US006946276B2

(12) United States Patent
Webster et al.

(10) Patent No.: US 6,946,276 B2
(45) **Date of Patent: *Sep. 20, 2005**

(54) ISOLATED HUMAN KINASE PROTEINS, NUCLEIC ACID MOLECULES ENCODING HUMAN KINASE PROTEINS, AND USES THEREOF

(75) Inventors: Marion Webster, San Francisco, CA (US); Chunhua Yan, Boyds, MD (US); Valentina Di Francesco, Rockville, MD (US); Ellen M. Beasley, Damestown, MD (US)

(73) Assignee: Applera Corporation, Norwalk, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/724,594

(22) Filed: Dec. 2, 2003

(65) Prior Publication Data

US 2004/0091993 A1 May 13, 2004

Related U.S. Application Data

(62) Division of application No. 10/238,709, filed on Sep. 11, 2002, now Pat. No. 6,680,188, which is a division of application No. 09/804,471, filed on Mar. 13, 2001, now Pat. No. 6,479,269.

(51) Int. Cl.[7] ............................ C12N 9/20; C12N 1/20; C12N 15/00; C12N 5/00; C07H 21/04

(52) U.S. Cl. ................. 435/194; 435/252.3; 435/320.1; 435/325; 435/6; 536/23.2

(58) Field of Search .............................. 435/194, 252.3, 435/320.1, 325, 6; 536/23.2

(56) References Cited

U.S. PATENT DOCUMENTS 6,734,009 B2 * 5/2004 Yu et al. .................. 435/252.3
2004/0023242 A1 * 2/2004 Yue et al. ...................... 435/6

* cited by examiner

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

12 Claims, 105 Drawing Sheets

```
   1 GGGGAGATGT TGAAGTTCAA ATATGGAGCG CGGAATCCTT TGGATGCTGG
  51 TGCTGCTGAA CCCATTGCCA ACCGGGCCTC CAGGCTGAAT CTGTTCTTCC
 101 AGGGGAAACC ACCCTTTATG ACTCAACAGC AGATGTCTCC TCTTTCCCGA
 151 GAAGGGATAT TAGATGCCCT CTTTGTTCTC TTTGAAGAAT GCAGTCAGCC
 201 TGCTCTGATG AAGATTAAGC ACGTGAGCAA CTTTGTCCGG AAGTATTCCG
 251 ACACCATAGC TGAGTTACAG GAGCTCCAGC CTTCGGCAAA GGACTTCGAA
 301 GTCAGAAGTC TTGTAGGTTG TGGTCACTTT GCTGAAGTGC AGGTGGTAAG
 351 AGAGAAAGCA ACCGGGGACA TCTATGCTAT GAAAGTGATG AAGAAGAAGG
 401 CTTTATTGGC CCAGGAGCAG GTTTCATTTT TTGAGGAAGA GCGGAACATA
 451 TTATCTCGAA GCACAAGCCC GTGGATCCCC CAATTACAGT ATGCCTTTCA
 501 GGACAAAAAT CACCTTTATC TGGTCATGGA ATATCAGCCT GGAGGGGACT
 551 TGCTGTCACT TTTGAATAGA TATGAGGACC AGTTAGATGA AAACCTGATA
 601 CAGTTTTACC TAGCTGAGCT GATTTTGGCT GTTCACAGCG TTCATCTGAT
 651 GGGATACGTG CATCGAGACA TCAAGCCTGA GAACATTCTC GTTGACCGCA
 701 CAGGACACAT CAAGCTGGTG GATTTTGGAT CTGCCGCGAA AATGAATTCA
 751 AACAAGATGG TGAATGCCAA ACTCCCGATT GGGACCCCAG ATTACATGGC
 801 TCCTGAAGTG CTGACTGTGA TGAACGGGGA TGGAAAAGGC ACCTACGGCC
 851 TGGACTGTGA CTGGTGGTCA GTGGGCGTGA TTGCCTATGA GATGATTTAT
 901 GGGAGATCCC CCTTCGCAGA GGGAACCTCT GCCAGAACCT TCAATAACAT
 951 TATGAATTTC CAGCGGTTTT TGAAATTTCC AGATGACCCC AAAGTGAGCA
1001 GTGACTTTCT TGATCTGATT CAAAGCTTGT TGTGCGGCCA GAAAGAGAGA
1051 CTGAAGTTTG AAGGTCTTTG CTGCCATCCT TTCTTCTCTA AAATTGACTG
1101 GAACAACATT CGTAACTCTC CTCCCCCCTT CGTTCCCACC CTCAAGTCCG
1151 ACGATGACAC CTCCAATTTT GATGAACCAG AGAAGAATTC GTGGGTTTCA
1201 TCCTCTCCGT GCCAGCTGAG CCCCTCAGGC TTCTCGGGTG AAGAACTGCC
1251 GTTTGTGGGG TTTTCGTACA GCAAGGCACT GGGGATTCTT GGTAGATCTG
1301 AGTCTGTTGT GTCGGGTCTG GACTCCCCTG CCAAGACTAG CTCCATGGAA
1351 AAGAAACTTC TCATCAAAAG CAAAGAGCTA CAAGACTCTC AGGACAAGTG
1401 TCACAAGGTA TTTATTTCCG CAGCCGGCCT CCTTCCTTGC TCCAGGATCC
1451 TCCCGTCCGT ATATGCCAAG GGATCCGCCC GGGGCCGCTG CTGGCTCTGA
1501 GCCGCCTGAT CCGTA
(SEQ ID NO: 1)
FEATURES:
5'UTR:        1 - 6
Start Codon:  7
Stop Codon:   1498
3'UTR:        1501

Homologous proteins:
Top 10 BLAST Hits:

                                                                     Score    E
Sequences producing significant alignments:                          (bits) Value
CRA|18000005168810 /altid=gi|3599507 /def=gb|AAC72822.1| (AF086...   888   0.0
CRA|18000005168811 /altid=gi|3599509 /def=gb|AAC72823.1| (AF086...   850   0.0
CRA|18000005161385 /altid=gi|3360512 /def=gb|AAC27932.1| (AF070...   844   0.0
CRA|18000005075416 /altid=gi|7505496 /def=pir||T25808 hypotheti...   352   7e-96
CRA|89000000196974 /altid=gi|7294566 /def=gb|AAF49906.1| (AE003...   347   1e-94
CRA|18000005236627 /altid=gi|5174413 /def=ref|NP_006026.1| CDC4...   346   4e-94
CRA|335001098689373 /altid=gi|11433630 /def=ref|XP_007257.1| CD...   346   4e-94
CRA|18000005123191 /altid=gi|7446379 /def=pir||T14039 protein k...   343   3e-93
CRA|18000005057611 /altid=gi|4505831 /def=ref|NP_003598.1| ser-...   342   6e-93
CRA|18000005067765 /altid=gi|7495847 /def=pir||T25539 hypotheti...   340   2e-92
```

FIGURE 1A

EST:

| Sequences producing significant alignments: | Score (bits) | E Value |
|---|---|---|
| gi\|11292270 /dataset=dbest /taxon=96... | 630 | e-178 |
| gi\|11369862 /dataset=dbest /taxon=96... | 615 | e-173 |
| gi\|12111020 /dataset=dbest /taxon=96... | 517 | e-144 |
| gi\|12362084 /dataset=dbest /taxon=96... | 492 | e-136 |
| gi\|12349935 /dataset=dbest /taxon=96... | 492 | e-136 |

FIGURE 1B

EXPRESSION INFORMATION FOR MODULATORY USE:
gi|11292270 Brain- glioblastoma
gi|11369862 Uterus tumor
gi|12111020 Colon
gi|12362084 Nervous- normal
gi|12349935 Nervous- tumor Tissue Expression:
Pooled tissues

FIGURE 1C

```
  1 MLKFKYGARN PLDAGAAEPI ANRASRLNLF FQGKPPFMTQ QQMSPLSREG
 51 ILDALFVLFE ECSQPALMKI KHVSNFVRKY SDTIAELQEL QPSAKDFEVR
101 SLVGCGHFAE VQVVREKATG DIYAMKVMKK KALLAQEQVS FFEEERNILS
151 RSTSPWIPQL QYAFQDKNHL YLVMEYQPGG DLLSLLNRYE DQLDENLIQF
201 YLAELILAVH SVHLMGYVHR DIKPENILVD RTGHIKLVDF GSAAKMNSNK
251 MVNAKLPIGT PDYMAPEVLT VMNGDGKGTY GLDCDWWSVG VIAYEMIYGR
301 SPFAEGTSAR TFNNIMNFQR FLKFPDDPKV SSDFLDLIQS LLCGQKERLK
351 FEGLCCHPFF SKIDWNNIRN SPPPFVPTLK SDDDTSNFDE PEKNSWVSSS
401 PCQLSPSGFS GEELPFVGFS YSKALGILGR SESVVSGLDS PAKTSSMEKK
451 LLIKSKELQD SQDKCHKVFI SAAGLLPCSR ILPSVYAKGS ARGRCWL
      (SEQ ID NO:2)

FEATURES:
Functional domains and key regions:
Prosite results:

[1] PDOC00004 PS00004 CAMP_PHOSPHO_SITE
cAMP- and cGMP-dependent protein kinase phosphorylation site

              78-81 RKYS
--------------------------------------------------------------------
--
[2] PDOC00005 PS00005 PKC_PHOSPHO_SITE
Protein kinase C phosphorylation site

Number of matches: 5
      1       93-95 SAK
      2     248-250 SNK
      3     308-310 SAR
      4     490-492 SAR
      5     378-380 TLK
--------------------------------------------------------------------
---
[3] PDOC00006 PS00006 CK2_PHOSPHO_SITE
Casein kinase II phosphorylation site

Number of matches: 9
      1       83-86 TIAE
      2       93-96 SAKD
      3     140-143 SFFE
      4     361-364 SKID
      5     381-384 SDDD
      6     386-389 SNFD
      7     410-413 SGEE
      8     436-439 SGLD
      9     445-448 SSME
--------------------------------------------------------------------
----
[4] PDOC00008 PS00008 MYRISTYL
N-myristoylation site

Number of matches: 3
```

FIGURE 2A

```
      1      50-55 GILDAL
      2    474-479 GLLPCS
      3    489-494 GSARGR
----------------------------------------------------------------
------
[5] PDOC00100 PS00107 PROTEIN_KINASE_ATP
Protein kinases ATP-binding region signature

           103-126 VGCGHFAEVQVVREKATGDIYAMK
----------------------------------------------------------------
-----
[6] PDOC00100 PS00108 PROTEIN_KINASE_ST
Serine/Threonine protein kinases active-site signature

           217-229 YVHRDIKPENILV
```

Membrane spanning structure and domains:

```
Candidate membrane-spanning segments:
 Helix Begin   End   Score Certainity
     1   197   217   0.789 Putative
     2   467   487   0.714 Putative
```

FIGURE 2B

```
BLAST Alignment to Top Hit:
Alignment to top blast hit:

>CRA|18000005168810 /altid=gi|3599507 /def=gb|AAC72822.1|
(AF086823)
            rho/rac-interacting citron kinase short isoform [Mus
            musculus] /org=Mus musculus /taxon=10090
/dataset=nraa
            /length=494
          Length = 494

 Score =  888 bits (2270), Expect = 0.0
 Identities = 432/495 (87%), Positives = 459/495 (92%)
 Frame = +1

Query: 7
MLKFKYGARNPLDAGAAEPIANRASRLNLFFQGKPPFMTQQQMSPLSREGILDALFVLFE 186
MLKFKYG RNP +A A+EPIA+RASRLNLFFQGKPP MTQQQMS LSREG+LDALF LFE
Sbjct: 1 MLKFKYGVRNPPEASASEPIASRASRLNLFFQGKPPLMTQQQMSALSREGMLDALFALFE 60

Query: 187  ECSQPALMKIKHVSNFVRKYSDTIAELQELQPSAKDFEVRSLVGCGHFAEVQVVREKATG 366
            ECSQPALMK+KHVS+FV+KYSDTIAEL+ELQPSA+DFEVRSLVGCGHFAEVQVVREKATG
Sbjct: 61   ECSQPALMKMKHVSSFVQKYSDTIAELRELQPSARDFEVRSLVGCGHFAEVQVVREKATG 120

Query: 367  DIYAMKVMKKKALLAQEQVSFFEEERNILSRSTSPWIPQLQYAFQDKNHLYLVMEYQPGG 546
            D+YAMK+MKKKALLAQEQVSFFEEERNILSRSTSPWIPQLQYAFQDKN+LYLVMEYQPGG
Sbjct: 121  DVYAMKIMKKKALLAQEQVSFFEEERNILSRSTSPWIPQLQYAFQDKNNLYLVMEYQPGG 180

Query: 547  DLLSLLNRYEDQLDENLIQFYLAELILAVHSVHLMGYVHRDIKPENILVDRTGHIKLVDF 726
         D LSLLNRYEDQLDE++IQFYLAELILAVHSVH MGYVHRDIKPENIL+DRTG IKLVDF
Sbjct: 181  DFLSLLNRYEDQLDESMIQFYLAELILAVHSVHQMGYVHRDIKPENILIDRTGEIKLVDF 240

Query: 727  GSAAKMNSNKMVNAKLPIGTPDYMAPEVLTVMNGDGKGTYGLDCDWWSVGVIAYEMIYGR 906
            GSAAKMNSNK V+AKLPIGTPDYMAPEVLTVMN D +GTYGLDCDWWSVGV+AYEM+YG+
Sbjct: 241  GSAAKMNSNK-VDAKLPIGTPDYMAPEVLTVMNEDRRGTYGLDCDWWSVGVVAYEMVYGK 299

Query: 907  SPFAEGTSARTFNNIMNFQRFLKFPDDPKVSSDFLDLIQSLLCGQKERLKFEGLCCHPFF 1086
            +PF EGTSARTFNNIMNFQRFLKFPDDPKVSS+ LDL+QSLLC QKERLKFEGLCCHPFF
Sbjct: 300  TPFTEGTSARTFNNIMNFQRFLKFPDDPKVSSELLDLLQSLLCVQKERLKFEGLCCHPFF 359

Query: 1087 SKIDWNNIRNSPPPFVPTLKSDDDTSNFDEPEKNSWVSSSPCQLSPSGFSGEELPFVGFS 1266
            ++ DWNNIRNSPPPFVPTLKSDDDTSNFDEPEKNSW P FSGEELPFVGFS
Sbjct: 360  ARTDWNNIRNSPPPFVPTLKSDDDTSNFDEPEKNSWAFILCVPAEPLAFSGEELPFVGFS 419

Query: 1267 YSKALGILGRSESVVSGLDSPAKTSSMEKKLLIKSKELQDSQDKCHKVFISAAGLLPCSR 1446
            YSKALG LGRSESVVS LDSPAK SSMEKKLLIKSKELQDSQDKCHKV IS AGL PCSR
Sbjct: 420  YSKALGYLGRSESVVSSLDSPAKVSSMEKKLLIKSKELQDSQDKCHKVSISTAGLRPCSR 479

QuerySIYAEGSAGGHC 494 (SEQ ID NO:4)
: 1447 ILPSVYAKGSARGRC 1491
IL S+YA+GSA G C
Sbjct: 480  ILQ
```

FIGURE 2C

Hmmer search results (Pfam):
Scores for sequence family classification (score includes all domains):

| Model | Description | Score | E-value | N |
| --- | --- | --- | --- | --- |
| PF00069 | Eukaryotic protein kinase domain | 219.4 | 5.5e-62 | 1 |
| CE00022 | CE00022 MAGUK_subfamily_d | 28.0 | 3.5e-08 | 1 |
| CE00359 | E00359 bone_morphogenetic_protein_receptor | 21.4 | 2.4e-05 | 1 |
| PF00433 | Protein kinase C terminal domain | 15.4 | 0.0018 | 1 |
| CE00287 | CE00287 PTK_Eph_orphan_receptor | -56.4 | 0.00012 | 1 |
| CE00292 | CE00292 PTK_membrane_span | -91.3 | 0.0013 | 1 |
| CE00291 | CE00291 PTK_fgf_receptor | -110.8 | 0.021 | 1 |
| CE00286 | E00286 PTK_EGF_receptor | -122.6 | 0.0015 | 1 |
| CE00290 | CE00290 PTK_Trk_family | -180.0 | 0.0073 | 1 |
| CE00016 | CE00016 GSK_glycogen_synthase_kinase | -201.8 | 1.8e-05 | 1 |

FIGURE 2D

Parsed for domains:

| Model | Domain | seq-f | seq-t | | hmm-f | hmm-t | | score | E-value |
|---|---|---|---|---|---|---|---|---|---|
| CE00359 | 1/1 | 219 | 269 | .. | 274 | 327 | .. | 21.4 | 2.4e-05 |
| CE00022 | 1/1 | 218 | 316 | .. | 143 | 238 | .. | 28.0 | 3.5e-08 |
| CE00292 | 1/1 | 97 | 341 | .. | 1 | 288 | [] | -91.3 | 0.0013 |
| CE00290 | 1/1 | 99 | 341 | .. | 1 | 282 | [] | -180.0 | 0.0073 |
| CE00286 | 1/1 | 96 | 341 | .. | 1 | 263 | [] | -122.6 | 0.0015 |
| CE00291 | 1/1 | 97 | 341 | .. | 1 | 285 | [] | -110.8 | 0.021 |
| CE00287 | 1/1 | 97 | 358 | .. | 1 | 260 | [] | -56.4 | 0.00012 |
| PF00069 | 1/1 | 97 | 360 | .. | 1 | 278 | [] | 219.4 | 5.5e-62 |
| PF00433 | 1/1 | 361 | 390 | .. | 1 | 32 | [. | 15.4 | 0.0018 |
| CE00016 | 1/1 | 38 | 438 | .. | 1 | 433 | [] | -201.8 | 1.8e-05 |

FIGURE 2E

```
   1 TACACCTAGC AATAGTCATA GAATGCACAA ATCTTCAATG TTAGCAAATA
  51 ATGCCAAACT TTTTTTTCAA ATTTCAAAGA GATTGTATCC ATTTACACGC
 101 CTACGGGTAC TGTATAAGTG TGTGTACTTC CACATCTTCG CAAACACTGT
 151 CACATCCTTT TGTTGTTGTT GTTCTCGAAT TTGAGTGTTA TTCTTTCTCA
 201 CTGTGACTTT ATTTTTCATA TTTTCTGATT ATGAACGAGG TTGACAACTT
 251 TCACACATTT GTTGGTCATC TGGATTTCCT TTTTGGTGAA GTGCCTGTTT
 301 AAGTATCTCG TCTATAATTT ATTTTAAAGT GTCCTTTCAG ACAGTCTCAA
 351 TGACTGTCAC CAACTCCTTG CAGGGCAGTC AGCCCGGAGA TAGAGTAATC
 401 AAGGTAGGTT GAAGTCAAGC TCAAAACATT CGCTGCCTCA GCTGTAGCAG
 451 AGGACCACTG GGCTTCCCCA GGTAACAAGT ACTTCTACCT TAGCCACATG
 501 AGAGAGAAAG AAGACCAGGC AGAGCAGCCT GGCTGCCTTC CTCCTTGCAG
 551 GTGGCCGAGA GCAGGGGACA GCGCCCTGGC GACCTCCTCA GGGATCCTAG
 601 ATTAACAGTC GCGTCCTCAA ACGCAGCATC CTGCGTAACC GCCAATTTCA
 651 AACTTCCAAG ACCTGCCCTG CTGATTTTGC CCTTCCCTTT TTCCCGTTGG
 701 TCGCGAGTCA AAGGAAGATG CAATTTGATT GGCTCTCCCC TTCACTTTCC
 751 TCCATGCCTT TAGGGACATG GGCGGGGCCT GGCTGAGACG CCCATGTCTA
 801 TCATAGGAGC GGAGACGCTG ATTGGTCCAA ACACGGCTGA GACCCGCCCG
 851 CGCCGTTCCT CGGGTTCAAA CGCGGCGGCG GGAGGCGCGG GGCGGAACAG
 901 ATCGCAGACC TGGGGGTTCG CAGAGCGTGA GTCTGATCCC CCAGACCCAA
 951 TTCTACCGCA CCCGGCTCTG CAAGGCCAGG GGAGGGCCGC CTCCACCCAT
1001 ACAAGTCCCG GGTTTCCCTC CCGCCCCGGG GAGGGCGGCG ATTCCACCCC
1051 CAGGGCTGCG GGAGGCCTGG AGGGTCTTCC GGGGCTAGCT GTGCGCGCGC
1101 CCACCTTCCT TGGGAGCCGA GGGGTCAGCC GAGTGGTGCT GGGGCAGGAG
1151 GCTTGCTCCT CCCCTAAACC AGGCGGAGTG CTTTGTCTCT TCAGCTCTGC
1201 CTCCTGTCAG CACTAACTGC ATTATTCTGC CCAGTGTAGT CGGCCGGTTC
1251 CTTATTATCT GCGTGAACTT AGCCATTTAC TTAACCTCTC TGTTTCAGCG
1301 TATTCATACC CCGTGCCCAC CCCATCACCT CATGATGCCC CCGCCTCTTT
1351 CGCTCTGCTC CAGTCCGTCT GGCCTCGCTG TTGCTGGAGA GGCCAGGTCC
1401 TGCCTCAGTG CTTTTGGCTT GGCTGTTTCG TTTGCCACGG ATGTCTTTCT
1451 TTCCCCAGAT ATCAACATGG CTTGCTGGTC ATTCGCTTCA GGTCTTCAAG
1501 TCTTGGGTCA AATGGTGGCT TCTCAGTGAA GTCTTATTTG ACCACACTAA
1551 AAATTGCACC ATCTCACCCC CATTGTCCTT TTCTTGCTCG ATTTTGTTTT
1601 TACCCCATAG CACTTAACAC CTTACAACAA GCTATATATT TTGCTTATTT
1651 CAGTCATTCA TTTAATAACT ATTCGCACCT ATTTGTGTGC CAGGCTATGT
1701 GTGCCCCCAC TGCATGGGGG CAAACATCTC TGCCCTTGTG GAGCTTCCAT
1751 TCTAAGGGGG GAGATAATAA ACACATTTAT AAGTAAGAGA GTATGTCAGA
1801 TAAGTGTATC ATCTCCTGTC ACAGTGAGTT AAAATCTGGT GTTTAATCTC
1851 CATGATTAGA CTGAGCTTCC TAAAACTGGA GTGGTAGCTG ATTTTCACCT
1901 CCTTGTCCCT GATATCTTGA GGGAGATCAG GATCTCTCAG GCCCTTCCTG
1951 CTCAAAACAT AGGACACACT TGACTTTTCT GATATCCTTT CAGCGCCAGT
2001 GGGGAGATGT TGAAGTTCAA ATATGGAGCG CGGAATCCTT TGGATGCTGG
2051 TGCTGCTGAA CCCATTGCCA GCCGGGCCTC CAGGCTGAAT CTGTTCTTCC
2101 AGGTAACAGC CTACCCTGCC AACTTTGCTC ACCTGTGTGT GTCCTTGGAA
2151 TCTCCTTGTC ACTCACCTTT GCTTTTATTT ATTTGTTTAT TTATTTAGAG
2201 TCTCAGTCTC TCAGGCTGGA GTACAGTGGT GCAATCTCAG CTCACTGCAA
2251 CCTCCGCCTC CTGGGTTCAA GCGATTCTCC TGCCTCAGCC TCCAGAGTAG
2301 CTGGGACTAC AGCCGCCTGC CACCACACCC GGCTAAATTT TGTATTTTTC
2351 TTTTTAGTAG AGACGGGGTT TCACCATGTT GGCCAGGCTA GGGTCGAACT
2401 CCTGACCTCA AGTGATCCAC CTGCCTTGGC CTCCTAAAGT GCTGGGATTA
2451 CAGGCATGAA CCGTGCCCAG CTTGCTTTTA TTATAGGACC AGGGATAATA
2501 TTTTAGGGGA AATTCTGTTT TGTTTTGTTT GAAACAAGGT CTTCTGTCGA
2551 CTCTAGGCCT GTGCCACCAT GCCTGGCTAA TTTTTTAATT TTTTGTAGGG
2601 ATGGGGTCTC ACTGTGTTGC CCAGGCTGAT ATAGAACACC TGACTTCAAG
```

FIGURE 3A

2651 TGAGCCTCTT GCCTTGGCCT CCCAAAGCAC TGGGGTTATA GGTGTGAGCC
2701 ACTGCACCTG GCCCTCTATT TAGAGTTTTA TATGCACTGA TTCTTTTGGA
2751 AAAAAGACAC TGTGCAGAAG TAGATAGCTG AACTTGCCTT AGAAGGGAGA
2801 TCTTTTCATA TTTCTCACAC TTTACACTTC TGTACTAAAG TTTATTCATT
2851 CATTGATTGA TTGGTTGCTT GCAAGACAGG GTCTTGCTCT GTGGCTCAGG
2901 CTGGAGTGCA TTGGCACAAT CACGGCTTAC TGCAGCCTTG ACCTCCTGGG
2951 CTCAAACGAT CCTCCCACTT CAGCTTCCTG AGTAGCTGGG ACCACAGGTG
3001 TGTGCCACCA TACCTGGCTA ATTTTTGTAT TTTTTGTAGA GATGAGGTTT
3051 CACCATGTTG CCCAGGCAGG TCTCGAATTC CTGGGCTCAA GTGATCTACT
3101 TGTCACAGCT TCTGCAAGTG TTGGGCTTAC AGGCATAAGC CCCTGTACCA
3151 GGGCAAGTTT GTCCTTTTAT TGAAGAAAGA AAAATAAATG AACAAAGATG
3201 CTTTTTAAAA CTACAATTTC TGTGGGTATA ATCCTATTCA TTTTCATTGC
3251 AGGGATGTTT ATTTTTTAAG ATTTTTTTTT TTTTTTTTTG AGACAGAGTC
3301 TTCGCTGTCG CCCAGGCTGG AGTGCAGTGG CGCGATCTCG GCTCACTGCA
3351 GGCTCTGCCC CCCGGGGTTC ACGCCATTCT CCTGCCTCAG CCTCCCACGT
3401 AGCTGGGACT ACAGGCGCCC GTCACCTCGC CCGGCTAATT TTTTGTATTT
3451 TTAGTAGAGA CGGGGTTTCA CTGTGTTAGC CAGGATGGTA TTTTTTAAGA
3501 TTTTAAAAAA AGTTTTGATG AATACCACAC CTGTTTAACC CTCATTCCTC
3551 TCAAGATACA CATTTCTGTC ACCCCAGATG CGTTAAAACT TAATATCATA
3601 AGATTACTTC CAAATAGATT TTTAATTCTT TTGTTTCTGA TGTATGTGGA
3651 ACACTGGTGA AGTAGAAATC CTTGTTTGAT TTATGTATTC GTAAGTCAGG
3701 GGGACAATAG AGACCATGAA GATTTAGAAT TGAATCCCAG TCCCAGCACT
3751 AGTTAGCTGC ATTACTTTGG GTGAGTCAGT TACCTTTTCT GAGTCCATTT
3801 GCTATTCTTT AAAATAGGTT GTAGCCTGTA ATGCCAGTAT TTTCGGAGGC
3851 TGAGGCGGGC GGATTACTTG AGGTCACGGG TTCGAGACCA GCCTGGACAA
3901 CGTGGTGAAA CCCTGTCTCT ACTAAAAATA TAGAAAATTA GCTGGGCATG
3951 GTGGTCGCAT GTACCTGTAA TCCCAGCTAC TTGAAAAGCT GAAGCAGGAG
4001 AATCATTTGA ACCCGGGAGG CGGAGGTTGT CGTGAGCCGA GATGGTGCAC
4051 TGCACTCCAG CCTGGGCGAC AGAGTGGGTA AGACTCCATC TCAAAACAAA
4101 ACAAAACAAA AGAAAACAAA AAAAATAACA TAGAGGTTGT AGTACCTAAT
4151 CCACAGGGTT GTTGTGAGGA TTAGATGAGA TATTCGATTT AAAGCACTTA
4201 GCACCTTGCC TGGCTCTTAG TAAACTCCTT ATAAAAAATG GTAATTATTG
4251 TTAATACTCA GCATAGAATA GTATTAGTTA TAATATTAAT ACTAAATTTG
4301 TTTCCTTAAT AGTAATTATA TTTGGGAAGG TAGTTATGTA GGATACCTGT
4351 AAGATGATGA ATGATGAAGT ATTCTTGATA ACTTTTTTTT TTTTTCCAAA
4401 ATATTGGTAT TGGGTGTTTA AACAGATGAG AGTGGAAACA AATTGAAAGC
4451 TTAGGTTTTT CTGTGGGACC ATCCCCATCA GCATTTTAAG TCTTGACATA
4501 TCTTTCACAA ATGAATAGTC TGTCTTTAAC CTTAGATGGC TGGAGTGCTG
4551 CCACGTTTCA GCCCCTTTAT CATGCTACTT TAAAATATCT CCAACTTGCT
4601 GGGCGTGGTG GCTCACGCCT GTAATCCTAG CAATTTGGGA GGCTGAGGTG
4651 GGTGGATTGC TTGAGGTCAG GAGTTCGAGA GCAGCCCGGG CAACATGGTG
4701 AGCCCCTCCG TTTCTACTAA AAACACAAAA AATAGCTGAC TGTGATGGTG
4751 TGTGCCTGTA GTCCCAGCTA CTCGGGAGGC TGAGGCAGGA GGATCACTTG
4801 AGCCCTAGAG GCAGAGGTTG CAGTGAGCTA AGATTGTGCC ACTGCACTTC
4851 AGCACTTCAG CCTAGGCGAC AGAGCAAGAC CCTGTAAATT AAAAAAAAAA
4901 AAAAAAAGAA AAGGAAAAAA ATTTCCAACT TATTAAGGGC TTATAGTGTG
4951 CTGATTATGT AATAGTTATG GCTTCCAATG TGTCTGGCAT AGAACTGGCA
5001 TGTTTCTGAG TATCTCACTT CAGCCTCATG ACAGAGGTAA GGACTATTTT
5051 TAATTTAAAC TTTAAATAGG AGGCAACAGG CCAGGTGTGG TGGCTCACAC
5101 CTGTAATCCC AGTACTTTGG GAGGCTGAGG CAGGTGGATT GCTTGAGTCC
5151 AAGAGTTCAA GACTAGCCTG GGCAAAATGG TGAAACCCCA TCTCTACAAA
5201 AAATATAAAT AATTAGTCAG GCATGGCGGT GTGTGCCTGT AGTCCCAGCT
5251 ACTCAGGAGG CTGAGGTGGG GGCATCTCTG GGGCCCCGGA GGCAGAGGTT

FIGURE 3B

5301 GTAGTGAGTT GAGATTGCAA CACTGCACTC CAGCCTGGGC AACAGAACGA
5351 GACCCTGTTT CTAAATAAAT ACATAAATAG GAGGCAACAG ATATAGACAG
5401 ATATGGAGGT AGGTAAGGCC TTGCCCAAGA TCATACACGT TGGGTTTTGC
5451 AGATGAGGCC AAGATCAGAC TCCATCTTTG GTTGGTCTGA CTCCAAAGGC
5501 TGACCACATA GCCATTGGGC CACAGCACCT GTGCACGTCA GAATTTATTA
5551 AGTATATCTT GTATTTAGTC ATTATAACAG GAAGACTTAT GGGTAAACCC
5601 TCAGTTCATC TCTTTTTAAT GCTGAGATCC CCCTGCCCAG TAAAGCTATT
5651 ATTGCAAGTA TAGTATATAC CTATCATTTG CCTTGAGTTA TCAGGTAAGG
5701 ATGCTGTTTG TTCTTTTCCC ATATAGTGCT GTTTGAATGA GGTTGAGATA
5751 CAGTAGCAAT TTTGTTTTCC ATTCAGGTGA GTACCTTAGA CTGAGTGTCA
5801 TTTTGTCTTT TTTACTTCTA CTCAACAGGA TTTCCTGACA TGTTCGAGGT
5851 CAGTGATTGT CAGACTTTCT GAGCCAGCAA AATTTCCCAA ATTGCTGGGT
5901 AGACACAGGT TTTCCAACTT TTTATTTTGC CAAGTAAGGA TATATAAAAA
5951 AAAAATAAAA AGAAAGACCT ATTATTTTCT GGCCCTTGTA TTTCATAAAG
6001 GGCATTTTAA GAAACAACAA GACAGGAAGA ACATCATCTC AGAATAAAGG
6051 ACCATTTTTA AATTTGAATA CATTTAGTTT TATAAAAAAG ATATCATGTG
6101 GTGTTCATTT TTTCTCATTT CACTGCAGGC TGTTGAAAAC TTTGTTAAGA
6151 ACCAGTACTA TATTTGGGAA CCCCTGCTTT AATTGATCTA AACTCTTGAA
6201 GAATAGAAGA AACAAAGCAT TTTATTTTTC TGAGTTACTG GCAACTATTA
6251 CTAAAGTGAC AGATATGGTG GCCTTGAATG CAGTGCTTCC CAAACCTGAT
6301 TGAGGTCTGA CTCTCTTGGG GACCAGGGTC TCATTCTGTT GCCCAGGCTG
6351 GAGTGTGGCA GCACAATCTT GGCTCACTGC AGCCTTTACT TCTTGGGCTC
6401 AAGTGATCCT TCTACCTCAG TCTCACAAGT GGCTAGGACT ACAGGACCAT
6451 GGCACTACAC CTGGCTAATT TTTTTTTGTT TGTTTGTAGA GATGGGATCT
6501 CGCTGTGTTG CCCTGGCTGG TCTTGAACTC CTGGGCTCAA GTGATCCTCC
6551 CACCTTGGCC TCCCAAAGTG CTAGTATTCC AGGTGTGAGC CACCTCTCCC
6601 TGCTGGGGAA CTTGTTAATA AAACAGATTC TAGGCTACAG TCTGGAAAAT
6651 TCTAATTCAT TTGGTTGTGG GGGAGGGGGG CATAGGACCA GAGAATGTGT
6701 TTGTTTGTTT GTTTGTTTTT CTTAAATTCT CCAGTGCTGT TGTGATTCAA
6751 ATGCAGCCGG TCTGTTTCTG TTATCAAGTG CTGTGTAACA AAGCACTCAC
6801 AAAGTTTAAA GCAACAATGA TTTATTTTTT CTTAGGATTC TGTGGGTTGG
6851 CTGGACTCAG CTAGGTAGTT CTGCTTCATC CTGTGATGTC AGCTGGGGTC
6901 ACTTGTGGGG CTACATTCAG CTGGGATTAT GTCTGGGACT GGAACATGTG
6951 GGTGCTGACT GCTGGCTGGG GCACCTTAGT GTTTCTCACA TGGCCTCTCT
7001 TCTCCATGAG GTCTTTCAGT AGTATAGCCC AGGACTCGTA ACTTTTTTTT
7051 TTTTTTTAAG ACAGACTGTC GCCCTGTCGC CCAGGCTGGA GTGCAGTGGC
7101 ACGATCTCTG CTCACTGCAA CCTCCGCCTC CTGGGTTCAA GCAATTCTCC
7151 TGCCCCAGCC TCCCGAGTAG CTGGGATTAC AGGCACGTGC CTCCACGCCC
7201 GGCTAATGTT TGCATTTTTA GTAGAGATGG GGTTTCACCA CGTTGGTCAG
7251 GCTGGTCTCG AACTTCTGAC CTCGCGATCC GCCTGCCTCG GCCTCCCAAA
7301 GTGTTGGAAT TACAGGTGTG AGCCACTGCA CCTGGCTGAC TCGTAACTTT
7351 TTTTGTAAGT AATAAATATT TTAGGCTTTG TGGGTCCTGT AGTCTCTGTT
7401 GCAACCACTC AACTTGGCCA TGGTAGCACA AAAGCAGCTA AAGACAATAT
7451 GTAAATGATG GGTGTAGCTG TGTTCCAGTA AAACTTATAA AAAGTCCGTG
7501 GGCTGGATTT GGTCCAAGGG CTACAGATTG CACACCCCTG GTCTAGCCCA
7551 AGCATCTGTG CATGGTGGCT GGCTTCCCAA AAGTGGAAGC TGCTAAGCTG
7601 CCTTTTTTTT TTTTTTTTTT TTTTTTGAGA GGGAGTCTCA CTGTGTTGCC
7651 TAGGCTGGAG TGCGGTGGTG TGATCTCGGC TCACTGCAAC CTCCATCTCC
7701 CGGGTGCAGG CAATTCTCAT GCCTCAACCT CCCAGGTAGC TGGGATTACG
7751 GGTGCCTACC ACCACGCCTG GCTAATTTTT GTATTTTGGT AGAGACAGGG
7801 TTTCACCATG TTGGCCAGGC TGGTCTCAAA CTCCTGACCT CAAGTGATCC
7851 ACCCGTCTTG GCCTCCCAAA GTGCTGGGAT TACAGATGTG AGCCACCGTG
7901 TCTGGCCGCT TGACAAGCTT CTTAAAGGCA CTGCCCTGAA CTGGCACAGT

FIGURE 3C

7951 GTCACTTGTG TCACATTCTT TTGGTTGAAG AGAGTCTCAG AGATGGCACA
8001 GATTCAAAGG CAGGAGAAAT AGACTCCAGC GCTTAAAGTA AGGAGTAGCA
8051 TGTGCCTACA GAATTGGAGG AACTGTTGGA GGCCATCTTT GAAGAGAGAC
8101 CACCACTATC CATGGCTTGG CACGTGGGAA TCACTGCTCT ATACCAGGGT
8151 TGCAGACTCA TGTCTTTGGG GGCCAGGCAG TGAGTATAAA TGAGTCAAGT
8201 GGGCCAGTTG GAAGATGGAG TCAGACCTGC AGTGAACTCC CAAACACATC
8251 TGCTACCGGG AGGGGCAGCA TTACTCAGCT CCAGCTCAGC GTCATCAGGC
8301 AGGAAGGCGA GGCAGTGTTG CCGGATGTGC CAGTGTTTCA AAAGAAGCCA
8351 GAGACTCCAT TTTTATTTTT TTGTATGGAA TCTCCTGATT TTGAAATATT
8401 GGCAGATAAT TCAAATTATC TTAAACACTA CAGGCCAAAC AAAACATATC
8451 TGTGGGCTAG AGACAGTCTG CCAGTTTGTA ACTATTTCTC CAGATCATGA
8501 GTAAATTTGG CTTTACGATG GTCACTCAGT TCTTATTACT CTAGGTTGTT
8551 CAAATGAATT AAAAAAGCTG AAATTATATG AATAAACCCC TGGGCACACA
8601 TGAAAGAAGT GAAAAACCCA TTGTTTCCTA TTGTAGAAAC ATGGAAGCAT
8651 GTCAGAGCCA GAGGATCCAG AGGAAATATT CTCACTAGCC TCAGACCCTC
8701 AGGAGTGAGG GAGCTTTTCT TGTTAATGGC CACGCTTGTG CAGTTTTCCT
8751 TCCCAGGTGC TGGTGAAAGA AACCCACAGT CTTGGAATCA TGGAAGTGAT
8801 ACCATAATGA CTGTCAGTTG ACGTTGCTTT AAAGAATGAA GCCACAGAAT
8851 TGTGCTGTTA GCATGTCGTG AGCAGTTAGT TGAGTTGGTG GCTTGTAATT
8901 TACTCTGTGT GGATGTTATT GATCAAAGCT TTTCATTATT GACAGTGTCT
8951 CCATCTGCTG TTTGCTGTTT TTAGGGGAAA CCACCCTTTA TGACTCAACA
9001 GCAGATGTCT CCTCTTTCCC GAGAAGGGAT ATTAGATGCC CTCTTTGTTC
9051 TCTTTGAAGA ATGCAGTCAG CCTGCTCTGA TGAAGATTAA GCACGTGAGC
9101 AACTTTGTCC CGGAAGTGTA AGTTTGGGGA ACTTTTTCTT GAAAACTGTC
9151 CTGAGAGAGA AAAACTAGAA AGATGCTTGA GGCAGAATGA GTTACTGGTT
9201 GATAGTAGTC GGTAAGAACT CTGGTTCTAT ATAAGACAGA TCCAGGTTCA
9251 AATTCAGGCT GCACCTCTTA TAGCTGGGAG ACCAGGTAAG TTGGGCTTCT
9301 TGGTTGCAAG CGACAAACTT AATTCAAAGA CTGAATTTAG GCCAGGTGCA
9351 ATGGCTCATA CCTATAATCT CAGCCCTTTG GGAAGCTGAG GTGGGTGAAT
9401 CGCTTGAGCC CAGGAGTTCA AGACCAGCTT GGGCAACATG GTGAAACCCC
9451 ATCTCTACAA AAAATACAAA AATTAGCTGG GTATGGTGGC TTGCACCCGT
9501 GGTCCCAGCT GCTGAGGAGG CTGAGGTGGG AGGATCACTG GAGCCCGGGA
9551 GGTTGAGGCT CAATGAGCTG TGATTGTGCC ATTGCACTCC AGTCTGGGTG
9601 ACAGAGTGAG ACCCTGTGTG AATAAAAGAG TGAATTTATT GGCTCATGAA
9651 ACTGAGAAAT CCAGGAATGA GTTAAGTTTT AGCTTTAGGC ATAGCTAGTT
9701 CCAGAGACCT CAATAATATC CCGTGGCCCT GTCCTTATAC TCACTCAGGG
9751 CTGACTTTCT ATTAGGCAGA GTAGGCACGG TGCTTAGGAT CTGTGATATT
9801 TAATTTTAAT GAATTTAATT ACTTTTAATT AACTGAATTA AATTTTAATT
9851 TGTTTTAAAA TTATAGGAAA AATGAATATA ATAATGTATA ATGATTCTGG
9901 ATTACATTCA TCTTTATACT AATGTAGTCA TAAAATATAA TTTTTGTTTT
9951 TTTTGGAGAC AGAGTCTTGC CCTATTACCC AGGCTGGATT GCAGTGGTAT
10001 ATCATGGCTC ACTGCAGTTT CAACCTTCTA GGCTCAAGCA ATCCTTCCAC
10051 CCCAGTGGCT GGGACTACAG GCTCACACTA CCACGCCCAG CTAATTTTTG
10101 CTTTTTTCTC TGTAGAGATA GGGTCTTACT ATGTTACCCA GGCTGGTTTC
10151 AAACTCCAGG CTTGAAGCAG TCTTCCTGCC TCAGCCTCCC AAAGCTTTGG
10201 GATTACAGGT GTGAGCCACC ATGCCTGGCC CCATAAAATA TAATTTTTGA
10251 ATTCTTTTTT GTTTTTAATG GAGGAAGGGG CTGAGGAAGG CAAAAGTACC
10301 TAGGGCCTAT GAAGTCATAT ATTGGCCTTG CCTTCACCCT GTTTCTGACT
10351 TTGCTTGACT TCCATGTGAT GAGGCAGTTG GCTGTTAGTG TCCCAGTTTC
10401 ATACTCTTAC ATTAGTGTTT TTCAACCAGT GGGTGATTTG ACGTTTTCGG
10451 TTGTCAGAGC TAGTTGGGGG TGGTGGTGTG TGAGTTTGGG GGGAAGGGTC
10501 CTACTGTCAG TTAATGGGTG AGGCCAGAGA TGCCACCAAA CACCTTACAG
10551 TGCACAAAGC AGCCCCCATA ACACAGAATT ATGTAGCCCA CAATGCCAAC

FIGURE 3D

```
10601 AGTGCTGAAT TTGAGAAACC CCACCTTGTA CAACATTGCT GTGCAACCAA
10651 CCACCCTAAA TATTACTGAC TTAAAACAAT AGTCACTGTG GCTGGGCGCG
10701 GTGGCTCATG CGTGTAAGCC CAGCGCTTTG GGAGGCTGAG GCGGCGGATC
10751 ACTTGAGGTC AGGAGTTCCA GACCAGCCTG GCCAACATGG TGAAACCTTG
10801 TCTCTACTAA AAATACAAGA ATTAGCTGAA TGTGGCAGCG GGCGCCTGTA
10851 ATCCCAGCCA TTTGGGAGGC AGAGGCAGGA GAATCGCTTG AACCTGGGAG
10901 GTGGAGGTTG CAGTGAGCCA AGATCTCACC ATTGCACTCC AGCTTGGGCA
10951 ATGAGTGAGA CTCTGTCTTA AAAAAAAAAA AAAGTTATTG TATTACCTCT
11001 TGTGTGTGTA GGTTAATTGG ACTCAGCTGG GGATTCCTCT GCTCTGTATT
11051 ACATTGGCCA GGATTGCAGT CACCTGGGGC TCTCCTGGGC TGGAATGTGT
11101 GAGAGGGCTT ACTCAGTGTT TGGTGCCCTG GCTTGGAGGC TGGGCCCAGC
11151 TGGGCCTCTC TCTCTTCATG AAGTTTCAGG GCCTTTTGCT GTCCACATGG
11201 CACCTCTATG TGGTCTCCAA ATCAGAAGTC AAGGAACTAC AGCCTGTGAT
11251 GCCTATTTTG TAAAGAAGGT TTTACTGGAA CACAGCCCTA CCCATGTGTT
11301 TGTACAGTGC CTATGGCTGC TTTCACATCA TAACAGCATT TTATTTCATT
11351 TTATTTATTT TTTTTTGAGA CAAAGTCTCA CTCTGGCTGG AGTGCAGCAG
11401 CACAATCATA GCTCACTGCA GCCTCCAACT CTTGGGCTCA AGCAATCCTC
11451 CTGTCTCAGC CTCCTCAGTA GCTAGTACTA CAGGCCCATG CCACCACTAA
11501 TGGCTAATTT TTTAATTTTG TGTAGAGATG GGACCTTGTG AGATTGCCTA
11551 GGCTGGTCTT GAACTCCTGG CCTCAAGAAA TCCTCCCACC TTGGCCTCCC
11601 AAAATGCTTG GATTACAGGC ATGAGCCACT GTGCCCAGCC CACAACAGCA
11651 TTTGAGTAGT TGTGATAGAG ACCAAATGGC CTACAAAGCC CAAAATAGTT
11701 CCTGTTTGGC CCATTTCGAA AAGGCTTGCT GACCTCTGAG CTACATGGTC
11751 TCTCTAGCAG GACAGCCTCG ACGGTAGCTC AGGTTTCCAA AACACAAAAG
11801 TGGAAGCTGC CAGGCTTTCT TAGGGGTTAT CCTAGGAGGG ACATAGGATC
11851 TCTTTGACTG CATTTTATTG TTTGATGCAT GCTCTGGGGC TGCTCAAATT
11901 CCACCTGAGA GGAAACTACA CAAGGTCATG AATCCCAAGA GGACTGGGGC
11951 ATTGGGTGCT ATTTTTGGAG ACTGGCTACC ACACCCTGCC CAATGGTAAT
12001 CTTCCCTTAT CTAGATTAAT ACAACCCCAG GGAAGATTCT AACTTGGCTC
12051 TGCTTTGGGT CATTTGCCTC CCTGGAGGTG AGGTGTTGTG ATCGGTTTTG
12101 TTGGAATGCC CAAAGGGGTC AGGGCAGTGT GATTACCAGG ACCTCATGGA
12151 ATGGGGGATG CGTGGTTATG CAAAGGAGCC GGGGATGCTG GGTAGAAAAA
12201 AAATCAGCAT ATGTTCACTA TAGTGCTCTT CAGTATTTTA CATGTACTTT
12251 GTTCTCAGTT TTCTCATCTG TAAAATAGGA ATAATGTATA TCCTTTTTTT
12301 TTTTTTTTTT TTGGAGTCTT GCTCTGTTGT CCAGGCTGGA GTACAGTGGC
12351 ACAATCTCAG CTCACTGCAA CCTCCGCATC CCGGGTTCAA GTGATTCTCC
12401 TGCCTCAGCC TCCTCAGTAG CTGGGACTAC AGGCGTGCAC CACCACACTC
12451 AGCTAGTTTT TGTATTTTTA GTAGAGATGG GGTTTCGCCA TGTTGGCCAG
12501 GCTGGTCTCA AACTCCTGAC CTCAAGTGAT CTGCCTGCCT CGGCCTCCGA
12551 AAGTGCTGGA ATTACAGGCA TGAGCCACCA CGCCCATTGG GAATAATGTA
12601 TATCTAATGA GGCTGTGTTG GAATTGAATG AGTTAATGCA CAGACCAGAT
12651 TTGTCATGTT GCCTGGCCCA TAGGAGACAA TAAATGGTAC CCAGTATTAA
12701 TAACTGTGAA TGTCAACAAC ATTTAATATA TTGTATATCT TCAAAATGTA
12751 CTTGAGGTAT TTGTTCATCA TTCTGTTTTT GTTTGAATAA GCTCGTGCCT
12801 TCTTTTTGTG AATATTTAAA TTTATAAGTA GCGAGTGGGA GGGGAAGGAA
12851 GTTATGTGAT GAGGCTAGCT TACTGAGCCA TCTGCAGGCA CCTTCATTAG
12901 TCTTGAGACT GTCCTCTGGT TACTTAACAG CAGTGAATTA TCTAGAATCA
12951 TTTAGTGATC AGAAGACTTG GTTTAGTGGA ATGTAGATTT TTTTCTAATA
13001 GACCCCTCTT CCAGGGAAAT GTTTCATATT TTTGAAGAGG TTTCCTGGGG
13051 AGTGTTTAAG AGGCCATGAT TGAAAATGGG TGATTACATT AGTGTGTTTT
13101 CTATTCCTCC CCTTTTTGAG TTTCTGTTTT GGAATGTAAG CTTTGTTTTT
13151 CTACGTGGAG AAGGGTCCCT CAGCTGCTTC TGCCCAGGTT TTTTGAATCT
13201 TCCTATAGGG ATGGAGATTT TCTTTGGGGA CTGTTAGAGA AAATGGAATA
```

FIGURE 3E

```
13251 GAGTGTAGCT CTGAAGGAGA AGGATGTCTC CAGCAGAAGT ACCTCTAGCC
13301 TTGGGCCAAG GGAGGGAAGG GAAGGGAACG AGCATCTGGG AACCAGGGAA
13351 GGGATTTTTG TCTTTCTTAA TTACTCTTAC ATCCCCAGTG CCCAAAATAG
13401 TGTCTGGCAT ATGTTAAGTC CTTAGTAAAT ACTTGTTGAA TGAGTGTATG
13451 CTCAGTGAAC AAAATAAATG GCAAACATTA AGCACAGTAT CAGATAATTT
13501 GTGTAAAAAA TATACAGCAG TGTTATACTA AAACTTGCAC AGAGGCCAGG
13551 TGCAGTGGCT CACGCCTGTA ATCCCAGCAC TGGGAGGCCG AGGTGGGCAG
13601 ATCTTTGAGC TCAGGAGTTT GAGACCAACC TGGGCAACAT GCTGAAACCC
13651 TGTCTATACA AAAAATACAA AAAGTAGCTG GGGCATGGGG ACGCACATCT
13701 GTGGTCCCAG CTACTTGGGA GGCTGAGGCT GGAGTAATTG CTTGAAGCTG
13751 GGAGGTGGAG GTTGCAGTAA GCCAAGATTG TGCCACTGCA CCCCAGCCTG
13801 GGTGACAGAG TAAGACCCTG TCTCAAAACA CAAAACAACA CCCCCTTCAA
13851 AAAAAATCCA AAACCACCAC CACAACAAAA AAACTTACAC AGAAAAGTGT
13901 TGATAATTGT CAAAATTGGG CTGTTATTGG CAATTTGACA GTAGCTGAAT
13951 TACTACCATT TGAGCTATAT TCACTATAGA TAAGATCTTC AATATATTTA
14001 CAACTTTAGT ACTAATGGGA AAATGATAAC TTTTGAAAAG TTTTTTTTTT
14051 TTCTTATTGC AAACAATACA CAATACAATG TTAAATATAG AAGGTTAAAC
14101 GTGCATCTGA GTCTGTTTGG GCTGCGATAA TAGATACCTT AGACTTGGCA
14151 ATTTATAAAC AATAGAAATT CATTGCTGAC AGTTGTGAAG ACTGGGAAGT
14201 CCAAGATCAA GGCGCCAGCG AATCTGGTAT CTGGTGATGG CTCCCTGCTT
14251 CAAAAATGGC GCCTTCTTGC TGCATCTTCA CCTGGCAGAA GGGGCAAACA
14301 TGAGTCCTTC AGCTTCTTTT TTTTTTTTTT TCTATGTTTA AAACTTTTGG
14351 TCCGGCGTGG TGGCTCATGC CTGTAATCCT AGCACTTTGG GAGGCCGAGG
14401 CAGGTGCATC ATGAGGTCAA GAGATCGAGA CCATCCTGGC CAACATGGTG
14451 AAACCCCCCC GTCTCTATAC TAAAAATACA AAAATTAGCC AGGCATGGTG
14501 GCGTGTGCTT GTAGTCCCAG CTACTCAGGA GGCTGAGGCA GGAGAATTGC
14551 TTGAACCTGG GAGGCAGAGG TTGCAGTGAG CCAAGATTGC GCCACTGCAC
14601 TCCAGCCTGG CAACAGAGTA AGACTCCGTC TCAAAACAAA CAAACAAAAA
14651 AAACAAAAAA AAACTTTTAT TTTAGGTTCA TGGGTAAATG TACAGGTTTG
14701 TTATGTAGGT AAACTTGTCT TGGGGTTTGT TATAGATTAT TTCGTCACCC
14751 AGGTACTAAG CCTAGTAACC AATAGTTATT TTTTCAGATT GTCCTCCCTC
14801 CTCCCACCCT CTGTCCTCTA GTAGGCTCCA ATGTCTGTTG TTCCCTTCTT
14851 AGTGTCCTTG TGTTCTCATC CTTTAGCTCC CATTTATATG TGAGAACATG
14901 TGGTATTTGG TTTTCTGTTC CTGCATTAGT TTGCTAAGGA TAATGTCAGC
14951 CTCTTTTTTT TTTTTTTTTT TTTTTTTGAT ACAGAGTCTC GCTCTGTTGC
15001 CCAGGTTGGA GTGCAGTGGT GCGATCTTGG CTCACTGCAA CCTCTGCCTC
15051 CCGGGTTCAA GTGATTCTCT TGCCTTAGCC TCCTGAGTAG CTGGGACTAC
15101 AGGTGCGCAC CACCATGCCA GGCTAATTTT TGTATTTTAG TAGAGATAGG
15151 GTTTCACCAT GCTGGCCACG CTGGTCTCCA ACTCTTGACC TTGTGATCCG
15201 CCGGCCTCGT CTTTTTCCCA AAGTGCTGAG ATTACAGGTG TGAGTCACTG
15251 CACCCGGCCC AATGTCAGCC TCTTTTTTAG GGAAGTGATT TAATCACTTC
15301 CCTAAAAGTC CTACCTCGTT TTTTTTTTTG GTTTTTTCTT TTTTTTTTTT
15351 TTTTTTTTTT TTTTTTTTTA GGTAGAGTCT TGCTCTGTCA CCCAGGCTGG
15401 AGTGCAGTGG TGCGATCTTG GCTCACTGCA ACCTCCACCT CCTGAGTTCA
15451 AGCAATTCTC CTGCCTCAGC CTCCTGAGTA GCTGGGATTA TAGGTGCCTG
15501 CCACCACGCC TGGCTAATTT TTTTGTATTT TTAGTAGAGT TGGGGTTTCA
15551 CCATGTTGGC CAGGCTGGTC TTGAACTCCT GACCTCAAGT GATCTGCCCA
15601 AAATGCTGGG ATTACAGGCG GGAGCCACTG TGGCCAGCCC CTGCAAGTCC
15651 TACCTCTTAA TAGTATTACA CTGGGGATTA CATTTCAACA TGAATTTTGT
15701 AGGGGCGAGG GGCACAAACG TTTAGAATAT AGCACATCAC ATACATAGTG
15751 AGAGAAAAAT CCCTCAAAAT CTTACCTGAG ACAATCACTG CCAACAGATT
15801 GCTGTATAGT GTGCCAATTT TGTTTGTGTG TGTGTGTGCC TTAAAAATAT
15851 TTATTATGGA AATTTAAAAA CGTACCCCAA GGTGGCCAGG TGTAGGGCTC
```

FIGURE 3F

15901 ACGCCTGTAA TCCTGGCACT TTGGGAGCCC GAGGTGGGTG TATTACTTGA
15951 GGTCAGGAGT TTGAGACCAG CCTGGCCAAA ATGGTGATAC CAGTCTCCTA
16001 AAAATACAAA AATTAGCCGG GTGTGGTGGG CACCTGTAGT TCCAGCTACT
16051 CGGGAGACCA AGTCATGAGA ATTGCTTGAA CCCTGGAGGC AGAGGTTGCA
16101 GTGAGCCAAG ACCATGCCAC TGCACTCCAG CCAGGGTGAC AGAGTGAGAC
16151 TCCATCCTAG TAAACAAACA AACAAACAAA CAAACCAACT AACCAACCAG
16201 GATAAAACTC CCTGTCTGTA AGGAGTATGT GTTCTAATGG ATACTGAGCC
16251 ATCTTGTTCT GTTTAACATG TGCCTAATGT TCTTTTATAT GGGCGGACTT
16301 GTAGGTTGTT TCAACTTTTC TGTTGATGAA CCTTTAGGTG GTTTCTGATT
16351 ATTTTTGTGT TACAACAGTT TTCATCATTC ACATCTTTGT ATGCATCTTT
16401 TTTGAGCACA TGTGCAAGTA TTTCTGTGGA CAATGGATGA TTCCTAGAAA
16451 TTGAAAGTTT GGATTACTGT GTTCCAAAAA AGGAAGCAAT ACACCCAGCT
16501 ATGTTGGCTT TTGCTCTTGG GTCCAGATGA TTATCTGACA AAGTTATTCT
16551 CTGATTGCAT TTTCTTTTCT TTTCTTTTCT TTTTTTTTTT TGAGATGGAG
16601 TTTCGCTCTT GTTGCCCAGG TTGGAGTGCA ATGGCGCGAT CTTGGCTCAC
16651 TGCAACCTCT GCCTCCCAGG TTCAAGCGAT TCTCCTGCCT CAGCCTCCTA
16701 AGTAGCTGGC ATTGCAGGCA TGCGCCACGA CACCTGGCTA ATTTTTTGTA
16751 TTTTTAGTAG AGATGGGATT TCTCCATATT GGTCAGGCTG GTCTTGAACT
16801 CTTGACCTCA GGTGATCCAC CCGCTTCAGC CTCCCAAAGT GCTGGGATTA
16851 CAGGCGTGAG CCACAGTGCC TGGCCCTCTG ACTGCATTTT CACAGTGTTT
16901 TGGGTCCTTA TCTCTACCTC AGTACCTCAA TATTCAGTGC CCACTGGGCC
16951 CTTAGATACT GCAGCTAAAA GTGCACAGGG GTGGAGTGAT GTGACGGTTT
17001 TGGGGTCACA GAAGCAGCTG GTATAGAGAG AAGTTGTGAA GTTTTTTTTT
17051 TTTTTCCTGA GACAGAGTCT CGCTGTATCC CCTAGGCTGG AGTGCAGTGG
17101 CTTGATCTCG GCTCACTGCA ACCTCTGTCT CCCTGGTTCA AGTGATTCTT
17151 ATGCCTCAGC CTCCCGAGTA GCTGGGATTA TAGGCATGTG TCACCATACC
17201 CAGCTAATTT TTGTGTTTTT AGTAGAGATG GGGTTTCACC ATGTTGGCCA
17251 GGCTGGTCTT GAGCTCCTGA CCTCAGGTGA TCCGCCCACC TGGGCCTCCC
17301 AAAGTGCTGG GATTACAGGC CTGAGCCATT GCGCCTGGTC TTTTTTTTTT
17351 TTTTTTAAGT AATCATAGGC TTGAATGTAG CCTCTCATCT GTTCACCTTA
17401 ATAATCCAAA AGCCTTTAGA TAAAGAAATG GAGATTTGGA ATGGCTTCTC
17451 AGAATTCCAA GAGAGTATTG TCATGGTTTT GCCTGCAAAG CACCGTGGTC
17501 TGTCTCCTTG TGCAGTTGAG AAAGCTGGTG GTCGCCACTG ACAGGCCCAG
17551 AGTTATTAAG TTGGACACTG CTTTAAGCAA CTTTGTAAAC AATCCAAGGC
17601 ATACTAGAGA ATTAGGAGAG ATTGGCTTTG TGTATGAGCA ATAACAAAAT
17651 CAAGTTCAAT CCAGCAAGTT TTTGGGGAAT TATAATTCAA AACTCAAATA
17701 CTTGATCTGG AAGAAACTTG GAAAGAGGGA AGGAAGACAG GCTTGTTACA
17751 GCATTGTCAG GGTAAAAGGA AAATACCGTG CAGCTTTTAA TTTTGCTTCT
17801 TCATGGCATT CCCCATGTAG GTGCCCTAGA TTTGTTTTTT ACAGTGGTCA
17851 CGACTTCATG TGGATCCACC CACCACTCTT GCCTGGTTCC CCAAGGGACC
17901 AAGGGAAGGT GTATTCAGGA TGATTGCTGA AGTGAGGGGT GGGGTCTGTG
17951 GCTGAGAAGA CTCTCAATAC CGCGGCACTC ATTATAAGCC TCTGACACAG
18001 GAGATTTCAA CTCCACCCGT GCAACAAAGG AACAGGGTGG GCAAGAGTAG
18051 TTACAGTTGC AGGCTGAGTG CGATGGTTCA TGCCTGTAAT CCCAGTGCTT
18101 TGGGAAGCCA AGGTGGGAGG ATTGCTTGAG TCTAGGAGTT TGAGACCAGC
18151 CTGGGTGACA TAATGAGACC CTACCTGTAC AAAAAAATTT TAAAAATTAG
18201 CCAGATTGGT GGTGTGCGCC TATAGTCCCA GCTACTCTGG AGAATGAGGT
18251 GGGTGAGGGT CCCTTGAGTC CAGGAGTTCG AGGCTGCAGT GAGTTATGAT
18301 TCTATGATTT CACCACTGCA TTCCAGCCTG GGCGACAGAG CAAGATTGTG
18351 TTCTTTTTTT TTTTTGAGAC GGAGTCTCAC TCTGTCACCC AGGCTGAAGT
18401 GCAGTGGTAC GATCTCTGCT CACTACAACC TGCACCTCCC AGGTTCAAGT
18451 GATTCTCTCC CTCAGCCTCC CGAGCAGCTG AGATTAAAAG CGGCCGCTTG
18501 TGTGCAGCTA ATTTTTGTAT TGTTAGTAGA GATGGGGTTT CATCATGTTG

FIGURE 3G

18551 GTCAGGCTTG TCTTGAACTC CTGACCTCAG GTGATCCACC CGCCTCGCCC
18601 TCCCAAAATG CTGGGATTAC AGGCGTGAGC TACTGCGCCC AGCCATTTGT
18651 GTCTCTTAAA AAAAAAACTA AGAAAATGAA AAAAATGACA TTGGCCAATT
18701 CATTAAAATG CCACTCACTG ACTGTGGTAT GAAATGGCTT TCCCTTTGAT
18751 GGACCGAGTC TGTCTCATTG TGTGAGCCAC TTGCAGGGCT GAGTATGACT
18801 CTGGAATGTA GCTCCTAACC TTATCTGCTG CCCAGCCATT GAAATGGCCA
18851 TCCCTTCCAG TTCCCAGAAG ATTCCAGTGT GTGTTTGGGA TTTTAAGACA
18901 GTCTCTTGGT CTTCAGTGTG GCATCTTTCT GCCGGATTTT CCAGGATAAT
18951 TTTGATTATA AGCATTGCAT TGCCCTTGGT GTGTAATGCC TGTGTATGAT
19001 GCTGTTCCCT TGTAACGTGC AGGATTAAAT TTTTGGGTCA GCCACTGCTG
19051 CTCCCCTTCA TTCCTGCAGG TCATTAGAGT CATCGTACAT TTAGCGATGT
19101 CTCAGATCAG TGTATCTAGA GTGTTAATAA ACATGTTAGA TTCCAAATCT
19151 ACTGTCCATT TAATCCATAC TTCATACGTT GAGGATCTCT GACTGAAAGA
19201 TTAGACTTGG AAAAATAATA AGACTGTATG GTAAGAAAAC TATAGTTGCA
19251 AATCCATTTG GACATGTAGT ATGTCAGCCC TGCAGAGCAG ATGTCAGAAC
19301 CCCATTTAGT TCTCTGAGTG CTAAGCCCTT CTGCCCACCA CGCTGTTTTT
19351 TTTTTTTGAG ATGGAGTCTC GCTCTGTCAC TCAGGCTGGA GTGCAGTGGT
19401 GTGATCTCGG CTCACTGCAA GCTCTGTCTC CCAGGTTCAC GCCATTCTCC
19451 TGCCTCAGCC TCCCAAGTAG CTGGGACTAC AGGTGCTCAC CACCATGCCC
19501 AGCTAATTTT TTGTATGTTT TTGGTAGAGA CGGGGTTTCA CTGTGTTAGC
19551 CAGGATGGTC TGGATCTCCT GACCTTGTGA TCCACCCGCT TCGGCCTCCC
19601 AAAGTGCTGG GATTACAGGC GTGAGCCACT GCTCCTGGCC CCCACGCCTT
19651 TTTTTTTTTT TGGAGACAGA GTTTCACTCT GTCACCCAGA TTGGAGTGCT
19701 GTGGCACAAT CTCAGCTCAT TGTGTCCTCT GCCTCCCAGG TTCAAGTGAT
19751 TCTTGTGCCT CAGCCTCCTG AGTAGGTGGA ATTACAGGCG TGCACCACAA
19801 CACCTGGCTA ATTTTTGTAT TTTTAGTAGA GATGGGGTTT CACCATGTTG
19851 GCCAGGCTGG TCTCGATCTC CTGACCTCCA GTGATCCACT TGCCTAGGCC
19901 TCCCAAAGTG TTGGGATTAC AGGCGTCAGC CACCATGCCT GGACCCCTCT
19951 GCCCCTTTAA GCACTGCCAC ATATTAGATC TACGAAGGCT TTATGGATAC
20001 AATCCAAGGA AGATGAACCT TGGGCTAGTG GGATAAAACT AAGCGCATGT
20051 AGTTAGAATG GAATGATCTG GAAACCAGGT CCCAAGTTGG TCTAAATTAG
20101 ACTCATGTTG ACTATGTCAC ACTGTAAACC AGTCTAAATG CTAATAAGCA
20151 TGCTTGACCA AACACTGCCC TGCAGCCTTC AGAGAGGAAG AAGGAAAACA
20201 TAATTTGTAT CCTCTCTCCC TATTTTCTGA GTCTATGGGA TTCAAATTGT
20251 AGCTGCCATG GAAACTGTAC TTTGGAATTT CTAGAGCCCT TAATTTTAAC
20301 TTAACATATA AAAACACTTT TGTACTGATT TTATAATTAT TCATGATGGA
20351 TGAGAAAGTG AATGTCTTTG ACAGTGAGGG AAGCTATCCG AATGCTATTT
20401 TCTTTTTTTT TTTTCTTTCA TAAAGATGCA TATATTTGCA TGCTTTATTT
20451 ACCTGGGGCT AACTCTTGCA TCTTTTGCAG ATTCCGACAC CATAGCTGAG
20501 TTACAGGAGC TCCAGCCTTC GGCAAAGGAC TTCGAAGTCA GAAGTCTTGT
20551 AGGTTGTGGT CACTTTGCTG AAGTGCAGGT GGTAAGAGAG AAAGCAACCG
20601 GGGACATCTA TGCTATGAAA GTGATGAAGA AGAAGGCTTT ATTGGCCCAG
20651 GAGCAGGTAG GAGGATTTTA ACATCATGCT TTTCCACTTT CTGTACCGGA
20701 GTGTTCATTG CAAAGACGAT AATCTGCTGC ACTGGCGTCT AGGATCAAGC
20751 ACGTTTTCCT CTGTGACTCT ATATTTAATT ATAGTTGGGG CAAAAAGGTC
20801 TCTCATGTTC TTAGCTCATC TTCTTGAACT GATGTTGGCT AATTTTGAAG
20851 GCTCACAAAT TCCTCTTGAT GTATCATGTT TCTATCGTTG TAATTTATTT
20901 CAGAACCAAG GTGGCCTTTT AGCTAATGAA TTTAAGATGA TCTTTTATGA
20951 CCATTAGCTG AGGACTCAGG ATATACATAT GGTGGGGTGA ATCAGATTGC
21001 TTTTGTACAC GCTTTAGGTA TTTGTGTTGT GGGCATATGG ATTTGGTTTT
21051 AAAACAGGCC TTTGAAGAAA TCAAATAACA TTCTTTGTTA TGTGGCTAGG
21101 GAGTTGCTTG TTTGAGAGCA GGTAGAACGT TATCTTTTTT GTTGTGGTAT
21151 TTTTCTTTCT TTTAAACAAG GCTACTGTCT CTAGACATAT TGATTCATTT

FIGURE 3H

21201 GCTGTGTTTT AGAGAGATGG CCGTCAGCCT TGGAATTCAG AGAGTAATTT
21251 ATTACTTACA GACATTTTAG TGCACATGAT ATGTCTGATA ATGTACCCAG
21301 CTCTGCAGGA AGCTTGCAAA AGGAATAGAA GTCCCATGGT TGCTATTTTC
21351 AGTGTTTAAA AACAACCTTG GAAAGTGGAG GAAAAATGCA AATGTATAAA
21401 GCAGGTGCTT ACCAGCTAAA GTATCACAGA AGTGGGAGAG CAATTAGCAA
21451 ATTAATTAAC GATGATGTGA GGGGAGATGT TGTGGGTGAG CAAGGGACAG
21501 TTAGGGACAG TTCTCACCGA TGGGGGGAAA TGTAGGTTCT CGGCAGAGAG
21551 AAGTGATGAG AACATGTTGG GTAGAAGTGT GACATTCTGG AGTACTAGAA
21601 TGCTATGCAA GTGTGTGTGT GTGGGTGTGT GTGTGTGTTC AGTGGTTCAG
21651 AACAGACTGG GAAATGGCGA AATGAGGACA TTTGGGTGGG GAGGGGGAAA
21701 TGGGTGGGAA ACTCAAGAAC CTTTTTTTAA AAAATTGTGG TAAAATATAT
21751 ATAACATAAA GTGTACCATT TTAACCATTT TTAAATGTGC AACTGAGTGG
21801 TATTCAGTGC ATTCATGATG TTGTACAACC ATGACCGCTC TCCATTTCTA
21851 GAATTTTTCT ATCATCCCAA ACAGAAACTC TCTATCCATT ATACAATACC
21901 TCCCCATTCC CCCAAGAACC AGTTTTTGAA TTGCAGTTTA CTTTGTGAGG
21951 CTGTTGGGGA TTATTTAGGC CTCTGGAAGG AGGAGGTTGG GATCAGAGTC
22001 TGGCCCTGTG GACTTCAATG ACTTTGTGTG GCCTCCAATC AGAGAAGCAG
22051 CGGAGGGCAG GAAGCTGCTT GTCAGAATCT GAGAGTGATG TGGCTTCTTT
22101 GTTTAGCAAT AAAATGTGAG CACATAATAG AAAGGAAAAG TGACAGGACA
22151 TGGCAGATAA TTTGGAAGAG AGGAGTGGAA GATGCTCACT CAGCCTCCCA
22201 GCTCCTGAGA AAGAACTGTG TCTCATCAGT TCATACTACC TGAGCATCTG
22251 TTGTATCTGG TGTGTTTCTA GGTCCTGGAG AAGAGGCATT ACGTGTAGCC
22301 CTGACCTTGT GATGCTTATG TTTTTGATGG GAAATAGTGC GTGTAAAAAG
22351 AAAATAATCC AACAGGCCAC ACGGCAGGCA AACAATAGAG ATATTCAAAT
22401 AGGTATACCT TCCTCCAGGT GAATGGCCTG AAATGACCGT GTGGAAGTGT
22451 GGGCTGGGGG CTTATAAAAT TATACACATA CAGGCGCTAA CTAAAGCCGC
22501 CTATTCATTC CTTAAGAGGA TGCATAGAAA AGAAAAGTAG GGTCCTTAAC
22551 TGAGCCATTT GGAATTTAAG GGCATGAGAG AAGCCAGCAC AAGCAGTGAA
22601 GGGAAGGAAA AGAAGTGCCC GAGAGGAGGG AGGGATGCTG TTCTGCAGAC
22651 AAGGCCTGCC GCCTGGGAGA GGCCCGCACG CCCACCCAGG GTTCTCTGAC
22701 AGCTGGAAGG GGTCTTCAGA GACTGTTTAT ATTTTATTTA TTTATTTATT
22751 TATTTATTTT GAGACAGAGT CTCTGTCACC CAGGCTGGAG TGCAGTGGTG
22801 CGATCTCAGC TCACTGCAAG CTCCGCCTCC CAGGTTCACA CCATTCTCCT
22851 ATCTCAGCCT CCCGAGTAGC TGGGACTACA GGCGCCTGCC ACAATGCCCG
22901 GCTAATTTTT TTGTAATTTT AGTAGAGACG GGGTTTTACC TCGTTAGCCA
22951 GGATGGTCTT GATCTCCTGA CCTCATGATT CGCCCACCTC GGCCTCCCAA
23001 AGTGCTGGGA TTACAGGTGT GAGCCACTGT GCCTGGCCGA CTGTTTCTAC
23051 TATTTTAGAG AGAGGGTCTC ACTGTCATCT GTGCTGGAAT GCAGTGATGC
23101 AGTCATAGCT CACTGCACCC TCAAACTCCT GGGCTTAAGC GACCCTCCCG
23151 CCTCAGCCTC TTAAGTAGCT GGGACCATAG GCATGTGCTG CCACACCCAG
23201 TTAACTTTAT TATTTATTTA TTTATTTAGA GAATGAGTCT CATTCTGTTG
23251 CCCAGGCTAG AGGTGCAGTG GCACGATCTC GGCTCACTGC AACCCCGCCT
23301 CCCAGGTTCA AGCGATTCTT CTTGCTCAGC CTCCTGAATA GCTGGGATTA
23351 CAGGCACCTG CCACCACACC TGGCTAATTT TTGTATTTTT AGTGCAGAGG
23401 GGGGGGTTTC ACCATGTTGG TCAGGCTGGT CTCGAACTCC TGACCTTGTG
23451 ATCTGCCTGC CTCGGCCTCC CAAAGTGCTG GGATTACAGG CGTGAGCCAC
23501 CGTGCCCGGC CCACTTTATT ATTTTAAAAA CATTGTTTTA TTTTTATTTT
23551 TTTGAGACAG AGTCCGCTGG AGTTCAGTGG CCGGATCTCA CTCACTGCAA
23601 CCTCTGCCTC CTGGGTTCAA GTGATTCTTG TGCTTCAGCC TCTCTAGTAG
23651 CTGGGACTAC AGGCGGGTGC CACCATGCCT GGCTAATGTT TTTTGTATCT
23701 TTTTAGTAGA GACGGGGTTT TGCCCATGTT GGCCAGGCTG GTCTCGAACT
23751 CCTGACCTCA AGTGATCTGC CCACTTTAGC CTCTCAAAGT ACTTGGGATT
23801 ACAGGCGTGA GCCACTGTGG CTAGCCCCCA GCTAACTTTA AAAAAAAATT

FIGURE 3I

23851 TTGTGGGCCG GGTGCAGTGG CTCACGCCTG TAATCCCAGC ACTTTGGAGG
23901 CCAAGCAGGG CGGATCACTT GAGGTCGGGA GTTTGAGACC AGCCTGACCA
23951 ACATGGAGAA ACCCTGTCTC TACTAAAAAT ACAAAAAATT AGCCGGGTGT
24001 GGTGGTGCAT GCCTGTAATC CCAGCTACTT GGGAGCTGAG GCAGGAGAAT
24051 TGCTTGAATC TGGGAGGCAG AGGTTGCAGT GAGCTTAGAT CACGCCACTG
24101 CACTACAGCC TGGGCAACAA GAGCGAACAC TCCGTCTCAA AAAAAAAAAA
24151 TAAATTATGT AGAGGTGGGA TCTCCCTATG TTGCCCGGAC TGGTCTTGAA
24201 CTCCTGGCCT CAAGTGATCC TTCCATCTCC CCCTCCCAAA GTGTTGGGAT
24251 TACAGGCATG AGCCACCCCT CCTGGCTGAG ACTGCTTATT TTATTTATTT
24301 TTAATTTTTT TTGTTTTGAG ACTGCTTATT TTAATGGAAG CTTCAGGGGT
24351 CAGACGGGGT CAGACAGAGT CATTGGTGAG CAAGCAAAGG TGTAGACTGT
24401 TCAGTTCAGC CTTCCTTGGA CACCTTTTAT GTGCCAGACA AAAGAAGGAT
24451 CAGCATATCA GGTGCAGTAA ATTATTGGGG TTATGTTGGT GTTTCCCAAA
24501 TGTGTTAGAT TTATCCCTGG TAGTGTTAAA TCTCATGATT TTAGGTAGTA
24551 TATGGACAAC CTATGTAAAA ACATTTAATA GTTTAATATT AACTAGCATA
24601 TCAAAACCTG TGACTTTGCT CACGCCTGTA ATCCCAGCAC TTTGGGAGGC
24651 CAAGGCGGGA GGATGGTTTG GGCCCAGGAG TTTGAGGCCA GCCTAGGTAA
24701 CATGGTGAGA CCCTGTCTCT AAAACAAAAC AAAACAAAAC AAACAAACAA
24751 ACAAATAAAC AAATCCCCTG TAACTTGTTC TAACAATAAC CTAAACAATT
24801 TTTTATTTAA AATTAAATAA AAAAATTGAA ACAGTAACCA TTTTTTTTTT
24851 TTTTTTTGGA GACAGAGTCT TGCTTTGTCA CCTAGTCTAG AGTGCAGTGG
24901 CACAATCTCT GCTCACTGCA ACCTCTGCCT TCAAACAATT CTCCTGCCTC
24951 AGGCTTCTGA GTAGGTGGGA TTGATTACAG GTGCACTCCA CCATGCCCAG
25001 CTAATTTTTG TATTTTTAGT AGAGACGGGG TTTCACCATG TTGGCTAGGC
25051 TAGTCTTGAA CTCCTGACCT GCAGTAGTCC ACGTGCCTTG GCCTCCCAAA
25101 GTGCTGGGAT TACAATCACA AATTTATAGA AAAGTTGCAA GTACCATGTA
25151 GTCAGGGTTC TTAAGAGAAA TGGAACCAGT AGGAGATAGA TATATAATCA
25201 TCTCCTAGGA TTATAAGTTG ACACATAAGA CTAACCGTCA CATACAGTAT
25251 AAACAACTTT TTTTCTTAAA CCATTTGATA GATACACACA CACTGATATA
25301 CATAGAATAT ATATACACAC ACACAGAATG TATATACACA TAGAATATAT
25351 GTGCATACAG AATATATACA CAGAAATATA TATGTACACA TGCATAGAAT
25401 ATATTTACAT ATATATGCAT ATATATAATT TATTTATTTT AAGCAGTTGA
25451 TTTATACAGT TTTTGTTTTT GTTTTTTTTT TGAGACAGAG TCTCACTCTG
25501 TCACCCAGGC TAGAGTGCAG TGGCGAGATC TCAGCTCACT GCAACCTCTG
25551 CCCCCGGGTT CCAGTGATTC TCCTGCCTCA GCTCCACAAG TAGCACACCA
25601 CCATGCCCAG CTAATTTTTG TATTTTTTTT AGTAGAGACG AGGTTTCATC
25651 ATGTTGGCCA GGCTGGTCTC GAACTCCTGA CCTCAAGTGA TCCGCCCGCC
25701 TTGGCCTCCC AAAGTGCTGG GATTTCAGGC GTGAGCCACC ACACCTGGCT
25751 CCCATAATGT CTTTTAGAAT AAAACGATCG AGTTGAGGAT CACACGTGAC
25801 ACTTAATTGT CCTGTCTCTT TAGTCTCCTT CAATCTGGAG CAGTTCTTTG
25851 ATTTTTCCTG GACTCTCATG ACCTTGACAA TTCTGATGAT TATAGGCCAG
25901 TTATTTTGTA AAATTTGAAT TTGTCTGATG TTGCTTATGT TTAGATTTAG
25951 GGTCTTGGTC TTTGGCCGGA ATATCTCAGA CAAGATGCTC TGTTCTTATT
26001 GCATCAGAGC AGAAGACTCT CTGTTTCAGT TGATCACATT TATGTTGATG
26051 CTCACTTTGA TCACTTGATT AAGGTGGTGT CAGTTATGCC TTTCTACTTG
26101 TAGGGTTACT CCTTCCTCCT TCGTGATTTT ATTTATTTTA TTTTTCTTAG
26151 AGACAGGGTC TTGCTTGGTT GCCCAAGCTG GAGTGCAGTG GTGGGATCTT
26201 GGCTCACTGC AGCCTTGAAC TCCTGGGCTC AAGTAATCCA CCTGCCACAG
26251 CCTCCTGAGT AACTGGGACT GTAAGCGAAC ACCACCACAC CCAGCTACTT
26301 TTTGTATTGT AGAGATGGGG TCTCACTGTG TTGTCCAGGC TGGTCTGTAA
26351 CTCCTGGCCT CAAGCAGTCT TCCGGCCTTG GCCTCCCGAA GTGCTGGGAT
26401 TACAGGCATG AGCCACTGCA CCCAGCCTCC TTTGTAATTA AAAAAGTATT
26451 TTATGGGGAG TTACTTTCAA GTGATGGAAA TATTTTATAT CTATGTGGAC

FIGURE 3J

26501 TTGGATTTTC CTATTTCAGT CAGTGAGTTA TAATCCATTT CTGTCACTAG
26551 TTTTATACTT AAATTGTTCC CAACTTGGCC ACTGAGAACC TTTTTAGGTT
26601 AGCTTTTGTG TCCTTTTCAC ATGTCTCCAA GATTCATTGA ATACTTTCCT
26651 GCTTTCTGGT ATAGCAAGAT GTTCAGGTTC TTTTGGTACT TTTACTTTCT
26701 CTGCCCTGGC TCTGGCATCA GTCATTTCTC AGAGGAGCCC TGTGCCTTTC
26751 AGTGGACAAT GGTGTTTAGA GGCCAAGATC TGGACATTGG GTGTTTTCAT
26801 TGCTACCGGT GTGTCACTAC TCCCAGACCC CTTTCAGTGG ACAGCACTAA
26851 GGAATACACA TACGTATATA CAATATATCC ACCTACACAT GTGCGTGCAC
26901 TCACACACAC ACATATACAT TACATCTATA TTTGTGTATC CATGTCTATA
26951 TATTGAAAAT TGTGGCTGGG CACAGTGGCT TATGCCTTTA ATCTCAGCAT
27001 TTTGGGAGGC TGAGGCAAGA GGATCACCTG AAGCCAGGAG TTCAACACCA
27051 GCTTGGGAAA CAGAGAGAGA CTCTGTCTCT ACAAAAATAA AAAGGGAAAA
27101 CCATGAGTTC ACACCCGTGC CCCCAGTTCC AATCCAACTT CACAGGGTTC
27151 ATTTTAGTTT TCACCCTTTC CATGTTTGTA ATTCTCTTCT CTGACATTAT
27201 ACCCTTAATA TGTTTACTTA TTTTATGCAT CTGTATGCAT CCAATCTACT
27251 GTCTTTGTTG GTATCCCACC TCCCCTTGGT GGGTCCAGAT AATCTGCTCT
27301 GGGTTGCCCT TTCACGTGGA TGTCTTCCTT ACCCTGTGTG GGCCTGTGAT
27351 ACTGGGCTGC CCCCACACAT GAGTGCTGCC CTCCTCACGT TGCTTGGGAC
27401 GGCACTGTGT CCTGGGCCAC CATGACTTTT CTCATAACTA GCGTGGATGC
27451 TTACCTTGTT CCACACCAGT GAATGGCTTC AGGAAGAGAA GAGGAAGAGA
27501 AAAATATTTA CATTTAAAGA AAGGTAGTTT AAAGAAATAT GTTAGGTAAA
27551 GAATTGAGCA GGTAATATAC GGAGCTGGCA AAAATTGTGA CCAAAGTAGG
27601 TGAATGATTG AGATTTATGC AATTCTGGGC TAAGTGACAG CCCCTTCCCT
27651 TTCCCTTCCC TTCCCCTTCC CTTCCCTTTT CTTCCCTTTC CCTTCCCTTT
27701 CCTTCCCTTT CCCTTCCCCT TCCCTTCCCT TTCCTTCCCT TTCCCTCTTC
27751 TTCCTTCCTT CCTTCTGTTT TCTTTTCCCT TCTTTCCTTT GCCTTTTTTT
27801 TTTTTTTAAA GCTAGAAACA TCAGTTTAGG CATAAAGACA GAGGAAAAGG
27851 CTTCTTTTTC CTCTCACAGT TCTTTATAAT TGTCTAAGCA GTTTCTTTTT
27901 TCCCTAGGTT TCATTTTTTG AGGAAGAGCG GAACATATTA TCTCGAAGCA
27951 CAAGCCCGTG GATCCCCCAA TTACAGTATG CCTTTCAGGA CAAAAATCAC
28001 CTTTATCTGG TGAGTCTTTA CATCTGTCTC TCTGGAATTA GCCTAGCACT
28051 CTGACACTCA GATGCCTGTG GTAGAACTGA ATGTTGTTCT TGCCCATGTG
28101 GTCTCATTCA TGCAAAGACT TTCTTACCTT ACAGGTGTCT CCCTGGTTTC
28151 CTCGTTATAA AGATCAAGAG CTAACCCATT TAGAAACAGC CTCATTGGGC
28201 TGAACGTGGT GGCTCACGCC TGTAATCCCA GCATTTTGGG AGGCCGAGGC
28251 GGGTGGATCA CGAGGTCAGG AGATCAAGAC CATCCTGGCT AACACAGTGA
28301 AACCCCGTCT CTACTAAAAA TACAGAAAAA TTAGCCGGGC ATGGTGTCGG
28351 GTGCCTGTAG TCCCAGCTAC TCAGGTGGCT AAGGCAGGAC AATCGCTTGA
28401 ACCTGGGAAG CGGAGCTTGC AGTGAGCCGA GATTGCGCCA CTGCACTCCA
28451 GCCTGGGTGA CAGAGCAAGA CTCTATCTCA AAAAAAAAAA AAAGAAAAAA
28501 AAAGAAACAG CCTCATTGAC AGTTGGATAT TGTAGCTGTG GCTTTCAGGC
28551 AATAATAGGG AATCATTTAT TGGGGAATAG TCTGTCATTA TGTATAAGAT
28601 AATCTTGCTT TAATTTTTAA AAACTTCCTG TGTTAGCTTG CTTAGGATTA
28651 AAAAAATGAT AATAGTGCAT GGTTGTTATA AGAAAATGCA AACACTGCAG
28701 ACATGCATGA AGTTGAAGGG AAAGCCCCCC ATTTTCTTTT CCTTTTCTTT
28751 TTTTTTGAGA CAGAGTCTCG CTTTGTCACC CAGGCTGGAG TGCGGTGGCA
28801 CTATCTCGGC TCACTGCAAT CTCCACCTCC CAGGTTCAAG AGATTCTTCT
28851 GCCTCAGCTT CCCTAGTAGC TGGGATTACA GGCACGTGTC ACCACGCCCA
28901 ACTAATTTTT GTATTTTTAG TAGAGATGGG GTTTTACCAC GTTGGCCGGG
28951 CTGGCCGCAA ACTCCTGACC TCAAATGATC CACCTGCCTC GGCCTCCCAA
29001 AGTGTTGTGA TTACAGGAGT GAGCCACTGT GCCCGGCCTC TCCGTTTTAT
29051 TTTCTAATCC TCCTCCCTAG GGGAAGAAAT GTTAAATGGT TACATAAGCT
29101 TTCCCTTTCT GACCCTTAAC TGTGCTCTGT AGGAGCATGG TGGGGGATGT

FIGURE 3K

29151 TTCTTTTCTT TTCTTCTTTT TTTGAGACCA GGTCTCACTT TGCCACCCAG
29201 GCTGGAGTTC AGTGGCATGA ACATGGCTCA CTGCAGCCTC GACTTCCTGG
29251 GCTCCAGCAA ACCTCCCACC TCAGCCTCCC GGGCATACAC CACTGTGCCT
29301 GGCTAATTTT TGTATTTTTA GTAGAGACGG GGTTTTGCCA TGTTGCCCAG
29351 GCTGGTTTCG AAGTCCTGAG CTCAAGAGAT CTTCCTGCCT TGGCCTTCCA
29401 AAGTGCTGGG ATTACAGGTG TGAGCCACCA TGCCCAGCTC CGGTGGGGGA
29451 TATTTCTATA TCCACATGTG TATAGTTTAC TTTATAAAAA TGGTATGTTA
29501 CTCTGTGCTT GGCTCTCCAG CTTGCTGTTG CCTTTCACCA GTGTATCCCA
29551 GACATCCTTT CTTCCTTGTC AGTAACGCAG GTCTACTTTA TTCTTTGAGC
29601 AGTGGCATAA TTTTCCCTGA TGTGTATATA TCATAAGTTA GAGAATGCTA
29651 AAATTCATTT TGGGGCCTTG TTTAGGTTCT TGAGGGATTA AATTCCTAAA
29701 TTTAACAAGT GTATCCTGGA AACAATTTTT GTTCCTGATT CAGCCCTTAA
29751 AAGAGGACTA TCATGTTACC TTGAATGGAG ATAAACAGGC TCACGTAAGA
29801 GAAAAGGGTA AGAGGGATGA ACTCCCACTT ATCTTAAACT TCTACTGGCC
29851 CGTTTTTGGG GAATTTGCTG CTTTTATTCC TGACCTAAAA TAAATAAGTT
29901 TATGTGTCTT GGTTTCATAT TAGTTGAGAA CCCAGTGCCT GGAGAGAAGT
29951 TTTCCTTGTC CTCTGAGTGA GGACATTCAC ATATGAATCT ATTGGCAGAC
30001 TGGCTTTGAC TGACCACACG TGCCTTCAGA ACCAATGCCA CAGCTCTTAG
30051 GTTTATGGCC TGAAACACCC TTTCCTTACA TATTGCCTTA GAAACTTTCC
30101 TTCCTTGAGA CATGGGGCAT GGAACCCTCA CCTTCACAGA TGACCTTGGT
30151 GTGTTTCTAG GGTTGCTGGT GTTCCAGGAC ATCTGTTGCA GATGCAGTAT
30201 TTACCTTGTG CTCTCTGCAT CATAAGCAGC TTCTCATGTT TGAATGTATT
30251 AACAGACTTT TAATTTTTTT TATTTTTGAG ACAAAGTCTC ACTCTGTCAC
30301 CCAGGCTAGT GTTACCCAGG CTGGAGTGCA ATGGCTCAAT CTCAGCTCAC
30351 TGCAACCTCC ACCTCCTGGG TTCAAGCGAT TCTCTTGCCT CAGCCTCCCG
30401 AGTAGCTGGG ATTACAGGTG CATGACACCA CGCCCTGCTA ATTTTTGTAT
30451 TTTTAGTAGA GACGGGGTTT CGCCATGTTG GTGGGGCTGG TCTCAAACTC
30501 CTGACCTCAG ATGATCTGCC CGCCTTGGCC TCCCAAAGTG CTGGGATTAC
30551 AGGCGTGAGC CACTGCGCCT TTTCTTTTCA TTTTTTTTCT GAGATGGAGT
30601 CTTTCTCTGT CACCAGGCTG GAGTACAGTC ATGCAATCTC AGCTCACTGC
30651 AACTTCCACC TCCTGGGTTA AAGTGATTCT CCTGTCTTAG CCTCCTGTGT
30701 AGCTGGGACT ACAGGCGTGT GCCACTGTGC CCAGCTAATT TTTATATTTT
30751 TAGTAGAGAC GGGGTTTTGC CATGTGGGTT AGGCTGGTCT TGAACTCCTG
30801 ACCTCAGGTG ATCCACCCGT CTTGGCCTCC CAAAGTGCTG GGGTTATAGG
30851 CGTGAGCCAC TGTGCCCAGC CTCAGGCTTC TTTATTAAGA AGAAGTTCGG
30901 GCCAGGTGTG GTGGCTTACA CCTGTAATCC CAGCAATTTG GGAGGCCGAG
30951 GTGGGCAGAT CAGGAGGTCA GGAGATCGAG ACCATCCTGG CTAACATGGT
31001 GAAACCTCGT CTCTACTAAA AATATAAAAA ATTAGGCAGG TATGGTGGCG
31051 GGTGCCTGTA GTCCCAGCTA CTCGGGAGGC TGAGGGAGGA GAACGGTGTG
31101 AACCTGGGAG GCGGAGCTTG CAGTGAGCCC AGATTGTGCC AGTGCACTCC
31151 AGCCTGGGTG ACAGAGCGAG GCTCCGTCTC AAGAAAAAAA AAAAAGACGT
31201 TCCCTTGAAA CAACAGGGCT TTTGTTTGTT TTGGTTTGTG TTTGTTTGTT
31251 ATTGTTGTTT TAGATACGTA TTTTTTTCTT TCTTTTTTTT TTTTAAGTGA
31301 TGATGTCTCT GTTGCAGTGG CATGATCATA GCTCACTGTA ACCTCAAATT
31351 GCAGGGCTCA AGTGATTCTC CTGCTTCACC TTCCTGATTA GCTGGGACAA
31401 CAGGTACAAA CCACCATGCC TAGCGAATTT TTAAATTTTT CATAGAGACT
31451 AGGGTCTCAC TATGTTGCCT AGGCTGGTTT CGAACTCCTG GCCCCAAGTC
31501 ATCCTCCTGC CTTGGCTTCC CAAATTGTTG GGATCACAGG CATGAATCAC
31551 CACACCCAGC CTATTTTTAG ATATTTTAAT TCGAGCTCTA CAGGAGGTTT
31601 AGAACACTAG CTTGTGAAGA TAAACTTCAT TTTCAAGGCC ACACAGAATC
31651 TAAGTGGTCC TGGAATTAGG AAGGGCTTTG ATTTTTTGGA CCAAAGTTGA
31701 GAGTCCACAG TTTTCTGGTC TACCTTGCAC TGCTCCATAA ACTCATATTT
31751 CTTTTCTCTG AGCTGAAGAG CTCCCCTTCT TGGTGTCTAG TCTCAGGCAA

FIGURE 3L

31801 CTTATTCTTA AAAGTAAGCA TTATTGAAAT GCTTTGGGAT TTTCACATCA
31851 TCAAGGTCCA TTTTGGTAGA GGCACTGACA GATTTTGAGT GTTCTGTGTG
31901 AAGGAACTCA GTTGAGGATT TAGTGGTCCA TGTGGCAGGC TACTGCTCAG
31951 TAGCTTCAGG GAAACCACTG CTTGCCTCCC CTGTGGCCAG TGAGGATGAT
32001 CAGAGGAGTC CCAGCAGGAA TGCCCAAATG TAGTTTTCTT ACATGTTGAT
32051 GGGAGTGCAT TGTTTCATGT CTAAACAGTT CTCAAATCAC ATCTTCAGGA
32101 GGGTACTATC TGGGCACTTT GATAATTTCT CACTTTGATG TCACCGTTCT
32151 TATTACCATC ACCTAGTTTT GTCATAGTAG AAATAACTTT CCTTTTTCTG
32201 TGTGTGTGTG TGTGTGTGTG TGTGTGTGTG TGTGTGTGTT TTGAGATGGA
32251 GTCTTGCCGT GTTGCCCAGG CTGTAGTGCA GTGGCGTGTT CTCGGCTCAC
32301 TGCAACCTCT GCCTCCCGGG TTCTCCTGCC TCAGCCTCCC GAGTAGTTGG
32351 GATTACAGGC GTGTGACACC ACGCCTGGCT CATTTTTGTA TTTTCAGTAG
32401 AGATGGGGTT TCACCACTTT GGCCAGGCTG GTCTTGAACT CCTGACCTTG
32451 TGATCCGCCC ACCTTGACCT CCCAAAGTGC TGGGATTGCA GGTGTGAGCC
32501 ACCACGCCTG GCTTTTTTTT TTTTTTTTTT TGAGACAGAG TCTTGCTCTG
32551 TTGCCCAGGC TGGAGTGCAG TGGCGGGATC TTGGCTCACT GCAGCCTCCA
32601 CCTCCTAGGT TCAAGCAATT CTTCTGCCTC AGCCTCCTGA GTAGCTGGGA
32651 TTACAGGTGC CCACCACCAT GTCCGGCAAA TTTTTGTATT TTTAGTAGAG
32701 ACAGGGTTTC ACCATGTTGG CCAGGCTGGT TTCTAACTCC TGACCCCAGG
32751 TGATCCGCCT GCCTCAGCCT CCCAGAGTGA TGGAATTACA GGCATGAGCC
32801 ACTGCGCCTG GCCACCTTTG TCTTCTTAGT TGTGGATTTA ACTGCTGTGG
32851 ACATCTGCTT GGGCATAGCC TTCCCGGAGT ACCTCTTGGA TTGGGACTGT
32901 CTGTGGGTTT CTGTGCTAGG ACAGGCTCCC AGATGTAGGA GGCTTCCCCA
32951 ATGATCTCAC CACTGGCATC GGCATCCTTA GCTTCTACTC AGCTTTTCCA
33001 TCTGCCATCT TGCAAGATGG AAGGTTGTTT TGTTTTTGTT TTTGTTTTTT
33051 GGTTTATTTT TTTTGAGATA GAGTCTCGCT CTGTTGCCAA GGCTGGAGTT
33101 CAGTGGCGCA ATCTCGGCTC AGTGCAACCT CCACCTCCTG GGTTCAAGTG
33151 ATTCACCTGC CTCAGCCTCT GGAGTAGCTG GGATTACAGG CGCGTGCCAC
33201 CATGTTCGTT TAATTTTTTG TATTTTTAGT AGAGACGGGG TTTCACCGTG
33251 TTAGCCAGGA TGGTCTCGAT CTTCTGACCT CATGATCCGC CTGCTTCAGC
33301 CTCCCAGAGT GCTGGGATTA CAGGCGTGAG CCACCGTGCC CAGCCTAGGA
33351 GGGTTCTTAA TGCAGCTGTT TTTTGGAGTT CTGGTTGCCT CAGCACACTG
33401 CTACTTGGGT CAATGACATT TTTACTCCCT TGTTTTGTAG CTCAATTGGG
33451 TATTACTGAT GGGATTTTGT AATTATTAAT ATTTTCTTGT CTCCATTTTC
33501 TTCTCAAGTA CTTTGTTGCT TTTGAGTAAA ATGCTTGCTA AGGGTATAGT
33551 TTTCACATAA AAGCTCAAAT TTAGCATGGA AATTAAGATA TGCTCATACG
33601 TCTGCCATCC CTTATCTGTA ATTCTGAAAT ACCTAGAGTT CTGAATAACC
33651 TCAAATTCTT TTGTTACTTG TTTATCAGCA AAACCTGATT TGAACTCAGT
33701 TTTTGGCAAA ACTTGATCCA AGCTCTCTTA AGGCTCTTTT TAGTCTTTAT
33751 TCATTCCCTT TAGTGTGACT TCCCATTTTG CTATAAAATT ATGAGTGTGT
33801 TTGATTACAA GGTGATGTCC CAGACCCTAC TGAGGGTGTT ACATAATATA
33851 AACTGTATGT ATGGCTGGGC GCGGTGGCTT ATACCTGTAA TCCCAGCAAC
33901 TTTGGGAGGC CGAGGCGAGC GGATAACCTT AGTTCAGGAG TTCAAGCCCA
33951 GCCTGGCCAA CATGGTGAAA CCCCGTCTCT ACTAAGAATA CAAAAATTAG
34001 CCAGGCATGA TGGTGGGCGC CTGTAATCCC AGCTACTCCT TAGGCTGAGG
34051 CAGGAGAATC ACTTGAACCC AGGAGGTGGA GGTTGCAGTG AGCCAAGGTC
34101 ATGCCACTGC ACTCCAGCCT GGGCGACAAA GCAAGAATCT GTCTCAAAAA
34151 AAAAAAAAAA AAAGTGTGTG TACCACTTTA CCTTTCTAAA ATCTGAAAAA
34201 TTCTGAATCT GGAAACCCAT TCTGCTTCAA GATAAATGGA TCCTAGATTT
34251 ATATCGGTAC CGTACAGTCC TGAAATTCCA TCCTATCTAT TGGCCACTTT
34301 TACATCAACA AACCTTTGAA GTTTGGGGAA ACTTACATAT CACGCTCCCT
34351 TGGCAGTTGA ACATTATTTA TTTATTTTGA GATGGAGTAC TCGCTTTGCC
34401 CAGGCTGGAG TGCAGTGGCG CGATCTTGGC TCACTGCAAC CTCTGCCTCC

FIGURE 3M

34451 CGGGTTCAAG CAATTCTCCT GCCTCAGCCT CCTGAGTAGC TGGGATTATA
34501 GGCATGCAAC ACCATGCCCA GCTAATTTTT GTCTTTTTAG TAGAGACGGG
34551 GTTTCACTAT GTTAACCAGG CTGTTCTCGA ACTCCTGACC TTGTAATCTT
34601 CCCTCCTCGG CCTCCCAAAG TGCTGGAATT ACAGGCGTGA ACCACCACGC
34651 CTGGCCCTGA AGATACATTT TAAATCAATG AAAAAAACAA CAGGATTCTA
34701 CCTCCTATGG TATATCCCTC CTGGCTGTCT CTTCTCTCCA GTCTTGCCTC
34751 TGCTGTGTGG GTTTCAGGCA TCCATCTTCT CTACTCTGAA TTACTGTGAT
34801 AACCTCTGAA GTATTTTCCC TGCCATCTGT CTGGCCCTTC TCCCAGGTCT
34851 TCCACATACT GCAGCCAAGT CAGCCCGCTG TTGAAACCCT TCAAGACTCC
34901 CTGCTGTCCT CTGGATGAAG TCCAGACTCT TCCACGTGAC TTACCAGGCC
34951 TTTCTTGCAC TTGTCCCCAG CCACTTACTG TTTCTCTCTT TCTACCTTAA
35001 CATCCTGAAC TTCCTTTGGT TCTTTGACCT TGCCTCTGAC CTTTTTCCAT
35051 GCTGTTCACT CTTTCCCTGT TCACCTTGCT AACTCCTCTT TCTCTTTCTG
35101 GGTTGGATCA GATTTCACTT CTTCCAGAAG CCCTTCCTAG ACCCTATACT
35151 TCTGGAATGG CGCCTTTTGA CTGTACGCTC ATTGCACCCT GTACTTCTCC
35201 TTTATGAGTG GGTGCTGGTC TGTCCCACTA GGCTACTTCA TCCATAAAGG
35251 GAGAGTAGAG CTTTACCAAG TCAATGCTTA AGCAATATTT ATTGGATGAA
35301 TGTGTGATTA ATTTCATAGA AATTTGATGT GCATTCAAAT TTACTTATTG
35351 TATTACGGAA CTTGCATTAT ATTCTCAGTG GAGTTATTTT CTTTCACGTG
35401 TGTAATTCAA GATAGACTCA GTGAGATTTT CAAAATTTGG AATGCAGTGC
35451 AAGGAAATTG AACTTGAGTT CTTTTGCATT TTGATGGTTA AAAATTTCCC
35501 ATTTGTGGTG ACATACCACA ATAAGCCAGT GAATGTGGCT TATTGTTTTC
35551 TGGTCTATAG AAAATTGTCG CAAACTCTGT CATAATGTCT GGTTCTATAT
35601 AACAAAGCTA GTCCTGTATT CTGCATGTGG CTGATGGAAA CAGTGCTCTG
35651 TTGATCTGGT TCATGAAGAA ATCTGTTCAA TTCTGCATAA CAGATGCCTT
35701 CATCAGTGTC CTTCCATGAA GGAGCTGATC TTCACAAAGA ACACATAGTT
35751 TTGCATCCCA CCACTTGCAG TATTTTTTTT TTTTTTTTTT TTTTTTTGAG
35801 ATGCAGTCTC GCTCTGTCAC CCTGGCTGGA GTGCAGTGGC ATGATCTCAG
35851 CTCAGTGCAA CCTCTACCTC CTGGGTTCAA TTGATTCTCC TGCCTCAGCC
35901 TCCTGAGTAG CTGGGATTAC AGGCGCACAC CACCATGCCT GGCTAATTTT
35951 TGTTGTTTTA GTAGAGACGG AGTTTCACCA TATTGGTCAG GCTGGTCTCA
36001 AACTCTTGAC CTCATGATCT GCCTGCCTTG GCGTCCCAAA GTGTTGGGAT
36051 TACAGGCGTG AGTCACTGTG CCCTGCCAGT ATTGTTTTGT CTAAATTATT
36101 TGTGCTGATG TTTTTCCTAC TGTGGTTTTC TTCAGATTAC CCTTGCTCTG
36151 AGCCTGCAAT TGACTCATGA ACTTCTTTTC CATGTTCTAA CCTTACAATG
36201 ACTTCCTTGT GTTCACTCCA AATGTTTTTC CCTGGTTGCA TGTAGAGATG
36251 TATTAGCTAA GGTACATGCT TAGCTGCTGT ATCAAAGAGA CCCTAATGTA
36301 CAACCCAGGC TGGTAGAGCA GCTCTGCTGT ATGTGTTAAT TCAGGGACCC
36351 AGGTTCCTTC CATGTTGTGA CTCCCCCCTT CCTTAGGATG TTGTCTTCTT
36401 TTACATGGCT GAAGTTGGGC CATTTCATGT CTCTGTTCCA GCTGCCTGGT
36451 AGGAAAAAAG AACAGAAATT CAGAGTAAGC AAATTCTTTT TCTATAGATG
36501 GATGCGGAAG TTGGACACAT CATTTCCTCT CACATTTTCT CGGCCAGAAC
36551 GTAGTCATGT GACTGCACGT CTAGCTGCTA AGGAGACTGG GAATTTACTG
36601 TCGGCTGTGT GGCCTCTGTC AAGCTAAAAT TCTTATTACT GTGGAATAAG
36651 GGAAGGATGG ATTTGGGGGC ACAATTAATA GTCTGTCACA GAGGCTAAAA
36701 CAGCTGCTTT TGGCTGGGCA CGGTGGCTCA CACATGTAAT TTCAGCACTT
36751 TGGGAGGCCG AGGCAAGTGG ATCACTTGAG ATCAGGAATT TGAGACCAGC
36801 CTGGCCAACA TGGTGAAACC CTGTCTCTCC TAAAAATATA GAAATTAGCC
36851 GGGCATGGTG GCGGGTACCT GTAATCCGAG CTACTCCAGA GGTTGAGGCA
36901 GGAGAATTGC TTGAACCTGG AAGGCAGAGG TTGCAGTGAG CCAAGATGGT
36951 GCCACTGCAC TCCAGCCTGG GCGACAGAGC AAGACTCCAT CTCAAAAAAA
37001 AAAAAAAAGG TTAAATAAAC AGCTGCTTTT GTAGGTGATA CAAGGTACAG
37051 CTAAGCTTTG AAGCCAGGCC TGTAGTTTCA CCTTCCATAT TCTTACTCAA

FIGURE 3N

37101 GGCATTATAC TTCTGGATCT GAAACCACTG GATCTGATGC CCTGCTTGGG
37151 ATGAGTTCTT TATATTATCT TGCTTTCAAC CCACACCTGT GTAATTTTAT
37201 GGGCAGCGTT TGTTTCCTAT ATAGGAACAA TTTGAAAGTG GGCTGTTTCT
37251 AGGCTTTCAT GAATAGCAGG CTATGCTGTC ATTGGGAATC TGGAGGGAGT
37301 TAATGAACAC AACTTCATTG TTTACTTTAG TGAAATGTGG CAGCTTATGA
37351 TAGTTTTGAC AGTGAGACAT GTGCTGTTTT GATCTCTCAG CTAAGATTAT
37401 CTGATTTTTC AGGCATGTCT CAAAACTCAC CAGGCCTGCT CACATGCTGC
37451 TGCTTCTGAA GCCAGGGTTT GGAAACCAGC TGCCCATCAG AATGAGGCTG
37501 TGACTTAGAA TATTGGTTCT TGTTTTATTA CCATTCCTTG TTTGGTCTCT
37551 CCAGAGTCAC TGGCCTTTTC CGCTTCAATT TTCTTATCGG TGAAATGAGA
37601 TATTAATTCC TCTTATTGAC TTCAATTCAA TTGCTGAGTG TATTGTTGCC
37651 TTTGGGAAGT TCTTTGAGTT TTCTGTGCCT TTGAAATAGT TGTTTTTTTT
37701 TATTCTGGTG TTTTGAGGCA TGTTTCAAGT GAGTGCATTT ACACTTCTAC
37751 CATTTTAGGA GCCACAATTC AGTTATGTTG TCCCAGCTTG CTTGGCCCCA
37801 TCCCCAGAGT TTCTGATTCA GTAGGTCTGG GGTGGGGCCC AATAATTTGC
37851 ATTTCTTCTT CTTTTTTCGA GACAGAGTCT GACTGTGTCA TCCAAGCTGG
37901 AGTGCAGTGG CACGATCGTA GCTCATTGTA GCCTCAAACT CCTGGGCTCA
37951 AGCCGTCCTC CCACCTCACC CTCCTGAGTA GCTGGGACTA TAGGCATATA
38001 CTACCATGCC CTGCCACCTT TTTAATTTTT TGTAAGGATG GGGGTCTCAC
38051 TGTGTTGCTC AGGCTGGTCT TGAATTCCTG GGCTGAAGTG ATCCTCCTGC
38101 TTCAGCCTCC CCAAATGCCG GCATTCCTGG CATGAGCCAC TGCACTTGGC
38151 CAAGACTTTG CATTTCTAAC TAGTTTCCAG GTAATGCTGC TGCTGGTGTA
38201 GGGACCTCAT TTTGAGAACC ATTGTTCTAT AGCTGTAGCT ATAGTTAGTT
38251 TCTGGTTATA GCTTCTTCCT TTTGTCCCTT CAGTAATAGT GTACACATCC
38301 GAAATCCCTG TCCTTGCTCT TTCAGGCCCA GGCATGGTAT CTGGTCCTCT
38351 TCTGTTGCTA GCCCTGGGGT GCTTCATCAT CCCAAGTTTA TTTTTCTTCT
38401 CCTAACCTGA ACCTTTGTAA ATAGCCCCTT CCCTAATGAA CGTCCTCAAT
38451 TCCCTGTTTT GCGTGTCCTG TCTGTTTCTT GGCAAGACTC TGGATGATTC
38501 AGTACTCAAT GAGGATTTTT CGCATAGATG GATGAAACAG GCTGGGTTTC
38551 ATGTTTTCTA AGATAAAGGT GCTTCTCTCT TTTTCTCTTG GTCACTTTGA
38601 CCAAGAAGAA AATAACAGAG TTTTTATTCT CAAGAAGAAT AATATCGGGG
38651 CCACTCTGCT CAGAGGCCAC TCTGCTTTGA GGACCCCTTC TCTCCTCCCT
38701 CATGCCAAAG ATCAGGAACA TTGGGCAGAG CGGATAACGA TGCCGCCAGC
38751 GTCATTACAT TTTCACGGCA CTTTCAGTTG TGCTGAGCGT GCAAACATTT
38801 CAAGGAGACA TTTCTAAGAG GTGGCTAGCA CAGCATGCCT CTAATGCCCT
38851 ATGTGAATTG GAATAGAGTA CTAAAGAACT GTTCAATATT CACCCCATCC
38901 CCGCATATGC AAGCATGCAC GTGGGTTCAT TGTATATGTG TGTGTGCACG
38951 TGTGCACAGA CACATTTGTC CTTCGTTTCA AATGCAACAC AATGGATGGA
39001 AATTGCCTTC CTGGTACTGG GGTATGGATG CAAACACCAA CAGAGAAGCA
39051 GCCGCTACTT CCAAACTGAA CACATGTGAG ATTTGCCCTT TAATTAGCAT
39101 CTGCAGCTGC TGCCATCAGA AGGGTCTGTC TCTGTTGGCC TGAAAGTCTT
39151 TGCTTTAAAA GAGCAAGTCC ATTATAGCTC CAAGCCAGGC TCGTCTGTCA
39201 GCTGCTGTGC TTTCTCTGCC ATCAGCGGGG TTGCCACATT GTTTTGGGCT
39251 GTTTCACTCT AGGACTCTTT CCTCCTCCTG TGCCCCCAGC CTTTGATTAC
39301 CATGCCTTGG TGATCCTCAT TTGGGTGACC TGCAGCTGCT CATTGTGTGT
39351 GCAGGAGACA TCTCCAGTCC TTGTAAGGAG GGAAGATCAC TGGCTTCAGT
39401 GCTGATGGAC TGGTTATTTT CCAGCCCTTT GTCGTCAGTG ATCTTGTCTT
39451 GATATGCAGA AAGGCTCCAG GTAGTCACTG AAAAAAATAT AAGCAGCAGA
39501 GGTGATGGCT ATATGAAAGT CACGTTTCAT CAAGGGCATT GCTGCTATGG
39551 AAACTTTCAA TTCACTTGGA GTAGGGAGCC ATATTGGTTC CACAGCCTCC
39601 TCAGCAGTGG GTCCCAACAC AGTGCTGGGC TAGCTGCCTC TGAATCACCG
39651 CAGTAGCTCC TTTTACTATA GATTCCTGGG TCCCACCCAT GGAATGTGAT
39701 CCATGAAGTC TGGGGTTATT CCCTGGAATC CTTTAAGCTC CCTAAGTGGT

FIGURE 3O

39751 TGGGATGGGA AAGAGATATG CTTTATGTTA CTATACTTCT TATTATTATT
39801 ATTTTAAAAT TCTTGCCGGG CGCAGTGGCT CACACCTGTA ATCCCAGCAC
39851 ATTGGGAGAC CGAGGCGGGT GGATCACTTG AGGTCAGGAG TTCGAGACTG
39901 GCCTGGCCAA CATGATGAAA TCCCGTCTCT ACTAAAAATA CAAAAATTAG
39951 CTGGGCATGG TGGCGCATGA CTGTAGTCCC AGCCACTCCG GAGGCTGAGG
40001 CAGGAGAATC GCTTGAACCC GGGAGGCAGA GGTTGCAGTG AGCCGAGATC
40051 GTGGCACTGC ACTCCAGCCT GGGTAACAGA GTGAGACTTC ATCTCAAAAA
40101 AAACCCAAAA AAACAAAACT CTTTTTCATT ATACCGGAAC GTCAGCTTTA
40151 TGGAGTCGGG GATTTTTTCT GTTTTATTCA CTGCTGTTTC CCTAACATCT
40201 AGAATAGTGG CTGGCACGAT AGGCACTCAA GTATTGATTT AGATGAGTCT
40251 ATTTTATTTT CTTTTAAATT TTTAATTTTT ATTAGAGGTG GGGTCTGGCT
40301 TTGTTGCCCA AGCTGGTCTC AAAACTCCTG GCCTCAAGCG ATTGTACTGC
40351 CTCAGCCTCC CAAAGGGCTA GGATAGGCAT GAGCCAACAT GCCTGGCTTG
40401 TCTTATTTTT AACAAGCACT TCTGGTGATT CTGATGGACA ATCAGGCTTG
40451 GGAAGTTCTA ACCTAGAGGA CCTACAGTTG TCTTGGGGTA GAAGCCAAGG
40501 CTATCCTGGT TTTTAGAATC AGTGCCTTAC TGGGCATCTC TGAAGAGTAA
40551 AAGTCAGGGA CAGAGTTACA TTTTTGGACA AAACCAGATG CTGTGAATGG
40601 ACTCTTGGTC ACAACCTGGG TGGCGACTTG GTCCTTAACT TCTTCATCAT
40651 TTTCTGCTGA CCCTGTTCTT TGGTTCACAG CAAGTCACCT GATAAGAAGA
40701 CTCAAAGACT GCTAGTTTGT TACTTTAGAT GATGCTTTTG GAACCTCTTG
40751 GTACCATTTT AACAATCCAA ACGTATTTTA TGAAAGCACT CAAGTCCTGG
40801 GTCTTTATTG TATCTTTAAG CTCTAACAGC ATGATGATTG AATAAGCTGT
40851 GGTTGGCCAC ACACAAGCCA TCTTCCCCAT GGCCTCCATT CATACTAGAA
40901 TGAGCAGCTA TACCCCAGTA GTATAGTTTT GGGATATGGG TAACATCTTG
40951 GGATAGCCAC ATTTACTTAG TAAATGTCTG GCTTACATTC TCCTAATGGT
41001 GCACTGTTGG AATTTTTGGT GTGGTAACCT GGAATAGTGT TGGTGGGTCA
41051 AGTTTGATTA GCATCTTTGA TAAGGACCCG GTCTATTTAG AGGTTTGTCA
41101 TTGAGTGTGT CTGTTTTGGC CTCATGTTGT GAAGCATGCT GTGTAGCAGC
41151 TGTTGTAATT TTTGTTGCTT GTTTTCTCAA TCAACCCTGG TTTTGAAGAA
41201 ATGGGAAGTT GTTCCACTCT TAGACTGATC TGACTTGGGA GGGGATTTTC
41251 AGTTCAGGAA GTTGGATCTT CTGAATGGAA GCAAAGAATA CATGTCTTTT
41301 TGCCACTTTA CAAGCTGGCT CTTGTTTTCT GAACTATTTT ACTGGTCATT
41351 GCAAATAGAA TGTCAGGAGT AGCTGCCAAA TACTAAGTTG TGTTCAGTTT
41401 GTCAGTTCTT AAGAGTTGCC GGTGGCTGCT CTGCTATGCG TATGACTTTC
41451 TCAGCCTTAA ACTTACAAGC CATACTGTTT TTTTCACATC TTTAATACAG
41501 CCATAGGAAA TTTATAACTG TGGCGTGTCG TCATAAATAT GCATTGTTCT
41551 TATTTTAAGA CATTTCAGTA CTAAAAGTAT AAGTACTTCT GTTATTATCT
41601 GTGAATTTCT TTCCTTCTTC TTTTTTTGGA TATTTAAGAC CTTTTCGATG
41651 TCAATATATA TTTAAAACAG ACATATAAAT TAGCATTCAC CCACATACCC
41701 AGGGCCTATG GAGAACCAGG TTGGGATGAG TGGGTGAGCT ACAGGCAGCC
41751 AGGTGGCTCC TGTGGGCTCC TCGAGGACTG GGGTGAGTAA CTAATGTCTG
41801 CTAGGAACTT GGGGGAAAGA AGGTGTGTAT GTTAGGTGCT GCCCCCTTCT
41851 AAGTGTTCCT CTTGTTCATA ATTGATTTTT TTTTTTTTTT TTTTTTTTTT
41901 TTTAGAAGGA GTCTCGCTCT GTTGCCAGGC TGGAGTGCAG TGGTGTGATC
41951 TCAGCTCACT GCAACCTCTG CCTCCCGGGT TCAAGTGATT CTCCTGCCTC
42001 AGCCTCCCGA GTAGCTGGGA CTACAGGCAT GCACCACCAT GCCCAGCTAA
42051 TTTTTGTATT TTNNNNNNNN NNNNNNNNNN NNNNNNNNNN NNNNNNNNNN
42101 NNNNNNNNNN NNNNNNNNNN NNNNNNNNNN NNNNNNNNNN NNNNNNNNNN
42151 NNNNNNNNNN NNNNNNNNNN NNNNNNNNNN NNNNNNNNNN NNNNNNNNNN
42201 NNNNNNNNNN NNNNNNNNNN NNNNNNNNNN NNNNNNNNNN NNNNNNNNNN
42251 NNNNNNNNNN NNNNNNNNNN NNNNNNNNNN NNNNNNNNNN NNNNNNNNNN
42301 NNNNNNNNNN NNNNNNNNNN NNNNNNNNNN NNNNNNNNNN NNNNNNNNNN
42351 NNNNNNNNNN NNNNNNNNNN NNNNNNNNNN NNNNNNNNNN NNNNNNNNNN

FIGURE 3P

```
42401 NNNNNNNNNN NNNNNNNNNN NNNNNNNNNN NNNNNNNNNN NNNNNNNNNN
42451 NNNNNNNNNN NNNNNNNNNN NNNNNNNNNN NNNNNNNNNN NNNNNNNNNN
42501 NNNNNNNNNN NNNNNNNNNN NNNNNNNNNN NNNNNNNNNN NNNNNNNNNN
42551 NNNNNNNNNN NNNNNNNNNN NNNNNNNNNN NNNNNNNNNN NNNNNNNNNN
42601 NNNNNNNNNN NNNNNNNNNN NNNNNNNNNN NNNNNNNNNN NNNNNNNNNN
42651 NNNNNNNNNN NNNNNNNNNN NNNNNNNNNN NNNNNNNNNN NNNNNNNNNN
42701 NNNNNNNNNN NNNNNNNNNN NNNNNNNNNN NNNNNNNNNN NNNNNNNNNN
42751 NNNNNNNNNN NNNNNNNNNN NNNNNNNNNN NNNNNNNNNN NNNNNNNNNN
42801 NNNNNNNNNN NNNNNNNNNN NNNNNNNNNN NNNNNNNNNN NNNNNNNNNN
42851 NNNNNNNNNN NNNNNNNNNN NNNNNNNNNN NNNNNNNNNN NNNNNNNNNN
42901 NNNNNNNNNN NNNNNNNNNN NNNNNNNNNN NNNNNNNNNN NNNNNNNNNN
42951 NNNNNNNNNN NNNNNNNNNN NNNNNNNNNN NNNNNNNNNN NNNNNNNNNN
43001 NNNNNNNNNN NNNNNNNNNN NNNNNNNNNN NNNNNNNNNN NNNNNNNNNN
43051 NNNNNNNNNN NNNNNNNNNN NNNNNNNNNN NNNNNNNNNN NNNNNNNNNN
43101 NNNNNNNNNN NNNNNNNNNN NNNNNNNNNN NNNNNNNNNN NNNNNNNNNN
43151 NNNNNNNNNN NNNNNNNNNN NNNNNNNNNN NNNNNNNNNN NNNNNNNNNN
43201 NNNNNNNNNN NNNNNNNNNN NNNNNNNNNN NNNNNNNNNN NNNNNNNNNN
43251 NNNNNNNNNN NNNNNNNNNN NNNNNNNNNN NNNNNNNNNN NNNNNNNNNN
43301 NNNNNNNNNN NNNNNNNNNN NNNNNNNNNN NNNNNNNNNN NNNNNNNNNN
43351 NNNNNNNNNN NNNNNNNNNN NNNNNNNNNN NNNNNNNNNN NNNNNNNNNN
43401 NNNNNNNNNN NNNNNNNNNN NNNNNNNNNN NNNNNNNNNN NNNNNNNNNN
43451 NNNNNNNNNN NNNNNNNNNN NNNNNNNNNN NNNNNNNNNN NNNNNNNNNN
43501 NNNNNNNNNN NNNNNNNNNN NNNNNNNNNN NNNNNNNNNN NNNNNNNNNN
43551 NNNNNNNNNN NNNNNNNNNN NNNNNNNNNN NNNNNNNNNN NNNNNNNNNN
43601 NNNNNNNNNN NNNNNNNNNN NNNNNNNNNN NNNNNNNNNN NNNNNNNNNN
43651 NNNNNNNNNN NNNNNNNNNN NNNNNNNNNN NNNNNNNNNN NNNNNNNNNN
43701 NNNNNNNNNN NNNNNNNNNN NNNNNNNNNN NNNNNNNNNN NNNNNNNNNN
43751 NNNNNNNNNN NNNNNNNNNN NNNNNNNNNN NNNNNNNNNN NNNNNNNNNN
43801 NNNNNNNNNN NNNNNNNNNN NNNNNNNNNN NNNNNNNNNN NNNNNNNNNN
43851 NNNNNNNNNN NNNNNNNNNN NNNNNNNNNN NNNNNNNNNN NNNNNNNNNN
43901 NNNNNNNNNN NNNNNNNNNN NNNNNNNNNN NNNNNNNNNN NNNNNNNNNN
43951 NNNNNNNNNN NNNNNNNNNN NNNNNNNNNN NNNNNNNNNN NNNNNNNNNN
44001 NNNNNNNNNN NNNNNNNNNN NNNNNNNNNN NNNNNNNNNN NNNNNNNNNN
44051 NNNNNNNNNN NNNNNNNNNN NNNNNNNNNN NNNNNNNNNN NNNNNNNNNN
44101 NNNNNNNNNN NNNNNNNNNN NNNNNNNNNN NNNNNNNNNN NNNNNNNNNN
44151 NNNNNNNNNN NNNNNNNNNN NNNNNNNNNN NNNNNNNNNN NNNNNNNNNN
44201 NNNNNNNNNN NNNNNNNNNN NNNNNNNNNN NNNNNNNNNN NNNNNNNNNN
44251 NNNNNNNNNN NNNNNNNNNN NNNNNNNNNN NNNNNNNNNN NNNNNNNNNN
44301 NNNNNNNNNN NNNNNNNNNN NNNNNNNNNN NNNNNNNNNN NNNNNNNNNN
44351 NNNNNNNNNN NNNNNNNNNN NNNNNNNNNN NNNNNNNNNN NNNNNNNNNN
44401 NNNNNNNNNN NNNNNNNNNN NNNNNNNNNN NNNNNNNNNN NNNNNNNNNN
44451 NNNNNNNNNN NNNNNNNNNN NNNNNNNNNN NNNNNNNNNN NNNNNNNNNN
44501 NNNNNNNNNN NNNNNNNNNN NNNNNNNNNN NNNNNNNNNN NNNNNNNNNN
44551 NNNNNNNNNN NNNNNNNNNN NNNNNNNNNN NNNNNNNNNN NNNNNNNNNN
44601 NNNNNNNNNN NNNNNNNNNN NNNNNNNNNN NNNNNNNNNN NNNNNNNNNN
44651 NNNNNNNNNN NNNNNNNNNN NNNNNNNNNN NNNNNNNNNN NNNNNNNNNN
44701 NNNNNNNNNN NNNNNNNNNN NNNNNNNNNN NNNNNNNNNN NNNNNNNNNN
44751 NNNNNNNNNN NNNNNNNNNN NNNNNNNNNN NNNNNNNNNN NNNNNNNNNN
44801 NNNNNNNNNN NNNNNNNNNN NNNNNNNNNN NNNNNNNNNN NNNNNNNNNN
44851 NNNNNNNNNN NNNNNNNNNN NNNNNNNNNN NNNNNNNNNN NNNNNNNNNN
44901 NNNNNNNNNN NNNNNNNNNN NNNNNNNNNN NNNNNNNNNN NNNNNNNNNN
44951 NNNNNNNNNN NNNNNNNNNN NNNNNNNNNN NNNNNNNNNN NNNNNNNNNN
45001 NNNNNNNNNN NNNNNNNNNN NNNNNNNNNN NNNNNNNNNN NNNNNNNNNN
```

FIGURE 3Q

45051 NNNNNNNNNN NNNNNNNNNN NNNNNNNNNN NNNNNNNNNN NNNNNNNNNN
45101 NNNNNNNNNN NNNNNNNNNN NNNNNNNNNN NNNNNNNNNN NNNNNNNNNN
45151 NNNNNNNNNN NNNNNNNNNN NNNNNNNNNN NNNNNNNNNN NNNNNNNNNN
45201 NNNNNNNNNN NNNNNNNNNN NNNNNNNNNN NNNNNNNNNN NNNNNNNNNN
45251 NNNNNNNNNN NNNNNNNNNN NNNNNNNNNN NNNNNNNNNN NNNNNNNNNN
45301 NNNNNNNNNN NNNNNNNNNN NNNNNNNNNN NNNNNNNNNN NNNNNNNNNN
45351 NNNNNNNNNN NNNNNNNNNN NNNNNNNNNN NNNNNNNNNN NNNNNNNNNN
45401 NNNNNNNNNN NNNNNNNNNN NNNNNNNNNN NNNNNNNNNN NNNNNNNNNN
45451 NNNNNNNNNN NNNNNNNNNN NNNNNNNNNN NNNNNNNNNN NNNNNNNNNN
45501 NNNNNNNNNN NNNNNNNNNN NNNNNNNNNN NNNNNNNNNN NNNNNNNNNN
45551 NNNNNNNNNN NNNNNNNNNN NNNNNNNNNN NNNNNNNNNN NNNNNNNNNN
45601 NNNNNNNNNN NNNNNNNNNN NNNNNNNNNN NNNNNNNNNN NNNNNNNNNN
45651 NNNNNNNNNN NNNNNNNNNN NNNNNNNNNN NNNNNNNNNN NNNNNNNNNN
45701 NNNNNNNNNN NNNNNNNNNN NNNNNNNNNN NNNNNNNNNN NNNNNNNNNN
45751 NNNNNNNNNN NNNNNNNNNN NNNNNNNNNN NNNNNNNNNN NNNNNNNNNN
45801 NNNNNNNNNN NNNNNNNNNN NNNNNNNNNN NNNNNNNNNN NNNNNNNNNN
45851 NNNNNNNNNN NNNNNNNNNN NNNNNNNNNN NNNNNNNNNN NNNNNNNNNN
45901 NNNNNNNNNN NNNNNNNNNN NNNNNNNNNN NNNNNNNNNN NNNNNNNNNN
45951 NNNNNNNNNN NNNNNNNNNN NNNNNNNNNN NNNNNNNNNN NNNNNNNNNN
46001 NNNNNNNNNN NNNNNNNNNN NNNNNNNNNN NNNNNNNNNN NNNNNNNNNN
46051 NNNNNNNNNN NNNNNNNNNN NNNNNNNNNN NNNNNNNNNN NNNNNNNNNN
46101 NNNNNNNNNN NNNNNNNNNN NNNNNNNNNN NNNNNNNNNN NNNNNNNNNN
46151 NNNNNNNNNN NNNNNNNNNN NNNNNNNNNN NNNNNNNNNN NNNNNNNNNN
46201 NNNNNNNNNN NNNNNNNNNN NNNNNNNNNN NNNNNNNNNN NNNNNNNNNN
46251 NNNNNNNNNN NNNNNNNNNN NNNNNNNNNN NNNNNNNNNN NNNNNNNNNN
46301 NNNNNNNNNN NNNNNNNNNN NNNNNNNNNN NNNNNNNNNN NNNNNNNNNN
46351 NNNNNNNNNN NNNNNNNNNN NNNNNNNNNN NNNNNNNNNN NNNNNNNNNN
46401 NNNNNNNNNN NNNNNNNNNN NNNNNNNNNN NNNNNNNNNN NNNNNNNNNN
46451 NNNNNNNNNN NNNNNNNNNN NNNNNNNNNN NNNNNNNNNN NNNNNNNNNN
46501 NNNNNNNNNN NNNNNNNNNN NNNNNNNNNN NNNNNNNNNN NNNNNNNNNN
46551 NNNNNNNNNN NNNNNNNNNN NNNNNNNNNN NNNNNNNNNN NNNNNNNNNN
46601 NNNNNNNNNN NNNNNNNNNN NNNNNNNNNN NNNNNNNNNN NNNNNNNNNN
46651 NNNNNNNNNN NNNNNNNNNN NNNNNNNNNN NNNNNNNNNN NNNNNNNNNN
46701 NNNNNNNNNN NNNNNNNNNN NNNNNNNNNN NNNNNNNNNN NNNNNNNNNN
46751 NNNNNNNNNN NNNNNNNNNN NNNNNNNNNN NNNNNNNNNN NNNNNNNNNN
46801 NNNNNNNNNN NNNNNNNNNN NNNNNNNNNN NNNNNNNNNN NNNNNNNNNN
46851 NNNNNNNNNN NNNNNNNNNN NNNNNNNNNN NNNNNNNNNN NNNNNNNNNN
46901 NNNNNNNNNN NNNNNNNNNN NNNNNNNNNN NNNNNNNNNN NNNNNNNNNN
46951 NNNNNNNNNN NNNNNNNNNN NNNNNNNNNN NNNNNNNNNN NNNNNNNNNN
47001 NNNNNNNNNN NNNNNNNNNN NNNNNNNNNN NNNNNNNNNN NNNNNNNNNN
47051 NNNNNNNNNN NNNNNNNNNN NNNNNNNNNN NNNNNNNNNN NNNNNNNNNN
47101 NNNNNNNNNN NNNNNNNNNN NNNNNNNNNN NNNNNNNNNN NNNNNNNNNN
47151 NNNNNNNNNN NNNNNNNNNN NNNNNNNNNN NNNNNNNNNN NNNNNNNNNN
47201 NNNNNNNNNN NNNNNNNNNN NNNNNNNNNN NNNNNNNNNN NNNNNNNNNN
47251 NNNNNNNNNN NNNNNNNNNN NNNNNNNNNN NNNNNNNNNN NNNNNNNNNN
47301 NNNNNNNNNN NNNNNNNNNN NNNNNNNNNN NNNNNNNNNN NNNNNNNNNN
47351 NNNNNNNNNN NNNNNNNNNN NNNNNNNNNN NNNNNNNNNN NNNNNNNNNN
47401 NNNNNNNNNN NNNNNNNNNN NNNNNNNNNN NNNNNNNNNN NNNNNNNNNN
47451 NNNNNNNNNN NNNNNNNNNN NNNNNNNNNN NNNNNNNNNN NNNNNNNNNN
47501 NNNNNNNNNN NNNNNNNNNN NNNNNNNNNN NNNNNNNNNN NNNNNNNNNN
47551 NNNNNNNNNN NNNNNNNNNN NNNNNNNNNN NNNNNNNNNN NNNNNNNNNN
47601 NNNNNNNNNN NNNNNNNNNN NNNNNNNNNN NNNNNNNNNN NNNNNNNNNN
47651 NNNNNNNNNN NNNNNNNNNN NNNNNNNNNN NNNNNNNNNN NNNNNNNNNN

FIGURE 3R

47701 NNNNNNNNNN NNNNNNNNNN NNNNNNNNNN NNNNNNNNNN NNNNNNNNNN
47751 NNNNNNNNNN NNNNNNNNNN NNNNNNNNNN NNNNNNNNNN NNNNNNNNNN
47801 NNNNNNNNNN NNNNNNNNNN NNNNNNNNNN NNNNNNNNNN NNNNNNNNNN
47851 NNNNNNNNNN NNNNNNNNNN NNNNNNNNNN NNNNNNNNNN NNNNNNNNNN
47901 NNNNNNNNNN NNNNNNNNNN NNNNNNNNNN NNNNNNNNNN NNNNNNNNNN
47951 NNNNNNNNNN NNNNNNNNNN NNNNNNNNNN NNNNNNNNNN NNNNNNNNNN
48001 NNNNNNNNNN NNNNNNNNNN NNNNNNNNNN NNNNNNNNNN NNNNNNNNNN
48051 NNNNNNNNNN NNNNNNNNNN NNNNNNNNNN NNNNNNNNNN NNNNNNNNNN
48101 NNNNNNNNNN NNNNNNNNNN NNNNNNNNNN NNNNNNNNNN NNNNNNNNNN
48151 NNNNNNNNNN NNNNNNNNNN NNNNNNNNNN NNNNNNNNNN NNNNNNNNNN
48201 NNNNNNNNNN NNNNNNNNNN NNNNNNNNNN NNNNNNNNNN NNNNNNNNNN
48251 NNNNNNNNNN NNNNNNNNNN NNNNNNNNNN NNNNNNNNNN NNNNNNNNNN
48301 NNNNNNNNNN NNNNNNNNNN NNNNNNNNNN NNNNNNNNNN NNNNNNNNNN
48351 NNNNNNNNNN NNNNNNNNNN NNNNNNNNNN NNNNNNNNNN NNNNNNNNNN
48401 NNNNNNNNNN NNNNNNNNNN NNNNNNNNNN NNNNNNNNNN NNNNNNNNNN
48451 NNNNNNNNNN NNNNNNNNNN NNNNNNNNNN NNNNNNNNNN NNNNNNNNNN
48501 NNNNNNNNNN NNNNNNNNNN NNNNNNNNNN NNNNNNNNNN NNNNNNNNNN
48551 NNNNNNNNNN NNNNNNNNNN NNNNNNNNNN NNNNNNNNNN NNNNNNNNNN
48601 NNNNNNNNNN NNNNNNNNNN NNNNNNNNNN NNNNNNNNNN NNNNNNNNNN
48651 NNNNNNNNNN NNNNNNNNNN NNNNNNNNNN NNNNNNNNNN NNNNNNNNNN
48701 NNNNNNNNNN NNNNNNNNNN NNNNNNNNNN NNNNNNNNNN NNNNNNNNNN
48751 NNNNNNNNNN NNNNNNNNNN NNNNNNNNNN NNNNNNNNNN NNNNNNNNNN
48801 NNNNNNNNNN NNNNNNNNNN NNNNNNNNNN NNNNNNNNNN NNNNNNNNNN
48851 NNNNNNNNNN NNNNNNNNNN NNNNNNNNNN NNNNNNNNNN NNNNNNNNNN
48901 NNNNNNNNNN NNNNNNNNNN NNNNNNNNNN NNNNNNNNNN NNNNNNNNNN
48951 NNNNNNNNNN NNNNNNNNNN NNNNNNNNNN NNNNNNNNNN NNNNNNNNNN
49001 NNNNNNNNNN NNNNNNNNNN NNNNNNNNNN NNNNNNNNNN NNNNNNNNNN
49051 NNNNNNNNNN NNNNNNNNNN NNNNNNNNNN NNNNNNNNNN NNNNNNNNNN
49101 NNNNNNNNNN NNNNNNNNNN NNNNNNNNNN NNNNNNNNNN NNNNNNNNNN
49151 NNNNNNNNNN NNNNNNNNNN NNNNNNNNNN NNNNNNNNNN NNNNNNNNNN
49201 NNNNNNNNNN NNNNNNNNNN NNNNNNNNNN NNNNNNNNNN NNNNNNNNNN
49251 NNNNNNNNNN NNNNNNNNNN NNNNNNNNNN NNNNNNNNNN NNNNNNNNNN
49301 NNNNNNNNNN NNNNNNNNNN NNNNNNNNNN NNNNNNNNNN NNNNNNNNNN
49351 NNNNNNNNNN NNNNNNNNNN NNNNNNNNNN NNNNNNNNNN NNNNNNNNNN
49401 NNNNNNNNNN NNNNNNNNNN NNNNNNNNNN NNNNNNNNNN NNNNNNNNNN
49451 NNNNNNNNNN NNNNNNNNNN NNNNNNNNNN NNNNNNNNNN NNNNNNNNNN
49501 NNNNNNNNNN NNNNNNNNNN NNNNNNNNNN NNNNNNNNNN NNNNNNNNNN
49551 NNNNNNNNNN NNNNNNNNNN NNNNNNNNNN NNNNNNNNNN NNNNNNNNNN
49601 NNNNNNNNNN NNNNNNNNNN NNNNNNNNNN NNNNNNNNNN NNNNNNNNNN
49651 NNNNNNNNNN NNNNNNNNNN NNNNNNNNNN NNNNNNNNNN NNNNNNNNNN
49701 NNNNNNNNNN NNNNNNNNNN NNNNNNNNNN NNNNNNNNNN NNNNNNNNNN
49751 NNNNNNNNNN NNNNNNNNNN NNNNNNNNNN NNNNNNNNNN NNNNNNNNNN
49801 NNNNNNNNNN NNNNNNNNNN NNNNNNNNNN NNNNNNNNNN NNNNNNNNNN
49851 NNNNNNNNNN NNNNNNNNNN NNNNNNNNNN NNNNNNNNNN NNNNNNNNNN
49901 NNNNNNNNNN NNNNNNNNNN NNNNNNNNNN NNNNNNNNNN NNNNNNNNNN
49951 NNNNNNNNNN NNNNNNNNNN NNNNNNNNNN NNNNNNNNNN NNNNNNNNNN
50001 NNNNNNNNNN NNNNNNNNNN NNNNNNNNNN NNNNNNNNNN NNNNNNNNNN
50051 NNNNNNNNNN NNNNNNNNNN NNNNNNNNNN NNNNNNNNNN NNNNNNNNNN
50101 NNNNNNNNNN NNNNNNNNNN NNNNNNNNNN NNNNNNNNNN NNNNNNNNNN
50151 NNNNNNNNNN NNNNNNNNNN NNNNNNNNNN NNNNNNNNNN NNNNNNNNNN
50201 NNNNNNNNNN NNNNNNNNNN NNNNNNNNNN NNNNNNNNNN NNNNNNNNNN
50251 NNNNNNNNNN NNNNNNNNNN NNNNNNNNNN NNNNNNNNNN NNNNNNNNNN
50301 NNNNNNNNNN NNNNNNNNNN NNNNNNNNNN NNNNNNNNNN NNNNNNNNNN

FIGURE 3S

50351 NNNNNNNNNN NNNNNNNNNN NNNNNNNNNN NNNNNNNNNN NNNNNNNNNN
50401 NNNNNNNNNN NNNNNNNNNN NNNNNNNNNN NNNNNNNNNN NNNNNNNNNN
50451 NNNNNNNNNN NNNNNNNNNN NNNNNNNNNN NNNNNNNNNN NNNNNNNNNN
50501 NNNNNNNNNN NNNNNNNNNN NNNNNNNNNN NNNNNNNNNN NNNNNNNNNN
50551 NNNNNNNNNN NNNNNNNNNN NNNNNNNNNN NNNNNNNNNN NNNNNNNNNN
50601 NNNNNNNNNN NNNNNNNNNN NNNNNNNNNN NNNNNNNNNN NNNNNNNNNN
50651 NNNNNNNNNN NNNNNNNNNN NNNNNNNNNN NNNNNNNNNN NNNNNNNNNN
50701 NNNNNNNNNN NNNNNNNNNN NNNNNNNNNN NNNNNNNNNN NNNNNNNNNN
50751 NNNNNNNNNN NNNNNNNNNN NNNNNNNNNN NNNNNNNNNN NNNNNNNNNN
50801 NNNNNNNNNN NNNNNNNNNN NNNNNNNNNN NNNNNNNNNN NNNNNNNNNN
50851 NNNNNNNNNN NNNNNNNNNN NNNNNNNNNN NNNNNNNNNN NNNNNNNNNN
50901 NNNNNNNNNN NNNNNNNNNN NNNNNNNNNN NNNNNNNNNN NNNNNNNNNN
50951 NNNNNNNNNN NNNNNNNNNN NNNNNNNNNN NNNNNNNNNN NNNNNNNNNN
51001 NNNNNNNNNN NNNNNNNNNN NNNNNNNNNN NNNNNNNNNN NNNNNNNNNN
51051 NNNNNNNNNN NNNNNNNNNN NNNNNNNNNN NNNNNNNNNN NNNNNNNNNN
51101 NNNNNNNNNN NNNNNNNNNN NNNNNNNNNN NNNNNNNNNN NNNNNNNNNN
51151 NNNNNNNNNN NNNNNNNNNN NNNNNNNNNN NNNNNNNNNN NNNNNNNNNN
51201 NNNNNNNNNN NNNNNNNNNN NNNNNNNNNN NNNNNNNNNN NNNNNNNNNN
51251 NNNNNNNNNN NNNNNNNNNN NNNNNNNNNN NNNNNNNNNN NNNNNNNNNN
51301 NNNNNNNNNN NNNNNNNNNN NNNNNNNNNN NNNNNNNNNN NNNNNNNNNN
51351 NNNNNNNNNN NNNNNNNNNN NNNNNNNNNN NNNNNNNNNN NNNNNNNNNN
51401 NNNNNNNNNN NNNNNNNNNN NNNNNNNNNN NNNNNNNNNN NNNNNNNNNN
51451 NNNNNNNNNN NNNNNNNNNN NNNNNNNNNN NNNNNNNNNN NNNNNNNNNN
51501 NNNNNNNNNN NNNNNNNNNN NNNNNNNNNN NNNNNNNNNN NNNNNNNNNN
51551 NNNNNNNNNN NNNNNNNNNN NNNNNNNNNN NNNNNNNNNN NNNNNNNNNN
51601 NNNNNNNNNN NNNNNNNNNN NNNNNNNNNN NNNNNNNNNN NNNNNNNNNN
51651 NNNNNNNNNN NNNNNNNNNN NNNNNNNNNN NNNNNNNNNN NNNNNNNNNN
51701 NNNNNNNNNN NNNNNNNNNN NNNNNNNNNN NNNNNNNNNN NNNNNNNNNN
51751 NNNNNNNNNN NNNNNNNNNN NNNNNNNNNN NNNNNNNNNN NNNNNNNNNN
51801 NNNNNNNNNN NNNNNNNNNN NNNNNNNNNN NNNNNNNNNN NNNNNNNNNN
51851 NNNNNNNNNN NNNNNNNNNN NNNNNNNNNN NNNNNNNNNN NNNNNNNNNN
51901 NNNNNNNNNN NNNNNNNNNN NNNNNNNNNN NNNNNNNNNN NNNNNNNNNN
51951 NNNNNNNNNN NNNNNNNNNN NNNNNNNNNN NNNNNNNNNN NNNNNNNNNN
52001 NNNNNNNNNN NNNNNNNNNN NNNNNNNNNN NNNNNNNNNN NNNNNNNNNN
52051 NNNNNNNNNN NNNNNNNNNN NNNNNNNNNN NNNNNNNNNN NNNNNNNNNN
52101 NNNNNNNNNN NNNNNNNNNN NNNNNNNNNN NNNNNNNNNN NNNNNNNNNN
52151 NNNNNNNNNN NNNNNNNNNN NNNNNNNNNN NNNNNNNNNN NNNNNNNNNN
52201 NNNNNNNNNN NNNNNNNNNN NNNNNNNNNN NNNNNNNNNN NNNNNNNNNN
52251 NNNNNNNNNN NNNNNNNNNN NNNNNNNNNN NNNNNNNNNN NNNNNNNNNN
52301 NNNNNNNNNN NNNNNNNNNN NNNNNNNNNN NNNNNNNNNN NNNNNNNNNN
52351 NNNNNNNNNN NNNNNNNNNN NNNNNNNNNN NNNNNNNNNN NNNNNNNNNN
52401 NNNNNNNNNN NNNNNNNNNN NNNNNNNNNN NNNNNNNNNN NNNNNNNNNN
52451 NNNNNNNNNN NNNNNNNNNN NNNNNNNNNN NNNNNNNNNN NNNNNNNNNN
52501 NNNNNNNNNN NNNNNNNNNN NNNNNNNNNN NNNNNNNNNN NNNNNNNNNN
52551 NNNNNNNNNN NNNNNNNNNN NNNNNNNNNN NNNNNNNNNN NNNNNNNNNN
52601 NNNNNNNNNN NNNNNNNNNN NNNNNNNNNN NNNNNNNNNN NNNNNNNNNN
52651 NNNNNNNNNN NNNNNNNNNN NNNNNNNNNN NNNNNNNNNN NNNNNNNNNN
52701 NNNNNNNNNN NNNNNNNNNN NNNNNNNNNN NNNNNNNNNN NNNNNNNNNN
52751 NNNNNNNNNN NNNNNNNNNN NNNNNNNNNN NNNNNNNNNN NNNNNNNNNN
52801 NNNNNNNNNN NNNNNNNNNN NNNNNNNNNN NNNNNNNNNN NNNNNNNNNN
52851 NNNNNNNNNN NNNNNNNNNN NNNNNNNNNN NNNNNNNNNN NNNNNNNNNN
52901 NNNNNNNNNN NNNNNNNNNN NNNNNNNNNN NNNNNNNNNN NNNNNNNNNN
52951 NNNNNNNNNN NNNNNNNNNN NNNNNNNNNN NNNNNNNNNN NNNNNNNNNN

FIGURE 3T

53001 NNNNNNNNNN NNNNNNNNNN NNNNNNNNNN NNNNNNNNNN NNNNNNNNNN
53051 NNNNNNNNNN NNNNNNNNNN NNNNNNNNNN NNNNNNNNNN NNNNNNNNNN
53101 NNNNNNNNNN NNNNNNNNNN NNNNNNNNNN NNNNNNNNNN NNNNNNNNNN
53151 NNNNNNNNNN NNNNNNNNNN NNNNNNNNNN NNNNNNNNNN NNNNNNNNNN
53201 NNNNNNNNNN NNNNNNNNNN NNNNNNNNNN NNNNNNNNNN NNNNNNNNNN
53251 NNNNNNNNNN NNNNNNNNNN NNNNNNNNNN NNNNNNNNNN NNNNNNNNNN
53301 NNNNNNNNNN NNNNNNNNNN NNNNNNNNNN NNNNNNNNNN NNNNNNNNNN
53351 NNNNNNNNNN NNNNNNNNNN NNNNNNNNNN NNNNNNNNNN NNNNNNNNNN
53401 NNNNNNNNNN NNNNNNNNNN NNNNNNNNNN NNNNNNNNNN NNNNNNNNNN
53451 NNNNNNNNNN NNNNNNNNNN NNNNNNNNNN NNNNNNNNNN NNNNNNNNNN
53501 NNNNNNNNNN NNNNNNNNNN NNNNNNNNNN NNNNNNNNNN NNNNNNNNNN
53551 NNNNNNNNNN NNNNNNNNNN NNNNNNNNNN NNNNNNNNNN NNNNNNNNNN
53601 NNNNNNNNNN NNNNNNNNNN NNNNNNNNNN NNNNNNNNNN NNNNNNNNNN
53651 NNNNNNNNNN NNNNNNNNNN NNNNNNNNNN NNNNNNNNNN NNNNNNNNNN
53701 NNNNNNNNNN NNNNNNNNNN NNNNNNNNNN NNNNNNNNNN NNNNNNNNNN
53751 NNNNNNNNNN NNNNNNNNNN NNNNNNNNNN NNNNNNNNNN NNNNNNNNNN
53801 NNNNNNNNNN NNNNNNNNNN NNNNNNNNNN NNNNNNNNNN NNNNNNNNNN
53851 NNNNNNNNNN NNNNNNNNNN NNNNNNNNNN NNNNNNNNNN NNNNNNNNNN
53901 NNNNNNNNNN NNNNNNNNNN NNNNNNNNNN NNNNNNNNNN NNNNNNNNNN
53951 NNNNNNNNNN NNNNNNNNNN NNNNNNNNNN NNNNNNNNNN NNNNNNNNNN
54001 NNNNNNNNNN NNNNNNNNNN NNNNNNNNNN NNNNNNNNNN NNNNNNNNNN
54051 NNNNNNNNNN NNNNNNNNNN NNNNNNNNNN NNNNNNNNNN NNNNNNNNNN
54101 NNNNNNNNNN NNNNNNNNNN NNNNNNNNNN NNNNNNNNNN NNNNNNNNNN
54151 NNNNNNNNNN NNNNNNNNNN NNNNNNNNNN NNNNNNNNNN NNNNNNNNNN
54201 NNNNNNNNNN NNNNNNNNNN NNNNNNNNNN NNNNNNNNNN NNNNNNNNNN
54251 NNNNNNNNNN NNNNNNNNNN NNNNNNNNNN NNNNNNNNNN NNNNNNNNNN
54301 NNNNNNNNNN NNNNNNNNNN NNNNNNNNNN NNNNNNNNNN NNNNNNNNNN
54351 NNNNNNNNNN NNNNNNNNNN NNNNNNNNNN NNNNNNNNNN NNNNNNNNNN
54401 NNNNNNNNNN NNNNNNNNNN NNNNNNNNNN NNNNNNNNNN NNNNNNNNNN
54451 NNNNNNNNNN NNNNNNNNNN NNNNNNNNNN NNNNNNNNNN NNNNNNNNNN
54501 NNNNNNNNNN NNNNNNNNNN NNNNNNNNNN NNNNNNNNNN NNNNNNNNNN
54551 NNNNNNNNNN NNNNNNNNNN NNNNNNNNNN NNNNNNNNNN NNNNNNNNNN
54601 NNNNNNNNNN NNNNNNNNNN NNNNNNNNNN NNNNNNNNNN NNNNNNNNNN
54651 NNNNNNNNNN NNNNNNNNNN NNNNNNNNNN NNNNNNNNNN NNNNNNNNNN
54701 NNNNNNNNNN NNNNNNNNNN NNNNNNNNNN NNNNNNNNNN NNNNNNNNNN
54751 NNNNNNNNNN NNNNNNNNNN NNNNNNNNNN NNNNTTCTAA TAACTGTGCT
54801 TTCTACTACA TTAAGCCTAT TTTTTTTTTT TTTTTTTTTT TTTGAGATGG
54851 AGTCTTGCTC TGTTACCCAG GCTGGAGTGC AGTGGCACAA TATCGGCTCA
54901 CTGCAACCCT GCCTCCTGGG TTCAAGCGAT TTTCCTGCCT CAGCCTCCTG
54951 AGTAGCTGGG ATCACGGGTG CCCACCACCA TGCCTGGCTA ATTTTTGTAT
55001 TTTTAGTAGA GATGGGGTTT CACCATGTTG GCTAGGCTGG TCTTGAACTC
55051 TTGACCTTAG GTGATCCGCC TGCCTCGGCC TCCCAAAGTA TTGGGATTAC
55101 AGGCATGAGC CACTGTGCCT AGCCTGTGAA GCTCATTTCT TAAGGCTCTG
55151 ATAAATGTAT ATGTTTTAGT TTCAACCAAA AGGAAAAGGA ACGTATTTCC
55201 TAGATTTTTG TATCTCACCT AATTTTCATC TTTCTGGAAT GCTTAATACA
55251 TATTTTTATG TACATACATT ATTTGTTATT CTTGAGCCTC CTCTTGAGTG
55301 AAAATTTCCC CTTAGATGAC TCTTGGAGCT AATTTATTTC CTTCCCTTTA
55351 GCTCACTCAC TCATTCAATC ATTCAATAAC GAGTGCGTTA TCATACCAGG
55401 TACTGTTAGG TAGCAGGTTT ACAGGGATGA GCAGAAGAAG CAGGCCCTCT
55451 CTGCCTTCTT TCTTTTTCAT CACACTGAAA TCACAGCGCA TTGTGTGTGT
55501 GCAAAAGTAG AGTGCAGAGG GAACATGCAG AAAGGAGTTA TAGGATAGAA
55551 AAGGTAGCCA AGGAAAGCAG CAAGAACAGC ATGATTTGTT CAGGGATCTT
55601 TAAATAGCTC ATCATTGTTG GACAGCAAAG GGAGAGATGG GGAACGTGGC

FIGURE 3U

55651 AAGATGAGAT GAGAAGGGGA GCCGGGGTCA AGCCATGGAG GACGCTGAAC
55701 CCCTACAAAG GAACTAAGCC TATTGATGTG AACAGGCCAC TTATTTTGGG
55751 AACACGCCTT TGGTCCAAAG GGAAGAGGGC ACGAAACTTC CTTCTCTAAA
55801 AAACAAAAAA AAAGAAACTT GCATATATGA GAAATACTTT CTTCACTTTG
55851 CAGCATGAGA AACGGAATCC CTACTAAGGA AATAATTCTC TTATTTTTTT
55901 TGGAACAGCG GTTTTTGAAA TTTCCAGATG ACCCCAAAGT GAGCAGTGAC
55951 TTTCTTGATC TGATTCAAAG CTTGTTGTGC GGCCAGAAAG AGAGACTGAA
56001 GTTTGAAGGT CTTTGCTGCC ATCCTTTCTT CTCTAAAATT GACTGGAACA
56051 ACATTCGTAA CTGTAAGTAG GGCTGTTTTC CTTAATTTGG GATGTTGGGA
56101 TTATGAAACA CTCAAGAGAG ATCTGAGATT GTTCTGGCCC AAAGAAGCTT
56151 CTGTAAATTA CATAAATAAA GGCTTTAATT ATCTACAGGA GTAGTAAAGG
56201 CTAATGATGT AGCTGTCTTT GAGTAATAAT TCTGCCTTAA AATTGTTTGT
56251 GTAGAACTGG GTCATTTATC AAACTCTGTG TTTATGTGGC CTTTAGAATA
56301 TTATCCCTCA GTAAGTTAGA GGCACAGATT AATGGAGTTT GAAGGTTGTC
56351 ACTTGGTTTG ACACAGTTTC TTCCAAAAAA GTGGATCTAG GTATTTCATT
56401 CACATATCAG GAAAAAGACT CAGATTAGGC AACATGCCCA GGTTGTTCTG
56451 CTAATGGCTG AGTTTAAACA AAAACCATAA ACACCTCCCT GTGTTTATTC
56501 ATTTGTTTCC CTCGATAATA TTTGTCTTTG CTCACAAGCA TGTAAAACCT
56551 ATAATGTATA TGCACAGTAG ATTCATTCAT ACATCACTTT TTATAATCAG
56601 TTAGTGCAAA CTGAATGAAT TCATTAAAAA CAAAGACCTG GTTTATTATC
56651 AACAGAAACC ACACAATGCT CTTTTTTCTT TTACCAGTTG GTGATCTTTT
56701 AAAAATCCTT TTAATTCTTG GATGTGTTGT TGATTGAATG TGTTCTACTG
56751 AATGATCAGC ACGGATTAGA GCCAGTAGGA AAGCAGTTAT CCTGTTTGAG
56801 TATGTGTTTT GTTTTTGGTG ATGGAGGGAG GTTGGGAAAT GGAATCTGTT
56851 TCTAGGTGTC AAAACCAGGC TTCTGATTGG AGATGTGTTA TAATTATAAT
56901 TGCTTGCACC TTCAGCTAGG ACATAGTATG GTAAAAAATC AGTATTGTCC
56951 AGTTGTAAAC CATTTTGATG GTTTCTCTAA CCTTCTGCTG AAATATTTAA
57001 GTAGGTAGCA TTTCCATAAA TCTTTCTTGG CAAATGTTTT TATTATTCGG
57051 GTGGCCACAT TGCTTTATTT TTCTAAATAA ATAGACATCT CCCCCCAAAT
57101 CTCCAAGGTT CAGACCTTCT AATCAGTAAT ATATTTTCAG GGCATTCTTC
57151 CTTTTATGCT TTTAGAAAGA TGTAATAGAC TTTCTTTTAG ATGCTGTTCA
57201 AGTACTTAAT CTTTTCTTGT CTTGCCTTTT TATCTCTGTA ATCTTCTTGA
57251 ATAAGCAGTT AATTTTTTTT ATTCATGAAC CTGCTGATCA TGTCTAAGAA
57301 TGTATCTCCA CTTAAGTAAG TCAGTGAATG GTGATTACCT GAGTAGAGTT
57351 AAAGTAGTCC CCCACCCTCC TATCTGTGGC ACATATGTTC CAAGTCTCCC
57401 AGTGGATGTG TGAAACTGAT GATAGTACTG AAACCCATCT ACCTTTTTTC
57451 CTGTGCATAC ATACCTATGT TATATAAAGC TTAACTTATA AATTAGGCAT
57501 AATATATTTG ACTCCCAGCT CCCAGTGTAG TGGCTCTGAA GACTCACAAA
57551 ATGTATTTGC TTTAAAAAAT TCTTTTTTTT TTTTTTGAGA CGGAGTTTTG
57601 CTCTTGTTGC CCAGGCTGGA GTGCAGTGGT GCGACCTCAG CTCACTGCAA
57651 CCTCCGCCTC TTGGGTTCAA GCGATTCTCC TGCCTCAGCC TCCCAAGTAG
57701 CTGGGATTAT AGGCATGCAC CACCACACCC AGCTAATTTT CTATTTTTCG
57751 TAGAAACGGT TTTTCCATGT TGGTCAGGCT GATCTTGAAC TCCTGACCTC
57801 AGGTGATCTG CCTGCCTCGG CCTTCCAAAG TGCTGGGATT ACAGGTGTGA
57851 GCCACCACGC CTGGCCAAAA AATTCTTTTA ATTTAAGTAA ATCTTTATTT
57901 ATTTACTTTT GAGACAGAGT CTCACTCTGT GGGCCAGGCA GGAATGCAGT
57951 GGTGTGATCA CGGCTCACTG CAGCCTCGAC CTCCCATGCT CAAGCAGTCC
58001 TCCCACCTCA GCCTCCTAAG TAGCTAGGAC TACAGGTGTG TGCCATCACA
58051 CTCTGCTAAT TTTTTTGTAT TTGTAGAGAC GCGGTTTCAC CAGGTTGCCC
58101 AGGCTGGTCT TGAACTCCTG AGCTCAAGTG ATCCTCCTGC TTTGGCCTCC
58151 CAAAATACTG GGATTACAGG CGTGAGCCAT TGCACCCAGC CCTAATTTTA
58201 ATAAATCTTT TATTTTGGAA TAGTATTAGA TTTATAGAAA AGTTGCAAAG
58251 ATAGTATGGA AGAGTTCCCA CATACCCTTC ACCCAGTTTT CCCCAACGTT

FIGURE 3V

58301 AACTCTTTTT TATATTTATT TATTTATTTT TTGAGACACA GTCTTCCCGT
58351 CGCCCAGGCT GGAGTGTGGT GGCACGATCT CGGCTCACTG CAACCTCCGC
58401 CTCCTGGGTT CAAGTGATTC TTCTGCCTCA GCCTCCGAGT AGCTGGGACC
58451 ACAGGTGTGC GCCACCATGC CCGGCTACTT TTTGTATTTT CAGTAGAGAC
58501 AGGGTTTCAC CATGTTGGTC AGGCTGATCT CAAGCTCCTG ACCTCAGGTG
58551 ATCTGCCTAC CTTAGCCTCC CAAAGTGCTG GGATTACAGA CATGAGCCAC
58601 CGCACCCAGC CCCCAGTGTT AACTCTTACA TAACAGTGTC ACTGTCTAAG
58651 TGTTTGAAAA ACTATTTGTC AAAACTAATA TTGGTACATT ATTGTTAACT
58701 ACACTTCAGA CTTTTTTTGG ATTTTACCAA TTCTCCCACT CATGTCCCTT
58751 TTCTGTTTCA GGAATCAATC CGTGGTACCA TATTGCAGTT AGGGTGTTTA
58801 TATTTGATGG GACTGGTCCT AGTTTAGATA CTTAGTGTAG CTCAGCCAGC
58851 AGGTGGGATC TTCATGCCCA CCGAGGATTG GTATTGTGTT TTCCTGGTGG
58901 TTTTATGGCA TTTCCGACTA TGCAGAGAGG CATGGTATTA ACTTCAGTGT
58951 CTCCTAGCAA ATTTTCCTGT TTTTCACCAA CCTCTGATCC CTGCATTATT
59001 TGCAATCAAC TCAGAGATTT GTGATTGAAA ACATTGCTTG ACTCCATGCT
59051 CTTTAAGCTA TTTTCTAACT AGGTAACTGT AACATAAATT ATGCTTTTAT
59101 CTAGCACTGT TTTTCATAAA CACATGTTGA GTGATTTTCA TCAACCGAAA
59151 TACTTCGAAT CATTAAGTTT CCCAAGTTCA TGGATGCTGC TTAAATGCCT
59201 GGTGGTTCCA GGCTGTCGAA TATTTCTGCC TTCTGCAATA AGAGATTGTC
59251 CCTTGTTAAA AGCAACATTA GCCTTTGTGC GGTTTCACCC CCAATTCTTC
59301 TTTTTCTTGT TGTAACCAAT GAAAGGAAGT ACTGCTTAAC ACAGCAGGTA
59351 ATAATCTTCT AAAACTCATT ATCTCAAGAG GTGGTCCTGG CAGGATATAT
59401 AAATGCAATT TAAGAAAGGT CTTGGCAAAT TTATGAATGA CAGAACTGGG
59451 AGTGGCTACC GAGAGAAACT AGGATGCGCC TTTGCTTTGA CACTGAGGTC
59501 AGGCGTAGCT TCTGTACCCT CCTGGGTCCT GCCTCTTGGG GTTGCTGCAG
59551 GCAGCACCCC ATGAACCAGG CATCTGACCC AGTTCCAGGA TACTTATTCT
59601 TCCAGCAAGT CGAACACTCT GTGATGAGTG ACTGCCATGC TCATGGGTCA
59651 CCAGGCTCTC ATTATTCTGT TTCATTTCCA GCCTCCCACA AGATTGGTTT
59701 TTCAGCTGCT TATTTATTAT TATCATTATT TCAAGGCTGC TTTCCAAGTT
59751 TCAGTGGGGG GTTTCCTAAG CGTACCAGCT GCCCTGGTTG TGCAGTTCCG
59801 GTGATGTTTC AGATGCTGGG CCGGATTCTG GCTGTACCCA GCCTGATCTT
59851 TCTGGGCTTC AGGAAAGCTG AAGCCAATCA GAGCTCCTCT TTCATGCCTT
59901 TGGGATTATG CTTACCTTGC CTGGCATCGT GTACCTGCTC CCATCCATGG
59951 GAAAGTTTTG CTGTCTGGTA CTGTCTTCTA TCAACATCTT TTAAGATATC
60001 TTCCCCCGAG GCATCGTGAT GTCAACGGAA CCAGCACACT TGTACGTTTT
60051 ATGCAAGACT GCCATATCTC AACAGTGAGA AATGCATAAT GGAAGTGGTG
60101 ATCACGGATT ATTTCCTAGG ACATTATGGC TAATGCGCTA GAGAACTCGG
60151 ATGGTCTGTT GCGTCTGACA TGGGCTTTTT CTCTTGAGTT GTCTTTCTTT
60201 TGCTATTCTC TGAAAGAAAC AATTCTTGCC ACATGATCCT GATTTTTCAG
60251 GTCCTCAGCA TTTGTTAGCA GAAAGTACAC TTTGTTTCCA TCCGGCAGTG
60301 ACTCAGTGGT GGTCCCATGC TGATGAAACG CTGAGATAGT CTTCTTCCAA
60351 ATAGGTATCG TTTTGATTGT TGCTGCTTAT TTGCTAGCTG GCCCTCAATA
60401 GTGACAATGA AACCTCAAGT GTATAATATG GTTGCTCAGT AATCCTGAGG
60451 GAAGACAGTC TTTGGTTTGG GGGATAGGGA TTCTGTGCCT ACTTAGCTTC
60501 AGGTGAAAGT CTTACAAATT TTTGTGTGTA GAAATAAGCA CCATGTACCT
60551 CCTTGGGTTT TTTCTTTTTT TTTCTAGTCC TTTAGTATGG TCAACAATAT
60601 TGTTTAGGGA GTACCTATTC TGTGCTAACC ACTAGGCATT CAAGTATATT
60651 ACACTATGCT CCTTCAAAAC ACTTCTGTCA AATGTAAGGA TTATTATACC
60701 CATTTTACAG ATGTGGTTAC TGTGGTAACT TGGCCAAGGT CATAGGGCAA
60751 GTGAATAAGG GATTCTGGAT TTGGGTGGAG GTCTGTGTGA TTCCAAAGCC
60801 CATGCTCTTT CTACAATACT ATATATGCCT TTGCATAAGT TATTGTTATT
60851 AGTAATAATA TTTGTGATGA TGGCAAATAA TAAACCATGT CACACTAGAG
60901 AGTGATTTAA TCTCTAGGTC TATTTAAGAA CATTTGGAAT TGCAGGAATT

FIGURE 3W

60951 GGATTTTTTT TTTTTTTTAA GTGATGGAGT CTTGCCATCT TTGCCCAGGC
61001 TGGTCTCAAA CTTGTGGGCT CAAGTGATCA TCCTCCCTCT GCCTCCCAAA
61051 GTGATGGGAT TACAGATATG AGCCACCATG CCCAGCCTAG AATTGCAGGA
61101 ATTTTTGAAT TGATGATTCA TTCTGATATT TGAATTTCTA CAGTATGTTA
61151 AGTGCAATGT CAGGTGCTGG TGCTGTGGCT CCATTGATGA ACACATTTGG
61201 GTATGGCCCT ACCTTCATTG AATTTAGAGT CTAAGAGCCT AACCGGTCTT
61251 TTGCTTGAAT AGAGCTGTAG TCCTGTTAAA TTGCTGTACC TCCAAATGGT
61301 GGGAAGTTTA ATGCTTCGTA GGCCTCCCCT CACTAGTTTA CTGAACCACA
61351 TGTGCTTGAT TTTTTTTTGA GATGGGGTCT CGCTCTGTTG CCCAGGCCGG
61401 AGTGCAGTGG CGTGATCTCG GCTCACTGCA AGCTCCGCCT CCCAGGTTCA
61451 CGCCATTCTT CTGCCTCAGC CTCCCGAGTA GCTGGGACTA CAGGTGCCCG
61501 CCAACACGCC CGGCTAATTT TTTTGTATTT TTAGTAGAGA CAGGGTTTTA
61551 CCATGTTAGC CAGGATGGTC TCGGTCTGCT GACCTCGTGA TCCACCTGCC
61601 TCAGCCTCCC AAAGTGCTGG GATTACAGGC ATGAGCCACT GTGCCTGGCC
61651 CCACATGTGC TTGATTTTAA GCAAAATACA GACTATAGGC TGTGACCTGG
61701 TGATCTCTTC CCCACATACA GCATCCTGCT AACCTATAAC TCTCCCCATG
61751 TCTCAGATCT AGCCTGGGAA AGGACAATGT TGGATCGATG GCCCACTTCT
61801 AATCTTGGGA TTTCTAATCT CAAGATGAGT TGAGAAGACT CAGGATGTGT
61851 CCTGTTTTCT GTTTATTTAG AACAGGGTTT CTCAGCCTTG GCACTGTTGA
61901 CATTTGGGGC CAGATAATTC TTTGCTGTGG GGGCTGTTGT GTGAATTGCA
61951 GGATGTTGAA CAGCATCGCT GTGCTTTCTC CATGGATACC AGTAGCACCC
62001 TCCCCCTGCA GTTGCAACAA CCAAAAATGA CTCTAGACAT TGCCCAGTCT
62051 CCCCTTGGGG GCTACAGTCA CCTTCAGTTG AGAACCATTG ATTTAGAAGA
62101 ATTGGCCAGG TTATTATCAG GAGAGGGAAC ATCACAGTAA TCTGAATCTC
62151 TCAATACTGC CACTGTTACT GTTAACGAAC AGCAAAACTA TTACGTGGAG
62201 GCAGTAGGAC CTTGCTACTC AGAGTGTGGT CCGTGGACCG GCAGCATCGG
62251 AATCATCTAG GAGCTTGTTA GAGCTTCAGA GACTCAGGCC TACTGAGTCA
62301 GAAGCTGCAT TTTAATAAGG ATCCCCAGGG GATTTCTGTG CATATTAGAG
62351 TTGTGAAGCC CTGCAAGAGG AAGAAATTGG ATGCTAGCCT CAGAGTTTCT
62401 TGCTCATCTT TGTGGGTCTT CCTCGTTTTG TCTTCGGGCT TAAGGTATGG
62451 GGAGGCCACT TTTTGGCTCA GGACTCCTAT GGGTGAATGG GACTGCTTAG
62501 AACTGCTGGG TTTTAGGCCT TGCTTTGAGG AATTTAAAGC TTTTCTCTTA
62551 GATGGACATT ACATCGTTCA TATACTTCAA AATGGTGGTT TGACCTAATC
62601 TCTGCCTTCT GATAGCAAAA AGATATTTCC TTGACTCCCT GAACCCCACT
62651 TTACTGTTGT CCCATATTGG ATTTTAATTA AGGGTGGAAT AAGTATTCTT
62701 CACTAACATG TTTATACATG TATGATATTA CCATGCCATT TATTGAGTGC
62751 CTAGTATGTG CCAGGAGCTC TGCAAAGTGC TTTATGCTTA TTATTGTTCC
62801 ATTTATTCTT CCCCAAACCT CTGTGAGGCA GGTCCTATCA CTAGTCCACA
62851 ATACAAATGA GGTCATGGAG CCCGAAGTTG GCAGTGGTAG GAATCAAACT
62901 CAGGTCTCCC TGACTCTAAA TTCTCTTTGC CTTTGTTTTT TTGAAAAAGT
62951 GGTATAGCCC ATAGCAGAAA ATTCACATTA TACAGAAGGT TATACGGCGA
63001 AAAATGCCTC CTTCCCACCC CACGCTCAAC CCCTCTCCCT CAAGCGAACC
63051 ACTATTGTCA GTTTCTCATA GAACTTTCCA GAATATTCTA TGCTCCTATA
63101 ACACTAGCAC AACCTATCCT CTTAACAACA TCTTTATGCT GCCTCCCAAG
63151 AATTCAGTAA TTTTTTTTTT TTTGAGATGG AGTTTTGCTC TAGTTGCCCA
63201 GGCTGGAGTG CAATGGCGTG ATCTCGGCTC ATTGCAACCT CTGCCTCCCA
63251 CGTTCAAGTG ATTCTCTTGC CTCAGCCTCC CGAGTAGCTG GGATTACAGG
63301 CATGCGCCAC TATGCTTGGC TAATTTTGTA TTTTTAGTAG AGATGGGGTT
63351 TCTCCATGTT GGTCAGGCTG GTCTTGAACT CCCAACCTCA GGTAATCCGC
63401 CCACCTCGGC CTCCCAAAGT GTTGAGATTA CAGGCGTGAG CCACCGCACC
63451 TGGCCAAATT CAGTAATTTT TATTGGCAGG TTATTTTCCC GCATCATTGA
63501 AATGAATGAA GCAATCTTTA TACTTCATTC ATTTAAGCAT GGCCCTACCA
63551 TGCTTATCCT TCGAATCTGC CACTCAGCCA TTGGTTTCTG ATAAGCAGTG

FIGURE 3X

63601 CTCTTCTCAA ATGAAAACCC CTTATGGCTT TTTTTTTTTT TTAAACAAGG
63651 CCACAGGTGA TATCATGATT TTGACATTAT TTTTTCATTT ATTTTGTTTA
63701 GTGTCCTGCC TTTAGAATTG CATTATCTCA ATGGCTTGTG CATTTAGTGT
63751 GTGTGTGTGT GTGTGTGTTG TGTGTGTGTG TGTGTGGTAT GTGAGCACGC
63801 ACATATTTGT TTTGGGCCCT TTTTTTTTTT TTTTTTGAGA CAGAGTCTTC
63851 CTCTGTCAGC CAGGCTGGAG TGCAGTGGCA CAATCTCGGC TCACTGCAAC
63901 TTCTGCCTCC TGGGTTCAAG CAATTCTCCT GCCTCAGCCT CCCACGCAGC
63951 TGGGATTACA GGCATGCGCC ACCACGCCTG GCTAATTTTT TTGTATTTTT
64001 AGTAGAGACG GGTTTCACCG TGTTGGCCAG GCTGGTCTCG AACTCCTGAC
64051 CTCAGGTAAT CCGCCCGCCT CGGCCTCCCA AAGTGCTGGG ATTACAGGCG
64101 TGATGTTTTG GGCCTTTTAA AGTTCATCTT GTTTGTGTAT TCATTTGTTT
64151 GGGGCCTTTT AAAGTTCTTC TTGTTTGAGG CTTCCTGTCA TTTGAAGGGT
64201 TATCTGGTCA TGTTTTGTTT TCTAAGCTAG TTCCATGAGG ATCATAGATA
64251 TGCTTCTCTG TTAGGCTTGG TTGGCCCTTA AACTTGTCTT CCTTTTGGAC
64301 ACTCACTTAC TTCAGGGGCA GGAGGAAGTG AGGAAGAGGA GTTGGGTCTG
64351 TTTGGAGTAT CAGCATGGAC GGGAAGGGGA GCAAGAGGGA TGGGATGGTA
64401 AAGTAGTGAT GGTAGAAATT CAACTTACTA GACCAGGAGC GTGTGGGCGC
64451 CACCTACTAA AACAAAAAAG GAATAATGAA GAGCTATAGT CAGTAGCTCT
64501 TATAATCTCT TATGGGATAT GTAGGCAAAT ATTTATGTGT CTCTTCGGGG
64551 CTGTTCTGTT TTTAGAAGGT AAATGATTGG TAAGAAAAAA TAGGCCAAAA
64601 AGAGCTAAAT GCTTATGAAT TAGGATTATA GGATTTTCCC CCACTAGTCT
64651 GAATTTAGAA GCTACTTCCA GAGATGTCAA AAATATGTAA TATTCTACTT
64701 TATTCCAAGA TAAATTGAGG GCAACTTATT CTAGAAATAA TTGCAATATT
64751 AAAAATATAA CAATGAATAA ATAGAGAAAT CTAGATGAAA GGAGTATGAG
64801 GATAGGGAAA TAAAGTTAGG GTTGAAAGTA AAAACAAGGA AGTTCCTGTT
64851 AAGTTGCCAA AGGAAGAATG ATTTGGGACT CTCAGTCTCC CAGTGACCAA
64901 AGCAGAAAGG AGAATATAAA CAGTTACAAG AGCCCCAGTC GCATGAAAAA
64951 AAAGTCCAGA ATGCTCTGCT CAGAGGAGAC CCAATTTTCT GAATACTGAG
65001 CCCTGAGGAA TTTCACCACT GGGTTTCCCA TAAATGAGAC CCCCTGTGAC
65051 CTGGTGGGCC CCATCCCTCG GAAGTGTACC CTGGCATTTC CATAGGACTG
65101 CTTCCTTCTG GGCCTCTTAG TGCAAGCCAG CAGTGCAATG CCACATCCAA
65151 GTTTGGTAAA TCAATTCTAA GTGAGATAAA TTAATGCCTT TTTTGGGGGA
65201 AGATGGGAAA CAGAGTGGGT TTGTTGGAGA GCCCATAAAT TGGAGTCTTC
65251 AACCCTTAAA TTCTCACTTG CGGGAAAACC TTTCACAACC AAGCAAACGT
65301 GGAAATGATT TGGCCAAAGA TTCAAAATTA TATTAAACAT CTGGGACTAT
65351 ATTCAGCAGC CAACTTTCTA ATCAATTCTA TGAGTGTGGT GATTGCAGTT
65401 ATGCTCATTT TCTGAGGGTG AAGTTTGGAT AGAACTAAAA AGGGCGGTTG
65451 GCAGGAATCA AAAGAGATGA AAGCCTCAGG ACAAAGAGTT AGAGGCCCAG
65501 GTGGTTCATG ACTGAGAGTT TGGAAATGAT TTCTGGTGTC TCACTTCAGA
65551 GAAAATAAAT ATAGCCAACT CTGTTCATCC GTGGTGATGG AACATTCAAC
65601 TACAGCACTG GCAGTTTGGG ATCTAAGACC ACCCTTCCAG CACTTCAAAA
65651 TTCTGACTTA TAAAGGACAC ACACAAAGAA CAGATAGCCA GATAGAGACC
65701 AAAATACCCA CTTTATTCTT GGCAGGGCAA GCACCCAGTA AGCTCTGATG
65751 CAGGGCTCTG GTAAATTTGC CCATCCTACC AACAGAGAAG AATGGTGGCC
65801 TCCCCTCATG AACGGGGTCG GAGGGGGGCC TTGCCACAAC AGGGGGCCTG
65851 ATGGAAATAA GGGGGACAAG AGTGTTCGGT TGGTTGAGTG CCTGCTATGC
65901 CTGTGCCTAG GCAGTAAAAG GGGAAGTTTT AAGTTTGGCC CTTACTTTCA
65951 AGACATAGTA ATTCTACCTT CTAGTAAAAC ATGGCCAAAT AAATGTCTGC
66001 TTTTCATGAG CCAGATAACC TCCTTCTTCT TTATTGGAGG AGTGAGTAGA
66051 AGGGTGAGAC TAGCCGGGTG CGATGTCTCC AACCTGGGCG AAAGAGCAAG
66101 ACTCCATCTC AAAAAAAAAA AAAAAAATTA AGAATAAATC TTTTCACTGT
66151 TGGAGAAAAG TTTTGAGAGG CCGAGGTGAG AGGATCACTT GAGGCCAGGA
66201 GTTTGAGACT AGCCTGGGCA ACATAGCAAG ACCCCTGTCT CTATCAAAAA

FIGURE 3Y

66251 ATAATAATAA AAAAAGCTAG CTGGGTATGG TGGTGTGCAC CTGTAATCCC
66301 AGCTACTTGG GAGGCTGAGG TGGGAGGATT GCTTGAGCCC AGGAGTTCAA
66351 GCTTATAGTG AACTATGATT GCACCCCTGC ACTCCCTCCT GGGCATCAGA
66401 GTGAGACACT GTCTCTAAAA AAAAAAAGTT GGAGAAAAGG ATACTAAAGA
66451 GATAAAAGGG TACTAAAGAG ATCGGGAAGG CAGCAAAGAA TGAATCTAGT
66501 CTGATGTGTT ATTGGGTGTA CGTAATTCAT GGCGGAAGGT GCTGAAAGGG
66551 AAGGTTGCCT GGGCCTACAG CAAGCAGGTG CTGATGAACT AGCTCCTTTG
66601 CTATTACTTA AATGTGTCCT GGTTGGGCCA GATGTGGTGG CTCACACCTG
66651 TAATCCCAGC ACTTTGGGAG GCCAAGGCGG ACGGATCACT TGAGGTCAGG
66701 AGTTCGAGAC CAGCCTGGCC AACATGGTAA AACCCCGTCT CTACTAAAAA
66751 TACAAAAAAA GTATCCAGGC ATGGTGGCAG GTGCTTGTAA TCCCAGCTAC
66801 TTGGGAGGCT GAAGCATGAG AATTCCTTGA ACCCGGGAGG TGGAGGTTGC
66851 AGTGAGCCGA GATCATGCCA CTGCACTTCC AACCTGGGCA AAAGAGCAAG
66901 ACTGAGTTCT CAAAAAAAAA AAAAAAAAAA ATTCCTGGGG AATATCCACC
66951 AGGGTGAAAA ATTGGGTATA TCCAAATTCA GCTTTGCAAA GAAATGCACT
67001 CATGACTAGT TGCAATTTGA AACGTTCCTC TTCTGAGTAT TTCTAGCCTA
67051 TGTAGGTGTT TCACAGATTG CTGAGTACCT AGACTGAGAG GGAGAGAAAA
67101 AAACAAAGTA AAGCTAAAAT GTTAAGAAGT CTGGTTAAAG TGCAATCCAG
67151 AAGTGAGGGA AAGCATCTCT AAAAGTATGA ATCTTTGGGG AAACATAACT
67201 TGATTACCAA AAACTTAATA TTAAGCAGCC TCATAGGAAC ATGGCTTTTG
67251 GGTATGGCGA GAGCCAGCTA GAGCTCACAT CTCCATTGAA ATCCACCACC
67301 AGAGAGGTTA TCTGCCTAGT TGTTGGCAGC CAGACCCTGG CATTGTTTAG
67351 ATTGATTGAT GGAAGGCTAC TTTGGGAATG CTGGCTTCCT TATTCATTGA
67401 CTTTAAAGAC AGCATTGTAA AAATTGATCA CCAGCCCAAA TCAATGTTAC
67451 CCTGAAGTAT TTTTATGACT TTTTGGGGAG GCAAAGAGAT GGGATAATTT
67501 TTGATTTATT TAAGTCTATT GCAAACTGGA ACTCCTTTGT CTTCTTTTTG
67551 AACTACCTTT TTTGTTTTTT TGAGAGAGAG TCTTGCTTTG TTACCCAGAC
67601 TAGAAAGCAG TGATGCAGTC ACAGCTGACT GCAGCCTTGA CCTCCCAGAC
67651 TCCGATGATC CTCCCATCTC TCCCATGTGC ATCACCACAC CCGGCTAATT
67701 TTTTGTATTT TTTGTAGAGA CAGGGTTTTG CCATGTTGCC CAGGCTGGTC
67751 TTGAACTCCT AGACTGAAGT GATCCACCTG CTTTGGCCTC CTAAAATGCT
67801 GGGATTACAA GTGTTAGCCA CCAGGCCCGG TCTTGAACTT CGTATATACA
67851 GTGTGTTGTG TGGGCAAGTC ATGCCTGACC ACTTCCTAGT GGGAGGGGAG
67901 AAACTAGAGG GCTTGCCTGA GGCTTTAGGC AATGTAATCT GTTCTCTTGG
67951 GATCAATTAC TTATGCATAT TTAGTAGCCA GCTCTATTTG CTGATCACCT
68001 AATCTGTTCT CTTCGTTCAT TCCCATGAGA CTTCGATATG GGATATCTTC
68051 CTCTTCTTCC CATTGCAGCC TTTTCTCTCA GAGTTGTTCC CATGATAAGA
68101 ACTCCCATCA AAATCTCTGC TCTAACATCA GTTGTCAGAT TTTGCCACTT
68151 TTTTTTTTTT TTTTTTTCTG AGATGATGGA ATCTCACTCT GCTGCCCAGG
68201 CTGGAGGCAG TGCCACCATC TCGGCTCATT GCAACCTCTG TCTCCCGGGT
68251 TTGAGGGATT CTCCTGCCTC AGCCTCCCGA GTAGCTGAGA TTACAGGAGC
68301 ACCCCACCAC TCCAGGCTAA TTTTTGTATT TTTTTTAGTA GAGATGGGCT
68351 TTCACCATAT TGGCCAGGTT GGTCTCAAAC TCCTGACCTT AAATGATCTG
68401 CCTGTCTCTG CTTCCCAAAG TGCTGGGATT ACAGGTGTGA GCCACTACGC
68451 CCAGCCACAT TTTGTTACTT CTTTCTGTAA CCTGAATGTG GAAAAACTCA
68501 CTGTCTTTCC TCCACTCTCA CACCATAACT GTCAACACCA CAGAAGACTT
68551 CTGTGACCAA ATATGTGGTC ACCACCAAGC AAGCAGTAAG TTCTGCAGTG
68601 GACACCACTA GGCGTCCTCC AGTTCAGTTC TGGCACTATC CGCCTGGAGA
68651 TAGGGCTCAA TCCCACAGGT GGAGGTCTCA GTCCCCAAGA ATGTCCCCTC
68701 TTCAGGCACC AGTTGCAAGT CCAGGCCTCT GGAACTTCTC GCTGACTGGC
68751 TTCAAATTGG GGTTCCTGCA GCCCCCTCTT TGAGTTCAAT TAATTGGCTA
68801 GAGCTGCTCA CAGAACTTGG GAAAACACAT TTACTGGTTT ATTCTAAAGG
68851 ACATTGCAAA GGATAAAGAT GAAGAAATGC ATAGGGCGAG GTATGGGGGA

FIGURE 3Z

68901 AGGGTTGCGA GCTTCCACGC CCTCCCTGGT CGCCCTCCAG GAACCTCCAC
68951 GTGTTCAGCT ATCCGGAAGC TCTCCAAACT CTGTCCTCTT GGGACCTTTC
69001 ATGGAGACGC CATTGGATAG GCATGATCAA CAACCATGTA GAAATGGGAT
69051 TGCACGAAAA GGCTATGATC TAATCCTCAT AGGCTGAGTG GGGAATCCCA
69101 GCAAGGCCTG TTTGTTCAGA TCCTTCTGTA GCATTCATTC CTCCAGGTTA
69151 TGGGGCAGGA CCCCTTCTGA AATGGGGTCT TCTGACCTAC AATCAGACAA
69201 GGCAGAGGAA ATTTCTTTAT GGCCAGCTCC AAGTCAGAAA GGTGGGGGAA
69251 GATTAGAGTC CTGCCTTGAG CAGATGAAAG GAGGGCTGGA GGAGGTCAGA
69301 GAGAGAGAGA TTCTGTTTTT CAAGGCCTGC TTCTAAAGCC TAAAGCACCC
69351 CTAAATAACA AAAGATTGTA ACAAGGACTA TGGGAGTCAT AAGCCAGGAA
69401 CCGTGGATGA AAACCTATAT ATATGTATAT ATATATCTCA TAATAATTCA
69451 AACCTGTCTC CTGTTAATCC CATCCTCTCT GTTTCTGTTA TCATTTCCTT
69501 AGTGTAGATC TGCCTAAGTG TAGAATTTGT AGAATTTGTC ATGTTGACTA
69551 TTGTAGACTT GTCTTTTAGA GTTTCTAGCA CTAGCCTCTT CCACCCATCA
69601 CTATTGAGAT GATTGTATCC GTCTCAGTAC TGACACTAAC CCAGCACTCT
69651 GGTTTTACAT CTGTCAATCC ATCAAGACTT CACTTTCACT TTCTTCCCTG
69701 CCTCATTATT CACTATGCTC TTGGGCCATT GCTCTGGCTT CTGGGGCTTT
69751 TCTAAAGTAG CACTTTTCCC CACTCCAGCC CATGAAGATA CCTTTTAACC
69801 AGCTCTTGAG ATTAAATCCC CTCCGTGACA CTTTCCTGCA GGAACTTGCA
69851 AAAAAGTACT GCATTCCCCA CTGGCAAAAC TTGCCATCAG CCAGTTTATG
69901 TATTCTCTGC TTTTCACACC CATATCTTGA CCTCTGAACA ACACACATAT
69951 TCTCCTCTTC ATTTATTTCA CAGTTCTGTC TTCATAACAT TGATAAGTAT
70001 GATCACATTA GCGCTCTAGA TTTTAAGCAA CTGGAAGATA GCTATTTTTT
70051 TGGTACTCTT CCTTTAAATT TGAACATAGT GTCTAATTAG TCAATTAACA
70101 TTTTTTTAAA AGGGCGAGGG ACATCATGGT AGAGAGAACG AAGTTGAACG
70151 TGTTTTTGGT TGAATATTAG CGCATGCCCA CTGTATTCTA GGCACAGTCC
70201 TGATTCATTA TATCATCACA CAATAATTAT TTATGTGCCT TCATCCTTTA
70251 TGACACAGTG CTGGCTCTTA TTCATCTCCC ATTTCTGCAA TCCATGGTGA
70301 TGATTAAAAG TCTTAGGAGT TTTACGAGGC TCAGTATTTT TTTTTTTTAA
70351 TATGCTAGTT CTTCATGAAT ACATTGGGTA CTCTGAAGCA TATCATTTCC
70401 TGGGTTTCCT GAAGTGGTAT GTTGCGTGGA ATGGCACATT AGGTCTAAAT
70451 AATTATCCCC TATGTAAGGT TCTTGTTTTT CATTCATTCT CTTAAAAAAT
70501 AGATATTAAA CATTAAATAA GGACAGCCAG GTATTGTTTG AGGTGTTAGT
70551 GGGCTATGCT AAAAAATCAA AGGTGGGAAT GAGGCAGCTG GAGCTCAAAG
70601 GAGCATGTTA GAAGGAGTCC CAAGAGGACA AATCCATTTG GTTCTTCTTT
70651 CCTTGTTTTT TTTCGAATAT TTTTGAGGAT GATAATTTTT TTCCCCTCAA
70701 AAGCTTTTAA TGAATGTTAG GATTAAAAAA GAGAGAGAGA GAATTTATAG
70751 AAGAGAAATT AACTATAGCT CCTAAAATAG CTCTTTGTTT CTGAAAGCCT
70801 TGATTCTGCT ATCTATTTTA TAACTGAAAC AAAAACAAAA ACAAAAACAA
70851 AAAACAACCT CAAGAAGTTA CTTGTATAGC CTCTGCCACT AAGGAGACTG
70901 TGTTCTGATG TTACCTCAAA CAGGCTGATT TATTAAAATA TTTAAAAATA
70951 TATATGGAAA TATTTTTTTC TATTTTTTTT TTTAGTGGCT TTTCCCAGTG
71001 AACAATAGGT CTTACTATAT GATTTCTTAT TTGTCATTAG TGAATGTGGT
71051 GGGTATGTGG CAGCTGGGGG AGCTGATGAT TTTATAATAC TGTATCAGAA
71101 ATGATTAGTG TAGGTACTTA TTAACATATT TCTCAGACAG AACAATCTTG
71151 ACTTTTAAAA CCTCTTCATT TAATTCAAAC ATCAAGTACC CTGTTTGTGG
71201 CCTGTGTTAT GTTAGGTGCT CTCTTTACAA GACCTATTTT CTTGCTATTT
71251 AATTATATAT TTGCTTAGCA AATATTTACT CTGCACCTAC TAGGTACCTG
71301 GCACTGTGCT GTGTACTGAG GTGCCATGTG TACCTCCATC AACATAGACT
71351 CAAGATCAAT ATGATTTCAG TGAACTAAAA ATACCTTTAT TGAAGCAAAA
71401 AAAAATCACA TTTTGTAAGG ATCAAAAAAG AGACATTTTA TATAAGGTAC
71451 AAGAAATAGA AGAATTATAT CCCCAAGATA TATGTGATAA CATACTTGTT
71501 AGTTTTTGGA CGTGACCAGA TTTTACACAA TCCTTAAAAA ATGCAGCAAC

FIGURE 3AA

71551 CAGATTTTAA AGTAGTTCTC TAATCTCTCT TTCTGTGCCC CATTAGATGT
71601 ATATTGGATC TTCTCATTCT GTCTTTGTCT TTTGACCTCT CATGTTTTCC
71651 GTCTCTTTGT CTCTGTGTGT TGCATTGTAC ACAAATGCTT CTTGAACTGT
71701 GGTGTGCACA TGAATCACCT GGGGACCTTG TTACAACGTA GGTTCTGATT
71751 CCATGGGTAT GGGGCAGGGC CTGAGATTCT TAGAGAATTA AATTCTAACC
71801 AGCTCCTGAG TGGTGGTGAT AATGCCAGTG TGTAGACCAT AGCTTAAGTA
71851 TCAAGGTTCT ATGTGATTCC CTCAGATCTA ACTGCTAGTT CACTAAGTTT
71901 CTCTTCAGCT GTATCTAGTC TGCTATTTAA CATATTCAGT GAATTTTTAA
71951 CCTTAAATTC AAGAACAAGA CTTTTTATTT CTGGAAGTTC AGTTTGGTTC
72001 CTTTCAAATG TACCTGGTTC TTTTTCAAAG TGTCATGTTC TTTGATAAGA
72051 ATTTCTACTA ATTTACCTTG ATAATAAAAA TTTGTTTCAT GGCTCATTTT
72101 AGATTGTTCT TTTATCTGCA GTTTTTGGAG GGCTAATTCT CCCATTTCTT
72151 GTATCTGTTG TTGCACCCGT AAGGTGTAGT TGTTGATTTT TACTTTTTAA
72201 TTGTGAATTT ATTTCTGGTA GGGATTGGAA GGAGGTTGTT GGGGTGGGGG
72251 TGGGGTGGGG AGAAAATCCT GTGTGCCCTG GGTTGCAAAA ACACCCCTAC
72301 AAGTTGTTCT CCACTTGCAT CTGCCAGTGC TCCAAGGGCT CAGTGATCCT
72351 GGACCAGTAG TCATGATAAT TTCTTGAATT GTAACAGGAT ACTGTAAATG
72401 TGGACACTCT ACCTGAGGTT ACTGCTTCTT TCTATCTGCT TTATTTCCTT
72451 CCCACTGAAG GGCCCTGGAC AAGGGTAAAC ATCTCATCAC TTTCTGGGTG
72501 GCAGAATATT TCCAGTTCCC CCACTTCTTT TTGGCTTAAG GCTGTGGCTT
72551 TTTCCTCTGC CTGAATGTGG CCCTAAGAAG CCCTTCTTTT CAAACTTTCC
72601 TGTTGTACTT GACCGACTAG CTGTCTAGAG GTTTATATCC CTAGCTTTTA
72651 ATCTTTGCTG TGAATATCTT ACCTGTTACC AGCTAGTATA TTTCACATTG
72701 ACTTCTCTTT CCTTTTTTTT TTTTTTTTTT TTTTTGAGAC GGTGTTTCGC
72751 TCTTGTTCCC CAGGCTGGAG TGCAGTGGCA CGATCTTGGC TCACTGCAAC
72801 CTCCACCTCC CAGGTTCAAG CGATTCTCTT GCCTCAGCCT CCCAAGTAGC
72851 TGGGACTACA GGCATGCACC ATCACATCTG GCTAATTTTT TTGTATTTTT
72901 AATAGAGATG GGGTTTTACC ATGTTGGCCA GGCTGGCCTT GAACTCCTGA
72951 CCTCAGGTGA TCCACCTGCC TCGCCCTCCC AAGGTGCTGG GATTACAGGC
73001 ATGAGCCACT GTGCCTGGCC TACTTCTTCT TCCTTTTAAC TTGAAGATTA
73051 TCTGCCCCTT TTTCTAATCT TAACCGCATT AAGCTGGCTT TGAGCATGGC
73101 AAGAGTTTTA TAGATGAATC TTATTTTATA GTACAGGATT TCAAAATCAT
73151 AATTATTTCA CTGAGGGTGG CTTTTACCCT CCATTAATTA TACTTCTCAC
73201 TCAGAAATGG AATTCTATTT TGGTCTCCTA AAGATAAATT AGTATATAGT
73251 GGAAAGGAAT TATAAAGTTC TGCTAGGAAT TAAATGATAT GATTAACACA
73301 AACATCCACA TGGATGTGTC TCTGCCCTGT GCAGGAAAGA TGAACATTCA
73351 GTACAGATTC TGCTCTATGT CACTAGCTTT CAAGACCTGC AGGTTCTCTC
73401 CTAAGCATGC AATTCCTGTG AGCAGTAGCA ATAATAGCAG GTCATATTTG
73451 TGGAGTGATT ACTGTATGCT AAGAACTGTG GTAAACACTT TTATATGGAT
73501 TATTTTATTT AAACCTCCTA ATAGTCCATT GAAATAGATA TTGCCATGTT
73551 GAAAACTGAG GTTCAGAGAG GTTAAGTGAC TTACCCAGTG TCACAGAACT
73601 AGTAAGTGGT GCAGCTGGGA TTTGAACTGA GATTCCAGAA CAATTGCCAT
73651 TAACCACTTT GCTTCCATAT TAGTATCATC TGCAAATCTC TCTCCATAAA
73701 TTTCCTCAGT CTTTATCTGA GTTTCCTTAT TTCAGGAAGG AAAACTTCTG
73751 TTTTTGATCC TTATGAAATA CAATTTCCAT TAAAACTTTT TTTTTTTGCT
73801 ATTAAAAAAG GTACCGGATA ATTGAAACCA GACTGGATTT GAGCCTGTGT
73851 TGATGGAAGT ACACATGGGA TGTGGGCTGA AGTGTTCAAT CTAATTTTTC
73901 TTTCCATCAG CTAATTTTTA AAGTATTAAG CAAGTAGATT CTGACACTAA
73951 CAGGGAAGAT TTAAATTCTC TTGAGAGACT GGAGGTGTTA AATAATTTTC
74001 TGGTAGTGCA CATTTTACAT CTTAAATCTT CCTCACTCTC CCACCTCATC
74051 TCAATGTACC TGAAGCTCTG GGAATGTTCT TTTGTACTTC TCAGGAACAG
74101 CCAGACCTCT GGCTTCATCT CCTCTCCCCT CCACATCCCT TTCCTGCTCC
74151 AATTACTTCC CAGCGCCACT TGGATGTTGT TGTCATCGGG GAACTTTGGA

FIGURE 3BB

74201 AACAGCCAGA TTTTTTTGGA GTCTGTAAGC AGAAAACAGA CTGCTTGCTG
74251 CTCATATCTG GCACCCAGCT TTGTCCAGAA AACGAGGAGT TAAAAAGAAG
74301 TCTGGGCTGT GAAGGGCTGT GACAACTGTC CTAGGGGGAG CTCTAGCGAG
74351 CCCTGGCGGG CAGTGACTCA TGCTGCTCTG TCACTGGGAT CAGCACTGGC
74401 CCCTGGCAGG CAGGCGGCAG CCAGGTGGGG TTCCAGCCAG AGCACGCACG
74451 CACGGAGCCG GGAGCATGCA GCCTGCACTG CGGGGGATGT GATGCTCGGC
74501 TCTAACTCGC CTGGCTGGCC CGCCACGGAC GCCTCAGCTT GCAACCATGG
74551 TAACGTTTCT GGCGGGGGAC ACCCCCGGGA GCCCACCGCG ATGGGCAGCC
74601 TCCTGGTGAC TGATGGACGA GTGTCCACCT CCCAGACCGA GAGCGCTTAG
74651 TAGGTCGGAG GAAGTGGAGA GGATGTAACA CGCCCCCAGC CGGGAGTGAA
74701 GCCCTGAGGA GGTAGGAGCC GCATATGTCC ATCCGTGCAT TCCCACCGTC
74751 AGCGCGCAGG GGTGCTGTAG ATCACCGGTA GGAACTTTAT TTGGCTGGTG
74801 CTTCATTATG CTGATTAAAC TGCAGTGGAT TTGATGGGCA TGATTGCGCT
74851 GGGGAAGATG CATAATGAAC TAAAAAAAAA AAAAAGTGGT TAATAAGATC
74901 TCGGAGTCGA CTTGTCCGGG TATGAATGAA GTAGACTGCA GTGGTATCCT
74951 AACAGGAGTT CCAGAACCTC ACACATCCCT TTTCCTGGTC CTTCCTCTTA
75001 TCCCGGTTAA TCCACGAAAT GTAGAAGTTC CATCTTATTT CAACGATTAG
75051 TGCTAATCAT TAATAATTTA GACCTGTCTG GAGGAGGGAA TCCATAGGTT
75101 TAGGTCTCCT AGCATCCTGG CACTAGCCAG CAGCTGCTCT GTAGGAGCCT
75151 TCTGGAAACA GCAGGAAGGA GCGGCTTCCC CACGAGTTCC CCAAGTGCTT
75201 TCGTTGGCCC AAGTGCTTTC GTTGGCCCAA GTGACCTGTT TGAGTTTGCT
75251 CTTCAGTTTA CCCCAGGCGG GAAGGCAGCC TGTCTGCGGG TTGGTGGCCA
75301 TGTTGGCAGA GAAGGGGTTA ATCTCTTGTT GCTGTAGGAG CCGAGGTTGC
75351 GAGCTAGATT GAAAGCAGGC GCTGCAGTGC CATCGCCAGC GCCGAAGGAG
75401 TAAGACGATC TTCTCCGCAA CAGTGTTGAA TCCGGCTGAA ATTTTTTTTC
75451 CTCCCCGCCT CCTTTCTTGT TTTTCTTTAA CCAGCTCCTC CCCCCTTCGT
75501 TCCCACCCTC AAGTCTGACG ATGACACCTC CAATTTTGAT GAACCAGAGA
75551 AGAATTCGTG GGTTTCATCC TCTCCGTGCC AGCTGAGCCC CTCAGGCTTC
75601 TCGGGTGAAG AACTGCCGTT TGTGGGGTTT TCGTACAGCA AGGCACTGGG
75651 GATTCTTGGT AGATCTGAGT AAGTGAAAAT TTGACTTTCT AAAGGGACCT
75701 GCATTGATGC AAGGCTTTTG GAGCCAAAGG TGGTGGTGGG GGGGTGGGGG
75751 AATAGGTGGG GGGAGTGCAG TGGAGGGAAG CTGCTAGTCA CCTGCATTGG
75801 GAAAGCAGTC TACCTGTTAG GGCTTTGCGG GGGTAGCCTG TTAATATTCT
75851 CATTTTGCAG TGTGTAAGGT ACCTGTTCCT GTCTGTGGTA TGATAATTGT
75901 CAATTGGGTA CTTTGGGTTA GTTTTCCAAT CTTTGGTCTT CTTTAAAGGG
75951 GAGAGAGTGG GAGATTTCCA GCAGTGCAGA TCCCCGGTCA AAGGAGAAAT
76001 GTGCAGGAGT TAAGATGAGC TGCCCATCTA TCTAACCATC TATGTATCTG
76051 TCTCTCAAGT GGGTGGATGG GGGTTGCTAT CTTGGCTGTA TAAAGAATCC
76101 TAAAAACCTT GTCTCATAAG CTAGAGGTTT CCTGATGGGT TTAACTGAGC
76151 TGCAAGTGGC TGAACCAGAG CTCTAACAGA GAGATGGTGC TCGGCTCCTC
76201 TCCAAGTATG CTGCAAGATC AGGGATCTGG CAGCTGAGCC TCTCTGAGCT
76251 GGTGGAGCGC TGGCAGCCAG AGAAAGCCCC GTTACTGTGA GCCACCAGGA
76301 GGGAGTGTGA TGTAGCCGAG TCATTGATTC ACAGAAACTG GGCTTCATAG
76351 GGGGAAAAAA AACCAGGAGA CTAGAAAATG GAAATATAAA TATCACTGTA
76401 AACCTCTTGA TCTGGTAGGT CTTTCTCCAT TCTCATAAAA GCTATTGAAA
76451 AATGCATTAA CAGAGCACTT GGAATTAGAG GGTCGAGGCT TCCAGGAGCC
76501 TCCTGGAATT TCTGTAAAAT GCAGTAGCTT CTGTGGATGT GGGAGGTCAG
76551 TATCTTGCCT CATTCTCTCA TGATACAATG ACATTCTGTT TTCAGAGGAG
76601 TGAGTTCCCC AGAAGATCTT GGACTGATGG TGTTATTTGC CAGCCACCCT
76651 GGTCCCTGCA CTTTCAGGTT CTCAGAGGGT AATGTTGGGT TAGTTGCTGC
76701 CCACTTAGGA GACGAGCAGA ATTTGATATT CTTCTTGGCA GCATCTTTCC
76751 CTCTTTGTGG TATTTGTAGC TTAGATATCG ATTTATAGGG ATGTTATGTT
76801 GGTTCCTGGA TGGTGTCTCC CTATGGGTGC TATTTTGACA GTAACGTTCC

FIGURE 3CC

76851 TGAAAAGATT TCAGAGTGTT GTGGGGAATT GGGCATTTGA TACGAAATAA
76901 GGTTGTGGGC TGTGATTGAA TGTGAGGGAG GTTTTTATGT TGCAAGATGT
76951 TGAAGTGGTC TTTCTTGATC CCCTCTCTGG GGGCTGGGTT TCAAATTCAG
77001 GTTGGATTTT GGTAGTGTTA GATGTGCCTC TCTGTCTGAT TTGCTCCACA
77051 ACCCCAAAGC AATCTGGATG GTGGTGGGAG AGGCAGAGTG CTAACTAGCT
77101 GTTGAATGTG CCATCAGATG GGTTTGAAAC GGCTCAGCAG GATTGGGAGG
77151 TTTTGCCATT GGCATCAAAG AGCAGGGCAG AAGCGGAGGC CTGATGTTGA
77201 AGGATGCATG GTTAGTGGGC AGTATAACCT TGACACACGC AGCACACTGA
77251 AGGTCACACG TCGTACTGGA AGGACGTGTG GAGAGTTCTA GTTCTGGTTA
77301 GCAGTGGGCT GGCTGGGTCA GAATGCAAGC TTGCTTGGGT GTTGGTCAGT
77351 GATCTGAAAG ACGAGGGAGG ATTCGAGGGA GTTAGATTTC AGGGGAAAAG
77401 GCAGAATGAT ATGGGAGATC TTAGGCATTG CAATTAATCT GAAGCAGTGT
77451 GTGATTAATT GCTTATTTTT CAGGAAGACT TGAATGACAT CTTTCTGTTT
77501 CTCACAGAAA GCTCAGTTTA GGGAGCTCTC TGACAGGGAC ATCTCAGTAT
77551 TAAGGCTGAG GCACTCGATA AATATTTGTT GATTTAATTT ACCTATGATC
77601 CTTTCCTCCA GAAGTGTTTA TATTGCTTAT TGTATTTGAA GATGTGCTAT
77651 CTCACCTCTG GTAGTTTAAA CTATATCCTT AGAGCACAAA ACGAGCTGCT
77701 GTTCCTGACC CAACAGAATG TTTAATAAGA TTCTTATTTC AAAAAAGGTC
77751 CATGCAAATA AAACTGTGTA TTTCTTATTT GGACGATGGC ATCAGAGTAT
77801 TCCTATCATT GGGGAACTTT AACGTTTTTT CAAAGCTTGG CAACGGGGTT
77851 GGAATCAGAA AGATTTTCTT TCATCTTGCG TCTTGTTATG TGTTATTGCT
77901 ATTGGACTTG GCTACTCTGC TGTAGGCAGC CCTGTGGGTG ATACCTACAA
77951 GCATCATTTT AGAAATTCAT CCACCTGTTG GATGTAGATG ACCCTGGACA
78001 TATCAGATTG TGATTAATTA GAAATCTAAT AAAAGAGAGG CAGTGATGAA
78051 ATTACTTAGC AGCTCCTGCA GTTTTATTGA CAAAATTTAC TTGGAGAGAG
78101 GGGGAGACAT TTTCTGGGGG TACCACCTTT GCTGCCAGCG ACCCTGTGTT
78151 TCTTCCTGAG TTTCTTTTTC TTTTCTCACC ATTTTCAGCA TCACAGGTTT
78201 TTATTTACAC ACATTGATTA CCTGTGCTGT TACTCATTCT TCACACCACT
78251 GAGGAAATTG CAGATGCTGC TGTACTGTGC TAGGTAAATT GACCTCAGAT
78301 TTGTTACCAG TGAATTGAAT GAAATGTTCA GAGGTGGAGC TGAATGAACG
78351 AGGAGTTTTT GTGGAGAAAT TGGCAGTGAG AATGATTTAA ATTCTGTGAT
78401 AGCTCCTCGT TTTTTGGGAT CCTTATTTTG GGACCCCAGA CTATTTTTAA
78451 GCCATTGAGT GCATCATTAT TTTAGGCTGA GCAAGAATCT TGATGACAGC
78501 GTTTCAATGG CTGAGGCGTA GTGGGAGTTC CTTGCAGCTT GAGTTGGTGG
78551 GAGCTGGAGA GTTTCTAGAG AACTAGGTTT GGTTGTCTTT GGGGTGGGGT
78601 TATGGTGAAA TTAGTCTTGG AGAGTGAGTA GCTGTCTGAT GCTTCTTTTC
78651 CTTTTTAACC AGCAAGAGCC CAAACCAAAT CCCCAAGCTC TGAATGCCTG
78701 GCTGTTCCTC TCAGCCTTTC TTTGCTTGAA CTTGACAATA GTAGGGTAGT
78751 AACAGGAAAC AGCATGTTAA AGTTTTAAAA ATAAAATAGA TCTCAGCTCT
78801 TTTCCTTCCC ATTAGCAAGG GGTACATTTA TTTAGGTTTT TCCTTCTAGA
78851 TTGAGGCACT GCCTCATTTA AGTTCTTGGT GAAGCCATGC ATTTCTGCAA
78901 ACCATAAGTA TAAACTCTAG AACGGGGGTG TCCAATCTTT TGGCTTCCTT
78951 GGGCCACATG GGAAGAAGAA GAATTGTCTT GAGGCACACA TAAAATACAC
79001 TAATGATAGC TGATGAGCTA AAAAAAAAAA AAAACTCATA AAGTTTTAAG
79051 AAAGCTTACA AACTTGTAAG TTTTGAGCCA CATTAAAAAC CATCCTGGGC
79101 TGCATGCAGC CCCCGGGGCC TTGGGTTGGA CAAGCTTGCT GTAGAAGGTA
79151 AAAATCAGTT GGTTTTATGT TTTTGTTTTA AACATGCTGG TTGTATGCTT
79201 TTGGAAGAGT TGGGGAACAC TGAGGGTAAT GGGATCTTGA TGGGGCTGGA
79251 ATTTGTGGGA AGATGGTGTC TGGGTAGGCT GTTTTTAGGA AGGGGCACTC
79301 TCTTCCTTTT GATTCAGAGA TTTTTCCTTT CTTTTCGGGT GGTTCTGAAA
79351 ACACAGCGAT GGATCCAGGC ATTCAAACAC CATGGAGGAA GGAAGAGTGG
79401 CTGTTGCCAT TGCTTCCCGA GTTTTCTGGG AACCAGTTTT TGGTGCCTCT
79451 TCCTTGCTCT ACTGGGGCTT CTCTGCATGT CAGTTTCTTC AACTGCGAAG

FIGURE 3DD

79501 TGGAAGGACA GCGATACTTT TCTTACAGGA CTTTTGCGGG GATGGATGAA
79551 ATACGTAAAA CACTTGGTCT AGTACCTGGC ACATGGAAAA GCCTTGGTAA
79601 ATGTTCACTG TTGTTATTTT TGTTATTACT AATACACTAG TCCATGTATG
79651 TATAGTGTCC TCCTATACAC ACCAAGAGAA TATGGAAAGG ACTCAGCAAT
79701 GATTAGGTAG TCCAAAGTCA TACCAGATTG GAAACCAAGC TTCCCAGGCC
79751 CTGGGACTTT TCTGCTAGAG ACACTTCACG GTTCTGACCA ACTACAAAGA
79801 GTTAATATGC AGTTGCCAAA TACCTGTTGG TAAAAGGTGG ATGTTGGGGA
79851 GGAGTGGATT GGGGAACAGA ATTAGAAGGT CCAGTCCCAG AATGGGTACC
79901 TTCCCATCAA GTTGAACAAG TCAAAACAGG TTATGTTGAA ACAACTGAGA
79951 GAAAGTAAAG CAAACACCAT TGCTGCAGAA TATCATGGTA CAAATTGGAC
80001 ATCTTTGGGA GTTAGCGGAG TAAGGCAAAA TCCAGTGAGG GACGCTTAAT
80051 GGGTAATGCC AATTCACAAT TCTTGTTAAA TTACATTGCT GATCTTCCTT
80101 GGAATGTCTG TCCATTCCCC CAAGTAGACT GTGATCTCAA GGCAAGGCTG
80151 GGTCTTATTC ATCCTGGTTT TCCTGGAGCA GTAAATACTT GTGCTGGGAC
80201 TGGGCTTATA AGCATACTAA TGGAAAGTAA AATATTTGGG TTGGTTTTTT
80251 AAAAAGACAG TGGATTTGGA TCAGTGGAGA GGAAGGTAGA GGGAATTTCA
80301 GGTGGGCAGG GTGCTAACAA CAGCCCATCC TTACAGGGCA CCAACTGTGT
80351 TCTAGGCTGT GTTCCAACCA CTTTACACAG ATGAATTCAT TTAAATTGCA
80401 CAACCAGCCC AAGAGGAAGG TACCATTATT ATTCTCATTT TGGATGTGAG
80451 GAAACTGAGG CGTGGGGAGA TCAAACAACT TGCCTAAAGT TATGTAGCTT
80501 TGAGTGGCTT AGCTGAGATT TGAACCCTGT GGGTATAAAC GCCACAGATG
80551 GGAAATTTGT GTGGGGTACC CAGGTTCATG TGCTTGTTAG AAGTGGAAGC
80601 TATTTGTAGA GAATCACGAA TGATGAGGTT GGGGCAGGGT GTGATGGGAG
80651 CTGACAGGCA GGTCTAAATG CTGGGATTCA TTTTCAGTCT CTGTGTTTAT
80701 TGAGTAGGTA GACGGTATAG CTCTTGGATT TCTCAGATTT TTTCCTCTTT
80751 TCATTTAGAG ACTCTTATCT GGTGTGTGTG TGCCCGCACA CATACATAAA
80801 CCCACGCGTA TATACTCTTT CCCTGAATGT TCTTATTTGC TAAAGCTTAA
80851 GCTTGGCAAA GAGAGGAAAC TGCACTGACC TTACTCTCCA CCATATCTTC
80901 AGGCTGATCA TACACAAGTT GCTTAATAAG CATTTGGTTA ATCCATCTAA
80951 ATCATTCTTA TGGCTGCAAC TCTCATTTTG TTGATGACTC TACTATCTAT
81001 GTCTATTCAC ATCTACATTT TGTACTTTTG TTTGCCTCCC ATCTGTCCTG
81051 GGATGGCTGA TACCAGTGGA AGACAGCCTG AACTCTCCAA TCAGTCCTGT
81101 TTCCTTTTTA TGAAATACTT GGAGGTTGGA GGATCTTCCC TTAAAAAGTG
81151 TTTTCCTTTC TACATCCAGC CAAAGGCTCT TGGTCCTTGT GCTTGCTACC
81201 TAGATCCCTA TTGGAAAGAG TCTTGCCTGC AATTTGATTT TTTAAATAGC
81251 AGCAATAACA GAGTCGTCTC TGCTACACGA AGACATGCAT CTGCTGTATT
81301 TCCCAGACAA GTTCAAAAAC CTTAACTAGC TTCTGCCCAT GGTTATTGCT
81351 CTCAAGTGCC TTGTGTTGTT CCCATCCCCT CATTATCTGG ATTAGATGTT
81401 TAACATTTGC CTGTGTGTGT TGTGTTGGAT TTTCTCCTCT CCTCTTGCTC
81451 ATTCAATTTC TTCCTTCTCT TAGCCAAGCA CAGCTTGTTC TCCTACTTGC
81501 CTTATTCTGT TCTCTATTTA GACTGTGCGT GCCTGCCTTG CAGCCCTGGC
81551 AGGACCATTC CACCGCCTTC TCATTTGTCT TAAAGATACC TTTAGGAAAT
81601 CTAATCCAGA CAATCCTAGC CCAGTCCTGA AGATTAGGCT CCAGAAGATC
81651 TGTCAAGTGT GTTTTTTGCT GGCCTACACA TGCTAATTTG CATGGTTGCC
81701 TGGGATCCCT TAAGAAGACA GTCATTGACT AAATGGCGCT ACATGTTCCC
81751 AAGCTCTGCG CCAGTCTGGC AACTCTTCCT TTGTCTACGT GAATTTCTCC
81801 TAGTTCTTTC TGCTTTGCTT GCTGTTCATC TCCTGACCTC TCTCCGACAA
81851 ACTTCCTGAA AGAAGAGCCT GCACTCAACA CCTCTTTTTT CCACCTCTTC
81901 AACAATACTG AAATGACTGT CTCAGAAGCC GTTGATTGTA CCTAACCACC
81951 AAATCTGGTG ATTTCCATCT CACCACGTGA TACCATTAAT ACTACCTTTC
82001 TTCGAGACAA CGTTCTACTT TCTTCTCTTC TGTATTATGG ACACTTGGTT
82051 TCCCTCCTAC CTCTCTGACT GTCATTCTCA CTCTTTTGTG GCTGCCATCA
82101 GGCTCTTGCA ATGTACGTAC CATCTCCTCA AGTTCCATCC TCAGTTATCT

FIGURE 3EE

82151 TTCTAGTTGG TTCTTGGTGA TCTCATTCAG TTCCTTGACT TTAGTTCTTA
82201 CCTCCCCATG GCCTCCTCCC ATCGTACACT GTGTTCCTCA TCACCAGGAT
82251 GTTTTACCAG TTTCTCACCA TCCCATCCTC TGTTCCCTTC CTACATAGAC
82301 AGACCCACTC GCTCACTCAG TAAGCCACTA GGTGCTAGTT TTGGCTTCTT
82351 CATTTTATGT AAGAAACTAC CACCTTCCCT ACCCTTCTAG GCAAGAAAGC
82401 TGAGTCATCG TAAATTCTTT TCTGCCTCCC CCGCCATCCC ATCAGTTGCC
82451 AATTTCTCCA AGTGGTGCCT CTAGGATGCC ACTTGCATCC ATACCCATCT
82501 TTCTTCCTCA TTGGCACCCA TCATGGACTC TTGCTTGGTC TGGTGCAGTA
82551 GCCTCCTCAG TGATTCCCTT GCCTCTGGTT TTCCTGGCTG TAATCCATTC
82601 TCCACAAAGG GTGGAATTCT TCCAAAGCAT AGGTTGGATG ATGTCATTCA
82651 CCGGCTTACA CCTTCAACAG CATCCCAGTG TGCTCATAAT TAATGGCTGC
82701 TCCTGAACTT GGTATTCAGT CTTGGTATGC CAAGACCCCA GCCTGCCGGC
82751 TCATTTGTGT CTCCTCATCC CCTACTGAAT CACTTCAATA GTGTTGTCTG
82801 GCCAAGCTGT TCAAGGCTCA TTAAGGACAG GACCAGGTCT TCCTTCTTTT
82851 GCCTGAAACA GTGCCTTGCC CCTGGCAGGT CTTCAATGAA CATTTGTTGA
82901 ATTGAATTAG ACTAAAATGG CCAGGGATTA TACCAATTCC TTCTGCACAG
82951 TGTAGACAAC TGCTAATGGA ACCTGTTTTC TGTAGAGCAC TTCTTGTGTT
83001 CCCAGAACTA TGCGAGTACT TTATGTGCAT TATCTCATTA AATCATCACA
83051 ATCTCACTGT AACTCTATGA GGTAGCTGAT ATTATCCCCA TTTTACAAAT
83101 GAAGACACTG ATTCAGGAAG ATTAGATTAT TTTCCTGAGG TTCTGAAGGT
83151 AGAAACACAT CTAAGACTTG GAGCAATATC TGGTTGCCTC TAGACCACTG
83201 TACTATCTAC CCTGCCTCTA AGAGCCATGA CTTTGCTAGA TTATGCAGGA
83251 GTTATGGACT TGTCTAATAG TAAAGGTAAA AGAATTGGTT TTAATGAGAA
83301 TCTACTCTTC TAGGTACTAT TCTGAGTGCC TGACAAGCAT TCTCATGTAG
83351 ACCCAGCAAT AACTCATTAT TTTACAGATA GAGAAAATGA TGATCATGAT
83401 GCTTGGGTTA CTTCTTAGGT TCACTCAGCT CACATCTGGC AGAGGGTGGT
83451 CAACTTTTCC AAGTTTTAAC TTATTTATTT ATTTATTTTG AGACAGAGTC
83501 TCATTCTGTT GCCCACGCTG GAGTACGGTG ACACAATCTC AGCTTATTGC
83551 AACCTCCGCC TCCCAGGTTC AAGCGATTCT TGTGCCTCAG CCTCCCGTGT
83601 AGCTGGGATT ACAGGTGCCT GCCACCACGC CCAGCTAATT TTGTTTTTGT
83651 ATTTTTAGTA GAGGCTGGGT TTCACCATGT TGGCCAGGCC TGTCTTGAAC
83701 TCCTGACCTC AAGTGATCTG CCAGCCTCGG CCTCCCAAAG TGTTGTGATT
83751 ACAGATGTGA GCCACCACGC CTGGCTCAAC TTTTAACTTT AGAACTGATA
83801 TAAACATGCC TATTTTTTTG GGACTGACTG TAGCATACCC ATTCAAAGTC
83851 CAGGCTTTGG AATCAGACAG ACGTGGGCTG AACTCAGGGT TTCACCCCTT
83901 GCTTGTTGTG TGAATGAGAC ATTTCACTGC TTTCAGCCTC AATTCCCTCA
83951 TCTGTAAAGT GGAAGGTGTA AGGTCGCCTA TCTGATAGGT TTGCCATGGG
84001 GATATGAAGC ACACTTAGTG TTGGTGCCAT GAGTAGAATG AGTGTTCATT
84051 TCATATTTGT TAATGTTATT TAGGTCCGAG GATGGGTATG GGGTGCTTTG
84101 GACTCTCTTT TTCTCCCTGC TTCCGCCTTA TAAAGACATC TTGCTGGTTT
84151 CTGCCCATTG AGAGAATCCA GCTCCACGTG GGGGGCCTGA CAGATGTCCT
84201 AATATCTCCA TCCAATTTTT TACTCTGAAT GGAGTCTGTG ATGTATCACT
84251 TCAACCTGCA CTTTCTATAA AATGCTCTCC AGGCTTCTGG TAGGATCCAG
84301 TGCCAGTGGG AAGTGTGCAT GTTCCCAGCC TAGATGTCAC ATGCTCCCAC
84351 CCACCCTGGA AGCACTTGGG TATCCCCTGG ATGGGTAAGT CTGTGTGTCA
84401 TTGTGCCATT CCTGTCTCAG AACCAATGCT GGGCATCTCT ACTTGCAGGT
84451 GCTGGAAAGC TTTTTCATGC CAGCATACAT GCAGCACACT TCTCATTTTG
84501 GATTCCTTTA TCCCACGGTG ACCTTTAAAC TGGCTGCCTG GGGGCACAGA
84551 AGTACTAGCA CACCATTCAC TTATTTATTC ATTCATTCAT TCATTCATTC
84601 ATTCACTCAA CAAATATATT GTTCTAGTCC TTAAGGCACA ACTCTGAGCA
84651 AGACAGGTAA GGTCTTTACT CTCAAGAAGC TAGCATTTGG TGGGGAGAAA
84701 CAAAGGAGAA ATAACTACTG TGCACATGTG AGGCAATTGC AGATGGTGGT
84751 CTGCAGAATT GGGATTGAGA CTGCCTGGGG GTGGCCACTT TAGACTGGGT

FIGURE 3FF

84801 CCGCAAGGAA AGGTTCTCTG AGCTGAGCAT GAGTATTTGT TCAAGAAGGC
84851 TGAGTTGCAT CCCAAGGTGA CACAGCTTTT AAGCCCACAC TGAGCAGCTC
84901 TGAGGTCCTA GGGGCTGTTC GAGAACCTGG GATATAGCAC TGACTATGAG
84951 ACAAAAATCC CTGTCTTCAT GGAGCTTACA TGATGGGGGC AGATTCACAT
85001 TCATTCATTT GTTCATTAAT TCATTAATTC ATTCAGCTAT TTGAGAGCCT
85051 ACTATGTGCC AAGCACTTTC TAGGCACTGG AGAAGTAACA GTGAATGCAA
85101 AGGAGCAAGC ATCCCTGCCC ACACAGAGTG CATTCTTCCA GAATATCAAT
85151 AAGGAGTCGG TTAGCAAAAA TAAGTGGGAA GAGTATTCCA GAGAGAGGAA
85201 AAAAGGGCAA AGGCCCTGAG GCTGCCACTA ACCTATGGGT GCTCAATGAA
85251 CAGAAGGCAT GTTTGGGTAG GGGGTACTTA AGGATACACA AGGAACATGG
85301 TCTGAGCTGA GGTCATCAGG GCCTTTAGGT ATGGACTTTG CTCTAAATTG
85351 CACTGAGTAG GAAGCTTTTG CAGGATTTTG AATAGGGTCA TGGAATATCT
85401 GGGTCTTATT TCACAAAGTG TGCCTCTGAC CATTGTGTGG AGGGTGGATA
85451 GTGAGGGACA AGAGTTGGAT CCAGGGAGGT AAGTGTGGTT ATTGCAGTCA
85501 TCCCAGGTGA GAGGCAATGA AATTAACCTG CAAAGTGAGG CACTGGCTTA
85551 GAGGTGGGAA CTGAATTAAA AATCATGGGA CTAGCTATTC TTTTATTAAT
85601 AGCATGATTT TTGATAAATG ATTCTGGAGC TACATATTAA TCATTTCAAA
85651 GCAAGTGCTC TAATTTAACT AGAGACCACT GCTGGTTGTG TGTGTGAGTG
85701 CATATGTGTG TATGTATATG AGTATGTGTG GTGTGTGTCA GTATGTATAT
85751 GTGTGTATGG TATATATATA AATATATATA TTGTGTGTGG TGGGGGAGGG
85801 GGGGTGCCCC AAAGCTAGAC AGACTCTGAC TGTCTTTAGG GGAATAGTGT
85851 TTTTGATATT TCCAGGTGTT CCTGATGGGC ACCATTGTTA TTTTATTTTA
85901 TTTTTATTTT ATTTTTGAGA CGGAGTCTCA CTCTGTCGCC AGGCTGGAGT
85951 GCAGTGGCGC TATCTCGGCT CAAGACAACC TCCGCCTCCC AGGTTCAAGC
86001 AATTCTCCTG CCTCAGCCTC CCGAGTAGCT AGGACTACAG GTGCGTGCCA
86051 CCACACCCGG CCACCATTGT GTATTTTAAA GTGTGCTTAT AAAATTAGTT
86101 CAGAGCCAGA TGTGGTGGCC CACGCCTGTA ATCCAAGCAC TTTGGGAGGC
86151 CGAGGCGGGT GGATCATGAG GTCAGGAGAC CGAGACCATC CTTGCCAACG
86201 GGGTGGTGAA ACCCCATCTC TACTAAAAAT ACAAAAAAAT TAGCTGGGTA
86251 CAGTGGCGCG TGCCTGTAGT CCCAACTACT CCGGAGGACA AGGCAGGAGA
86301 ATTGCTTGAA CCTGGGAGGT AGAGGTTGCA GTGAGCCGAG ATCGCACCAC
86351 TGCACTCCAG CCTGGTGACA GAACAAGACT CCATCTCTAA ATAAATAAAT
86401 AAAACAAGTT CACAAATTTC GGAATGCTCA ATCTTAAAAG CCAGTATATT
86451 TTTGGAAACG GAATGCTGAT GAGTTTTTTA TTTTTTGCAG CATATTACAT
86501 CTTGCAGTTG CATGTATTTT TAGTGCTGTT GGCCAGCACT AAAGGTGGGG
86551 CCCTCAGCTG AGCTAATTTT GAGTCCCCTC ATTTTGGCTT CAAGTATACT
86601 CATTCTTGGT TTTCCCAAGA ATATCTGGGA TTTGTGATCT GTGTTATCTG
86651 TGGTTTGGTG TCGTATTTTG CAGGCATAGG GTCCTATTCC TAAGGGAATA
86701 AATGGATGGC TTGATGCTTA AGCACGAACT TAATCATCGC AGTAGTGATT
86751 AAAGAGTATT CAACATGTAC ACTTGCTTGT AGGAAGGAGT ACACATTGTA
86801 TTCTCTTTTG ATATGCAATA TTTTATTCAT AGCCCTATTA AGTAATTTTT
86851 TTTAACAAAG TTATATGGAT TATTTACAGG TACATCACGG GAAAACTGCA
86901 TTTTATAATT TTCACTGAAA TGTTGAGGTT ACATGTAAAG CAATTTTTAT
86951 GTCATATCTG ATACATTTTA AGAAAACATG TCTTCCTGTT ACAGCGGTAA
87001 TGACCATGCC TGCTCTTTCT TCTGTGTCAT ATGCCATTAT CCCTATTAAT
87051 ACTCTTTGGG CTTCTATAAT TATAAAGCAG ATGTGTATAT CAGGGAGAGA
87101 TGTTGATTTC AGAGTAAGTT TTTCTAGAAA ATAGAAGCTG GAAAAAAAAG
87151 GAAAACCCAA ACTTGGCTTC GTGCTCGAAG AGACAGCACT GCTGTGTGTG
87201 GGCGGGTGGC TGCGTGCACC CGCTGCTCAG AAGTGCCTTT TCTCTCCATG
87251 GGGATAACTG GCTGTGTATC CGAGATGTGG CCAGGAGTAG GCAAGCAACG
87301 TGTGGGCAGG CTGCATGTTC TTTTATTAGC ATCTTCATTG TACTGCATCT
87351 CGTCGAGCCC AGAGCATGAA CTGGCCTGGG TTTCTAATAT CTACCCTGCT
87401 TCCCACCTAA TTACTCCCCT GAACCCTAAA GTGAGGGAGG GAGAGTTGCT

FIGURE 3GG

87451 CTTGTGGGGT GAGCTTTCCC TGGGGTGGCT GTGAACCAAC CTGGCATGTG
87501 GATGTTCTTG GGTATCCAGA GCTGTCCTGG ACTCAGGCTT GGAGTCAGCT
87551 TCTTAGCACT GAATGCAGCC AGTCATGGAT GGAGGTCACT GTATCTCACA
87601 TGTTCCGCTC TCCCTTTCCT CCATGACCTT GCCCCTCTGA GCCTCTGTAG
87651 CACTTTTCTT GAGTGTGTCC AAGGCCATCT AGCTAAGAAG TAGCAGAAAT
87701 GGGATTTGAA GCCATGACTG TTTGGTGATA GAGCCTCAGC TTTGAACTGG
87751 GGTTCTACTG CCTGGCACCC CTGCACAAAT CATGGTAACG TGGTAGGAGA
87801 ACATAGAGGT ATAGGGCAAG CCCCTCCTTA ATGCCATGAA TAATACCCAT
87851 CTTATAGGAT TGTGGGGAGG ACTCAGTGAA GTAACCCGTG AAGCACTAAA
87901 CACGTGCCTG ACACGTGCTC AATAAATGAG CACTTGTCCT GATGACAAAG
87951 GTCGTGGCAT TAATTCTCTC TCCTAGGTTG TTACTTCCTT GAGGACAGGA
88001 ATTGTGGCTT CCTTAATGGC CACTGCAGCA GAGTTTCTCA AGTTGGCACT
88051 ATTGACATTT TGGGCTGGAT AATTCTTGTT GTGGGAGCTG TCCTGTGGAT
88101 TGTAGGATGT TGAGCAGCAT CTTTGGCCTC TACCCGCTAC ATATTAATAG
88151 CACCCCTAGT CATGAAAATA AAATGTCTAG ACATTGCCAA ACTGCCCCTG
88201 TTGAGAACCA CTGGTCTGCA GGTATCTCTC ATGGGGATCA CAGGGCTTTT
88251 ATATTCTCTT CTCTGTCTCT CTCTCTCCCT CTCTGGGTGT CTCTCTCTCT
88301 CACACACACG CTTAGAGAAG GTGGTTAAAA AAAATTTTGT TGAAGTTTGA
88351 GAATTTTGAG AACAAAGGAA AAATTTTGGA AGGCATTTTA ATGAACAGAT
88401 AGACTCTGTC CCATTCCATG GTCAACAGAA TTTCATAATT AGATAGTTTG
88451 TTTACTGCAA CTCTGCACCC CATTGCCCAT CATTTTAGAG TTCCAACCAG
88501 TTAGAGGATT TTTCTTGCAA ACTTTCCTTA AAGCAGTGAT AGTATCAGCT
88551 CTTTAAATAA TACTATGCTT GATGAAGTGG TACTTTTCGG GATAATTTGA
88601 GACCAGCCGA CTTGCTGCTT GAAGAGGACA GGGCTATATT TGGTAATAAT
88651 ATATATGTGA TAATATGTAT GTAATATTAT TATAATGTAA TATACAATAA
88701 TATTTGGTGT AACTGGTGAC TCTGAGGCCA GTCTTTGATC GAACCTCTCA
88751 AGCTATGATT TACATTATGG TCAATGTTAG CATAATGCAA TTATCAGCAA
88801 TCACTTGCTG TTGCTTTGAA AGTCAGAAGG ATGGCTAATA AAAATCTTAG
88851 AAAAAGAAAA CAGGCTGGGC GCAGTGGCTC ACCCCTGTAA TCCCAGCACT
88901 TTGGGAGGCT GAGGCGGGCA GATCATGAGG TCAGGAGATC GAGACCATCC
88951 TGGCCAACAT GGTGAAACCC CATCTGTACT AGAATACAAA AAAAAAAAAA
89001 AAATTTGCTG GGCGTGGTGG CGTGCGCCTG TAGTCCCAGC TACTCGGGAG
89051 CTGAGTCAGG GGAATCGCTT GAACCCGGGA GGTGGAGGTT GCAGTGAGCC
89101 GAGATTGTGC CACTGCACTC CAGCCTGGTG ACAGAGTGAG ACTCCGTCTC
89151 AAACAAAACA AAACAAAACA AAAAACAAAA AAAGAAAATC TTAGAAAAAG
89201 AAAATAAATT GTAATATTTC AGAATATTTG TTGGGGAGGA TATGTGTGCT
89251 CAAGAAATAT ATACTGAGAA CTTACCATTG ATGCTAGAGA TTGAATTGCC
89301 CCATGTCTAC ATGAAAAATG AATAGAATAT AAACATTTTA AATTGAGCCA
89351 TGTCTATCTG TATTATATTT CTTTTATAGA AATTCATGGA AATGGTATAT
89401 TTTAACTGAA TTATTAACAC TGGGGACAAT AGGCTTTAAT CATTATCTAA
89451 TACCTGTACG TTGTTTTGAA ATTCATAGCC CACCACCATT AATTTCAAAA
89501 TTGGGTTCTT ACTCAAAGAG TGATGAAAAG GCACCAGTAC CAAATGGTCT
89551 GGCCAAAATG CTACATGGAA CTAAATGCTG GGGATGGTCA TACAATGAGT
89601 TTTAAGTGGC TAGACCCTAA ATCAGAAGCA CTTTCTTCTA ATTAGCACCA
89651 TGGTTCTTAA TCCTTTCTGT ACATTACAAT CGCTCAGCAG CTTAATACAA
89701 ATGTTGCTTC CCGGGGCCAC ACTCCACATC TTTCTGACTC TCTGATTTAA
89751 TTGGTCCGAA TGGGGCCTAT ACATCAGGTG TTTTTTAAAA GGTCTCCAAG
89801 TGATTCTAAT GTGTACCTGC ATTGAGGACC AGGGAAGGTG TAGGAAGCCT
89851 GATAACCTTT ACTCTCCAGC CTCATCCTCC AATCCCATGA TTGTTTATGG
89901 GATTGTTGCT ACACACCCAG CTTAGTCATA GCATTCTTAC TCTAGCTTTT
89951 TTTTAGATGC AATTTTTATT TATTCTTAAA GAAAAAGATT TCTTTAGCAC
90001 CTTTATTCTA AAGAGCTCTT AATTGCTGTG CTTAGAACTT CTAAACAGTG
90051 AGCATTTGTC AAACATAGAA TAGCAGAATG AAGGGGTTGG ACCTCGGGTG

FIGURE 3HH

90101 AGGAGGGCTG TCGCATGGTC TCTTTCGAGT GCCGGCGGGT GGGGGCTGCA
90151 CATCTCCTCG CTTCTGGGCC CATTGATAAG TGACCTAAAA GTGCCTTTCG
90201 TTTTTTTTGG TGGGGGGTGA AAAAGCAATC TGTTTTGTAC CCACAGCGGT
90251 GCACTTTAAA CAGGAAGCCC TACTGGGGCC AGCCTTCTAT GTGTCATTAA
90301 GTTTTTCACG CCACATCCTA CCTATCATCA TGCACCCATG TCATCGTTCT
90351 TTTAAAGGGT GCCAGTTTTT TGCTTAAGCA CAAGGAGCTG TGACCTGTGT
90401 TGTCATCCCT GATGCATGTC ATGCATGTGA CTTCATGACA TGTGGGTGAC
90451 TTTTGATCTC TGAAGGACCA GGGACCCAGT CTGTGGATCA CCACTCTCTC
90501 CGTGGGTGGT TTGGGTCTTG TTCTCTAGCC CACCCAGCCA GGTGCAATTA
90551 GGAATAAAGG AAATAGCAAA GGAATTTTGC TCAAGGCCAT GCCAAGCATT
90601 TCATCTCATA TGAAAAGGAA AAGAGAGAGA GTGTGTGTGT GTTGGCTAGA
90651 TTTAGGTAGA AAACAGGCTG GTGAGAAGCG TAGAACTTGG TTAAAATTTC
90701 TAGCCAAAAG TAAGATTTTT AAAAAGATTT ATTTCTGGAT CCAATCCCTG
90751 TTGCCCATTT CTATGAATAA TCACCATTTG TTTTAATGTG AATAATAGCA
90801 CACAGCAAAT TCAGCCCCCT GAGTTTTACC ATTTTAAGCA ATTGCTTTAG
90851 GCCCGTGAGG CATGTACTAT TTATGAAGTT GCATGGGTAG TAATGGAAAA
90901 CACAACAATG ACAGTAGTAA CAGGTGACAT TTGTCGAACA CTTGCAGTGT
90951 GCCAGGCACT GTGCTGAGAG CATTACATGC ATTATTTCAT TTAATCCTTC
91001 CAAGAACTCT TTGAAGTAGG TTGGTAATTA TGGCCATTTT ACAATTGAGG
91051 AAACTGAGGT TCGGAGATGT CAAATAACTA GTCAGTGGTG GGGGTCAGAT
91101 TTTTCTTTTT TTTTTAAATT TATTTGCTTT TTTTTTTTTT TTTTTTGAGA
91151 CGGAGTCTCA CTCTGTTGCC CAGGCTGAGT GCTGTGGTGC CATCTTGGCT
91201 CACTGCAAGT TCCGCCTCCC GGGTTCACGC CATTCTCCTG CCTCAGCCTC
91251 CGGAGTAGCT GGGACTACAG GCGCCCACCA CCAGGCCTGG CTAATTTTTT
91301 GTATTTTTAG TAGAGACGAG GTTTCACCGT GTTAGCCAGG ATGGTCTGGA
91351 TCTCCTGACC TCGTGATCCG CTTGCCTCGG CCCCCCAAAG TGCTGAGATT
91401 ACAGGCATCA GCCACCGCGC CCGGCCTATT TGTTTTTTTT TTTAAGAGAC
91451 AAGGTCTTGC TGTGTTACCC AGACTGGAGT GCAGTGGTAC AATCGTAGCT
91501 CACTGTAGCC TTGAACTCCT GGGCTCGAGC GATCCTCCCA CCCCAGCCTC
91551 CCACGTAGCT GGGACTAGAG GCATGAGCCA CTATGCCCGA CTCATTTTTA
91601 AACATTTTTT ATAGAGACGG CTGGGTGTGG TACCTGTAAT CCCAGCACTT
91651 TGGGAGACTG AGGCGGGCGG ATTGCTTGAG CCCAGGAATT TGAGACCAGC
91701 CTGGGCAACA TGGAGAAACC CCGTGTCTAC AAAAAATACA AAAATCAGCT
91751 GGGTGTGGTG GTGCGTGCCT GTAGTTCCAG TTACTGGGGA GGCTGAGGTA
91801 AGAGAATCAC TTGAGTCTGG GAAGTCGAGG CTGCAGTGAC CTGGGACCAC
91851 CGCACTCCAG CCTGGGCATC GGAGTGAGAC TGTCTTTCAA AAAATAATTT
91901 ATTTATTTAT TTTAAAAATA GAGACAGGGT ATTGCTGTGT TGCCCAGGCC
91951 CGTCTTGAAC TTCTGGCCTC AAGTGATCCT TCTGCCTCGG CCTCCCAAAG
92001 TGTTGAGATT ATAGGCATGT GCCACTGTGC CCAGCCTGAG ATTTTGAACA
92051 GAGGAGCATG ATGCTGGGCG TTGACTCATT TGGCTGTGAG TGTGGAAAGC
92101 TGTCACTGGA GTACAGCAAG TCAGCACTAT CAAGCCAGCC CTTGTCATTG
92151 CCAGGAGCTG CGGGGAGAGA GGTGTTTTGC ATTGCTGCAG GGAACTGACC
92201 TCTTTTAGTC AGGGAAGTAG TTTGGGCAGT AGAAAGCAGA ACTTGCACCT
92251 GCTGGTAAGA TCTGAGTGGT CACTGACAAC CAGCTCTGCA ACCCTGTTAC
92301 CAGGGCAACA AAGATGGGCC CAGGGGTAGT GGTGGGCTCT GCCACATCTC
92351 TCTGTGCATA AGAACCTTTG GCCACTTGCT CTGGCCTTGT CTTTCACCAA
92401 TCCCAGTGTT CATATCCAGT GTACCAACCA CTGAGGGCAG CTGTCCTGGA
92451 ATCTGTCTCT CATCTCTGCC CATAATTAAC TGCTTCTGGG CACAGTGCAT
92501 GAGTTACATA GATGAGTGTG GGTAAGTTTG CCCTTTCTGT GGGGGGAGCA
92551 TCCTTTTGGT CCACTCTCAG GAGGGCATCC TATGTTATTT TTGTGATATT
92601 TTCCTAAGAG TTGTATAAGC AAGTGCATCA AGCCAACTTG TCTACCCCAG
92651 CTCCCTCTTG AGACCAGCAG AAACTATTTA TCAACTGGCA GTTTACGTAA
92701 CCTCTCTGGG CCTCAATTTC CTCATATAAA ATGAGGATAA TAAATCGTAT

FIGURE 3II

92751 CTGCTCATAG AGTTGCTGTG GGGAGTAAAG AGTTCAAATG TATCTGTCAG
92801 TGAAGGAAAA AAGAAAAAAA AACAAAAACA AAGAGTTCAA ATATATCTAG
92851 CGTTCAAACA GAACCAGGTA TGCAGCCAGT GCCCAATAGG TGTATGAGTT
92901 TCCTATGGCC AATGTAACAA ATGACCACAA ACTTAGTGGC TTAAAACAAC
92951 ACACATTTAT TATTTTACAG TTCTGGAGGT CAGAAGTCTA AGATGATGCC
93001 AGGCTTGGTG GCTCAAGCCT GTAATCCCAG CACTTTGGGA GGCTGAGGTG
93051 GCAGGATCAC TTGAGGTCAG GAGTTCCAGA CTAGCCTAGC CAACATGGTG
93101 AAACCCCATC TCTACTAAAA ATACAAAAAT TAGTCAGGCA CGGTCACGAG
93151 CACCTGTAAT CCCAACTACT CAGGAGGCTG AGGCAGGAGA ATTGCTTGAA
93201 CCCAGGAGGT GGAGGTTGCA GTGAGCCGAG GTTGCAGTGA GCCGAGGTTG
93251 CACCACTGCA CTCCAGCCTG GGCAACAGAA CGCGACCCTG TTTCCAAGAA
93301 AAAAAAAAAG TCCGGGATGA GTTTTACTGG GCTGAGATCA GTGTAGACAA
93351 GGCTGCCCTC TCTCTGGAGG CTCTAGGGCA GAATCTGTTT CCTTGTCTTT
93401 TCCAGCTTCT AGAGGTTGCC TGCATTCCTT GGCTTGTGGC CCCTTCCTCC
93451 GTGTTCAAAG CCATTGGTGT AACATCTTCA GGTCTCTGTG ACTCCGATCC
93501 TTGCTTCCAT CTTATAAGGA TCCTTGTGAT TTCATTGTAC CCATCCAGAT
93551 ATCCCAGGAG AATCTTTCCA TCCCAAGATC CATAACTTAA ATCCCATCTG
93601 CAAAGTCCCT TTTGCCATGT GTGGTAATAT ATTCACAGCT TGCAGAGATC
93651 AGGACATGGG CATCTTTGGG AAACGGGAAG GGGGCATTAT TTGACCTAAC
93701 ATCAAGAGCA TGAGATGTTT TTGTAAAATG AAACAAATGT TGCAGCTTCC
93751 TAATGCAGCT TCTTAGGCCC ACCTGCAGGC CCCCTTGACG TTGGTTTTTC
93801 TCTACCTAGG TCTGTTGTGT CGGGTCTGGA CTCCCCTGCC AAGACTAGCT
93851 CCATGGAAAA GAAACTTCTC ATCAAAAGCA AAGAGCTACA AGACTCTCAG
93901 GACAAGTGTC ACAAGGTATT TATTTCCGCA GCCGGCCTCC TTCCTTGCTC
93951 CAGGATCCTC CCGTCCGTAT ATGCCAAGGG ATCCGCCCGG GGCCGCTGCT
94001 GGCTCTGAGC CGCCTGATCC GTAGAGAGTG AGGCGCTCCT GCCTTCGCTG
94051 AAGTCGCGCC TCCAGCAGCT CAGAGGGAGA TGAATTCGGG CCTTGCTGTT
94101 GCTGTAAATC CTTTAAATCT AAACCAGAGG AGGCCCTGGA TTTAAACAGT
94151 CCGTTTCTCA GCATGACCCA GCCAGATGTC TGCTTCTTCC GGCAGGTGGC
94201 CTGGGTCCTC ACCTGTGGCT GAGATACATC CCATCTGCTT TGAGTGATGC
94251 GAAGTCTCTC TTCCTAGTCT TTTAAAACTC CTGCTTATGT CACTGCGGCC
94301 ACTGTGTTGA TTACGCTCAA CGTCTCTTAA CATTCACTGT TCCTGCCCAG
94351 AGGCAACGCT CTGGAAACTA ATAAGTCACT GCTTGCCTGG GACTCCTAAG
94401 AGTGCAGACG AATAAATATC TCCTTGCCCT GTCCTGGATT TGTCCTCTAG
94451 ATCTTTGCAA GGAGATGGGG GGGGATCAAG ATGGATTTGG GATAAAATTA
94501 AAGTGACGTC TGCAAAAACA AAACAAAAAC AAAAGCAAAC AGGTGAAAAA
94551 TGATGATTGT GGCTTCCTTG CTAACTGGGT TAGAGAAGTG ATCAAGTGTG
94601 AACCGGGACT TGAATGAGAG GAGTGACTTA GCATTTGGTG ACTGTCCTTA
94651 ACGAAGAACT GTGCGCTCCT GGGCGAAGAA ACAATGGTAT TTCCATCCCA
94701 ACTTAACTTT TGGCGAATTA GCCTTAGCCC AGACCACCAG GTGGTTTCGG
94751 AGGCTACTTG AGATGTGATT GCTCCTAATG AACCTCCACG GGCCTTTTTA
94801 ACCTGTCGAT GTGTTTATTT CAGATGGAGC AGGAAATGAC CCGGTTACAT
94851 CGGAGAGTGT CAGAGGTGGA GGCTGTGCTT AGTCAGAAGG AGGTGGAGCT
94901 GAAGGCCTCT GAGACTCAGA GATCCCTCCT GGAGCAGGAC CTTGCTACCT
94951 ACATCACAGA ATGCAGTGTG AGCCTTCCCT GAAGCCCCCT TCCCTTGGAG
95001 GTGGCACTTC CTGTTGTGTG TGTCTCATCC TGTTTCATGA TGACTCCATG
95051 AGGCACATCA CAGCCAATGG CAGAGAGTAG AGAGAGGGAG AGCACAAAAG
95101 CAAGATCTGT GTTTTGCAGA GTAGTGAGAG CCAGGCGTAA GGTCCCCAAG
95151 AAATGAGATT GGACTCATTT CCAGCAGAAA GTGCAGGTAG ACGGCTGGTA
95201 CCATGGAGTC TGGAGATGGG AGTAATTCAT CTTTGCCGCA AGTTGCAAAA
95251 GATCTTAACA TCTCCCATCC CAGCCTCTGT GGTCTGCGTT GTGTCTGACA
95301 TGAGCAGCCT TGAGAACCAG ACTCCCAACT ATGTACAAGA AAACTTACTT
95351 TCAATCTTCC TGACATCAAA TTTTCCATTG GCCAGAACCA GTGTAGTGAC

FIGURE 3JJ

95401 AAGAAAATAG CCTTGAAAAC CCAGACCCTC TGTCATTATT TACCATGTGA
95451 CTTTCATTTT TTCTTTCCTT CACAAGAGTA GACTGTCTTC TTCTCCATTG
95501 TCTTGTTAAA TTTTTCATTC AGGTGTTTTT TAATGTGCCC AATTAAACAG
95551 TCTCAAGAAG TTGAATCACA CATTTCTAAA GTTTTTTTCA CAAGGGAGAG
95601 GAAATCTATA GAACGTGGCT GATTAAGAAT AACTGCTATG TTTCCATTCC
95651 AGACTTGGCT GCCTTTCAGT GGTGGGTGAA GTTATTCAGC TATGTATTTC
95701 AGATATAGAT TTCAGTGCCA TTGAAGCATT AAGGGATTCT TATGGATGAA
95751 AGGTGTCCAG GAAAAATAAG CCAGGAGGTA GAAATAGACC ACTTGGAGTC
95801 TTAAATGACA ACTGGGCAGA GGATATGAAG TCATTGCTAC TTTGAAAGAG
95851 GCATATGTAC TTTAGGGCCC ACAAATAACT GTAGAAAACA CTTTGTAGCT
95901 ATCCACATGG TGGCTGTAAT AGCTACTGGG TCTTAATAGG TTTTAGTCCT
95951 GAACATGCAA GTAAGTATCT CCTAGGACAG GTAGATGGTG GCAGGAGACA
96001 GGCTGATGCA GTTTCCGGCT GGACTAATTT TTGTATTGTT AGTAGAGATG
96051 GGGTTTCATC ATGTTGGTCA GGCTTGTCTT GAACTCCTGA CCTCAGGTGA
96101 TCCACCCGCC TCGCCCTCCC AAAATGCTGG GATTACAGGC GTGAGCTACT
96151 GCGCCCAGCC ATTTGTGTCT CTTAAAAAAA AAACTAAGAA AATGAAAAAA
96201 ATGACATTGG CCAATTCATT AAAATGCCAC TCACTGACTG TGGTATGAAA
96251 TGGCTTTCCC TTTGATGGAC CGAAGTCTGT CTCATTGTGT GAGCCACTTG
96301 CAGGGCTGAG TATGACTNNN NNNNNNNNNN NNNNNNNNNN NNNNNNNNNN
96351 NNNNNNNNNN NNNNNNNNNN NNNNNNNNNN NNNNNNNNNN NNNNNNNNNN
96401 NNNNNNNNNN NNNNNNNNNN NNNNNNNNNN NNNNNNNNNN NNNNNNNNNN
96451 NNNNNNNNNN NNNNNNNNNN NNNNNNNNNN NNNNNNNNNN NNNNNNNNNN
96501 NNNNNNNNNN NNNNNNNNNN NNNNNNNNNN NNNNNNNNNN NNNNNNNNNN
96551 NNNNNNNNNN NNNNNNNNNN NNNNNNNNNN NNNNNNNNNN NNNNNNNNNN
96601 NNNNNNNNNN NNNNNNNNNN NNNNNNNNNN NNNNNNNNNN NNNNNNNNNN
96651 NNNNNNNNNN NNNNNNNNNN NNNNNNNNNN NNNNNNNNNN NNNNNNNNNN
96701 NNNNNNNNNN NNNNNNNNNN NNNNNNNNNN NNNNNNNNNN NNNNNNNNNN
96751 NNNNNNNNNN NNNNNNNNNN NNNNNNNNNN NNNNNNNNNN NNNNNNNNNN
96801 NNNNNNNNNN NNNNNNNNNN NNNNNNNNNN NNNNNNNNNN NNNNNNNNNN
96851 NNNNNNNNNN NNNNNNNNNN NNNNNNNNNN NNNNNNNNNN NNNNNNNNNN
96901 NNNNNNNNNN NNNNNNNNNN NNNNNNNNNN NNNNNNNNNN NNNNNNNNNN
96951 NNNNNNNNNN NNNNNNNNNN NNNNNNNNNN NNNNNNNNNN NNNNNNNNNN
97001 NNNNNNNNNN NNNNNNNNNN NNNNNNNNNN NNNNNNNNNN NNNNNNNNNN
97051 NNNNNNNNNN NNNNNNNNNN NNNNNNNNNN NNNNNNNNNN NNNNNNNNNN
97101 NNNNNNNNNN NNNNNNNNNN NNNNNNNNNN NNNNTCGGCC TCCCAAGTGC
97151 TGGGATTACA GGCGTGAGCC ACTGCTCCTG GCCCCCACGC CTTTTTTTTT
97201 TTTTGGAGAC AGAGTTTCAC TCTGTCACCC AGATTGGAGT GCTGTGGCAC
97251 AATCTCAGCT CATTGTGTCC TCTGCCTCCC AGGTTCAAGT GATTCTTGTG
97301 CCTCAGCCTC CTGAGTAGGT GGAATTACAG GCGTGCACCA CAACACCTGG
97351 CTAATTTTTG TATTTTTAGT AGAGATGGGG TTTCACCATG TTGGCCAGGC
97401 TGGTCTCGAT CTCCTGACCT CCAGTGATCC ACTTGCCTAG GCCTCCCAAA
97451 GTGTTGGGAT TACAGGCGTC AGCCACCATG CCTGGACCCC TCTGCCCCTT
97501 TAAGCACTGC CACATATTAG ATCTACGAAG GCTTTATGGA TACAATCCAA
97551 GGAAGATGAA CCTTGGGCTA GTGGGATAAA ACTAAGCGCA TGTAGTTAGA
97601 ATGGAATGAT CTGGAAACCA GGTCCCAAGT TGGTCTAAAT TAGACTCATG
97651 TTGACTATGT CACACTGTAA ACCAGTCTAA ATGCTAATAA GCATGCTTGA
97701 CCAAACACTG CCCTGCAGCC TTCAGAGAGG AAGAAGGAAA ACATAATTTG
97751 TATCCTCTCT CCCTATTTTC TGAGTCTATG GGATTCAAAT TGTAGCTGCC
97801 ATGGAAACTG TACTTTGGAA TTTCTAGAGC CCTTAATTTT AACTTAACAT
97851 ATAAAAACAC TTTTGTACTG ATTTTATAAT TATTCATGAT GGATGAGAAA
97901 GTGAATGTCT TTGACAGTGA GGGAAGCTAT CCGAATGCTA TTTTCTTTTT
97951 TTTTTTTCTT TCATAAAGAT GCATATATTT GCATGCTTTA TTTACCTGGG
98001 GCTAACTCTT GCATCTTTTG CAGATTCCGA CACCATAGCT GAGTTACAGG

FIGURE 3KK

98051 AGCTCCAGCC TTCGGCAAAG GACTTCGAAG TCAGAAGTCT TGTAGGTTGT
98101 GGTCACTTTG CTGAAGTGCA GGTGGTAAGA GAGAAAGCAA CCGGGGACAT
98151 CTATGCTATG AAAGTGATGA AGAAGAAGGC TTTATTGGCC CAGGAGCAGG
98201 TAGGAGGATT TTAACATCAT GCTTTTCCAC TTTCTGTACC GGAGTGTTCA
98251 TTGCAAAGAC GATAATCTGC TGCACTGGCG TCTAGGATCA AGCACGTTTT
98301 CCTCTGTGAC TCTATATTTA ATTATAGTTG GGGCAAAAAG GTCTCTCATG
98351 TTCTTAGCTC ATCTTCTTGA ACTGATGTTG GCTAATTTTG AAGGCTCACA
98401 AATTCCTCTT GATGTATCAT GTTTCTATCG TTGTAATTTA TTTCAGAACC
98451 AAGGTGGCCT TTTAGCTAAT GAATTTAAGA TGATCTTTTA TGACCATTAG
98501 CTGAGGACTC AGGATATACA TATGGTGGGG TGAATCAGAT TGCTTTTGTA
98551 CACGCTTTAG GTATTTGTGT TGTGGGCATA TGGATTTGGT TTTAAAACAG
98601 GCCTTTGAAG AAATCAAATA ACATTCTTTG TTATGTGGCT AGGGAGTTGC
98651 TTGTTTGAGA GCAGGTAGAA CGTTATCTTT TTTGTTGTGG TATTTTTCTT
98701 TCTTTTAAAC AAGGCTACTG TCTCTAGACA TATTGATTCA TTTGCTGTGT
98751 TTTAGAGAGA TGGCCGTCAG CCTTGGAATT CAGAGAGTAA TTTATTACTT
98801 ACAGACATTT TAGTGCACAT GATATGTCTG ATAATGTACC CAGCTCTGCA
98851 GGAAGCTTGC AAAAGGAATA GAAGTCCCAT GGTTGCTATT TTCAGTGTTT
98901 AAAAACAACC TTGGAAAGTG GAGGAAAAAT GCAAATGTAT AAAGCAGGTG
98951 CTTACCAGCT AAAGTATCAC AGAAGTGGGA GAGCAATTAG CAAATTAATT
99001 AACGATGATG TGAGGGGAGA TGTTGTGGGT GAGCAAGGGA CAGTTAGGGA
99051 CAGTTCTCAC CGATGGGGGG AAATGTAGGT TCTCGGCAGA GAGAAGTGAT
99101 GAGAACATGT TGGGTAGAAG TGTGACATTC TGGAGTACTA GAATGCTATG
99151 CAAGTGTGTG TGTGTGGGTG TGTGTGTGTG TTCAGTGGTT CAGAACAGAC
99201 TGGGAAATGG CGAAATGAGG ACATTTGGGT GGGGAGGGGG AAATGGGTGG
99251 GAAACTCAAG AACCTTTTTT TAAAAAATTG TGGTAAAATA TATATAACAT
99301 AAAGTGTACC ATTTTAACCA TTTTTAAATG TGCAACTGAG TGGTATTCAG
99351 TGCATTCATG ATGTTGTACA ACCATGACCG CTCTCCATTT CTAGAATTTT
99401 TCTATCATCC CAAACAGAAA CTCTCTATCC ATTATACAAT ACCTCCCCAT
99451 TCCCCCAAGA ACCAGTTTTT GAATTGCAGT TTACTTTGTG AGGCTGTTGG
99501 GGATTATTTA GGCCTCTGGA AGGAGGAGGT TGGGATCAGA GTCTGGCCCT
99551 GTGGACTTCA ATGACTTTGT GTGGCCTCCA ATCAGAGAAG CAGCGGAGGG
99601 CAGGAAGCTG CTTGTCAGAA TCTGAGAGTG ATGTGGCTTC TTTGTTTAGC
99651 AATAAAATGT GAGCACATAA TAGAAAGGAA AAGTGACAGG ACATGGCAGA
99701 TAATTTGGAA GAGAGGAGTG GAAGATGCTC ACTCAGCCTC CCAGCTCCTG
99751 AGAAAGAACT GTGTCTCATC AGTTCATACT ACCTGAGCAT CTGTTGTATC
99801 TGGTGTGTTT CTAGGTACCT GGAGAAGAGG CATTACGTGT AGCCCTGACC
99851 TTGTGATGCT TATGTTTTTG ATGGGAAATA GTGCGTGTAA AAAGAAAATA
99901 ATCCAACAGG CCACACGGCA GGCAAACAAT AGAGATATTC AAATAGGTAT
99951 ACCTTCCTCC AGGTGAATGG CCTGAAATGA CCGTGTGGAA GTGTGGGCTG
100001 GGGGCTTATA AAATTATACA CATACAGGCG CTAACTAAAG CCGCCTATTC
100051 ATTCCTTAAG AGGATGCATA GAAAAGAAAA GTAGGGTCCT TTAACTGAGC
100101 CCATTTGAAT TTAGGGCCTG AGAGAAGCAG CACAAGCAGT GAAGGGAAGA
100151 AAAAGAAGTG CCCGAGAGGA GGGAGGGATT CTGTTCTGCA GACAAGGCCT
100201 GCCGCCTGGG AGAGGCCCGC ACGCCCACCC AGGGTTCTCT GACAGCTGGA
100251 AGGGGTCTTC AGAGACTGTT TATATTTTAT TTATTTATTT ATTTATTTAT
100301 TNTGAGACAG AGTCTCTGTC ACCCAGGCTG GAGTGCAGTG GTGCGATCTC
100351 AGCTCACTGC AAGCTCCGCC TCCCAGGTTC ACACCATTCT CCTATCTCAG
100401 CCTCCCGAGT AGCTGGGACT ACAGGCGCCT GCCACAATGC CCGGCTAATT
100451 TTTTTGTAAT TTTAGTAGAG ACGGGGTTTT ACCTGCGTTA GCCAGGTATG
100501 GTCTTGATCT CCTGACCTCA TGATTCGCCC ACCTCGGCCT CCCAAAGTGC
100551 TGGGATTACA GGTGTGAGCC ACTGTGCCTG GCCGACTGTT TCTACTATTT
100601 TAGAGAGAGG GTCTCACTGT CATCTGTGCT GGAATGCAGT GATGCAGTCA
100651 TAGCTCACTG CACCCTCAAA CTCCTGGGCT TAAGCGACCC TCCCGCCTCA

FIGURE 3LL

100701 GCCTCTTAAG TAGCTGGGAC CATAGGCATG TGCTGCCACA CCCAGTTAAC
100751 TTTATTATTT ATTTATTTAT TTAGAGAATG AGTCTCATTC TGTTGCCCAG
100801 GCTAGAGGTG CAGTGGCACG ATCTCGGCTC ACTGCAACCC CGCCTCCCAG
100851 GTTCAAGCGA TTCTTCTTGC TCAGCCTCCT GAATAGCTGG GATTACAGGC
100901 ACCTGCCACC ACACCTGGCT AATTTTTGTA TTTTTAGTGC AGAGGGGGGN
100951 NNNNNNNNNN NNNNNNNNNN NNNNNNNNNN NNNNNNNNNN NNNNNNNNNN
101001 NNNNNNNNNN NNNNNNNNNN NNNNNNNNNN NNNNNNNNNN NNNNNNNNNN
101051 NNNNNNNNNN NNNNNNNNNN NNNNNNNNNN NNNNNNNNNN NNNNNNNNNN
101101 NNNNNNNNNN NNNNNNNNNN NNNNNNNNNN NNNNNNNNNN NNNNNNNNNN
101151 NNNNNNNNNN NNNNNNNNNN NNNNNNNNNN NNNNNNNNNN NNNNNNNNNN
101201 NNNNNNNNNN NNNNNNNNNN NNNNNNNNNN NNNNNNNNNN NNNNNNNNNN
101251 NNNNNNNNNN NNNNNNNNNN NNNNNNNNNN NNNNNNNNNN NNNNNNNNNN
101301 NNNNNNNNNN NNNNNNNNNN NNNNNNNNNN NNNNNNNNNN NNNNNNNNNN
101351 NNNNNNNNNN NNNNNNNNNN NNNNNNNNNN NNNNNNNNNN NNNNNNNNNN
101401 NNNNNNNNNN NNNNNNNNNN NNNNNNNNNN NNNNNNNNNN NNNNNNNNNN
101451 NNNNNNNNNN NNNNNNNNNN NNNNNNNNNN NNNNNNNNNN NNNNNNNNNN
101501 NNNNNNNNNN NNNNNNNNNN NNNNNNNNNN NNNNNNNNNN NNNNNNNNNN
101551 NNNNNNNNNN NNNNNNNNNN NNNNNNNNNN NNNNNNNNNN NNNNNNNNNN
101601 NNNNNNNNNN NNNNNNNNNN NNNNNNNNNN NNNNNNNNNN NNNNNNNNNN
101651 NNNNNNNNNN NNNNNNNNNN NNNNNNNNNN NNNNNNNNNN NNNNNNNNNN
101701 NNNNNNNNNN NNNNNNNNNN NNNNNNNNNN NNNNNNNNNN NNNNNNNNNN
101751 NNNNNNNNNN NNNNNNNNNN NNNNNNNNNN NNNNNNNNNN NNNNNNNNNN
101801 NNNNNNNNNN NNNNNNNNNN NNNNNNNNNN NNNNNNNNNN NNNNNNNNNN
101851 NNNNNNNNNN NNNNNNNNNN NNNNNNNNNN NNNNNNNNNN NNNNNNNNNN
101901 NNNNNNNNNN NNNNNNNNNN NNNNNNNNNN NNNNNNNNNN NNNNNNNNNN
101951 NNNNNNNNNN NNNNNNNNNN NNNNNNNNNN NNNNNNNNNN NNNNNNNNNN
102001 NNNNNNNNNN NNNNNNNNNN NNNNNNNNNN NNNNNNNNNN NNNNNNNNNN
102051 NNNNNNNNNN NNNNNNNNNN NNNNNNNNNN NNNNNNNNNN NNNNNNNNNN
102101 NNNNNNNNNN NNNNNNNNNN NNNNNNNNNN NNNNNNNNNN NNNNNNNNNN
102151 NNNNNNNNNN NNNNNNNNNN NNNNNNNNNN NNNNNNNNNN NNNNNNNNNN
102201 NNNNNNNNNN NNNNNNNNNN NNNNNNNNNN NNNNNNNNNN NNNNNNNNNN
102251 NNNNNNNNNN NNNNNNNNNN NNNNNNNNNN NNNNNNNNNN NNNNNNNNNN
102301 NNNNNNNNNN NNNNNNNNNN NNNNNNNNNN NNNNNNNNNN NNNNNNNNNN
102351 NNNNNNNNNN NNNNNNNNNN NNNNNNNNNN NNNNNNNNNN NNNNNNNNNN
102401 NNNNNNNNNN NNNNNNNNNN NNNNNNNNNN NNNNNNNNNN NNNNNNNNNN
102451 NNNNNNNNNN NNNNNNNNNN NNNNNNNNNN NNNNNNNNNN NNNNNNNNNN
102501 NNNNNNNNNN NNNNNNNNNN NNNNNNNNNN NNNNNNNNNN NNNNNNNNNN
102551 NNNNNNNNNN NNNNNNNNNN NNNNNNNNNN NNNNNNNNNN NNNNNNNNNN
102601 NNNNNNNNNN NNNNNNNNNN NNNNNNNNNN NNNNNNNNNN NNNNNNNNNN
102651 NNNNNNNNNN NNNNNNNNNN NNNNNNNNNN NNNNNNNNNN NNNNNNNNNN
102701 NNNNNNNNNN NNNNNNNNNN NNNNNNNNNN NNNNNNNNNN NNNNNNNNNN
102751 NNNNNNNNNN NNNNNNNNNN NNNNNNNNNN NNNNNNNNNN NNNNNNNNNN
102801 NNNNNNNNNN NNNNNNTATA TGTGCATACA GAATATATAC ACAGAAATAT
102851 ATATGTACAC ATGCATAGAA TATATTTACA TATATATGCA TATATATAAT
102901 TTATTTATTT TAAGCAGTTG ATTTATACAG TTTTTGTTTT TGTTTTTTTT
102951 TTGAGACAGA GTCTCACTCT GTCACCCAGG CTAGAGTGCA GTGGCGAGAT
103001 CTCAGCTCAC TGCAACCTCT GCCCCCGGGT TCCAGTGATT CTCCTGCCTC
103051 AGCTCCACAA GTAGCACACC ACCATGCCCA GCTAATTTTT GTATTTTTTT
103101 TAGTAGAGAC GAGGTTTCAT CATGTTGGCC AGGCTGGTCT CGAACTCCTG
103151 ACCTCAAGTG ATCCGCCCGC CTTGGCCTCC CAAAGTGCTG GGATTTCAGG
103201 CGTGAGCCAC CACACCTGGC TCCCATAATG TCTTTTAGAA TAAAACGATC
103251 GAGTTGAGGA TCACACGTGA CACTTAATTG TCCTGTCTCT TTAGTCTCCT
103301 TCAATCTGGA GCAGTTCTTT GATTTTTCCT GGACTCTCAT GACCTTGACA

FIGURE 3MM

103351 ATTCTGATGA TTATAGGCCA GTTATTTTGT AAAATTTGAA TTTGTCTGAT
103401 GTTGCTTATG TTTAGATTTA GGGTCTTGGT CTTTGGCCGG AATATCTCAG
103451 ACAAGATGCT CTGTTCTTAT TGCATCAGAG CAGAAGACTC TCTGTTTCAG
103501 TTGATCACAT TTATGTTGAT GCTCACTTTG ATCACTTGAT TAAGGTGGTG
103551 TCAGTTATGC CTTTCTACTT GTAGGGTTAC TCCTTCCTCC TTCGTGATTT
103601 TATTTATTTT ATTTTTCTTA GAGACAGGGT CTTGCTTGGT TGCCCAAGCT
103651 GGAGTGCAGT GGTGGGATCT TGGCTCACTG CAGCCTTGAA CTCCTGGGCT
103701 CAAGTAATCC ACCTGCCACA GCCTCCTGAG TAACTGGGAC TGTAAGCGAA
103751 CACCACCACA CCCAGCTACT TTTTGTATTG TAGAGATGGG GTCTCACTGT
103801 GTTGTCCAGG CTGGTCTGTA ACTCCTGGCC TCAAGCAGTC TTCCGGCCTT
103851 GGCCTCCCGA AGTGCTGGGA TTACAGGCAT GAGCCACTGC ACCCAGCCTC
103901 CTTTGTAATT AAAAAAGTAT TTTATGGGGA GTTACTTTCA AGTGATGGAA
103951 ATATTTTATA TCTATGTGGA CTTGGATTTT CCTATTTCAG TCAGTGAGTT
104001 ATAATCCATT TCTGTCACTA GTTTTATACT TAAATTGTTC CCAACTTGGC
104051 CACTGAGAAC CTTTTTAGGT TAGCTTTTGT GTCCTTTTCA CATGTCTCCA
104101 AGATTCATTG AATACTTTCC TGCTTTCTGG TATAGCAAGA TGTTCAGGTT
104151 CTTTTGGTAC TTTTACTTTC TCTGCCCTGG CTCTGGCATC AGTCATTTCT
104201 CAGAGGAGCC CTGTGCCTTT CAGTGGACAA TGGTGTTTAG AGGCCAAGAT
104251 CTGGACATTG GGTGTTTTCA TTGCTACCGG TGTGTCACTA CTCCCAGACC
104301 CCTTTCAGTG GACAGCACTA AGGAATACAC ATACGTATAT ACAATATATC
104351 CACCTACACA TGTGCGTGCA CTCACACACA CACATATACA TTACATCTAT
104401 ATTTGTGTAT CCATGTCTAT ATATTGAAAA TTGTGGCTGG GCACAGTGGC
104451 TTATGCCTTT AATCTCAGCA TTTTGGGAGG CTGAGGCAAG AGGATCACCT
104501 GAAGCCAGGA GTTCAACACC AGCTTGGGAA ACAGAGAGAG ACTCTGTCTC
104551 TACAAAAATA AAAAGGGAAA ACCATGAGTT CACACCCGTG CCCCCAGTTC
104601 CAATCCAACT TCACAGGGTT CATTTTAGTT TTCACCCTTT CCATGTTTGT
104651 AATTCTCTTC TCTGACATTA TACCCTTAAT ATGTTTACTT ATTTTATGCA
104701 TCTGTATGCA TCCAATCTAC TGTCTTTGTT GGTATCCCAC CTCCCCTTGG
104751 TGGGTCCAGA TAATCTGCTC TGGGTTGCCC TTTCACGTGG ATGTCTTCCT
104801 TACCCTGTGT GGGCCTGTGA TACTGGGCTG CCCCCACACA TGAGTGCTGC
104851 CCTCCTCACG TTGCTTGGGA CGGCACTGTG TCCTGGGCCA CCATGACTTT
104901 TCTCATAACT AGCGTGGATG CTTACCTTGT TCCACACCAG TGAATGGCTT
104951 CAGGAAGAGA AGAGGAAGAG AAAAATATTT ACATTTAAAG AAAGGTAGTT
105001 TAAAGAAATA TGTTAGGTAA AGAATTGAGC AGGTAATATA CGGAGCTGGC
105051 AAAAATTGTG ACCAAAGTAG GTGAATGATT GAGATTTATG CAATTCTGGG
105101 CTAAGTGACA GCCCCTTCCC TTTCCCTTCC CTTCCCCTTC CCTTCCCTTT
105151 TCTTCCCTTT CCCTTCCCTT TCCTTCCCTT TCCCTTCCCC TTCCCTTCCC
105201 TTTCCTTCCC TTTCCCTCTT CTTCCTTCCT TCCTTCTGTT TTCTTTTCCC
105251 TTCTTTCCTT TGCCTTTTTT TTTTTTTTAA AGCTAGAAAC ATCAGTTTAG
105301 GCATAAAGAC AGAGGAAAAG GCTTCTTTTT CCTCTCACAG TTCTTTATAA
105351 TTGTCTAAGC AGTTTCTTTT TTCCCTAGGT TTCATTTTTT GAGGAAGAGC
105401 GGAACATATT ATCTCGAAGC ACAAGCCCGG GATCCCCCAA TTANNNNNNN
105451 NNNNNNNNNN NNNNNNNNNN NNNNNNNNNN NNNNNNNNNN NNNNNNNNNN
105501 NNNNNNNNNN NNNNNNNNNN NNNNNNNNNN NNNNNNNNNN NNNNNNNNNN
105551 NNNNNNNNNN NNNNNNNNNN NNNNNNNNNN NNNNNNNNNN NNNNNNNNNN
105601 NNNNNNNNNN NNNNNNNNNN NNNNNNNNNN NNNNNNNNNN NNNNNNNNNN
105651 NNNNNNNNNN NNNNNNNNNN NNNNNNNNNN NNNNNNNNNN NNNNNNNNNN
105701 NNNNNNNNNN NNNNNNNNNN NNNNNNNNNN NNNNNNNNNN NNNNNNNNNN
105751 NNNNNNNNNN NNNNNNNNNN NNNNNNNNNN NNNNNNNNNN NNNNNNNNNN
105801 NNNNNNNNNN NNNNNNNNNN NNNNNNNNNN NNNNNNNNNN NNNNNNNNNN
105851 NNNNNNNNNN NNNNNNNNNN NNNNNNNNNN NNNNNNNNNN NNNNNNNNNN
105901 NNNNNNNNNN NNNNNNNNNN NNNNNNNNNN NNNNNNNNNN NNNNNNNNNN
105951 NNNNNNNNNN NNNNNNNNNN NNNNNNNNNN NNNNNNNNNN NNNNNNNNNN

FIGURE 3NN

106001 NNNNNNNNNN NNNNNNNNNN NNNNNNNNNN NNNNNNNNNN NNNNNNNNNN
106051 NNNNNNNNNN NNNNNNNNNN NNNNNNNNNN NNNNNNNNNN NNNNNNNNNN
106101 NNNNNNNNNN NNNNNNNNNN NNNNNNNNNN NNNNNNNNNN NNNNNNNNNN
106151 NNNNNNNNNN NNNNNNNNNN NNNNNNNNNN NNNNNNNNNN NNNNNNNNNN
106201 NNNNNNNNNN NNNNNNNNNN NNNNNNNNNN NNNNNNNNNN NNNNNNNNNN
106251 NNNNNNNNNN NNNNNNNNNN NNNNNNNNNN NNNNNNNNNN NNNNNNNNNN
106301 NNNNNNNNNN NNNNNNNNNN NNNNNNNNNN NNNNNNNNNN NNNNNNNNNN
106351 NNNNNNNNNN NNNNNNNNNN NNNNNNNNNN NNNNNNNNNN NNNNNNNNNN
106401 NNNNNNNNNN NNNNNNNNNN NNNNNNNNNN NNNNNNNNNN NNNNNNNNNN
106451 NNNNNNNNNN NNNNNNNNNN NNNNNNNNNN NNNNNNNNNN NNNATGGAGT
106501 CTTGCTCTGT TGTCCAGGCT GGAGTGCAGT GGTGTGATCT TGGCTCACTG
106551 CAACCTCCGC CTCCTGGGTT GAAGCGATTC TCCTGCCTCA GCCCCCTGAA
106601 TAGCTGGGAT TACAGGCATG TGCCACCACG CCTGGCTAAT TTTTGTATTT
106651 TTAATAGACA CGGGGTTTCA CCATGTTGGT CAGGCTGGTC TCGAACTCCT
106701 GACCTCAGGT GATCTGCATG CCTAGGCCTC CCAAAGTGCT GGGATTACAG
106751 GCATGAGCCA CTGCGCCTGG CCAACTTATT TAACTTTTTT GAGACAGGGT
106801 CTCACTCTGT CACCCAGGCT GGAGTGCAGT GGCATGATCA TGGCTCACTG
106851 CAGCCTCAAA TTGCAGGGCT CAAGTGATTC TCCTGCTTCA CCTTCCTGAT
106901 TAGCTGGGAC AACAGGTACA AACCACCATG CCTAGCTAAT TTTTAAATTT
106951 TCTGTAGAGA CTAGGGTCTC ACTATGTTGC CCAGGCTGGT TTCGAACTCC
107001 TGAGCTCAAG AGATCTTCCT GCCTTGGCCT TCCAAAGTGC TGGGATTACA
107051 GGTGTGAGCC CCATGCCCAG CTCCGGTGGG GGATATTTCT ATATCCACAT
107101 GTGTATAGTT TACTTTATAA AAATGGTATG TTACTCTGTG CTTGGCTCTC
107151 CAGCTTGCTG TTGCCTTTCA CCAGTGTATC CCAGACATCC TTTCTTCCTT
107201 GTCAGTAACG CAGGTCTACT TTATTCTTTG AGCAGTGGCA TAATTTTCCC
107251 TGATGTGTAT ATATCATAAG TTAGAGAATG CTAAAATTCA TTTTGGGGCC
107301 TTGTTTAGGT TCTTGAGGGA TTAAATTCCT AAATTTAACA AGTGTATCCT
107351 GGAAACAATT TTTGTTCCTG ATTCAGCCCT TAAAAGAGGA CTATCATGTT
107401 ACCTTGAATG GAGATAAACA GGCTCACGTA AGAGAAAAGG GTAAGAGGGA
107451 TGAACTCCCA CTTATCTTAA ACTTCTACTG GCCCGTTTTT GGGGAATTTG
107501 CTGCTTTTAT TCCTGACCTA AAATAAATAA GTTTATGTGT CTTGGTTTCA
107551 TATTAGTTGA GAACCCAGTG CCTGGAGAGA AGTTTTCCTT GTCCTCTGAG
107601 TGAGGACATT CACATATGAA TCTATTGGCA GACTGGCTTT GACTGACCAC
107651 ACGTGCCTTC AGAACCAATG CCACAGCTCT TAGGTTTATG GCCTGAAACA
107701 CCCTTTCCTT ACATATTGCC TTAGAAACTT TCCTTCCTTG AGACATGGGG
107751 CATGGAACCC TCACCTTCAC AGATGACCTT GGTGTGTTTC TAGGGTTGCT
107801 GGTGTTCCAG GACATCTGTT GCAGATGCAG TATTTACCTT GTGCTCTCTG
107851 CATCATAAGC AGCTTCTCAT GTTTGAATGT ATTAACAGAC TTTTAATTTT
107901 TTTTATTTTT GAGACAAAGT CTCACTCTGT CACCCAGGCT AGTGTTACCC
107951 AGGCTGGAGT GCAATGNNNN NNNNNNNNNN NNNNNNNNNN NNNNNNNNNN
108001 NNNNNNNNNN NNNNNNNNNN NNNNNNNNNN NNNNNNNNNN NNNNNNNNNN
108051 NNNNNNNNNN NNNNNNNNNN NNNNNNNNNN NNNNNNNNNN NNNNNNNNNN
108101 NNNNNNNNNN NNNNNNNNNN NNNNNNNNNN NNNNNNNNNN NNNNNNNNNN
108151 NNNNNNNNNN NNNNNNNNNN NNNNNNNNNN NNNNNNNNNN NNNNNNNNNN
108201 NNNNNNNNNN NNNNNNNNNN NNNNNNNNNN NNNNNNNNNN NNNNNNNNNN
108251 NNNNNNNNNN NNNNNNNNNN NNNNNNNNNN NNNNNNNNNN NNNNNNNNNN
108301 NNNNNNNNNN NNNNNNNNNN NNNNNNNNNN NNNNNNNNNN NNNNNNNNNN
108351 NNNNNNNNNN NNNNNNNNNN NNNNNNNNNN NNNNNNNNNN NNNNNNNNNN
108401 NNNNNNNNNN NNNNNNNNNN NNNNNNNNNN NNNNNNNNNN NNNNNNNNNN
108451 NNNNNNNNNN NNNNNNNNNN NNNNNNNNNN NNNNNNNNNN NNNNNNNNNN
108501 NNNNNNNNNN NNNNNNNNNN NNNNNNNNNN NNNNNNNNNN NNNNNNNNNN
108551 NNNNNNNNNN NNNNNNNNNN NNNNNNNNNN NNNNNNNNNN NNNNNNNNNN
108601 NNNNNNNNNN NNNNNNNNNN NNNNNNNNNN NNNNNNNNNN NNNNNNNNNN

FIGURE 3OO

108651 NNNNNNNNNN NNNNNNNNNN NNNNNNNNNN NNNNNNNNNN NNNNNNNNNN
108701 NNNNNNNNNN NNNNNNNNNN NNNNNNNNNN NNNNNNNNNN NNNNNNNNNN
108751 NNNNNNNNNN NNNNNNNNNN NNNNNNNNNN NNNNNNNNNN NNNNNNNNNN
108801 NNNNNNNNNN NNNNNNNNNN NNNNNNNNNN NNNNNNNNNN NNNNNNNNNN
108851 NNNNNNNNNN NNNNNNNNNN NNNNNNNNNN NNNNNNNNNN NNNNNNNNNN
108901 NNNNNNNNNN NNNNNNNNNN NNNNNNNNNN NNNNNNNNNN NNNNNNNNNN
108951 NNNNNNNNNN NNNNNNNNNN NNNNNNNNNN NNNNNNNNNN NNNNNNNNNN
109001 NNNNNNNNNN NNNNNNNNNN NNNNNNNNNN NNNNNNNNNN NNNNNNNNNN
109051 NNNNNNNNNN NNNNNNNNNN NNNNNNNNNN NNNNNNNNNN NNNNNNNNNN
109101 NNNNNNNNNN NNNNNNNNNN NNNNNNNNNN NNNNNNNNNN NNNNNNNNNN
109151 NNNNNNNNNN NNNNNNNNNN NNNNNNNNNN NNNNNNNNNN NNNNNNNNNN
109201 NNNNNNNNNN NNNNNNNNNN NNNNNNNNNN NNNNNNNNNN NNNNNNNNNN
109251 NNNNNNNNNN NNNNNNNNNN NNNNNNNNNN NNNNNNNNNN NNNNNNNNNN
109301 NNNNNNNNNN NNNNNNNNNN NNNNNNNNNN NNNNNNNNNN NNNNNNNNNN
109351 NNNNNNNNNN NNNNNNNNNN NNNNNNNNNN NNNNNNNNNN NNNNNNNNNN
109401 NNNNNNNNNN NNNNNNNNNN NNNNNNNNNN NNNNNNNNNN NNNNNNNNNN
109451 NNNNNNNNNN NNNNNNNNNN NNNNNNNNNN NNNNNNNNNN NNNNNNNNNN
109501 NNNNNNNNNN NNNNNNNNNN NNNNNNNNNN NNNNNNNNNN NNNNNNNNNN
109551 NNNNNNNNNN NNNNNNNNNN NNNNNNNNNN NNNNNNNNNN NNNNNNNNNN
109601 NNNNNNNNNN NNNNNNNNNN NNNNNNNNNN NNNNNNNNNN NNNNNNNNNN
109651 NNNNNNNNNN NNNNNNNNNN NNNNNNNNNN NNNNNNNNNN NNNNNNNNNN
109701 NNNNNNNNNN NNNNNNNNNN NNNNNNNNNN NNNNNNNNNN NNNNNNNNNN
109751 NNNNNNNNNN NNNNNNNNNN NNNNNNNNNN NNNNNNNNNN NNNNNNNNNN
109801 NNNNNNNNNN NNNNNNNNNN NNNNNNNNNN NNNNNNNNNN NNNNNNNNNN
109851 NNNNNNNNNN NNNNNNNNNN NNNNNNNNNN NNNNNNNNNN NNNNNNNNNN
109901 NNNNNNNNNN NNNNNNNNNN NNNNNNNNNN NNNNNNNNNN NNNNNNNNNN
109951 NNNNNNNNNN NNNNNNNNNN NNNNNNNNNN NNNNNNNNNN NNNNNNNNNN
110001 NNNNNNNNNN NNNNNNNNNN NNNNNNNNNN NNNNNNNNNN NNNNNNNNNN
110051 NNNNNNNNNN NNNNNNNNNN NNNNNNNNNN NNNNNNNNNN NNNNNNNNNN
110101 NNNNNNNNNN NNNNNNNNNN NNNNNNNNNN NNNNNNNNNN NNNNNNNNNN
110151 NNNNNNNNNN NNNNNNNNNN NNNNNNNNNN NNNNNNNNNN NNNNNNNNNN
110201 NNNNNNNNNN NNNNNNNNNN NNNNNNNNNN NNNNNNNNNN NNNNNNNNNN
110251 NNNNNNNNNN NNNNNNNNNN NNNNNNNNNN NNNNNNNNNN NNNNNNNNNN
110301 NNNNNNNNNN NNNNNNNNNN NNNNNNNNNN NNNNNNNNNN NNNNNNNNNN
110351 NNNNNNNNNN NNNNNNNNNN NNNNNNNNNN NNNNNNNNNN NNNNNNNNNN
110401 NNNNNNNNNN NNNNNNNNNN NNNNNNNNNN NNNNNNNNNN NNNNNNNNNN
110451 NNNNNNNNNN NNNNNNNNNN NNNNNNNNNN NNNNNNNNNN NNNNNNNNNN
110501 NNNNNNNNNN NNNNNNNNNN NNNNNNNNNN NNNNNNNNNN NNNNNNNNNN
110551 NNNNNNNNNN NNNNNNNNNN NNNNNNNNNN NNNNNNNNNN NNNNNNNNNN
110601 NNNNNNNNNN NNNNNNNNNN NNNNNNNNNN NNNNNNNNNN NNNNNNNNNN
110651 NNNNNNNNNN NNNNNNNNNN NNNNNNNNNN NNNNNNNNNN NNNNNNNNNN
110701 NNNNNNNNNN NNNNNNNNNN NNNNNNNNNN NNNNNNNNNN NNNNNNNNNN
110751 NNNNNNNNNN NNNNNNNNNN NNNNNNNNNN NNNNNNNNNN NNNNNNNNNN
110801 NNNNNNNNNN NNNNNNNNNN NNNNNNNNNN NNNNNNNNNN NNNNNNNNNN
110851 NNNNNNNNNN NNNNNNNNNN NNNNNNNNNN NNNNNNNNNN NNNNNNNNNN
110901 NNNNNNNNNN NNNNNNNNNN NNNNNNNNNN NNNNNNNNNN NNNNNNNNNN
110951 NNNNNNNNNN NNNNNNNNNN NNNNNNNNNN NNNNNNNNNN NNNNNNNNNN
111001 NNNNNNNNNN NNNNNNNNNN NNNNNNNNNN NNNNNNNNNN NNNNNNNNNN
111051 NNNNNNNNNN NNNNNNNNNN NNNNNNNNNN NNNNNNNNNN NNNNNNNNNN
111101 NNNNNNNNNN NNNNNNNNNN NNNNNNNNNN NNNNNNNNNN NNNNNNNNNN
111151 NNNNNNNNNN NNNNNNNNNN NNNNNNNNNN NNNNNNNNNN NNNNNNNNNN
111201 NNNNNNNNNN NNNNNNNNNN NNNNNNNNNN NNNNNNNNNN NNNNNNNNNN
111251 NNNNNNNNNN NNNNNNNNNN NNNNNNNNNN NNNNNNNNNN NNNNNNNNNN

FIGURE 3PP

111301 NNNNNNNNNN NNNNNNNNNN NNNNNNNNNN NNNNNNNNNN NNNNNNNNNN
111351 NNNNNNNNNN NNNNNNNNNN NNNNNNNNNN NNNNNNNNNN NNNNNNNNNN
111401 NNNNNNNNNN NNNNNNNNNN NNNNNNNNNN NNNNNNNNNN NNNNNNNNNN
111451 NNNNNNNNNN ATATTGAATC TGTGCAAAGT CAGCTATCAG TCTGATTGCC
111501 CTATCCCACA AATTGCATCC CAGGAGATGA TTAGATGCAA TAGGTGAAAG
111551 TTTTCATGTT CCTCAGTGGC ATTCAGTGCA TGAACAACCA TTGTCCACCT
111601 AATTCCTCTG CATCTACAGC AAGAAATAGA ATTTTTGTGG AGACTTAACA
111651 TGCTGTGTCT TACTTACATA TGTATGCAAA AAAAAAAAAA AAAGTCACTT
111701 TTTTTCTTTT TTGAGACCGA GTCTTGCTCT GTGGCCCAGG CTGGAGCACA
111751 ATCACGGCTC ACTGTAACCT CCGCTACCCA GGTTCAAGTG ATTCTCCTGC
111801 CTCAGCCTCC TTGAGTAGCT GGGACTACAG GCACGTGCCA CCATGCCCAG
111851 CTAATTTTTG TACTTTTAGT AGAAATGGGG TTTTGCCATG TTGGCCAGGC
111901 TGGTCTCGAA CTCCTGACCT CAGGTGATCC ACCTGTCTTG GCCTCCCAAA
111951 GTGTGGGATT ACAGGCGTGA ACCACCAACG CCTGGCCCTG AAGATACATT
112001 TTAAATCAAT GAAAAAAAAC AACAGGATTC TACCTCCTAT GGTATATCCC
112051 TCCTGGCTGT CTCTTCTCTC CAGTCTTGCC TCTGCTGTGT GGGTTTCAGG
112101 CATCCATCTT CTCTACTCTG AATTACTGTG ATAACCTCTG AAGTATTTTC
112151 CCTGCCATCT GTCTGGCCCT TCTCCCAGGT CTTCCACATA CTGCAGCCAA
112201 GTCAGCCCGC TGTTGAAACC CTTCAAGACT CCCTGCTGTC CTCTGGATGA
112251 AGTCCAGACT CTTCCACGTG ACTTACCAGG CCTTTCTTGC ACTTGTCCCC
112301 AGCCACTTAC TGTTTCTCTC TTTCTACCTT AACATCCTGA ACTTCCTTTG
112351 GTTCTTTGAC CTTGCCTCTG ACCTTTTTCC ATGCTGTTCA CTCTTTCCCT
112401 GTTCACCTTG CTAACTCCTC TTTCTCTTTC TGGGTTGGAT CAGATTTCAC
112451 TTCTTCCAGA AGCCCTTCCT AGACCCTATA CTTCTGGAAT GGCGCCTTTT
112501 GACTGTACGC TCATTGCACC CTGTACTTCT CCTTTATGAG TGGGTGCTGG
112551 TCTGTCCCAC TAGGCTACTT CATCCATAAA GGGAGAGTAG AGCTTTACCA
112601 AGTCAATGCT TAAGCAATAT TTATTGGATG AATGTGTGAT TAATTTCATA
112651 GAAATTTGAT GTGCATTCAA ATTTACTTAT TGTATTACGG AACTTGCATT
112701 ATATTCTCAG TGGAGTTATT TTCTTTCACG TGTGTAATTC AAGATAGACT
112751 CAGTGAGATT TTCAAAATTT GGAATGCAGT GCAAGGAAAT TGAACTTGAG
112801 TTCTTTTGCA TTTTGATGGT TAAAAATTTC CCATTTGTGG TGACATACCA
112851 CAATAAGCCA GTGAATGTGG CTTATTGTTT TCTGGTCTAT AGAAAATTGT
112901 CGCAAACTCT GTCATAATGT CTGGTTCTAT ATAACAAAGC TAGTCCTGTA
112951 TTCTGCATGT GGCTGATGGA AACAGTGCTC TGTTGATCTG GTTCATGAAG
113001 AAATCTGTTC AATTCTGCAT AACAGATGCC TTCATCAGTG TCCTTCCATG
113051 AAGGAGCTGA TCTTCACAAA GAACACATAG TTTTGCATCC CACCACTTGC
113101 AGTNNNNNNN NNNNNNNNNN NNNNNNNNNN NNNNNNNNNN NNNNNNNNNN
113151 NNNNNNNNNN NNNNNNNNNN NNNNNNNNNN NNNNNNNNNN NNNNNNNNNN
113201 NNNNNNNNNN NNNNNNNNNN NNNNNNNNNN NNNNNNNNNN NNNNNNNNNN
113251 NNNNNNNNNN NNNNNNNNNN NNNNNNNNNN NNNNNNNNNN NNNNNNNNNN
113301 NNNNNNNNNN NNNNNNNNNN NNNNNNNNNN NNNNNNNNNN NNNNNNNNNN
113351 NNNNNNNNNN NNNNNNNNNN NNNNNNNNNN NNNNNNNNNN NNNNNNNNNN
113401 NNNNNNNCCT ACTGTGGTTT TCTTCAGAAT TACCCTTGCT CTGAGCCTGC
113451 AATTGACTCA TGAACTTCTT TTCCATGTTC TAACCTTACA ATGACTTCCT
113501 TGTGTTCACT CCAAATGTTT TTCCCTGGTT GCATGTAGAG ATGTATTAGC
113551 TAAGGTACAT GCTTAGCTGC TGTATCAAAG AGACCCTAAT GTACAACCCA
113601 GGCTGGTAGA GCAGCTCTGC TGTATGTGTT AATTCAGGGA CCCAGGTTCC
113651 TTCCATGTTG TGACTCCCCC CTTCCTTAGG ATGTTGTCTT CTTTTACATG
113701 GCTGAAGTTG GGCCATTTCA TGTCTCTGTT CCAGCTGCCT GGTAGGAAAA
113751 AAGAACAGAA ATTCAGAGTA AGCAAATTCT TTTTCTATAG ATGGATGCGG
113801 AAGTTGGACA CATCATTTCC TCTCACATTT TCTCGGCCAG AACGTAGTCA
113851 TGTGACTGCA CGTCTAGCTG CTAAGGAGAC TGGGAATTTA CTGTCGGCTG
113901 TGTGGCCTCT GTCAAGCTAA AATTCTTATT ACTGTGGAAT AAGGGAAGGA

FIGURE 3QQ

113951 TGGATTTGGG GGCACAATTA ATAGTCTGTC ACAGAGGCTA AAACAGCTGC
114001 TTTTGGCTGG GCACGGTGGC TCACACATGT AATTTCAGCA CTTTGGGAGG
114051 CCGAGGCAAG TGGATCACTT GAGATCAGGA ATTTGAGACC AGCCTGGCCA
114101 ACATGGTGAA ACCCTGTCTC TCCTAAAAAT ATAGAAATTA GCCGGGCATG
114151 GTGGCGGGTA CCTGTAATCC GAGCTACTCC AGAGGTTGAG GCAGGAGAAT
114201 TGCTTGAACC TGGAAGGCAG AGGTTGCAGT GAGCCAAGAT GGTGCCACTG
114251 CACTCCAGCC TGGGCGACAG AGCAAGACTC CATCTCAAAA AAAAAAAAAA
114301 AGGTTAAATA AACAGCTGCT TTTGTAGGTG ATACAAGGTA CAGCTAAGCT
114351 TTGAAGCCAG GCCTGTAGTT TCACCTTCCA TATTCTTACT CAAGGCATTA
114401 TACTTCTGGA TCTGAAACCA CTGGATCTGA TGCCCTGCTT GGGATGAGTT
114451 CTTTATATTA TCTTGCTTTC AACCCACACC TGTGTAATTT TATGGGCAGC
114501 GTTTGTTTCC TATATAGGAA CAATTTGAAA GTGGGCTGTT TCTAGGCTTT
114551 CATGAATAGC AGGCTATGCT GTCATTGGGA ATCTGGAGGG AGTTAATGAA
114601 CACAACTTCA TTGTTTACTT TAGTGAAATG TGGCAGCTTA TGATAGTTTT
114651 GACAGTGAGA CATGTGCTGT TTTGATCTCT CAGCTAAGAT TATCTGATTT
114701 TTCAGGCATG TCTCAAAACT CACCAGGCCT GCTCACATGC TGCTGCTTCT
114751 GAAGCCAGGG TTTGGAAACC AGCTGCCCAT CAGAATGAGG CTGTGACTTA
114801 GAATATTGGT TCTTGTTTTA TTACCATTCC TTGTTTGGTC TCTCCAGAGT
114851 CACTGGCCTT TTCCGCTTCA ATTTTCTTAT CGGTGAAATG AGATATTAAT
114901 TCCTCTTATT GACTTCAATT CAATTGCTGA GTGTATTGTT GCCTTTGGGA
114951 AGTTCTTTGA GTTTTCTGTG CCTTTGAAAT AGTTGTTTTT TTTTATTCTG
115001 GTGTTTTGAG GCATGTTTCA AGTGAGTGCA TTTACACTTC TACCATTTTA
115051 GGAGCCACAA TTCAGTTATG TTGTCCCAGC TTGCTTGGCC CCATCCCCAG
115101 AGTTTCTGAT TCAGTAGGTC TGGGGTGGGG CCCAATAATT TGCATTTCTT
115151 CTTCTTTTTT CGAGACAGAG TCTGACTGTG TCATCCAAGC TGGAGTGCAG
115201 TGGCACGATC GTAGCTCATT GTAGCCTCAA ACTCCTGGGC TCAAGCCGTC
115251 CTCCCACCTC ACCCTCCTGA GTAGCTGGGA CTATAGGCAT ATACTACCAT
115301 GCCCTGCCAC CTTTTTAATT TTTTGTAAGG ATGGGGGTCT CACTGTGTTG
115351 CTCAGGCTGG TCTTGAATTC CTGGGCTGAA GTGATCCTCC TGCTTCAGCC
115401 TCCCCAAATG CCGGCATTCC TGGCATGAGC CACTGCACTT GGCCAAGACT
115451 TTGCATTTCT AACTAGTTTC CAGGTAATGC TGCTGCTGGT GTAGGGACCT
115501 CATTTTGAGA ACCATTGTTC TATAGCTGTA GCTATAGTTA GTTTCTGGTT
115551 ATAGCTTCTT CCTTTTGTCC CTTCAGTAAT AGTGTACACA TCCGAAATCC
115601 CTGTCCTTGC TCTTTCAGGC CCAGGCATGG TATCTGGTCC TCTTCTGTTG
115651 CTAGCCCTGG GGTGCTTCAT CATCCCAAGT TTATTTTTCT TCTCCTAACC
115701 TGAACCTTTG TAAATAGCCC CTTCCCTAAT GAACGTCCTC AATTCCCTGT
115751 TTTGCGTGTC CTGTCTGTTT CTTGGCAAGA CTCTGGATGA TTCAGTACTC
115801 AATGAGGATT TTTCGCATAG ATGGATGAAA CAGGCTGGGT TTCATGTTTT
115851 CTAAGATAAA GGTGCTTCTC TCTTTTTCTC TTGGTCACTT TGACCAAGAA
115901 GAAAATAACA GAGTTTTTAT TCTCAAGAAG AATAATATCG GGGCCACTCT
115951 GCTCAGAGGC CACTCTGCTT TGAGGACCCC TTCTCTCCTC CCTCATGCCA
116001 AAGATCAGGA ACATTGGGCA GAGCGGATAA CGATGCCGCC AGCGTCATTA
116051 CATTTTCACG GCACTTTCAG TTGTGCTGAG CGTGCAAACA TTTCAAGGAG
116101 ACATTTCTAA GAGGTGGCTA GCACAGCATG CCTCTAATGC CCTATGTGAA
116151 TTGGAATAGA GTACTAAAGA ACTGTTCAAT ATTCACCCCA TCCCCGCATA
116201 TGCAAGCATG CACGTGGGTT CATTGTATAT GTGTGTGTGC ACGTGTGCAC
116251 AGACACATTT GTCCTTCGTT TCAAATGCAA CACAATGGAT GGAAATTGCC
116301 TTCCTGGTAC TGGGGTATGG ATGCAAACAC CAACAGAGAA GCAGCCGCTA
116351 CTTCCAAACT GAACACATGT GAGATTTGCC CTTTAATTAG CATCTGCAGC
116401 TGCTGCCATC AGAAGGGTCT GTCTCTGTTG GCCTGAAAGT CTTTGCTTTA
116451 AAAGAGCAAG TCCATTATAG CTCCAAGCCA GGCTCGTCTG TCAGCTGCTG
116501 TGCTTTCTCT GCCATCAGCG GGGTTGCCAC ATTGTTTTGG GCTGTTTCAC
116551 TCTAGGACTC TTTCCTCCTC CTGTGCCCCC AGCCTTTGAT TACCATGCCT

FIGURE 3RR

116601 TGGTGATCCT CATTTGGGTG ACCTGCAGCT GCTCATTGTG TGTGCAGGAG
116651 ACATCTCCAG TCCTTGTAAG GAGGGAAGAT CACTGGCTTC AGTGCTGATG
116701 GACTGGTTAT TTTCCAGCCC TTTGTCGTCA GTGATCTTGT CTTGATATGC
116751 AGAAAGGCTC CAGGTAGTCA CTGAAAAAAA TATAAGCAGC AGAGGTGATG
116801 GCTATATGAA AGTCACGTTT CATCAAGGGC ATTGCTGCTA TGGAAACTTT
116851 CAATTCACTT GGAGTAGGGA GCCATATTGG TTCCACAGCC TCCTCAGCAG
116901 TGGGTCCCAA CACAGTGCTG GGCTAGCTGC CTCTGAATCA CCGCAGTAGC
116951 TCCTTTTACT ATAGATTCCT GGGTCCCACC CATGGAATGT GATCCATGAA
117001 GTCTGGGGTT ATTCCCTGGA ATCCTTTAAG CTCCCTAAGT GGTTGGGATG
117051 GGAAAGAGAT ATGCTTTATG TTACTATACT TCTTATTATT ATTATTTTAA
117101 AATTCTTGCC GGGCGCAGTG GCTCACACCT GTAATCCCAG CACATTGGGA
117151 GACCGAGGCG GGTGGATCAC TTGAGGTCAG GAGTTCGAGA CTGGCCTGGC
117201 CAACATGATG AAATCCCGTC TCTACTAAAA ATACAAAAAT TAGCTGGGCA
117251 TGGTGGCGCA TGACTGTAGT CCCAGCCACT CCGGAGGCTG AGGCAGGAGA
117301 ATCGCTTGAA CCCGGGAGGC AGAGGTTGCA GTGAGCCGAG ATCGTGGCAC
117351 TGCACTCCAG CCTGGGTAAC AGAGTGAGAC TTCATCTCAA AAAAAACCCA
117401 AAAAAACAAA ACTCTTTTTC ATTATACCGG AACGTCAGCT TTATGGAGTC
117451 GGGGATTTTT TCTGTTTTAT TCACTGCTGT TTCCCTAACA TCTAGAATAG
117501 TGGCTGGCAC GATAGGCACT CAAGTATTGA TTTAGATGAG TCTATTTTAT
117551 TTTCTTTTAA ATTTTTAATT TTTATTAGAG GTGGGGTCTG GCTTTGTTGC
117601 CCAAGCTGGT CTCAAAACTC CTGGCCTCAA GCGATTGTAC TGCCTCAGCC
117651 TCCCAAAGGG CTAGGATAGG CATGAGCCAA CATGCCTGGC TTGTCTTATT
117701 TTTAACAAGC ACTTCTGGTG ATTCTGATGG ACAATCAGGC TTGGGAAGTT
117751 CTAACCTAGA GGACCTACAG TTGTCTTGGG GTAGAAGCCA AGGCTATCCT
117801 GGTTTTTAGA ATCAGTGCCT TACTGGGCAT CTCTGAAGAG TAAAAGTCAG
117851 GGACAGAGTT ACATTTTTGG ACAAAACCAG ATGCTGTGAA TGGACTCTTG
117901 GTCACAACCT GGGTGGCGAC TTGGTCCTTA ACTTCTTCAT CATTTTCTGC
117951 TGACCCTGTT CTTTGGTTCA CAGCAAGTCA CCTGATAAGA AGACTCAAAG
118001 ACTGCTAGTT TGTTACTTTA GATGATGCTT TTGGAACCTC TTGGTACCAT
118051 TTTAACAATC CAAACGTATT TTATGAAAGC ACTCAAGTCC TGGGTCTTTA
118101 TTGTATCTTT AAGCTCTAAC AGCATGATGA TTGAATAAGC TGTGGTTGGC
118151 CACACACAAG CCATCTTCCC CATGGCCTCC ATTCATACTA GAATGAGCAG
118201 CTATACCCCA GTAGTATAGT TTTGGGATAT GGGTAACATC TTGGGATAGC
118251 CACATTTACT TAGTAAATGT CTGGCTTACA TTCTCCTAAT GGTGCACTGT
118301 TGGAATTTTT GGTGTGGTAA CCTGGAATAG TGTTGGTGGG TCAAGTTTGA
118351 TTAGCATCTT TGATAAGGAC CCGGTCTATT TAGAGGTTTG TCATTGAGTG
118401 TGTCTGTTTT GGCCTCATGT TGTGAAGCAT GCTGTGTAGC AGCTGTTGTA
118451 ATTTTTGTTG CTTGTTTTCT CAATCAACCC TGGTTTTGAA GAAATGGGAA
118501 GTTGTTCCAC TCTTAGACTG ATCTGACTTG GGAGGGGATT TTCAGTTCAG
118551 GAAGTTGGAT CTTCTGAATG GAAGCAAAGA ATACATGTCT TTTTGCCACT
118601 TTACAAGCTG GCTCTTGTTT TCTGAACTAT TTTACTGGTC ATTGCAAATA
118651 GAATGTCAGG AGTAGCTGCC AAATACTAAG TTGTGTTCAG TTTGTCAGTT
118701 CTTAAGAGTT GCCGGTGGCT GCTCTGCTAT GCGTATGACT TTCTCAGCCT
118751 TAAACTTACA AGCCATACTG TTTTTTTCAC ATCTTTAATA CAGCCATAGG
118801 AAATTTATAA CTGTGGCGTG TCGTCATAAA TATGCATTGT TCTTATTTTA
118851 AGACATTTCA GTACTAAAAG TATAAGTACT TCTGTTATTA TCTGTGAATT
118901 TCTTTCCTTC TTCTTTTTTT GGATATTTAA GACCTTTTCG ATGTCAATAT
118951 ATATTTAAAA CAGACATATA AATTAGCATT CACCCACATA CCCAGGGCCT
119001 ATGGAGAACC AGGTTGGGAT GAGTGGGTGA GCTACAGGCA GCCAGGTGGC
119051 TCCTGTGGGC TCCTCGAGGA CTGGGGTGAG TAACTAATGT CTGCTAGGAA
119101 CTTGGGGGAA AGAAGGTGTG TATGTTAGGT GCTGCCCCCT TCTAAGTGTT
119151 CCTCTTGTTC ATAATTGAGT TTTTTTTTTT TTTTTTTTTT TTTTAGAAGG
119201 AGTCTCGCTC TGTTGCCAGG CTGGAGTGCA GTGGTGTGAT CTCAGCTCAC

FIGURE 3SS

119251 TGCAACCTCT GCCTCCCGGG TTCAAGTGAT TCTCCTGCCT CAGCCTCCCG
119301 AGTAGCTGGG ACTACAGGCA TGCACCACCA TGCCCAGCTA ATTTTTGTAT
119351 TTTTAGTAAA GACGGGGTTT CACCATGTTG GCCAGGGTGG TCTCGATCTC
119401 TTGACCTTGT GATCCGCCTG CCTCGGCCTC CCAAAGTGCT GGGATTACAG
119451 GTGTGAGCCA CTGTGCCCAG CCCATAAATC AAAATTTTTT CAGCAATTGT
119501 TATACAAGTG GAACCTTACT CTTCAAATGC AATTGTCCAG TGTCTGGCTT
119551 AATGTCTGCT GTTGTCAGAA ACCATGTGAA TGGAGTAGAT TCCCAGGTTA
119601 TAAGGAGCCC CCAGGGAGGA TGCGCGAGTC ACTGGCTTCT CCAGGGGTCT
119651 CTGGTTTGGG GTTGCCTTGG TGCTGGGCAC ACTTCCTGGA GATTTTACTG
119701 GACCAGCCTG AGGCCTTTGG GGCTCTGTGC AGATGCTCTA CTTCTGACTT
119751 GTCTAGAGCT TTCTTCTAAT TCTGGACTAA AAGCAAGCAG GAGTTTGGAG
119801 GATGATGGTG AGAATTCACA TCCCCGAGTT GGCTTTTGGA ATGCAGTAGT
119851 TTGTGAGATT TAGTGTTTTT TTTAAGAAGT ATATTCAGAT CTTGCCTTTT
119901 TCCCAGAAAG CATATGAGAC AACTTCCAAG ACATTTATAG CATGGCTAAT
119951 AAAATGGGAA ATCAGGGCGA AGGACAGGAG AACTCAATAA GGGTTAACAT
120001 GGCTACAGCG ATTGTCTAAA TGGGTTCTTT TTGCTGGCCA GAGCAGAAAG
120051 GATCATGCAG TAAAGTGGGG GGGAAGAAAG GGAATTGAAT GGTAGGTGAA
120101 GACTTCATGT TGGTGCCAGG CACTGTGCCA GGCCCTCCTA GGACCTTGTC
120151 TTACTCAATC CTCACACAGT GCTGCAAGAG GATTAGTCTT ATCCCTGTTT
120201 TAGAGAGGAT GAAACTGAAA GGCAGCGAGG TGAAGTCACC AGCAGGAGGC
120251 TGAAGCCGCC CAGGCTAACT GGCCTTATAG CTACCTAGGG ACTCAGGAAT
120301 ATCACACCTG TTTATCATCA AAAGGAGAAA GGATTTCAGT TCCTTGGGGT
120351 AGAAGAGTTT CTTTTTGCTA ATCAAACATT TTACTTGAGG CTTCATATTC
120401 TTCTTCAAGA TTTTTTTCCT GTGTATGTAC CAACACATGT AATAATTCCT
120451 TGTTTATTTC AAAAAAGGGG TTGTACTTTA TTCTTTACAA GATTTCACTT
120501 TATATTGTCA TGGACAATTT TCCATGGCAG TATGAATAAA TGGAATCTGT
120551 TTGTTTTTAA TATCTTTGTC TTATCCCATT GTTTACATAT GTCATATTTT
120601 AGCCAGTCTC TAACTGATGG ATAGCTGAAT GATTTCCATG TTTTTTTCCC
120651 CTGTTACAAA CAATACTGCA AGGAATCTAT TTATCTTTCT ATTTATCTGC
120701 AAACTATTGT AAGTACCTGT AAATTGTTAG AAGTGGAATT ACTAGGTCAA
120751 AGGGGATATT TTCACATTTA AATTTTGAAT AGAGGCTGTC AGTTGCCTTC
120801 CACACTGACT ATAAAAGGAA AAGATTGTAT CACATTTATT GCAAGCCTTC
120851 TGTATTCTGC TGGGTGCTGA GGGGAATACA GAAAGGATAT AAGAGTGGTT
120901 GCCCTCTAGG AATATCCGTC TACACTGTAC CTAATCCTAG GGAATGTCTG
120951 GGGTGTCAAC TTGTGGGTGG GAAAGTGGGT GGATTTAATT CAACTGTTCA
121001 AGCTTGCCTT GCAAACACTG TGCATGGTGT CTGGGACTAG TCTTTCATTA
121051 TATTGATTCC CCTGGGTAAC AGATGTAATT TCCTTAGGGC AGGGACTTCA
121101 TCCTACATGA CTTACAGCGT GCCTTACACA TCTTCTTTGC TTTGTGGAGA
121151 CCTTGTTATT ATAACACGTC AGGTGATATT CGAGGATCTA ATTGAGGCAT
121201 TCCCTATTTT TGGGTGTGTG AAGAATTAAT AACTTTGGCA TTCTATACAG
121251 GTCATGGAAT ATCAGCCTGG AGGGGACTTG CTGTCACTTT TGAATAGATA
121301 TGAGGACCAG TTAGATGAAA ACCTGATACA GTTTTACCTA GCTGAGCTGA
121351 TTTTGGCTGT TCACAGCGTT CATCTGATGG GATACGTGCA TCGGTAAGTG
121401 AGACTCTGGT AGCATTTTTA TGCTGAGGAT TTTCCTGTGT CGCATAAGAG
121451 TTCCTGCATG GAAATGAGTG GATGAGTGAT TTCAAGATCA AGATAACGCC
121501 NNNNNNNNNN NNNNNNNNNN NNNNNNNNNN NNNNNNNNNN NNNNNNNNNN
121551 NNNNNNNNNN NNNNNNNNNN NNNNNNNNNN NNNNNNNNNN NNNNNNNNNN
121601 NNNNNNNNNN NNNNNNNNNN NNNNNNNNNN NNNNNNNNNN NNNNNNNNNN
121651 NNNNNNNNNN NNNNNNNNNN NNNNNNNNNN NNNNNNNNNN NNNNNNNNNN
121701 NNNNNNNNNN NNNNNNNNNN NNNNNNNNNN NNNNNNNNNN NNNNNNNNNN
121751 NNNNNNNNNN NNNNNNNNNN NNNNNNNNNN NNNNNNNNNN NNNNNNNNNN
121801 NNNNNNNNNN NNNNNNNNNN NNNNNNNNNN NNNNNNNNNN NNNNNNNNNN
121851 NNNNNNNNNN NNNNNNNNNN NNNNNNNNNN NNNNNNNNNN NNNNNNNNNN

FIGURE 3TT

121901 NNNNNNNNNN NNNNNNNNNN NNNNNNNNNN NNNNNNNNNN NNNNNNNNNN
121951 NNNNNNNNNN NNNNNNNNNN NNNNNNNNNN NNNNNNNNNN NNNNNNNNNN
122001 NNNNNNNNNN NNNNNNNNNN NNNNNNNNNN NNNNNNNNNN NNNNNNNNNN
122051 NNNNNNNNNN NNNNNNNNNN NNNNNNNNNN NNNNNNNNNN NNNNNNNNNN
122101 NNNNNNNNNN NNNNNNNNNN NNNNNNNNNN NNNNNNNNNN NNNNNNNNNN
122151 NNNNNNNNNN NNNNNNNNNN NNNNNNNNNN NNNNNNNNNN NNNNNNNNNN
122201 NNNNNNNNNN NNNNNNNNNN NNNNNNNNNN NNNNNNNNNN NNNNNNNNNN
122251 NNNNNNNNNN NNNNNNNNNN NNNNNNNNNN NNNNNNNNNN NNNNNNNNNN
122301 NNNNNNNNNN NNNNNNNNNN NNNNNNNNNN NNNNNNNNNN NNNNNNNNNN
122351 NNNNNNNNNN NNNNNNNNNN NNNNNNNNNN NNNNNNNNNN NNNNNNNNNN
122401 NNNNNNNNNN NNNNNNNNNN NNNNNNNNNN NNNNNNNNNN NNNNNNNNNN
122451 NNNNNNNNNN NNNNNNNNNN NNNNNNNNNN NNNNNNNNNN NNNNNNNNNN
122501 NNNNNNNNNN NNNNNNNNNN NNNNNNNNNN NNNNNNNNNN NNNNNNNNNN
122551 NNNNNNNNNN NNNNNNNNNN NNNNNNNNNN NNNNNNNNNN NNNNNNNNNN
122601 NNNNNNNNNN NNNNNNNNNN NNNNNNNNNN NNNNNNNNNN NNNNNNNNNN
122651 NNNNNNNNNN NNNNNNNNNN NNNNNNNNNN NNNNNNNNNN NNNNNNNNNN
122701 NNNNNNNNNN NNNNNNNNNN NNNNNNNNNN NNNNNNNNNN NNNNNNNNNN
122751 NNNNNNNNNN NNNNNNNNNN NNNNNNNNNN NNNNNNNNNN NNNNNNNNNN
122801 NNNNNNNNNN NNNNNNNNNN NNNNNNNNNN NNNNNNNNNN NNNNNNNNNN
122851 NNNNNNNNNN NNNNNNNNNN NNNNNNNNNN NNNNNNNNNN NNNNNNNNNN
122901 NNNNNNNNNN NNNNNNNNNN NNNNNNNNNN NNNNNNNNNN NNNNNNNNNN
122951 NNNNNNNNNN NNNNNNNNNN NNNNNNNNNN NNNNNNNNNN NNNNNNNNNN
123001 NNNNNNNNNN NNNNNNNNNN NNNNNNNNNN NNNNNNNNNN NNNNNNNNNN
123051 NNNNNNNNNN NNNNNNNNNN NNNNNNNNNN NNNNNNNNNN NNNNNNNNNN
123101 NNNNNNNNNN NNNNNNNNNN NNNNNNNNNN NNNNNNNNNN NNNNNNNNNN
123151 NNNNNNNNNN NNNNNNNNNN NNNNNNNNNN NNNNNNNNNN NNNNNNNNNN
123201 NNNNNNNNNN NNNNNNNNNN NNNNNNNNNN NNNNNNNNNN NNNNNNNNNN
123251 NNNNNNNNNN NNNNNNNNNN NNNNNNNNNN NNNNNNNNNN NNNNNNNNNN
123301 NNNNNNNNNN NNNNNNNNNN NNNNNNNNNN NNNNNNNNNN NNNNNNNNNN
123351 NNNNNNNNNN NNNNNNNNNN NNNNNNNNNN NNNNNNNNNN NNNNNNNNNN
123401 NNNNNNNNNN NNNNNNNNNN NNNNNNNNNN NNNNNNNNNN NNNNNNNNNN
123451 NNNNNNNNNN NNNNNNNNNN NNNNNNNNNN NNNNNNNNNN NNNNNNNNNN
123501 NNNNNNNNNN NNNNNNNNNN NNNNNNNNNN NNNNNNNNNN NNNNNNNNNN
123551 NNNNNNNNNN NNNNNNNNNN NNNNNNNNNN NNNNNNNNNN NNNNNNNNNN
123601 NNNNNNNNNN NNNNNNNNNN NNNNNNNNNN NNNNNNNNNN NNNNNNNNNN
123651 NNNNNNNNNN NNNNNNNNNN NNNNNNNNNN NNNNNNNNNN NNNNNNNNNN
123701 NNNNNNNNNN NNNNNNNNNN NNNNNNNNNN NNNNAAAAAA CTGATGCTAG
123751 TGAAAATGCA TAATTTAAGA GGTTAGAGAA GCTGCTCTTC AAAATGCCCC
123801 CCAAGTCTGA GAGTTAAATC CTTTACATAA AGGACAATAT GTAAAATTTT
123851 CTTTTTCTTT TTTCTTTTTT TTTGAGACGG AGTCTCGCTC TGTCCCCCAG
123901 GCTGGAGTGC AGTGGCGCGA TCTCGGCTCA CTGCAAGCTC CGCCCCCCTG
123951 GGTTCACGCC ATTCTCCTGC CTCAGCCTCC CGAGTAGCTG GGACTGCAAG
124001 CGCCCGCCAC CATGCCCAGC TAATTTTTTG TATTTTTAGT AGAGACGGGG
124051 TTTCACCGTG TTAGCCAGGA TGGTCTCGAT CTCCTGACCT CGTGATCCAC
124101 TCGCTTCGGC CTCCCAAAGT GCTGGGATTA CAGGCATAAG CCACTGCGCC
124151 CGGCTCTTTT TTTTCTTAAA CTGCTTCCAG AAAAGTGGAT ATTATTAGGT
124201 TGATGTTAAG AAAAGGCTTG GAGTTGCATT AACTTTTTGC TTTCTAGCAT
124251 CTGGCCTGTC TGTTCTGCAG ACCTGAGACC TACTTGAGAT AATTTTCTTG
124301 GTGTTCAGGC CCTTGGAAAA ATAAGTTCCC TATGTTGTCC AGTGTCAAAG
124351 TTTCTCAACC TCAGCACTAT TCTTTTTTTC AGGTTATTTT CTTGTAATCT
124401 GTTCACTTGA TCATTACATT AAGAATTAGA TTATATTGCT ATAACTACAA
124451 AGCATTTTAT GTTTTAAAAA TTATGTACAA TTTAGAAACA GGCATGAAAA
124501 CTTAGGTATT AAATTTAGTG GAATAAAGCA CAGAAAAAAA GTTAAAATAA

FIGURE 3UU

124551 TGCAGTTTTA TCACTTAGGA TTAAACATTT ATATGGGCCG GGTGTAGTGC
124601 CTCACACCTG TAATCCCAGC ACGTTTGGAG GTCGAGGCGG GAGGATTGCT
124651 GGAGTTTGAG ACCAGCCTGG GCAACAAAAT GAGACCTAGT CTCTACAAAA
124701 AATCAAAAAA TTAGCCAGAC ATGGTAGTAC ATGCTTGTAG CTCCAGCCAC
124751 ATGGGAGGCC AAGACAGTAG GATCGCTGGA GCGAAGGAGG TTGAGGCTGC
124801 AATGACCGTG TTTGCACCAT TGCATTCCAG CCTGGGCGAC AGAACAAGAC
124851 CCTGTCTTAA AACAAATTTA TATGCTGCAT TCGTGAAATT AAAAAAAAAT
124901 CATGGATTTA GAAATAAATT GAAGCAAGGT ACATTGACAG TGTAACCTCA
124951 GCACTACTGA CATTTTGATC TGAATAATTC TTTGTTGTGG GGGATGCGCT
125001 GTATAAGATG TTTAGCTGCA TCCCTGACTC CTACCTCCTA GATGCCATTA
125051 GCACCCTCCC CTCCAGATGT GATAACCAAA AATGTCTCTA GACATTGCCA
125101 GATGTGCCTG GGGTAGGAGG GTTGGGGGAA GTGGGGTTTG AGAACCCTTA
125151 GTTGATCATG CCTGCAGTAG GTTGAGAAGC ATCAGAAAGC TAATTAATTA
125201 GACAGGAATA TGTGTTTGCA GTAAGAAAAC CTCAGCAAAC TAATCAAGTT
125251 CCAAAGTTAC TGCTTGGTAA ATAAATAGGA ATTAAGAATA AGACCCTATC
125301 TCTGTGTCTG GGGTCATTCT CTTCGGAGCT CTTGGTGGAG AGACAGGGTT
125351 CCCAGTTTCA ATTTTTTAGT GCTTCAGACT GCCCTTTTCA GTTATAATTG
125401 TAACAACCTT CACTCCAGGT GGGGAGCCTC CCAGGTTTAT TTACAACAAG
125451 GCTCAATCTC TGATTATTTT GGTCAAGGAG ATATGACACT CTATACCACA
125501 CACTTGAGAA TATTGCCTCT CTTTTTCTCT TGAGCTTTTA GGGTTGGAAC
125551 GTGACAGGCA GATAAGGAAT TTTTTGCATT AAGTGCAAAG TCCTTTTTCT
125601 TATAGAAGAG CAATAATCTG CACACTAGAT CAAGTCAAGT GTGGATATAA
125651 AATTATAATT TTTGGGGGGA TATTTTTAAT AGTGGTTTTG GGTTAAACAT
125701 ATTTCCTTTA AATGAAATGT CTGTAGGCCT AAAGTAGGTT CTAAATGTTG
125751 CCTGTACTCA TAGTATACCA TATAAAATAT AATCCACATT TACTGGAACT
125801 ACCATATATT ACTTACCCCA AATCAATCAA TCCCTTCCCT ATCACCCCCA
125851 CGTAAGATCT TCGTATTTTG GATACCTGTG AATCTTAGAT CTGTTCAGTT
125901 TTCCATTATC CATTGTCTTA TTTCAAGCTT CTCATTCAGA ATGTTGCTTT
125951 GGAGTATTTT CTGTTAGTAA ACACAGGGCC TAGTGACTCT AGGACCTGCT
126001 GTGTGACTTA GGTCACCCAC TTCACTTTAT TAGAATCTCA AAGAATGGTG
126051 AACAGCTGAG TTCCAATCTG TCTCATTTGG CTCTCATGAA AACAGTCATA
126101 AGGAGATTGT AGATAAACCA CATTATATAG CATAGTAAGT GATAATCAAC
126151 CCCATTTGGC AGTTGCAACC CCACAAGAGA TAGCCCTTTT TAGATTTGTG
126201 TAGGAGTGAA AAGCTTTATT TTCCACAAGA GGAACGACAT AGTAAGAACT
126251 CCTTTCCCCC CTGCTTCTGC AGGTATATGC TTATGCCCTA GGCAACTTGA
126301 TGGGTAAAGT TAGGTTTAAA TAGTTTTATT TGTAAGCTCT TCTCTTCTCT
126351 TCTCTTCTCT TCTCTTCTCT TCTCTTCTCT TCTTTTCTTT CAAGACAGAG
126401 TCTTGCTCTG TCACCCAGGC TGGAGTGCAG TGGGCGACCT TGGCTCACTG
126451 CAACCTCCGC CTCCTGGGTT CAAGAGATTC TCCTGCCTCA GCTCCCCGAG
126501 TAGCTGGGAT TACAGGTGCC CGCCACCATG CCTGGCTAAT TTTTGTATTT
126551 TTAGTAGAGA TGGGGTTTCA CCATGTTGAA GCATTTTAGG AAAGGGGTTA
126601 GGAGGAGGAA GACANNNNNN NNNNNNNNNN NNNNNNNNNN NNNNNNNNNN
126651 NNNNNNNNNN NNNNNNNNNN NNNNNNTCTC CCCCTTTCTC CCAAAATATG
126701 GCAGACTCTT CTGTCCCCTA GTCATTCTCA TATAGTCTTC TGAACTTGTT
126751 TATTTTCTTC CCTGTTAATA CAGTAAAAAT TAACTAAGTT GGCCAGGAGT
126801 GGTGGCACAT GCCTGTAATC CCAGCACTTT GGGAGGCCGA GGCGAGCAGA
126851 TCACCTGAGG TCAGGAGTTT GAGACCAGCC TGGCCAACAT GGTGAAACCC
126901 TGTCTCTACT AAAAAAAAAT TGTAAAAGTT AGCTGGGTGT GGTGGTGCGC
126951 ACCTGTAGTC CCAGCTATTC GGGAGGCTGA GGCAGGAGAA TTGCTTGAAC
127001 CCAGGGGGCTG GAGGTTGCAG TGAGCCAAGA TCGCGCCACT GCACTCTAGC
127051 CTGGGCGACA GAGCAGTCTT TAAAAAAAAA AAAAAATTAA CTAAGTTAAG
127101 TAGTACTTGG GCCCTATCAG ATAGTGTCCT CCTGCAGGCA GGCTGGGCCC
127151 CTACTACAGT TTCACTTTTA ATATCTCACC GAGATTAGCT GACTGAATTG

FIGURE 3VV

127201 CCACCAGAGG AGAGTGAAAG CATATTGCAA AATCATAATC AGGACATGTG
127251 AGATTATGTG TTGAACAGGT TTAATGTGCT TGGGGGTCAG TGACTAATGG
127301 GAACTTAGCA GTCATTAACT GTCATTAAAA ACGTTTGTTA ATTACTATTA
127351 CACACTTAGA GATTTGTTAA TTAACAAAGA GTAATGCCTT TGCTAATCAC
127401 TATTATGCAC TTAAGAGGAA GCCAGTGGGT ATTTTTCCCT TCATAGCTTT
127451 CTAGTACAAA TTAATAAAAT TTAGAAAATT AGAAAATGAT TGTGCATAAA
127501 TGTGTATAAT CATGTATCTG TTAGGGGGCA AAAATTAGTT GGGGAATTAT
127551 CTTTCTTTGA TAAGTCTTAT CATTAGTTTG AAAATGGGGC ATTGGCAATT
127601 CATACTGTTT GGCTGGGTTG TCCTGAGAAA CACTCCCCAG TCAATTCTGT
127651 TTTTGCAACT CTTTGGTTGT GAACAAGTGA CTGCCCTGTG AGCTGCAAAT
127701 AAGGAGAACT GAATATTCCT GAACAGTCTG TGGCAATAAA AATGAAATCC
127751 AGTAAGTGCA AATGGTATGT ATTCAACAAT TGCGTAGTTA GGTCCTGCAA
127801 GGTAATTAGA CATAAAGGAT AAGTATTTAA TCAACAATAT AGTAGCATTT
127851 TCATTACCTA GTCAAATCAA GATGTTACAG TTTTCCTTCT CTTGTTTTGT
127901 TATTTAAAAA ATATCTATTG TGGCCAGGCT CCGTGGCTCA CACTTGTAAT
127951 CCCAGCACTT TGGGAGGCCA AGATGGGTGG ATCACGAGGT CAAGAGATCG
128001 AGACCATCCT GGCCAAACAT AGTGAAACCC CGTCTCTACT AAAAATACAA
128051 AAATTATCTG GGTGTGGTGG CATGCACCTG TAGTCGCAGT TACTCGAGAG
128101 GCTGAGGCAA GAGAATTGCT TGAACCTGGG AGGAGGAGGT TGCAGTGAGC
128151 TGAGATCGCA GCACTGCACT CCAGCCTGGT GACAGAGCGA GACTCCATCT
128201 CGGAAAAAAA AAAAAATCTA TTGGTTATTG TTGGTGCATT TTAACCAAAA
128251 CCCTTTAGTT TAACCCTAAC CTGTGCTGAG CTCTTTAACA TTTACATACA
128301 TATTAAAAAA CAGAATCAGC CCAGATTTCC CAACATATTA AGTCTTCTCC
128351 TTGACTTAAG CTACTTTCAG TTCTTCAAGC TTAAGTCACC CTGTGGTTTT
128401 GTCTTAGGCC AAATATTTTC CCCTTTGTCT CCCCTTCTGT CTATCAAGCC
128451 AAGCCTGCCT GTGGGTTTTG GATAGTGTGA CCATCTGGCT TTCTTGAAGG
128501 GGCACTTACA GGGGAAGTTT TATTGCCCAA ACCGGTGGAC AATCCATGTC
128551 AGGAATGATT ATATCACACT GCTTTCTGGG TTTAGGGCTT GGAAAAACCT
128601 GTATCAGAGC GTGGGCCCTA GGGAAGAGGT AAAAAGAGAG GAGAGGGAAG
128651 AATAGGTCTG TTTCATATAA CGAGAAAGTC TCATGGCAGA GGAATGGATG
128701 AGATTCAAGT TACAGGCTGG AAGAGCTTCA TCCAGAATCA GCCCCGGGGA
128751 GAGGAGACCT CATCACGTCC TCACTAAACA TTCACTTTCC TCTCCACACC
128801 CAGTTAAAGT AAAGCAAATT TACTTCCTTG GTGAAAAGCC CAGCCTTCAA
128851 GGTATGTGGA CTTACCCACA AAATCTCTTG GCTCACTCAG TTTCACTTAC
128901 CATCGTTTAA TGAGGAAAAA GTTCTTTTGT ACCATGTAAC TGCTGACCTG
128951 AGAGAAGCCC ATTATGATAT AGAGTTATAG GACAGCTGGC CAACACACTA
129001 TATAGCTAAA ATCAGGGCCT CTCTGTTTTG ATGGGGAGAA AAGTTAGAGA
129051 AGGAATCTTT AGACTTCAAA TTTCATGGCT CAGTAAAACG TCAAAATAAT
129101 TTTGAAGACC AAAGGGGTTG CCAGCTTACT AGGCTGCCTA GACAGGGGTG
129151 GGTATGAGGG GAAGAAAGCC TGCTTCTTTC ATCAACAGCA TATCCAGAAA
129201 CAAAGGACAT TTAAACACTA AAAAAGTCAG AAGGACAAAT TCTCAGAAAA
129251 AAAGGACAGT CCTTTAAATG GGTTACATTT AGCTTTATAA AATGCCCTCC
129301 TGTATTGTCC TAATCTTTCT TTGCCAAGGT CAAGTGCTTG GGTGCCATTG
129351 GATTATAAGC CCCTGGGTTT CTGAACGGTG GGGGAGGGAA CCACAGGAAC
129401 AAGGGTTAGG GGTGAGGAAA AAGAACTCAT TAACCTTGGG CCCTGGGTGG
129451 AAGTTAATTA TCATGTCTTG CCCTGTGGGT GGGTTGAAGT AGGAACGTTA
129501 ATTCCAAAGG CAGTTTTCCA AATTTTTGAA CTTGAGATTT GTAATATTAT
129551 CTTGCCAGTT AGCCACCAGT TCTCTTCTCT TTTTTCTTTT CTTTTCTTAC
129601 AGTCTCGCTG TCACCCAGGC TGCAGTGTAA TGGCGCAATC TTGGCTCACT
129651 GCAACCTCCG CCTCCCAGGT TCAAGCGATT CTTGTGCCTC AGCCTCCCGA
129701 GTAGCTGGGA CCACAGGTGT GCACCACCAC ACCTGACTAA TTTTTGTATT
129751 TTTAATAGAG ATGGGGCTTC ACCATGTTGG CCATGCTGGT CTCAAACTCC
129801 TGGCCTCAAA TGATCCACCC ACCTTGGCCT CCCAAAGTGT TGGGATTACA

FIGURE 3WW

129851 GGCATGGGCC ACTGCACCTG GCCAACTGCC AGTTTTCTAG TAATGGTTAG
129901 GTTGATATTT TAGATTCATT TTTAGAGTTT ATTATCATTT TGCTGTTATC
129951 ATAAGAGAAG TTCCATCATG TCAATAACTT GTATTAGGAA AGACATCTTC
130001 CATTCCCGGT ATATCCAACT CTCATTCGTA TAACTGAAGG CTGTGTGTAT
130051 ATCATCAACA ATTCTTGCCC TTTTGCCCTT GGATTGCATT ATATGCTGTG
130101 TGCTTTTTTT TTTTTTTAAA TTAGTAAAGC GTTTGCATTT CCTGACAGTG
130151 TGCCACTTGA CAGCTGGTTT AAGTGCCTGG GAGAATAGTA ATCAGTGGCA
130201 AATCAGCTTG TGTCTGAAAT GTGGCTGTTG GCAGTCTACT TGAGGATAAT
130251 TGAAAGTTTG CTGTATTCGT TTTATTGATG GGATTCTAGG TGAATGCCAA
130301 ACTCCCGATT GGGACCCCAG ATTACATGGC TCCTGAAGTG CTGACTGTGA
130351 TGAACGGGGA TGGAAAAGGC ACCTACGGCC TGGACTGTGA CTGGTGGTCA
130401 GTGGGCGTGA TTGCCTATGA GATGATTTAT GGGAGATCCC CCTTCGCAGA
130451 GGGAACCTCT GCCAGAACCT TCAATAACAT TATGAATTTC CAGGTAAAGA
130501 GTCCTTAGAA GATTTCGAAG TCACATTGAG AAACGTTATT TAAAAATTGT
130551 GCGAATGAGG CTGGGCCGTG GGTGGCTCAT GCCTGTAATC CCGGCACTTT
130601 GGGAGGCCGA GGTGGGTGGA TCACGAGGTC AGGAGATCGA GACCATCCTG
130651 GCTAACATGG TGAAACCCCA TCTCTACTAA AAAATACAAA AAAATTAGCC
130701 AGTTGTGGTG GTGGGCGCCT GTAGTCCCAG CTANNNNNNN NNNNNNNNNN
130751 NNNNNNNNNN NNNNNNNNNN NNNNNNNNNN NNNNNNNNNN NNNNNNNNNN
130801 NNNNNNNNNN NNNNNNNNNN NNNNNNNNNN NNNNNNNNNN NNNNNNNNNN
130851 NNNNNNNNNN NNNNNNNNNN NNNNNNNNNN NNNNNNNNNN NNNNNNNNNN
130901 NNNNNNNNNN NNNNNNNNNN NNNNNNNNNN NNNNNNNNNN NNNNNNNNNN
130951 NNNNNNNNNN NNNNNNNNNN NNNNNNNNNN NNNNNNNNNN NNNNNNNNNN
131001 NNNNNNNNNN NNNNNNNNNN NNNNNNNNNN NNNNNNNNNN NNNNNNNNNN
131051 NNNNNNNNNN NNNNNNNNNN NNNNNNNNNN NNNNNNNNNN NNNNNNNNNN
131101 NNNNNNNNNN NNNNNNNNNN NNNNNNNNNN NNNNNNNNNN NNNNNNNNNN
131151 NNNNNNNNNN NNNNNNNNNN NNNNNNNNNN NNNNNNNNNN NNNNNNNNNN
131201 NNNNNNNNNN NNNNNNNNNN NNNNNNNNNN NNNNNNNNNN NNNNNNNNNN
131251 NNNNNNNNNN NNNNNNNNNN NNNNNNNNNN NNNNNNNNNN NNNNNNNNNN
131301 NNNNNNNNNN NNNNNNNNNN NNNNNNNNNN NNNNNNNNNN NNNNNNNNNN
131351 NNNNNNNNNN NNNNNNNNNN NNNNNNNNNN NNNNNNNNNN NNNNNNNNNN
131401 NNNNNNNNNN NNNNNNNNNN NNNNNNNNNN NNNNNNNNNN NNNNNNNNNN
131451 NNNNNNNNNN NNNNNNNNNN NNNNNNNNNN NNNNNNNNNN NNNNNNNNNN
131501 NNNNNNNNNN NNNNNNNNNN NNNNNNNNNN NNNNNNNNNN NNNNNNNNNN
131551 NNNNNNNNNN NNNNNNNNNN NNNNNNNNNN NNNNNNNNNN NNNNNNNNNN
131601 NNNNNNNNNN NNNNNNNNNN NNNNNNNNNN NNNNNNNNNN NNNNNNNNNN
131651 NNNNNNNNNN NNNNNNNNNN NNNNNNNNNN NNNNNNNNNN NNNNNNNNNN
131701 NNNNNNNNNN NNNNNNNNNN NNNNNNNNNN NNNNNNNNNN NNNNNNNNNN
131751 NNNNNNNNNN NNNNNNNNNN NNNNNNNNNN NNNNNNNNNN NNNNNNNNNN
131801 NNNNNNNNNN NNNNNNNNNN NNNNNNNNNN NNNNNNNNNN NNNNNNNNNN
131851 NNNNNNNNNN NNNNNNNNNN NNNNNNNNNN NNNNNNNNNN NNNNNNNNNN
131901 NNNNNNNNNN NNNNNNNNNN NNNNNNNNNN NNNNNNNNNN NNNNNNNNNN
131951 NNNNNNNNNN NNNNNNNNNN NNNNNNNNNN NNNNNNNNNN NNNNNNNNNN
132001 NNNNNNNNNN NNNNNNNNNN NNNNNNNNNN NNNNNNNNNN NNNNNNNNNN
132051 NNNNNNNNNN NNNNNNNNNN NNNNNNNNNN NNNNNNNNNN NNNNNNNNNN
132101 NNNNNNNNNN NNNNNNNNNN NNNNNNNNNN NNNNNNNNNN NNNNNNNNNN
132151 NNNNNNNNNN NNNNNNNNNN NNNNNNNNNN NNNNNNNNNN NNNNNNNNNN
132201 NNNNNNNNNN NNNNNNNNNN NNNNNNNNNN NNNNNNNNNN NNNNNNNNNN
132251 NNNNNNNNNN NNNNNNNNNN NNNNNNNNNN NNNNNNNNNN NNNNNNNNNN
132301 NNNNNNNNNN NNNNNNNNNN NNNNNNNNNN NNNNNNNNNN NNNNNNNNNN
132351 NNNNNNNNNN NNNNNNNNNN NNNNNNNNNN NNNNNNNNNN NNNNNNNNNN
132401 NNNNNNNNNN NNNNNNNNNN NNNNNNNNNN NNNNNNNNNN NNNNNNNNNN
132451 NNNNNNNNNN NNNNNNNNNN NNNNNNNNNN NNNNNNNNNN NNNNNNNNNN

FIGURE 3XX

132501 NNNNNNNNNN NNNNNNNNNN NNNNNNNNNN NNNNNNNNNN NNNNNNNNNN
132551 NNNNNNNNNN NNNNNNNNNN NNNNNNNNNN NNNNNNNNNN NNNNNNNNNN
132601 NNNNNNNNNN NNNNNNNNNN NNNNNNNNNN NNNNNNNNNN NNNNNNNNNN
132651 NNNNNNNNNN NNNNNNNNNN NNNNNNNNNN NNNNNNNNNN NNNNNNNNNN
132701 NNNNNNNNNN NNNNNNNNNN NNNNNNNNNN NNNNNNNNNN NNNNNNNNNN
132751 NNNNNNNNNN NNNNNNNNNN NNNNNNNNNN NNNNNNNNNN NNNNNNNNNN
132801 NNNNNNNNNN NNNNNNNNNN NNNNNNNNNN NNNNNNNNNN NNNNNNNNNN
132851 NNNNNNNNNN NNNNNNNNNN NNNNNNNNNN NNNNNNNNNN NNNNNNNNNN
132901 NNNNNNNNNN NNNNNNNNNN NNNNNNNNNN NNNNNNNNNN NNNNNNNNNN
132951 NNNNNNNNNN NNNNNNNNNN NNNNNNNNNN NNNNNNNNNN NNNNNNNNNN
133001 NNNNNNNNNN NNNNNNNNNN NNNNNNNNNN NNNNNNNNNN NNNNNNNNNN
133051 NNNNNNNNNN NNNNNNNNNN NNNNNNNNNN NNNNNNNNNN NNNNNNNNNN
133101 NNNNNNNNNN NNNNNNNNNN NNNNNNNNNN NNNNNNNNNN NNNNNNNNNN
133151 NNNNNNNNNN NNNNNNNNNN NNNNNNNNNN NNNNNNNNNN NNNNNNNNNN
133201 NNNNNNNNNN NNNNNNNNNN NNNNNNNNNN NNNNNNNNNN NNNNNNNNNN
133251 NNNNNNNNNN NNNNNNNNNN NNNNNNNNNN NNNNNNNNNN NNNNNNNNNN
133301 NNNNNNNNNN NNNNNNNNNN NNNNNNNNNN NNNNNNNNNN NNNNNNNNNN
133351 NNNNNNNNNN NNNNNNNNNN NNNNNNNNNN NNNNNNNNNN NNNNNNNNNN
133401 NNNNNNNNNN NNNNNNNNNN NNNNNNNNNN NNNNNNNNNN NNNNNNNNNN
133451 NNNNNNNNNN NNNNNNNNNN NNNNNNNNNN NNNNNNNNNN NNNNNNNNNN
133501 NNNNNNNNNN NNNNNNNNNN NNNNNNNNNN NNNNNNNNNN NNNNNNNNNN
133551 NNNNNNNNNN NNNNNNNNNN NNNNNNNNNN NNNNNNNNNN NNNNNNNNNN
133601 NNNNNNNNNN NNNNNNNNNN NNNNNNNNNN NNNNNNNNNN NNNNNNNNNN
133651 NNNNNNNNNN NNNNNNNNNN NNNNNNNNNN NNNNNNNNNN NNNNNNNNNN
133701 NNNNNNNNNN NNNNNNNNNN NNNNNNNNNN NNNNNNNNNN NNNNNNNNNN
133751 NNNNNNNNNN NNNNNNNNNN NNNNNNNNNN NNNNNNNNNN NNNNNNNNNN
133801 NNNNNNNNNN NNNNNNNNNN NNNNNNNNNN NNNNNNNNNN NNNNNNNNNN
133851 NNNNNNNNNN NNNNNNNNNN NNNNNNNNNN NNNNNNNNNN NNNNNNNNNN
133901 NNNNNNNNNN NNNNNNNNNN NNNNNNNNNN NNNNNNNNNN NNNNNNNNNN
133951 NNNNNNNNNN NNNNNNNNNN NNNNNNNNNN NNNNNNNNNN NNNNNNNNNN
134001 NNNNNNNNNN NNNNNNNNNN NNNNNNNNNN NNNNNNNNNN NNNNNNNNNN
134051 NNNNNNNNNN NNNNNNNNNN NNNNNNNNNN NNNNNNNNNN NNNNNNNNNN
134101 NNNNNNNNNN NNNNNNNNNN NNNNNNNNNN NNNNNNNNNN NNNNNNNNNN
134151 NNNNNNNNNN NNNNNNNNNN NNNNNNNNNN NNNNNNNNNN NNNNNNNNNN
134201 NNNNNNNNNN NNNNNNNNNN NNNNNNNNNN NNNNNNNNNN NNNNNNNNNN
134251 NNNNNNNNNN NNNNNNNNNN NNNNNNNNNN NNNNNNNNNN NNNNNNNNNN
134301 NNNNNNNNNN NNNNNNNNNN NNNNNNNNNN NNNNNNNNNN NNNNNNNNNN
134351 NNNNNNNNNN NNNNNNNNNN NNNNNNNNNN NNNNNNNNNN NNNNNNNNNN
134401 NNNNNNNNNN NNATTGCTTT ATTTTTCTAA ATAAATAGAC ATCTCCCCCC
134451 AAATCTCCAA GGTTCAGACC TTCTAATCAG TAATATATTT TCAGGGCATT
134501 CTTCCTTTTA TGCTTTTAGA AAGATGTAAT AGACTTTCTT TTAGATGCTG
134551 TTCAAGTACT TAATCTTTTC TTGTCTTGCC TTTTTATCTC TGTAATCTTC
134601 TTGAATAAGC AGTTAATTTT TTTTATTCAT GAACCTGCTG ATCATGTCTA
134651 AGAATGTATC TCCACTTAAG TAAGTCAGTG AATGGTGATT ACCTGAGTAG
134701 AGTTAAAGTA GTCCCCCACC CTCCTATCTG TGGCACATAT GTTCCAAGTC
134751 TCCCAGTGGA TGTGTGAAAC TGATGATAGT ACTGAAACCC ATCTACCTTT
134801 TTTCCTGTGC ATACATACCT ATGTTATATA AAGCTTAACT TATAAATTAG
134851 GCATAATATA TTTGACTCCC AGCTCCCAGT GTAGTGGCTC TGCAGACTCA
134901 CAAAATGTAT TTGCTTTAAA AAATTCTTTT TTTTTTTTTT GAGACGGAGT
134951 TTTGCTCTTG TTGCCCAGGC TGGAGTGCAG TGGTGCGACC TCAGCTCACT
135001 GCAACCTCCG CCTCTTGGGT TCAAGCGATT CTCCTGCCTC AGCCTCCCAA
135051 GTAGCTGGGA TTATAGGCAT GCACCACCAC ACCCAGCTAA TTTTCTATTT
135101 TTCGTAGAAA CGGTTTTTCC ATGTTGGTCA GGCTGATCTT GAACTCCTGA

FIGURE 3YY

135151 CCTCAGGTGA TCTGCCTGCC TCGGCCTTCC AAAGTGCTGG GATTACAGGT
135201 GTGAGCCACC ACGCCTGGCC AAAAAATTCT TTTAATTTAA GTAAATCTTT
135251 ATTTATTTAC TTTTGAGACA GAGTCTCACT CTGTGGGCCA GGCAGGAATG
135301 CAGTGGTGTG ATCACGGCTC ACTGCAGCCT CGACCTCCCA TGCTCAAGCA
135351 GTCCTCCCAC CTCAGCCTCC TAAGTAGCTA GGACTACAGG TGTGTGCCAT
135401 CACACTCTGC TAATTTTTTT GTATTTGTAG AGACGCGGTT TCACCAGGTT
135451 GCCCAGGCTG GTCTTGAACT CCTGAGCTCA AGTGATCCTC CTGCTTTGGC
135501 CTCCCAAAAT ACTGGGATTA CAGGCGTGAG CCATTGCACC CAGCCCTAAT
135551 TTTAATAAAT CTTTTATTTT GGAATAGTAT TAGATTTATA GAAAAGTTGC
135601 AAAGATAGTA TGGAAGAGTT CCCACATACC CTTCACCCAG TTTTCCCCAA
135651 NNNNNNNNNN NNNNNNNNNN NNNNNNNNNN NNNNNNNNNN NNNNNNNNNN
135701 TATTTATTTA TTTATTTTTT GAGACACAGT CTTCCCGTCG CCCAGGCTGG
135751 AGTGTGGTGG CACGATCTCG GCTCACTGCA ACCTCCGCCT CCTGGGTTCA
135801 AGTGATTCTT CTGCCTCAGC CTCCGAGTAG CTGGGACCAC AGGTGTGCGC
135851 CACCATGCCC GGCTACTTTT TGTATTTTCA GTAGAGACAG GGTTTCACCA
135901 TGTTGGTCAG GCTGATCTCA AGCTCCTGAC CTCAGGTGAT CTGCCTACCT
135951 TAGCCTCCCA AAGTGCTGGG ATTACAGACA TGAGCCACCG CACCCAGCCC
136001 CCAGTGTTAA CTCTTACATA ACAGTGTCAC TGTCTAAGTG TTTGAAAAAC
136051 TATTTGTCAA AACTAATATT GGTACATTAT TGTTAACTAC ACTTCAGACT
136101 TTTTTTGGAT TTTACCAATT CTCCCACTCA TGTCCCTTTT CTGTTTCAGG
136151 AATCAATCCG TGGTACCATA TTGCAGTTAG GGTGTTTATA TTTGATGGGA
136201 CTGGTCCTAG TTTAGATACT TAGTGTAGCT CAGCCAGCAG GTGGGATCTT
136251 CATGCCCACC GAGGATTGGT ATTGTGTTTT CCTGGTGGTT TTATGGCATT
136301 TCCGACTATG CAGAGAGGCA TGGTATTAAC TTCAGTGTCT CCTAGCAAAT
136351 TTTCCTGTTT TTCACCAACC TCTGATCCCT GCATTATTTG CAATCAACTC
136401 AGAGATTTGT GATTGAAAAC ATTGCTTGAC TCCATGCTCT TTAAGCTATT
136451 TTCTAACTAG GTAACTGTAA CATAAATTAT GCTTTTATCT AGCACTGTTT
136501 TTCATAAACA CATGTTGAGT GATTTTCATC AACCGAAATA CTTCGAATCA
136551 TTAAGTTTCC CAAGTTCATG GATGCTGCTT AAATGCCTGG TGGTTCCAGG
136601 CTGTCGAATA TTTCTGCCTT CTGCAATAAG AGATTGTCCC TTGTTAAAAG
136651 CAACATTAGC CTTTGTGCGG TTTCACCCCC AATTCTTCTT TTTCTTGTTG
136701 TAACCAATGA AAGGAAGTAC TGCTTAACAC AGCAGGTAAT AATCTTCTAA
136751 AACTCATTAT CTCAAGAGGT GGTCCTGGCA GGATATATAA ATGCAATTTA
136801 AGAAAGGTCT TGGCAAATTT ATGAATGACA GAACTGGGAG TGGCTACCGA
136851 GAGAAACTAG GATGCGCCTT TGCTTTGACA CTGAGGTCAG GCGTAGCTTC
136901 TGTACCCTCC TGGGTCCTGC CTCTTGGGGT TGCTGCAGGC AGCACCCCAT
136951 GAACCAGGCA TCTGACCCAG TTCCAGGATA CTTATTCTTC CAGCAAGTCG
137001 AACACTCTGT GATGAGTGAC TGCCATGCTC ATGGGTCACC AGGCTCTCAT
137051 TATTCTGTTT CATTTCCAGC CTCCCACAAG ATTGGTTTTT CAGCTGCTTA
137101 TTTATTATTA TCATTATTTC AAGGCTGCTT TCCAAGTTTC AGTGGGGGGT
137151 TTCCTAAGCG TACCAGCTGC CCTGGTTGTG CAGTTCCGGT GATGTTTCAG
137201 ATGCTGGGCC GGATTCTGGC TGTACCCAGC CTGATCTTTC TGGGCTTCAG
137251 GAAAGCTGAA GCCAATCAGA GCTCCTCTTT CATGCCTTTG GGATTATGCT
137301 TACCTTGCCT GGCATCGTGT ACCTGCTCCC ATCCATGGGA AAGTTTTGCT
137351 GTCTGGTACT GTCTTCTATC AACATCTTTT AAGATATCTT CCCCCGAGGC
137401 ATCGTGATGT CAACGGAACC AGCACACTTG TACGTTTTAT GCAAGACTGC
137451 CATATCTCAA CAGTGAGAAA TGCATAATGG AAGTGGTGAT CACGGATTAT
137501 TTCCTAGGAC ATTATGGCTA ATGCGCTAGA GAACTCGGAT GGTCTGTTGC
137551 GTCTGACATG GGCTTTTTCT CTTGAGTTGT CTTTCTTTTG CTATTCTCTG
137601 AAAGAAACAA TTCTTGCCAC ATGATCCTGA TTTTTCAGGT CCTCAGCATT
137651 TGTTAGCAGA AAGTACACTT TGTTTCCATC CGGCAGTGAC TCAGTGGTGG
137701 TCCCATGCTG ATGAAACGCT GAGATAGTCT TCTTCCAAAT AGGTATCGTT
137751 TTGATTGTTG CTGCTTATTT GCTAGCTGGC CCTCAATAGT GACAATGAAA

FIGURE 3ZZ

137801 CCTCAAGTGT ATAATATGGT TGCTCAGTAA TCCTGAGGGA AGACAGTCTT
137851 TGGTTTGGGG GATAGGGATT CTGTGCCTAC TTAGCTTCAG GTGAAAGTCT
137901 TACAAATTTT TGTGTGTAGA AATAAGCACC ATGTACCTCC TTGGGTTTTT
137951 TCTTTTTTTT TCTAGTCCTT TAGTATGGTC AACAATATTG TTTAGGGAGT
138001 ACCTATTCTG TGCTAACCAC TAGGCATTCA AGTATATTAC ACTATGCTCC
138051 TTCAAAACAC TTCTGTCAAA TGTAAGGATT ATTATACCCA TTTTACAGAT
138101 GTGGTTACTG TGGTAACTTG GCCAAGGTCA TAGGGCAAGT GAATAAGGGA
138151 TTCTGGATTT GGGTGGAGGT CTGTGTGATT CCAAAGCCCA TGCTCTTTCT
138201 ACAATACTAT ATATGCCTTT GCATAAGTTA TTGTTATTAG TAATAATATT
138251 TGTGATGATG GCAAATAATA AACCATGTCA CACTAGAGAG TGATTTAATC
138301 TCTAGGTCTA TTTAAGAACA TTTGGAATTG CAGGAATTGG ATTTTTTTTT
138351 TTTTTTAAGT GATGGAGTCT TGCCATCTTT GCCCAGGCTG GTCTCAAACT
138401 TGTGGGCTCA AGTGATCATC CTCCCTCTGC CTCCCAAAGT GATGGGATTA
138451 CAGATATGAG CCACCATGCC CAGCCTAGAA TTGCAGGAAT TTTTGAATTG
138501 ATGATTCATT CTGATATTTG AATTTCTACA GTATGTTAAG TGCAATGTCA
138551 GGTGCTGGTG CTGTGGCTCC ATTGATGAAC ACATTTGGGT ATGGCCCTAC
138601 CTTCATTGAA TTTAGAGTCT AAGAGCCTAA CCGGTCTTTT GCTTGAATAG
138651 AGCTGTAGTC CTGTTAAATT GCTGTACCTC CAAATGGTGG GAAGTTTAAT
138701 GCTTCGTAGG CCTCCCCTCA CTAGTTTACT GAACCACATG TGCTTGATTT
138751 TTTTTTGANN NNNNNNNNNN NNNNNNNNNN NNNNNNNNNN NNNNNNNNNN
138801 NNNNNNNNNN NNNNNNNNNN NNNNNNNNNN CTCACTGCAA GCTCCGCCTC
138851 CCAGGTTCAC GCCATTCTTC TGCCTCAGCC TCCCGAGTAG CTGGGACTAC
138901 AGGTGCCCGC CAACACGGCC CGGCTAATTT TTTTGTATTT TTAGTAGAGA
138951 CAGGGTTTTA CCATGTTAGC CAGGATGGTC TCGGTCTGCT GACCTCGTGA
139001 TCCACCTGCC TCAGCCTCCC AAAGTGCTGG GATTACAGGC ATGAGCCACT
139051 GTGCCTGGCC CCACATGTGC TTGATTTTAA GCAAAATACA GACTATAGGC
139101 TGTGACCTGG TGATCTCTTC CCCACATACA GCATCCTGCT AACCTATAAC
139151 TCTCCCCATG TCTCAGATCT AGCCTGGGAA AGGACAATGT TGGATCGATG
139201 GCCCACTTCT AATCTTGGGA TTTCTAATCT CAAGATGAGT TGAGAAGACT
139251 CAGGATGTGT CCTGTTTTCT GTTTATTTAG AACAGGGTTT CTCAGCCTTG
139301 GCACTGTTGA CATTTGGGGC CAGATAATTC TTTGCTGTGG GGGCTGTTGT
139351 GTGAATTGCA GGATGTTGAA CAGCATCGCT GTGCTTTCTC CATGGATACC
139401 AGTAGCACCC TCCCCCTGCA GTTGCAACAA CCAAAAATGA CTCTAGACAT
139451 TGCCCAGTCT CCCCTTGGGG GCTACAGTCA CCTTCAGTTG AGAACCATTG
139501 ATTTAGAAGA ATTGGCCAGG TTATTATCAG GAGAGGGAAC ATCACAGTAA
139551 TCTGAATCTC TCAATACTGC CACTGTTACT GTTAACGAAC AGCAAAACTA
139601 TTACGTGGAG GCAGTAGGAC CTTGCTACTC AGAGTGTGGT CCGTGGACCG
139651 GCAGCATCGG AATCATCTAG GAGCTTGTTA GAGCTTCAGA GACTCAGGCC
139701 TACTGAGTCA GAAGCTGCAT TTTAATAAGG ATCCCCAGGG GATTTCTGTG
139751 CATATTAGAG TTGTGAAGCC CTGCAAGAGG AAGAAATTGG ATGCTAGCCT
139801 CAGAGTTTCT TGCTCATCTT TGTGGGTCTT CCTACGTTTT GTCTTCGGGC
139851 TTAAGGTATG GGGAGGCCAC TTTTTGGCTC AGGACTCCTA TGGGTGAATG
139901 GGACTGCTTA GAACTGCTGG GTTTTAGGCC TTGCTTTGAG GAATTTAAAG
139951 CTTTTCTCTT AGATGGACAT TACATCGTTC ATATACTTCA AAATGGTGGT
140001 TTGACCTAAT CTCTGCCTTC TGATAGCAAA AAGATATTTC CTTGACTCCC
140051 TGAACCCCAC TTTACTGTTG TCCCATATTG GATTTTAATT AAGGGTGGAA
140101 TAAGTATTCT TCACTAACAT GTTTATACAT GTATGATATT ACCATGCCAT
140151 TTATTGAGTG CCTAGTATGT GCCAGGAGCT CTGCAAAGTG CTTTATGCTT
140201 ATTATTGTTC CATTTATTCT TCCCCAAACC TCTGTGAGGC AGGTCCTATC
140251 ACTAGTCCAC AATACAAATG AGGTCATGGA GCCCGAAGTT GGCAGTGGTA
140301 GGAATCAAAC TCAGGTCTCC CTGACTCTAA ATTCTCTTTG CCTTTGTTTT
140351 TTTGAAAAAG TGGTATAGCC CATAGCAGAA AATTCACATT ATACAGAAGG
140401 TTATACGGCG AAAAATGCCT CCTTCCCACC CCACGCTCAA CCCCTCTCCC

FIGURE 3AAA

140451 TCAAGCGGAA CCACTATTGT CAGTTTCTCA TAGAACTTTC CAGAATATTC
140501 TATGCTCCTA TAACACTAGC ACAACCTATC CTCTTAACAA CATCTTTATG
140551 CTGCCTCCCA AGAATTCAGT AATTTTTTTT TTTTTGAGAT GGAGTTTTGC
140601 TCTAGTTGCC CAGGCTGGAG TGCAATGGCG TGATCTCGGC TCATTGCAAC
140651 CTCTGCCTCC CACGTTCAAG TGATTCTCTT GCCTCAGCCT CCCGAGTAGC
140701 TGGGATTACA GGCATGCGCC ACTATGCTTG GCTAATTTTG TATTTTTAGT
140751 AGAGATGGGG TTTCTCCCAT GTTGGTCAGG CTGGTCTTGA ACTCCCAACC
140801 TCAGGTAATC CGCCCACCTC GGCCTCCCAA AGTGTTGAGA TTACAGGCGT
140851 GAGCCACCGC ACCTGGCCAA ATTCAGTAAT TTTTATTGGC AGGTTATTTT
140901 CCCGCATCAT TNNNNNNNNN NNNNNNNNNN NNNNNNNNNN NNNNNNNNNN
140951 NNNNNNNNNN NNNNNNNNNN NNNNNNNNNN NNNNNNNNNN NNNNNNNNNN
141001 NNNNNNNNNN NNNNNNNNNN NNNNNNNNNN NNNNNNNNNN NNNNNNNNNN
141051 NNNNNNNNNN NNNNNNNNNN NNNNNNNNNN NNNNNNNNNN NNNNNNNNNN
141101 NNNNNNNNNN NNNNNNNNNN NNNNNNNNNN NNNNNNNNNN NNNNNNNNNN
141151 NNNNNNNNNN NNNNNNNNNN NNNNNNNNNN NNNNNNNNNN NNNNNNNNNN
141201 NNNNNNNNNN NNNNNNNNNN NNNNNNNNNN NNNNNNNNNN NNNNNNNNNN
141251 NNNNNNNNNN NNNNNNNNNN NNNNNNNNNN NNNNNNNNNN NNNNNNNNNN
141301 NNNNNNNNNN NNNNNNNNNN NNNNNNNNNN NNNNNNNNNN NNNNNNNNNN
141351 NNNNNNNNNN NNNNNNNNNN NNNNNNNNNN NNNNNNNNNN NNNNNNNNNN
141401 NNNNNNNNNN NNNNNNNNNN NNNNNNNNNN NNNNNNNNNN NNNNNNNNNN
141451 NNNNNNNNNN NNNNNNNNNN NNNNNNNNNN NNNNNNNNNN NNNNNNNNNN
141501 NNNNNNNNNN NNNNNNNNNN NNNNNNNNNN NNNNNNNNNN NNNNNNNNNN
141551 NNNNNNNNNN NNNNNNNNNN NNNNNNNNNN NNNNNNNNNN NNNNNNNNNN
141601 NNNNNNNNNN NNNNNNNNNN NNNNNNNNNN NNNNNNNNNN NNNNNNNNNN
141651 NNNNNNNNNN NNNNNNNNNN NNNNNNNNNN NNNNNNNNNN NNNNNNNNNN
141701 NNNNNNNNNN NNNNNNNNNN NNNNNNNNNN NNNNNNNNNN NNNNNNNNNN
141751 NNNNNNNNNN NNNNNNNNNN NNNNNNNNNN NNNNNNNNNN NNNNNNNNNN
141801 NNNNNNNNNN NNNNNNNNNN NNNNNNNNNN NNNNNNNNNN NNNNNNNNNN
141851 NNNNNNNNNN NNNNNNNNNN NNNNNNNNNN NNNNNNNNNN NNNNNNNNNN
141901 NNNNNNNNNN NNNNNNNNNN NNNNNNNNNN NNNNNNNNNN NNNNNNNNNN
141951 NNNNNNNNNN NNNNNNNNNN NNNNNNNNNN NNNNNNNNNN NNNNNNNNNN
142001 NNNNNNNNNN NNNNNNNNNN NNNNNNNNNN NNNNNNNNNN NNNNNNNNNN
142051 NNNNNNNNNN NNNNNNNNNN NNNNNNNNNN NNNNNNNNNN NNNNNNNNNN
142101 NNNNNNNNNN NNNNNNNNNN NNNNNNNNNN NNNNNNNNNN NNNNNNNNNN
142151 NNNNNNNNNN NNNNNNNNNN NNNNNNNNNN NNNNNNNNNN NNNNNNNNNN
142201 NNNNNNNNNN NNNNNNNNNN NNNNNNNNNN NNNNNNNNNN NNNNNNNNNN
142251 NNNNNNNNNN NNNNNNNNNN NNNNNNNNNN NNNNNNNNNN NNNNNNNNNN
142301 NNNNNNNNNN NNNNNNNNNN NNNNNNNNNN NNNNNNNNNN NNNNNNNNNN
142351 NNNNNNNNNN NNNNNNNNNN NNNNNNNNNN NNNNNNNNNN NNNNNNNNNN
142401 NNNNNNNNNN NNNNNNNNNN NNNNNNNNNN NNNNNNNNNN NNNNNNNNNN
142451 NNNNNNNNNN NNNNNNNNNN NNNNNNNNNN NNNNNNNNNN NNNNNNNNNN
142501 NNNNNNNNNN NNNNNNNNNN NNNNNNNNNN NNNNNNNNNN NNNNNNNNNN
142551 NNNNNNNNNN NNNNNNNNNN NNNNNNNNNN NNNNNNNNNN NNNNNNNNNN
142601 NNNNNNNNNN NNNNNNNNNN NNNNNNNNNN NNNNNNNNNN NNNNNNNNNN
142651 NNNNNNNNNN NNNNNNNNNN NNNNNNNNNN NNNNNNNNNN NNNNNNNNNN
142701 NNNNNNNNNN NNNNNNNNNN NNNNNNNNNN NNNNNNNNNN NNNNNNNNNN
142751 NNNNNNNNNN NNNNNNNNNN NNNNNNNNNN NNNNNNNNNN NNNNNNNNNN
142801 NNNNNNNNNN NNNNNNNNNN NNNNNNNNNN NNNNNNNNNN NNNNNNNNNN
142851 NNNNNNNNNN NNNNNNNNNN NNNNNNNNNN NNNNNNNNNN NNNNNNNNNN
142901 NNNNNNNNNN NNNNNNNNNN NNNNNNNNNN NNNNNNNNNN NNNNNNNNNN
142951 NNNNNNNNNN NNNNNNNNNN NNNNNNNNNN NNNNNNNNNN NNNNNNNNNN
143001 NNNNNNNNNN NNNNNNNNNN NNNNNNNNNN NNNNNNNNNN NNNNNNNNNN
143051 NNNNNNNNNN NNNNNNNNNN NNNNNNNNNN NNNNNNNNNN NNNNNNNNNN

FIGURE 3BBB

143101 NNNNNNNNNN NNNNNNNNNN NNNNNNNNNN NNNNNNNNNN NNNNNNNNNN
143151 NNNNNNNNNN NNNNNNNNNN NNNNNNNNNN NNNNNNNNNN NNNNNNNNNN
143201 NNNNNNNNNN NNNNNNNNNN NNNNNNNNNN NNNNNNNNNN NNNNNNNNNN
143251 NNNNNNNNNN NNNNNNNNNN NNNNNNNNNN NNNNNNNNNN NNNNNNNNNN
143301 NNNNNNNNNN NNNNNNNNNN NNNNNNNNNN NNNNNNNNNN NNNNNNNNNN
143351 NNNNNNNNNN NNNNNNNNNN NNNNNNNNNN NNNNNNNNNN NNNNNNNNNN
143401 NNNNNNNNNN NNNNNNNNNN NNNNNNNNNN NNNNNNNNNN NNNNNNNNNN
143451 NNNNNNNNNN NNNNNNNNNN NNNNNNNNNN NNNNNNNNNN NNNNNNNNNN
143501 NNNNNNNNNN NNNNNNNNNN NNNNNNNNNN NNNNNNNNNN NNNNNNNNNN
143551 NNNNNNNNNN NNNNNNNNNN NNNNNNNNNN NNNNNNNNNN NNNNNNNNNN
143601 NNNNNNNNNN NNNNNNNNNN NNNNNNNNNN NNNNNNNNNN NNNNNNNNNN
143651 NNNNNNNNNN NNNNNNNNNN NNNNNNNNNN NNNNNNNNNN NNNNNNNNNN
143701 NNNNNNNNNN NNNNNNNNNN NNNNNNNNNN NNNNNNNNNN NNNNNNNNNN
143751 NNNNNNNNNN NNNNNNNNNN NNNNNNNNNN NNNNNNNNNN NNNNNNNNNN
143801 NNNNNNNNNN NNNNNNNNNN NNNNNNNNNN NNNNNNNNNN NNNNNNNNNN
143851 NNNNNNNNNN NNNNNNNNNN NNNNNNNNNN NNNNNNNNNN NNNNNNNNNN
143901 NNNNNNNNNN NNNNNNNNNN NNNNNNNNNN NNNNNNNNNN NNNNNNNNNN
143951 NNNNNNNNNN NNNNNNNNNN NNNNNNNNNN NNNNNNNNNN NNNNNNNNNN
144001 NNNNNNNNNN NNNNNNNNNN NNNNNNNNNN NNNNNNNNNN NNNNNNNNNN
144051 NNNNNNNNNN NNNNNNNNNN NNNNNNNNNN NNNNNNNNNN NNNNNNNNNN
144101 NNNNNNNNNN NNNNNNNNNN NNNNNNNNNN NNNNNNNNNN NNNNNNNNNN
144151 NNNNNNNNNN NNNNNNNNNN NNNNNNNNNN NNNNNNNNNN NNNNNNNNNN
144201 NNNNNNNNNN NNNNNNNNNN NNNNNNNNNN NNNNNNNNNN NNNNNNNNNN
144251 NNNNNNNNNN NNNNNNNNNN NNNNNNNNNN NNNNNNNNNN NNNNNNNNNN
144301 NNNNNNNNNN NNNNNNNNNN NNNNNNNNNN NNNNNNNNNN NNNNNNNNNN
144351 NNNNNNNNNN NNNNNNNNNN NNNNNNNNNN NNNNNNNNNN NNNNNNNNNN
144401 NNNNNNNNNN NNNNNNNNNN NNNNNNNNNN NNNNNNNNNN NNNNNNNNNN
144451 NNNNNNNNNN NNNNNNNNNN NNNNNNNNNN NNNNNNNNNN NNNNNNNNNN
144501 NNNNNNNNNN NNNNNNNNNN NNNNNNNNNN NNNNNNNNNN NNNNNNNNNN
144551 NNNNNNNNNN NNNNNNNNNN NNNNNNNNNN NNNNNNNNNN NNNNNNNNNN
144601 NNNNNNNNNN NNNNNNNNNN NNNNNNNNNN NNNNNNNNNN NNNNNNNNNN
144651 NNNNNNNNNN NNNNNNNNNN NNNNNNNNNN NNNNNNNNNN NNNNNNNNNN
144701 NNNNNNNNNN NNNNNNNNNN NNNNNNNNNN NNNNNNNNNN NNNNNNNNNN
144751 NNNNNNNNNN NNNNNNNNNN NNNNNNNNNN NNNNNNNNNN NNNNNNNNNN
144801 NNNNNNNNNN NNNNNNNNNN NNNNNNNNNN NNNNNNNNNN NNNNNNNNNN
144851 NNNNNNNNNN NNNNNNNNNN NNNNNNNNNN NNNNNNNNNN NNNNNNNNNN
144901 NNNNNNNNNN NNNNNNNNNN NNNNNNNNNN NNNNNNNNNN NNNNNNNNNN
144951 NNNNNNNNNN NNNNNNNNNN NNNNNNNNNN NNNNNNNNNN NNNNNNNNNN
145001 NNNNNNNNNN NNNNNNNNNN NNNNNNNNNN NNNNNNNNNN NNNNNNNNNN
145051 NNNNNNNNNN NNNNNNNNNN NNNNNNNNNN NNNNNNNNNN NNNNNNNNNN
145101 NNNNNNNNNN NNNNNNNNNN NNNNNNNNNN NNNNNNNNNN NNNNNNNNNN
145151 NNNNNNNNNN NNNNNNNNNN NNNNNNNNNN NNNNNNNNNN NNNNNNNNNN
145201 NNNNNNNNNN NNNNNNNNNN NNNNNNNNNN NNNNNNNNNN NNNNNNNNNN
145251 NNNNNNNNNN NNNNNNNNNN NNNNNNNNNN NNNNNNNNNN NNNNNNNNNN
145301 NNNNNNNNNN NNNNNNNNNN NNNNNNNNNN NNNNNNNNNN NNNNNNNNNN
145351 NNNNNNNNNN NNNNNNNNNN NNNNNNNNNN NNNNNNNNNN NNNNNNNNNN
145401 NNNNNNNNNN NNNNNNNNNN NNNNNNNNNN NNNNNNNNNN NNNNNNNNNN
145451 NNNNNNNNNN NNNNNNNNNN NNNNNNNNNN NNNNNNNNNN NNNNNNNNNN
145501 NNNNNNNNNN NNNNNNNNNN NNNNNNNNNN NNNNNNNNNN NNNNNNNNNN
145551 NNNNNNNNNN NNNNNNNNNN NNNNNNNNNN NNNNNNNNNN NNNNNNNNNN
145601 NNNNNNNNNN NNNNNNNNNN NNNNNNNNNN NNNNNNNNNN NNNNNNNNNN
145651 NNNNNNNNNN NNNNNNNNNN NNNNNNNNNN NNNNNNNNNN NNNNNNNNNN
145701 NNNNNNNNNN NNNNNNNNNN NNNNNNNNNN NNNNNNNNNN NNNNNNNNNN

FIGURE 3CCC

145751 NNNNNNNNNN NNNNNNNNNN NNNNNNNNNN NNNNNNNNNN NNNNNNNNNN
145801 NNNNNNNNNN NNNNNNNNNN NNNNNNNNNN NNNNNNNNNN NNNNNNNNNN
145851 NNNNNNNNNN NNNNNNNNNN NNNNNNNNNN NNNNNNNNNN NNNNNNNNNN
145901 NNNNNNNNNN NNNNNNNNNN NNNNNNNNNN NNNNNNNNNN NNNNNNNNNN
145951 NNNNNNNNNN NNNNNNNNNN NNNNNNNNNN NNNNNNNNNN NNNNNNNNNN
146001 NNNNNNNNNN NNNNNNNNNN NNNNNNNNNN NNNNNNNNNN NNNNNNNNNN
146051 NNNNNNNNNN NNNNNNNNNN NNNNNNNNNN NNNNNNNNNN NNNNNNNNNN
146101 NNNNNNNNNN NNNNNNNNNN NNNNNNNNNN NNNNNNNNNN NNNNNNNNNN
146151 NNNNNNNNNN NNNNNNNNNN NNNNNNNNNN NNNNNNNNNN NNNNNNNNNN
146201 NNNNNNNNNN NNNNNNNNNN NNNNNNNNNN NNNNNNNNNN NNNNNNNNNN
146251 NNNNNNNNNN NNNNNNNNNN NNNNNNNNNN NNNNNNNNNN NNNNNNNNNN
146301 NNNNNNNNNN NNNNNNNNNN NNNNNNNNNN NNNNNNNNNN NNNNNNNNNN
146351 NNNNNNNNNN NNNNNNNNNN NNNNNNNNNN NNNNNNNNNN NNNNNNAATT
146401 CAAAACCTGT CTCCTGTTAA TCCCATCCTC TCTGTTTCTG TTATCATTTC
146451 CTTAGTGTAG ATCTGCCTAA GTGTAGAATT TGTAGAATTT GTCATGTTGA
146501 CTATTGTAGA CTTGTCTTTT AGAGTTTCTA GCACTAGCCT CTTCCACCCA
146551 TCACTATTGA GATGATTGTA TCCGTCTCAG TACTGACACT AACCCAGCAC
146601 TCTGGTTTTA CATCTGTCAA TCCATCAAGA CTTCACTTTC ACTTTCTTCC
146651 CTGCCTCATT ATTCACTATG CTCTTGGGCC ATTGCTCTGG CTTCTGGGGC
146701 TTTTCTAAAG TAGCACTTTT CCCCACTCCA GCCCATGAAG ATACCTTTTA
146751 ACCAGCTCTT GAGATTAAAT CCCCTCCGTG ACACTTTCCT GCAGGAACTT
146801 GCAAAAAAGT ACTGCATTCC CCACTGGCAA AACTTGCCAT CAGCCAGTTT
146851 ATGTATTCTC TGCTTTTCAC ACCCATATCT TGACCTCTGA ACAACACACA
146901 TATTCTCCTC TTCATTTATT TCACAGTTCT GTCTTCATAA CATTGATAAG
146951 TATGATCACA TTAGCGCTCT AGATTTTAAG CAACTGGAAG ATAGCTATTT
147001 TTTTGGTACT CTTCCTTTAA ATTTGAACAT AGTGTCTAAT TAGTCAATTA
147051 ACATTTTTTT AAAAGGGCGA GGGACATCAT GGTAGAGAGA ACGAAGTTGA
147101 ACGTGTTTTT GGTTGAATAT TAGCGCATGC CCACTGTATT CTAGGCACAG
147151 TCCTGATTCA TTATATCATC ACACAATAAT TATTTATGTG CCTTCATCCT
147201 TTATGACACA GTGCTGGCTC TTATTCATCT CCCATTTCTG CAATCCATGG
147251 TGATGATTAA AAGTCTTAGG AGTTTTACGA GGCTCAGTAT TTTTTTTTTT
147301 TAATATGCTA GTTCTTCATG AATACATTGG GTACTCTGAA GCATATCATT
147351 TCCTGGGTTT CCTGAAGTGG TATGTTGCGT GGAATGGCAC ATTAGGTCTA
147401 AATAATTATC CCCTATGTAA GGGGTCTTGT TTTTCATTCA TTCTCTTAAA
147451 AAATAGATAT TAAACATTAA ATAAGGACAG CCAGGNNNNN NNNNNNNNNN
147501 NNNNNNNNNN NNNNNNNNNN NNNNNNNNNN NNNNNNNNNN NNNNNNNNNN
147551 NNNNNNNNNN NNNNNNNNNN NNNNNNNNNN NNNNNNNNNN NNNNNNNNNN
147601 NNNNNNNNNN NNNNNNNNNN NNNNNNNNNN NNNNNNNNNN NNNNNNNNNN
147651 NNNNNNNNNN NNNNNNNNNN NNNNNNNNNN NNNNNNNNNN NNNNNNNNNN
147701 NNNNNNNNNN NNNNNNNNNN NNNNNNNNNN NNNNNNNNNN NNNNNNNNNN
147751 NNNNNNNNNN NNNNNNNNNN NNNNNNNNNN NNNNNNNNNN NNNNNNNNNN
147801 NNNNNNNNNN NNNNNNNNNN NNNNNNNNNN NNNNNNNNNN NNNNNNNNNN
147851 NNNNNNNNNN NNNNNNNNNN NNNNNNNNNN NNNNNNNNNN NNNNNNNNNN
147901 NNNNNNNNNN NNNNNNNNNN NNNNNNNNNN NNNNNNNNNN NNNNNNNNNN
147951 NNNNNNNNNN NNNNNNNNNN NNNNNNNNNN NNNNNNNNNN NNNNNNNNNN
148001 NNNNNNNNNN NNNNNNNNNN NNNNNNNNNN NNNNNNNNNN NNNNNNNNNN
148051 NNNNNNNNNN NNNNNNNNNN NNNNNNNNNN NNNNNNNNNN NNNNNNNNNN
148101 NNNNNNNNNN NNNNNNNNNN NNNNNNNNNN NNNNNNNNNN NNNNNNNNNN
148151 NNNNNNNNNN NNNNNNNNNN NNNNNNNNNN NNNNNNNNNN NNNNNNNNNN
148201 NNNNNNNNNN NNNNNNNNNN NNNNNNNNNN NNNNNNNNNN NNNNNNNNNN
148251 NNNNNNNNNN NNNNNNNNNN NNNNNNNNNN NNNNNNNNNN NNNNNNNNNN
148301 NNNNNNNNNN NNNNNNNNNN NNNNNNNNNN NNNNNNNNNN NNNNNNNNNN
148351 NNNNNNNNNN NNNNNNNNNN NNNNNNNNNN NNNNNNNNNN NNNNNNNNNN

FIGURE 3DDD

| | | | | | |
|---|---|---|---|---|---|
| 148401 | NNNNNNNNNN | NNNNNNNNNN | NNNNNNNNNN | NNNNNNNNNN | NNNNNNNNNN |
| 148451 | NNNNNNNNNN | NNNNNNNNNN | NNNNNNNNNN | NNNNNNNNNN | NNNNNNNNNN |
| 148501 | NNNNNNNNNN | NNNNNNNNNN | NNNNNNNNNN | NNNNNNNNNN | NNNNNNNNNN |
| 148551 | NNNNNNNNNN | NNNNNNNNNN | NNNNNNNNNN | NNNNNNNNNN | NNNNNNNNNN |
| 148601 | NNNNNNNNNN | NNNNNNNNNN | NNNNNNNNNN | NNNNNNNNNN | NNNNNNNNNN |
| 148651 | NNNNNNNNNN | NNNNNNNNNN | NNNNNNNNNN | NNNNNNNNNN | NNNNNNNNNN |
| 148701 | NNNNNNNNNN | NNNNNNNNNN | NNNNNNNNNN | NNNNNNNNNN | NNNNNNNNNN |
| 148751 | NNNNNNNNNN | NNNNNNNNNN | NNNNNNNNNN | NNNNNNNNNN | NNNNNNNNNN |
| 148801 | NNNNNNNNNN | NNNNNNNNNN | NNNNNNNNNN | NNNNNNNNNN | NNNNNNNNNN |
| 148851 | NNNNNNNNNN | NNNNNNNNNN | NNNNNNNNNN | NNNNNNNNNN | NNNNNNNNNN |
| 148901 | NNNNNNNNNN | NNNNNNNNNN | NNNNNNNNNN | NNNNNNNNNN | NNNNNNNNNN |
| 148951 | NNNNNNNNNN | NNNNNNNNNN | NNNNNNNNNN | NNNNNNNNNN | NNNNNNNNNN |
| 149001 | NNNNNNNNNN | NNNNNNNNNN | NNNNNNNNNN | NNNNNNNNNN | NNNNNNNNNN |
| 149051 | NNNNNNNNNN | NNNNNNNNNN | NNNNNNNNNN | NNNNNNNNNN | NNNNNNNNNN |
| 149101 | NNNNNNNNNN | NNNNNNNNNN | NNNNNNNNNN | NNNNNNNNNN | NNNNNNNNNN |
| 149151 | NNNNNNNNNN | NNNNNNNNNN | NNNNNNNNNN | NNNNNNNNNN | NNNNNNNNNN |
| 149201 | NNNNNNNNNN | NNNNNNNNNN | NNNNNNNNNN | NNNNNNNNNN | NNNNNNNNNN |
| 149251 | NNNNNNNNNN | NNNNNNNNNN | NNNNNNNNNN | NNNNNNNNNN | NNNNNNNNNN |
| 149301 | NNNNNNNNNN | NNNNNNNNNN | NNNNNNNNNN | NNNNNNNNNN | NNNNNNNNNN |
| 149351 | NNNNNNNNNN | NNNNNNNNNN | NNNNNNNNNN | NNNNNNNNNN | NNNNNNNNNN |
| 149401 | NNNNNNNNNN | NNNNNNNNNN | NNNNNNNNNN | NNNNNNNNNN | NNNNNNNNNN |
| 149451 | NNNNNNNNNN | NNNNNNNNNN | NNNNNNNNNN | NNNNNNNNNN | NNNNNNNNNN |
| 149501 | NNNNNNNNNN | NNNNNNNNNN | NNNNNNNNNN | NNNNNNNNNN | NNNNNNNNNN |
| 149551 | NNNNNNNNNN | NNNNNNNNNN | NNNNNNNNNN | NNNNNNNNNN | NNNNNNNNNN |
| 149601 | NNNNNNNNNN | NNNNNNNNNN | NNNNNNNNNN | NNNNNNNNNN | NNNNNNNNNN |
| 149651 | NNNNNNNNNN | NNNNNNNNNN | NNNNNNNNNN | NNNNNNNNNN | NNNNNNNNNN |
| 149701 | NNNNNNNNNN | NNNNNNNNNN | NNNNNNNNNN | NNNNNNNNNN | NNNNNNNNNN |
| 149751 | NNNNNNNNNN | NNNNNNNNNN | NNNNNNNNNN | NNNNNNNNNN | NNNNNNNNNN |
| 149801 | NNNNNNNNNN | NNNNNNNNNN | NNNNNNNNNN | NNNNNNNNNN | NNNNNNNNNN |
| 149851 | NNNNNNNNNN | NNNNNNNNNN | NNNNNNNNNN | NNNNNNNNNN | NNNNNNNNNN |
| 149901 | NNNNNNNNNN | NNNNNNNNNT | TCCTTTTTTT | TTTTTTTTTT | TTTTTTGAGA |
| 149951 | CGGTGTTTCG | CTCTTGTTCC | CCAGGCTGGA | GTGCAGTGGC | ACGATCTTGG |
| 150001 | CTCACTGCAA | CCTCCACCTC | CCAGGTTCAA | GCGATTCTCT | TGCCTCAGCC |
| 150051 | TCCCAAGTAG | CTGGGACTAC | AGGCATGCAC | CATCACATCT | GGCTAATTTT |
| 150101 | TTTGTATTTT | TAATAGAGAT | GGGGTTTTAC | CATGTTGGCC | AGGCTGGCCT |
| 150151 | TGAACTCCTG | ACCTCAGGTG | ATCCACCTGC | CTCGCCCTCC | CAAGGTGCTG |
| 150201 | GGATTACAGG | CATGAGCCAC | TGTGCCTGGC | CTACTTCTTC | TTCCTTTTAA |
| 150251 | CTTGAAGATT | ATCTGCCCCT | TTTTCTAATC | TTAACCGCAT | TAAGCTGGCT |
| 150301 | TTGAGCATGG | CAAGAGTTTT | ATAGATGAAT | CTTATTTTAT | AGTACAGGAT |
| 150351 | TTCAAAATCA | TAATTATTTC | ACTGAGGGTG | GCTTTTACCC | TCCATTAATT |
| 150401 | ATACTTCTCA | CTCAGAAATG | GAATTCTATT | TTGGTCTCCT | AAAGATAAAT |
| 150451 | TAGTATATAG | TGGAAAGGAA | TTATAAAGTT | CTGCTAGGAA | TTAAATGATA |
| 150501 | TGATTAACAC | AAACATCCAC | ATGGATGTGT | CTCTGCCCTG | TGCAGGAAAG |
| 150551 | ATGAACATTC | AGTACAGATT | CTGCTCTATG | TCACTAGCTT | TCAAGACCTG |
| 150601 | CAGGTTCTCT | CCTAAGCATG | CAATTCCTGT | GAGCAGTAGC | AATAATAGCA |
| 150651 | GGTCATATTT | GTGGAGTGAT | TACTGTATGC | TAAGAACTGT | GGTAAACACT |
| 150701 | TTTATATGGA | TTATTTTATT | TAAACCTCCT | AATAGTCCAT | TGAAATAGAT |
| 150751 | ATTGCCATGT | TGAAAACTGA | GGTTCAGAGA | GGTTAAGTGA | CTTACCCAGT |
| 150801 | GTCACAGAAC | TAGTAAGTGG | TGCAGCTGGG | ATTTGAACTG | AGATTCCAGA |
| 150851 | ACAATTGCCA | TTAACCACTT | TGCTTCCATA | TTAGTATCAT | CTGCAAATCT |
| 150901 | CTCTCCATAA | ATTTCCTCAG | TCTTTATCTG | AGTTTCCTTA | TTTCAGGAAG |
| 150951 | GAAAACTTCT | GTTTTTGATC | CTTATGAAAT | ACAATTTCCA | TTAAAACTTT |
| 151001 | TTTTTTTTGC | TATTAAAAAA | GGTACCGGAT | AATTGAAACC | AGACTGGATT |

FIGURE 3EEE

151051 TGAGCCTGTG TTGATGGAAG TACACATGGG ATGTGGGCTG AAGTGTTCAA
151101 TCTAATTTTT CTTTCCATCA GCTAATTTTT AAAGTATTAA GCAAGTAGAT
151151 TCTGACACTA ACAGGGAAGA TTTAAATTCT CTTGAGAGAC TGGAGGTGTT
151201 AAATAATTTT CTGGTAGTGC ACATTTTACA TCTTAAATCT TCCTCACTCT
151251 CCCACCTCAT CTCAATGTAC CTGAAGCTCT GGGAATGTTC TTTTGTACTT
151301 CTCAGGAACA GCCAGACCTC TGGCTTCATC TCCTCTCCCC TCCACATCCC
151351 TTTCCTGCTC CAATTACTTC CCAGCGCCAC TTGGATGTTG TTGTCATCGG
151401 GGAACTTTGG AAACAGCCAG ATTTTTTTGG AGTCTGTAAG CAGAAAACAG
151451 ACTGCTTGCT GCTCATATCT GGCACCCAGC TTTGTCCAGA AAACGAGGAG
151501 TTAAAAAGAA GTCTGGGCTG TGAAGGGCTG TGACAACTGT CCTAGGGGGA
151551 GCTCTAGCGA GCCCTGGCGG GCAGTGACTC ATGCTGCTCT GTCACTGGGA
151601 TCAGCACTGG CCCCTGGCAG GCAGGCGGCA GCCAGGTGGG GTTCCAGCCA
151651 GAGCACGCAC GCACGGAGCC GGGAGCATGC AGCCTGCACT GCGGGGGATG
151701 TGATGCTCGG CTCTAACTCG CCTGGCTGGC CCGCCACGGA CGCCTCAGCT
151751 TGCAACCATG GTAACGTTTC TGGCGGGGGA CACCCCCGGG AGCCCACCGC
151801 GATGGGCAGC CTCCTGGTGA CTGATGGACG AGTGTCCACC TCCCAGACCG
151851 AGAGCGCTTA GTAGGTCGGA GGAAGTGGAG AGGATGTAAC ACGCCCCCAG
151901 CCGGGAGTGA AGCCCTGAGG AGGTAGGAGC CGCATATGTC CATCCGTGCA
151951 TTCCCACCGT CAGCGCGCAG GGGTGCTGTA GATCACCGGT AGGAACTTTA
152001 TTTGGCTGGT GCTTCATTAT GCTGATTAAA CTGCAGTGGA TTTGATGGGC
152051 ATGATTGCGC TGGGGAAGAT GCATAATGAA CTAAAAAAAA AAAAAAGTGG
152101 TTAATAAGAT CTCGGAGTCG ACTTGTCCGG GTATGAATGA AGTAGACTGC
152151 AGTGGTATCC TAACAGGAGT TCCAGAACCT CACACATCCC TTTTCCTGGT
152201 CCTTCCTCTT ATCCCGGTTA ATCCACGAAA TGTAGAAGTT CCATCTTATT
152251 TCAACGATTA GTGCTAATCA TTAATAATTT AGACCTGTCT GGAGGAGGGA
152301 ATCCATAGGT TTAGGTCTCC TAGCATCCTG GCACTAGCCA GCAGCTGCTC
152351 TGTAGGAGCC TTCTGGAAAC AGCAGGAAGG AGCGGCTTCC CCACGAGTTC
152401 CCCAAGTGCT TTCGTTGGCC CAAGTGCTTT CGTTGGCCCA AGTGACCTGT
152451 TTGAGTTTGC TCTTCAGTTT ACCCCAGGCG GGAAGGCAGC CTGTCTGCGG
152501 GTTGGTGGCC ATGTTGGCAG AGAAGGGGTT AATCTCTTGT TGCTGTAGGA
152551 GCCGAGGTTG CGAGCTAGAT TGAAAGCAGG CGCTGCAGTG CCATCGCCAG
152601 CGCCGAAGGA GTAAGACGAT CTTCTCCGCA ACAGTGTTGA ATCCGGCTGA
152651 AATTTTTTTT CCTCCCCGCC TCCTTTCTTG TTTTTCTTTA ACCAGCTCCT
152701 CCCCCCTTCG TTCCCACCCT CAAGTCTGAC GATGACACCT CCAATTTTGA
152751 TGAACCAGAG AAGAATTCGT GGGTTTCATC CTCTCCGTGC CAGCTGAGCC
152801 CCTCAGGCTT CTCGGGTGAA GAACTGCCGT TTGTGGGGTT TTCGTACAGC
152851 AAGGCACTGG GGATTCTTGG TAGATCTGAG TAAGTGAAAA TTTGACTTTC
152901 TAAAGGGACC TGCATTGATG CAAGGCTTTT GGAGCCAAAG GTGGTGGTGG
152951 GGGGGTGGGG GAATAGGTGG GGGGAGTGCA GTGGAGGGAA GCTGCTAGTC
153001 ACCTGCATTG GGAAAGCAGT CTACCTGTTA GGGCTTTGCG GGGGTAGCCT
153051 GTTAATATTC TCATTTTGCA GTGTGTAAGG TACCTGTTCC TGTCTGTGGT
153101 ATGATAATTG TCAATTGGGT ACTTTGGGTT AGTTTTCCAA TCTTTGGTCT
153151 TCTTTAAAGG GGAGAGAGTG GGAGATTTCC AGCAGTGCAG ATCCCCGGTC
153201 AAAGGAGAAA TGTGCAGGAG TTAAGATGAG CTGCCCATCT ATCTAACCAT
153251 CTATGTATCT GTCTCTCAAG TGGGTGGATG GGGGTTGCTA TCTTGGCTGT
153301 ATAAAGAATC CTAAAAACCT TGTCTCATAA GCTAGAGGTT TCCTGATGGG
153351 TTTAACTGAG CTGCAAGTGG CTGAACCAGA GCTCTAACAG AGAGATGGTG
153401 CTCGGCTCCT CTCCAAGTAT GCTGCAAGAT CAGGGATCTG GCAGCTGAGC
153451 CTCTCTGAGC TGGTGGAGCG CTGGCAGCCA GAGAAAGCCC CGTTACTGTG
153501 AGCCACCAGG AGGGAGTGTG ATGTAGCCGA GTCATTGATT CACAGAAACT
153551 GGGCTTCATA GGGGGAAAAA AAACCAGGAG ACTAGAAAAT GGAAATATAA
153601 ATATCACTGT AAACCTCTTG ATCTGGTAGG TCTTTCTCCA TTCTCATAAA
153651 AGCTATTGAA AAATGCATTA ACAGAGCACT TGGAATTAGA GGGTCGAGGC

FIGURE 3FFF

153701 TTCCAGGAGC CTCCTGGAAT TTCTGTAAAA TGCAGTAGCT TCTGTGGATG
153751 TGGGAGGTCA GTATCTTGCC TCATTCTCTC ATGATACAAT GACATTCTGT
153801 TTTCAGAGGA GTGAGTTCCC CAGAAGATCT TGGACTGATG GTGTTATTTG
153851 CCAGCCACCC TGGTCCCTGC ACTTTCAGGT TCTCAGAGGG TAATGTTGGG
153901 TTAGTTGCTG CCCACTTAGG AGACGAGCAG AATTTGATAT TCTTCTTGGC
153951 AGCATCTTTC CCTCTTTGTG GTATTTGTAG CTTAGATATC GATTTATAGG
154001 GATGTTATGT TGGTTCCTGG ATGGTGTCTC CCTATGGGTG CTATTTTGAC
154051 AGTAACGTTC CTGAAAAGAT TTCAGAGTGT TGTGGGGAAT TGGGCATTTG
154101 ATACGAAATA AGGTTGTGGG CTGTGATTGA ATGTGAGGGA GGTTTTTATG
154151 TTGCAAGATG TTGAAGTGGT CTTTCTTGAT CCCCTCTCTG GGGGCTGGGT
154201 TTCAAATTCA GGTTGGATTT TGGTAGTGTT AGATGTGCCT CTCTGTCTGA
154251 TTTGCTCCAC AACCCCAAAG CAATCTGGAT GGTGGTGGGA GAGGCAGAGT
154301 GCTAACTAGC TGTTGAATGT GCCATCAGAT GGGTTTGAAA CGGCTCAGCA
154351 GGATTGGGAG GTTTTGCCAT TGGCATCAAA GAGCAGGGCA GAAGCGGAGG
154401 CCTGATGTTG AAGGATGCAT GGTTAGTGGG CAGTATAACC TTGACACACG
154451 CAGCACACTG AAGGTCACAC GTCGTACTGG AAGGACGTGT GGAGAGTTCT
154501 AGTTCTGGTT AGCAGTGGGC TGGCTGGGTC AGAATGCAAG CTTGCTTGGG
154551 TGTTGGTCAG TGATCTGAAA GACGAGGGAG GATTCGAGGG AGTTAGATTT
154601 CAGGGGAAAA GGCAGAATGA TATGGGAGAT CTTAGGCATT GCAATTAATC
154651 TGAAGCAGTG TGTGATTAAT TGCTTATTTT TCAGGAAGAC TTGAATGACA
154701 TCTTTCTGTT TCTCACAGAA AGCTCAGTTT AGGGAGCTCT CTGACAGGGA
154751 CATCTCAGTA TTAAGGCTGA GGCACTCGAT AAATATTTGT TGATTTAATT
154801 TACCTATGAT CCTTTCCTCC AGAAGTGTTT ATATTGCTTA TTGTATTTGA
154851 AGATGTGCTA TCTCACCTCT GGTAGTTTAA ACTATATCCT TAGAGCACAA
154901 AACGAGCTGC TGTTCCTGAC CCAACAGAAT GTTTAATAAG ATTCTTATTT
154951 CAAAAAAGGT CCATGCAAAT AAAACTGTGT ATTTCTTATT TGGACGATGG
155001 CATCAGAGTA TTCCTATCAT TGGGGAACTT TAACGTTTTT TCAAAGCTTG
155051 GCAACGGGGT TGGAATCAGA AAGATTTTCT TTCATCTTGC GTCTTGTTAT
155101 GTGTTATTGC TATTGGACTT GGCTACTCTG CTGTAGGCAG CCCTGTGGGT
155151 GATACCTACA AGCATCATTT TAGAAATTCA TCCACCTGTT GGATGTAGAT
155201 GACCCTGGAC ATATCAGATT GTGATTAATT AGAAATCTAA TAAAAGAGAG
155251 GCAGTGATGA AATTACTTAG CAGCTCCTGC AGTTTTATTG ACAAAATTTA
155301 CTTGGAGAGA GGGGGAGACA TTTTCTGGGG GTACCACCTT TGCTGCCAGC
155351 GACCCTGTGT TTCTTCCTGA GTTTCTTTTT CTTTTCTCAC CATTTTCAGC
155401 ATCACAGGTT TTTATTTACA CACATTGATT ACCTGTGCTG TTACTCATTC
155451 TTCACACCAC TGAGGAAATT GCAGATGCTG CTGTACTGTG CTAGGTAAAT
155501 TGACCTCAGA TTTGTTACCA GTGAATTGAA TGAAATGTTC AGAGGTGGAG
155551 CTGAATGAAC GAGGAGTTTT TGTGGAGAAA TTGGCAGTGA GAATGATTTA
155601 AATTCTGTGA TAGCTCCTCG TTTTTTGGGA TCCTTATTTT GGGACCCCAG
155651 ACTATTTTTA AGCCATTGAG TGCATCATTA TTTTAGGCTG AGCAAGAATC
155701 TTGATGACAG CGTTTCAATG GCTGAGGCGT AGTGGGAGTT CCTTGCAGCT
155751 TGAGTTGGTG GGAGCTGGAG AGTTTCTAGA GAACTAGGTT TGGTTGTCTT
155801 TGGGGTGGGG TTATGGTGAA ATTAGTCTTG GAGAGTGAGT AGCTGTCTGA
155851 TGCTTCTTTT CCTTTTTAAC CAGCAAGAGC CCAAACCAAA TCCCCAAGCT
155901 CTGAATGCCT GGCTGTTCCT CTCAGCCTTT CTTTGCTTGA ACTTGACAAT
155951 AGTAGGGTAG TAACAGGAAA CAGCATGTTA AAGTTTTAAA AATAAAATAG
156001 ATCTCAGCTC TTTTCCTTCC CATTAGCAAG GGGTACATTT ATTTAGGTTT
156051 TTCCTTCTAG ATTGAGGCAC TGCCTCATTT AAGTTCTTGG TGAAGCCATG
156101 CATTTCTGCA AACCATAAGT ATAAACTCTA GAACGGGGGT GTCCAATCTT
156151 TTGGCTTCCT TGGGCCACAT GGGAAGAAGA AGAATTGTCT TGAGGCACAC
156201 ATAAAATACA CTAATGATAG CTGATGAGCT AAAAAAAAAA AAAAACTCAT
156251 AAAGTTTTAA GAAAGCTTAC AAACTTGTAA GTTTTGAGCC ACATTAAAAA
156301 CCATCCTGGG CTGCATGCAG CCCCCGGGGC CTTGGGTTGG ACAAGCTTGC

FIGURE 3GGG

156351 TGTAGAAGGT AAAAATCAGT TGGTTTTATG TTTTTGTTTT AAACATGCTG
156401 GTTGTATGCT TTTGGAAGAG TTGGGGAACA CTGAGGGTAA TGGGATCTTG
156451 ATGGGGCTGG AATTTGTGGG AAGATGGTGT CTGGGTAGGC TGTTTTTAGG
156501 AAGGGGCACT CTCTTCCTTT TGATTCAGAG ATTTTTCCTT TCTTTTCGGG
156551 TGGTTCTGAA AACACAGCGA TGGATCCAGG CATTCAAACA CCATGGAGGA
156601 AGGAAGAGTG GCTGTTGCCA TTGCTTCCCG AGTTTTCTGG GAACCAGTTT
156651 TTGGTGCCTC TTCCTTGCTC TACTGGGGCT TCTCTGCATG TCAGTTTCTT
156701 CAACTGCGAA GTGGAAGGAC AGCGATACTT TTCTTACAGG ACTTTTGCGG
156751 GGATGGATGA AATACGTAAA ACACTTGGTC TAGTACCTGG CACATGGAAA
156801 AGCCTTGGTA AATGTTCACT GTTGTTATTT TTGTTATTAC TAATACACTA
156851 GTCCATGTAT GTATAGTGTC CTCCTATACA CACCAAGAGA ATATGGAAAG
156901 GACTCAGCAA TGATTAGGTA GTCCAAAGTC ATACCAGATT GGAAACCAAG
156951 CTTCCCAGGC CCTGGGACTT TTCTGCTAGA GACACTTCAC GGTTCTGACC
157001 AACTACAAAG AGTTAATATG CAGTTGCCAA ATACCTGTTG GTAAAAGGTG
157051 GATGTTGGGG AGGAGTGGAT TGGGGAACAG AATTAGAAGG TCCAGTCCCA
157101 GAATGGGTAC CTTCCCATCA AGTTGAACAA GTCAAAACAG GTTATGTTGA
157151 AACAACTGAG AGAAAGTAAA GCAAACACCA TTGCTGCAGA ATATCATGGT
157201 ACAAATTGGA CATCTTTGGG AGTTAGCGGA GTAAGGCAAA ATCCAGTGAG
157251 GGACGCTTAA TGGGTAATGC CAATTCACAA TTCTTGTTAA ATTACATTGC
157301 TGATCTTCCT TGGAATGTCT GTCCATTCCC CCAAGTAGAC TGTGATCTCA
157351 AGGCAAGGCT GGGTCTTATT CATCCTGGTT TTCCTGGAGC AGTAAATACT
157401 TGTGCTGGGA CTGGGCTTAT AAGCATACTA ATGGAAAGTA AAATATTTGG
157451 GTTGGTTTTT TAAAAAGACA GTGGATTTGG ATCAGTGGAG AGGAAGGTAG
157501 AGGGAATTTC AGGTGGGCAG GGTGCTAACA ACAGCCCATC CTTACAGGGC
157551 ACCAACTGTG TTCTAGGCTG TGTTCCAACC ACTTTACACA GATGAATTCA
157601 TTTAAATTGC ACAACCAGCC CAAGAGGAAG GTACCATTAT TATTCTCATT
157651 TTGGATGTGA GGAAACTGAG GCGTGGGGAG ATCAAACAAC TTGCCTAAAG
157701 TTATGTAGCT TTGAGTGGCT TAGCTGAGAT TTGAACCCTG TGGGTATAAA
157751 TGCCACAGAT GGGAAATTTG TGTGGGGTAC CCCAGGGTTC ATGTGCTTGT
157801 TAGAAGTGGA AGCTATTTGT AGAGAATCAC GAATGATGAG GTTGGGGCAG
157851 GGTGTGATGG GAGCTGACAG GCAGGTCTAA ATGCTGGGAT TCCATTTTCA
157901 GTCTCTGTGT TTATTGAGTA GGTAGACGGT ATAGCTCTTG GATTTCTCAG
157951 ATTTTTTCCT CTTTTCATTT AGAGACTCTT ATCTGGTGTG TGTGTGCCCG
158001 CACACATACA TAAACCCACG CGTATATACT CTTTCCCTGA ATGTTCTTAT
158051 TTGCTAAAGC TTAAGCTTGG CAAAGAGAGG AAACTGCACT GACCTTACTC
158101 TCCACCATAT CTTCAGGCTG ATCATACACA AGTTGCTTAA TAAGCATTTG
158151 GTTAATCCAT CTAAATCATT CTTATGGCTG CAACTCTCAT TTTGTTGATG
158201 ACTCTACTAT CTATGTCTAT TCACATCTAC ATTTTGTACT TTTGTTTGCC
158251 TCCCATCTGT CCTGGGATGG CTGATACCAG TGGAAGACAG CCTGAACTCT
158301 CCAATCAGTC CTGTTTCCTT TTTATGAAAT ACTTGGAGGT TGGAGGATCT
158351 TCCCTTAAAA AGTGTTTTCC TTTCTACATC CAGCCAAAGG CTCTTGGTCC
158401 TTGTGCTTGC TACCTAGATC CCTATTGGAA AGAGTCTTGC CTGCAATTTG
158451 ATTTTTTAAA TAGCAGCAAT AACAGAGTCG TCTCTGCTAC ACGAAGACAT
158501 GCATCTGCTG TATTTCCCAG ACAAGTTCAA AAACCTTAAC TAGCTTCTGC
158551 CCATGGTTAT TGCTCTCAAG TGCCTTGTGT TGTTCCCATC CCCTCATTAT
158601 CTGGATTAGA TGTTTAACAT TTGCCTGTGT GTGTTGTGTT GGATTTTCTC
158651 CTCTCCTCTT GCTCATTCAA TTTCTTCCTT CTCTTAGCCA AGCACAGCTT
158701 GTTCTCCTAC TTGCCTTATT CTGTTCTCTA TTTAGACTGT GCGTGCCTGC
158751 CTTGCAGCCC TGGCAGGACC ATTCCACCGC CTTCTCATTT GTCTTAAAGA
158801 TACCTTTAGG AAATCTAATC CAGACAATCC TAGCCCAGTC CTGAAGATTA
158851 GGCTCCAGAA GATTCTGTCA AGTGTGTTTT TTGCTGGCCT ACACATGCTA
158901 ATTTGCATGG TTGCCTGGGA TCCCTTAAGA AGACAGTCAT TGACTAAATG
158951 GCGCTACATG TTCCCAAGCT CTGCGCCAGT CTGGCAACTC TTCCTTTGTC

FIGURE 3HHH

159001 TACGTGAATT TCTCCTAGTT CTTTCTGCTT TGCTTGCTGT TCATCTCCTG
159051 ACCTCTCTCC GACAAACTTC NNNNNNNNNN NNNNNNNNNN NNNNNNNNNN
159101 NNNNNNNNNN NNNNNNNNNN NNNNNNNNNN NNNNNNNNNN NNNNNNNNNN
159151 NNNNNNNNNN NNNNNNNNNN NNNNNNNNNN NNNNNNNNNN NNNNNNNNNN
159201 NNNNNNNNNN NNNNNNNNNN NNNNNNNNNN NNNNNNNNNN NNNNNNNNNN
159251 NNNNNNNNNN NNNNNNNNNN NNNNNNNNNN NNNNNNNNNN NNNNNNNNNN
159301 NNNNNNNNNN NNNNNNNNNN NNNNNNNNNN NNNNNNNNNN NNNNNNNNNN
159351 NNNNNNNNNN NNNNNNNNNN NNNNNNNNNN NNNNNNNNNN NNNNNNNNNN
159401 NNNNNNNNNN NNNNNNNNNN NNNNNNNNNN NNNNNNNNNN NNNNNNNNNN
159451 NNNNNNNNNN NNNNNNNNNN NNNNNNNNNN NNNNNNNNNN NNNNNNNNNN
159501 NNNNNNNNNN NNNNNNNNNN NNNNNNNNNN NNNNNNNNNN NNNNNNNNNN
159551 NNNNNNNNNN NNNNNNNNNN NNNNNNNNNN NNNNNNNNNN NNNNNNNNNN
159601 NNNNNNNNNN NNNNNNNNNN NNNNNNNNNN NNNNNNNNNN NNNNNNNNNN
159651 NNNNNNNNNN NNNNNNNNNN NNNNNNNNNN NNNNNNNNNN NNNNNNNNNN
159701 NNNNNNNNNN NNNNNNNNNN NNNNNNNNNN NNNNNNNNNN NNNNNNNNNN
159751 NNNNNNNNNN NNNNNNNNNN NNNNNNNNNN NNNNNNNNNN NNNNNNNNNN
159801 NNNNNNNNNN NNNNNNNNNN NNNNNNNNNN NNNNNNNNNN NNNNNNNNNN
159851 NNNNNNNNNN NNNNNNNNNN NNNNNNNNNN NNNNNNNNNN NNNNNNNNNN
159901 NNNNNNNNNN NNNNNNNNNN NNNNNNNNNN NNNNNNNNNN NNNNNNNNNN
159951 NNNNNNNNNN NNNNNNNNNN NNNNNNNNNN NNNNNNNNNN NNNNNNNNNN
160001 NNNNNNNNNN NNNNNNNNNN NNNNNNNNNN NNNNNNNNNN NNNNNNNNNN
160051 NNNNNNNNNN NNNNNNNNNN NNNNNNNNNN NNNNNNNNNN NNNNNNNNNN
160101 NNNNNNNNNN NNNNNNNNNN NNNNNNNNNN NNNNNNNNNN NNNNNNNNNN
160151 NNNNNNNNNN NNNNNNNNNN NNNNNNNNNN NNNNNNNNNN NNNNNNNNNN
160201 NNNNNNNNNN NNNNNNNNNN NNNNNNNNNN NNNNNNNNNN NNNNNNNNNN
160251 NNNNNNNNNN NNNNNNNNNN NNNNNNNNNN NNNNNNNNNN NNNNNNNNNN
160301 NNNNNNNNNN NNNNNNNNNN NNNNNNNNNN NNNNNNNNNN NNNNNNNNNN
160351 NNNNNNNNNN NNNNNNNNNN NNNNNNNNNN NNNNNNNNNN NNNNNNNNNN
160401 NNNNNNNNNN NNNNNNNNNN NNNNNNNNNN NNNNNNNNNN NNNNNNNNNN
160451 NNNNNNNNNN NNNNNNNNNN NNNNNNNNNN NNNNNNNNNN NNNNNNNNNN
160501 NNNNNNNNNN NNNNNNNNNN NNNNNNNNNN NNNNNNNNNN NNNNNNNNNN
160551 NNNNNNNNNN NNNNNNNNNN NNNNNNNNNN NNNNNNNNNN NNNNNNNNNN
160601 NNNNNNNNNN NNNNNNNNNN NNNNNNNNNN NNNNNNNNNN NNNNNNNNNN
160651 NNNNNNNNNN NNNNNNNNNN NNNNNNNNNN NNNNNNNNNN NNNNNNNNNN
160701 NNNNNNNNNN NNNNNNNNNN NNNNNNNNNN NNNNNNNNNN NNNNNNNNNN
160751 NNNNNNNNNN NNNNNNNNNN NNNNNNNNNN NNNNNNNNNN NNNNNNNNNN
160801 NNNNNNNNNN NNNNNNNNNN NNNNNNNNNN NNNNNNNNNN NNNNNNNNNN
160851 NNNNNNNNNN NNNNNNNNNN NNNNNNNNNN NNNNNNNNNN NNNNNNNNNN
160901 NNNNNNNNNN NNNNNNNNNN NNNNNNNNNN NNNNNNNNNN NNNNNNNNNN
160951 NNNNNNNNNN NNNNNNNNNN NNNNNNNNNN NNNNNNNNNN NNNNNNNNNN
161001 NNNNNNNNNN NNNNNNNNNN NNNNNNNNNN NNNNNNNNNN NNNNNNNNNN
161051 NNNNNNNNNN NNNNNNNNNN NNNNNNNNNN NNNNNNNNNN NNNNNNNNNN
161101 NNNNNNNNNN NNNNNNNNNN NNNNNNNNNN NNNNNNNNNN NNNNNNNNNN
161151 NNNNNNNNNN NNNNNNNNNN NNNNNNNNNN NNNNNNNNNN NNNNNNNNNN
161201 NNNNNNNNNN NNNNNNNNNN NNNNNNNNNN NNNNNNNNNN NNNNNNNNNN
161251 NNNNNNNNNN NNNNNNNNNN NNNNNNNNNN NNNNNNNNNN NNNNNNNNNN
161301 NNNNNNNNNN NNNNNNNNNN NNNNNNNNNN NNNNNNNNNN NNNNNNNNNN
161351 NNNNNNNNNN NNNNNNNNNN NNNNNNNNNN NNNNNNNNNN NNNNNNNNNN
161401 NNNNNNNNNN NNNNNNNNNN NNNNNNNNNN NNNNNNNNNN NNNNNNNNNN
161451 NNNNNNNNNN NNNNNNNNNN NNNNNNNNNN NNNNNNNNNN NNNNNNNNNN
161501 NNNNNNNNNN NNNNNNNNNN NNNNNNNNNN NNNNNNNNNN NNNNNNNNNN
161551 NNNNNNNNNN NNNNNNNNNN NNNNNNNNNN NNNNNNNNNN NNNNNNNNNN
161601 NNNNNNNNNN NNNNNNNNNN NNNNNNNNNN NNNNNNNNNN NNNNNNNNNN

FIGURE 3III

161651 NNNNNNNNNN NNNNNNNNNN NNNNNNNNNN NNNNNNNNNN NNNNNNNNNN
161701 NNNNNNNNNN NNNNNNNNNN NNNNNNNNNN NNNNNNNNNN NNNNNNNNNN
161751 NNNNNNNNNN NNNNNNNNNN NNNNNNNNNN NNNNNNNNNN NNNNNNNNNN
161801 NNNNNNNNNN NNNNNNNNNN NNNNNNNNNN NNNNNNNNNN NNNNNNNNNN
161851 NNNNNNNNNN NNNNNNNNNN NNNNNNNNNN NNNNNNNNNN NNNNNNNNNN
161901 NNNNNNNNNN NNNNNNNNNN NNNNNNNNNN NNNNNNNNNN NNNNNNNNNN
161951 NNNNNNNNNN NNNNNNNNNN NNNNNNNNNN NNNNNNNNNN NNNNNNNNNN
162001 NNNNNNNNNN NNNNNNNNNN NNNNNNNNNN NNNNNNNNNN NNNNNNNNNN
162051 NNNNNNNNNN NNNNNNNNNN NNNNNNNNNN NNNNNNNNNN NNNNNNNNNN
162101 NNNNNNNNNN NNNNNNNNNN NNNNNNNNNN NNNNNNNNNN NNNNNNNNNN
162151 NNNNNNNNNN NNNNNNNNNN NNNNNNNNNN NNNNNNNNNN NNNNNNNNNN
162201 NNNNNNNNNN NNNNNNNNNN NNNNNNNNNN NNNNNNNNNN NNNNNNNNNN
162251 NNNNNNNNNN NNNNNNNNNN NNNNNNNNNN NNNNNNNNNN NNNNNNNNNN
162301 NNNNNNNNNN NNNNNNNNNN NNNNNNNNNN NNNNNNNNNN NNNNNNNNNN
162351 NNNNNNNNNN NNNNNNNNNN NNNNNNNNNN NNNNNNNNNN NNNNNNNNNN
162401 NNNNNNNNNN NNNNNNNNNN NNNNNNNNNN NNNNNNNNNN NNNNNNNNNN
162451 NNNNNNNNNN NNNNNNNNNN NNNNNNNNNN NNNNNNNNNN NNNNNNNNNN
162501 NNNNNNNNNN NNNNNNNNNN NNNNNNNNNN NNNNNNNNNN NNNNNNNNNN
162551 NNNNNNNNNN NNNNNNNNNN NNNNNNNNNN NNNNNNNNNN NNNNNNNNNN
162601 NNNNNNNNNN NNNNNNNNNN NNNNNNNNNN NNNNNNNNNN NNNNNNNNNN
162651 NNNNNNNNNN NNNNNNNNNN NNNNNNNNNN NNNNNNNNNN NNNNNNNNNN
162701 NNNNNNNNNN NNNNNNNNNN NNNNNNNNNN NNNNNNNNNN NNNNNNNNNN
162751 NNNNNNNNNN NNNNNNNNNN NNNNNNNNNN NNNNNNNNNN NNNNNNNNNN
162801 NNNNNNNNNN NNNNNNNNNN NNNNNNNNNN NNNNNNNNNN NNNNNNNNNN
162851 NNNNNNNNNN NNNNNNNNNN NNNNNNNNNN NNNNNNNNNN NNNNNNNNNN
162901 NNNNNNNNNN NNNNNNNNNN NNNNNNNNNN NNNNNNNNNN NNNNNNNNNN
162951 NNNNNNNNNN NNNNNNNNNN NNNNNNNNNN NNNNNNNNNN NNNNNNNNNN
163001 NNNNNNNNNN NNNNNNNNNN NNNNNNNNNN NNNNNNNNNN NNNNNNNNNN
163051 NNNNNNNNNN NNNNNNNNNN NNNNNNNNNN NNNNNNNNNN NNNNNNNNNN
163101 NNNNNNNNNN NNNNNNNNNN NNNNNNNNNN NNNNNNNNNN NNNNNNNNNN
163151 NNNNNNNNNN NNNNNNNNNN NNNNNNNNNN NNNNNNNNNN NNNNNNNNNN
163201 NNNNNNNNNN NNNNNNNNNN NNNNNNNNNN NNNNNNNNNN NNNNNNNNNN
163251 NNNNNNNNNN NNNNNNNNNN NNNNNNNNNN NNNNNNNNNN NNNNNNNNNN
163301 NNNNNNNNNN NNNNNNNNNN NNNNNNNNNN NNNNNNNNNN NNNNNNNNNN
163351 NNNNNNNNNN NNNNNNNNNN NNNNNNNNNN NNNNNNNNNN NNNNNNNNNN
163401 NNNNNNNNNN NNNNNNNNNN NNNNNNNNNN NNNNNNNNNN NNNNNNNNNN
163451 NNNNNNNNNN NNNNNNNNNN NNNNNNNNNN NNNNNNNNNN NNNNNNNNNN
163501 NNNNNNNNNN NNNNNNNNNN NNNNNNNNNN NNNNNNNNNN NNNNNNNNNN
163551 NNNNNNNNNN NNNNNNNNNN NNNNNNNNNN NNNNNNNNNN NNNNNNNNNN
163601 NNNNNNNNNN NNNNNNNNNN NNNNNNNNNN NNNNNNNNNN NNNNNNNNNN
163651 NNNNNNNNNN NNNNNNNNNN NNNNNNNNNN NNNNNNNNNN NNNNNNNNNN
163701 NNNNNNNNNN NNNNNNNNNN NNNNNNNNNN NNNNNNNNNN NNNNNNNNNN
163751 NNNNNNNNNN NNNNNNNNNN NNNNNNNNNN NNNNNNNNNN NNNNNNNNNN
163801 NNNNNNNNNN NNNNNNNNNN NNNNNNNNNN NNNNNNNNNN NNNNNNNNNN
163851 NNNNNNNNNN NNNNNNNNNN NNNNNNNNNN NNNNNNNNNN NNNNNNNNNN
163901 NNNNNNNNNN NNNNNNNNNN NNNNNNNNNN NNNNNNNNNN NNNNNNNNNN
163951 NNNNNNNNNN NNNNNNNNNN NNNNNNNNNN NNNNNNNNNN NNNNNNNNNN
164001 NNNNNNNNNN NNNNNNNNNN NNNNNNNNNN NNNNNNNNNN NNNNNNNNNN
164051 NNNNNNNNNN NNNNNNNNNN NNNNNNNNNN NNNNNNNNNN NNNNNNNNNN
164101 NNNNNNNNNN NNNNNNNNNN NNNNNNNNNN NNNNNNNNNN NNNNNNNNNN
164151 NNNNNNNNNN NNNNNNNNNN NNNNNNNNNN NNNNNNNNNN NNNNNNNNNN
164201 NNNNNNNNNN NNNNNNNNNN NNNNNNNNNN NNNNNNNNNN NNNNNNNNNN
164251 NNNNNNNNNN NNNNNNNNNN NNNNNNNNNN NNNNNNNNNN NNNNNNNNNN

FIGURE 3JJJ

164301 NNNNNNNNNN NNNNNNNNNN NNNNNNNNNN NNNNNNNNNN NNNNNNNNNN
164351 NNNNNNNNNN NNNNNNNNNN NNNNATTTCA GAGTAAGTTT TTCTAGAAAA
164401 TAGAAGCTGG AAAAAAAAGG AAAACCCAAA CTTGGCTTCG TGCTCGAAGA
164451 GACAGCACTG CTGTGTGTGG GCGGGTGGCT GCGTGCACCC GCTGCTCAGA
164501 AGTGCCTTTT CTCTCCATGG GGATAACTGG CTGTGTATCC GAGATGTGGC
164551 CAGGAGTAGG CAAGCAACGT GTGGGCAGGC TGCATGTTCT TTTATTAGCA
164601 TCTTCATTGT ACTGCATCTC GTCGAGCCCA GAGCATGAAC TGGCCTGGGT
164651 TTCTAATATC TACCCTGCTT CCCACCTAAT TACTCCCCTG AACCCTAAAG
164701 TGAGGGAGGG AGAGTTGCTC TTGTGGGGTG AGCTTTCCCT GGGGTGGCTG
164751 TGAACCAACC TGGCATGTGG ATGTTCTTGG GTATCCAGAG CTGTCCTGGA
164801 CTCAGGCTTG GAGTCAGCTT CTTAGCACTG AATGCAGCCA GTCATGGATG
164851 GAGGTCACTG TATCTCACAT GTTCCGCTCT CCCTTTCCTC CATGACCTTG
164901 CCCCTCTGAG CCTCTGTAGC ACTTTTCTTG AGTGTGTCCA AGGCCATCTA
164951 GCTAAGAAGT AGCAGAAATG GGATTTGAAG CCATGACTGT TTGGTGATAG
165001 AGCCTCAGCT TTGAACTGGG GTTCTACTGC CTGGCACCCC TGCACAAATC
165051 ATGGTAACGT GGTAGGAGAA CATAGAGGTA TAGGGCAAGC CCCTCCTTAA
165101 TGCCATGAAT AATACCCATC TTATAGGATT GTGGGGAGGA CTCAGTGAAG
165151 TAACCCGTGA AGCACTAAAC ACGTGCCTGA CACGTGCTCA ATAAATGAGC
165201 ACTTGTCCTG ATGACAAAGG TCGTGGCATT AATTCTCTCT CCTAGGTTGT
165251 TACTTCCTTG AGGACAGGAA TTGTGGCTTC CTTAATGGCC ACTGCAGCAG
165301 AGTTTCTCAA GTTGGCACTA TTGACATTTT GGGCTGGATA ATTCTTGTTG
165351 TGGGAGCTGT CCTGTGGATT GTAGGATGTT GAGCAGCATC TTTGGCCTCT
165401 ACCCGCTACA TATTAATAGC ACCCCTAGTC ATGAAAATAA AATGTCTAGA
165451 CATTGCCAAA CTGCCCCTGT TGAGAACCAC TGGTCTGCAG GTATCTCTCA
165501 TGGGGATCAC AGGGCTTTTA TATTCTCTTC TCTGTCTCTC TCTCTCCCTC
165551 TCTGGGTGTC TCTCTCTCTC ACACACACGC TTAGAGAAGG TGGTTAAAAA
165601 AAATTTTGTT GAAGTTTGAG AATTTTGAGA ACAAAGGAAA AATTTTGGAA
165651 GGCATTTTAA TGAACAGATA GACTCTGTCC CATTCCATGG TCAACAGAAT
165701 TTCATAATTA GATAGTTTGT TTACTGCAAC TCTGCACCCC ATTGCCCATC
165751 ATTTTAGAGT TCCAACCAGT TAGAGGATTT TTCTTGCAAA CTTTCCTTAA
165801 AGCAGTGATA GTATCAGCTC TTTAAATAAT ACTATGCTTG ATGAAGTGGT
165851 ACTTTTCGGG ATAATTTGAG ACCAGCCGAC TTGCTGCTTG AAGAGGACAG
165901 GGCTATATTT GGTAATAATA TATATGTGAT AATATGTATG TAATATTATT
165951 ATAATGTAAT ATACAATAAT ATTTGGTGTA ACTGGTGACT CTGAGGCCAG
166001 TCTTTGATCG AACCTCTCAA GCTATGATTT ACATTATGGT CAATGTTAGC
166051 ATAATGCAAT TATCAGCAAT CACTTGCTGT TGCTTTGAAA GTCAGAAGGA
166101 TGGCTAATAA AAATCTTAGA AAAAGAAAAC AGGCCGGGTG CAGTGGCTCA
166151 CCCCTGTAAT CCCAGCACTT TGGGAGGCTG AGGCGGACAG ATCATGAGGT
166201 CAGGAGATCG AGACCATCCT GGCCAACATG GTGAAACCCC ATCTGTACTA
166251 GAATACAAAA AAAAAAAAAA AATTTGCTGG GCGTGGTGGC GTGCGCCTGT
166301 AGTCCCAGCT ACTCGGGAGC TGAGTCAGGG GAATCGCTTG AACCCGGGAG
166351 GTGGAGGTTG CAGTGAGCCG AGATTGTGCC ACTGCACTCC AGCCTGGTGA
166401 CAGAGTGAGA CTCCGTCTCA AACAAAACAA AACAAAACAA AAAACAAAAA
166451 AAGAAAATCT TAGAAAAAGA AAATAAATTG TAATATTTCA GAATATTTGT
166501 TGGGGAGGAT ATGTGTGCTC AAGAAATATA TACTGAGAAC TTACCATTGA
166551 TGCTAGAGAT TGAATTGCCC CATGTCTACA TGAAAAATGA ATAGAATATA
166601 AACATTTTAA ATTGAGCCAT GTCTATCTGT ATTATATTTC TTTTATAGAA
166651 ATTCATGGAA ATGGTATATT TTAACTGAAT TATTAACACT GGGGACAATA
166701 GGCTTTAATC ATTATCTAAT ACCTGTACGT TGTTTTGAAA TTCATAGCCC
166751 ACCACCATTA ATTTCAAAAT TGGGTTCTTA CTCAAAGAGT GATGAAAAGG
166801 CACCAGTACC AAATGGTCTG GCCAAAATGC TACATGGAAC TAAATGCTGG
166851 GGATGGTCAT ACAATGAGTT TTAAGTGGCT AGACCCTAAA TCAGAAGCAC
166901 TTTCTTCTAA TTAGCACCAT GGTTCTTAAT CCTTTCTGTA CATTACAATC

FIGURE 3KKK

166951 GCTCAGCAGC TTAATACAAA TGTTGCTTCC CGGGGCCACA CTCCACATCT
167001 TTCTGACTCT CTGATTTAAT TGGTCCGAAT GGGGCCTATA CATCAGGTGT
167051 TTTTTAAAAG GTCTCCAAGT GATTCTAATG TGTACCTGCA TTGAGGACCA
167101 GGGAAGGTGT AGGAAGCCTG ATAACCTTTA CTCTCCAGCC TCATCCTCCA
167151 ATCCCATGAT TGTTTATGGG ATTGTTGCTA CACACCCAGC TTAGTCATAG
167201 CATTCTTACT CTAGCTTTTT TTTAGATGCA ATTTTTATTT ATTCTTAAAG
167251 AAAAAGATTT CTTTAGCACC TTTATTCTAA AGAGCTCTTA ATTGCTGTGC
167301 TTAGAACTTC TAAACAGTGA GCATTTGTCA AACATAGAAT AGCAGAATGA
167351 AGGGGTTGGA CCTCGGGTGA GGAGGGCTGT CGCATGGTCT CTTTCGAGTG
167401 CCGGCGGGTG GGGGCTGCAC ATCTCCTCGC TTCTGGGCCC ATTGATAAGT
167451 GACCTAAAAG TGCCTTTCGT TTTTTTTGGT GGGGGGTGAA AAAGCAATCT
167501 GTTTTGTACC CACAGCGGTG CACTTTAAAC AGGAAGCCCT ACTGGGGCCA
167551 GCCTTCTATG TGTCATTAAG TTTTTCACGC CACATCCTAC CTATCATCAT
167601 GCACCCATGT CATCGTTCTT TTAAAGGGTG CCAGTTTTTT GCTTAAGCAC
167651 AAGGAGCTGT GACCTGTGTT GTCATCCCTG ATGCATGTCA TGCATGTGAC
167701 TTCATGACAT GTGGGTGACT TTTGATCTCT GAAGGACCAG GGACCCAGTC
167751 TGTGGATCAC CACTCTCTCC GTGGGTGGTT TGGGTCTTGT TCTCTAGCCC
167801 ACCCAGCCAG GTGCAATTAG GAATAAAGGA AATAGCAAAG GAATTTTGCT
167851 CAAGGCCATG CCAAGCATTT CATCTCATAT GAAAAGGAAA AGAGAGAGAG
167901 TGTGTGTGTG TTGGCTAGAT TTAGGTAGAA AACAGGCTGG TGAGAAGCGT
167951 AGAACTTGGT TAAAATTTCT AGCCAAAAGT AAGATTTTTA AAAAGATTTA
168001 TTTCTGGATC CAATCCCTGT TGCCCATTTC TATGAATAAT CACCATTTGT
168051 TTTAATGTGA ATAATAGCAC ACAGCAAATT CAGCCCCCTG AGTTTTACCA
168101 TTTTAAGCAA TTGCTTTAGG CCCGTGAGGC ATGTACTATT TATGAAGTTG
168151 CATGGGTAGT AATGGAAAAC ACAACAATGA CAGTAGTAAC AGGTGACATT
168201 TGTCGAACAC TTGCAGTGTG CCAGGCACTG TGCTGAGAGC ATTACATGCA
168251 TTATTTCATT TAATCCTTCC AAGAACTCTT TGAAGTAGGT TGGTAATTAT
168301 GGCCATTTTA CAATTGAGGA AACTGAGGTT CGGAGATGTC AAATAACTAG
168351 TCAGTGGTGG GGTCAGATTT TTCTTTTTTT TTTAAATTTA TTTGCTTTTT
168401 TTTTTTTTTT TTTTTTTTTG AGACGGAGTC TCACTCTGTT GCCCAGGCTG
168451 ANNNNNNNNN NNNNNNNNNN NNNNNNNNNN NNNNNNNNNN NNNNNNNNNN
168501 NNNNNNNNNN NNNNNNNNNN NNNNNNNNNN NNNNNNNNNN NNNNNNNNNN
168551 NNNNNNNNNN NNNNNNNNNN NNNNNNNNNN NNNNNNNNNN NNNNNNNNNN
168601 NNNNNNNNNN NNNNNNNNNN NNNNNNNNNN NNNNNNNNNN NNNNNNNNNN
168651 NNNNNNNNNN NNNNNNNNNN NNNNNNNNNN NNNNNNNNNN NNNNNNNNNN
168701 NNNNNNNNNN NNNNNNNNNN NNNNNNNNNN NNNNNNNNNN NNNNNNNNNN
168751 NNNNNNNNNN NNNNNNNNNN NNNNNNNNNN NNNNNNNNNN NNNNNNNNNN
168801 NNNNNNNNNN NNNNNNNNNN NNNNNNNNNN NNNNNNNNNN NNNNNNNNNN
168851 NNNNNNNNNN NNNNNNNNNN NNNNNNNNNN NNNNNNNNNN NNNNNNNNNN
168901 NNNNNNNNNN NNNNNNNNNN NNNNNNNNNN NNNNNNNNNN NNNNNNNNNN
168951 NNNNNNNNNN NNNNNNNNNN NNNNNNNNNN NNNNNNNNNN NNNNNNNNNN
169001 NNNNNNNNNN NNNNNNNNNN NNNNNNNNNN NNNNNNNNNN NNNNNNNNNN
169051 NNNNNNNNNN NNNNNNNNNN NNNNNNNNNN NNNNNNNNNN NNNNNNNNNN
169101 NNNNNNNNNN NNNNNNNNNN NNNNNNNNNN NNNNNNNNNN NNNNNNNNNN
169151 NNNNNNNNNN NNNNNNNNNN NNNNNNNNNN NNNNNNNNNN NNNNNNNNNN
169201 NNNNNNNNNN NNNNNNNNNN NNNNNNNNNN NNNNNNNNNN NNNNNNNNNN
169251 NNNNNNNNNN NNNNNNNNNN NNNNNNNNNN NNNNNNNNNN NNNNNNNNNN
169301 NNNNNNNNNN NNNNNNNNNN NNNNNNNNNN NNNNNNNNNN NNNNNNNNNN
169351 NNNNNNNNNN NNNNNNNNNN NNNNNNNNNN NNNNNNNNNN NNNNNNNNNN
169401 NNNNNNNNNN NNNNNNNNNN NNNNNNNNNN NNNNNNNNNN NNNNNNNNNN
169451 NNNNNNNNNN NNNNNNNNNN NNNNNNNNNN NNNNNNNNNN NNNNNNNNNN
169501 NNNNNNNNNN NNNNNNNNNN NNNNNNNNNN NNNNNNNNNN NNNNNNNNNN
169551 NNNNNNNNNN NNNNNNNNNN NNNNNNNNNN NNNNNNNNNN NNNNNNNNNN

FIGURE 3LLL

169601 NNNNNNNNNN NNNNNNNNNN NNNNNNNNNN NNNNNNNNNN NNNNNNNNNN
169651 NNNNNNNNNN NNNNNNNNNN NNNNNNNNNN NNNNNNNNNN NNNNNNNNNN
169701 NNNNNNNNNN NNNNNNNNNN NNNNNNNNNN NNNNNNNNNN NNNNNNNNNN
169751 NNNNNNNNNN NNNNNNNNNN NNNNNNNNNN NNNNNNNNNN NNNNNNNNNN
169801 NNNNNNNNNN NNNNNNNNNN NNNNNNNNNN NNNNNNNNNN NNNNNNNNNN
169851 NNNNNNNNNN NNNNNNNNNN NNNNNNNNNN NNNNNNNNNN NNNNNNNNNN
169901 NNNNNNNNNN NNNNNNNNNN NNNNNNNNNN NNNNNNNNNN NNNNNNNNNN
169951 NNNNNNNNNN NNNNNNNNNN NNNNNNNNNN NNNNNNNNNN NNNNNNNNNN
170001 NNNNNNNNNN NNNNNNNNNN NNNNNNNNNN NNNNNNNNNN NNNNNNNNNN
170051 NNNNNNNNNN NNNNNNNNNN NNNNNNNNNN NNNNNNNNNN NNNNNNNNNN
170101 NNNNNNNNNN NNNNNNNNNN NNNNNNNNNN NNNNNNNNNN NNNNNNNNNN
170151 NNNNNNNNNN NNNNNNNNNN NNNNNNNNNN NNNNNNNNNN NNNNNNNNNN
170201 NNNNNNNNNN NNNNNNNNNN NNNNNNNNNN NNNNNNNNNN NNNNNNNNNN
170251 NNNNNNNNNN NNNNNNNNNN NNNNNNNNNN NNNNNNNNNN NNNNNNNNNN
170301 NNNNNNNNNN NNNNNNNNNN NNNNNNNNNN NNNNNNNNNN NNNNNNNNNN
170351 NNNNNNNNNN NNNNNNNNNN NNNNNNNNNN NNNNNNNNNN NNNNNNNNNN
170401 NNNNNNNNNN NNNNNNNNNN NNNTGGCTTA AAACAACACA CATTTATTAT
170451 TTTACAGTTC TGGAGGTCAG AAGTCTAAGA TGATGCCAGG CTTGGTGGCT
170501 CAAGCCTGTA ATCCCAGCAC TTTGGGAGGC TGAGGTGGCA GGATCACTTG
170551 AGGTCAGGAG TTCCAGACTA GCCTAGCCAA CATGGTGAAA CCCCATCTCT
170601 ACTAAAAATA CAAAAATTAG TCAGGCACGG TCACGAGCAC CTGTAATCCC
170651 AACTACTCAG GAGGCTGAGG CAGGAGAATT GCTTGAACCC AGGAGGTGGA
170701 GGTTGCAGTG AGCCGAGGTT GCAGTGAGCC GAGGTTGCAC CACTGCACTC
170751 CAGCCTGGGC AACAGAACGC GACCCTGTTT CCAAGAAAAA AAAAAAGTCC
170801 GGGATGAGTT TTACTGGGCT GAGATCAGTG TAGACAAGGC TGCCCTCTCT
170851 CTGGAGGCTC TAGGGCAGAA TCTGTTTCCT TGTCTTTTCC AGCTTCTAGA
170901 GGTTGCCTGC ATTCCTTGGC TTGTGGCCCC TTCCTCCGTG TTCAAAGCCA
170951 TTGGTGTAAC ATCTTCAGGT CTCTGTGACT CCGATCCTTG CTTCCATCTT
171001 ATAAGGATCC TTGTGATTTC ATTGTACCCA TCCAGATATC CCAGGAGAAT
171051 CTTTCCATCC CAAGATCCAT AACTTAAATC CCATCTGCAA AGTCCCTTTT
171101 GCCATGTGTG GTAATATATT CACAGCTTGC AGAGATCAGG ACATGGGCAT
171151 CTTTGGGAAA CGGGAAGGGG GCATTATTTG ACCTAACATC AAGAGCATGA
171201 GATGTTTTTG TAAAATGAAA CAAATGTTGC AGCTTCCTAA TGCAGCTTCT
171251 TAGGCCCACC TGCAGGCCCC CTTGACGTTG GTTTTTCTCT ACCTAGGTCT
171301 GTTGTGTCGG GTCTGGACTC CCCTGCCAAG ACTAGCTCCA TGGAAAAGAA
171351 ACTTCTCATC AAAAGCAAAG AGCTACAAGA CTCTCAGGAC AAGTGTCACA
171401 AGGTATTTAT TTCCGCAGCC GGCCTCCTTC CTTGCTCCAG GATCCTCCCG
171451 TCCGTATATG CCAAGGGATC CGCCCGGGGC CGCTGCTGGC TCTGAGCCGC
171501 CTGATCCGTA GAGAGTGAGG CGCTCCTGCC TTCGCTGAAG TCGCGCCTCC
171551 AGCAGCTCAG AGGGAGATGA ATTCGGGCCT TGCTGTTGCT GTAAATCCTT
171601 TAAATCTAAA CCAGAGGAGG CCCTGGATTT AAACAGTCCG TTTCTCAGCA
171651 TGACCCAGCC AGATGTCTGC TTCTTCCGGC AGGTGGCCTG GGTCCTCACC
171701 TGTGGCTGAG ATACATCCCA TCTGCTTTGA GTGATGCGAA GTCTCTCTTC
171751 CTAGTCTTTT AAAACTCCTG CTTATGTCAC TGCGGCCACT GTGTTGATTA
171801 CGCTCAACGT CTCTTAACAT TCACTGTTCC TGCCCAGAGG CAACGCTCTG
171851 GAAACTAATA AGTCACTGCT TGCCTGGGAC TCCTAAGAGT GCAGACGAAT
171901 AAATATCTCC TTGCCCTGTC CTGGATTTGT CCTCTAGATC TTTGCAAGGA
171951 GATGGGGGGG GATCAAGATG GATTTGGGAT AAAATTAAAG TGACGTCTGC
172001 AAAAACAAAA CAAAAACAAA AGCAAACAGG TGAAAAATGA TGATTGTGGC
172051 TTCCTTGCTA ACTGGGTTAG AGAAGTGATC AAGTGTGAAC CGGGACTTGA
172101 ATGAGAGGAG TGACTTAGCA TTTGGTGACT GTCCTTAACG AAGAACTGTG
172151 CGCTCCTGGG CGAAGAAACA ATGGTATTTC CATCCCAACT TAACTTTTGG
172201 CGAATTAGCC TTAGCCCAGA CCACCAGGTG GTTTCGGAGG CTACTTGAGA

FIGURE 3MMM

172251 TGTGATTGCT CCTAATGAAC CTCCACGGGC CTTTTTAACC TGTCGATGTG
172301 TTTATTTCAG ATGGAGCAGG AAATGACCCG GTTACATCGG AGAGTGTCAG
172351 AGGTGGAGGC TGTGCTTAGT CAGAAGGAGG TGGAGCTGAA GGCCTCTGAG
172401 ACTCAGAGAT CCCTCCTGGA GCAGGACCTT GCTACCTACA TCACAGAATG
172451 CAGTGTGAGC CTTCCCTGAA GCCCCCTTCC CTTGGAGGTG GCACTTCCTG
172501 TTGTGTGTGT CTCATCCTGT TTCATGATGA CTCCATGAGG CACATCACAG
172551 CCAATGGCAG AGAGTAGAGA GAGGGAGAGC ACAAAAGCAA GATCTGTGTT
172601 TTGCAGAGTA GTGAGAGCCA GGCGTAAGGT CCCCAAGAAA TGAGATTGGA
172651 CTCATTTCCA GCAGAAAGTG CAGGTAGACG GCTGGTACCA TGGAGTCTGG
172701 AGATGGGAGT AATTCATCTT TGCCGCAAGT TGCAAAAGAT CTTAACATCT
172751 CCCATCCCAG CCTCTGTGGT CTGCGTTGTG TCTGACATGA GCAGCCTTGA
172801 GAACCAGACT CCCAACTATG TACAAGAAAA CTTACTTTCA ATCTTCCTGA
172851 CATCAAATTT TCCATTGGCC AGAACCAGTG TAGTGACAAG AAAATAGCCT
172901 TGAAAACCCA GACCCTCTGT CATTATTTAC CATGTGACTT TCATTTTTTC
172951 TTTCCTTCAC AAGAGTAGAC TGTCTTCTTC TCCATTGTCT TGTTAAATTT
173001 TTCATTCAGG TGTTTTTTAA TGTGCCCAAT TAAACAGTCT CAAGAAGTTG
173051 AATCACACAT TTCTAAAGTT TTTTTCACAA GGGAGAGGAA ATCTATAGAA
173101 CGTGGCTGAT TAAGAATAAC TGCTATGTTT CCATTCCAGA CTTGGCTGCC
173151 TTTCAGTGGT GGGTGAAGTT ATTCAGCTAT GTATTTCAGA TATAGATTTC
173201 AGTGCCATGA AGCATAAGGG NNNNNNNNNN NNNNNNNNNN NNNNNNNNNN
173251 NNNNNNNNNN NNNNNNNNNN NNNNNNNNNN NNNNNNNNNN NNNNNNNNNN
173301 NNNNNNNNNN NNNNNNNNNN NNNNNNNNNN NNNNNNNNNN NNNNNNNNNN
173351 NNNNNNNNNN NNNNNNNNNN NNNNNNNNNN NNNNNNNNNN NNNNNNNNNN
173401 NNNNNNNNNN NNNNNNNNNN NNNNNNNNNN NNNNNNNNNN NNNNNNNNNN
173451 NNNNNNNNNN NNNNNNNNNN NNNNNNNNNN NNNNNNNNNN NNNNNNNNNN
173501 NNNNNNNNNN TGATTCTCCT GCCTCAGCCT CCCGAGTAGC TGGGACTACA
173551 GGCATGCACC ACCATGCCCA GCTAATTTTT GTATTTTTAG TAAAGACGGG
173601 GTTTCACCAT GTTGGCCAGG GTGGTCTCGA TCTCTTGACC TTGTGATCCG
173651 CCTGCCTCGG CCTCCCAAAG TGCTGGGATT ACAGGTGTGA GCCACTGTGC
173701 CCAGCCCATA AATCAAAATT TTTTCAGCAA TTGTTATACA AGTGGAACCT
173751 TACTCTTCAA ATGCAATTGT CCAGTGTCTG GCTTAATGTC TGCTGTTGTC
173801 AGAAACCATG TGAATGGAGT AGATTCCCAG GTTATAAGGA GCCCCCAGGG
173851 AGGATGCGCG AGTCACTGGC TTCTCCAGGG GTCTCTGGTT TGGGGTTGCC
173901 TTGGTGCTGG GCACACTTCC TGGAGATTTT ACTGGACCAG CCTGAGGCCT
173951 TTGGGGCTCT GTGCAGATGC TCTACTTCTG ACTTGTCTAG AGCTTTCTTC
174001 TAATTCTGGA CTAAAAGCAA GCAGGAGTTT GGAGGATGAT GGTGAGAATT
174051 CACATCCCCG AGTTGGCTTT TGGAATGCAG TAGTTTGTGA GATTTAGTGT
174101 TTTTTTTAAG AAGTATATTC AGATCTTGCC TTTTTCCCAG AAAGCATATG
174151 AGACAACTTC CAAGACATTT ATAGCATGGC TAATAAAATG GGAAATCAGG
174201 GCGAAGGACA GGAGAACTCA ATAAGGGTTA ACATGGCTAC AGCGATTGTC
174251 TAAATGGGTT CTTTTTGCTG GCCAGAGCAG AAAGGATCAT GCAGTAAAGT
174301 GGGGGGGAAG AAAGGGAATT GAATGGTAGG TGAAGACTTC ATGTTGGTGC
174351 CAGGCACTGT GCCAGGCCCT CCTAGGACCT TGTCTTACTC AATCCTCACA
174401 CAGTGCTGCA AGAGGATTAG TCTTATCCCT GTTTTAGAGA GGATGAAACT
174451 GAAAGGCAGC GAGGTGAAGT CACCAGCAGG AGGCTGAAGC CGC
(SEQ ID NO:3)

FEATURES:
Start: 2007
Exon: 2007-2102
Intron: 2103-8974
Exon: 8975-9117
Intron: 9118-15407

FIGURE 3NNN

Exon:     15408-15409
Intron:   15410-20480
Exon:     20481-20656
Intron:   20657-27907
Exon:     27908-28013
Intron:   28014-72738
Exon:     72739-72741
Intron:   72742-105286
Exon:     105287-105294
Intron:   105295-121265
Exon:     121266-121393
Intron:   121394-123900
Exon:     123901-123911
Intron:   123912-126394
Exon:     126395-126467
Intron:   126468-129602
Exon:     129603-129609
Intron:   129610-130289
Exon:     130290-130493
Intron:   130494-149974
Exon:     149975-150024
Intron:   150025-150920
Exon:     150921-151021
Intron:   151022-152695
Exon:     152696-152879
Intron:   152880-171296
Exon:     171297-171492
Stop:     171493

SNPs:

| DNA Position | Major | Minor | Domain | Protein Position | Major | Minor |
|---|---|---|---|---|---|---|
| 10267 | - | T A | Intron | | | |
| 11548 | C | T | Intron | | | |
| 13169 | G | C | Intron | | | |
| 16643 | T | C | Intron | | | |
| 22293 | A | G | Intron | | | |
| 24151 | T | C | Intron | | | |
| 24523 | G | T | Intron | | | |
| 25268 | G | A | Intron | | | |
| 29374 | A | G | Intron | | | |
| 29795 | G | A | Intron | | | |
| 30861 | T | C | Intron | | | |
| 32238 | G | - | Intron | | | |
| 32242 | T | - | Intron | | | |
| 37658 | A | G | Intron | | | |
| 37749 | A | G | Intron | | | |
| 39924 | C | T | Intron | | | |
| 55645 | C | T | Intron | | | |
| 57539 | A | C | Intron | | | |

FIGURE 3000

| | | | |
|---|---|---|---|
| 58604 | C | G A | Intron |
| 58861 | T | G | Intron |
| 59060 | G | A | Intron |
| 59518 | C | A | Intron |
| 59802 | T | C | Intron |
| 60083 | T | G | Intron |
| 60525 | T | C | Intron |
| 61078 | A | G | Intron |
| 63026 | T | C | Intron |
| 63231 | G | A | Intron |
| 65298 | C | T | Intron |
| 66172 | C | T | Intron |
| 66244 | T | C | Intron |
| 66700 | G | A | Intron |
| 67029 | G | T | Intron |
| 67140 | A | G | Intron |
| 68038 | G | A | Intron |
| 69852 | G | A | Intron |
| 71083 | T | C | Intron |
| 71098 | G | A | Intron |
| 71445 | A | C | Intron |
| 71981 | C | A | Intron |
| 72366 | T | A | Intron |
| 73797 | T | - | Intron |
| 74416 | G | A | Intron |
| 74664 | G | C | Intron |
| 76330 | T | C | Intron |
| 78181 | A | G | Intron |
| 78685 | C | A | Intron |
| 79926 | G | A | Intron |
| 80198 | G | A | Intron |
| 80540 | T | C | Intron |
| 81810 | C | T | Intron |
| 82211 | G | A | Intron |
| 82304 | C | G | Intron |
| 82452 | A | G | Intron |
| 82539 | T | A | Intron |
| 83079 | A | G | Intron |
| 83350 | T | G | Intron |
| 83407 | A | G | Intron |
| 83434 | G | A | Intron |
| 83527 | A | G | Intron |
| 83699 | G | A | Intron |
| 83729 | A | G | Intron |
| 84000 | T | G | Intron |
| 84034 | C | T | Intron |
| 84213 | C | T | Intron |
| 84803 | A | G | Intron |
| 85027 | G | A | Intron |
| 85275 | A | T | Intron |
| 87009 | T | C | Intron |
| 87888 | G | A | Intron |
| 88136 | G | A | Intron |

FIGURE 3PPP

| | | | | | |
|---|---|---|---|---|---|
| 88231 | G | A | Intron | | |
| 88482 | A | G | Intron | | |
| 88608 | C | A | Intron | | |
| 88866 | T | C | Intron | | |
| 88870 | C | T | Intron | | |
| 88918 | G | A | Intron | | |
| 88940 | C | T | Intron | | |
| 89133 | A | G | Intron | | |
| 89260 | T | C | Intron | | |
| 89298 | G | T | Intron | | |
| 89682 | G | A | Intron | | |
| 89757 | C | T | Intron | | |
| 89817 | C | T | Intron | | |
| 90248 | G | A | Intron | | |
| 90283 | G | C | Intron | | |
| 90506 | C | G | Intron | | |
| 90607 | C | T | Intron | | |
| 92329 | A | G | Intron | | |
| 92912 | C | A | Intron | | |
| 95043 | A | G | Intron | | |
| 95227 | T | C | Intron | | |
| 107428 | G | A | Intron | | |
| 114951 | A | G | Intron | | |
| 115042 | A | G | Intron | | |
| 117217 | C | T | Intron | | |
| 120452 | A | G | Intron | | |
| 124035 | G | A T | Intron | | |
| 124589 | C | T | Intron | | |
| 125136 | G | - | Intron | | |
| 125856 | G | T | Intron | | |
| 126256 | C | T | Intron | | |
| 127332 | C | T | Intron | | |
| 128302 | G | A | Intron | | |
| 129122 | C | T | Intron | | |
| 129376 | T | C | Intron | | |
| 134893 | A | C | Intron | | |
| 136001 | C | G | Intron | | |
| 136249 | T | G | Intron | | |
| 136448 | G | A | Intron | | |
| 136906 | C | A | Intron | | |
| 137190 | T | C | Intron | | |
| 137471 | T | G | Intron | | |
| 137913 | T | C | Intron | | |
| 138466 | A | G | Intron | | |
| 146805 | G | A | Intron | | |
| 151008 | T | - | Exon | 365 | C |
| 151627 | G | A | Intron | | |
| 151875 | G | C | Intron | | |
| 153541 | T | C | Intron | | |
| 155392 | A | G | Intron | | |
| 155896 | C | A | Intron | | |
| 157137 | G | A | Intron | | |
| 157409 | G | A | Intron | | |

FIGURE 3QQQ

| | | | |
|---|---|---|---|
| 164675 | T | C | Intron |
| 165157 | G | A | Intron |
| 165405 | G | A | Intron |
| 165500 | G | A | Intron |
| 165751 | A | G | Intron |
| 165877 | C | A | Intron |
| 166135 | T | C | Intron |
| 166139 | C | T | Intron |
| 166187 | G | A | Intron |
| 166209 | C | T | Intron |
| 166402 | A | G | Intron |
| 166529 | T | C | Intron |
| 166567 | G | T | Intron |
| 166951 | G | A | Intron |
| 167026 | C | T | Intron |
| 167086 | C | T | Intron |
| 167517 | G | A | Intron |
| 167552 | G | C | Intron |
| 167775 | C | G | Intron |
| 167876 | C | T | Intron |
| 172530 | A | G | Beyond ORF(3') |
| 172714 | T | C | Beyond ORF(3') |
| 173811 | C | T | Beyond ORF(3') |
| 173812 | C | T G | Beyond ORF(3') |

Context:

DNA
Position

10267 TTGCCCTATTACCCAGGCTGGATTGCAGTGGTATATCATGGCTCACTGCAGTTTCAACCT
TCTAGGCTCAAGCAATCCTTCCACCCCAGTGGCTGGGACTACAGGCTCACACTACCACGC
CCAGCTAATTTTTGCTTTTTTCTCTGTAGAGATAGGGTCTTACTATGTTACCCAGGCTGG
TTTCAAACTCCAGGCTTGAAGCAGTCTTCCTGCCTCAGCCTCCCAAAGCTTTGGGATTAC
AGGTGTGAGCCACCATGCCTGGCCCCATAAAATATAATTTTTGAATTCTTTTTTGTTTTT
[-,T,A]
ATGGAGGAAGGGGCTGAGGAAGGCAAAAGTACCTAGGGCCTATGAAGTCATATATTGGCC
TTGCCTTCACCCTGTTTCTGACTTTGCTTGACTTCCATGTGATGAGGCAGTTGGCTGTTA
GTGTCCCAGTTTCATACTCTTACATTAGTGTTTTTCAACCAGTGGGTGATTTGACGTTTT
CGGTTGTCAGAGCTAGTTGGGGGTGGTGGTGTGTGAGTTTGGGGGGAAGGGTCCTACTGT
CAGTTAATGGGTGAGGCCAGAGATGCCACCAAACACCTTACAGTGCACAAAGCAGCCCCC

11548 GATGCCTATTTTGTAAAGAAGGTTTTACTGGAACACAGCCCTACCCATGTGTTTGTACAG
TGCCTATGGCTGCTTTCACATCATAACAGCATTTTATTTCATTTTATTTATTTTTTTTTG
AGACAAAGTCTCACTCTGGCTGGAGTGCAGCAGCACAATCATAGCTCACTGCAGCCTCCA
ACTCTTGGGCTCAAGCAATCCTCCTGTCTCAGCCTCCTCAGTAGCTAGTACTACAGGCCC
ATGCCACCACTAATGGCTAATTTTTTAATTTTGTGTAGAGATGGGACCTTGTGAGATTGC
[C,T]
TAGGCTGGTCTTGAACTCCTGGCCTCAAGAAATCCTCCCACCTTGGCCTCCCAAAATGCT
TGGATTACAGGCATGAGCCACTGTGCCCAGCCCACAACAGCATTTGAGTAGTTGTGATAG
AGACCAAATGGCCTACAAAGCCCAAAATAGTTCCTGTTTGGCCCATTTCGAAAAGGCTTG
CTGACCTCTGAGCTACATGGTCTCTCTAGCAGGACAGCCTCGACGGTAGCTCAGGTTTCC
AAAACACAAAAGTGGAAGCTGCCAGGCTTTCTTAGGGGTTATCCTAGGAGGGACATAGGA

13169 CTTACTGAGCCATCTGCAGGCACCTTCATTAGTCTTGAGACTGTCCTCTGGTTACTTAAC
AGCAGTGAATTATCTAGAATCATTTAGTGATCAGAAGACTTGGTTTAGTGGAATGTAGAT

FIGURE 3RRR

TTTTTTCTAATAGACCCCTCTTCCAGGGAAATGTTTCATATTTTTGAAGAGGTTTCCTGG
GGAGTGTTTAAGAGGCCATGATTGAAAATGGGTGATTACATTAGTGTGTTTTCTATTCCT
CCCCTTTTTGAGTTTCTGTTTTGGAATGTAAGCTTTGTTTTTCTACGTGGAGAAGGGTCC
[G,C]
TCAGCTGCTTCTGCCCAGGTTTTTTGAATCTTCCTATAGGGATGGAGATTTTCTTTGGGG
ACTGTTAGAGAAAATGGAATAGAGTGTAGCTCTGAAGGAGAAGGATGTCTCCAGCAGAAG
TACCTCTAGCCTTGGGCCAAGGGAGGGAAGGGAAGGGAACGAGCATCTGGGAACCAGGGA
AGGGATTTTTGTCTTTCTTAATTACTCTTACATCCCCAGTGCCCAAAATAGTGTCTGGCA
TATGTTAAGTCCTTAGTAAATACTTGTTGAATGAGTGTATGCTCAGTGAACAAAATAAAT

16643 TTCTGATTATTTTTGTGTTACAACAGTTTTCATCATTCACATCTTTGTATGCATCTTTTT
TGAGCACATGTGCAAGTATTTCTGTGGACAATGGATGATTCCTAGAAATTGAAAGTTTGG
ATTACTGTGTTCCAAAAAAGGAAGCAATACACCCAGCTATGTTGGCTTTTGCTCTTGGGT
CCAGATGATTATCTGACAAAGTTATTCTCTGATTGCATTTTCTTTTCTTTTCTTTTCTTT
TTTTTTTTTGAGATGGAGTTTCGCTCTTGTTGCCCAGGTTGGAGTGCAATGGCGCGATCT
[T,C]
GGCTCACTGCAACCTCTGCCTCCCAGGTTCAAGCGATTCTCCTGCCTCAGCCTCCTAAGT
AGCTGGCATTGCAGGCATGCGCCACGACACCTGGCTAATTTTTTGTATTTTTAGTAGAGA
TGGGATTTCTCCATATTGGTCAGGCTGGTCTTGAACTCTTGACCTCAGGTGATCCACCCG
CTTCAGCCTCCCAAAGTGCTGGGATTACAGGCGTGAGCCACAGTGCCTGGCCCTCTGACT
GCATTTTCACAGTGTTTTGGGTCCTTATCTCTACCTCAGTACCTCAATATTCAGTGCCCA

22293 TCAGAGTCTGGCCCTGTGGACTTCAATGACTTTGTGTGGCCTCCAATCAGAGAAGCAGCG
GAGGGCAGGAAGCTGCTTGTCAGAATCTGAGAGTGATGTGGCTTCTTTGTTTAGCAATAA
AATGTGAGCACATAATAGAAAGGAAAAGTGACAGGACATGGCAGATAATTTGGAAGAGAG
GAGTGGAAGATGCTCACTCAGCCTCCCAGCTCCTGAGAAAGAACTGTGTCTCATCAGTTC
ATACTACCTGAGCATCTGTTGTATCTGGTGTGTTTCTAGGTCCTGGAGAAGAGGCATTAC
[A,G]
TGTAGCCCTGACCTTGTGATGCTTATGTTTTTGATGGGAAATAGTGCGTGTAAAAAGAAA
ATAATCCAACAGGCCACACGGCAGGCAAACAATAGAGATATTCAAATAGGTATACCTTCC
TCCAGGTGAATGGCCTGAAATGACCGTGTGGAAGTGTGGGCTGGGGGCTTATAAAATTAT
ACACATACAGGCGCTAACTAAAGCCGCCTATTCATTCCTTAAGAGGATGCATAGAAAAGA
AAAGTAGGGTCCTTAACTGAGCCATTTGGAATTTAAGGGCATGAGAGAAGCCAGCACAAG

24151 TTGTGGGCCGGGTGCAGTGGCTCACGCCTGTAATCCCAGCACTTTGGAGGCCAAGCAGGG
CGGATCACTTGAGGTCGGGAGTTTGAGACCAGCCTGACCAACATGGAGAAACCCTGTCTC
TACTAAAAATACAAAAAATTAGCCGGGTGTGGTGGTGCATGCCTGTAATCCCAGCTACTT
GGGAGCTGAGGCAGGAGAATTGCTTGAATCTGGGAGGCAGAGGTTGCAGTGAGCTTAGAT
CACGCCACTGCACTACAGCCTGGGCAACAAGAGCGAACACTCCGTCTCAAAAAAAAAAAA
[T,C]
AAATTATGTAGAGGTGGGATCTCCCTATGTTGCCCGGACTGGTCTTGAACTCCTGGCCTC
AAGTGATCCTTCCATCTCCCCCTCCCAAAGTGTTGGGATTACAGGCATGAGCCACCCCTC
CTGGCTGAGACTGCTTATTTTATTTATTTTTAATTTTTTTTGTTTTGAGACTGCTTATTT
TAATGGAAGCTTCAGGGGTCAGACGGGGTCAGACAGAGTCATTGGTGAGCAAGCAAAGGT
GTAGACTGTTCAGTTCAGCCTTCCTTGGACACCTTTTATGTGCCAGACAAAAGAAGGATC

24523 CCATCTCCCCCTCCCAAAGTGTTGGGATTACAGGCATGAGCCACCCCTCCTGGCTGAGAC
TGCTTATTTTATTTATTTTTAATTTTTTTTGTTTTGAGACTGCTTATTTTAATGGAAGCT
TCAGGGGTCAGACGGGGTCAGACAGAGTCATTGGTGAGCAAGCAAAGGTGTAGACTGTTC
AGTTCAGCCTTCCTTGGACACCTTTTATGTGCCAGACAAAAGAAGGATCAGCATATCAGG
TGCAGTAAATTATTGGGGTTATGTTGGTGTTTCCCAAATGTGTTAGATTTATCCCTGGTA
[G,T]
TGTTAAATCTCATGATTTTAGGTAGTATATGGACAACCTATGTAAAAACATTTAATAGTT
TAATATTAACTAGCATATCAAAACCTGTGACTTTGCTCACGCCTGTAATCCCAGCACTTT
GGGAGGCCAAGGCGGGAGGATGGTTTGGGCCCAGGAGTTTGAGGCCAGCCTAGGTAACAT
GGTGAGACCCTGTCTCTAAAACAAAACAAAACAAAACAAACAAACAAACAAATAAACAAA
TCCCCTGTAACTTGTTCTAACAATAACCTAAACAATTTTTTATTTAAAATTAAATAAAAA

25268 GGATTGATTACAGGTGCACTCCACCATGCCCAGCTAATTTTTGTATTTTTAGTAGAGACG
GGGTTTCACCATGTTGGCTAGGCTAGTCTTGAACTCCTGACCTGCAGTAGTCCACGTGCC
TTGGCCTCCCAAAGTGCTGGGATTACAATCACAAATTTATAGAAAAGTTGCAAGTACCAT
GTAGTCAGGGTTCTTAAGAGAAATGGAACCAGTAGGAGATAGATATATAATCATCTCCTA
GGATTATAAGTTGACACATAAGACTAACCGTCACATACAGTATAAACAACTTTTTTTCTT
[G,A]
AACCATTTGATAGATACACACACACTGATATACATAGAATATATATACACACACACAGAA

FIGURE 3SSS

TGTATATACACATAGAATATATGTGCATACAGAATATATACACAGAAATATATATGTACA
CATGCATAGAATATATTTACATATATATGCATATATATAATTTATTTATTTTAAGCAGTT
GATTTATACAGTTTTTGTTTTTGTTTTTTTTTGAGACAGAGTCTCACTCTGTCACCCAG
GCTAGAGTGCAGTGGCGAGATCTCAGCTCACTGCAACCTCTGCCCCCGGGTTCCAGTGAT

29374 AAGAAATGTTAAATGGTTACATAAGCTTTCCCTTTCTGACCCTTAACTGTGCTCTGTAGG
AGCATGGTGGGGGATGTTTCTTTTCTTTTCTTCTTTTTTTGAGACCAGGTCTCACTTTGC
CACCCAGGCTGGAGTTCAGTGGCATGAACATGGCTCACTGCAGCCTCGACTTCCTGGGCT
CCAGCAAACCTCCCACCTCAGCCTCCCGGGCATACACCACTGTGCCTGGCTAATTTTTGT
ATTTTTAGTAGAGACGGGGTTTTGCCATGTTGCCCAGGCTGGTTTCGAAGTCCTGAGCTC
[A,G]
AGAGATCTTCCTGCCTTGGCCTTCCAAAGTGCTGGGATTACAGGTGTGAGCCACCATGCC
CAGCTCCGGTGGGGGATATTTCTATATCCACATGTGTATAGTTTACTTTATAAAAATGGT
ATGTTACTCTGTGCTTGGCTCTCCAGCTTGCTGTTGCCTTTCACCAGTGTATCCCAGACA
TCCTTTCTTCCTTGTCAGTAACGCAGGTCTACTTTATTCTTTGAGCAGTGGCATAATTTT
CCCTGATGTGTATATATCATAAGTTAGAGAATGCTAAAATTCATTTTGGGGCCTTGTTTA

29795 ATGTTACTCTGTGCTTGGCTCTCCAGCTTGCTGTTGCCTTTCACCAGTGTATCCCAGACA
TCCTTTCTTCCTTGTCAGTAACGCAGGTCTACTTTATTCTTTGAGCAGTGGCATAATTTT
CCCTGATGTGTATATATCATAAGTTAGAGAATGCTAAAATTCATTTTGGGGCCTTGTTTA
GGTTCTTGAGGGATTAAATTCCTAAATTTAACAAGTGTATCCTGGAAACAATTTTTGTTC
CTGATTCAGCCCTTAAAAGAGGACTATCATGTTACCTTGAATGGAGATAAACAGGCTCAC
[G,A]
TAAGAGAAAAGGGTAAGAGGGATGAACTCCCACTTATCTTAAACTTCTACTGGCCCGTTT
TTGGGGAATTTGCTGCTTTTATTCCTGACCTAAAATAAATAAGTTTATGTGTCTTGGTTT
CATATTAGTTGAGAACCCAGTGCCTGGAGAGAAGTTTTCCTTGTCCTCTGAGTGAGGACA
TTCACATATGAATCTATTGGCAGACTGGCTTTGACTGACCACACGTGCCTTCAGAACCAA
TGCCACAGCTCTTAGGTTTATGGCCTGAAACACCCTTTCCTTACATATTGCCTTAGAAAC

30861 CACTGCGCCTTTTCTTTTCATTTTTTTTCTGAGATGGAGTCTTTCTCTGTCACCAGGCTG
GAGTACAGTCATGCAATCTCAGCTCACTGCAACTTCCACCTCCTGGGTTAAAGTGATTCT
CTGTCTTAGCCTCCTGTGTAGCTGGGACTACAGGCGTGTGCCACTGTGCCCAGCTAATT
TTTATATTTTTAGTAGAGACGGGGTTTTGCCATGTGGGTTAGGCTGGTCTTGAACTCCTG
ACCTCAGGTGATCCACCCGTCTTGGCCTCCCAAAGTGCTGGGGTTATAGGCGTGAGCCAC
[T,C]
GTGCCCAGCCTCAGGCTTCTTTATTAAGAAGAAGTTCGGGCCAGGTGTGGTGGCTTACAC
CTGTAATCCCAGCAATTTGGGAGGCCGAGGTGGGCAGATCAGGAGGTCAGGAGATCGAGA
CCATCCTGGCTAACATGGTGAAACCTCGTCTCTACTAAAAATATAAAAAATTAGGCAGGT
ATGGTGGCGGGTGCCTGTAGTCCCAGCTACTCGGGAGGCTGAGGGAGGAGAACGGTGTGA
ACCTGGGAGGCGGAGCTTGCAGTGAGCCCAGATTGTGCCAGTGCACTCCAGCCTGGGTGA

32238 GGCTACTGCTCAGTAGCTTCAGGGAAACCACTGCTTGCCTCCCCTGTGGCCAGTGAGGAT
GATCAGAGGAGTCCCAGCAGGAATGCCCAAATGTAGTTTTCTTACATGTTGATGGGAGTG
CATTGTTTCATGTCTAAACAGTTCTCAAATCACATCTTCAGGAGGGTACTATCTGGGCAC
TTTGATAATTTCTCACTTTGATGTCACCGTTCTTATTACCATCACCTAGTTTTGTCATAG
TAGAAATAACTTTCCTTTTTCTGTGTGTGTGTGTGTGTGTGTGTGTGTGTGTGTGTGTGT
[G,-]
TTTTGAGATGGAGTCTTGCCGTGTTGCCCAGGCTGTAGTGCAGTGGCGTGTTCTCGGCTC
ACTGCAACCTCTGCCTCCCGGGTTCTCCTGCCTCAGCCTCCCGAGTAGTTGGGATTACAG
GCGTGTGACACCACGCCTGGCTCATTTTTGTATTTTCAGTAGAGATGGGGTTTCACCACT
TTGGCCAGGCTGGTCTTGAACTCCTGACCTTGTGATCCGCCCACCTTGACCTCCCAAAGT
GCTGGGATTGCAGGTGTGAGCCACCACGCCTGGCTTTTTTTTTTTTTTTTTTTGAGACAG

32242 ACTGCTCAGTAGCTTCAGGGAAACCACTGCTTGCCTCCCCTGTGGCCAGTGAGGATGATC
AGAGGAGTCCCAGCAGGAATGCCCAAATGTAGTTTTCTTACATGTTGATGGGAGTGCATT
GTTTCATGTCTAAACAGTTCTCAAATCACATCTTCAGGAGGGTACTATCTGGGCACTTTG
ATAATTTCTCACTTTGATGTCACCGTTCTTATTACCATCACCTAGTTTTGTCATAGTAGA
AATAACTTTCCTTTTTCTGTGTGTGTGTGTGTGTGTGTGTGTGTGTGTGTGTGTGTGTTT
[T,-]
GAGATGGAGTCTTGCCGTGTTGCCCAGGCTGTAGTGCAGTGGCGTGTTCTCGGCTCACTG
CAACCTCTGCCTCCCGGGTTCTCCTGCCTCAGCCTCCCGAGTAGTTGGGATTACAGGCGT
GTGACACCACGCCTGGCTCATTTTTGTATTTTCAGTAGAGATGGGGTTTCACCACTTTGG
CCAGGCTGGTCTTGAACTCCTGACCTTGTGATCCGCCCACCTTGACCTCCCAAAGTGCTG
GGATTGCAGGTGTGAGCCACCACGCCTGGCTTTTTTTTTTTTTTTTTTTGAGACAGAGTC

FIGURE 3TTT

37658 GACAGTGAGACATGTGCTGTTTTGATCTCTCAGCTAAGATTATCTGATTTTTCAGGCATG
TCTCAAAACTCACCAGGCCTGCTCACATGCTGCTGCTTCTGAAGCCAGGGTTTGGAAACC
AGCTGCCCATCAGAATGAGGCTGTGACTTAGAATATTGGTTCTTGTTTTATTACCATTCC
TTGTTTGGTCTCTCCAGAGTCACTGGCCTTTTCCGCTTCAATTTTCTTATCGGTGAAATG
AGATATTAATTCCTCTTATTGACTTCAATTCAATTGCTGAGTGTATTGTTGCCTTTGGGA
[A,G]
GTTCTTTGAGTTTTCTGTGCCTTTGAAATAGTTGTTTTTTTTTATTCTGGTGTTTTGAGG
CATGTTTCAAGTGAGTGCATTTACACTTCTACCATTTTAGGAGCCACAATTCAGTTATGT
TGTCCCAGCTTGCTTGGCCCCATCCCCAGAGTTTCTGATTCAGTAGGTCTGGGGTGGGGC
CCAATAATTTGCATTTCTTCTTCTTTTTTCGAGACAGAGTCTGACTGTGTCATCCAAGCT
GGAGTGCAGTGGCACGATCGTAGCTCATTGTAGCCTCAAACTCCTGGGCTCAAGCCGTCC

37749 GCTGCTTCTGAAGCCAGGGTTTGGAAACCAGCTGCCCATCAGAATGAGGCTGTGACTTAG
AATATTGGTTCTTGTTTTATTACCATTCCTTGTTTGGTCTCTCCAGAGTCACTGGCCTTT
TCCGCTTCAATTTTCTTATCGGTGAAATGAGATATTAATTCCTCTTATTGACTTCAATTC
AATTGCTGAGTGTATTGTTGCCTTTGGGAAGTTCTTTGAGTTTTCTGTGCCTTTGAAATA
GTTGTTTTTTTTTATTCTGGTGTTTTGAGGCATGTTTCAAGTGAGTGCATTTACACTTCT
[A,G]
CCATTTTAGGAGCCACAATTCAGTTATGTTGTCCCAGCTTGCTTGGCCCCATCCCCAGAG
TTTCTGATTCAGTAGGTCTGGGGTGGGGCCCAATAATTTGCATTTCTTCTTCTTTTTTCG
AGACAGAGTCTGACTGTGTCATCCAAGCTGGAGTGCAGTGGCACGATCGTAGCTCATTGT
AGCCTCAAACTCCTGGGCTCAAGCCGTCCTCCCACCTCACCCTCCTGAGTAGCTGGGACT
ATAGGCATATACTACCATGCCCTGCCACCTTTTTAATTTTTTGTAAGGATGGGGGTCTCA

39924 GCTGGGCTAGCTGCCTCTGAATCACCGCAGTAGCTCCTTTTACTATAGATTCCTGGGTCC
CACCCATGGAATGTGATCCATGAAGTCTGGGGTTATTCCCTGGAATCCTTTAAGCTCCCT
AAGTGGTTGGGATGGGAAAGAGATATGCTTTATGTTACTATACTTCTTATTATTATTATT
TTAAAATTCTTGCCGGGCGCAGTGGCTCACACCTGTAATCCCAGCACATTGGGAGACCGA
GGCGGGTGGATCACTTGAGGTCAGGAGTTCGAGACTGGCCTGGCCAACATGATGAAATCC
[C,T]
GTCTCTACTAAAAATACAAAAATTAGCTGGGCATGGTGGCGCATGACTGTAGTCCCAGCC
ACTCCGGAGGCTGAGGCAGGAGAATCGCTTGAACCCGGGAGGCAGAGGTTGCAGTGAGCC
GAGATCGTGGCACTGCACTCCAGCCTGGGTAACAGAGTGAGACTTCATCTCAAAAAAAAC
CCAAAAAAACAAAACTCTTTTTCATTATACCGGAACGTCAGCTTTATGGAGTCGGGGATT
TTTTCTGTTTTATTCACTGCTGTTTCCCTAACATCTAGAATAGTGGCTGGCACGATAGGC

55645 CCTTTAGCTCACTCACTCATTCAATCATTCAATAACGAGTGCGTTATCATACCAGGTACT
GTTAGGTAGCAGGTTTACAGGGATGAGCAGAAGAAGCAGGCCCTCTCTGCCTTCTTTCTT
TTTCATCACACTGAAATCACAGCGCATTGTGTGTGTGCAAAAGTAGAGTGCAGAGGGAAC
ATGCAGAAAGGAGTTATAGGATAGAAAAGGTAGCCAAGGAAAGCAGCAAGAACAGCATGA
TTTGTTCAGGGATCTTTAAATAGCTCATCATTGTTGGACAGCAAAGGGAGAGATGGGGAA
[C,T]
GTGGCAAGATGAGATGAGAAGGGGAGCCGGGGTCAAGCCATGGAGGACGCTGAACCCCTA
CAAAGGAACTAAGCCTATTGATGTGAACAGGCCACTTATTTTGGGAACACGCCTTTGGTC
CAAAGGGAAGAGGGCACGAAACTTCCTTCTCTAAAAAACAAAAAAAAAGAAACTTGCATA
TATGAGAAATACTTTCTTCACTTTGCAGCATGAGAAACGGAATCCCTACTAAGGAAATAA
TTCTCTTATTTTTTTTTGGAACAGCGGTTTTTGAAATTTCCAGATGACCCCAAAGTGAGCA

57539 TAATCTTCTTGAATAAGCAGTTAATTTTTTTTTATTCATGAACCTGCTGATCATGTCTAAG
AATGTATCTCCACTTAAGTAAGTCAGTGAATGGTGATTACCTGAGTAGAGTTAAAGTAGT
CCCCCACCCTCCTATCTGTGGCACATATGTTCCAAGTCTCCCAGTGGATGTGTGAAACTG
ATGATAGTACTGAAACCCATCTACCTTTTTTCCTGTGCATACATACCTATGTTATATAAA
GCTTAACTTATAAATTAGGCATAATATATTTGACTCCCAGCTCCCAGTGTAGTGGCTCTG
[A,C]
AGACTCACAAAATGTATTTGCTTTAAAAAATTCTTTTTTTTTTTTTTTGAGACGGAGTTTT
GCTCTTGTTGCCCAGGCTGGAGTGCAGTGGTGCGACCTCAGCTCACTGCAACCTCCGCCT
CTTGGGTTCAAGCGATTCTCCTGCCTCAGCCTCCCAAGTAGCTGGGATTATAGGCATGCA
CCACCACACCCAGCTAATTTTCTATTTTTCGTAGAAACGGTTTTTCCATGTTGGTCAGGC
TGATCTTGAACTCCTGACCTCAGGTGATCTGCCTGCCTCGGCCTTCCAAAGTGCTGGGAT

58604 TCTTTTTTATATTTATTTATTTATTTTTTGAGACACAGTCTTCCCGTCGCCCAGGCTGGA
GTGTGGTGGCACGATCTCGGCTCACTGCAACCTCCGCCTCCTGGGTTCAAGTGATTCTTC
TGCCTCAGCCTCCGAGTAGCTGGGACCACAGGTGTGCGCCACCATGCCCGGCTACTTTTT
GTATTTTCAGTAGAGACAGGGTTTCACCATGTTGGTCAGGCTGATCTCAAGCTCCTGACC

FIGURE 3UUU

TCAGGTGATCTGCCTACCTTAGCCTCCCAAAGTGCTGGGATTACAGACATGAGCCACCGC
[C,G,A]
CCCAGCCCCCAGTGTTAACTCTTACATAACAGTGTCACTGTCTAAGTGTTTGAAAAACTA
TTTGTCAAAACTAATATTGGTACATTATTGTTAACTACACTTCAGACTTTTTTTGGATTT
TACCAATTCTCCCACTCATGTCCCTTTTCTGTTTCAGGAATCAATCCGTGGTACCATATT
GCAGTTAGGGTGTTTATATTTGATGGGACTGGTCCTAGTTTAGATACTTAGTGTAGCTCA
GCCAGCAGGTGGGATCTTCATGCCCACCGAGGATTGGTATTGTGTTTTCCTGGTGGTTTT

58861 CTTAGCCTCCCAAAGTGCTGGGATTACAGACATGAGCCACCGCACCCAGCCCCCAGTGTT
AACTCTTACATAACAGTGTCACTGTCTAAGTGTTTGAAAAACTATTTGTCAAAACTAATA
TTGGTACATTATTGTTAACTACACTTCAGACTTTTTTTGGATTTTACCAATTCTCCCACT
CATGTCCCTTTTCTGTTTCAGGAATCAATCCGTGGTACCATATTGCAGTTAGGGTGTTTA
TATTTGATGGGACTGGTCCTAGTTTAGATACTTAGTGTAGCTCAGCCAGCAGGTGGGATC
[T,G]
TCATGCCCACCGAGGATTGGTATTGTGTTTTCCTGGTGGTTTTATGGCATTTCCGACTAT
GCAGAGAGGCATGGTATTAACTTCAGTGTCTCCTAGCAAATTTTCCTGTTTTTCACCAAC
CTCTGATCCCTGCATTATTTGCAATCAACTCAGAGATTTGTGATTGAAAACATTGCTTGA
CTCCATGCTCTTTAAGCTATTTTCTAACTAGGTAACTGTAACATAAATTATGCTTTTATC
TAGCACTGTTTTTCATAAACACATGTTGAGTGATTTTCATCAACCGAAATACTTCGAATC

59060 AGGAATCAATCCGTGGTACCATATTGCAGTTAGGGTGTTTATATTTGATGGGACTGGTCC
TAGTTTAGATACTTAGTGTAGCTCAGCCAGCAGGTGGGATCTTCATGCCCACCGAGGATT
GGTATTGTGTTTTCCTGGTGGTTTTATGGCATTTCCGACTATGCAGAGAGGCATGGTATT
AACTTCAGTGTCTCCTAGCAAATTTTCCTGTTTTTCACCAACCTCTGATCCCTGCATTAT
TTGCAATCAACTCAGAGATTTGTGATTGAAAACATTGCTTGACTCCATGCTCTTTAAGCT
[G,A]
TTTTCTAACTAGGTAACTGTAACATAAATTATGCTTTTATCTAGCACTGTTTTTCATAAA
CACATGTTGAGTGATTTTCATCAACCGAAATACTTCGAATCATTAAGTTTCCCAAGTTCA
TGGATGCTGCTTAAATGCCTGGTGGTTCCAGGCTGTCGAATATTTCTGCCTTCTGCAATA
AGAGATTGTCCCTTGTTAAAAGCAACATTAGCCTTTGTGCGGTTTCACCCCCAATTCTTC
TTTTTCTTGTTGTAACCAATGAAAGGAAGTACTGCTTAACACAGCAGGTAATAATCTTCT

59518 GAATATTTCTGCCTTCTGCAATAAGAGATTGTCCCTTGTTAAAAGCAACATTAGCCTTTG
TGCGGTTTCACCCCCAATTCTTCTTTTTCTTGTTGTAACCAATGAAAGGAAGTACTGCTT
AACACAGCAGGTAATAATCTTCTAAAACTCATTATCTCAAGAGGTGGTCCTGGCAGGATA
TATAAATGCAATTTAAGAAAGGTCTTGGCAAATTTATGAATGACAGAACTGGGAGTGGCT
ACCGAGAGAAACTAGGATGCGCCTTTGCTTTGACACTGAGGTCAGGCGTAGCTTCTGTAC
[C,A]
CTCCTGGGTCCTGCCTCTTGGGGTTGCTGCAGGCAGCACCCCATGAACCAGGCATCTGAC
CCAGTTCCAGGATACTTATTCTTCCAGCAAGTCGAACACTCTGTGATGAGTGACTGCCAT
GCTCATGGGTCACCAGGCTCTCATTATTCTGTTTCATTTCCAGCCTCCCACAAGATTGGT
TTTTCAGCTGCTTATTTATTATTATCATTATTTCAAGGCTGCTTTCCAAGTTTCAGTGGG
GGGTTTCCTAAGCGTACCAGCTGCCCTGGTTGTGCAGTTCCGGTGATGTTTCAGATGCTG

59802 GGCGTAGCTTCTGTACCCTCCTGGGTCCTGCCTCTTGGGGTTGCTGCAGGCAGCACCCCA
TGAACCAGGCATCTGACCCAGTTCCAGGATACTTATTCTTCCAGCAAGTCGAACACTCTG
TGATGAGTGACTGCCATGCTCATGGGTCACCAGGCTCTCATTATTCTGTTTCATTTCCAG
CCTCCCACAAGATTGGTTTTTCAGCTGCTTATTTATTATTATCATTATTTCAAGGCTGCT
TTCCAAGTTTCAGTGGGGGGTTTCCTAAGCGTACCAGCTGCCCTGGTTGTGCAGTTCCGG
[T,C]
GATGTTTCAGATGCTGGGCCGGATTCTGGCTGTACCCAGCCTGATCTTTCTGGGCTTCAG
GAAAGCTGAAGCCAATCAGAGCTCCTCTTTCATGCCTTTGGGATTATGCTTACCTTGCCT
GGCATCGTGTACCTGCTCCCATCCATGGGAAAGTTTTGCTGTCTGGTACTGTCTTCTATC
AACATCTTTTAAGATATCTTCCCCCGAGGCATCGTGATGTCAACGGAACCAGCACACTTG
TACGTTTTATGCAAGACTGCCATATCTCAACAGTGAGAAATGCATAATGGAAGTGGTGAT

60083 CCTGGTTGTGCAGTTCCGGTGATGTTTCAGATGCTGGGCCGGATTCTGGCTGTACCCAGC
CTGATCTTTCTGGGCTTCAGGAAAGCTGAAGCCAATCAGAGCTCCTCTTTCATGCCTTTG
GGATTATGCTTACCTTGCCTGGCATCGTGTACCTGCTCCCATCCATGGGAAAGTTTTGCT
GTCTGGTACTGTCTTCTATCAACATCTTTTAAGATATCTTCCCCCGAGGCATCGTGATGT
CAACGGAACCAGCACACTTGTACGTTTTATGCAAGACTGCCATATCTCAACAGTGAGAAA
[T,G]
GCATAATGGAAGTGGTGATCACGGATTATTTCCTAGGACATTATGGCTAATGCGCTAGAG
AACTCGGATGGTCTGTTGCGTCTGACATGGGCTTTTTCTCTTGAGTTGTCTTTCTTTTGC
TATTCTCTGAAAGAAACAATTCTTGCCACATGATCCTGATTTTTCAGGTCCTCAGCATTT

FIGURE 3VVV

GTTAGCAGAAAGTACACTTTGTTTCCATCCGGCAGTGACTCAGTGGTGGTCCCATGCTGA
TGAAACGCTGAGATAGTCTTCTTCCAAATAGGTATCGTTTTGATTGTTGCTGCTTATTTG

60525 CTTGCCACATGATCCTGATTTTTCAGGTCCTCAGCATTTGTTAGCAGAAAGTACACTTTG
TTTCCATCCGGCAGTGACTCAGTGGTGGTCCCATGCTGATGAAACGCTGAGATAGTCTTC
TTCCAAATAGGTATCGTTTTGATTGTTGCTGCTTATTTGCTAGCTGGCCCTCAATAGTGA
CAATGAAACCTCAAGTGTATAATATGGTTGCTCAGTAATCCTGAGGGAAGACAGTCTTTG
GTTTGGGGGATAGGGATTCTGTGCCTACTTAGCTTCAGGTGAAAGTCTTACAAATTTTTG
[T,C]
GTGTAGAAATAAGCACCATGTACCTCCTTGGGTTTTTTCTTTTTTTTTCTAGTCCTTTAG
TATGGTCAACAATATTGTTTAGGGAGTACCTATTCTGTGCTAACCACTAGGCATTCAAGT
ATATTACACTATGCTCCTTCAAAACACTTCTGTCAAATGTAAGGATTATTATACCCATTT
TACAGATGTGGTTACTGTGGTAACTTGGCCAAGGTCATAGGGCAAGTGAATAAGGGATTC
TGGATTTGGGTGGAGGTCTGTGTGATTCCAAAGCCCATGCTCTTTCTACAATACTATATA

61078 GAGGTCTGTGTGATTCCAAAGCCCATGCTCTTTCTACAATACTATATATGCCTTTGCATA
AGTTATTGTTATTAGTAATAATATTTGTGATGATGGCAAATAATAAACCATGTCACACTA
GAGAGTGATTTAATCTCTAGGTCTATTTAAGAACATTTGGAATTGCAGGAATTGGATTTT
TTTTTTTTTTTTAAGTGATGGAGTCTTGCCATCTTTGCCCAGGCTGGTCTCAAACTTGTGG
GCTCAAGTGATCATCCTCCCTCTGCCTCCCAAAGTGATGGGATTACAGATATGAGCCACC
[A,G]
TGCCCAGCCTAGAATTGCAGGAATTTTTGAATTGATGATTCATTCTGATATTTGAATTTC
TACAGTATGTTAAGTGCAATGTCAGGTGCTGGTGCTGTGGCTCCATTGATGAACACATTT
GGGTATGGCCCTACCTTCATTGAATTTAGAGTCTAAGAGCCTAACCGGTCTTTTGCTTGA
ATAGAGCTGTAGTCCTGTTAAATTGCTGTACCTCCAAATGGTGGGAAGTTTAATGCTTCG
TAGGCCTCCCCTCACTAGTTTACTGAACCACATGTGCTTGATTTTTTTTTGAGATGGGGT

63026 TATTACCATGCCATTTATTGAGTGCCTAGTATGTGCCAGGAGCTCTGCAAAGTGCTTTAT
GCTTATTATTGTTCCATTTATTCTTCCCCAAACCTCTGTGAGGCAGGTCCTATCACTAGT
CCACAATACAAATGAGGTCATGGAGCCCGAAGTTGGCAGTGGTAGGAATCAAACTCAGGT
CTCCCTGACTCTAAATTCTCTTTGCCTTTGTTTTTTTGAAAAAGTGGTATAGCCCATAGC
AGAAAATTCACATTATACAGAAGGTTATACGGCGAAAAATGCCTCCTTCCCACCCCACGC
[T,C]
CAACCCCTCTCCCTCAAGCGAACCACTATTGTCAGTTTCTCATAGAACTTTCCAGAATAT
TCTATGCTCCTATAACACTAGCACAACCTATCCTCTTAACAACATCTTTATGCTGCCTCC
CAAGAATTCAGTAATTTTTTTTTTTTTTGAGATGGAGTTTTGCTCTAGTTGCCCAGGCTGG
AGTGCAATGGCGTGATCTCGGCTCATTGCAACCTCTGCCTCCCACGTTCAAGTGATTCTC
TTGCCTCAGCCTCCCGAGTAGCTGGGATTACAGGCATGCGCCACTATGCTTGGCTAATTT

63231 CTTTGTTTTTTTGAAAAAGTGGTATAGCCCATAGCAGAAAATTCACATTATACAGAAGGT
TATACGGCGAAAAATGCCTCCTTCCCACCCCACGCTCAACCCCTCTCCCTCAAGCGAACC
ACTATTGTCAGTTTCTCATAGAACTTTCCAGAATATTCTATGCTCCTATAACACTAGCAC
AACCTATCCTCTTAACAACATCTTTATGCTGCCTCCCAAGAATTCAGTAATTTTTTTTTT
TTTGAGATGGAGTTTTGCTCTAGTTGCCCAGGCTGGAGTGCAATGGCGTGATCTCGGCTC
[G,A]
TTGCAACCTCTGCCTCCCACGTTCAAGTGATTCTCTTGCCTCAGCCTCCCGAGTAGCTGG
GATTACAGGCATGCGCCACTATGCTTGGCTAATTTTGTATTTTTAGTAGAGATGGGGTTT
CTCCATGTTGGTCAGGCTGGTCTTGAACTCCCAACCTCAGGTAATCCGCCCACCTCGGCC
TCCCAAAGTGTTGAGATTACAGGCGTGAGCCACCGCACCTGGCCAAATTCAGTAATTTTT
ATTGGCAGGTTATTTTCCCGCATCATTGAAATGAATGAAGCAATCTTTATACTTCATTCA

65298 GAGCCCTGAGGAATTTCACCACTGGGTTTCCCATAAATGAGACCCCCTGTGACCTGGTGG
GCCCCATCCCTCGGAAGTGTACCCTGGCATTTCCATAGGACTGCTTCCTTCTGGGCCTCT
TAGTGCAAGCCAGCAGTGCAATGCCACATCCAAGTTTGGTAAATCAATTCTAAGTGAGAT
AAATTAATGCCTTTTTTGGGGGAAGATGGGAAACAGAGTGGGTTTGTTGGAGAGCCCATA
AATTGGAGTCTTCAACCCTTAAATTCTCACTTGCGGGAAAACCTTTCACAACCAAGCAAA
[C,T]
GTGGAAATGATTTGGCCAAAGATTCAAAATTATATTAAACATCTGGGACTATATTCAGCA
GCCAACTTTCTAATCAATTCTATGAGTGTGGTGATTGCAGTTATGCTCATTTTCTGAGGG
TGAAGTTTGGATAGAACTAAAAAGGGCGGTTGGCAGGAATCAAAAGAGATGAAAGCCTCA
GGACAAAGAGTTAGAGGCCCAGGTGGTTCATGACTGAGAGTTTGGAAATGATTTCTGGTG
TCTCACTTCAGAGAAAATAAATATAGCCAACTCTGTTCATCCGTGGTGATGGAACATTCA

66172 GTGTTCGGTTGGTTGAGTGCCTGCTATGCCTGTGCCTAGGCAGTAAAAGGGGAAGTTTTA
AGTTTGGCCCTTACTTTCAAGACATAGTAATTCTACCTTCTAGTAAAACATGGCCAAATA

FIGURE 3WWW

AATGTCTGCTTTTCATGAGCCAGATAACCTCCTTCTTCTTTATTGGAGGAGTGAGTAGAA
GGGTGAGACTAGCCGGGTGCGATGTCTCCAACCTGGGCGAAAGAGCAAGACTCCATCTCA
AAAAAAAAAAAAAAAATTAAGAATAAATCTTTTCACTGTTGGAGAAAAGTTTTGAGAGGC
[C,T]
GAGGTGAGAGGATCACTTGAGGCCAGGAGTTTGAGACTAGCCTGGGCAACATAGCAAGAC
CCCTGTCTCTATCAAAAAATAATAATAAAAAAAGCTAGCTGGGTATGGTGGTGTGCACCT
GTAATCCCAGCTACTTGGGAGGCTGAGGTGGGAGGATTGCTTGAGCCCAGGAGTTCAAGC
TTATAGTGAACTATGATTGCACCCCTGCACTCCCTCCTGGGCATCAGAGTGAGACACTGT
CTCTAAAAAAAAAAAGTTGGAGAAAAGGATACTAAAGAGATAAAAGGGTACTAAAGAGAT

66244 ACTTTCAAGACATAGTAATTCTACCTTCTAGTAAAACATGGCCAAATAAATGTCTGCTTT
TCATGAGCCAGATAACCTCCTTCTTCTTTATTGGAGGAGTGAGTAGAAGGGTGAGACTAG
CCGGGTGCGATGTCTCCAACCTGGGCGAAAGAGCAAGACTCCATCTCAAAAAAAAAAAAA
AAAATTAAGAATAAATCTTTTCACTGTTGGAGAAAAGTTTTGAGAGGCCGAGGTGAGAGG
ATCACTTGAGGCCAGGAGTTTGAGACTAGCCTGGGCAACATAGCAAGACCCCTGTCTCTA
[T,C]
CAAAAAATAATAATAAAAAAAGCTAGCTGGGTATGGTGGTGTGCACCTGTAATCCCAGCT
ACTTGGGAGGCTGAGGTGGGAGGATTGCTTGAGCCCAGGAGTTCAAGCTTATAGTGAACT
ATGATTGCACCCCTGCACTCCCTCCTGGGCATCAGAGTGAGACACTGTCTCTAAAAAAAA
AAAGTTGGAGAAAAGGATACTAAAGAGATAAAAGGGTACTAAAGAGATCGGGAAGGCAGC
AAAGAATGAATCTAGTCTGATGTGTTATTGGGTGTACGTAATTCATGGCGGAAGGTGCTG

66700 AGTGAGACACTGTCTCTAAAAAAAAAAAGTTGGAGAAAAGGATACTAAAGAGATAAAAGG
GTACTAAAGAGATCGGGAAGGCAGCAAAGAATGAATCTAGTCTGATGTGTTATTGGGTGT
ACGTAATTCATGGCGGAAGGTGCTGAAAGGGAAGGTTGCCTGGGCCTACAGCAAGCAGGT
GCTGATGAACTAGCTCCTTTGCTATTACTTAAATGTGTCCTGGTTGGGCCAGATGTGGTG
GCTCACACCTGTAATCCCAGCACTTTGGGAGGCCAAGGCGGACGGATCACTTGAGGTCAG
[G,A]
AGTTCGAGACCAGCCTGGCCAACATGGTAAAACCCCGTCTCTACTAAAAATACAAAAAAA
GTATCCAGGCATGGTGGCAGGTGCTTGTAATCCCAGCTACTTGGGAGGCTGAAGCATGAG
AATTCCTTGAACCCGGGAGGTGGAGGTTGCAGTGAGCCGAGATCATGCCACTGCACTTCC
AACCTGGGCAAAAGAGCAAGACTGAGTTCTCAAAAAAAAAAAAAAAAAAAAATTCCTGGGG
AATATCCACCAGGGTGAAAAATTGGGTATATCCAAATTCAGCTTTGCAAAGAAATGCACT

67029 AAAACCCCGTCTCTACTAAAAATACAAAAAAAGTATCCAGGCATGGTGGCAGGTGCTTGT
AATCCCAGCTACTTGGGAGGCTGAAGCATGAGAATTCCTTGAACCCGGGAGGTGGAGGTT
GCAGTGAGCCGAGATCATGCCACTGCACTTCCAACCTGGGCAAAAGAGCAAGACTGAGTT
CTCAAAAAAAAAAAAAAAAAAAAATTCCTGGGGAATATCCACCAGGGTGAAAAATTGGGTA
TATCCAAATTCAGCTTTGCAAAGAAATGCACTCATGACTAGTTGCAATTTGAAACGTTCC
[G,T]
CTTCTGAGTATTTCTAGCCTATGTAGGTGTTTCACAGATTGCTGAGTACCTAGACTGAGA
GGGAGAGAAAAAAACAAAGTAAAGCTAAAATGTTAAGAAGTCTGGTTAAAGTGCAATCCA
GAAGTGAGGGAAAGCATCTCTAAAAGTATGAATCTTTGGGGAAACATAACTTGATTACCA
AAAACTTAATATTAAGCAGCCTCATAGGAACATGGCTTTTGGGTATGGCGAGAGCCAGCT
AGAGCTCACATCTCCATTGAAATCCACCACCAGAGAGGTTATCTGCCTAGTTGTTGGCAG

67140 GTGGAGGTTGCAGTGAGCCGAGATCATGCCACTGCACTTCCAACCTGGGCAAAAGAGCAA
GACTGAGTTCTCAAAAAAAAAAAAAAAAAAAAATTCCTGGGGAATATCCACCAGGGTGAAA
AATTGGGTATATCCAAATTCAGCTTTGCAAAGAAATGCACTCATGACTAGTTGCAATTTG
AAACGTTCCTCTTCTGAGTATTTCTAGCCTATGTAGGTGTTTCACAGATTGCTGAGTACC
TAGACTGAGAGGGAGAGAAAAAAACAAAGTAAAGCTAAAATGTTAAGAAGTCTGGTTAAA
[A,G]
TGCAATCCAGAAGTGAGGGAAAGCATCTCTAAAAGTATGAATCTTTGGGGAAACATAACT
TGATTACCAAAAACTTAATATTAAGCAGCCTCATAGGAACATGGCTTTTGGGTATGGCGA
GAGCCAGCTAGAGCTCACATCTCCATTGAAATCCACCACCAGAGAGGTTATCTGCCTAGT
TGTTGGCAGCCAGACCCTGGCATTGTTTAGATTGATTGATGGAAGGCTACTTTGGGAATG
CTGGCTTCCTTATTCATTGACTTTAAAGACAGCATTGTAAAAATTGATCACCAGCCCAAA

68038 GCCCAGGCTGGTCTTGAACTCCTAGACTGAAGTGATCCACCTGCTTTGGCCTCCTAAAAT
GCTGGGATTACAAGTGTTAGCCACCAGGCCCGGTCTTGAACTTCGTATATACAGTGTGTT
GTGTGGGCAAGTCATGCCTGACCACTTCCTAGTGGGAGGGGAGAAACTAGAGGGCTTGCC
TGAGGCTTTAGGCAATGTAATCTGTTCTCTTGGGATCAATTACTTATGCATATTTAGTAG
CCAGCTCTATTTGCTGATCACCTAATCTGTTCTCTTCGTTCATTCCCATGAGACTTCGAT
[G,A]
TGGGATATCTTCCTCTTCTTCCCATTGCAGCCTTTTCTCTCAGAGTTGTTCCCATGATAA

FIGURE 3XXX

GAACTCCCATCAAAATCTCTGCTCTAACATCAGTTGTCAGATTTTGCCACTTTTTTTTTT
TTTTTTTTTCTGAGATGATGGAATCTCACTCTGCTGCCCAGGCTGGAGGCAGTGCCACCA
TCTCGGCTCATTGCAACCTCTGTCTCCCGGGTTTGAGGGATTCTCCTGCCTCAGCCTCCC
GAGTAGCTGAGATTACAGGAGCACCCCACCACTCCAGGCTAATTTTTGTATTTTTTTTAG

69852 GGCTTTTCTAAAGTAGCACTTTTCCCCACTCCAGCCCATGAAGATACCTTTTAACCAGCT
CTTGAGATTAAATCCCCTCCGTGACACTTTCCTGCAGGAACTTGCAA
[G,A]
AAAGTACTGCATTCCCCACTGGCAAAACTTGCCATCAGCCAGTTTATGTATTCTCTGCTT
TTCACACCCATATCTTGACCTCTGAACAACACACATATTCTCCTCTT

71083 CTTTGTTTCTGAAAGCCTTGATTCTGCTATCTATTTTATAACTGAAACAAAAACAAAAAC
AAAAACAAAAAACAACCTCAAGAAGTTACTTGTATAGCCTCTGCCACTAAGGAGACTGTG
TTCTGATGTTACCTCAAACAGGCTGATTTATTAAAATATTTAAAAATATATATGGAAATA
TTTTTTTCTATTTTTTTTTTTTAGTGGCTTTTCCCAGTGAACAATAGGTCTTACTATATGA
TTTCTTATTTGTCATTAGTGAATGTGGTGGGTATGTGGCAGCTGGGGGAGCTGATGATTT
[T,C]
ATAATACTGTATCAGAAATGATTAGTGTAGGTACTTATTAACATATTTCTCAGACAGAAC
AATCTTGACTTTTAAAACCTCTTCATTTAATTCAAACATCAAGTACCCTGTTTGTGGCCT
GTGTTATGTTAGGTGCTCTCTTTACAAGACCTATTTTCTTGCTATTTAATTATATATTTG
CTTAGCAAATATTTACTCTGCACCTACTAGGTACCTGGCACTGTGCTGTGTACTGAGGTG
CCATGTGTACCTCCATCAACATAGACTCAAGATCAATATGATTTCAGTGAACTAAAAATA

71098 CCTTGATTCTGCTATCTATTTTATAACTGAAACAAAAACAAAAACAAAAACAAAAAACAA
CCTCAAGAAGTTACTTGTATAGCCTCTGCCACTAAGGAGACTGTGTTCTGATGTTACCTC
AAACAGGCTGATTTATTAAAATATTTAAAAATATATATGGAAATATTTTTTTCTATTTTT
TTTTTTAGTGGCTTTTCCCAGTGAACAATAGGTCTTACTATATGATTTCTTATTTGTCAT
TAGTGAATGTGGTGGGTATGTGGCAGCTGGGGGAGCTGATGATTTTATAATACTGTATCA
[G,A]
AAATGATTAGTGTAGGTACTTATTAACATATTTCTCAGACAGAACAATCTTGACTTTTAA
AACCTCTTCATTTAATTCAAACATCAAGTACCCTGTTTGTGGCCTGTGTTATGTTAGGTG
CTCTCTTTACAAGACCTATTTTCTTGCTATTTAATTATATATTTGCTTAGCAAATATTTA
CTCTGCACCTACTAGGTACCTGGCACTGTGCTGTGTACTGAGGTGCCATGTGTACCTCCA
TCAACATAGACTCAAGATCAATATGATTTCAGTGAACTAAAAATACCTTTATTGAAGCAA

71445 ATCTTGACTTTTAAAACCTCTTCATTTAATTCAAACATCAAGTACCCTGTTTGTGGCCTG
TGTTATGTTAGGTGCTCTCTTTACAAGACCTATTTTCTTGCTATTTAATTATATATTTGC
TTAGCAAATATTTACTCTGCACCTACTAGGTACCTGGCACTGTGCTGTGTACTGAGGTGC
CATGTGTACCTCCATCAACATAGACTCAAGATCAATATGATTTCAGTGAACTAAAAATAC
CTTTATTGAAGCAAAAAAAAAATCACATTTTGTAAGGATCAAAAAAGAGACATTTTATATA
[A,C]
GGTACAAGAAATAGAAGAATTATATCCCCAAGATATATGTGATAACATACTTGTTAGTTT
TTGGACGTGACCAGATTTTACACAATCCTTAAAAAATGCAGCAACCAGATTTTAAAGTAG
TTCTCTAATCTCTCTTTCTGTGCCCCATTAGATGTATATTGGATCTTCTCATTCTGTCTT
TGTCTTTTGACCTCTCATGTTTTCCGTCTCTTTGTCTCTGTGTGTTGCATTGTACACAAA
TGCTTCTTGAACTGTGGTGTGCACATGAATCACCTGGGGACCTTGTTACAACGTAGGTTC

71981 ACAAATGCTTCTTGAACTGTGGTGTGCACATGAATCACCTGGGGACCTTGTTACAACGTA
GGTTCTGATTCCATGGGTATGGGGCAGGGCCTGAGATTCTTAGAGAATTAAATTCTAACC
AGCTCCTGAGTGGTGGTGATAATGCCAGTGTGTAGACCATAGCTTAAGTATCAAGGTTCT
ATGTGATTCCCTCAGATCTAACTGCTAGTTCACTAAGTTTCTCTTCAGCTGTATCTAGTC
TGCTATTTAACATATTCAGTGAATTTTTAACCTTAAATTCAAGAACAAGACTTTTTATTT
[C,A]
TGGAAGTTCAGTTTGGTTCCTTTCAAATGTACCTGGTTCTTTTTCAAAGTGTCATGTTCT
TTGATAAGAATTTCTACTAATTTACCTTGATAATAAAAATTTGTTTCATGGCTCATTTTA
GATTGTTCTTTTATCTGCAGTTTTTGGAGGGCTAATTCTCCCATTTCTTGTATCTGTTGT
TGCACCCGTAAGGTGTAGTTGTTGATTTTTACTTTTTAATTGTGAATTTATTTCTGGTAG
GGATTGGAAGGAGGTTGTTGGGGTGGGGGTGGGGTGGGGAGAAAATCCTGTGTGCCCTGG

72366 CCTTGATAATAAAAATTTGTTTCATGGCTCATTTTAGATTGTTCTTTTATCTGCAGTTTT
TGGAGGGCTAATTCTCCCATTTCTTGTATCTGTTGTTGCACCCGTAAGGTGTAGTTGTTG
ATTTTTACTTTTTAATTGTGAATTTATTTCTGGTAGGGATTGGAAGGAGGTTGTTGGGGT
GGGGGTGGGGTGGGGAGAAAATCCTGTGTGCCCTGGGTTGCAAAAACACCCCTACAAGTT
GTTCTCCACTTGCATCTGCCAGTGCTCCAAGGGCTCAGTGATCCTGGACCAGTAGTCATG

FIGURE 3YYY

[T,A]
TAATTTCTTGAATTGTAACAGGATACTGTAAATGTGGACACTCTACCTGAGGTTACTGCT
TCTTTCTATCTGCTTTATTTCCTTCCCACTGAAGGGCCCTGGACAAGGGTAAACATCTCA
TCACTTTCTGGGTGGCAGAATATTTCCAGTTCCCCCACTTCTTTTTGGCTTAAGGCTGTG
GCTTTTTCCTCTGCCTGAATGTGGCCCTAAGAAGCCCTTCTTTTCAAACTTTCCTGTTGT
ACTTGACCGACTAGCTGTCTAGAGGTTTATATCCCTAGCTTTTAATCTTTGCTGTGAATA

73797 GGATTATTTTATTTAAACCTCCTAATAGTCCATTGAAATAGATATTGCCATGTTGAAAAC
TGAGGTTCAGAGAGGTTAAGTGACTTACCCAGTGTCACAGAACTAGTAAGTGGTGCAGCT
GGGATTTGAACTGAGATTCCAGAACAATTGCCATTAACCACTTTGCTTCCATATTAGTAT
CATCTGCAAATCTCTCTCCATAAATTTCCTCAGTCTTTATCTGAGTTTCCTTATTTCAGG
AAGGAAAACTTCTGTTTTTGATCCTTATGAAATACAATTTCCATTAAAACTTTTTTTTTT
[T,-]
GCTATTAAAAAAGGTACCGGATAATTGAAACCAGACTGGATTTGAGCCTGTGTTGATGGA
AGTACACATGGGATGTGGGCTGAAGTGTTCAATCTAATTTTTCTTTCCATCAGCTAATTT
TTAAAGTATTAAGCAAGTAGATTCTGACACTAACAGGGAAGATTTAAATTCTCTTGAGAG
ACTGGAGGTGTTAAATAATTTTCTGGTAGTGCACATTTTACATCTTAAATCTTCCTCACT
CTCCCACCTCATCTCAATGTACCTGAAGCTCTGGGAATGTTCTTTTGTACTTCTCAGGAA

74416 CATCTCCTCTCCCCTCCACATCCCTTTCCTGCTCCAATTACTTCCCAGCGCCACTTGGAT
GTTGTTGTCATCGGGGAACTTTGGAAACAGCCAGATTTTTTTGGAGTCTGTAAGCAGAAA
ACAGACTGCTTGCTGCTCATATCTGGCACCCAGCTTTGTCCAGAAAACGAGGAGTTAAAA
AGAAGTCTGGGCTGTGAAGGGCTGTGACAACTGTCCTAGGGGGAGCTCTAGCGAGCCCTG
GCGGGCAGTGACTCATGCTGCTCTGTCACTGGGATCAGCACTGGCCCCTGGCAGGCAGGC
[G,A]
GCAGCCAGGTGGGGTTCCAGCCAGAGCACGCACGCACGGAGCCGGGAGCATGCAGCCTGC
ACTGCGGGGGATGTGATGCTCGGCTCTAACTCGCCTGGCTGGCCCGCCACGGACGCCTCA
GCTTGCAACCATGGTAACGTTTCTGGCGGGGGACACCCCCGGGAGCCCACCGCGATGGGC
AGCCTCCTGGTGACTGATGGACGAGTGTCCACCTCCCAGACCGAGAGCGCTTAGTAGGTC
GGAGGAAGTGGAGAGGATGTAACACGCCCCCAGCCGGGAGTGAAGCCCTGAGGAGGTAGG

74664 TGACTCATGCTGCTCTGTCACTGGGATCAGCACTGGCCCCTGGCAGGCAGGCGGCAGCCA
GGTGGGGTTCCAGCCAGAGCACGCACGCACGGAGCCGGGAGCATGCAGCCTGCACTGCGG
GGGATGTGATGCTCGGCTCTAACTCGCCTGGCTGGCCCGCCACGGACGCCTCAGCTTGCA
ACCATGGTAACGTTTCTGGCGGGGGACACCCCCGGGAGCCCACCGCGATGGGCAGCCTCC
TGGTGACTGATGGACGAGTGTCCACCTCCCAGACCGAGAGCGCTTAGTAGGTCGGAGGAA
[G,C]
TGGAGAGGATGTAACACGCCCCCAGCCGGGAGTGAAGCCCTGAGGAGGTAGGAGCCGCAT
ATGTCCATCCGTGCATTCCCACCGTCAGCGCGCAGGGGTGCTGTAGATCACCGGTAGGAA
CTTTATTTGGCTGGTGCTTCATTATGCTGATTAAACTGCAGTGGATTTGATGGGCATGAT
TGCGCTGGGGAAGATGCATAATGAACTAAAAAAAAAAAAAAGTGGTTAATAAGATCTCGG
AGTCGACTTGTCCGGGTATGAATGAAGTAGACTGCAGTGGTATCCTAACAGGAGTTCCAG

76330 ATCTAACCATCTATGTATCTGTCTCTCAAGTGGGTGGATGGGGGTTGCTATCTTGGCTGT
ATAAAGAATCCTAAAAACCTTGTCTCATAAGCTAGAGGTTTCCTGATGGGTTTAACTGAG
CTGCAAGTGGCTGAACCAGAGCTCTAACAGAGAGATGGTGCTCGGCTCCTCTCCAAGTAT
GCTGCAAGATCAGGGATCTGGCAGCTGAGCCTCTCTGAGCTGGTGGAGCGCTGGCAGCCA
GAGAAAGCCCCGTTACTGTGAGCCACCAGGAGGGAGTGTGATGTAGCCGAGTCATTGATT
[T,C]
ACAGAAACTGGGCTTCATAGGGGGAAAAAAAAACCAGGAGACTAGAAAATGGAAATATAAA
TATCACTGTAAACCTCTTGATCTGGTAGGTCTTTCTCCATTCTCATAAAAGCTATTGAAA
AATGCATTAACAGAGCACTTGGAATTAGAGGGTCGAGGCTTCCAGGAGCCTCCTGGAATT
TCTGTAAAATGCAGTAGCTTCTGTGGATGTGGGAGGTCAGTATCTTGCCTCATTCTCTCA
TGATACAATGACATTCTGTTTTCAGAGGAGTGAGTTCCCCAGAAGATCTTGGACTGATGG

78181 TCTTGTTATGTGTTATTGCTATTGGACTTGGCTACTCTGCTGTAGGCAGCCCTGTGGGTG
ATACCTACAAGCATCATTTTAGAAATTCATCCACCTGTTGGATGTAGATGACCCTGGACA
TATCAGATTGTGATTAATTAGAAATCTAATAAAAGAGAGGCAGTGATGAAATTACTTAGC
AGCTCCTGCAGTTTTATTGACAAAATTTACTTGGAGAGAGGGGGAGACATTTTCTGGGGG
TACCACCTTTGCTGCCAGCGACCCTGTGTTTCTTCCTGAGTTTCTTTTTCTTTTCTCACC
[A,G]
TTTTCAGCATCACAGGTTTTTATTTACACACATTGATTACCTGTGCTGTTACTCATTCTT
CACACCACTGAGGAAATTGCAGATGCTGCTGTACTGTGCTAGGTAAATTGACCTCAGATT
TGTTACCAGTGAATTGAATGAAATGTTCAGAGGTGGAGCTGAATGAACGAGGAGTTTTTG
TGGAGAAATTGGCAGTGAGAATGATTTAAATTCTGTGATAGCTCCTCGTTTTTTGGGATC

FIGURE 3ZZZ

CTTATTTTGGGACCCCAGACTATTTTTAAGCCATTGAGTGCATCATTATTTTAGGCTGAG

78685 ATTTAAATTCTGTGATAGCTCCTCGTTTTTTGGGATCCTTATTTTGGGACCCCAGACTAT
TTTTAAGCCATTGAGTGCATCATTATTTTAGGCTGAGCAAGAATCTTGATGACAGCGTTT
CAATGGCTGAGGCGTAGTGGGAGTTCCTTGCAGCTTGAGTTGGTGGGAGCTGGAGAGTTT
CTAGAGAACTAGGTTTGGTTGTCTTTGGGGTGGGGTTATGGTGAAATTAGTCTTGGAGAG
TGAGTAGCTGTCTGATGCTTCTTTTCCTTTTTAACCAGCAAGAGCCCAAACCAAATCCCC
[C,A]
AGCTCTGAATGCCTGGCTGTTCCTCTCAGCCTTTCTTTGCTTGAACTTGACAATAGTAGG
GTAGTAACAGGAAACAGCATGTTAAAGTTTTAAAAATAAAATAGATCTCAGCTCTTTTCC
TTCCCATTAGCAAGGGGTACATTTATTTAGGTTTTTCCTTCTAGATTGAGGCACTGCCTC
ATTTAAGTTCTTGGTGAAGCCATGCATTTCTGCAAACCATAAGTATAAACTCTAGAACGG
GGGTGTCCAATCTTTTGGCTTCCTTGGGCCACATGGGAAGAAGAAGAATTGTCTTGAGGC

79926 TTACTAATACACTAGTCCATGTATGTATAGTGTCCTCCTATACACACCAAGAGAATATGG
AAAGGACTCAGCAATGATTAGGTAGTCCAAAGTCATACCAGATTGGAAACCAAGCTTCCC
AGGCCCTGGGACTTTTCTGCTAGAGACACTTCACGGTTCTGACCAACTACAAAGAGTTAA
TATGCAGTTGCCAAATACCTGTTGGTAAAAGGTGGATGTTGGGGAGGAGTGGATTGGGGA
ACAGAATTAGAAGGTCCAGTCCCAGAATGGGTACCTTCCCATCAAGTTGAACAAGTCAAA
[G,A]
CAGGTTATGTTGAAACAACTGAGAGAAAGTAAAGCAAACACCATTGCTGCAGAATATCAT
GGTACAAATTGGACATCTTTGGGAGTTAGCGGAGTAAGGCAAAATCCAGTGAGGGACGCT
TAATGGGTAATGCCAATTCACAATTCTTGTTAAATTACATTGCTGATCTTCCTTGGAATG
TCTGTCCATTCCCCCAAGTAGACTGTGATCTCAAGGCAAGGCTGGGTCTTATTCATCCTG
GTTTTCCTGGAGCAGTAAATACTTGTGCTGGGACTGGGCTTATAAGCATACTAATGGAAA

80198 ACCTTCCCATCAAGTTGAACAAGTCAAAACAGGTTATGTTGAAACAACTGAGAGAAAGTA
AAGCAAACACCATTGCTGCAGAATATCATGGTACAAATTGGACATCTTTGGGAGTTAGCG
GAGTAAGGCAAAATCCAGTGAGGGACGCTTAATGGGTAATGCCAATTCACAATTCTTGTT
AAATTACATTGCTGATCTTCCTTGGAATGTCTGTCCATTCCCCCAAGTAGACTGTGATCT
CAAGGCAAGGCTGGGTCTTATTCATCCTGGTTTTCCTGGAGCAGTAAATACTTGTGCTGG
[G,A]
ACTGGGCTTATAAGCATACTAATGGAAAGTAAAATATTTGGGTTGGTTTTTTAAAAAGAC
AGTGGATTTGGATCAGTGGAGAGGAAGGTAGAGGGAATTTCAGGTGGGCAGGGTGCTAAC
AACAGCCCATCCTTACAGGGCACCAACTGTGTTCTAGGCTGTGTTCCAACCACTTTACAC
AGATGAATTCATTTAAATTGCACAACCAGCCCAAGAGGAAGGTACCATTATTATTCTCAT
TTTGGATGTGAGGAAACTGAGGCGTGGGGAGATCAAACAACTTGCCTAAAGTTATGTAGC

80540 GTTGGTTTTTTAAAAAGACAGTGGATTTGGATCAGTGGAGAGGAAGGTAGAGGGAATTTC
AGGTGGGCAGGGTGCTAACAACAGCCCATCCTTACAGGGCACCAACTGTGTTCTAGGCTG
TGTTCCAACCACTTTACACAGATGAATTCATTTAAATTGCACAACCAGCCCAAGAGGAAG
GTACCATTATTATTCTCATTTTGGATGTGAGGAAACTGAGGCGTGGGGAGATCAAACAAC
TTGCCTAAAGTTATGTAGCTTTGAGTGGCTTAGCTGAGATTTGAACCCTGTGGGTATAAA
[T,C]
GCCACAGATGGGAAATTTGTGTGGGGTACCCAGGTTCATGTGCTTGTTAGAAGTGGAAGC
TATTTGTAGAGAATCACGAATGATGAGGTTGGGGCAGGGTGTGATGGGAGCTGACAGGCA
GGTCTAAATGCTGGGATTCATTTTCAGTCTCTGTGTTTATTGAGTAGGTAGACGGTATAG
CTCTTGGATTTCTCAGATTTTTTCCTCTTTTCATTTAGAGACTCTTATCTGGTGTGTGTG
TGCCCGCACACATACATAAACCCACGCGTATATACTCTTTCCCTGAATGTTCTTATTTGC

81810 TTCTCTATTTAGACTGTGCGTGCCTGCCTTGCAGCCCTGGCAGGACCATTCCACCGCCTT
CTCATTTGTCTTAAAGATACCTTTAGGAAATCTAATCCAGACAATCCTAGCCCAGTCCTG
AAGATTAGGCTCCAGAAGATCTGTCAAGTGTGTTTTTTGCTGGCCTACACATGCTAATTT
GCATGGTTGCCTGGGATCCCTTAAGAAGACAGTCATTGACTAAATGGCGCTACATGTTCC
CAAGCTCTGCGCCAGTCTGGCAACTCTTCCTTTGTCTACGTGAATTTCTCCTAGTTCTTT
[C,T]
TGCTTTGCTTGCTGTTCATCTCCTGACCTCTCTCCGACAAACTTCCTGAAAGAAGAGCCT
GCACTCAACACCTCTTTTTTCCACCTCTTCAACAATACTGAAATGACTGTCTCAGAAGCC
GTTGATTGTACCTAACCACCAAATCTGGTGATTTCCATCTCACCACGTGATACCATTAAT
ACTACCTTTCTTCGAGACAACGTTCTACTTTCTTCTCTTCTGTATTATGGACACTTGGTT
TCCCTCCTACCTCTCTGACTGTCATTCTCACTCTTTTGTGGCTGCCATCAGGCTCTTGCA

82211 AAATGACTGTCTCAGAAGCCGTTGATTGTACCTAACCACCAAATCTGGTGATTTCCATCT
CACCACGTGATACCATTAATACTACCTTTCTTCGAGACAACGTTCTACTTTCTTCTCTTC
TGTATTATGGACACTTGGTTTCCCTCCTACCTCTCTGACTGTCATTCTCACTCTTTTGTG

FIGURE 3AAAA

GCTGCCATCAGGCTCTTGCAATGTACGTACCATCTCCTCAAGTTCCATCCTCAGTTATCT
TTCTAGTTGGTTCTTGGTGATCTCATTCAGTTCCTTGACTTTAGTTCTTACCTCCCCATG
[G,A]
CCTCCTCCCATCGTACACTGTGTTCCTCATCACCAGGATGTTTTACCAGTTTCTCACCAT
CCCATCCTCTGTTCCCTTCCTACATAGACAGACCCACTCGCTCACTCAGTAAGCCACTAG
GTGCTAGTTTTGGCTTCTTCATTTTATGTAAGAAACTACCACCTTCCCTACCCTTCTAGG
CAAGAAAGCTGAGTCATCGTAAATTCTTTTCTGCCTCCCCCGCCATCCCATCAGTTGCCA
ATTTCTCCAAGTGGTGCCTCTAGGATGCCACTTGCATCCATACCCATCTTTCTTCCTCAT

82304 GAGACAACGTTCTACTTTCTTCTCTTCTGTATTATGGACACTTGGTTTCCCTCCTACCTC
TCTGACTGTCATTCTCACTCTTTTGTGGCTGCCATCAGGCTCTTGCAATGTACGTACCAT
CTCCTCAAGTTCCATCCTCAGTTATCTTTCTAGTTGGTTCTTGGTGATCTCATTCAGTTC
CTTGACTTTAGTTCTTACCTCCCCATGGCCTCCTCCCATCGTACACTGTGTTCCTCATCA
CCAGGATGTTTTACCAGTTTCTCACCATCCCATCCTCTGTTCCCTTCCTACATAGACAGA
[C,G]
CCACTCGCTCACTCAGTAAGCCACTAGGTGCTAGTTTTGGCTTCTTCATTTTATGTAAGA
AACTACCACCTTCCCTACCCTTCTAGGCAAGAAAGCTGAGTCATCGTAAATTCTTTTCTG
CCTCCCCCGCCATCCCATCAGTTGCCAATTTCTCCAAGTGGTGCCTCTAGGATGCCACTT
GCATCCATACCCATCTTTCTTCCTCATTGGCACCCATCATGGACTCTTGCTTGGTCTGGT
GCAGTAGCCTCCTCAGTGATTCCCTTGCCTCTGGTTTTCCTGGCTGTAATCCATTCTCCA

82452 TCTAGTTGGTTCTTGGTGATCTCATTCAGTTCCTTGACTTTAGTTCTTACCTCCCCATGG
CCTCCTCCCATCGTACACTGTGTTCCTCATCACCAGGATGTTTTACCAGTTTCTCACCAT
CCCATCCTCTGTTCCCTTCCTACATAGACAGACCCACTCGCTCACTCAGTAAGCCACTAG
GTGCTAGTTTTGGCTTCTTCATTTTATGTAAGAAACTACCACCTTCCCTACCCTTCTAGG
CAAGAAAGCTGAGTCATCGTAAATTCTTTTCTGCCTCCCCCGCCATCCCATCAGTTGCCA
[A,G]
TTTCTCCAAGTGGTGCCTCTAGGATGCCACTTGCATCCATACCCATCTTTCTTCCTCATT
GGCACCCATCATGGACTCTTGCTTGGTCTGGTGCAGTAGCCTCCTCAGTGATTCCCTTGC
CTCTGGTTTTCCTGGCTGTAATCCATTCTCCACAAAGGGTGGAATTCTTCCAAAGCATAG
GTTGGATGATGTCATTCACCGGCTTACACCTTCAACAGCATCCCAGTGTGCTCATAATTA
ATGGCTGCTCCTGAACTTGGTATTCAGTCTTGGTATGCCAAGACCCCAGCCTGCCGGCTC

82539 CATCACCAGGATGTTTTACCAGTTTCTCACCATCCCATCCTCTGTTCCCTTCCTACATAG
ACAGACCCACTCGCTCACTCAGTAAGCCACTAGGTGCTAGTTTTGGCTTCTTCATTTTAT
GTAAGAAACTACCACCTTCCCTACCCTTCTAGGCAAGAAAGCTGAGTCATCGTAAATTCT
TTTCTGCCTCCCCCGCCATCCCATCAGTTGCCAATTTCTCCAAGTGGTGCCTCTAGGATG
CCACTTGCATCCATACCCATCTTTCTTCCTCATTGGCACCCATCATGGACTCTTGCTTGG
[T,A]
CTGGTGCAGTAGCCTCCTCAGTGATTCCCTTGCCTCTGGTTTTCCTGGCTGTAATCCATT
CTCCACAAAGGGTGGAATTCTTCCAAAGCATAGGTTGGATGATGTCATTCACCGGCTTAC
ACCTTCAACAGCATCCCAGTGTGCTCATAATTAATGGCTGCTCCTGAACTTGGTATTCAG
TCTTGGTATGCCAAGACCCCAGCCTGCCGGCTCATTTGTGTCTCCTCATCCCCTACTGAA
TCACTTCAATAGTGTTGTCTGGCCAAGCTGTTCAAGGCTCATTAAGGACAGGACCAGGTC

83079 ATCACTTCAATAGTGTTGTCTGGCCAAGCTGTTCAAGGCTCATTAAGGACAGGACCAGGT
CTTCCTTCTTTTGCCTGAAACAGTGCCTTGCCCCTGGCAGGTCTTCAATGAACATTTGTT
GAATTGAATTAGACTAAAATGGCCAGGGATTATACCAATTCCTTCTGCACAGTGTAGACA
ACTGCTAATGGAACCTGTTTTCTGTAGAGCACTTCTTGTGTTCCCAGAACTATGCGAGTA
CTTTATGTGCATTATCTCATTAAATCATCACAATCTCACTGTAACTCTATGAGGTAGCTG
[A,G]
TATTATCCCCATTTTACAAATGAAGACACTGATTCAGGAAGATTAGATTATTTTCCTGAG
GTTCTGAAGGTAGAAACACATCTAAGACTTGGAGCAATATCTGGTTGCCTCTAGACCACT
GTACTATCTACCCTGCCTCTAAGAGCCATGACTTTGCTAGATTATGCAGGAGTTATGGAC
TTGTCTAATAGTAAAGGTAAAAGAATTGGTTTTAATGAGAATCTACTCTTCTAGGTACTA
TTCTGAGTGCCTGACAAGCATTCTCATGTAGACCCAGCAATAACTCATTATTTTACAGAT

83350 AATCTCACTGTAACTCTATGAGGTAGCTGATATTATCCCCATTTTACAAATGAAGACACT
GATTCAGGAAGATTAGATTATTTTCCTGAGGTTCTGAAGGTAGAAACACATCTAAGACTT
GGAGCAATATCTGGTTGCCTCTAGACCACTGTACTATCTACCCTGCCTCTAAGAGCCATG
ACTTTGCTAGATTATGCAGGAGTTATGGACTTGTCTAATAGTAAAGGTAAAAGAATTGGT
TTTAATGAGAATCTACTCTTCTAGGTACTATTCTGAGTGCCTGACAAGCATTCTCATGTA
[T,G]
ACCCAGCAATAACTCATTATTTTACAGATAGAGAAAATGATGATCATGATGCTTGGGTTA
CTTCTTAGGTTCACTCAGCTCACATCTGGCAGAGGGTGGTCAACTTTTCCAAGTTTTAAC

FIGURE 3BBBB

TTATTTATTTATTTATTTTGAGACAGAGTCTCATTCTGTTGCCCACGCTGGAGTACGGTG
ACACAATCTCAGCTTATTGCAACCTCCGCCTCCCAGGTTCAAGCGATTCTTGTGCCTCAG
CCTCCCGTGTAGCTGGGATTACAGGTGCCTGCCACCACGCCCAGCTAATTTTGTTTTTGT

83407 ACTGATTCAGGAAGATTAGATTATTTTCCTGAGGTTCTGAAGGTAGAAACACATCTAAGA
CTTGGAGCAATATCTGGTTGCCTCTAGACCACTGTACTATCTACCCTGCCTCTAAGAGCC
ATGACTTTGCTAGATTATGCAGGAGTTATGGACTTGTCTAATAGTAAAGGTAAAAGAATT
GGTTTTAATGAGAATCTACTCTTCTAGGTACTATTCTGAGTGCCTGACAAGCATTCTCAT
GTAGACCCAGCAATAACTCATTATTTTACAGATAGAGAAAATGATGATCATGATGCTTGG
[A,G]
TTACTTCTTAGGTTCACTCAGCTCACATCTGGCAGAGGGTGGTCAACTTTTCCAAGTTTT
AACTTATTTATTTATTTATTTTGAGACAGAGTCTCATTCTGTTGCCCACGCTGGAGTACG
GTGACACAATCTCAGCTTATTGCAACCTCCGCCTCCCAGGTTCAAGCGATTCTTGTGCCT
CAGCCTCCCGTGTAGCTGGGATTACAGGTGCCTGCCACCACGCCCAGCTAATTTTGTTTT
TGTATTTTTAGTAGAGGCTGGGTTTCACCATGTTGGCCAGGCCTGTCTTGAACTCCTGAC

83434 CCTGAGGTTCTGAAGGTAGAAACACATCTAAGACTTGGAGCAATATCTGGTTGCCTCTAG
ACCACTGTACTATCTACCCTGCCTCTAAGAGCCATGACTTTGCTAGATTATGCAGGAGTT
ATGGACTTGTCTAATAGTAAAGGTAAAAGAATTGGTTTTAATGAGAATCTACTCTTCTAG
GTACTATTCTGAGTGCCTGACAAGCATTCTCATGTAGACCCAGCAATAACTCATTATTTT
ACAGATAGAGAAAATGATGATCATGATGCTTGGGTTACTTCTTAGGTTCACTCAGCTCAC
[G,A]
TCTGGCAGAGGGTGGTCAACTTTTCCAAGTTTTAACTTATTTATTTATTTATTTTGAGAC
AGAGTCTCATTCTGTTGCCCACGCTGGAGTACGGTGACACAATCTCAGCTTATTGCAACC
TCCGCCTCCCAGGTTCAAGCGATTCTTGTGCCTCAGCCTCCCGTGTAGCTGGGATTACAG
GTGCCTGCCACCACGCCCAGCTAATTTTGTTTTTGTATTTTTAGTAGAGGCTGGGTTTCA
CCATGTTGGCCAGGCCTGTCTTGAACTCCTGACCTCAAGTGATCTGCCAGCCTCGGCCTC

83527 ATGACTTTGCTAGATTATGCAGGAGTTATGGACTTGTCTAATAGTAAAGGTAAAAGAATT
GGTTTTAATGAGAATCTACTCTTCTAGGTACTATTCTGAGTGCCTGACAAGCATTCTCAT
GTAGACCCAGCAATAACTCATTATTTTACAGATAGAGAAAATGATGATCATGATGCTTGG
GTTACTTCTTAGGTTCACTCAGCTCACATCTGGCAGAGGGTGGTCAACTTTTCCAAGTTT
TAACTTATTTATTTATTTATTTTGAGACAGAGTCTCATTCTGTTGCCCACGCTGGAGTAC
[A,G]
GTGACACAATCTCAGCTTATTGCAACCTCCGCCTCCCAGGTTCAAGCGATTCTTGTGCCT
CAGCCTCCCGTGTAGCTGGGATTACAGGTGCCTGCCACCACGCCCAGCTAATTTTGTTTT
TGTATTTTTAGTAGAGGCTGGGTTTCACCATGTTGGCCAGGCCTGTCTTGAACTCCTGAC
CTCAAGTGATCTGCCAGCCTCGGCCTCCCAAAGTGTTGTGATTACAGATGTGAGCCACCA
CGCCTGGCTCAACTTTTAACTTTAGAACTGATATAAACATGCCTATTTTTTTGGGACTGA

83699 ATGCTTGGGTTACTTCTTAGGTTCACTCAGCTCACATCTGGCAGAGGGTGGTCAACTTTT
CCAAGTTTTAACTTATTTATTTATTTATTTTGAGACAGAGTCTCATTCTGTTGCCCACGC
TGGAGTACGGTGACACAATCTCAGCTTATTGCAACCTCCGCCTCCCAGGTTCAAGCGATT
CTTGTGCCTCAGCCTCCCGTGTAGCTGGGATTACAGGTGCCTGCCACCACGCCCAGCTAA
TTTTGTTTTTGTATTTTTAGTAGAGGCTGGGTTTCACCATGTTGGCCAGGCCTGTCTTGA
[G,A]
CTCCTGACCTCAAGTGATCTGCCAGCCTCGGCCTCCCAAAGTGTTGTGATTACAGATGTG
AGCCACCACGCCTGGCTCAACTTTTAACTTTAGAACTGATATAAACATGCCTATTTTTTT
GGGACTGACTGTAGCATACCCATTCAAAGTCCAGGCTTTGGAATCAGACAGACGTGGGCT
GAACTCAGGGTTTCACCCCTTGCTTGTTGTGTGAATGAGACATTTCACTGCTTTCAGCCT
CAATTCCCTCATCTGTAAAGTGGAAGGTGTAAGGTCGCCTATCTGATAGGTTTGCCATGG

83729 CTCACATCTGGCAGAGGGTGGTCAACTTTTCCAAGTTTTAACTTATTTATTTATTTATTT
TGAGACAGAGTCTCATTCTGTTGCCCACGCTGGAGTACGGTGACACAATCTCAGCTTATT
GCAACCTCCGCCTCCCAGGTTCAAGCGATTCTTGTGCCTCAGCCTCCCGTGTAGCTGGGA
TTACAGGTGCCTGCCACCACGCCCAGCTAATTTTGTTTTTGTATTTTTAGTAGAGGCTGG
GTTTCACCATGTTGGCCAGGCCTGTCTTGAACTCCTGACCTCAAGTGATCTGCCAGCCTC
[A,G]
GCCTCCCAAAGTGTTGTGATTACAGATGTGAGCCACCACGCCTGGCTCAACTTTTAACTT
TAGAACTGATATAAACATGCCTATTTTTTTGGGACTGACTGTAGCATACCCATTCAAAGT
CCAGGCTTTGGAATCAGACAGACGTGGGCTGAACTCAGGGTTTCACCCCTTGCTTGTTGT
GTGAATGAGACATTTCACTGCTTTCAGCCTCAATTCCCTCATCTGTAAAGTGGAAGGTGT
AAGGTCGCCTATCTGATAGGTTTGCCATGGGGATATGAAGCACACTTAGTGTTGGTGCCA

84000 CTCCTGACCTCAAGTGATCTGCCAGCCTCGGCCTCCCAAAGTGTTGTGATTACAGATGTG

FIGURE 3CCCC

AGCCACCACGCCTGGCTCAACTTTTAACTTTAGAACTGATATAAACATGCCTATTTTTTT
GGGACTGACTGTAGCATACCCATTCAAAGTCCAGGCTTTGGAATCAGACAGACGTGGGCT
GAACTCAGGGTTTCACCCCTTGCTTGTTGTGTGAATGAGACATTTCACTGCTTTCAGCCT
CAATTCCCTCATCTGTAAAGTGGAAGGTGTAAGGTCGCCTATCTGATAGGTTTGCCATGG
[T,G]
GATATGAAGCACACTTAGTGTTGGTGCCATGAGTAGAATGAGTGTTCATTTCATATTTGT
TAATGTTATTTAGGTCCGAGGATGGGTATGGGGTGCTTTGGACTCTCTTTTTCTCCCTGC
TTCCGCCTTATAAAGACATCTTGCTGGTTTCTGCCCATTGAGAGAATCCAGCTCCACGTG
GGGGGCCTGACAGATGTCCTAATATCTCCATCCAATTTTTTACTCTGAATGGAGTCTGTG
ATGTATCACTTCAACCTGCACTTTCTATAAAATGCTCTCCAGGCTTCTGGTAGGATCCAG

84034 CCCAAAGTGTTGTGATTACAGATGTGAGCCACCACGCCTGGCTCAACTTTTAACTTTAGA
ACTGATATAAACATGCCTATTTTTTTGGGACTGACTGTAGCATACCCATTCAAAGTCCAG
GCTTTGGAATCAGACAGACGTGGGCTGAACTCAGGGTTTCACCCCTTGCTTGTTGTGTGA
ATGAGACATTTCACTGCTTTCAGCCTCAATTCCCTCATCTGTAAAGTGGAAGGTGTAAGG
TCGCCTATCTGATAGGTTTGCCATGGGGATATGAAGCACACTTAGTGTTGGTGCCATGAG
[C,T]
AGAATGAGTGTTCATTTCATATTTGTTAATGTTATTTAGGTCCGAGGATGGGTATGGGGT
GCTTTGGACTCTCTTTTTCTCCCTGCTTCCGCCTTATAAAGACATCTTGCTGGTTTCTGC
CCATTGAGAGAATCCAGCTCCACGTGGGGGGCCTGACAGATGTCCTAATATCTCCATCCA
ATTTTTTACTCTGAATGGAGTCTGTGATGTATCACTTCAACCTGCACTTTCTATAAAATG
CTCTCCAGGCTTCTGGTAGGATCCAGTGCCAGTGGGAAGTGTGCATGTTCCCAGCCTAGA

84213 AATGAGACATTTCACTGCTTTCAGCCTCAATTCCCTCATCTGTAAAGTGGAAGGTGTAAG
GTCGCCTATCTGATAGGTTTGCCATGGGGATATGAAGCACACTTAGTGTTGGTGCCATGA
GTAGAATGAGTGTTCATTTCATATTTGTTAATGTTATTTAGGTCCGAGGATGGGTATGGG
GTGCTTTGGACTCTCTTTTTCTCCCTGCTTCCGCCTTATAAAGACATCTTGCTGGTTTCT
GCCCATTGAGAGAATCCAGCTCCACGTGGGGGGCCTGACAGATGTCCTAATATCTCCATC
[C,T]
AATTTTTTACTCTGAATGGAGTCTGTGATGTATCACTTCAACCTGCACTTTCTATAAAAT
GCTCTCCAGGCTTCTGGTAGGATCCAGTGCCAGTGGGAAGTGTGCATGTTCCCAGCCTAG
ATGTCACATGCTCCCACCCACCCTGGAAGCACTTGGGTATCCCCTGGATGGGTAAGTCTG
TGTGTCATTGTGCCATTCCTGTCTCAGAACCAATGCTGGGCATCTCTACTTGCAGGTGCT
GGAAAGCTTTTTCATGCCAGCATACATGCAGCACACTTCTCATTTTGGATTCCTTTATCC

84803 TTCCTTTATCCCACGGTGACCTTTAAACTGGCTGCCTGGGGGCACAGAAGTACTAGCACA
CCATTCACTTATTTATTCATTCATTCATTCATTCATTCATTCACTCAACAAATATATTGT
TCTAGTCCTTAAGGCACAACTCTGAGCAAGACAGGTAAGGTCTTTACTCTCAAGAAGCTA
GCATTTGGTGGGGAGAAACAAAGGAGAAATAACTACTGTGCACATGTGAGGCAATTGCAG
ATGGTGGTCTGCAGAATTGGGATTGAGACTGCCTGGGGGTGGCCACTTTAGACTGGGTCC
[A,G]
CAAGGAAAGGTTCTCTGAGCTGAGCATGAGTATTTGTTCAAGAAGGCTGAGTTGCATCCC
AAGGTGACACAGCTTTTAAGCCCACACTGAGCAGCTCTGAGGTCCTAGGGGCTGTTCGAG
AACCTGGGATATAGCACTGACTATGAGACAAAAATCCCTGTCTTCATGGAGCTTACATGA
TGGGGGCAGATTCACATTCATTCATTTGTTCATTAATTCATTAATTCATTCAGCTATTTG
AGAGCCTACTATGTGCCAAGCACTTTCTAGGCACTGGAGAAGTAACAGTGAATGCAAAGG

85027 TGTGAGGCAATTGCAGATGGTGGTCTGCAGAATTGGGATTGAGACTGCCTGGGGGTGGCC
ACTTTAGACTGGGTCCGCAAGGAAAGGTTCTCTGAGCTGAGCATGAGTATTTGTTCAAGA
AGGCTGAGTTGCATCCCAAGGTGACACAGCTTTTAAGCCCACACTGAGCAGCTCTGAGGT
CCTAGGGGCTGTTCGAGAACCTGGGATATAGCACTGACTATGAGACAAAAATCCCTGTCT
TCATGGAGCTTACATGATGGGGGCAGATTCACATTCATTCATTTGTTCATTAATTCATTA
[G,A]
TTCATTCAGCTATTTGAGAGCCTACTATGTGCCAAGCACTTTCTAGGCACTGGAGAAGTA
ACAGTGAATGCAAAGGAGCAAGCATCCCTGCCCACACAGAGTGCATTCTTCCAGAATATC
AATAAGGAGTCGGTTAGCAAAAATAAGTGGGAAGAGTATTCCAGAGAGAGGAAAAAAGGG
CAAAGGCCCTGAGGCTGCCACTAACCTATGGGTGCTCAATGAACAGAAGGCATGTTTGGG
TAGGGGGTACTTAAGGATACACAAGGAACATGGTCTGAGCTGAGGTCATCAGGGCCTTTA

85275 CTTACATGATGGGGGCAGATTCACATTCATTCATTTGTTCATTAATTCATTAATTCATTC
AGCTATTTGAGAGCCTACTATGTGCCAAGCACTTTCTAGGCACTGGAGAAGTAACAGTGA
ATGCAAAGGAGCAAGCATCCCTGCCCACACAGAGTGCATTCTTCCAGAATATCAATAAGG
AGTCGGTTAGCAAAAATAAGTGGGAAGAGTATTCCAGAGAGAGGAAAAAAGGGCAAAGGC
CCTGAGGCTGCCACTAACCTATGGGTGCTCAATGAACAGAAGGCATGTTTGGGTAGGGGG
[A,T]

FIGURE 3DDDD

ACTTAAGGATACACAAGGAACATGGTCTGAGCTGAGGTCATCAGGGCCTTTAGGTATGGA
CTTTGCTCTAAATTGCACTGAGTAGGAAGCTTTTGCAGGATTTTGAATAGGGTCATGGAA
TATCTGGGTCTTATTTCACAAAGTGTGCCTCTGACCATTGTGTGGAGGGTGGATAGTGAG
GGACAAGAGTTGGATCCAGGGAGGTAAGTGTGGTTATTGCAGTCATCCCAGGTGAGAGGC
AATGAAATTAACCTGCAAAGTGAGGCACTGGCTTAGAGGTGGGAACTGAATTAAAAATCA

87009 GCTTGATGCTTAAGCACGAACTTAATCATCGCAGTAGTGATTAAAGAGTATTCAACATGT
ACACTTGCTTGTAGGAAGGAGTACACATTGTATTCTCTTTTGATATGCAATATTTTATTC
ATAGCCCTATTAAGTAATTTTTTTTAACAAAGTTATATGGATTATTTACAGGTACATCAC
GGGAAAACTGCATTTTATAATTTTCACTGAAATGTTGAGGTTACATGTAAAGCAATTTTT
ATGTCATATCTGATACATTTTAAGAAAACATGTCTTCCTGTTACAGCGGTAATGACCATG
[T,C]
CTGCTCTTTCTTCTGTGTCATATGCCATTATCCCTATTAATACTCTTTGGGCTTCTATAA
TTATAAAGCAGATGTGTATATCAGGGAGAGATGTTGATTTCAGAGTAAGTTTTTCTAGAA
AATAGAAGCTGGAAAAAAAAGGAAAACCCAAACTTGGCTTCGTGCTCGAAGAGACAGCAC
TGCTGTGTGTGGGCGGGTGGCTGCGTGCACCCGCTGCTCAGAAGTGCCTTTTCTCTCCAT
GGGGATAACTGGCTGTGTATCCGAGATGTGGCCAGGAGTAGGCAAGCAACGTGTGGGCAG

87888 ACTGTATCTCACATGTTCCGCTCTCCCTTTCCTCCATGACCTTGCCCCTCTGAGCCTCTG
TAGCACTTTTCTTGAGTGTGTCCAAGGCCATCTAGCTAAGAAGTAGCAGAAATGGGATTT
GAAGCCATGACTGTTTGGTGATAGAGCCTCAGCTTTGAACTGGGGTTCTACTGCCTGGCA
CCCCTGCACAAATCATGGTAACGTGGTAGGAGAACATAGAGGTATAGGGCAAGCCCCTCC
TTAATGCCATGAATAATACCCATCTTATAGGATTGTGGGGAGGACTCAGTGAAGTAACCC
[G,A]
TGAAGCACTAAACACGTGCCTGACACGTGCTCAATAAATGAGCACTTGTCCTGATGACAA
AGGTCGTGGCATTAATTCTCTCTCCTAGGTTGTTACTTCCTTGAGGACAGGAATTGTGGC
TTCCTTAATGGCCACTGCAGCAGAGTTTCTCAAGTTGGCACTATTGACATTTTGGGCTGG
ATAATTCTTGTTGTGGGAGCTGTCCTGTGGATTGTAGGATGTTGAGCAGCATCTTTGGCC
TCTACCCGCTACATATTAATAGCACCCCTAGTCATGAAAATAAAATGTCTAGACATTGCC

88136 ATGAATAATACCCATCTTATAGGATTGTGGGGAGGACTCAGTGAAGTAACCCGTGAAGCA
CTAAACACGTGCCTGACACGTGCTCAATAAATGAGCACTTGTCCTGATGACAAAGGTCGT
GGCATTAATTCTCTCTCCTAGGTTGTTACTTCCTTGAGGACAGGAATTGTGGCTTCCTTA
ATGGCCACTGCAGCAGAGTTTCTCAAGTTGGCACTATTGACATTTTGGGCTGGATAATTC
TTGTTGTGGGAGCTGTCCTGTGGATTGTAGGATGTTGAGCAGCATCTTTGGCCTCTACCC
[G,A]
CTACATATTAATAGCACCCCTAGTCATGAAAATAAAATGTCTAGACATTGCCAAACTGCC
CCTGTTGAGAACCACTGGTCTGCAGGTATCTCTCATGGGGATCACAGGGCTTTTATATTC
TCTTCTCTGTCTCTCTCTCTCCCTCTCTGGGTGTCTCTCTCTCTCACACACACGCTTAGA
GAAGGTGGTTAAAAAAAATTTTGTTGAAGTTTGAGAATTTTGAGAACAAAGGAAAAATTT
TGGAAGGCATTTTAATGAACAGATAGACTCTGTCCCATTCCATGGTCAACAGAATTTCAT

88231 CACTTGTCCTGATGACAAAGGTCGTGGCATTAATTCTCTCTCCTAGGTTGTTACTTCCTT
GAGGACAGGAATTGTGGCTTCCTTAATGGCCACTGCAGCAGAGTTTCTCAAGTTGGCACT
ATTGACATTTTGGGCTGGATAATTCTTGTTGTGGGAGCTGTCCTGTGGATTGTAGGATGT
TGAGCAGCATCTTTGGCCTCTACCCGCTACATATTAATAGCACCCCTAGTCATGAAAATA
AAATGTCTAGACATTGCCAAACTGCCCCTGTTGAGAACCACTGGTCTGCAGGTATCTCTC
[G,A]
TGGGGATCACAGGGCTTTTATATTCTCTTCTCTGTCTCTCTCTCTCCCTCTCTGGGTGTC
TCTCTCTCTCACACACACGCTTAGAGAAGGTGGTTAAAAAAAATTTTGTTGAAGTTTGAG
AATTTTGAGAACAAAGGAAAAATTTTGGAAGGCATTTTAATGAACAGATAGACTCTGTCC
CATTCCATGGTCAACAGAATTTCATAATTAGATAGTTTGTTTACTGCAACTCTGCACCCC
ATTGCCCATCATTTTAGAGTTCCAACCAGTTAGAGGATTTTTCTTGCAAACTTTCCTTAA

88482 CATTGCCAAACTGCCCCTGTTGAGAACCACTGGTCTGCAGGTATCTCTCATGGGGATCAC
AGGGCTTTTATATTCTCTTCTCTGTCTCTCTCTCTCCCTCTCTGGGTGTCTCTCTCTCTC
ACACACACGCTTAGAGAAGGTGGTTAAAAAAAATTTTGTTGAAGTTTGAGAATTTTGAGA
ACAAAGGAAAAATTTTGGAAGGCATTTTAATGAACAGATAGACTCTGTCCCATTCCATGG
TCAACAGAATTTCATAATTAGATAGTTTGTTTACTGCAACTCTGCACCCCATTGCCCATC
[A,G]
TTTTAGAGTTCCAACCAGTTAGAGGATTTTTCTTGCAAACTTTCCTTAAAGCAGTGATAG
TATCAGCTCTTTAAATAATACTATGCTTGATGAAGTGGTACTTTTCGGGATAATTTGAGA
CCAGCCGACTTGCTGCTTGAAGAGGACAGGGCTATATTTGGTAATAATATATATGTGATA
ATATGTATGTAATATTATTATAATGTAATATACAATAATATTTGGTGTAACTGGTGACTC
TGAGGCCAGTCTTTGATCGAACCTCTCAAGCTATGATTTACATTATGGTCAATGTTAGCA

FIGURE 3EEEE

88608 ACGCTTAGAGAAGGTGGTTAAAAAAAATTTTGTTGAAGTTTGAGAATTTTGAGAACAAAG
GAAAAATTTTGGAAGGCATTTTAATGAACAGATAGACTCTGTCCCATTCCATGGTCAACA
GAATTTCATAATTAGATAGTTTGTTTACTGCAACTCTGCACCCCATTGCCCATCATTTTA
GAGTTCCAACCAGTTAGAGGATTTTTCTTGCAAACTTTCCTTAAAGCAGTGATAGTATCA
GCTCTTTAAATAATACTATGCTTGATGAAGTGGTACTTTTCGGGATAATTTGAGACCAGC
[C,A]
GACTTGCTGCTTGAAGAGGACAGGGCTATATTTGGTAATAATATATATGTGATAATATGT
ATGTAATATTATTATAATGTAATATACAATAATATTTGGTGTAACTGGTGACTCTGAGGC
CAGTCTTTGATCGAACCTCTCAAGCTATGATTTACATTATGGTCAATGTTAGCATAATGC
AATTATCAGCAATCACTTGCTGTTGCTTTGAAAGTCAGAAGGATGGCTAATAAAAATCTT
AGAAAAAGAAAACAGGCTGGGCGCAGTGGCTCACCCCTGTAATCCCAGCACTTTGGGAGG

88866 TGCTTGATGAAGTGGTACTTTTCGGGATAATTTGAGACCAGCCGACTTGCTGCTTGAAGA
GGACAGGGCTATATTTGGTAATAATATATATGTGATAATATGTATGTAATATTATTATAA
TGTAATATACAATAATATTTGGTGTAACTGGTGACTCTGAGGCCAGTCTTTGATCGAACC
TCTCAAGCTATGATTTACATTATGGTCAATGTTAGCATAATGCAATTATCAGCAATCACT
TGCTGTTGCTTTGAAAGTCAGAAGGATGGCTAATAAAAATCTTAGAAAAAGAAAACAGGC
[T,C]
GGGCGCAGTGGCTCACCCCTGTAATCCCAGCACTTTGGGAGGCTGAGGCGGGCAGATCAT
GAGGTCAGGAGATCGAGACCATCCTGGCCAACATGGTGAAACCCCATCTGTACTAGAATA
CAAAAAAAAAAAAAAAATTTGCTGGGCGTGGTGGCGTGCGCCTGTAGTCCCAGCTACTCG
GGAGCTGAGTCAGGGGAATCGCTTGAACCCGGGAGGTGGAGGTTGCAGTGAGCCGAGATT
GTGCCACTGCACTCCAGCCTGGTGACAGAGTGAGACTCCGTCTCAAACAAAACAAAACAA

88870 TGATGAAGTGGTACTTTTCGGGATAATTTGAGACCAGCCGACTTGCTGCTTGAAGAGGAC
AGGGCTATATTTGGTAATAATATATATGTGATAATATGTATGTAATATTATTATAATGTA
ATATACAATAATATTTGGTGTAACTGGTGACTCTGAGGCCAGTCTTTGATCGAACCTCTC
AAGCTATGATTTACATTATGGTCAATGTTAGCATAATGCAATTATCAGCAATCACTTGCT
GTTGCTTTGAAAGTCAGAAGGATGGCTAATAAAAATCTTAGAAAAAGAAAACAGGCTGGG
[C,T]
GCAGTGGCTCACCCCTGTAATCCCAGCACTTTGGGAGGCTGAGGCGGGCAGATCATGAGG
TCAGGAGATCGAGACCATCCTGGCCAACATGGTGAAACCCCATCTGTACTAGAATACAAA
AAAAAAAAAAAAATTTGCTGGGCGTGGTGGCGTGCGCCTGTAGTCCCAGCTACTCGGGAG
CTGAGTCAGGGGAATCGCTTGAACCCGGGAGGTGGAGGTTGCAGTGAGCCGAGATTGTGC
CACTGCACTCCAGCCTGGTGACAGAGTGAGACTCCGTCTCAAACAAAACAAAACAAAACA

88918 CTTGAAGAGGACAGGGCTATATTTGGTAATAATATATATGTGATAATATGTATGTAATAT
TATTATAATGTAATATACAATAATATTTGGTGTAACTGGTGACTCTGAGGCCAGTCTTTG
ATCGAACCTCTCAAGCTATGATTTACATTATGGTCAATGTTAGCATAATGCAATTATCAG
CAATCACTTGCTGTTGCTTTGAAAGTCAGAAGGATGGCTAATAAAAATCTTAGAAAAAGA
AAACAGGCTGGGCGCAGTGGCTCACCCCTGTAATCCCAGCACTTTGGGAGGCTGAGGCGG
[G,A]
CAGATCATGAGGTCAGGAGATCGAGACCATCCTGGCCAACATGGTGAAACCCCATCTGTA
CTAGAATACAAAAAAAAAAAAAAAATTTGCTGGGCGTGGTGGCGTGCGCCTGTAGTCCCA
GCTACTCGGGAGCTGAGTCAGGGGAATCGCTTGAACCCGGGAGGTGGAGGTTGCAGTGAG
CCGAGATTGTGCCACTGCACTCCAGCCTGGTGACAGAGTGAGACTCCGTCTCAAACAAAA
CAAAACAAAACAAAAAACAAAAAAAGAAAATCTTAGAAAAAGAAAATAAATTGTAATATT

88940 TTGGTAATAATATATATGTGATAATATGTATGTAATATTATTATAATGTAATATACAATA
ATATTTGGTGTAACTGGTGACTCTGAGGCCAGTCTTTGATCGAACCTCTCAAGCTATGAT
TTACATTATGGTCAATGTTAGCATAATGCAATTATCAGCAATCACTTGCTGTTGCTTTGA
AAGTCAGAAGGATGGCTAATAAAAATCTTAGAAAAAGAAAACAGGCTGGGCGCAGTGGCT
CACCCCTGTAATCCCAGCACTTTGGGAGGCTGAGGCGGGCAGATCATGAGGTCAGGAGAT
[C,T]
GAGACCATCCTGGCCAACATGGTGAAACCCCATCTGTACTAGAATACAAAAAAAAAAAAA
AAATTTGCTGGGCGTGGTGGCGTGCGCCTGTAGTCCCAGCTACTCGGGAGCTGAGTCAGG
GGAATCGCTTGAACCCGGGAGGTGGAGGTTGCAGTGAGCCGAGATTGTGCCACTGCACTC
CAGCCTGGTGACAGAGTGAGACTCCGTCTCAAACAAAACAAAACAAAACAAAAAACAAAA
AAAGAAAATCTTAGAAAAAGAAAATAAATTGTAATATTTCAGAATATTTGTTGGGGAGGA

89133 GGCTAATAAAAATCTTAGAAAAAGAAAACAGGCTGGGCGCAGTGGCTCACCCCTGTAATC
CCAGCACTTTGGGAGGCTGAGGCGGGCAGATCATGAGGTCAGGAGATCGAGACCATCCTG
GCCAACATGGTGAAACCCCATCTGTACTAGAATACAAAAAAAAAAAAAAAATTTGCTGGG

FIGURE 3FFFF

CGTGGTGGCGTGCGCCTGTAGTCCCAGCTACTCGGGAGCTGAGTCAGGGGAATCGCTTGA
ACCCGGGAGGTGGAGGTTGCAGTGAGCCGAGATTGTGCCACTGCACTCCAGCCTGGTGAC
[A,G]
GAGTGAGACTCCGTCTCAAACAAAACAAAACAAAACAAAAAACAAAAAAAGAAAATCTTA
GAAAAAGAAAATAAATTGTAATATTTCAGAATATTTGTTGGGGAGGATATGTGTGCTCAA
GAAATATATACTGAGAACTTACCATTGATGCTAGAGATTGAATTGCCCCATGTCTACATG
AAAAATGAATAGAATATAAACATTTTAAATTGAGCCATGTCTATCTGTATTATATTTCTT
TTATAGAAATTCATGGAAATGGTATATTTTAACTGAATTATTAACACTGGGGACAATAGG

89260 TGGTGAAACCCCATCTGTACTAGAATACAAAAAAAAAAAAAAAAATTTGCTGGGCGTGGTG
GCGTGCGCCTGTAGTCCCAGCTACTCGGGAGCTGAGTCAGGGGAATCGCTTGAACCCGGG
AGGTGGAGGTTGCAGTGAGCCGAGATTGTGCCACTGCACTCCAGCCTGGTGACAGAGTGA
GACTCCGTCTCAAACAAAACAAAACAAAACAAAAAACAAAAAAAGAAAATCTTAGAAAAA
GAAAATAAATTGTAATATTTCAGAATATTTGTTGGGGAGGATATGTGTGCTCAAGAAATA
[T,C]
ATACTGAGAACTTACCATTGATGCTAGAGATTGAATTGCCCCATGTCTACATGAAAAATG
AATAGAATATAAACATTTTAAATTGAGCCATGTCTATCTGTATTATATTTCTTTTATAGA
AATTCATGGAAATGGTATATTTTAACTGAATTATTAACACTGGGGACAATAGGCTTTAAT
CATTATCTAATACCTGTACGTTGTTTTGAAATTCATAGCCCACCACCATTAATTTCAAAA
TTGGGTTCTTACTCAAAGAGTGATGAAAAGGCACCAGTACCAAATGGTCTGGCCAAAATG

89298 AAAAAATTTGCTGGGCGTGGTGGCGTGCGCCTGTAGTCCCAGCTACTCGGGAGCTGAGTC
AGGGGAATCGCTTGAACCCGGGAGGTGGAGGTTGCAGTGAGCCGAGATTGTGCCACTGCA
CTCCAGCCTGGTGACAGAGTGAGACTCCGTCTCAAACAAAACAAAACAAAACAAAAAACA
AAAAAAGAAAATCTTAGAAAAAGAAAATAAATTGTAATATTTCAGAATATTTGTTGGGGA
GGATATGTGTGCTCAAGAAATATATACTGAGAACTTACCATTGATGCTAGAGATTGAATT
[G,T]
CCCCATGTCTACATGAAAAATGAATAGAATATAAACATTTTAAATTGAGCCATGTCTATC
TGTATTATATTTCTTTTATAGAAATTCATGGAAATGGTATATTTTAACTGAATTATTAAC
ACTGGGGACAATAGGCTTTAATCATTATCTAATACCTGTACGTTGTTTTGAAATTCATAG
CCCACCACCATTAATTTCAAAATTGGGTTCTTACTCAAAGAGTGATGAAAAGGCACCAGT
ACCAAATGGTCTGGCCAAAATGCTACATGGAACTAAATGCTGGGGATGGTCATACAATGA

89682 ATTCATGGAAATGGTATATTTTAACTGAATTATTAACACTGGGGACAATAGGCTTTAATC
ATTATCTAATACCTGTACGTTGTTTTGAAATTCATAGCCCACCACCATTAATTTCAAAAT
TGGGTTCTTACTCAAAGAGTGATGAAAAGGCACCAGTACCAAATGGTCTGGCCAAAATGC
TACATGGAACTAAATGCTGGGGATGGTCATACAATGAGTTTTAAGTGGCTAGACCCTAAA
TCAGAAGCACTTTCTTCTAATTAGCACCATGGTTCTTAATCCTTTCTGTACATTACAATC
[G,A]
CTCAGCAGCTTAATACAAATGTTGCTTCCCGGGGCCACACTCCACATCTTTCTGACTCTC
TGATTTAATTGGTCCGAATGGGGCCTATACATCAGGTGTTTTTTAAAAGGTCTCCAAGTG
ATTCTAATGTGTACCTGCATTGAGGACCAGGGAAGGTGTAGGAAGCCTGATAACCTTTAC
TCTCCAGCCTCATCCTCCAATCCCATGATTGTTTATGGGATTGTTGCTACACACCCAGCT
TAGTCATAGCATTCTTACTCTAGCTTTTTTTTAGATGCAATTTTTATTTATTCTTAAAGA

89757 TACGTTGTTTTGAAATTCATAGCCCACCACCATTAATTTCAAAATTGGGTTCTTACTCAA
AGAGTGATGAAAAGGCACCAGTACCAAATGGTCTGGCCAAAATGCTACATGGAACTAAAT
GCTGGGGATGGTCATACAATGAGTTTTAAGTGGCTAGACCCTAAATCAGAAGCACTTTCT
TCTAATTAGCACCATGGTTCTTAATCCTTTCTGTACATTACAATCGCTCAGCAGCTTAAT
ACAAATGTTGCTTCCCGGGGCCACACTCCACATCTTTCTGACTCTCTGATTTAATTGGTC
[C,T]
GAATGGGGCCTATACATCAGGTGTTTTTTAAAAGGTCTCCAAGTGATTCTAATGTGTACC
TGCATTGAGGACCAGGGAAGGTGTAGGAAGCCTGATAACCTTTACTCTCCAGCCTCATCC
TCCAATCCCATGATTGTTTATGGGATTGTTGCTACACACCCAGCTTAGTCATAGCATTCT
TACTCTAGCTTTTTTTTAGATGCAATTTTTATTTATTCTTAAAGAAAAAGATTTCTTTAG
CACCTTTATTCTAAAGAGCTCTTAATTGCTGTGCTTAGAACTTCTAAACAGTGAGCATTT

89817 AGAGTGATGAAAAGGCACCAGTACCAAATGGTCTGGCCAAAATGCTACATGGAACTAAAT
GCTGGGGATGGTCATACAATGAGTTTTAAGTGGCTAGACCCTAAATCAGAAGCACTTTCT
TCTAATTAGCACCATGGTTCTTAATCCTTTCTGTACATTACAATCGCTCAGCAGCTTAAT
ACAAATGTTGCTTCCCGGGGCCACACTCCACATCTTTCTGACTCTCTGATTTAATTGGTC
CGAATGGGGCCTATACATCAGGTGTTTTTTAAAAGGTCTCCAAGTGATTCTAATGTGTAC
[C,T]
TGCATTGAGGACCAGGGAAGGTGTAGGAAGCCTGATAACCTTTACTCTCCAGCCTCATCC

FIGURE 3GGGG

TCCAATCCCATGATTGTTTATGGGATTGTTGCTACACACCCAGCTTAGTCATAGCATTCT
TACTCTAGCTTTTTTTTAGATGCAATTTTTATTTATTCTTAAAGAAAAAGATTTCTTTAG
CACCTTTATTCTAAAGAGCTCTTAATTGCTGTGCTTAGAACTTCTAAACAGTGAGCATTT
GTCAAACATAGAATAGCAGAATGAAGGGGTTGGACCTCGGGTGAGGAGGGCTGTCGCATG

90248 TTTTTTTAGATGCAATTTTTATTTATTCTTAAAGAAAAAGATTTCTTTAGCACCTTTATT
CTAAAGAGCTCTTAATTGCTGTGCTTAGAACTTCTAAACAGTGAGCATTTGTCAAACATA
GAATAGCAGAATGAAGGGGTTGGACCTCGGGTGAGGAGGGCTGTCGCATGGTCTCTTTCG
AGTGCCGGCGGGTGGGGGCTGCACATCTCCTCGCTTCTGGGCCCATTGATAAGTGACCTA
AAAGTGCCTTTCGTTTTTTTTGGTGGGGGGTGAAAAAGCAATCTGTTTTGTACCCACAGC
[G,A]
GTGCACTTTAAACAGGAAGCCCTACTGGGGCCAGCCTTCTATGTGTCATTAAGTTTTTCA
CGCCACATCCTACCTATCATCATGCACCCATGTCATCGTTCTTTTAAAGGGTGCCAGTTT
TTTGCTTAAGCACAAGGAGCTGTGACCTGTGTTGTCATCCCTGATGCATGTCATGCATGT
GACTTCATGACATGTGGGTGACTTTTGATCTCTGAAGGACCAGGGACCCAGTCTGTGGAT
CACCACTCTCTCCGTGGGTGGTTTGGGTCTTGTTCTCTAGCCCACCCAGCCAGGTGCAAT

90283 AAAAGATTTCTTTAGCACCTTTATTCTAAAGAGCTCTTAATTGCTGTGCTTAGAACTTCT
AAACAGTGAGCATTTGTCAAACATAGAATAGCAGAATGAAGGGGTTGGACCTCGGGTGAG
GAGGGCTGTCGCATGGTCTCTTTCGAGTGCCGGCGGGTGGGGGCTGCACATCTCCTCGCT
TCTGGGCCCATTGATAAGTGACCTAAAAGTGCCTTTCGTTTTTTTTGGTGGGGGGTGAAA
AAGCAATCTGTTTTGTACCCACAGCGGTGCACTTTAAACAGGAAGCCCTACTGGGGCCAG
[G,C]
CTTCTATGTGTCATTAAGTTTTTCACGCCACATCCTACCTATCATCATGCACCCATGTCA
TCGTTCTTTTAAAGGGTGCCAGTTTTTTGCTTAAGCACAAGGAGCTGTGACCTGTGTTGT
CATCCCTGATGCATGTCATGCATGTGACTTCATGACATGTGGGTGACTTTTGATCTCTGA
AGGACCAGGGACCCAGTCTGTGGATCACCACTCTCTCCGTGGGTGGTTTGGGTCTTGTTC
TCTAGCCCACCCAGCCAGGTGCAATTAGGAATAAAGGAAATAGCAAAGGAATTTTGCTCA

90506 TTTGGTGGGGGGTGAAAAAGCAATCTGTTTTGTACCCACAGCGGTGCACTTTAAACAGGA
AGCCCTACTGGGGCCAGCCTTCTATGTGTCATTAAGTTTTTCACGCCACATCCTACCTAT
CATCATGCACCCATGTCATCGTTCTTTTAAAGGGTGCCAGTTTTTTGCTTAAGCACAAGG
AGCTGTGACCTGTGTTGTCATCCCTGATGCATGTCATGCATGTGACTTCATGACATGTGG
GTGACTTTTGATCTCTGAAGGACCAGGGACCCAGTCTGTGGATCACCACTCTCTCCGTGG
[C,G]
TGGTTTGGGTCTTGTTCTCTAGCCCACCCAGCCAGGTGCAATTAGGAATAAAGGAAATAG
CAAAGGAATTTTGCTCAAGGCCATGCCAAGCATTTCATCTCATATGAAAAGGAAAAGAGA
GAGAGTGTGTGTGTGTTGGCTAGATTTAGGTAGAAAACAGGCTGGTGAGAAGCGTAGAAC
TTGGTTAAAATTTCTAGCCAAAAGTAAGATTTTTAAAAAGATTTATTTCTGGATCCAATC
CCTGTTGCCCATTTCTATGAATAATCACCATTTGTTTTAATGTGAATAATAGCACACAGC

90607 CACGCCACATCCTACCTATCATCATGCACCCATGTCATCGTTCTTTTAAAGGGTGCCAGT
TTTTTGCTTAAGCACAAGGAGCTGTGACCTGTGTTGTCATCCCTGATGCATGTCATGCAT
GTGACTTCATGACATGTGGGTGACTTTTGATCTCTGAAGGACCAGGGACCCAGTCTGTGG
ATCACCACTCTCTCCGTGGGTGGTTTGGGTCTTGTTCTCTAGCCCACCCAGCCAGGTGCA
ATTAGGAATAAAGGAAATAGCAAAGGAATTTTGCTCAAGGCCATGCCAAGCATTTCATCT
[C,T]
ATATGAAAAGGAAAAGAGAGAGAGTGTGTGTGTGTTGGCTAGATTTAGGTAGAAAACAGG
CTGGTGAGAAGCGTAGAACTTGGTTAAAATTTCTAGCCAAAAGTAAGATTTTTAAAAAGA
TTTATTTCTGGATCCAATCCCTGTTGCCCATTTCTATGAATAATCACCATTTGTTTTAAT
GTGAATAATAGCACACAGCAAATTCAGCCCCCTGAGTTTTACCATTTTAAGCAATTGCTT
TAGGCCCGTGAGGCATGTACTATTTATGAAGTTGCATGGGTAGTAATGGAAAACACAACA

92329 GCCCAGCCTGAGATTTTGAACAGAGGAGCATGATGCTGGGCGTTGACTCATTTGGCTGTG
AGTGTGGAAAGCTGTCACTGGAGTACAGCAAGTCAGCACTATCAAGCCAGCCCTTGTCAT
TGCCAGGAGCTGCGGGGAGAGAGGTGTTTTGCATTGCTGCAGGGAACTGACCTCTTTTAG
TCAGGGAAGTAGTTTGGGCAGTAGAAAGCAGAACTTGCACCTGCTGGTAAGATCTGAGTG
GTCACTGACAACCAGCTCTGCAACCCTGTTACCAGGGCAACAAAGATGGGCCCAGGGGTA
[A,G]
TGGTGGGCTCTGCCACATCTCTCTGTGCATAAGAACCTTTGGCCACTTGCTCTGGCCTTG
TCTTTCACCAATCCCAGTGTTCATATCCAGTGTACCAACCACTGAGGGCAGCTGTCCTGG
AATCTGTCTCTCATCTCTGCCCATAATTAACTGCTTCTGGGCACAGTGCATGAGTTACAT
AGATGAGTGTGGGTAAGTTTGCCCTTTCTGTGGGGGGAGCATCCTTTTGGTCCACTCTCA
GGAGGGCATCCTATGTTATTTTTGTGATATTTTCCTAAGAGTTGTATAAGCAAGTGCATC

FIGURE 3HHHH

92912 TGTATAAGCAAGTGCATCAAGCCAACTTGTCTACCCCAGCTCCCTCTTGAGACCAGCAGA
AACTATTTATCAACTGGCAGTTTACGTAACCTCTCTGGGCCTCAATTTCCTCATATAAAA
TGAGGATAATAAATCGTATCTGCTCATAGAGTTGCTGTGGGGAGTAAAGAGTTCAAATGT
ATCTGTCAGTGAAGGAAAAAAGAAAAAAAAACAAAAACAAAGAGTTCAAATATATCTAGC
GTTCAAACAGAACCAGGTATGCAGCCAGTGCCCAATAGGTGTATGAGTTTCCTATGGCCA
[C,A]
TGTAACAAATGACCACAAACTTAGTGGCTTAAAACAACACACATTTATTATTTTACAGTT
CTGGAGGTCAGAAGTCTAAGATGATGCCAGGCTTGGTGGCTCAAGCCTGTAATCCCAGCA
CTTTGGGAGGCTGAGGTGGCAGGATCACTTGAGGTCAGGAGTTCCAGACTAGCCTAGCCA
ACATGGTGAAACCCCATCTCTACTAAAAATACAAAAATTAGTCAGGCACGGTCACGAGCA
CCTGTAATCCCAACTACTCAGGAGGCTGAGGCAGGAGAATTGCTTGAACCCAGGAGGTGG

95043 GGTTTCGGAGGCTACTTGAGATGTGATTGCTCCTAATGAACCTCCACGGGCCTTTTTAAC
CTGTCGATGTGTTTATTTCAGATGGAGCAGGAAATGACCCGGTTACATCGGAGAGTGTCA
GAGGTGGAGGCTGTGCTTAGTCAGAAGGAGGTGGAGCTGAAGGCCTCTGAGACTCAGAGA
TCCCTCCTGGAGCAGGACCTTGCTACCTACATCACAGAATGCAGTGTGAGCCTTCCCTGA
AGCCCCCTTCCCTTGGAGGTGGCACTTCCTGTTGTGTGTGTCTCATCCTGTTTCATGATG
[A,G]
CTCCATGAGGCACATCACAGCCAATGGCAGAGAGTAGAGAGAGGGAGAGCACAAAAGCAA
GATCTGTGTTTTGCAGAGTAGTGAGAGCCAGGCGTAAGGTCCCCAAGAAATGAGATTGGA
CTCATTTCCAGCAGAAAGTGCAGGTAGACGGCTGGTACCATGGAGTCTGGAGATGGGAGT
AATTCATCTTTGCCGCAAGTTGCAAAAGATCTTAACATCTCCCATCCCAGCCTCTGTGGT
CTGCGTTGTGTCTGACATGAGCAGCCTTGAGAACCAGACTCCCAACTATGTACAAGAAAA

95227 TCCTGGAGCAGGACCTTGCTACCTACATCACAGAATGCAGTGTGAGCCTTCCCTGAAGCC
CCCTTCCCTTGGAGGTGGCACTTCCTGTTGTGTGTGTCTCATCCTGTTTCATGATGACTC
CATGAGGCACATCACAGCCAATGGCAGAGAGTAGAGAGAGGGAGAGCACAAAAGCAAGAT
CTGTGTTTTGCAGAGTAGTGAGAGCCAGGCGTAAGGTCCCCAAGAAATGAGATTGGACTC
ATTTCCAGCAGAAAGTGCAGGTAGACGGCTGGTACCATGGAGTCTGGAGATGGGAGTAAT
[T,C]
CATCTTTGCCGCAAGTTGCAAAAGATCTTAACATCTCCCATCCCAGCCTCTGTGGTCTGC
GTTGTGTCTGACATGAGCAGCCTTGAGAACCAGACTCCCAACTATGTACAAGAAAACTTA
CTTTCAATCTTCCTGACATCAAATTTTCCATTGGCCAGAACCAGTGTAGTGACAAGAAAA
TAGCCTTGAAAACCCAGACCCTCTGTCATTATTTACCATGTGACTTTCATTTTTTCTTTC
CTTCACAAGAGTAGACTGTCTTCTTCTCCATTGTCTTGTTAAATTTTTCATTCAGGTGTT

107428 ATGTTACTCTGTGCTTGGCTCTCCAGCTTGCTGTTGCCTTTCACCAGTGTATCCCAGACA
TCCTTTCTTCCTTGTCAGTAACGCAGGTCTACTTTATTCTTTGAGCAGTGGCATAATTTT
CCCTGATGTGTATATATCATAAGTTAGAGAATGCTAAAATTCATTTTGGGGCCTTGTTTA
GGTTCTTGAGGGATTAAATTCCTAAATTTAACAAGTGTATCCTGGAAACAATTTTTGTTC
CTGATTCAGCCCTTAAAAGAGGACTATCATGTTACCTTGAATGGAGATAAACAGGCTCAC
[G,A]
TAAGAGAAAAGGGTAAGAGGGATGAACTCCCACTTATCTTAAACTTCTACTGGCCCGTTT
TTGGGGAATTTGCTGCTTTTATTCCTGACCTAAAATAAATAAGTTTATGTGTCTTGGTTT
CATATTAGTTGAGAACCCAGTGCCTGGAGAGAAGTTTTCCTTGTCCTCTGAGTGAGGACA
TTCACATATGAATCTATTGGCAGACTGGCTTTGACTGACCACACGTGCCTTCAGAACCAA
TGCCACAGCTCTTAGGTTTATGGCCTGAAACACCCTTTCCTTACATATTGCCTTAGAAAC

114951 GACAGTGAGACATGTGCTGTTTTGATCTCTCAGCTAAGATTATCTGATTTTTCAGGCATG
TCTCAAAACTCACCAGGCCTGCTCACATGCTGCTGCTTCTGAAGCCAGGGTTTGGAAACC
AGCTGCCCATCAGAATGAGGCTGTGACTTAGAATATTGGTTCTTGTTTTATTACCATTCC
TTGTTTGGTCTCTCCAGAGTCACTGGCCTTTTCCGCTTCAATTTTCTTATCGGTGAAATG
AGATATTAATTCCTCTTATTGACTTCAATTCAATTGCTGAGTGTATTGTTGCCTTTGGGA
[A,G]
GTTCTTTGAGTTTTCTGTGCCTTTGAAATAGTTGTTTTTTTTTATTCTGGTGTTTTGAGG
CATGTTTCAAGTGAGTGCATTTACACTTCTACCATTTTAGGAGCCACAATTCAGTTATGT
TGTCCCAGCTTGCTTGGCCCCATCCCCAGAGTTTCTGATTCAGTAGGTCTGGGGTGGGGC
CCAATAATTTGCATTTCTTCTTCTTTTTTCGAGACAGAGTCTGACTGTGTCATCCAAGCT
GGAGTGCAGTGGCACGATCGTAGCTCATTGTAGCCTCAAACTCCTGGGCTCAAGCCGTCC

115042 GCTGCTTCTGAAGCCAGGGTTTGGAAACCAGCTGCCCATCAGAATGAGGCTGTGACTTAG
AATATTGGTTCTTGTTTTATTACCATTCCTTGTTTGGTCTCTCCAGAGTCACTGGCCTTT
TCCGCTTCAATTTTCTTATCGGTGAAATGAGATATTAATTCCTCTTATTGACTTCAATTC
AATTGCTGAGTGTATTGTTGCCTTTGGGAAGTTCTTTGAGTTTTCTGTGCCTTTGAAATA
GTTGTTTTTTTTTATTCTGGTGTTTTGAGGCATGTTTCAAGTGAGTGCATTTACACTTCT

FIGURE 3IIII

[A,G]
CCATTTTAGGAGCCACAATTCAGTTATGTTGTCCCAGCTTGCTTGGCCCCATCCCCAGAG
TTTCTGATTCAGTAGGTCTGGGGTGGGGCCCAATAATTTGCATTTCTTCTTCTTTTTTCG
AGACAGAGTCTGACTGTGTCATCCAAGCTGGAGTGCAGTGGCACGATCGTAGCTCATTGT
AGCCTCAAACTCCTGGGCTCAAGCCGTCCTCCCACCTCACCCTCCTGAGTAGCTGGGACT
ATAGGCATATACTACCATGCCCTGCCACCTTTTTAATTTTTTGTAAGGATGGGGGTCTCA

117217 GCTGGGCTAGCTGCCTCTGAATCACCGCAGTAGCTCCTTTTACTATAGATTCCTGGGTCC
CACCCATGGAATGTGATCCATGAAGTCTGGGGTTATTCCCTGGAATCCTTTAAGCTCCCT
AAGTGGTTGGGATGGGAAAGAGATATGCTTTATGTTACTATACTTCTTATTATTATTATT
TTAAAATTCTTGCCGGGCGCAGTGGCTCACACCTGTAATCCCAGCACATTGGGAGACCGA
GGCGGGTGGATCACTTGAGGTCAGGAGTTCGAGACTGGCCTGGCCAACATGATGAAATCC
[C,T]
GTCTCTACTAAAAATACAAAAATTAGCTGGGCATGGTGGCGCATGACTGTAGTCCCAGCC
ACTCCGGAGGCTGAGGCAGGAGAATCGCTTGAACCCGGGAGGCAGAGGTTGCAGTGAGCC
GAGATCGTGGCACTGCACTCCAGCCTGGGTAACAGAGTGAGACTTCATCTCAAAAAAAAC
CCAAAAAAACAAAACTCTTTTTCATTATACCGGAACGTCAGCTTTATGGAGTCGGGGATT
TTTTCTGTTTTATTCACTGCTGTTTCCCTAACATCTAGAATAGTGGCTGGCACGATAGGC

120452 TACTCAATCCTCACACAGTGCTGCAAGAGGATTAGTCTTATCCCTGTTTTAGAGAGGATG
AAACTGAAAGGCAGCGAGGTGAAGTCACCAGCAGGAGGCTGAAGCCGCCCAGGCTAACTG
GCCTTATAGCTACCTAGGGACTCAGGAATATCACACCTGTTTATCATCAAAAGGAGAAAG
GATTTCAGTTCCTTGGGGTAGAAGAGTTTCTTTTTGCTAATCAAACATTTTACTTGAGGC
TTCATATTCTTCTTCAAGATTTTTTTCCTGTGTATGTACCAACACATGTAATAATTCCTT
[A,G]
TTTATTTCAAAAAAGGGGTTGTACTTTATTCTTTACAAGATTTCACTTTATATTGTCATG
GACAATTTTCCATGGCAGTATGAATAAATGGAATCTGTTTGTTTTTAATATCTTTGTCTT
ATCCCATTGTTTACATATGTCATATTTTAGCCAGTCTCTAACTGATGGATAGCTGAATGA
TTTCCATGTTTTTTTCCCCTGTTACAAACAATACTGCAAGGAATCTATTTATCTTTCTAT
TTATCTGCAAACTATTGTAAGTACCTGTAAATTGTTAGAAGTGGAATTACTAGGTCAAAG

124035 AAAAAACTGATGCTAGTGAAAATGCATAATTTAAGAGGTTAGAGAAGCTGCTCTTCAAAA
TGCCCCCCAAGTCTGAGAGTTAAATCCTTTACATAAAGGACAATATGTAAAATTTTCTTT
TTCTTTTTTCTTTTTTTTTGAGACGGAGTCTCGCTCTGTCCCCCAGGCTGGAGTGCAGTG
GCGCGATCTCGGCTCACTGCAAGCTCCGCCCCCCTGGGTTCACGCCATTCTCCTGCCTCA
GCCTCCCGAGTAGCTGGGACTGCAAGCGCCCGCCACCATGCCCAGCTAATTTTTTGTATT
[G,A,T]
TTAGTAGAGACGGGGTTTCACCGTGTTAGCCAGGATGGTCTCGATCTCCTGACCTCGTGA
TCCACTCGCTTCGGCCTCCCAAAGTGCTGGGATTACAGGCATAAGCCACTGCGCCCGGCT
CTTTTTTTTCTTAAACTGCTTCCAGAAAAGTGGATATTATTAGGTTGATGTTAAGAAAAG
GCTTGGAGTTGCATTAACTTTTTGCTTTCTAGCATCTGGCCTGTCTGTTCTGCAGACCTG
AGACCTACTTGAGATAATTTTCTTGGTGTTCAGGCCCTTGGAAAAATAAGTTCCCTATGT

124589 ATAATTTTCTTGGTGTTCAGGCCCTTGGAAAAATAAGTTCCCTATGTTGTCCAGTGTCAA
AGTTTCTCAACCTCAGCACTATTCTTTTTTTCAGGTTATTTTCTTGTAATCTGTTCACTT
GATCATTACATTAAGAATTAGATTATATTGCTATAACTACAAAGCATTTTATGTTTTAAA
AATTATGTACAATTTAGAAACAGGCATGAAAACTTAGGTATTAAATTTAGTGGAATAAAG
CACAGAAAAAAAGTTAAAATAATGCAGTTTTATCACTTAGGATTAAACATTTATATGGGC
[C,T]
GGGTGTAGTGCCTCACACCTGTAATCCCAGCACGTTTGGAGGTCGAGGCGGGAGGATTGC
TGGAGTTTGAGACCAGCCTGGGCAACAAAATGAGACCTAGTCTCTACAAAAAATCAAAAA
ATTAGCCAGACATGGTAGTACATGCTTGTAGCTCCAGCCACATGGGAGGCCAAGACAGTA
GGATCGCTGGAGCGAAGGAGGTTGAGGCTGCAATGACCGTGTTTGCACCATTGCATTCCA
GCCTGGGCGACAGAACAAGACCCTGTCTTAAAACAAATTTATATGCTGCATTCGTGAAAT

125136 GCGACAGAACAAGACCCTGTCTTAAAACAAATTTATATGCTGCATTCGTGAAATTAAAAA
AAAATCATGGATTTAGAAATAAATTGAAGCAAGGTACATTGACAGTGTAACCTCAGCACT
ACTGACATTTTGATCTGAATAATTCTTTGTTGTGGGGGATGCGCTGTATAAGATGTTTAG
CTGCATCCCTGACTCCTACCTCCTAGATGCCATTAGCACCCTCCCCTCCAGATGTGATAA
CCAAAAATGTCTCTAGACATTGCCAGATGTGCCTGGGGTAGGAGGGTTGGGGGAAGTGGG
[G,-]
TTTGAGAACCCTTAGTTGATCATGCCTGCAGTAGGTTGAGAAGCATCAGAAAGCTAATTA
ATTAGACAGGAATATGTGTTTGCAGTAAGAAAACCTCAGCAAACTAATCAAGTTCCAAAG
TTACTGCTTGGTAAATAAATAGGAATTAAGAATAAGACCCTATCTCTGTGTCTGGGGTCA
TTCTCTTCGGAGCTCTTGGTGGAGAGACAGGGTTCCCAGTTTCAATTTTTTAGTGCTTCA

FIGURE 3JJJJ

GACTGCCCTTTTCAGTTATAATTGTAACAACCTTCACTCCAGGTGGGGAGCCTCCCAGGT

125856 AGGCAGATAAGGAATTTTTTTGCATTAAGTGCAAAGTCCTTTTTCTTATAGAAGAGCAATA
ATCTGCACACTAGATCAAGTCAAGTGTGGATATAAAATTATAATTTTTGGGGGGATATTT
TTAATAGTGGTTTTGGGTTAAACATATTTCCTTTAAATGAAATGTCTGTAGGCCTAAAGT
AGGTTCTAAATGTTGCCTGTACTCATAGTATACCATATAAAATATAATCCACATTTACTG
GAACTACCATATATTACTTACCCCAAATCAATCAATCCCTTCCCTATCACCCCCACGTAA
[G,T]
ATCTTCGTATTTTGGATACCTGTGAATCTTAGATCTGTTCAGTTTTCCATTATCCATTGT
CTTATTTCAAGCTTCTCATTCAGAATGTTGCTTTGGAGTATTTTCTGTTAGTAAACACAG
GGCCTAGTGACTCTAGGACCTGCTGTGTGACTTAGGTCACCCACTTCACTTTATTAGAAT
CTCAAAGAATGGTGAACAGCTGAGTTCCAATCTGTCTCATTTGGCTCTCATGAAAACAGT
CATAAGGAGATTGTAGATAAACCACATTATATAGCATAGTAAGTGATAATCAACCCCATT

126256 ATTTTCTGTTAGTAAACACAGGGCCTAGTGACTCTAGGACCTGCTGTGTGACTTAGGTCA
CCCACTTCACTTTATTAGAATCTCAAAGAATGGTGAACAGCTGAGTTCCAATCTGTCTCA
TTTGGCTCTCATGAAAACAGTCATAAGGAGATTGTAGATAAACCACATTATATAGCATAG
TAAGTGATAATCAACCCCATTTGGCAGTTGCAACCCCACAAGAGATAGCCCTTTTTAGAT
TTGTGTAGGAGTGAAAAGCTTTATTTTCCACAAGAGGAACGACATAGTAAGAACTCCTTT
[C,T]
CCCCCTGCTTCTGCAGGTATATGCTTATGCCCTAGGCAACTTGATGGGTAAAGTTAGGTT
TAAATAGTTTTATTTGTAAGCTCTTCTCTTCTCTTCTCTTCTCTTCTCTTCTCTTCTCTT
CTCTTCTTTTCTTTCAAGACAGAGTCTTGCTCTGTCACCCAGGCTGGAGTGCAGTGGGCG
ACCTTGGCTCACTGCAACCTCCGCCTCCTGGGTTCAAGAGATTCTCCTGCCTCAGCTCCC
CGAGTAGCTGGGATTACAGGTGCCCGCCACCATGCCTGGCTAATTTTTGTATTTTTAGTA

127332 CGCGCCACTGCACTCTAGCCTGGGCGACAGAGCAGTCTTTAAAAAAAAAAAAAAATTAAC
TAAGTTAAGTAGTACTTGGGCCCTATCAGATAGTGTCCTCCTGCAGGCAGGCTGGGCCCC
TACTACAGTTTCACTTTTAATATCTCACCGAGATTAGCTGACTGAATTGCCACCAGAGGA
GAGTGAAAGCATATTGCAAAATCATAATCAGGACATGTGAGATTATGTGTTGAACAGGTT
TAATGTGCTTGGGGGTCAGTGACTAATGGGAACTTAGCAGTCATTAACTGTCATTAAAAA
[C,T]
GTTTGTTAATTACTATTACACACTTAGAGATTTGTTAATTAACAAAGAGTAATGCCTTTG
CTAATCACTATTATGCACTTAAGAGGAAGCCAGTGGGTATTTTTCCCTTCATAGCTTTCT
AGTACAAATTAATAAAATTTAGAAAATTAGAAAATGATTGTGCATAAATGTGTATAATCA
TGTATCTGTTAGGGGGCAAAAATTAGTTGGGGAATTATCTTTCTTTGATAAGTCTTATCA
TTAGTTTGAAAATGGGGCATTGGCAATTCATACTGTTTGGCTGGGTTGTCCTGAGAAACA

128302 GACCATCCTGGCCAAACATAGTGAAACCCCGTCTCTACTAAAAATACAAAAATTATCTGG
GTGTGGTGGCATGCACCTGTAGTCGCAGTTACTCGAGAGGCTGAGGCAAGAGAATTGCTT
GAACCTGGGAGGAGGAGGTTGCAGTGAGCTGAGATCGCAGCACTGCACTCCAGCCTGGTG
ACAGAGCGAGACTCCATCTCGGAAAAAAAAAAAAAATCTATTGGTTATTGTTGGTGCATTT
TAACCAAAACCCTTTAGTTTAACCCTAACCTGTGCTGAGCTCTTTAACATTTACATACAT
[G,A]
TTAAAAAACAGAATCAGCCCAGATTTCCCAACATATTAAGTCTTCTCCTTGACTTAAGCT
ACTTTCAGTTCTTCAAGCTTAAGTCACCCTGTGGTTTTGTCTTAGGCCAAATATTTTCCC
CTTTGTCTCCCCTTCTGTCTATCAAGCCAAGCCTGCCTGTGGGTTTTGGATAGTGTGACC
ATCTGGCTTTCTTGAAGGGGCACTTACAGGGGAAGTTTTATTGCCCAAACCGGTGGACAA
TCCATGTCAGGAATGATTATATCACACTGCTTTCTGGGTTTAGGGCTTGGAAAAACCTGT

129122 ACTTCCTTGGTGAAAAGCCCAGCCTTCAAGGTATGTGGACTTACCCACAAAATCTCTTGG
CTCACTCAGTTTCACTTACCATCGTTTAATGAGGAAAAAGTTCTTTTGTACCATGTAACT
GCTGACCTGAGAGAAGCCCATTATGATATAGAGTTATAGGACAGCTGGCCAACACACTAT
ATAGCTAAAATCAGGGCCTCTCTGTTTTGATGGGGAGAAAAGTTAGAGAAGGAATCTTTA
GACTTCAAATTTCATGGCTCAGTAAAACGTCAAAATAATTTTGAAGACCAAAGGGGTTGC
[C,T]
AGCTTACTAGGCTGCCTAGACAGGGGTGGGTATGAGGGGAAGAAAGCCTGCTTCTTTCAT
CAACAGCATATCCAGAAACAAAGGACATTTAAACACTAAAAAAGTCAGAAGGACAAATTC
TCAGAAAAAAAGGACAGTCCTTTAAATGGGTTACATTTAGCTTTATAAAATGCCCTCCTG
TATTGTCCTAATCTTTCTTTGCCAAGGTCAAGTGCTTGGGTGCCATTGGATTATAAGCCC
CTGGGTTTCTGAACGGTGGGGGAGGGAACCACAGGAACAAGGGTTAGGGGTGAGGAAAAA

129376 TGGCTCAGTAAAACGTCAAAATAATTTTGAAGACCAAAGGGGTTGCCAGCTTACTAGGCT
GCCTAGACAGGGGTGGGTATGAGGGGAAGAAAGCCTGCTTCTTTCATCAACAGCATATCC
AGAAACAAAGGACATTTAAACACTAAAAAAGTCAGAAGGACAAATTCTCAGAAAAAAAGG

FIGURE 3KKKK

ACAGTCCTTTAAATGGGTTACATTTAGCTTTATAAAATGCCCTCCTGTATTGTCCTAATC
TTTCTTTGCCAAGGTCAAGTGCTTGGGTGCCATTGGATTATAAGCCCCTGGGTTTCTGAA
[T,C]
GGTGGGGGAGGGAACCACAGGAACAAGGGTTAGGGGTGAGGAAAAAGAACTCATTAACCT
TGGGCCCTGGGTGGAAGTTAATTATCATGTCTTGCCCTGTGGGTGGGTTGAAGTAGGAAC
GTTAATTCCAAAGGCAGTTTTCCAAATTTTTGAACTTGAGATTTGTAATATTATCTTGCC
AGTTAGCCACCAGTTCTCTTCTCTTTTTTCTTTTCTTTTCTTACAGTCTCGCTGTCACCC
AGGCTGCAGTGTAATGGCGCAATCTTGGCTCACTGCAACCTCCGCCTCCCAGGTTCAAGC

134893 TAATCTTCTTGAATAAGCAGTTAATTTTTTTTATTCATGAACCTGCTGATCATGTCTAAG
AATGTATCTCCACTTAAGTAAGTCAGTGAATGGTGATTACCTGAGTAGAGTTAAAGTAGT
CCCCCACCCTCCTATCTGTGGCACATATGTTCCAAGTCTCCCAGTGGATGTGTGAAACTG
ATGATAGTACTGAAACCCATCTACCTTTTTTCCTGTGCATACATACCTATGTTATATAAA
GCTTAACTTATAAATTAGGCATAATATATTTGACTCCCAGCTCCCAGTGTAGTGGCTCTG
[A,C]
AGACTCACAAAATGTATTTGCTTTAAAAAATTCTTTTTTTTTTTTTTGAGACGGAGTTTT
GCTCTTGTTGCCCAGGCTGGAGTGCAGTGGTGCGACCTCAGCTCACTGCAACCTCCGCCT
CTTGGGTTCAAGCGATTCTCCTGCCTCAGCCTCCCAAGTAGCTGGGATTATAGGCATGCA
CCACCACACCCAGCTAATTTTCTATTTTTCGTAGAAACGGTTTTTCCATGTTGGTCAGGC
TGATCTTGAACTCCTGACCTCAGGTGATCTGCCTGCCTCGGCCTTCCAAAGTGCTGGGAT

136001 TATTTATTTATTTATTTTTTGAGACACAGTCTTCCCGTCGCCCAGGCTGGAGTGTGGTGG
CACGATCTCGGCTCACTGCAACCTCCGCCTCCTGGGTTCAAGTGATTCTTCTGCCTCAGC
CTCCGAGTAGCTGGGACCACAGGTGTGCGCCACCATGCCCGGCTACTTTTTGTATTTTCA
GTAGAGACAGGGTTTCACCATGTTGGTCAGGCTGATCTCAAGCTCCTGACCTCAGGTGAT
CTGCCTACCTTAGCCTCCCAAAGTGCTGGGATTACAGACATGAGCCACCGCACCCAGCCC
[C,G]
CAGTGTTAACTCTTACATAACAGTGTCACTGTCTAAGTGTTTGAAAAACTATTTGTCAAA
ACTAATATTGGTACATTATTGTTAACTACACTTCAGACTTTTTTTGGATTTTACCAATTC
TCCCACTCATGTCCCTTTTCTGTTTCAGGAATCAATCCGTGGTACCATATTGCAGTTAGG
GTGTTTATATTTGATGGGACTGGTCCTAGTTTAGATACTTAGTGTAGCTCAGCCAGCAGG
TGGGATCTTCATGCCCACCGAGGATTGGTATTGTGTTTTCCTGGTGGTTTTATGGCATTT

136249 CTTAGCCTCCCAAAGTGCTGGGATTACAGACATGAGCCACCGCACCCAGCCCCCAGTGTT
AACTCTTACATAACAGTGTCACTGTCTAAGTGTTTGAAAAACTATTTGTCAAAACTAATA
TTGGTACATTATTGTTAACTACACTTCAGACTTTTTTTGGATTTTACCAATTCTCCCACT
CATGTCCCTTTTCTGTTTCAGGAATCAATCCGTGGTACCATATTGCAGTTAGGGTGTTTA
TATTTGATGGGACTGGTCCTAGTTTAGATACTTAGTGTAGCTCAGCCAGCAGGTGGGATC
[T,G]
TCATGCCCACCGAGGATTGGTATTGTGTTTTCCTGGTGGTTTTATGGCATTTCCGACTAT
GCAGAGAGGCATGGTATTAACTTCAGTGTCTCCTAGCAAATTTTCCTGTTTTTCACCAAC
CTCTGATCCCTGCATTATTTGCAATCAACTCAGAGATTTGTGATTGAAAACATTGCTTGA
CTCCATGCTCTTTAAGCTATTTTCTAACTAGGTAACTGTAACATAAATTATGCTTTTATC
TAGCACTGTTTTTCATAAACACATGTTGAGTGATTTTCATCAACCGAAATACTTCGAATC

136448 AGGAATCAATCCGTGGTACCATATTGCAGTTAGGGTGTTTATATTTGATGGGACTGGTCC
TAGTTTAGATACTTAGTGTAGCTCAGCCAGCAGGTGGGATCTTCATGCCCACCGAGGATT
GGTATTGTGTTTTCCTGGTGGTTTTATGGCATTTCCGACTATGCAGAGAGGCATGGTATT
AACTTCAGTGTCTCCTAGCAAATTTTCCTGTTTTTCACCAACCTCTGATCCCTGCATTAT
TTGCAATCAACTCAGAGATTTGTGATTGAAAACATTGCTTGACTCCATGCTCTTTAAGCT
[G,A]
TTTTCTAACTAGGTAACTGTAACATAAATTATGCTTTTATCTAGCACTGTTTTTCATAAA
CACATGTTGAGTGATTTTCATCAACCGAAATACTTCGAATCATTAAGTTTCCCAAGTTCA
TGGATGCTGCTTAAATGCCTGGTGGTTCCAGGCTGTCGAATATTTCTGCCTTCTGCAATA
AGAGATTGTCCCTTGTTAAAAGCAACATTAGCCTTTGTGCGGTTTCACCCCCAATTCTTC
TTTTTCTTGTTGTAACCAATGAAAGGAAGTACTGCTTAACACAGCAGGTAATAATCTTCT

136906 GAATATTTCTGCCTTCTGCAATAAGAGATTGTCCCTTGTTAAAAGCAACATTAGCCTTTG
TGCGGTTTCACCCCCAATTCTTCTTTTTCTTGTTGTAACCAATGAAAGGAAGTACTGCTT
AACACAGCAGGTAATAATCTTCTAAAACTCATTATCTCAAGAGGTGGTCCTGGCAGGATA
TATAAATGCAATTTAAGAAAGGTCTTGGCAAATTTATGAATGACAGAACTGGGAGTGGCT
ACCGAGAGAAACTAGGATGCGCCTTTGCTTTGACACTGAGGTCAGGCGTAGCTTCTGTAC
[C,A]
CTCCTGGGTCCTGCCTCTTGGGGTTGCTGCAGGCAGCACCCCATGAACCAGGCATCTGAC
CCAGTTCCAGGATACTTATTCTTCCAGCAAGTCGAACACTCTGTGATGAGTGACTGCCAT

FIGURE 3LLLL

GCTCATGGGTCACCAGGCTCTCATTATTCTGTTTCATTTCCAGCCTCCCACAAGATTGGT
TTTTCAGCTGCTTATTTATTATTATCATTATTTCAAGGCTGCTTTCCAAGTTTCAGTGGG
GGGTTTCCTAAGCGTACCAGCTGCCCTGGTTGTGCAGTTCCGGTGATGTTTCAGATGCTG

137190 GGCGTAGCTTCTGTACCCTCCTGGGTCCTGCCTCTTGGGGTTGCTGCAGGCAGCACCCCA
TGAACCAGGCATCTGACCCAGTTCCAGGATACTTATTCTTCCAGCAAGTCGAACACTCTG
TGATGAGTGACTGCCATGCTCATGGGTCACCAGGCTCTCATTATTCTGTTTCATTTCCAG
CCTCCCACAAGATTGGTTTTTCAGCTGCTTATTTATTATTATCATTATTTCAAGGCTGCT
TTCCAAGTTTCAGTGGGGGGTTTCCTAAGCGTACCAGCTGCCCTGGTTGTGCAGTTCCGG
[T,C]
GATGTTTCAGATGCTGGGCCGGATTCTGGCTGTACCCAGCCTGATCTTTCTGGGCTTCAG
GAAAGCTGAAGCCAATCAGAGCTCCTCTTTCATGCCTTTGGGATTATGCTTACCTTGCCT
GGCATCGTGTACCTGCTCCCATCCATGGGAAAGTTTTGCTGTCTGGTACTGTCTTCTATC
AACATCTTTTAAGATATCTTCCCCCGAGGCATCGTGATGTCAACGGAACCAGCACACTTG
TACGTTTTATGCAAGACTGCCATATCTCAACAGTGAGAAATGCATAATGGAAGTGGTGAT

137471 CCTGGTTGTGCAGTTCCGGTGATGTTTCAGATGCTGGGCCGGATTCTGGCTGTACCCAGC
CTGATCTTTCTGGGCTTCAGGAAAGCTGAAGCCAATCAGAGCTCCTCTTTCATGCCTTTG
GGATTATGCTTACCTTGCCTGGCATCGTGTACCTGCTCCCATCCATGGGAAAGTTTTGCT
GTCTGGTACTGTCTTCTATCAACATCTTTTAAGATATCTTCCCCCGAGGCATCGTGATGT
CAACGGAACCAGCACACTTGTACGTTTTATGCAAGACTGCCATATCTCAACAGTGAGAAA
[T,G]
GCATAATGGAAGTGGTGATCACGGATTATTTCCTAGGACATTATGGCTAATGCGCTAGAG
AACTCGGATGGTCTGTTGCGTCTGACATGGGCTTTTTCTCTTGAGTTGTCTTTCTTTTGC
TATTCTCTGAAAGAAACAATTCTTGCCACATGATCCTGATTTTTCAGGTCCTCAGCATTT
GTTAGCAGAAAGTACACTTTGTTTCCATCCGGCAGTGACTCAGTGGTGGTCCCATGCTGA
TGAAACGCTGAGATAGTCTTCTTCCAAATAGGTATCGTTTTGATTGTTGCTGCTTATTTG

137913 CTTGCCACATGATCCTGATTTTTCAGGTCCTCAGCATTTGTTAGCAGAAAGTACACTTTG
TTTCCATCCGGCAGTGACTCAGTGGTGGTCCCATGCTGATGAAACGCTGAGATAGTCTTC
TTCCAAATAGGTATCGTTTTGATTGTTGCTGCTTATTTGCTAGCTGGCCCTCAATAGTGA
CAATGAAACCTCAAGTGTATAATATGGTTGCTCAGTAATCCTGAGGGAAGACAGTCTTTG
GTTTGGGGGATAGGGATTCTGTGCCTACTTAGCTTCAGGTGAAAGTCTTACAAATTTTTG
[T,C]
GTGTAGAAATAAGCACCATGTACCTCCTTGGGTTTTTTTCTTTTTTTTTTCTAGTCCTTTAG
TATGGTCAACAATATTGTTTAGGGAGTACCTATTCTGTGCTAACCACTAGGCATTCAAGT
ATATTACACTATGCTCCTTCAAAACACTTCTGTCAAATGTAAGGATTATTATACCCATTT
TACAGATGTGGTTACTGTGGTAACTTGGCCAAGGTCATAGGGCAAGTGAATAAGGGATTC
TGGATTTGGGTGGAGGTCTGTGTGATTCCAAAGCCCATGCTCTTTCTACAATACTATATA

138466 GAGGTCTGTGTGATTCCAAAGCCCATGCTCTTTCTACAATACTATATATGCCTTTGCATA
AGTTATTGTTATTAGTAATAATATTTGTGATGATGGCAAATAATAAACCATGTCACACTA
GAGAGTGATTTAATCTCTAGGTCTATTTAAGAACATTTGGAATTGCAGGAATTGGATTTT
TTTTTTTTTTTAAGTGATGGAGTCTTGCCATCTTTGCCCAGGCTGGTCTCAAACTTGTGG
GCTCAAGTGATCATCCTCCCTCTGCCTCCCAAAGTGATGGGATTACAGATATGAGCCACC
[A,G]
TGCCCAGCCTAGAATTGCAGGAATTTTTGAATTGATGATTCATTCTGATATTTGAATTTC
TACAGTATGTTAAGTGCAATGTCAGGTGCTGGTGCTGTGGCTCCATTGATGAACACATTT
GGGTATGGCCCTACCTTCATTGAATTTAGAGTCTAAGAGCCTAACCGGTCTTTTGCTTGA
ATAGAGCTGTAGTCCTGTTAAATTGCTGTACCTCCAAATGGTGGGAAGTTTAATGCTTCG
TAGGCCTCCCCTCACTAGTTTACTGAACCACATGTGCTTGATTTTTTTTTGA

146805 GGCTTTTCTAAAGTAGCACTTTTCCCCACTCCAGCCCATGAAGATACCTTTTAACCAGCT
CTTGAGATTAAATCCCCTCCGTGACACTTTCCTGCAGGAACTTGCAA
[G,A]
AAAGTACTGCATTCCCCACTGGCAAAACTTGCCATCAGCCAGTTTATGTATTCTCTGCTT
TTCACACCCATATCTTGACCTCTGAACAACACACATATTCTCCTCTT

151008 GGATTATTTTATTTAAACCTCCTAATAGTCCATTGAAATAGATATTGCCATGTTGAAAAC
TGAGGTTCAGAGAGGTTAAGTGACTTACCCAGTGTCACAGAACTAGTAAGTGGTGCAGCT
GGGATTTGAACTGAGATTCCAGAACAATTGCCATTAACCACTTTGCTTCCATATTAGTAT
CATCTGCAAATCTCTCTCCATAAATTTCCTCAGTCTTTATCTGAGTTTCCTTATTTCAGG
AAGGAAAACTTCTGTTTTTGATCCTTATGAAATACAATTTCCATTAAAACTTTTTTTTTT
[T,-]
GCTATTAAAAAAGGTACCGGATAATTGAAACCAGACTGGATTTGAGCCTGTGTTGATGGA

FIGURE 3MMMM

AGTACACATGGGATGTGGGCTGAAGTGTTCAATCTAATTTTTCTTTCCATCAGCTAATTT
TTAAAGTATTAAGCAAGTAGATTCTGACACTAACAGGGAAGATTTAAATTCTCTTGAGAG
ACTGGAGGTGTTAAATAATTTTCTGGTAGTGCACATTTTACATCTTAAATCTTCCTCACT
CTCCCACCTCATCTCAATGTACCTGAAGCTCTGGGAATGTTCTTTTGTACTTCTCAGGAA

151627 CATCTCCTCTCCCCTCCACATCCCTTTCCTGCTCCAATTACTTCCCAGCGCCACTTGGAT
GTTGTTGTCATCGGGGAACTTTGGAAACAGCCAGATTTTTTTGGAGTCTGTAAGCAGAAA
ACAGACTGCTTGCTGCTCATATCTGGCACCCAGCTTTGTCCAGAAAACGAGGAGTTAAAA
AGAAGTCTGGGCTGTGAAGGGCTGTGACAACTGTCCTAGGGGGAGCTCTAGCGAGCCCTG
GCGGGCAGTGACTCATGCTGCTCTGTCACTGGGATCAGCACTGGCCCCTGGCAGGCAGGC
[G,A]
GCAGCCAGGTGGGGTTCCAGCCAGAGCACGCACGCACGGAGCCGGGAGCATGCAGCCTGC
ACTGCGGGGGATGTGATGCTCGGCTCTAACTCGCCTGGCTGGCCCGCCACGGACGCCTCA
GCTTGCAACCATGGTAACGTTTCTGGCGGGGGACACCCCCGGGAGCCCACCGCGATGGGC
AGCCTCCTGGTGACTGATGGACGAGTGTCCACCTCCCAGACCGAGAGCGCTTAGTAGGTC
GGAGGAAGTGGAGAGGATGTAACACGCCCCCAGCCGGGAGTGAAGCCCTGAGGAGGTAGG

151875 TGACTCATGCTGCTCTGTCACTGGGATCAGCACTGGCCCCTGGCAGGCAGGCGGCAGCCA
GGTGGGGTTCCAGCCAGAGCACGCACGCACGGAGCCGGGAGCATGCAGCCTGCACTGCGG
GGGATGTGATGCTCGGCTCTAACTCGCCTGGCTGGCCCGCCACGGACGCCTCAGCTTGCA
ACCATGGTAACGTTTCTGGCGGGGGACACCCCCGGGAGCCCACCGCGATGGGCAGCCTCC
TGGTGACTGATGGACGAGTGTCCACCTCCCAGACCGAGAGCGCTTAGTAGGTCGGAGGAA
[G,C]
TGGAGAGGATGTAACACGCCCCCAGCCGGGAGTGAAGCCCTGAGGAGGTAGGAGCCGCAT
ATGTCCATCCGTGCATTCCCACCGTCAGCGCGCAGGGGTGCTGTAGATCACCGGTAGGAA
CTTTATTTGGCTGGTGCTTCATTATGCTGATTAAACTGCAGTGGATTTGATGGGCATGAT
TGCGCTGGGGAAGATGCATAATGAACTAAAAAAAAAAAAAAAGTGGTTAATAAGATCTCGG
AGTCGACTTGTCCGGGTATGAATGAAGTAGACTGCAGTGGTATCCTAACAGGAGTTCCAG

153541 ATCTAACCATCTATGTATCTGTCTCTCAAGTGGGTGGATGGGGGTTGCTATCTTGGCTGT
ATAAAGAATCCTAAAAACCTTGTCTCATAAGCTAGAGGTTTCCTGATGGGTTTAACTGAG
CTGCAAGTGGCTGAACCAGAGCTCTAACAGAGAGATGGTGCTCGGCTCCTCTCCAAGTAT
GCTGCAAGATCAGGGATCTGGCAGCTGAGCCTCTCTGAGCTGGTGGAGCGCTGGCAGCCA
GAGAAAGCCCCGTTACTGTGAGCCACCAGGAGGGAGTGTGATGTAGCCGAGTCATTGATT
[T,C]
ACAGAAACTGGGCTTCATAGGGGGAAAAAAAACCAGGAGACTAGAAAATGGAAATATAAA
TATCACTGTAAACCTCTTGATCTGGTAGGTCTTTCTCCATTCTCATAAAAGCTATTGAAA
AATGCATTAACAGAGCACTTGGAATTAGAGGGTCGAGGCTTCCAGGAGCCTCCTGGAATT
TCTGTAAAATGCAGTAGCTTCTGTGGATGTGGGAGGTCAGTATCTTGCCTCATTCTCTCA
TGATACAATGACATTCTGTTTTCAGAGGAGTGAGTTCCCCAGAAGATCTTGGACTGATGG

155392 TCTTGTTATGTGTTATTGCTATTGGACTTGGCTACTCTGCTGTAGGCAGCCCTGTGGGTG
ATACCTACAAGCATCATTTTAGAAATTCATCCACCTGTTGGATGTAGATGACCCTGGACA
TATCAGATTGTGATTAATTAGAAATCTAATAAAAGAGAGGCAGTGATGAAATTACTTAGC
AGCTCCTGCAGTTTTATTGACAAAATTTACTTGGAGAGAGGGGGAGACATTTTCTGGGGG
TACCACCTTTGCTGCCAGCGACCCTGTGTTTCTTCCTGAGTTTCTTTTTCTTTTCTCACC
[A,G]
TTTTCAGCATCACAGGTTTTTATTTACACACATTGATTACCTGTGCTGTTACTCATTCTT
CACACCACTGAGGAAATTGCAGATGCTGCTGTACTGTGCTAGGTAAATTGACCTCAGATT
TGTTACCAGTGAATTGAATGAAATGTTCAGAGGTGGAGCTGAATGAACGAGGAGTTTTTG
TGGAGAAATTGGCAGTGAGAATGATTTAAATTCTGTGATAGCTCCTCGTTTTTTGGGATC
CTTATTTTGGGACCCCAGACTATTTTTAAGCCATTGAGTGCATCATTATTTTAGGCTGAG

155896 ATTTAAATTCTGTGATAGCTCCTCGTTTTTTGGGATCCTTATTTTGGGACCCCAGACTAT
TTTTAAGCCATTGAGTGCATCATTATTTTAGGCTGAGCAAGAATCTTGATGACAGCGTTT
CAATGGCTGAGGCGTAGTGGGAGTTCCTTGCAGCTTGAGTTGGTGGGAGCTGGAGAGTTT
CTAGAGAACTAGGTTTGGTTGTCTTTGGGGTGGGGTTATGGTGAAATTAGTCTTGGAGAG
TGAGTAGCTGTCTGATGCTTCTTTTCCTTTTTAACCAGCAAGAGCCCAAACCAAATCCCC
[C,A]
AGCTCTGAATGCCTGGCTGTTCCTCTCAGCCTTTCTTTGCTTGAACTTGACAATAGTAGG
GTAGTAACAGGAAACAGCATGTTAAAGTTTTAAAAATAAAATAGATCTCAGCTCTTTTCC
TTCCCATTAGCAAGGGGTACATTTATTTAGGTTTTTCCTTCTAGATTGAGGCACTGCCTC
ATTTAAGTTCTTGGTGAAGCCATGCATTTCTGCAAACCATAAGTATAAACTCTAGAACGG
GGGTGTCCAATCTTTTGGCTTCCTTGGGCCACATGGGAAGAAGAAGAATTGTCTTGAGGC

FIGURE 3NNNN

157137 TTACTAATACACTAGTCCATGTATGTATAGTGTCCTCCTATACACACCAAGAGAATATGG
AAAGGACTCAGCAATGATTAGGTAGTCCAAAGTCATACCAGATTGGAAACCAAGCTTCCC
AGGCCCTGGGACTTTTCTGCTAGAGACACTTCACGGTTCTGACCAACTACAAAGAGTTAA
TATGCAGTTGCCAAATACCTGTTGGTAAAAGGTGGATGTTGGGGAGGAGTGGATTGGGGA
ACAGAATTAGAAGGTCCAGTCCCAGAATGGGTACCTTCCCATCAAGTTGAACAAGTCAAA
[G,A]
CAGGTTATGTTGAAACAACTGAGAGAAAGTAAAGCAAACACCATTGCTGCAGAATATCAT
GGTACAAATTGGACATCTTTGGGAGTTAGCGGAGTAAGGCAAAATCCAGTGAGGGACGCT
TAATGGGTAATGCCAATTCACAATTCTTGTTAAATTACATTGCTGATCTTCCTTGGAATG
TCTGTCCATTCCCCCAAGTAGACTGTGATCTCAAGGCAAGGCTGGGTCTTATTCATCCTG
GTTTTCCTGGAGCAGTAAATACTTGTGCTGGGACTGGGCTTATAAGCATACTAATGGAAA

157409 ACCTTCCCATCAAGTTGAACAAGTCAAAACAGGTTATGTTGAAACAACTGAGAGAAAGTA
AAGCAAACACCATTGCTGCAGAATATCATGGTACAAATTGGACATCTTTGGGAGTTAGCG
GAGTAAGGCAAAATCCAGTGAGGGACGCTTAATGGGTAATGCCAATTCACAATTCTTGTT
AAATTACATTGCTGATCTTCCTTGGAATGTCTGTCCATTCCCCCAAGTAGACTGTGATCT
CAAGGCAAGGCTGGGTCTTATTCATCCTGGTTTTCCTGGAGCAGTAAATACTTGTGCTGG
[G,A]
ACTGGGCTTATAAGCATACTAATGGAAAGTAAAATATTTGGGTTGGTTTTTTAAAAAGAC
AGTGGATTTGGATCAGTGGAGAGGAAGGTAGAGGGAATTTCAGGTGGGCAGGGTGCTAAC
AACAGCCCATCCTTACAGGGCACCAACTGTGTTCTAGGCTGTGTTCCAACCACTTTACAC
AGATGAATTCATTTAAATTGCACAACCAGCCCAAGAGGAAGGTACCATTATTATTCTCAT
TTTGGATGTGAGGAAACTGAGGCGTGGGGAGATCAAACAACTTGCCTAAAGTTATGTAGC

164675 ATTTCAGAGTAAGTTTTTCTAGAAAATAGAAGCTGGAAAAAAAAGGAAAACCCAAACTTG
GCTTCGTGCTCGAAGAGACAGCACTGCTGTGTGTGGGCGGGTGGCTGCGTGCACCCGCTG
CTCAGAAGTGCCTTTTCTCTCCATGGGGATAACTGGCTGTGTATCCGAGATGTGGCCAGG
AGTAGGCAAGCAACGTGTGGGCAGGCTGCATGTTCTTTTATTAGCATCTTCATTGTACTG
CATCTCGTCGAGCCCAGAGCATGAACTGGCCTGGGTTTCTAATATCTACCCTGCTTCCCA
[T,C]
CTAATTACTCCCCTGAACCCTAAAGTGAGGGAGGGAGAGTTGCTCTTGTGGGGTGAGCTT
TCCCTGGGGTGGCTGTGAACCAACCTGGCATGTGGATGTTCTTGGGTATCCAGAGCTGTC
CTGGACTCAGGCTTGGAGTCAGCTTCTTAGCACTGAATGCAGCCAGTCATGGATGGAGGT
CACTGTATCTCACATGTTCCGCTCTCCCTTTCCTCCATGACCTTGCCCCTCTGAGCCTCT
GTAGCACTTTTCTTGAGTGTGTCCAAGGCCATCTAGCTAAGAAGTAGCAGAAATGGGATT

165157 ACTGTATCTCACATGTTCCGCTCTCCCTTTCCTCCATGACCTTGCCCCTCTGAGCCTCTG
TAGCACTTTTCTTGAGTGTGTCCAAGGCCATCTAGCTAAGAAGTAGCAGAAATGGGATTT
GAAGCCATGACTGTTTGGTGATAGAGCCTCAGCTTTGAACTGGGGTTCTACTGCCTGGCA
CCCCTGCACAAATCATGGTAACGTGGTAGGAGAACATAGAGGTATAGGGCAAGCCCCTCC
TTAATGCCATGAATAATACCCATCTTATAGGATTGTGGGGAGGACTCAGTGAAGTAACCC
[G,A]
TGAAGCACTAAACACGTGCCTGACACGTGCTCAATAAATGAGCACTTGTCCTGATGACAA
AGGTCGTGGCATTAATTCTCTCTCCTAGGTTGTTACTTCCTTGAGGACAGGAATTGTGGC
TTCCTTAATGGCCACTGCAGCAGAGTTTCTCAAGTTGGCACTATTGACATTTTGGGCTGG
ATAATTCTTGTTGTGGGAGCTGTCCTGTGGATTGTAGGATGTTGAGCAGCATCTTTGGCC
TCTACCCGCTACATATTAATAGCACCCCTAGTCATGAAAATAAAATGTCTAGACATTGCC

165405 ATGAATAATACCCATCTTATAGGATTGTGGGGAGGACTCAGTGAAGTAACCCGTGAAGCA
CTAAACACGTGCCTGACACGTGCTCAATAAATGAGCACTTGTCCTGATGACAAAGGTCGT
GGCATTAATTCTCTCTCCTAGGTTGTTACTTCCTTGAGGACAGGAATTGTGGCTTCCTTA
ATGGCCACTGCAGCAGAGTTTCTCAAGTTGGCACTATTGACATTTTGGGCTGGATAATTC
TTGTTGTGGGAGCTGTCCTGTGGATTGTAGGATGTTGAGCAGCATCTTTGGCCTCTACCC
[G,A]
CTACATATTAATAGCACCCCTAGTCATGAAAATAAAATGTCTAGACATTGCCAAACTGCC
CCTGTTGAGAACCACTGGTCTGCAGGTATCTCTCATGGGGATCACAGGGCTTTTATATTC
TCTTCTCTGTCTCTCTCTCTCCCTCTCTGGGTGTCTCTCTCTCTCACACACACGCTTAGA
GAAGGTGGTTAAAAAAAATTTTGTTGAAGTTTGAGAATTTTGAGAACAAAGGAAAAATTT
TGGAAGGCATTTTAATGAACAGATAGACTCTGTCCCATTCCATGGTCAACAGAATTTCAT

165500 CACTTGTCCTGATGACAAAGGTCGTGGCATTAATTCTCTCTCCTAGGTTGTTACTTCCTT
GAGGACAGGAATTGTGGCTTCCTTAATGGCCACTGCAGCAGAGTTTCTCAAGTTGGCACT
ATTGACATTTTGGGCTGGATAATTCTTGTTGTGGGAGCTGTCCTGTGGATTGTAGGATGT
TGAGCAGCATCTTTGGCCTCTACCCGCTACATATTAATAGCACCCCTAGTCATGAAAATA
AAATGTCTAGACATTGCCAAACTGCCCCTGTTGAGAACCACTGGTCTGCAGGTATCTCTC

FIGURE 3OOOO

```
         [G,A]
         TGGGGATCACAGGGCTTTTATATTCTCTTCTCTGTCTCTCTCTCTCCCTCTCTGGGTGTC
         TCTCTCTCTCACACACACGCTTAGAGAAGGTGGTTAAAAAAAATTTTGTTGAAGTTTGAG
         AATTTTGAGAACAAAGGAAAAATTTTGGAAGGCATTTTAATGAACAGATAGACTCTGTCC
         CATTCCATGGTCAACAGAATTTCATAATTAGATAGTTTGTTTACTGCAACTCTGCACCCC
         ATTGCCCATCATTTTAGAGTTCCAACCAGTTAGAGGATTTTTCTTGCAAACTTTCCTTAA

165751   CATTGCCAAACTGCCCCTGTTGAGAACCACTGGTCTGCAGGTATCTCTCATGGGGATCAC
         AGGGCTTTTATATTCTCTTCTCTGTCTCTCTCTCTCCCTCTCTGGGTGTCTCTCTCTCTC
         ACACACACGCTTAGAGAAGGTGGTTAAAAAAAATTTTGTTGAAGTTTGAGAATTTTGAGA
         ACAAAGGAAAAATTTTGGAAGGCATTTTAATGAACAGATAGACTCTGTCCCATTCCATGG
         TCAACAGAATTTCATAATTAGATAGTTTGTTTACTGCAACTCTGCACCCCATTGCCCATC
         [A,G]
         TTTTAGAGTTCCAACCAGTTAGAGGATTTTTCTTGCAAACTTTCCTTAAAGCAGTGATAG
         TATCAGCTCTTTAAATAATACTATGCTTGATGAAGTGGTACTTTTCGGGATAATTTGAGA
         CCAGCCGACTTGCTGCTTGAAGAGGACAGGGCTATATTTGGTAATAATATATATGTGATA
         ATATGTATGTAATATTATTATAATGTAATATACAATAATATTTGGTGTAACTGGTGACTC
         TGAGGCCAGTCTTTGATCGAACCTCTCAAGCTATGATTTACATTATGGTCAATGTTAGCA

165877   ACGCTTAGAGAAGGTGGTTAAAAAAAATTTTGTTGAAGTTTGAGAATTTTGAGAACAAAG
         GAAAAATTTTGGAAGGCATTTTAATGAACAGATAGACTCTGTCCCATTCCATGGTCAACA
         GAATTTCATAATTAGATAGTTTGTTTACTGCAACTCTGCACCCCATTGCCCATCATTTTA
         GAGTTCCAACCAGTTAGAGGATTTTTCTTGCAAACTTTCCTTAAAGCAGTGATAGTATCA
         GCTCTTTAAATAATACTATGCTTGATGAAGTGGTACTTTTCGGGATAATTTGAGACCAGC
         [C,A]
         GACTTGCTGCTTGAAGAGGACAGGGCTATATTTGGTAATAATATATATGTGATAATATGT
         ATGTAATATTATTATAATGTAATATACAATAATATTTGGTGTAACTGGTGACTCTGAGGC
         CAGTCTTTGATCGAACCTCTCAAGCTATGATTTACATTATGGTCAATGTTAGCATAATGC
         AATTATCAGCAATCACTTGCTGTTGCTTTGAAAGTCAGAAGGATGGCTAATAAAAATCTT
         AGAAAAAGAAAACAGGCCGGGTGCAGTGGCTCACCCCTGTAATCCCAGCACTTTGGGAGG

166135   TGCTTGATGAAGTGGTACTTTTCGGGATAATTTGAGACCAGCCGACTTGCTGCTTGAAGA
         GGACAGGGCTATATTTGGTAATAATATATATGTGATAATATGTATGTAATATTATTATAA
         TGTAATATACAATAATATTTGGTGTAACTGGTGACTCTGAGGCCAGTCTTTGATCGAACC
         TCTCAAGCTATGATTTACATTATGGTCAATGTTAGCATAATGCAATTATCAGCAATCACT
         TGCTGTTGCTTTGAAAGTCAGAAGGATGGCTAATAAAAATCTTAGAAAAAGAAAACAGGC
         [T,C]
         GGGTGCAGTGGCTCACCCCTGTAATCCCAGCACTTTGGGAGGCTGAGGCGGACAGATCAT
         GAGGTCAGGAGATCGAGACCATCCTGGCCAACATGGTGAAACCCCATCTGTACTAGAATA
         CAAAAAAAAAAAAAAAATTTGCTGGGCGTGGTGGCGTGCGCCTGTAGTCCCAGCTACTCG
         GGAGCTGAGTCAGGGGAATCGCTTGAACCCGGGAGGTGGAGGTTGCAGTGAGCCGAGATT
         GTGCCACTGCACTCCAGCCTGGTGACAGAGTGAGACTCCGTCTCAAACAAAACAAAACAA

166139   TGATGAAGTGGTACTTTTCGGGATAATTTGAGACCAGCCGACTTGCTGCTTGAAGAGGAC
         AGGGCTATATTTGGTAATAATATATATGTGATAATATGTATGTAATATTATTATAATGTA
         ATATACAATAATATTTGGTGTAACTGGTGACTCTGAGGCCAGTCTTTGATCGAACCTCTC
         AAGCTATGATTTACATTATGGTCAATGTTAGCATAATGCAATTATCAGCAATCACTTGCT
         GTTGCTTTGAAAGTCAGAAGGATGGCTAATAAAAATCTTAGAAAAAGAAAACAGGCCGGG
         [C,T]
         GCAGTGGCTCACCCCTGTAATCCCAGCACTTTGGGAGGCTGAGGCGGACAGATCATGAGG
         TCAGGAGATCGAGACCATCCTGGCCAACATGGTGAAACCCCATCTGTACTAGAATACAAA
         AAAAAAAAAAAAATTTGCTGGGCGTGGTGGCGTGCGCCTGTAGTCCCAGCTACTCGGGAG
         CTGAGTCAGGGGAATCGCTTGAACCCGGGAGGTGGAGGTTGCAGTGAGCCGAGATTGTGC
         CACTGCACTCCAGCCTGGTGACAGAGTGAGACTCCGTCTCAAACAAAACAAAACAAAACA

166187   CTTGAAGAGGACAGGGCTATATTTGGTAATAATATATATGTGATAATATGTATGTAATAT
         TATTATAATGTAATATACAATAATATTTGGTGTAACTGGTGACTCTGAGGCCAGTCTTTG
         ATCGAACCTCTCAAGCTATGATTTACATTATGGTCAATGTTAGCATAATGCAATTATCAG
         CAATCACTTGCTGTTGCTTTGAAAGTCAGAAGGATGGCTAATAAAAATCTTAGAAAAAGA
         AAACAGGCCGGGTGCAGTGGCTCACCCCTGTAATCCCAGCACTTTGGGAGGCTGAGGCGG
         [G,A]
         CAGATCATGAGGTCAGGAGATCGAGACCATCCTGGCCAACATGGTGAAACCCCATCTGTA
         CTAGAATACAAAAAAAAAAAAAAAATTTGCTGGGCGTGGTGGCGTGCGCCTGTAGTCCCA
         GCTACTCGGGAGCTGAGTCAGGGGAATCGCTTGAACCCGGGAGGTGGAGGTTGCAGTGAG
         CCGAGATTGTGCCACTGCACTCCAGCCTGGTGACAGAGTGAGACTCCGTCTCAAACAAAA
```

FIGURE 3PPPP

CAAAACAAAACAAAAAACAAAAAAAGAAAATCTTAGAAAAAGAAAATAAATTGTAATATT

166209 TTGGTAATAATATATATGTGATAATATGTATGTAATATTATTATAATGTAATATACAATA
ATATTTGGTGTAACTGGTGACTCTGAGGCCAGTCTTTGATCGAACCTCTCAAGCTATGAT
TTACATTATGGTCAATGTTAGCATAATGCAATTATCAGCAATCACTTGCTGTTGCTTTGA
AAGTCAGAAGGATGGCTAATAAAAATCTTAGAAAAAGAAAACAGGCCGGGTGCAGTGGCT
CACCCCTGTAATCCCAGCACTTTGGGAGGCTGAGGCGGACAGATCATGAGGTCAGGAGAT
[C,T]
GAGACCATCCTGGCCAACATGGTGAAACCCCATCTGTACTAGAATACAAAAAAAAAAAAA
AAATTTGCTGGGCGTGGTGGCGTGCGCCTGTAGTCCCAGCTACTCGGGAGCTGAGTCAGG
GGAATCGCTTGAACCCGGGAGGTGGAGGTTGCAGTGAGCCGAGATTGTGCCACTGCACTC
CAGCCTGGTGACAGAGTGAGACTCCGTCTCAAACAAAACAAAACAAAACAAAAAACAAAA
AAAGAAAATCTTAGAAAAAGAAAATAAATTGTAATATTTCAGAATATTTGTTGGGGAGGA

166402 GGCTAATAAAAATCTTAGAAAAAGAAAACAGGCCGGGTGCAGTGGCTCACCCCTGTAATC
CCAGCACTTTGGGAGGCTGAGGCGGACAGATCATGAGGTCAGGAGATCGAGACCATCCTG
GCCAACATGGTGAAACCCCATCTGTACTAGAATACAAAAAAAAAAAAAAAAATTTGCTGGG
CGTGGTGGCGTGCGCCTGTAGTCCCAGCTACTCGGGAGCTGAGTCAGGGGAATCGCTTGA
ACCCGGGAGGTGGAGGTTGCAGTGAGCCGAGATTGTGCCACTGCACTCCAGCCTGGTGAC
[A,G]
GAGTGAGACTCCGTCTCAAACAAAACAAAACAAAACAAAAAACAAAAAAAGAAAATCTTA
GAAAAAGAAAATAAATTGTAATATTTCAGAATATTTGTTGGGGAGGATATGTGTGCTCAA
GAAATATATACTGAGAACTTACCATTGATGCTAGAGATTGAATTGCCCCATGTCTACATG
AAAAATGAATAGAATATAAACATTTTAAATTGAGCCATGTCTATCTGTATTATATTTCTT
TTATAGAAATTCATGGAAATGGTATATTTTAACTGAATTATTAACACTGGGGACAATAGG

166529 TGGTGAAACCCCATCTGTACTAGAATACAAAAAAAAAAAAAAAAATTTGCTGGGCGTGGTG
GCGTGCGCCTGTAGTCCCAGCTACTCGGGAGCTGAGTCAGGGGAATCGCTTGAACCCGGG
AGGTGGAGGTTGCAGTGAGCCGAGATTGTGCCACTGCACTCCAGCCTGGTGACAGAGTGA
GACTCCGTCTCAAACAAAACAAAACAAAACAAAAAACAAAAAAAGAAAATCTTAGAAAAA
GAAAATAAATTGTAATATTTCAGAATATTTGTTGGGGAGGATATGTGTGCTCAAGAAATA
[T,C]
ATACTGAGAACTTACCATTGATGCTAGAGATTGAATTGCCCCATGTCTACATGAAAAATG
AATAGAATATAAACATTTTAAATTGAGCCATGTCTATCTGTATTATATTTCTTTTATAGA
AATTCATGGAAATGGTATATTTTAACTGAATTATTAACACTGGGGACAATAGGCTTTAAT
CATTATCTAATACCTGTACGTTGTTTTGAAATTCATAGCCCACCACCATTAATTTCAAAA
TTGGGTTCTTACTCAAAGAGTGATGAAAAGGCACCAGTACCAAATGGTCTGGCCAAAATG

166567 AAAAAATTTGCTGGGCGTGGTGGCGTGCGCCTGTAGTCCCAGCTACTCGGGAGCTGAGTC
AGGGGAATCGCTTGAACCCGGGAGGTGGAGGTTGCAGTGAGCCGAGATTGTGCCACTGCA
CTCCAGCCTGGTGACAGAGTGAGACTCCGTCTCAAACAAAACAAAACAAAACAAAAAACA
AAAAAAGAAAATCTTAGAAAAAGAAAATAAATTGTAATATTTCAGAATATTTGTTGGGGA
GGATATGTGTGCTCAAGAAATATATACTGAGAACTTACCATTGATGCTAGAGATTGAATT
[G,T]
CCCCATGTCTACATGAAAAATGAATAGAATATAAACATTTTAAATTGAGCCATGTCTATC
TGTATTATATTTCTTTTATAGAAATTCATGGAAATGGTATATTTTAACTGAATTATTAAC
ACTGGGGACAATAGGCTTTAATCATTATCTAATACCTGTACGTTGTTTTGAAATTCATAG
CCCACCACCATTAATTTCAAAATTGGGTTCTTACTCAAAGAGTGATGAAAAGGCACCAGT
ACCAAATGGTCTGGCCAAAATGCTACATGGAACTAAATGCTGGGGATGGTCATACAATGA

166951 ATTCATGGAAATGGTATATTTTAACTGAATTATTAACACTGGGGACAATAGGCTTTAATC
ATTATCTAATACCTGTACGTTGTTTTGAAATTCATAGCCCACCACCATTAATTTCAAAAT
TGGGTTCTTACTCAAAGAGTGATGAAAAGGCACCAGTACCAAATGGTCTGGCCAAAATGC
TACATGGAACTAAATGCTGGGGATGGTCATACAATGAGTTTTAAGTGGCTAGACCCTAAA
TCAGAAGCACTTTCTTCTAATTAGCACCATGGTTCTTAATCCTTTCTGTACATTACAATC
[G,A]
CTCAGCAGCTTAATACAAATGTTGCTTCCCGGGGCCACACTCCACATCTTTCTGACTCTC
TGATTTAATTGGTCCGAATGGGGCCTATACATCAGGTGTTTTTTAAAAGGTCTCCAAGTG
ATTCTAATGTGTACCTGCATTGAGGACCAGGGAAGGTGTAGGAAGCCTGATAACCTTTAC
TCTCCAGCCTCATCCTCCAATCCCATGATTGTTTATGGGATTGTTGCTACACACCCAGCT
TAGTCATAGCATTCTTACTCTAGCTTTTTTTTAGATGCAATTTTTATTTATTCTTAAAGA

167026 TACGTTGTTTTGAAATTCATAGCCCACCACCATTAATTTCAAAATTGGGTTCTTACTCAA
AGAGTGATGAAAAGGCACCAGTACCAAATGGTCTGGCCAAAATGCTACATGGAACTAAAT
GCTGGGGATGGTCATACAATGAGTTTTAAGTGGCTAGACCCTAAATCAGAAGCACTTTCT

FIGURE 3QQQQ

TCTAATTAGCACCATGGTTCTTAATCCTTTCTGTACATTACAATCGCTCAGCAGCTTAAT
ACAAATGTTGCTTCCCGGGGCCACACTCCACATCTTTCTGACTCTCTGATTTAATTGGTC
[C,T]
GAATGGGGCCTATACATCAGGTGTTTTTTAAAAGGTCTCCAAGTGATTCTAATGTGTACC
TGCATTGAGGACCAGGGAAGGTGTAGGAAGCCTGATAACCTTTACTCTCCAGCCTCATCC
TCCAATCCCATGATTGTTTATGGGATTGTTGCTACACACCCAGCTTAGTCATAGCATTCT
TACTCTAGCTTTTTTTTAGATGCAATTTTTATTTATTCTTAAAGAAAAAGATTTCTTTAG
CACCTTTATTCTAAAGAGCTCTTAATTGCTGTGCTTAGAACTTCTAAACAGTGAGCATTT

167086 AGAGTGATGAAAAGGCACCAGTACCAAATGGTCTGGCCAAAATGCTACATGGAACTAAAT
GCTGGGGATGGTCATACAATGAGTTTTAAGTGGCTAGACCCTAAATCAGAAGCACTTTCT
TCTAATTAGCACCATGGTTCTTAATCCTTTCTGTACATTACAATCGCTCAGCAGCTTAAT
ACAAATGTTGCTTCCCGGGGCCACACTCCACATCTTTCTGACTCTCTGATTTAATTGGTC
CGAATGGGGCCTATACATCAGGTGTTTTTTAAAAGGTCTCCAAGTGATTCTAATGTGTAC
[C,T]
TGCATTGAGGACCAGGGAAGGTGTAGGAAGCCTGATAACCTTTACTCTCCAGCCTCATCC
TCCAATCCCATGATTGTTTATGGGATTGTTGCTACACACCCAGCTTAGTCATAGCATTCT
TACTCTAGCTTTTTTTTAGATGCAATTTTTATTTATTCTTAAAGAAAAAGATTTCTTTAG
CACCTTTATTCTAAAGAGCTCTTAATTGCTGTGCTTAGAACTTCTAAACAGTGAGCATTT
GTCAAACATAGAATAGCAGAATGAAGGGGTTGGACCTCGGGTGAGGAGGGCTGTCGCATG

167517 TTTTTTTAGATGCAATTTTTATTTATTCTTAAAGAAAAAGATTTCTTTAGCACCTTTATT
CTAAAGAGCTCTTAATTGCTGTGCTTAGAACTTCTAAACAGTGAGCATTTGTCAAACATA
GAATAGCAGAATGAAGGGGTTGGACCTCGGGTGAGGAGGGCTGTCGCATGGTCTCTTTCG
AGTGCCGGCGGGTGGGGGCTGCACATCTCCTCGCTTCTGGGCCCATTGATAAGTGACCTA
AAAGTGCCTTTCGTTTTTTTTTGGTGGGGGGTGAAAAAGCAATCTGTTTTGTACCCACAGC
[G,A]
GTGCACTTTAAACAGGAAGCCCTACTGGGGCCAGCCTTCTATGTGTCATTAAGTTTTTCA
CGCCACATCCTACCTATCATCATGCACCCATGTCATCGTTCTTTTAAAGGGTGCCAGTTT
TTTGCTTAAGCACAAGGAGCTGTGACCTGTGTTGTCATCCCTGATGCATGTCATGCATGT
GACTTCATGACATGTGGGTGACTTTTGATCTCTGAAGGACCAGGGACCCAGTCTGTGGAT
CACCACTCTCTCCGTGGGTGGTTTGGGTCTTGTTCTCTAGCCCACCCAGCCAGGTGCAAT

167552 AAAAGATTTCTTTAGCACCTTTATTCTAAAGAGCTCTTAATTGCTGTGCTTAGAACTTCT
AAACAGTGAGCATTTGTCAAACATAGAATAGCAGAATGAAGGGGTTGGACCTCGGGTGAG
GAGGGCTGTCGCATGGTCTCTTTCGAGTGCCGGCGGGTGGGGGCTGCACATCTCCTCGCT
TCTGGGCCCATTGATAAGTGACCTAAAAGTGCCTTTCGTTTTTTTTTGGTGGGGGGTGAAA
AAGCAATCTGTTTTGTACCCACAGCGGTGCACTTTAAACAGGAAGCCCTACTGGGGCCAG
[G,C]
CTTCTATGTGTCATTAAGTTTTTCACGCCACATCCTACCTATCATCATGCACCCATGTCA
TCGTTCTTTTAAAGGGTGCCAGTTTTTTGCTTAAGCACAAGGAGCTGTGACCTGTGTTGT
CATCCCTGATGCATGTCATGCATGTGACTTCATGACATGTGGGTGACTTTTGATCTCTGA
AGGACCAGGGACCCAGTCTGTGGATCACCACTCTCTCCGTGGGTGGTTTGGGTCTTGTTC
TCTAGCCCACCCAGCCAGGTGCAATTAGGAATAAAGGAAATAGCAAAGGAATTTTGCTCA

167775 TTTGGTGGGGGGTGAAAAAGCAATCTGTTTTGTACCCACAGCGGTGCACTTTAAACAGGA
AGCCCTACTGGGGCCAGCCTTCTATGTGTCATTAAGTTTTTCACGCCACATCCTACCTAT
CATCATGCACCCATGTCATCGTTCTTTTAAAGGGTGCCAGTTTTTTGCTTAAGCACAAGG
AGCTGTGACCTGTGTTGTCATCCCTGATGCATGTCATGCATGTGACTTCATGACATGTGG
GTGACTTTTGATCTCTGAAGGACCAGGGACCCAGTCTGTGGATCACCACTCTCTCCGTGG
[C,G]
TGGTTTGGGTCTTGTTCTCTAGCCCACCCAGCCAGGTGCAATTAGGAATAAAGGAAATAG
CAAAGGAATTTTGCTCAAGGCCATGCCAAGCATTTCATCTCATATGAAAAGGAAAAGAGA
GAGAGTGTGTGTGTGTTGGCTAGATTTAGGTAGAAAACAGGCTGGTGAGAAGCGTAGAAC
TTGGTTAAAATTTCTAGCCAAAAGTAAGATTTTTAAAAAGATTTATTTCTGGATCCAATC
CCTGTTGCCCATTTCTATGAATAATCACCATTTGTTTTAATGTGAATAATAGCACACAGC

167876 CACGCCACATCCTACCTATCATCATGCACCCATGTCATCGTTCTTTTAAAGGGTGCCAGT
TTTTTGCTTAAGCACAAGGAGCTGTGACCTGTGTTGTCATCCCTGATGCATGTCATGCAT
GTGACTTCATGACATGTGGGTGACTTTTGATCTCTGAAGGACCAGGGACCCAGTCTGTGG
ATCACCACTCTCTCCGTGGGTGGTTTGGGTCTTGTTCTCTAGCCCACCCAGCCAGGTGCA
ATTAGGAATAAAGGAAATAGCAAAGGAATTTTGCTCAAGGCCATGCCAAGCATTTCATCT
[C,T]
ATATGAAAAGGAAAAGAGAGAGAGTGTGTGTGTGTTGGCTAGATTTAGGTAGAAAACAGG
CTGGTGAGAAGCGTAGAACTTGGTTAAAATTTCTAGCCAAAAGTAAGATTTTTAAAAAGA

FIGURE 3RRRR

TTTATTTCTGGATCCAATCCCTGTTGCCCATTTCTATGAATAATCACCATTTGTTTTAAT
GTGAATAATAGCACACAGCAAATTCAGCCCCCTGAGTTTTACCATTTTAAGCAATTGCTT
TAGGCCCGTGAGGCATGTACTATTTATGAAGTTGCATGGGTAGTAATGGAAAACACAACA

172530 GGTTTCGGAGGCTACTTGAGATGTGATTGCTCCTAATGAACCTCCACGGGCCTTTTTAAC
CTGTCGATGTGTTTATTTCAGATGGAGCAGGAAATGACCCGGTTACATCGGAGAGTGTCA
GAGGTGGAGGCTGTGCTTAGTCAGAAGGAGGTGGAGCTGAAGGCCTCTGAGACTCAGAGA
TCCCTCCTGGAGCAGGACCTTGCTACCTACATCACAGAATGCAGTGTGAGCCTTCCCTGA
AGCCCCCTTCCCTTGGAGGTGGCACTTCCTGTTGTGTGTGTCTCATCCTGTTTCATGATG
[A,G]
CTCCATGAGGCACATCACAGCCAATGGCAGAGAGTAGAGAGAGGGAGAGCACAAAAGCAA
GATCTGTGTTTTGCAGAGTAGTGAGAGCCAGGCGTAAGGTCCCCAAGAAATGAGATTGGA
CTCATTTCCAGCAGAAAGTGCAGGTAGACGGCTGGTACCATGGAGTCTGGAGATGGGAGT
AATTCATCTTTGCCGCAAGTTGCAAAAGATCTTAACATCTCCCATCCCAGCCTCTGTGGT
CTGCGTTGTGTCTGACATGAGCAGCCTTGAGAACCAGACTCCCAACTATGTACAAGAAAA

172714 TCCTGGAGCAGGACCTTGCTACCTACATCACAGAATGCAGTGTGAGCCTTCCCTGAAGCC
CCCTTCCCTTGGAGGTGGCACTTCCTGTTGTGTGTGTCTCATCCTGTTTCATGATGACTC
CATGAGGCACATCACAGCCAATGGCAGAGAGTAGAGAGAGGGAGAGCACAAAAGCAAGAT
CTGTGTTTTGCAGAGTAGTGAGAGCCAGGCGTAAGGTCCCCAAGAAATGAGATTGGACTC
ATTTCCAGCAGAAAGTGCAGGTAGACGGCTGGTACCATGGAGTCTGGAGATGGGAGTAAT
[T,C]
CATCTTTGCCGCAAGTTGCAAAAGATCTTAACATCTCCCATCCCAGCCTCTGTGGTCTGC
GTTGTGTCTGACATGAGCAGCCTTGAGAACCAGACTCCCAACTATGTACAAGAAAACTTA
CTTTCAATCTTCCTGACATCAAATTTTCCATTGGCCAGAACCAGTGTAGTGACAAGAAAA
TAGCCTTGAAAACCCAGACCCTCTGTCATTATTTACCATGTGACTTTCATTTTTTTCTTTC
CTTCACAAGAGTAGACTGTCTTCTTCTCCATTGTCTTGTTAAATTTTTCATTCAGGTGTT

173811 TGATTCTCCTGCCTCAGCCTCCCGAGTAGCTGGGACTACAGGCATGCACCACCATGCCCA
GCTAATTTTTGTATTTTTAGTAAAGACGGGGTTTCACCATGTTGGCCAGGGTGGTCTCGA
TCTCTTGACCTTGTGATCCGCCTGCCTCGGCCTCCCAAAGTGCTGGGATTACAGGTGTGA
GCCACTGTGCCCAGCCCATAAATCAAAATTTTTTCAGCAATTGTTATACAAGTGGAACCT
TACTCTTCAAATGCAATTGTCCAGTGTCTGGCTTAATGTCTGCTGTTGTCAGAAACCATG
[C,T]
GAATGGAGTAGATTCCCAGGTTATAAGGAGCCCCCAGGGAGGATGCGCGAGTCACTGGCT
TCTCCAGGGGTCTCTGGTTTGGGGTTGCCTTGGTGCTGGGCACACTTCCTGGAGATTTTA
CTGGACCAGCCTGAGGCCTTTGGGGCTCTGTGCAGATGCTCTACTTCTGACTTGTCTAGA
GCTTTCTTCTAATTCTGGACTAAAAGCAAGCAGGAGTTTGGAGGATGATGGTGAGAATTC
ACATCCCCGAGTTGGCTTTTGGAATGCAGTAGTTTGTGAGATTTAGTGTTTTTTTTAAGA

173812 GATTCTCCTGCCTCAGCCTCCCGAGTAGCTGGGACTACAGGCATGCACCACCATGCCCAG
CTAATTTTTGTATTTTTAGTAAAGACGGGGTTTCACCATGTTGGCCAGGGTGGTCTCGAT
CTCTTGACCTTGTGATCCGCCTGCCTCGGCCTCCCAAAGTGCTGGGATTACAGGTGTGAG
CCACTGTGCCCAGCCCATAAATCAAAATTTTTTCAGCAATTGTTATACAAGTGGAACCTT
ACTCTTCAAATGCAATTGTCCAGTGTCTGGCTTAATGTCTGCTGTTGTCAGAAACCATGT
[C,T,G]
AATGGAGTAGATTCCCAGGTTATAAGGAGCCCCCAGGGAGGATGCGCGAGTCACTGGCTT
CTCCAGGGGTCTCTGGTTTGGGGTTGCCTTGGTGCTGGGCACACTTCCTGGAGATTTTAC
TGGACCAGCCTGAGGCCTTTGGGGCTCTGTGCAGATGCTCTACTTCTGACTTGTCTAGAG
CTTTCTTCTAATTCTGGACTAAAAGCAAGCAGGAGTTTGGAGGATGATGGTGAGAATTCA
CATCCCCGAGTTGGCTTTTGGAATGCAGTAGTTTGTGAGATTTAGTGTTTTTTTTAAGAA

Chromosome map:
Chromosome 12

FIGURE 3SSSS

ISOLATED HUMAN KINASE PROTEINS, NUCLEIC ACID MOLECULES ENCODING HUMAN KINASE PROTEINS, AND USES THEREOF

This application is a Divisional of U.S. Ser. No. 10/238,709, filed Sep. 11, 2002, now U.S. Pat. No. 6,680,188 issued Jan. 20, 2004, which is a Divisional of U.S. Ser. No. 09/804,471 filed Mar. 13, 2001, now U.S. Pat. No. 6,479,269 issued Nov. 12, 2002.

FIELD OF THE INVENTION

The present invention is in the field of kinase proteins that are related to the rho/rac-interacting citron kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) EMBO *Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Activated Rho GTPases trigger distinctive kinase cascades. In particular, the Rho-binding serine/threonine kinase (ROCK) binds to Rho, and its kinase activity is moderately stimulated by this association. The citron molecule (Madaule et al., 1995), a specific interactor of Rho and Rac, shares a significant degree of structural homology with ROCK; however, its lack of a kinase domain raised the question of its biologic function. By PCR of a mouse primary keratinocyte cDNA library, Di Cunto et al. (1998) identified a novel serine/threonine kinase, CRIK (citron Rho-interacting kinase), belonging to the myotonic dystrophy kinase family. CRIK can be expressed as at least 2 isoforms, one of which encompasses the previously reported form of citron in almost its entirety. The long form of CRIK is a 240-kD protein in which the kinase domain is followed by the sequence of citron. The short form, CRIK-SK (short kinase), is an approximately 54-kD protein that consists mostly of the kinase domain. CRIK and CRIK-SK proteins are capable of phosphorylating exogenous substrates as well as of autophosphorylation, when tested by in vitro kinase assays after expression into COS-7 cells. CRIK kinase activity is increased several-fold by coexpression of constitutively active Rho, while active Rac has more limited effects. Kinase activity of the endogenous CRIK is indicated by in vitro kinase assays after immunoprecipitation with antibodies recognizing the citron moiety of the protein. When expressed in keratinocytes, full-length CRIK, but not CRIK-SK, localizes into corpuscular cytoplasmic structures and elicits recruitment of actin into these structures. The previously reported Rho-associated kinases ROCK1 and ROCK2 are ubiquitously expressed. Northern blot analysis of mouse tissues revealed a restricted pattern of expression limited to keratinocytes, brain, spleen, lung, kidney, and an especially strong signal in testis. No expression was detectable in heart, liver, or skeletal muscle. The CRIK protein contains a kinase domain, a coiled-coil domain, a leucine-rich domain, a Rho-Rac binding domain, a zinc finger region, a pleckstrin homology domain, and a putative SH3-binding domain. Di Cunto et al. (1998) reported cloning the human homolog of the CRIK kinase domain. They stated that the human homolog of citron is contained within a PAC clone mapping to chromosome 12q.

Di Cunto et al. (2000) generated mice deficient in citron kinase by targeted disruption. Citron-K −/− mice grow at slower rates, are severely ataxic, and die before adulthood as a consequence of fatal seizures. Their brains display defective neurogenesis, with dramatic depletion of microneurons in the olfactory bulb, hippocampus, and cerebellum. These abnormalities arise during development of the central nervous system due to altered cytokinesis and massive apoptosis. Di Cunto et al(2000) concluded that citron-K is essential for cytokinesis in vivo, in specific neuronal precursors only. Moreover, they suggested a novel molecular mechanism for a subset of human malformation syndromes of the central nervous system. For a review, see Di Cunto et al., *J Biol Chem* Nov. 6, 1998; 273(45):29706–11; Di Cunto, et al., *Neuron* 28: 115–127, 2000; Madaule et al., *FEBS Lett.* 377: 243–248, 1995; Nagase et al., *DNA Res.* 6:63–70, 1999.

Kinase proteins, particularly members of the rho/rac-interacting citron kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the rho/rac-interacting citron kinase subfamily.

SUMMARY OF THE INVENTION

The present invention is based in part on the identification of amino acid sequences of human kinase peptides and proteins that are related to the rho/racinteracting citron kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the brain glioblastoma, uterus tumor, colon, normal nervous system, tumor nervous system.

DESCRIPTION OF THE FIGURE SHEETS

FIGS. 1A–1C provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the brain glioblastoma, uterus tumor, colon, normal nervous system, tumor nervous system.

FIGS. 2A–2E provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3SSSS provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. 148 SNPs, including 6 indels, have been identified in the gene encoding the kinase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the rho/rac-interacting citron kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the rho/rac-interacting citron kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the rho/rac-interacting citron kinase subfamily and the expression pattern observed. Experimental data as provided in FIG. 1 indicates expression in the brain glioblastoma, uterus tumor, colon, normal nervous system, tumor nervous system. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known rho/rac-interacting citron kinase family or subfamily of kinase proteins.

Specific Embodiments

Peptide Molecules

The present invention provides nucleic acid sequences that encode protein molecules that have been identified as being members of the kinase family of proteins and are related to the rho/rac-interacting citron kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the brain glioblastoma, uterus tumor, colon, normal nervous system, tumor nervous system. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988*; Biocomputing: Informatics and Genome Projects*, Smith, D. W., ed., Academic Press, New York, 1993*; Computer Analysis of Sequence Data, Part* 1, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 12 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 12 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the rho/rac-interacting citron kinase protein described herein and mouse Cirton Rho-interacting kinase (CRIK) (see FIG. 1). As discussed in the background, mouse CRIK are known in the art to be involved in phosphorylating exogenous substrates as well as autophosphorylation., and have be may play a role in central nervous system s. Accordingly, the rho/rac-interacting citron kinase protein, and the encoding gene, provided by the present invention is useful for treating, preventing, and/or diagnosing disorder related to the cytokinesis and massive apoptosis.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. A large percentage of pharmaceutical agents are being developed that modulate the activity of kinase proteins, particularly members of the rho/rac-interacting citron kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the brain glioblastoma, uterus tumor, colon, normal nervous system, tumor nervous system. Such uses can readily be determined using the information provided herein, that which is known in the art, and routine experimentation.

The proteins of the present invention (including variants and fragments that may have been disclosed prior to the present invention) are useful for biological assays related to kinases that are related to members of the rho/rac-interacting citron kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the brain glioblastoma, uterus tumor, colon, normal nervous system, tumor nervous system. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g,. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the brain glioblastoma, uterus tumor, colon, normal nervous system, tumor nervous system. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) cell 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent W094/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the brain glioblastoma, uterus tumor, colon, normal nervous system, tumor nervous system. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the brain glioblastoma, uterus tumor, colon, normal nervous system, tumor nervous system. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase binding partner interaction.

FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the brain glioblastoma, uterus tumor, colon, normal nervous system, tumor nervous system. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the brain glioblastoma, uterus tumor, colon, normal nervous system, tumor nervous system. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the brain glioblastoma, uterus tumor, colon, normal nervous system, tumor nervous system. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 12 by ePCR.

FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 148 SNPs, including 6 indels, have been identified in the gene encoding the kinase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 12 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the brain glioblastoma, uterus tumor, colon, normal nervous system, tumor nervous system. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the brain glioblastoma, uterus tumor, colon, normal nervous system, tumor nervous system.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements. As indicated by the data presented in FIG. 3, the map position was determined to be on chromosome 12 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin *et al., Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis. (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al. (1996; Nat. Biotech.1675 –1680 and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule comprising a nucleotide sequence selected from the group consisting of:

(a) a transcript or cDNA sequence that encodes a polypeptide having an amino acid sequence comprising SEQ ID NO:2;

(b) SEQ ID NO:1;

(c) nucleotides 7–1497 of SEQ ID NO:1; and (d) a nucleotide sequence that is completely complementary to the nucleotide sequence of (a), (b), or (c).

2. An isolated nucleic acid molecule having a nucleotide sequence comprising SEQ ID NO:1 or the complement thereof.

3. An isolated nucleic acid molecule having a nucleotide sequence comprising nucleotides 7–1497 of SEQ ID NO:1 or the complement thereof.

4. An isolated transcript or cDNA nucleic acid molecule comprising a nucleotide sequence that encodes a polypeptide comprising SEQ ID NO:2, or the complement of said nucleotide sequence.

5. The isolated nucleic acid molecule of claim 1, further comprising a heterologous nucleotide sequence.

6. The isolated nucleic acid molecule of claim 5, wherein the heterologous nucleotide sequence encodes a heterologous amino acid sequence.

7. A vector comprising the nucleic acid molecule of any one of claims 1, and 2–6.

8. An isolated host cell containing the vector of claim 7.

9. A process for producing a producing a polypeptide comprising culturing the host cell of claim 8 under conditions sufficient for the production of said polypeptide, and recovering said polypeptide.

10. The vector of claim 7, wherein said vector is selected from the group consisting of a plasmid, a virus, and a bacteriophage.

11. The vector of claim 7, wherein said nucleic acid molecule is inserted into said vector in proper orientation and correct reading frame such that a polypeptide comprising an amino acid sequence of SEQ ID NO:2 is expressed by a cell transformed with said vector.

12. The vector of claim 11, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 1515
<212> TYPE: DNA
<213> ORGANISM: Homo sapiens

<400> SEQUENCE: 1

```
ggggagatgt tgaagttcaa atatggagcg cggaatcctt tggatgctgg tgctgctgaa     60

cccattgcca accgggcctc caggctgaat ctgttcttcc aggggaaacc accctttatg    120

actcaacagc agatgtctcc tctttcccga gaagggatat tagatgccct ctttgttctc    180

tttgaagaat gcagtcagcc tgctctgatg aagattaagc acgtgagcaa ctttgtccgg    240

aagtattccg acaccatagc tgagttacag gagctccagc cttcggcaaa ggacttcgaa    300

gtcagaagtc ttgtaggttg tggtcacttt gctgaagtgc aggtggtaag agagaaagca    360

accggggaca tctatgctat gaaagtgatg aagaagaagg ctttattggc ccaggagcag    420

gtttcatttt ttgaggaaga gcggaacata ttatctcgaa gcacaagccc gtggatcccc    480

caattacagt atgcctttca ggacaaaaat cacctttatc tggtcatgga atatcagcct    540

ggaggggact tgctgtcact tttgaataga tatgaggacc agttagatga aaacctgata    600

cagttttacc tagctgagct gattttggct gttcacagcg ttcatctgat gggatacgtg    660

catcgagaca tcaagcctga gaacattctc gttgaccgca caggacacat caagctggtg    720

gattttggat ctgccgcgaa aatgaattca aacaagatgg tgaatgccaa actcccgatt    780

gggaccccag attacatggc tcctgaagtg ctgactgtga tgaacgggga tggaaaaggc    840

acctacggcc tggactgtga ctggtggtca gtgggcgtga ttgcctatga gatgatttat    900

gggagatccc ccttcgcaga gggaacctct gccagaacct tcaataacat tatgaatttc    960

cagcggtttt tgaaatttcc agatgacccc aaagtgagca gtgactttct tgatctgatt   1020

caaagcttgt tgtgcggcca gaaagagaga ctgaagtttg aaggtctttg ctgccatcct   1080

ttcttctcta aaattgactg gaacaacatt cgtaactctc ctccccctt cgttcccacc    1140

ctcaagtccg acgatgacac ctccaatttt gatgaaccag agaagaattc gtgggtttca   1200

tcctctccgt gccagctgag cccctcaggc ttctcgggtg aagaactgcc gtttgtgggg   1260

ttttcgtaca gcaaggcact ggggattctt ggtagatctg agtctgttgt gtcgggtctg   1320

gactcccctg ccaagactag ctccatggaa aagaaacttc tcatcaaaag caaagagcta   1380

caagactctc aggacaagtg tcacaaggta tttatttccg cagccggcct ccttccttgc   1440

tccaggatcc tcccgtccgt atatgccaag ggatccgccc ggggccgctg ctggctctga   1500

gccgcctgat ccgta                                                    1515
```

<210> SEQ ID NO 2
<211> LENGTH: 497
<212> TYPE: PRT
<213> ORGANISM: Homo sapiens

<400> SEQUENCE: 2

```
Met Leu Lys Phe Lys Tyr Gly Ala Arg Asn Pro Leu Asp Ala Gly Ala
1               5                   10                  15

Ala Glu Pro Ile Ala Asn Arg Ala Ser Arg Leu Asn Leu Phe Phe Gln
            20                  25                  30

Gly Lys Pro Pro Phe Met Thr Gln Gln Gln Met Ser Pro Leu Ser Arg
```

-continued

```
        35                  40                  45

Glu Gly Ile Leu Asp Ala Leu Phe Val Leu Phe Glu Glu Cys Ser Gln
    50                  55                  60

Pro Ala Leu Met Lys Ile Lys His Val Ser Asn Phe Val Arg Lys Tyr
65                  70                  75                  80

Ser Asp Thr Ile Ala Glu Leu Gln Glu Leu Gln Pro Ser Ala Lys Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
            180                 185                 190

Leu Asp Glu Asn Leu Ile Gln Phe Tyr Leu Ala Glu Leu Ile Leu Ala
        195                 200                 205

Val His Ser Val His Leu Met Gly Tyr Val His Arg Asp Ile Lys Pro
    210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Met Val Asn Ala Lys Leu
                245                 250                 255

Pro Ile Gly Thr Pro Asp Tyr Met Ala Pro Glu Val Leu Thr Val Met
            260                 265                 270

Asn Gly Asp Gly Lys Gly Thr Tyr Gly Leu Asp Cys Asp Trp Trp Ser
        275                 280                 285

Val Gly Val Ile Ala Tyr Glu Met Ile Tyr Gly Arg Ser Pro Phe Ala
    290                 295                 300

Glu Gly Thr Ser Ala Arg Thr Phe Asn Asn Ile Met Asn Phe Gln Arg
305                 310                 315                 320

Phe Leu Lys Phe Pro Asp Asp Pro Lys Val Ser Ser Asp Phe Leu Asp
                325                 330                 335

Leu Ile Gln Ser Leu Leu Cys Gly Gln Lys Glu Arg Leu Lys Phe Glu
            340                 345                 350

Gly Leu Cys Cys His Pro Phe Phe Ser Lys Ile Asp Trp Asn Asn Ile
        355                 360                 365

Arg Asn Ser Pro Pro Pro Phe Val Pro Thr Leu Lys Ser Asp Asp Asp
    370                 375                 380

Thr Ser Asn Phe Asp Glu Pro Glu Lys Asn Ser Trp Val Ser Ser Ser
385                 390                 395                 400

Pro Cys Gln Leu Ser Pro Ser Gly Phe Ser Gly Glu Glu Leu Pro Phe
                405                 410                 415

Val Gly Phe Ser Tyr Ser Lys Ala Leu Gly Ile Leu Gly Arg Ser Glu
            420                 425                 430

Ser Val Val Ser Gly Leu Asp Ser Pro Ala Lys Thr Ser Ser Met Glu
        435                 440                 445

Lys Lys Leu Leu Ile Lys Ser Lys Glu Leu Gln Asp Ser Gln Asp Lys
    450                 455                 460
```

-continued

```
Cys His Lys Val Phe Ile Ser Ala Ala Gly Leu Leu Pro Cys Ser Arg
465                 470                 475                 480

Ile Leu Pro Ser Val Tyr Ala Lys Gly Ser Ala Arg Gly Arg Cys Trp
                485                 490                 495

Leu


<210> SEQ ID NO 3
<211> LENGTH: 174493
<212> TYPE: DNA
<213> ORGANISM: Homo sapiens
<220> FEATURE:
<221> NAME/KEY: misc_feature
<222> LOCATION: (1)...(174493)
<223> OTHER INFORMATION: n = A,T,C or G

<400> SEQUENCE: 3

tacacctagc aatagtcata gaatgcacaa atcttcaatg ttagcaaata atgccaaact     60

tttttttcaa atttcaaaga gattgtatcc atttacacgc ctacgggtac tgtataagtg    120

tgtgtacttc cacatcttcg caaacactgt cacatccttt tgttgttgtt gttctcgaat    180

ttgagtgtta ttctttctca ctgtgacttt atttttcata ttttctgatt atgaacgagg    240

ttgacaactt tcacacattt gttggtcatc tggatttcct ttttggtgaa gtgcctgttt    300

aagtatctcg tctataattt attttaaagt gtcctttcag acagtctcaa tgactgtcac    360

caactccttg cagggcagtc agcccggaga tagagtaatc aaggtaggtt gaagtcaagc    420

tcaaaacatt cgctgcctca gctgtagcag aggaccactg ggcttcccca ggtaacaagt    480

acttctacct tagccacatg agagagaaag aagaccaggc agagcagcct ggctgccttc    540

ctccttgcag gtggccgaga gcaggggaca gcgccctggc gacctcctca gggatcctag    600

attaacagtc gcgtcctcaa acgcagcatc ctgcgtaacc gccaatttca aacttccaag    660

acctgccctg ctgattttgc ccttcccttt ttcccgttgg tcgcgagtca aaggaagatg    720

caatttgatt ggctctcccc ttcactttcc tccatgcctt tagggacatg ggcggggcct    780

ggctgagacg cccatgtcta tcataggagc ggagacgctg attggtccaa acacggctga    840

gacccgcccg cgccgttcct cgggttcaaa cgcggcggcg ggaggcgcgg ggcggaacag    900

atcgcagacc tgggggttcg cagagcgtga gtctgatccc ccagacccaa ttctaccgca    960

cccggctctg caaggccagg ggagggccgc ctccacccat acaagtcccg ggtttccctc   1020

ccgccccggg gagggcggcg attccacccc cagggctgcg ggaggcctgg agggtcttcc   1080

ggggctagct gtgcgcgcgc ccaccttcct tgggagccga ggggtcagcc gagtggtgct   1140

ggggcaggag gcttgctcct cccctaaacc aggcggagtg ctttgtctct tcagctctgc   1200

ctcctgtcag cactaactgc attattctgc ccagtgtagt cggccggttc cttattatct   1260

gcgtgaactt agccatttac ttaacctctc tgtttcagcg tattcatacc ccgtgcccac   1320

cccatcacct catgatgccc ccgcctcttt cgctctgctc cagtccgtct ggcctcgctg   1380

ttgctggaga ggccaggtcc tgcctcagtg cttttggctt ggctgtttcg tttgccacgg   1440

atgtctttct ttccccagat atcaacatgg cttgctggtc attcgcttca ggtcttcaag   1500

tcttgggtca aatggtggct tctcagtgaa gtcttatttg accacactaa aaattgcacc   1560

atctcacccc cattgtcctt ttcttgctcg attttgtttt taccccatag cacttaacac   1620

cttacaacaa gctatatatt ttgcttattt cagtcattca tttaataact attcgcacct   1680

atttgtgtgc caggctatgt gtgcccccac tgcatggggg caaacatctc tgcccttgtg   1740
```

-continued

```
gagcttccat tctaaggggg gagataataa acacatttat aagtaagaga gtatgtcaga   1800
taagtgtatc atctcctgtc acagtgagtt aaaatctggt gtttaatctc catgattaga   1860
ctgagcttcc taaaactgga gtggtagctg attttcacct ccttgtccct gatatcttga   1920
gggagatcag gatctctcag gcccttcctg ctcaaaacat aggacacact tgacttttct   1980
gatatccttt cagcgccagt ggggagatgt tgaagttcaa atatggagcg cggaatcctt   2040
tggatgctgg tgctgctgaa cccattgcca gccgggcctc caggctgaat ctgttcttcc   2100
aggtaacagc ctaccctgcc aactttgctc acctgtgtgt gtccttggaa tctccttgtc   2160
actcaccttt gcttttattt atttgtttat ttatttagag tctcagtctc tcaggctgga   2220
gtacagtggt gcaatctcag ctcactgcaa cctccgcctc ctgggttcaa gcgattctcc   2280
tgcctcagcc tccagagtag ctgggactac agccgcctgc caccacaccc ggctaaattt   2340
tgtatttttc tttttagtag agacggggtt tcaccatgtt ggccaggcta gggtcgaact   2400
cctgacctca agtgatccac ctgccttggc ctcctaaagt gctgggatta caggcatgaa   2460
ccgtgcccag cttgctttta ttataggacc agggataata ttttagggga aattctgttt   2520
tgttttgttt gaaacaaggt cttctgtcga ctctaggcct gtgccaccat gcctggctaa   2580
ttttttaatt ttttgtaggg atggggtctc actgtgttgc ccaggctgat atagaacacc   2640
tgacttcaag tgagcctctt gccttggcct cccaaagcac tggggttata ggtgtgagcc   2700
actgcacctg gccctctatt tagagtttta tatgcactga ttcttttgga aaaaagacac   2760
tgtgcagaag tagatagctg aacttgcctt agaagggaga tcttttcata tttctcacac   2820
tttacacttc tgtactaaag tttattcatt cattgattga ttggttgctt gcaagacagg   2880
gtcttgctct gtggctcagg ctggagtgca ttggcacaat cacggcttac tgcagccttg   2940
acctcctggg ctcaaacgat cctcccactt cagcttcctg agtagctggg accacaggtg   3000
tgtgccacca tacctggcta atttttgtat tttttgtaga gatgaggttt caccatgttg   3060
cccaggcagg tctcgaattc ctgggctcaa gtgatctact tgtcacagct tctgcaagtg   3120
ttgggcttac aggcataagc cctgtaccca gggcaagttt gtccttttat tgaagaaaga   3180
aaaataaatg aacaaagatg ctttttaaaa ctacaatttc tgtgggtata atcctattca   3240
ttttcattgc agggatgttt attttttaag attttttttt ttttttttg agacagagtc   3300
ttcgctgtcg cccaggctgg agtgcagtgg cgcgatctcg gctcactgca ggctctgccc   3360
cccggggttc acgccattct cctgcctcag cctcccacgt agctgggact acaggcgccc   3420
gtcacctcgc ccggctaatt ttttgtattt ttagtagaga cggggtttca ctgtgttagc   3480
caggatggta ttttttaaga ttttaaaaaa agttttgatg aataccacac ctgtttaacc   3540
ctcattcctc tcaagataca catttctgtc accccagatg cgttaaaact taatatcata   3600
agattacttc caaatagatt tttaattctt ttgtttctga tgtatgtgga acactggtga   3660
agtagaaatc cttgtttgat ttatgtattc gtaagtcagg gggacaatag agaccatgaa   3720
gatttagaat tgaatcccag tcccagcact agttagctgc attactttgg gtgagtcagt   3780
taccttttct gagtccattt gctattcttt aaaataggtt gtagcctgta atgccagtat   3840
tttcggaggc tgaggcgggc ggattacttg aggtcacggg ttcgagacca gcctggacaa   3900
cgtggtgaaa ccctgtctct actaaaaata tagaaaatta gctgggcatg gtggtcgcat   3960
gtacctgtaa tcccagctac ttgaaaagct gaagcaggag aatcatttga acccgggagg   4020
cggaggttgt cgtgagccga gatggtgcac tgcactccag cctgggcgac agagtgggta   4080
agactccatc tcaaaacaaa acaaaacaaa agaaaacaaa aaaaataaca tagaggttgt   4140
```

-continued

```
agtacctaat ccacagggtt gttgtgagga ttagatgaga tattcgattt aaagcactta   4200
gcaccttgcc tggctcttag taaactcctt ataaaaaatg gtaattattg ttaatactca   4260
gcatagaata gtattagtta taatattaat actaaatttg tttccttaat agtaattata   4320
tttgggaagg tagttatgta ggatacctgt aagatgatga atgatgaagt attcttgata   4380
actttttttt tttttccaaa atattggtat tgggtgttta aacagatgag agtggaaaca   4440
aattgaaagc ttaggttttt ctgtgggacc atccccatca gcattttaag tcttgacata   4500
tctttcacaa atgaatagtc tgtctttaac cttagatggc tggagtgctg ccacgtttca   4560
gcccctttat catgctactt taaaatatct ccaacttgct gggcgtggtg gctcacgcct   4620
gtaatcctag caatttggga ggctgaggtg ggtggattgc ttgaggtcag gagttcgaga   4680
gcagcccggg caacatggtg agcccctccg tttctactaa aaacacaaaa aatagctgac   4740
tgtgatggtg tgtgcctgta gtcccagcta ctcgggaggc tgaggcagga ggatcacttg   4800
agccctagag gcagaggttg cagtgagcta agattgtgcc actgcacttc agcacttcag   4860
cctaggcgac agagcaagac cctgtaaatt aaaaaaaaaa aaaaaaagaa aaggaaaaaa   4920
atttccaact tattaagggc ttatagtgtg ctgattatgt aatagttatg gcttccaatg   4980
tgtctggcat agaactggca tgtttctgag tatctcactt cagcctcatg acagaggtaa   5040
ggactatttt taatttaaac tttaaatagg aggcaacagg ccaggtgtgg tggctcacac   5100
ctgtaatccc agtactttgg gaggctgagg caggtggatt gcttgagtcc aagagttcaa   5160
gactagcctg ggcaaaatgg tgaaacccca tctctacaaa aaatataaat aattagtcag   5220
gcatggcggt gtgtgcctgt agtcccagct actcaggagg ctgaggtggg ggcatctctg   5280
gggccccgga ggcagaggtt gtagtgagtt gagattgcaa cactgcactc cagcctgggc   5340
aacagaacga gaccctgttt ctaaataaat acataaatag gaggcaacag atatagacag   5400
atatggaggt aggtaaggcc ttgcccaaga tcatacacgt tgggttttgc agatgaggcc   5460
aagatcagac tccatctttg gttggtctga ctccaaaggc tgaccacata gccattgggc   5520
cacagcacct gtgcacgtca gaatttatta agtatatctt gtatttagtc attataacag   5580
gaagacttat gggtaaaccc tcagttcatc tctttttaat gctgagatcc ccctgcccag   5640
taaagctatt attgcaagta tagtatatac ctatcatttg ccttgagtta tcaggtaagg   5700
atgctgtttg ttcttttccc atatagtgct gtttgaatga ggttgagata cagtagcaat   5760
tttgttttcc attcaggtga gtaccttaga ctgagtgtca ttttgtcttt tttacttcta   5820
ctcaacagga tttcctgaca tgttcgaggt cagtgattgt cagactttct gagccagcaa   5880
aatttcccaa attgctgggt agacacaggt tttccaactt tttattttgc caagtaagga   5940
tatataaaaa aaaaataaaa agaaagacct attattttct ggcccttgta tttcataaag   6000
ggcattttaa gaaacaacaa gacaggaaga acatcatctc agaataaagg accattttta   6060
aatttgaata catttagttt tataaaaaag atatcatgtg gtgttcattt tttctcattt   6120
cactgcaggc tgttgaaaac tttgttaaga accagtacta tatttgggaa cccctgcttt   6180
aattgatcta aactcttgaa gaatagaaga aacaaagcat tttatttttc tgagttactg   6240
gcaactatta ctaaagtgac agatatggtg gccttgaatg cagtgcttcc caaacctgat   6300
tgaggtctga ctctcttggg gaccagggtc tcattctgtt gcccaggctg gagtgtggca   6360
gcacaatctt ggctcactgc agcctttact tcttgggctc aagtgatcct tctacctcag   6420
tctcacaagt ggctaggact acaggaccat ggcactacac ctggctaatt tttttttgtt   6480
```

-continued

```
tgtttgtaga gatgggatct cgctgtgttg ccctggctgg tcttgaactc ctgggctcaa   6540
gtgatcctcc caccttggcc tcccaaagtg ctagtattcc aggtgtgagc cacctctccc   6600
tgctggggaa cttgttaata aaacagattc taggctacag tctggaaaat tctaattcat   6660
ttggttgtgg gggagggggg cataggacca gagaatgtgt ttgtttgttt gtttgttttt   6720
cttaaattct ccagtgctgt tgtgattcaa atgcagccgg tctgtttctg ttatcaagtg   6780
ctgtgtaaca aagcactcac aaagtttaaa gcaacaatga tttatttttt cttaggattc   6840
tgtgggttgg ctggactcag ctaggtagtt ctgcttcatc ctgtgatgtc agctggggtc   6900
acttgtgggg ctacattcag ctgggattat gtctgggact ggaacatgtg ggtgctgact   6960
gctggctggg gcaccttagt gtttctcaca tggcctctct tctccatgag gtctttcagt   7020
agtatagccc aggactcgta actttttttt ttttttttaag acagactgtc gccctgtcgc   7080
ccaggctgga gtgcagtggc acgatctctg ctcactgcaa cctccgcctc ctgggttcaa   7140
gcaattctcc tgccccagcc tcccgagtag ctgggattac aggcacgtgc ctccacgccc   7200
ggctaatgtt tgcattttta gtagagatgg ggtttcacca cgttggtcag gctggtctcg   7260
aacttctgac ctcgcgatcc gcctgcctcg gcctcccaaa gtgttggaat tacaggtgtg   7320
agccactgca cctggctgac tcgtaacttt ttttgtaagt aataaatatt ttaggctttg   7380
tgggtcctgt agtctctgtt gcaaccactc aacttggcca tggtagcaca aaagcagcta   7440
aagacaatat gtaaatgatg ggtgtagctg tgttccagta aaacttataa aaagtccgtg   7500
ggctggattt ggtccaaggg ctacagattg cacacccctg gtctagccca agcatctgtg   7560
catggtggct ggcttcccaa aagtggaagc tgctaagctg cctttttttt tttttttttt   7620
tttttgaga gggagtctca ctgtgttgcc taggctggag tgcggtggtg tgatctcggc   7680
tcactgcaac ctccatctcc cgggtgcagg caattctcat gcctcaacct cccaggtagc   7740
tgggattacg ggtgcctacc accacgcctg gctaattttt gtatttttggt agagacaggg   7800
tttcaccatg ttggccaggc tggtctcaaa ctcctgacct caagtgatcc acccgtcttg   7860
gcctcccaaa gtgctgggat tacagatgtg agccaccgtg tctggccgct tgacaagctt   7920
cttaaaggca ctgccctgaa ctggcacagt gtcacttgtg tcacattctt ttggttgaag   7980
agagtctcag agatggcaca gattcaaagg caggagaaat agactccagc gcttaaagta   8040
aggagtagca tgtgcctaca gaattggagg aactgttgga ggccatcttt gaagagagac   8100
caccactatc catggcttgg cacgtgggaa tcactgctct ataccagggt tgcagactca   8160
tgtctttggg ggccaggcag tgagtataaa tgagtcaagt gggccagttg gaagatggag   8220
tcagacctgc agtgaactcc caaacacatc tgctaccggg aggggcagca ttactcagct   8280
ccagctcagc gtcatcaggc aggaaggcga ggcagtgttg ccggatgtgc cagtgtttca   8340
aaagaagcca gagactccat ttttattttt ttgtatggaa tctcctgatt ttgaaatatt   8400
ggcagataat tcaaattatc ttaaacacta caggccaaac aaaacatatc tgtgggctag   8460
agacagtctg ccagtttgta actatttctc cagatcatga gtaaatttgg ctttacgatg   8520
gtcactcagt tcttattact ctaggttgtt caaatgaatt aaaaaagctg aaattatatg   8580
aataaacccc tgggcacaca tgaaagaagt gaaaaaccca ttgtttccta ttgtagaaac   8640
atggaagcat gtcagagcca gaggatccag aggaaatatt ctcactagcc tcagaccctc   8700
aggagtgagg gagcttttct tgttaatggc cacgcttgtg cagttttcct tcccaggtgc   8760
tggtgaaaga aacccacagt cttggaatca tggaagtgat accataatga ctgtcagttg   8820
acgttgcttt aaagaatgaa gccacagaat tgtgctgtta gcatgtcgtg agcagttagt   8880
```

-continued

```
tgagttggtg gcttgtaatt tactctgtgt ggatgttatt gatcaaagct tttcattatt   8940
gacagtgtct ccatctgctg tttgctgttt ttaggggaaa ccaccettta tgactcaaca   9000
gcagatgtct cctctttccc gagaagggat attagatgcc ctctttgttc tctttgaaga   9060
atgcagtcag cctgctctga tgaagattaa gcacgtgagc aactttgtcc cggaagtgta   9120
agtttgggga actttttctt gaaaactgtc ctgagagaga aaaactagaa agatgcttga   9180
ggcagaatga gttactggtt gatagtagtc ggtaagaact ctggttctat ataagacaga   9240
tccaggttca aattcaggct gcacctctta tagctgggag accaggtaag ttgggcttct   9300
tggttgcaag cgacaaactt aattcaaaga ctgaatttag gccaggtgca atggctcata   9360
cctataatct cagccctttg ggaagctgag gtgggtgaat cgcttgagcc caggagttca   9420
agaccagctt gggcaacatg gtgaaacccc atctctacaa aaaatacaaa aattagctgg   9480
gtatggtggc ttgcacccgt ggtcccagct gctgaggagg ctgaggtggg aggatcactg   9540
gagcccggga ggttgaggct caatgagctg tgattgtgcc attgcactcc agtctgggtg   9600
acagagtgag accctgtgtg aataaaagag tgaatttatt ggctcatgaa actgagaaat   9660
ccaggaatga gttaagtttt agctttaggc atagctagtt ccagagacct caataatatc   9720
ccgtggccct gtccttatac tcactcaggg ctgactttct attaggcaga gtaggcacgg   9780
tgcttaggat ctgtgatatt taattttaat gaatttaatt acttttaatt aactgaatta   9840
aattttaatt tgttttaaaa ttataggaaa aatgaatata ataatgtata atgattctgg   9900
attacattca tctttatact aatgtagtca taaaatataa tttttgtttt ttttggagac   9960
agagtcttgc cctattaccc aggctggatt gcagtggtat atcatggctc actgcagttt  10020
caaccttcta ggctcaagca atccttccac cccagtggct gggactacag gctcacacta  10080
ccacgcccag ctaatttttg cttttttctc tgtagagata gggtcttact atgttaccca  10140
ggctggtttc aaactccagg cttgaagcag tcttcctgcc tcagcctccc aaagctttgg  10200
gattacaggt gtgagccacc atgcctggcc ccataaaata taatttttga attctttttt  10260
gtttttaatg gaggaagggg ctgaggaagg caaaagtacc tagggcctat gaagtcatat  10320
attggccttg ccttcaccct gtttctgact ttgcttgact tccatgtgat gaggcagttg  10380
gctgttagtg tcccagtttc atactcttac attagtgttt ttcaaccagt gggtgatttg  10440
acgttttcgg ttgtcagagc tagttggggg tggtggtgtg tgagtttggg gggaagggtc  10500
ctactgtcag ttaatgggtg aggccagaga tgccaccaaa caccttacag tgcacaaagc  10560
agccccccata acacagaatt atgtagccca caatgccaac agtgctgaat ttgagaaacc  10620
ccaccttgta caacattgct gtgcaaccaa ccaccctaaa tattactgac ttaaaacaat  10680
agtcactgtg gctgggcgcg gtggctcatg cgtgtaagcc cagcgctttg ggaggctgag  10740
gcggcggatc acttgaggtc aggagttcca gaccagcctg gccaacatgg tgaaaccttg  10800
tctctactaa aaatacaaga attagctgaa tgtggcagcg ggcgcctgta atcccagcca  10860
tttgggaggc agaggcagga gaatcgcttg aacctgggag gtggaggttg cagtgagcca  10920
agatctcacc attgcactcc agcttgggca atgagtgaga ctctgtctta aaaaaaaaaa  10980
aaagttattg tattacctct tgtgtgtgta ggttaattgg actcagctgg ggattcctct  11040
gctctgtatt acattggcca ggattgcagt cacctggggc tctcctgggc tggaatgtgt  11100
gagagggctt actcagtgtt tggtgccctg gcttggaggc tgggcccagc tgggcctctc  11160
tctcttcatg aagtttcagg gccttttgct gtccacatgg cacctctatg tggtctccaa  11220
```

-continued atcagaagtc aaggaactac agcctgtgat gcctattttg taaagaaggt tttactggaa 11280
cacagcccta cccatgtgtt tgtacagtgc ctatggctgc tttcacatca taacagcatt 11340
ttatttcatt ttatttattt ttttttgaga caaagtctca ctctggctgg agtgcagcag 11400
cacaatcata gctcactgca gcctccaact cttgggctca agcaatcctc ctgtctcagc 11460
ctcctcagta gctagtacta caggcccatg ccaccactaa tggctaattt tttaattttg 11520
tgtagagatg ggaccttgtg agattgccta ggctggtctt gaactcctgg cctcaagaaa 11580
tcctcccacc ttggcctccc aaaatgcttg gattacaggc atgagccact gtgcccagcc 11640
cacaacagca tttgagtagt tgtgatagag accaaatggc ctacaaagcc caaaatagtt 11700
cctgtttggc ccatttcgaa aaggcttgct gacctctgag ctacatggtc tctctagcag 11760
gacagcctcg acggtagctc aggtttccaa aacacaaaag tggaagctgc caggctttct 11820
taggggttat cctaggaggg acataggatc tctttgactg cattttattg tttgatgcat 11880
gctctggggc tgctcaaatt ccacctgaga ggaaactaca caaggtcatg aatcccaaga 11940
ggactggggc attgggtgct atttttggag actggctacc acaccctgcc caatggtaat 12000
cttcccttat ctagattaat acaaccccag ggaagattct aacttggctc tgctttgggt 12060
catttgcctc cctggaggtg aggtgttgtg atcggttttg ttggaatgcc caaaggggtc 12120
agggcagtgt gattaccagg acctcatgga atgggggatg cgtggttatg caaaggagcc 12180
ggggatgctg ggtagaaaaa aaatcagcat atgttcacta tagtgctctt cagtatttta 12240
catgtacttt gttctcagtt ttctcatctg taaaatagga ataatgtata tccttttttt 12300
tttttttttt ttggagtctt gctctgttgt ccaggctgga gtacagtggc acaatctcag 12360
ctcactgcaa cctccgcatc ccgggttcaa gtgattctcc tgcctcagcc tcctcagtag 12420
ctgggactac aggcgtgcac caccacactc agctagtttt tgtattttta gtagagatgg 12480
ggtttcgcca tgttggccag gctggtctca aactcctgac ctcaagtgat ctgcctgcct 12540
cggcctccga aagtgctgga attacaggca tgagccacca cgcccattgg gaataatgta 12600
tatctaatga ggctgtgttg gaattgaatg agttaatgca cagaccagat ttgtcatgtt 12660
gcctggccca taggagacaa taaatggtac ccagtattaa taactgtgaa tgtcaacaac 12720
atttaatata ttgtatatct tcaaaatgta cttgaggtat ttgttcatca ttctgttttt 12780
gtttgaataa gctcgtgcct tctttttgtg aatatttaaa tttataagta gcgagtggga 12840
ggggaaggaa gttatgtgat gaggctagct tactgagcca tctgcaggca ccttcattag 12900
tcttgagact gtcctctggt tacttaacag cagtgaatta tctagaatca tttagtgatc 12960
agaagacttg gtttagtgga atgtagattt ttttctaata gacccctctt ccagggaaat 13020
gtttcatatt tttgaagagg tttcctgggg agtgtttaag aggccatgat tgaaaatggg 13080
tgattacatt agtgtgtttt ctattcctcc cctttttgag tttctgtttt ggaatgtaag 13140
ctttgttttt ctacgtggag aagggtccct cagctgcttc tgcccaggtt ttttgaatct 13200
tcctataggg atggagattt tctttgggga ctgttagaga aaatggaata gagtgtagct 13260
ctgaaggaga aggatgtctc cagcagaagt acctctagcc ttgggccaag ggagggaagg 13320
gaagggaacg agcatctggg aaccagggaa gggatttttg tctttcttaa ttactcttac 13380
atccccagtg cccaaaatag tgtctggcat atgttaagtc cttagtaaat acttgttgaa 13440
tgagtgtatg ctcagtgaac aaaataaatg gcaaacatta agcacagtat cagataattt 13500
gtgtaaaaaa tatacagcag tgttatacta aaacttgcac agaggccagg tgcagtggct 13560
cacgcctgta atcccagcac tgggaggccg aggtgggcag atctttgagc tcaggagttt 13620

-continued

```
gagaccaacc tgggcaacat gctgaaaccc tgtctataca aaaaatacaa aaagtagctg  13680
gggcatgggg acgcacatct gtggtcccag ctacttggga ggctgaggct ggagtaattg  13740
cttgaagctg ggaggtggag gttgcagtaa gccaagattg tgccactgca ccccagcctg  13800
ggtgacagag taagaccctg tctcaaaaca caaaacaaca ccccccttcaa aaaaaatcca  13860
aaaccaccac cacaacaaaa aaacttacac agaaaagtgt tgataattgt caaaattggg  13920
ctgttattgg caatttgaca gtagctgaat tactaccatt tgagctatat tcactataga  13980
taagatcttc aatatattta caactttagt actaatggga aaatgataac ttttgaaaag  14040
tttttttttt ttcttattgc aaacaataca caatacaatg ttaaatatag aaggttaaac  14100
gtgcatctga gtctgtttgg gctgcgataa tagatacctt agacttggca atttataaac  14160
aatagaaatt cattgctgac agttgtgaag actgggaagt ccaagatcaa ggcgccagcg  14220
aatctggtat ctggtgatgg ctccctgctt caaaaatggc gccttcttgc tgcatcttca  14280
cctggcagaa ggggcaaaca tgagtccttc agcttctttt tttttttttt tctatgttta  14340
aaacttttgg tccggcgtgg tggctcatgc ctgtaatcct agcactttgg gaggccgagg  14400
caggtgcatc atgaggtcaa gagatcgaga ccatcctggc caacatggtg aaaccccccc  14460
gtctctatac taaaaataca aaaattagcc aggcatggtg gcgtgtgctt gtagtcccag  14520
ctactcagga ggctgaggca ggagaattgc ttgaacctgg gaggcagagg ttgcagtgag  14580
ccaagattgc gccactgcac tccagcctgg caacagagta agactccgtc tcaaaacaaa  14640
caaacaaaaa aaacaaaaaa aaacttttat tttaggttca tgggtaaatg tacaggtttg  14700
ttatgtaggt aaacttgtct tggggtttgt tatagattat ttcgtcaccc aggtactaag  14760
cctagtaacc aatagttatt ttttcagatt gtcctccctc ctcccaccct ctgtcctcta  14820
gtaggctcca atgtctgttg ttcccttctt agtgtccttg tgttctcatc ctttagctcc  14880
catttatatg tgagaacatg tggtatttgg ttttctgttc ctgcattagt ttgctaagga  14940
taatgtcagc ctcttttttt tttttttttt tttttttgat acagagtctc gctctgttgc  15000
ccaggttgga gtgcagtggt gcgatcttgg ctcactgcaa cctctgcctc ccgggttcaa  15060
gtgattctct tgccttagcc tcctgagtag ctgggactac aggtgcgcac caccatgcca  15120
ggctaatttt tgtattttag tagagatagg gtttcaccat gctggccacg ctggtctcca  15180
actcttgacc ttgtgatccg ccggcctcgt ctttttccca aagtgctgag attacaggtg  15240
tgagtcactg cacccggccc aatgtcagcc tctttttttag ggaagtgatt taatcacttc  15300
cctaaaagtc ctacctcgtt tttttttttg gttttttctt tttttttttt tttttttttt  15360
ttttttttta ggtagagtct tgctctgtca cccaggctgg agtgcagtgg tgcgatcttg  15420
gctcactgca acctccacct cctgagttca agcaattctc ctgcctcagc ctcctgagta  15480
gctgggatta taggtgcctg ccaccacgcc tggctaattt ttttgtattt ttagtagagt  15540
tggggtttca ccatgttggc caggctggtc ttgaactcct gacctcaagt gatctgccca  15600
aaatgctggg attacaggcg ggagccactg tggccagccc ctgcaagtcc tacctcttaa  15660
tagtattaca ctggggatta catttcaaca tgaattttgt aggggcgagg ggcacaaacg  15720
tttagaatat agcacatcac atacatagtg agagaaaaat ccctcaaaat cttacctgag  15780
acaatcactg ccaacagatt gctgtatagt gtgccaattt tgtttgtgtg tgtgtgtgcc  15840
ttaaaaatat ttattatgga aatttaaaaa cgtaccccaa ggtggccagg tgtagggctc  15900
acgcctgtaa tcctggcact ttgggagccc gaggtgggtg tattacttga ggtcaggagt  15960
```

-continued

```
ttgagaccag cctggccaaa atggtgatac cagtctccta aaaatacaaa aattagccgg  16020
gtgtggtggg cacctgtagt tccagctact cgggagacca agtcatgaga attgcttgaa  16080
ccctggaggc agaggttgca gtgagccaag accatgccac tgcactccag ccagggtgac  16140
agagtgagac tccatcctag taaacaaaca aacaaacaaa caaaccaact aaccaaccag  16200
gataaaactc cctgtctgta aggagtatgt gttctaatgg atactgagcc atcttgttct  16260
gtttaacatg tgcctaatgt tcttttatat gggcggactt gtaggttgtt tcaacttttc  16320
tgttgatgaa cctttaggtg gtttctgatt atttttgtgt tacaacagtt ttcatcattc  16380
acatctttgt atgcatcttt tttgagcaca tgtgcaagta tttctgtgga caatggatga  16440
ttcctagaaa ttgaaagttt ggattactgt gttccaaaaa aggaagcaat acacccagct  16500
atgttggctt ttgctcttgg gtccagatga ttatctgaca aagttattct ctgattgcat  16560
tttcttttct tttcttttct tttttttttt tgagatggag tttcgctctt gttgcccagg  16620
ttggagtgca atggcgcgat cttggctcac tgcaacctct gcctcccagg ttcaagcgat  16680
tctcctgcct cagcctccta agtagctggc attgcaggca tgcgccacga cacctggcta  16740
atttttgta tttttagtag agatgggatt tctccatatt ggtcaggctg gtcttgaact  16800
cttgacctca ggtgatccac ccgcttcagc ctcccaaagt gctgggatta caggcgtgag  16860
ccacagtgcc tggccctctg actgcatttt cacagtgttt tgggtcctta tctctacctc  16920
agtacctcaa tattcagtgc ccactgggcc cttagatact gcagctaaaa gtgcacaggg  16980
gtggagtgat gtgacggttt tggggtcaca gaagcagctg gtatagagag aagttgtgaa  17040
gttttttttt tttttcctga gacagagtct cgctgtatcc cctaggctgg agtgcagtgg  17100
cttgatctcg gctcactgca acctctgtct ccctggttca agtgattctt atgcctcagc  17160
ctcccgagta gctgggatta taggcatgtg tcaccatacc cagctaattt ttgtgttttt  17220
agtagagatg gggtttcacc atgttggcca ggctggtctt gagctcctga cctcaggtga  17280
tccgcccacc tgggcctccc aaagtgctgg gattacaggc ctgagccatt gcgcctggtc  17340
tttttttttt ttttttaagt aatcataggc ttgaatgtag cctctcatct gttcacctta  17400
ataatccaaa agcctttaga taaagaaatg gagatttgga atggcttctc agaattccaa  17460
gagagtattg tcatggtttt gcctgcaaag caccgtggtc tgtctccttg tgcagttgag  17520
aaagctggtg gtcgccactg acaggcccag agttattaag ttggacactg ctttaagcaa  17580
ctttgtaaac aatccaaggc atactagaga attaggagag attggctttg tgtatgagca  17640
ataacaaaat caagttcaat ccagcaagtt tttggggaat tataattcaa aactcaaata  17700
cttgatctgg aagaaacttg gaaagaggga aggaagacag gcttgttaca gcattgtcag  17760
ggtaaaagga aaataccgtg cagcttttaa ttttgcttct tcatggcatt ccccatgtag  17820
gtgccctaga tttgtttttt acagtggtca cgacttcatg tggatccacc caccactctt  17880
gcctggttcc cccaagggacc aagggaaggt gtattcagga tgattgctga agtgaggggt  17940
ggggtctgtg gctgagaaga ctctcaatac cgcggcactc attataagcc tctgacacag  18000
gagatttcaa ctccacccgt gcaacaaagg aacagggtgg gcaagagtag ttacagttgc  18060
aggctgagtg cgatggttca tgcctgtaat cccagtgctt tgggaagcca aggtgggagg  18120
attgcttgag tctaggagtt tgagaccagc ctgggtgaca taatgagacc ctacctgtac  18180
aaaaaaattt taaaaattag ccagattggt ggtgtgcgcc tatagtccca gctactctgg  18240
agaatgaggt gggtgagggt cccttgagtc caggagttcg aggctgcagt gagttatgat  18300
tctatgattt caccactgca ttccagcctg ggcgacagag caagattgtg ttcttttttt  18360
```

-continued

```
tttttgagac ggagtctcac tctgtcaccc aggctgaagt gcagtggtac gatctctgct  18420
cactacaacc tgcacctccc aggttcaagt gattctctcc ctcagcctcc cgagcagctg  18480
agattaaaag cggccgcttg tgtgcagcta atttttgtat tgttagtaga gatggggttt  18540
catcatgttg gtcaggcttg tcttgaactc ctgacctcag gtgatccacc cgcctcgccc  18600
tcccaaaatg ctgggattac aggcgtgagc tactgcgccc agccatttgt gtctcttaaa  18660
aaaaaaacta agaaaatgaa aaaaatgaca ttggccaatt cattaaaatg ccactcactg  18720
actgtggtat gaaatggctt tccctttgat ggaccgagtc tgtctcattg tgtgagccac  18780
ttgcagggct gagtatgact ctggaatgta gctcctaacc ttatctgctg cccagccatt  18840
gaaatggcca tcccttccag ttcccagaag attccagtgt gtgtttggga ttttaagaca  18900
gtctcttggt cttcagtgtg gcatctttct gccggatttt ccaggataat tttgattata  18960
agcattgcat tgcccttggt gtgtaatgcc tgtgtatgat gctgttccct tgtaacgtgc  19020
aggattaaat ttttgggtca gccactgctg ctccccttca ttcctgcagg tcattagagt  19080
catcgtacat ttagcgatgt ctcagatcag tgtatctaga gtgttaataa acatgttaga  19140
ttccaaatct actgtccatt taatccatac ttcatacgtt gaggatctct gactgaaaga  19200
ttagacttgg aaaaataata agactgtatg gtaagaaaac tatagttgca aatccatttg  19260
gacatgtagt atgtcagccc tgcagagcag atgtcagaac cccatttagt tctctgagtg  19320
ctaagccctt ctgcccacca cgctgttttt ttttttgag atggagtctc gctctgtcac  19380
tcaggctgga gtgcagtggt gtgatctcgg ctcactgcaa gctctgtctc ccaggttcac  19440
gccattctcc tgcctcagcc tcccaagtag ctgggactac aggtgctcac caccatgccc  19500
agctaatttt ttgtatgttt ttggtagaga cggggtttca ctgtgttagc caggatggtc  19560
tggatctcct gaccttgtga tccacccgct tcggcctccc aaagtgctgg gattacaggc  19620
gtgagccact gctcctggcc cccacgcctt tttttttttt tggagacaga gtttcactct  19680
gtcacccaga ttggagtgct gtggcacaat ctcagctcat tgtgtcctct gcctcccagg  19740
ttcaagtgat tcttgtgcct cagcctcctg agtaggtgga attacaggcg tgcaccacaa  19800
cacctggcta atttttgtat ttttagtaga gatggggttt caccatgttg gccaggctgg  19860
tctcgatctc ctgacctcca gtgatccact tgcctaggcc tcccaaagtg ttgggattac  19920
aggcgtcagc caccatgcct ggacccctct gcccctttaa gcactgccac atattagatc  19980
tacgaaggct ttatggatac aatccaagga agatgaacct tgggctagtg ggataaaact  20040
aagcgcatgt agttagaatg gaatgatctg gaaaccaggt cccaagttgg tctaaattag  20100
actcatgttg actatgtcac actgtaaacc agtctaaatg ctaataagca tgcttgacca  20160
aacactgccc tgcagccttc agagaggaag aaggaaaaca taatttgtat cctctctccc  20220
tattttctga gtctatggga ttcaaattgt agctgccatg gaaactgtac tttggaattt  20280
ctagagccct taattttaac ttaacatata aaaacacttt tgtactgatt ttataattat  20340
tcatgatgga tgagaaagtg aatgtctttg acagtgaggg aagctatccg aatgctattt  20400
tctttttttt ttttctttca taaagatgca tatatttgca tgctttattt acctggggct  20460
aactcttgca tcttttgcag attccgacac catagctgag ttacaggagc tccagccttc  20520
ggcaaaggac ttcgaagtca gaagtcttgt aggttgtggt cactttgctg aagtgcaggt  20580
ggtaagagag aaagcaaccg gggacatcta tgctatgaaa gtgatgaaga agaaggcttt  20640
attggcccag gagcaggtag gaggatttta acatcatgct tttccacttt ctgtaccgga  20700
```

-continued

```
gtgttcattg caaagacgat aatctgctgc actggcgtct aggatcaagc acgttttcct  20760
ctgtgactct atatttaatt atagttgggg caaaaaggtc tctcatgttc ttagctcatc  20820
ttcttgaact gatgttggct aattttgaag gctcacaaat tcctcttgat gtatcatgtt  20880
tctatcgttg taatttattt cagaaccaag gtggcctttt agctaatgaa tttaagatga  20940
tcttttatga ccattagctg aggactcagg atatacatat ggtggggtga atcagattgc  21000
ttttgtacac gctttaggta tttgtgttgt gggcatatgg atttggtttt aaaacaggcc  21060
tttgaagaaa tcaaataaca ttctttgtta tgtggctagg gagttgcttg tttgagagca  21120
ggtagaacgt tatctttttt gttgtggtat ttttctttct tttaaacaag gctactgtct  21180
ctagacatat tgattcattt gctgtgtttt agagagatgg ccgtcagcct tggaattcag  21240
agagtaattt attacttaca gacattttag tgcacatgat atgtctgata atgtacccag  21300
ctctgcagga agcttgcaaa aggaatagaa gtcccatggt tgctattttc agtgtttaaa  21360
aacaaccttg gaaagtggag gaaaaatgca aatgtataaa gcaggtgctt accagctaaa  21420
gtatcacaga agtgggagag caattagcaa attaattaac gatgatgtga ggggagatgt  21480
tgtgggtgag caagggacag ttagggacag ttctcaccga tggggggaaa tgtaggttct  21540
cggcagagag aagtgatgag aacatgttgg gtagaagtgt gacattctgg agtactagaa  21600
tgctatgcaa gtgtgtgtgt gtgggtgtgt gtgtgtgttc agtggttcag aacagactgg  21660
gaaatggcga aatgaggaca tttgggtggg gaggggggaaa tgggtgggaa actcaagaac  21720
cttttttttaa aaaattgtgg taaaatatat ataacataaa gtgtaccatt ttaaccattt  21780
ttaaatgtgc aactgagtgg tattcagtgc attcatgatg ttgtacaacc atgaccgctc  21840
tccatttcta gaatttttct atcatcccaa acagaaactc tctatccatt atacaatacc  21900
tccccattcc cccaagaacc agtttttgaa ttgcagttta ctttgtgagg ctgttgggga  21960
ttatttaggc ctctggaagg aggaggttgg gatcagagtc tggccctgtg gacttcaatg  22020
actttgtgtg gcctccaatc agagaagcag cggagggcag gaagctgctt gtcagaatct  22080
gagagtgatg tggcttcttt gtttagcaat aaaatgtgag cacataatag aaaggaaaag  22140
tgacaggaca tggcagataa tttggaagag aggagtggaa gatgctcact cagcctccca  22200
gctcctgaga aagaactgtg tctcatcagt tcatactacc tgagcatctg ttgtatctgg  22260
tgtgtttcta ggtcctggag aagaggcatt acgtgtagcc ctgaccttgt gatgcttatg  22320
tttttgatgg gaaatagtgc gtgtaaaaag aaaataatcc aacaggccac acggcaggca  22380
aacaatagag atattcaaat aggtatacct tcctccaggt gaatggcctg aaatgaccgt  22440
gtggaagtgt gggctggggg cttataaaat tatacacata caggcgctaa ctaaagccgc  22500
ctattcattc cttaagagga tgcatagaaa agaaaagtag ggtccttaac tgagccattt  22560
ggaatttaag ggcatgagag aagccagcac aagcagtgaa gggaaggaaa agaagtgccc  22620
gagaggaggg agggatgctg ttctgcagac aaggcctgcc gcctgggaga ggcccgcacg  22680
cccacccagg gttctctgac agctggaagg ggtcttcaga gactgtttat attttattta  22740
tttatttatt tatttatttt gagacagagt ctctgtcacc caggctggag tgcagtggtg  22800
cgatctcagc tcactgcaag ctccgcctcc caggttcaca ccattctcct atctcagcct  22860
cccgagtagc tgggactaca ggcgcctgcc acaatgcccg gctaattttt ttgtaatttt  22920
agtagagacg gggttttacc tcgttagcca ggatggtctt gatctcctga cctcatgatt  22980
cgcccacctc ggcctcccaa agtgctggga ttacaggtgt gagccactgt gcctggccga  23040
ctgtttctac tattttagag agagggtctc actgtcatct gtgctggaat gcagtgatgc  23100
```

-continued

```
agtcatagct cactgcaccc tcaaactcct gggcttaagc gaccctcccg cctcagcctc  23160
ttaagtagct gggaccatag gcatgtgctg ccacacccag ttaactttat tatttattta  23220
tttatttaga gaatgagtct cattctgttg cccaggctag aggtgcagtg gcacgatctc  23280
ggctcactgc aaccccgcct cccaggttca agcgattctt cttgctcagc ctcctgaata  23340
gctgggatta caggcacctg ccaccacacc tggctaattt ttgtattttt agtgcagagg  23400
gggggtttc accatgttgg tcaggctggt ctcgaactcc tgaccttgtg atctgcctgc  23460
ctcggcctcc caaagtgctg ggattacagg cgtgagccac cgtgcccggc ccactttatt  23520
attttaaaaa cattgtttta tttttatttt tttgagacag agtccgctgg agttcagtgg  23580
ccggatctca ctcactgcaa cctctgcctc ctgggttcaa gtgattcttg tgcttcagcc  23640
tctctagtag ctgggactac aggcgggtgc caccatgcct ggctaatgtt ttttgtatct  23700
ttttagtaga gacggggttt tgcccatgtt ggccaggctg gtctcgaact cctgacctca  23760
agtgatctgc ccactttagc ctctcaaagt acttgggatt acaggcgtga gccactgtgg  23820
ctagccccca gctaacttta aaaaaaaatt ttgtgggccg ggtgcagtgg ctcacgcctg  23880
taatcccagc actttggagg ccaagcaggg cggatcactt gaggtcggga gtttgagacc  23940
agcctgacca acatggagaa accctgtctc tactaaaaat acaaaaaatt agccgggtgt  24000
ggtggtgcat gcctgtaatc ccagctactt gggagctgag gcaggagaat tgcttgaatc  24060
tgggaggcag aggttgcagt gagcttagat cacgccactg cactacagcc tgggcaacaa  24120
gagcgaacac tccgtctcaa aaaaaaaaaa taaattatgt agaggtggga tctccctatg  24180
ttgcccggac tggtcttgaa ctcctggcct caagtgatcc ttccatctcc ccctcccaaa  24240
gtgttgggat tacaggcatg agccacccct cctggctgag actgcttatt ttatttattt  24300
ttaatttttt ttgttttgag actgcttatt ttaatggaag cttcaggggt cagacggggt  24360
cagacagagt cattggtgag caagcaaagg tgtagactgt tcagttcagc cttccttgga  24420
caccttttat gtgccagaca aaagaaggat cagcatatca ggtgcagtaa attattgggg  24480
ttatgttggt gtttcccaaa tgtgttagat ttatccctgg tagtgttaaa tctcatgatt  24540
ttaggtagta tatggacaac ctatgtaaaa acatttaata gtttaatatt aactagcata  24600
tcaaaacctg tgactttgct cacgcctgta atcccagcac tttgggaggc caaggcggga  24660
ggatggtttg ggcccaggag tttgaggcca gcctaggtaa catggtgaga ccctgtctct  24720
aaaacaaaac aaaacaaaac aaacaaacaa acaaataaac aaatcccctg taacttgttc  24780
taacaataac ctaaacaatt ttttatttaa aattaaataa aaaaattgaa acagtaacca  24840
tttttttttt tttttttgga gacagagtct tgctttgtca cctagtctag agtgcagtgg  24900
cacaatctct gctcactgca acctctgcct tcaaacaatt ctcctgcctc aggcttctga  24960
gtaggtggga ttgattacag gtgcactcca ccatgcccag ctaatttttg tatttttagt  25020
agagacgggg tttcaccatg ttggctaggc tagtcttgaa ctcctgacct gcagtagtcc  25080
acgtgccttg gcctcccaaa gtgctgggat tacaatcaca aatttataga aaagttgcaa  25140
gtaccatgta gtcagggttc ttaagagaaa tggaaccagt aggagataga tatataatca  25200
tctcctagga ttataagttg acacataaga ctaaccgtca catacagtat aaacaacttt  25260
ttttcttaaa ccatttgata gatacacaca cactgatata catagaatat atatacacac  25320
acacagaatg tatatacaca tagaatatat gtgcatacag aatatataca cagaaatata  25380
tatgtacaca tgcatagaat atatttacat atatatgcat atatataatt tatttatttt  25440
```

-continued

```
aagcagttga tttatacagt ttttgttttt gttttttttt tgagacagag tctcactctg  25500
tcacccaggc tagagtgcag tggcgagatc tcagctcact gcaacctctg cccccgggtt  25560
ccagtgattc tcctgcctca gctccacaag tagcacacca ccatgcccag ctaatttttg  25620
tatttttttt agtagagacg aggtttcatc atgttggcca ggctggtctc gaactcctga  25680
cctcaagtga tccgcccgcc ttggcctccc aaagtgctgg gatttcaggc gtgagccacc  25740
acacctggct cccataatgt cttttagaat aaaacgatcg agttgaggat cacacgtgac  25800
acttaattgt cctgtctctt tagtctcctt caatctggag cagttctttg atttttcctg  25860
gactctcatg accttgacaa ttctgatgat tataggccag ttattttgta aaatttgaat  25920
ttgtctgatg ttgcttatgt ttagatttag ggtcttggtc tttggccgga atatctcaga  25980
caagatgctc tgttcttatt gcatcagagc agaagactct ctgtttcagt tgatcacatt  26040
tatgttgatg ctcactttga tcacttgatt aaggtggtgt cagttatgcc tttctacttg  26100
tagggttact ccttcctcct tcgtgatttt atttatttta tttttcttag agacagggtc  26160
ttgcttggtt gcccaagctg gagtgcagtg gtgggatctt ggctcactgc agccttgaac  26220
tcctgggctc aagtaatcca cctgccacag cctcctgagt aactgggact gtaagcgaac  26280
accaccacac ccagctactt tttgtattgt agagatgggg tctcactgtg ttgtccaggc  26340
tggtctgtaa ctcctggcct caagcagtct tccggccttg gcctcccgaa gtgctgggat  26400
tacaggcatg agccactgca cccagcctcc tttgtaatta aaaaagtatt ttatggggag  26460
ttactttcaa gtgatggaaa tattttatat ctatgtggac ttggattttc ctatttcagt  26520
cagtgagtta taatccattt ctgtcactag ttttatactt aaattgttcc caacttggcc  26580
actgagaacc tttttaggtt agcttttgtg tccttttcac atgtctccaa gattcattga  26640
atactttcct gctttctggt atagcaagat gttcaggttc ttttggtact tttactttct  26700
ctgccctggc tctggcatca gtcatttctc agaggagccc tgtgcctttc agtggacaat  26760
ggtgtttaga ggccaagatc tggacattgg gtgttttcat tgctaccggt gtgtcactac  26820
tcccagaccc ctttcagtgg acagcactaa ggaatacaca tacgtatata caatatatcc  26880
acctacacat gtgcgtgcac tcacacacac acatatacat tacatctata tttgtgtatc  26940
catgtctata tattgaaaat tgtggctggg cacagtggct tatgccttta atctcagcat  27000
tttgggaggc tgaggcaaga ggatcacctg aagccaggag ttcaacacca gcttgggaaa  27060
cagagagaga ctctgtctct acaaaaaataa aaagggaaaa ccatgagttc acacccgtgc  27120
ccccagttcc aatccaactt cacagggttc attttagttt tcacccttc catgtttgta  27180
attctcttct ctgacattat acccttaata tgtttactta ttttatgcat ctgtatgcat  27240
ccaatctact gtctttgttg gtatcccacc tccccttggt gggtccagat aatctgctct  27300
gggttgccct ttcacgtgga tgtcttcctt accctgtgtg ggcctgtgat actgggctgc  27360
ccccacacat gagtgctgcc ctcctcacgt tgcttgggac ggcactgtgt cctgggccac  27420
catgactttt ctcataacta gcgtggatgc ttaccttgtt ccacaccagt gaatggcttc  27480
aggaagagaa gaggaagaga aaaatattta catttaaaga aaggtagttt aaagaaatat  27540
gttaggtaaa gaattgagca ggtaatatac ggagctggca aaaattgtga ccaaagtagg  27600
tgaatgattg agatttatgc aattctgggc taagtgacag ccccttccct ttcccttccc  27660
ttccccttcc cttccctttt cttccctttc ccttcccttt ccttcccttt cccttcccct  27720
tcccttccct ttccttccct ttccctcttc ttccttcctt ccttctgttt tcttttccct  27780
tctttccttt gccttttttt tttttttaaa gctagaaaca tcagtttagg cataaagaca  27840
```

-continued

```
gaggaaaagg cttctttttc ctctcacagt tctttataat tgtctaagca gtttcttttt  27900
tccctaggtt tcatttttg aggaagagcg gaacatatta tctcgaagca caagcccgtg  27960
gatcccccaa ttacagtatg cctttcagga caaaaatcac ctttatctgg tgagtcttta  28020
catctgtctc tctggaatta gcctagcact ctgacactca gatgcctgtg gtagaactga  28080
atgttgttct tgcccatgtg gtctcattca tgcaaagact ttcttacctt acaggtgtct  28140
ccctggtttc ctcgttataa agatcaagag ctaacccatt tagaaacagc ctcattgggc  28200
tgaacgtggt ggctcacgcc tgtaatccca gcattttggg aggccgaggc gggtggatca  28260
cgaggtcagg agatcaagac catcctggct aacacagtga aaccccgtct ctactaaaaa  28320
tacagaaaaa ttagccgggc atggtgtcgg gtgcctgtag tcccagctac tcaggtggct  28380
aaggcaggac aatcgcttga acctgggaag cggagcttgc agtgagccga gattgcgcca  28440
ctgcactcca gcctgggtga cagagcaaga ctctatctca aaaaaaaaaa aaagaaaaaa  28500
aaagaaacag cctcattgac agttggatat tgtagctgtg gctttcaggc aataataggg  28560
aatcatttat tggggaatag tctgtcatta tgtataagat aatcttgctt taatttttaa  28620
aaacttcctg tgttagcttg cttaggatta aaaaaatgat aatagtgcat ggttgttata  28680
agaaaatgca aacactgcag acatgcatga agttgaaggg aaagcccccc attttctttt  28740
ccttttcttt ttttttgaga cagagtctcg ctttgtcacc caggctggag tgcggtggca  28800
ctatctcggc tcactgcaat ctccacctcc caggttcaag agattcttct gcctcagctt  28860
ccctagtagc tgggattaca ggcacgtgtc accacgccca actaattttt gtatttttag  28920
tagagatggg gttttaccac gttggccggg ctggccgcaa actcctgacc tcaaatgatc  28980
cacctgcctc ggcctcccaa agtgttgtga ttacaggagt gagccactgt gcccggcctc  29040
tccgttttat tttctaatcc tcctccctag gggaagaaat gttaaatggt tacataagct  29100
ttccctttct gacccttaac tgtgctctgt aggagcatgg tgggggatgt ttcttttctt  29160
ttcttctttt tttgagacca ggtctcactt tgccacccag gctggagttc agtggcatga  29220
acatggctca ctgcagcctc gacttcctgg gctccagcaa acctcccacc tcagcctccc  29280
gggcatacac cactgtgcct ggctaatttt tgtattttta gtagagacgg ggttttgcca  29340
tgttgcccag gctggtttcg aagtcctgag ctcaagagat cttcctgcct tggccttcca  29400
aagtgctggg attacaggtg tgagccacca tgcccagctc cggtgggggga tatttctata  29460
tccacatgtg tatagtttac tttataaaaa tggtatgtta ctctgtgctt ggctctccag  29520
cttgctgttg cctttcacca gtgtatccca gacatccttt cttccttgtc agtaacgcag  29580
gtctacttta ttctttgagc agtggcataa ttttccctga tgtgtatata tcataagtta  29640
gagaatgcta aaattcattt tggggccttg tttaggttct tgagggatta aattcctaaa  29700
tttaacaagt gtatcctgga aacaattttt gttcctgatt cagcccttaa aagaggacta  29760
tcatgttacc ttgaatggag ataaacaggc tcacgtaaga gaaaagggta agagggatga  29820
actcccactt atcttaaact tctactggcc cgtttttggg gaatttgctg cttttattcc  29880
tgacctaaaa taaataagtt tatgtgtctt ggtttcatat tagttgagaa cccagtgcct  29940
ggagagaagt tttccttgtc ctctgagtga ggacattcac atatgaatct attggcagac  30000
tggctttgac tgaccacacg tgccttcaga accaatgcca cagctcttag gtttatggcc  30060
tgaaacaccc tttccttaca tattgcctta gaaactttcc ttccttgaga catggggcat  30120
ggaaccctca ccttcacaga tgaccttggt gtgtttctag ggttgctggt gttccaggac  30180
```

-continued

```
atctgttgca gatgcagtat ttaccttgtg ctctctgcat cataagcagc ttctcatgtt  30240
tgaatgtatt aacagacttt taattttttt tatttttgag acaaagtctc actctgtcac  30300
ccaggctagt gttacccagg ctggagtgca atggctcaat ctcagctcac tgcaacctcc  30360
acctcctggg ttcaagcgat tctcttgcct cagcctcccg agtagctggg attacaggtg  30420
catgacacca cgccctgcta atttttgtat ttttagtaga gacggggttt cgccatgttg  30480
gtggggctgg tctcaaactc ctgacctcag atgatctgcc cgccttggcc tcccaaagtg  30540
ctgggattac aggcgtgagc cactgcgcct tttcttttca ttttttttct gagatggagt  30600
ctttctctgt caccaggctg gagtacagtc atgcaatctc agctcactgc aacttccacc  30660
tcctgggtta aagtgattct cctgtcttag cctcctgtgt agctgggact acaggcgtgt  30720
gccactgtgc ccagctaatt tttatatttt tagtagagac ggggttttgc catgtgggtt  30780
aggctggtct tgaactcctg acctcaggtg atccacccgt cttggcctcc caaagtgctg  30840
gggttatagg cgtgagccac tgtgcccagc ctcaggcttc tttattaaga agaagttcgg  30900
gccaggtgtg gtggcttaca cctgtaatcc cagcaatttg ggaggccgag gtgggcagat  30960
caggaggtca ggagatcgag accatcctgg ctaacatggt gaaacctcgt ctctactaaa  31020
aatataaaaa attaggcagg tatggtggcg ggtgcctgta gtcccagcta ctcgggaggc  31080
tgagggagga gaacggtgtg aacctgggag gcggagcttg cagtgagccc agattgtgcc  31140
agtgcactcc agcctgggtg acagagcgag gctccgtctc aagaaaaaaa aaaaagacgt  31200
tcccttgaaa caacagggct tttgtttgtt ttggtttgtg tttgtttgtt attgttgttt  31260
tagatacgta ttttttttctt tcttttttttt ttttaagtga tgatgtctct gttgcagtgg  31320
catgatcata gctcactgta acctcaaatt gcagggctca agtgattctc ctgcttcacc  31380
ttcctgatta gctgggacaa caggtacaaa ccaccatgcc tagcgaattt ttaaattttt  31440
catagagact agggtctcac tatgttgcct aggctggttt cgaactcctg gccccaagtc  31500
atcctcctgc cttggcttcc caaattgttg ggatcacagg catgaatcac cacacccagc  31560
ctatttttag atattttaat tcgagctcta caggaggttt agaacactag cttgtgaaga  31620
taaacttcat tttcaaggcc acacagaatc taagtggtcc tggaattagg aagggctttg  31680
attttttgga ccaaagttga gagtccacag ttttctggtc taccttgcac tgctccataa  31740
actcatattt cttttctctg agctgaagag ctccccttct tggtgtctag tctcaggcaa  31800
cttattctta aaagtaagca ttattgaaat gctttgggat tttcacatca tcaaggtcca  31860
ttttggtaga ggcactgaca gattttgagt gttctgtgtg aaggaactca gttgaggatt  31920
tagtggtcca tgtggcaggc tactgctcag tagcttcagg gaaaccactg cttgcctccc  31980
ctgtggccag tgaggatgat cagaggagtc ccagcaggaa tgcccaaatg tagttttctt  32040
acatgttgat gggagtgcat tgtttcatgt ctaaacagtt ctcaaatcac atcttcagga  32100
gggtactatc tgggcacttt gataatttct cactttgatg tcaccgttct tattaccatc  32160
acctagtttt gtcatagtag aaataacttt cctttttctg tgtgtgtgtg tgtgtgtgtg  32220
tgtgtgtgtg tgtgtgtgtt ttgagatgga gtcttgccgt gttgcccagg ctgtagtgca  32280
gtggcgtgtt ctcggctcac tgcaacctct gcctcccggg ttctcctgcc tcagcctccc  32340
gagtagttgg gattacaggc gtgtgacacc acgcctggct catttttgta ttttcagtag  32400
agatggggtt tcaccacttt ggccaggctg gtcttgaact cctgaccttg tgatccgccc  32460
accttgacct cccaaagtgc tgggattgca ggtgtgagcc accacgcctg gctttttttt  32520
tttttttttt tgagacagag tcttgctctg ttgcccaggc tggagtgcag tggcgggatc  32580
```

-continued

```
ttggctcact gcagcctcca cctcctaggt tcaagcaatt cttctgcctc agcctcctga  32640
gtagctggga ttacaggtgc ccaccaccat gtccggcaaa tttttgtatt tttagtagag  32700
acagggtttc accatgttgg ccaggctggt ttctaactcc tgaccccagg tgatccgcct  32760
gcctcagcct cccagagtga tggaattaca ggcatgagcc actgcgcctg gccacctttg  32820
tcttcttagt tgtggattta actgctgtgg acatctgctt gggcatagcc ttcccggagt  32880
acctcttgga ttgggactgt ctgtgggttt ctgtgctagg acaggctccc agatgtagga  32940
ggcttcccca atgatctcac cactggcatc ggcatcctta gcttctactc agcttttcca  33000
tctgccatct tgcaagatgg aaggttgttt tgtttttgtt tttgtttttt ggtttatttt  33060
ttttgagata gagtctcgct ctgttgccaa ggctggagtt cagtggcgca atctcggctc  33120
agtgcaacct ccacctcctg ggttcaagtg attcacctgc ctcagcctct ggagtagctg  33180
ggattacagg cgcgtgccac catgttcgtt taatttttg tatttttagt agagacgggg  33240
tttcaccgtg ttagccagga tggtctcgat cttctgacct catgatccgc ctgcttcagc  33300
ctcccagagt gctgggatta caggcgtgag ccaccgtgcc cagcctagga gggttcttaa  33360
tgcagctgtt ttttggagtt ctggttgcct cagcacactg ctacttgggt caatgacatt  33420
tttactccct tgttttgtag ctcaattggg tattactgat gggattttgt aattattaat  33480
attttcttgt ctccattttc ttctcaagta ctttgttgct tttgagtaaa atgcttgcta  33540
agggtatagt tttcacataa aagctcaaat ttagcatgga aattaagata tgctcatacg  33600
tctgccatcc cttatctgta attctgaaat acctagagtt ctgaataacc tcaaattctt  33660
ttgttacttg tttatcagca aaacctgatt tgaactcagt ttttggcaaa acttgatcca  33720
agctctctta aggctctttt tagtctttat tcattccctt tagtgtgact tcccattttg  33780
ctataaaatt atgagtgtgt ttgattacaa ggtgatgtcc cagaccctac tgagggtgtt  33840
acataatata aactgtatgt atggctgggc gcggtggctt atacctgtaa tcccagcaac  33900
tttgggaggc cgaggcgagc ggataacctt agttcaggag ttcaagccca gcctggccaa  33960
catggtgaaa ccccgtctct actaagaata caaaaattag ccaggcatga tggtgggcgc  34020
ctgtaatccc agctactcct taggctgagg caggagaatc acttgaaccc aggaggtgga  34080
ggttgcagtg agccaaggtc atgccactgc actccagcct gggcgacaaa gcaagaatct  34140
gtctcaaaaa aaaaaaaaaa aaagtgtgtg taccacttta cctttctaaa atctgaaaaa  34200
ttctgaatct ggaaacccat tctgcttcaa gataaatgga tcctagattt atatcggtac  34260
cgtacagtcc tgaaattcca tcctatctat tggccacttt tacatcaaca aacctttgaa  34320
gtttggggaa acttacatat cacgctccct tggcagttga acattattta tttattttga  34380
gatggagtac tcgctttgcc caggctggag tgcagtggcg cgatcttggc tcactgcaac  34440
ctctgcctcc cgggttcaag caattctcct gcctcagcct cctgagtagc tgggattata  34500
ggcatgcaac accatgccca gctaattttt gtctttttag tagagacggg gtttcactat  34560
gttaaccagg ctgttctcga actcctgacc ttgtaatctt ccctcctcgg cctcccaaag  34620
tgctggaatt acaggcgtga accaccacgc ctggccctga agatacattt taaatcaatg  34680
aaaaaaacaa caggattcta cctcctatgg tatatccctc ctggctgtct cttctctcca  34740
gtcttgcctc tgctgtgtgg gtttcaggca tccatcttct ctactctgaa ttactgtgat  34800
aacctctgaa gtattttccc tgccatctgt ctggcccttc tcccaggtct tccacatact  34860
gcagccaagt cagcccgctg ttgaaaccct tcaagactcc ctgctgtcct ctggatgaag  34920
```

-continued

```
tccagactct tccacgtgac ttaccaggcc tttcttgcac ttgtccccag ccacttactg  34980
tttctctctt tctaccttaa catcctgaac ttcctttggt tctttgacct tgcctctgac  35040
ctttttccat gctgttcact ctttccctgt tcaccttgct aactcctctt tctctttctg  35100
ggttggatca gatttcactt cttccagaag cccttcctag accctatact tctggaatgg  35160
cgccttttga ctgtacgctc attgcaccct gtacttctcc tttatgagtg ggtgctggtc  35220
tgtcccacta ggctacttca tccataaagg gagagtagag ctttaccaag tcaatgctta  35280
agcaatattt attggatgaa tgtgtgatta atttcataga aatttgatgt gcattcaaat  35340
ttacttattg tattacggaa cttgcattat attctcagtg gagttatttt ctttcacgtg  35400
tgtaattcaa gatagactca gtgagatttt caaaatttgg aatgcagtgc aaggaaattg  35460
aacttgagtt cttttgcatt ttgatggtta aaaatttccc atttgtggtg acataccaca  35520
ataagccagt gaatgtggct tattgttttc tggtctatag aaaattgtcg caaactctgt  35580
cataatgtct ggttctatat aacaaagcta gtcctgtatt ctgcatgtgg ctgatggaaa  35640
cagtgctctg ttgatctggt tcatgaagaa atctgttcaa ttctgcataa cagatgcctt  35700
catcagtgtc cttccatgaa ggagctgatc ttcacaaaga acacatagtt ttgcatccca  35760
ccacttgcag tatttttttt tttttttttt tttttttgag atgcagtctc gctctgtcac  35820
cctggctgga gtgcagtggc atgatctcag ctcagtgcaa cctctacctc ctgggttcaa  35880
ttgattctcc tgcctcagcc tcctgagtag ctgggattac aggcgcacac caccatgcct  35940
ggctaatttt tgttgtttta gtagagacgg agtttcacca tattggtcag gctggtctca  36000
aactcttgac ctcatgatct gcctgccttg gcgtcccaaa gtgttgggat tacaggcgtg  36060
agtcactgtg ccctgccagt attgttttgt ctaaattatt tgtgctgatg tttttcctac  36120
tgtggttttc ttcagattac ccttgctctg agcctgcaat tgactcatga acttcttttc  36180
catgttctaa ccttacaatg acttccttgt gttcactcca aatgtttttc cctggttgca  36240
tgtagagatg tattagctaa ggtacatgct tagctgctgt atcaaagaga ccctaatgta  36300
caacccaggc tggtagagca gctctgctgt atgtgttaat tcagggaccc aggttccttc  36360
catgttgtga ctcccccctt ccttaggatg ttgtcttctt ttacatggct gaagttgggc  36420
catttcatgt ctctgttcca gctgcctggt aggaaaaaag aacagaaatt cagagtaagc  36480
aaattctttt tctatagatg gatgcggaag ttggacacat catttcctct cacattttct  36540
cggccagaac gtagtcatgt gactgcacgt ctagctgcta aggagactgg gaatttactg  36600
tcggctgtgt ggcctctgtc aagctaaaat tcttattact gtggaataag ggaaggatgg  36660
atttgggggc acaattaata gtctgtcaca gaggctaaaa cagctgcttt tggctgggca  36720
cggtggctca cacatgtaat ttcagcactt tgggaggccg aggcaagtgg atcacttgag  36780
atcaggaatt tgagaccagc ctggccaaca tggtgaaacc ctgtctctcc taaaaatata  36840
gaaattagcc gggcatggtg gcgggtacct gtaatccgag ctactccaga ggttgaggca  36900
ggagaattgc ttgaacctgg aaggcagagg ttgcagtgag ccaagatggt gccactgcac  36960
tccagcctgg gcgacagagc aagactccat ctcaaaaaaa aaaaaaaagg ttaaataaac  37020
agctgctttt gtaggtgata caaggtacag ctaagctttg aagccaggcc tgtagtttca  37080
ccttccatat tcttactcaa ggcattatac ttctggatct gaaaccactg gatctgatgc  37140
cctgcttggg atgagttctt tatattatct tgctttcaac ccacacctgt gtaattttat  37200
gggcagcgtt tgtttcctat ataggaacaa tttgaaagtg ggctgtttct aggctttcat  37260
gaatagcagg ctatgctgtc attgggaatc tggagggagt taatgaacac aacttcattg  37320
```

-continued

```
tttactttag tgaaatgtgg cagcttatga tagttttgac agtgagacat gtgctgtttt  37380
gatctctcag ctaagattat ctgatttttc aggcatgtct caaaactcac caggcctgct  37440
cacatgctgc tgcttctgaa gccagggttt ggaaaccagc tgcccatcag aatgaggctg  37500
tgacttagaa tattggttct tgttttatta ccattccttg tttggtctct ccagagtcac  37560
tggccttttc cgcttcaatt ttcttatcgg tgaaatgaga tattaattcc tcttattgac  37620
ttcaattcaa ttgctgagtg tattgttgcc tttgggaagt tctttgagtt ttctgtgcct  37680
ttgaaatagt tgtttttttt tattctggtg ttttgaggca tgtttcaagt gagtgcattt  37740
acacttctac cattttagga gccacaattc agttatgttg tcccagcttg cttggcccca  37800
tccccagagt ttctgattca gtaggtctgg ggtggggccc aataatttgc atttcttctt  37860
ctttttttcga gacagagtct gactgtgtca tccaagctgg agtgcagtgg cacgatcgta  37920
gctcattgta gcctcaaact cctgggctca agccgtcctc ccacctcacc ctcctgagta  37980
gctgggacta taggcatata ctaccatgcc ctgccacctt tttaattttt tgtaaggatg  38040
ggggtctcac tgtgttgctc aggctggtct tgaattcctg ggctgaagtg atcctcctgc  38100
ttcagcctcc ccaaatgccg gcattcctgg catgagccac tgcacttggc caagactttg  38160
catttctaac tagtttccag gtaatgctgc tgctggtgta gggacctcat tttgagaacc  38220
attgttctat agctgtagct atagttagtt tctggttata gcttcttcct tttgtccctt  38280
cagtaatagt gtacacatcc gaaatccctg tccttgctct ttcaggccca ggcatggtat  38340
ctggtcctct tctgttgcta gccctggggt gcttcatcat cccaagttta tttttcttct  38400
cctaacctga acctttgtaa atagcccctt ccctaatgaa cgtcctcaat tccctgtttt  38460
gcgtgtcctg tctgtttctt ggcaagactc tggatgattc agtactcaat gaggattttt  38520
cgcatagatg gatgaaacag gctgggtttc atgttttcta agataaaggt gcttctctct  38580
ttttctcttg gtcactttga ccaagaagaa aataacagag tttttattct caagaagaat  38640
aatatcgggg ccactctgct cagaggccac tctgctttga ggaccccttc tctcctccct  38700
catgccaaag atcaggaaca ttgggcagag cggataacga tgccgccagc gtcattacat  38760
tttcacggca ctttcagttg tgctgagcgt gcaaacattt caaggagaca tttctaagag  38820
gtggctagca cagcatgcct ctaatgccct atgtgaattg gaatagagta ctaaagaact  38880
gttcaatatt caccccatcc ccgcatatgc aagcatgcac gtgggttcat tgtatatgtg  38940
tgtgtgcacg tgtgcacaga cacatttgtc cttcgtttca aatgcaacac aatggatgga  39000
aattgccttc ctggtactgg ggtatggatg caaacaccaa cagagaagca gccgctactt  39060
ccaaactgaa cacatgtgag atttgccctt taattagcat ctgcagctgc tgccatcaga  39120
agggtctgtc tctgttggcc tgaaagtctt tgctttaaaa gagcaagtcc attatagctc  39180
caagccaggc tcgtctgtca gctgctgtgc tttctctgcc atcagcgggg ttgccacatt  39240
gttttgggct gtttcactct aggactcttt cctcctcctg tgcccccagc ctttgattac  39300
catgccttgg tgatcctcat ttgggtgacc tgcagctgct cattgtgtgt gcaggagaca  39360
tctccagtcc ttgtaaggag ggaagatcac tggcttcagt gctgatggac tggttatttt  39420
ccagcccttt gtcgtcagtg atcttgtctt gatatgcaga aaggctccag gtagtcactg  39480
aaaaaaatat aagcagcaga ggtgatggct atatgaaagt cacgtttcat caagggcatt  39540
gctgctatgg aaactttcaa ttcacttgga gtagggagcc atattggttc cacagcctcc  39600
tcagcagtgg gtcccaacac agtgctgggc tagctgcctc tgaatcaccg cagtagctcc  39660
```

-continued

```
ttttactata gattcctggg tcccacccat ggaatgtgat ccatgaagtc tggggttatt  39720
ccctggaatc ctttaagctc cctaagtggt tgggatggga aagagatatg ctttatgtta  39780
ctatacttct tattattatt attttaaaat tcttgccggg cgcagtggct cacacctgta  39840
atcccagcac attgggagac cgaggcgggt ggatcacttg aggtcaggag ttcgagactg  39900
gcctggccaa catgatgaaa tcccgtctct actaaaaata caaaaattag ctgggcatgg  39960
tggcgcatga ctgtagtccc agccactccg gaggctgagg caggagaatc gcttgaaccc  40020
gggaggcaga ggttgcagtg agccgagatc gtggcactgc actccagcct gggtaacaga  40080
gtgagacttc atctcaaaaa aaacccaaaa aaacaaaact ctttttcatt ataccggaac  40140
gtcagcttta tggagtcggg gatttttttct gttttattca ctgctgtttc cctaacatct  40200
agaatagtgg ctggcacgat aggcactcaa gtattgattt agatgagtct attttatttt  40260
cttttaaatt tttaattttt attagaggtg gggtctggct ttgttgccca agctggtctc  40320
aaaactcctg gcctcaagcg attgtactgc ctcagcctcc caaagggcta ggataggcat  40380
gagccaacat gcctggcttg tcttattttt aacaagcact tctggtgatt ctgatggaca  40440
atcaggcttg ggaagttcta acctagagga cctacagttg tcttggggta gaagccaagg  40500
ctatcctggt ttttagaatc agtgccttac tgggcatctc tgaagagtaa aagtcaggga  40560
cagagttaca tttttggaca aaaccagatg ctgtgaatgg actcttggtc acaacctggg  40620
tggcgacttg gtccttaact tcttcatcat tttctgctga ccctgttctt tggttcacag  40680
caagtcacct gataagaaga ctcaaagact gctagtttgt tactttagat gatgcttttg  40740
gaacctcttg gtaccatttt aacaatccaa acgtatttta tgaaagcact caagtcctgg  40800
gtctttattg tatctttaag ctctaacagc atgatgattg aataagctgt ggttggccac  40860
acacaagcca tcttccccat ggcctccatt catactagaa tgagcagcta taccccagta  40920
gtatagtttt gggatatggg taacatcttg ggatagccac atttacttag taaatgtctg  40980
gcttacattc tcctaatggt gcactgttgg aatttttggt gtggtaacct ggaatagtgt  41040
tggtgggtca agtttgatta gcatctttga taaggacccg gtctatttag aggtttgtca  41100
ttgagtgtgt ctgttttggc ctcatgttgt gaagcatgct gtgtagcagc tgttgtaatt  41160
tttgttgctt gttttctcaa tcaaccctgg ttttgaagaa atgggaagtt gttccactct  41220
tagactgatc tgacttggga ggggattttc agttcaggaa gttggatctt ctgaatggaa  41280
gcaaagaata catgtctttt tgccacttta caagctggct cttgttttct gaactatttt  41340
actggtcatt gcaaatagaa tgtcaggagt agctgccaaa tactaagttg tgttcagttt  41400
gtcagttctt aagagttgcc ggtggctgct ctgctatgcg tatgactttc tcagccttaa  41460
acttacaagc catactgttt ttttcacatc tttaatacag ccataggaaa tttataactg  41520
tggcgtgtcg tcataaatat gcattgttct tattttaaga catttcagta ctaaaagtat  41580
aagtacttct gttattatct gtgaatttct ttccttcttc tttttttgga tatttaagac  41640
cttttcgatg tcaatatata tttaaaacag acatataaat tagcattcac ccacataccc  41700
agggcctatg gagaaccagg ttgggatgag tgggtgagct acaggcagcc aggtggctcc  41760
tgtgggctcc tcgaggactg gggtgagtaa ctaatgtctg ctaggaactt gggggaaaga  41820
aggtgtgtat gttaggtgct gccccccttct aagtgttcct cttgttcata attgattttt  41880
tttttttttt tttttttttt tttagaagga gtctcgctct gttgccaggc tggagtgcag  41940
tggtgtgatc tcagctcact gcaacctctg cctcccgggt tcaagtgatt ctcctgcctc  42000
agcctcccga gtagctggga ctacaggcat gcaccaccat gcccagctaa tttttgtatt  42060
```

-continued

```
ttnnnnnnnn nnnnnnnnnn nnnnnnnnnn nnnnnnnnnn nnnnnnnnnn nnnnnnnnnn  42120
nnnnnnnnnn nnnnnnnnnn nnnnnnnnnn nnnnnnnnnn nnnnnnnnnn nnnnnnnnnn  42180
nnnnnnnnnn nnnnnnnnnn nnnnnnnnnn nnnnnnnnnn nnnnnnnnnn nnnnnnnnnn  42240
nnnnnnnnnn nnnnnnnnnn nnnnnnnnnn nnnnnnnnnn nnnnnnnnnn nnnnnnnnnn  42300
nnnnnnnnnn nnnnnnnnnn nnnnnnnnnn nnnnnnnnnn nnnnnnnnnn nnnnnnnnnn  42360
nnnnnnnnnn nnnnnnnnnn nnnnnnnnnn nnnnnnnnnn nnnnnnnnnn nnnnnnnnnn  42420
nnnnnnnnnn nnnnnnnnnn nnnnnnnnnn nnnnnnnnnn nnnnnnnnnn nnnnnnnnnn  42480
nnnnnnnnnn nnnnnnnnnn nnnnnnnnnn nnnnnnnnnn nnnnnnnnnn nnnnnnnnnn  42540
nnnnnnnnnn nnnnnnnnnn nnnnnnnnnn nnnnnnnnnn nnnnnnnnnn nnnnnnnnnn  42600
nnnnnnnnnn nnnnnnnnnn nnnnnnnnnn nnnnnnnnnn nnnnnnnnnn nnnnnnnnnn  42660
nnnnnnnnnn nnnnnnnnnn nnnnnnnnnn nnnnnnnnnn nnnnnnnnnn nnnnnnnnnn  42720
nnnnnnnnnn nnnnnnnnnn nnnnnnnnnn nnnnnnnnnn nnnnnnnnnn nnnnnnnnnn  42780
nnnnnnnnnn nnnnnnnnnn nnnnnnnnnn nnnnnnnnnn nnnnnnnnnn nnnnnnnnnn  42840
nnnnnnnnnn nnnnnnnnnn nnnnnnnnnn nnnnnnnnnn nnnnnnnnnn nnnnnnnnnn  42900
nnnnnnnnnn nnnnnnnnnn nnnnnnnnnn nnnnnnnnnn nnnnnnnnnn nnnnnnnnnn  42960
nnnnnnnnnn nnnnnnnnnn nnnnnnnnnn nnnnnnnnnn nnnnnnnnnn nnnnnnnnnn  43020
nnnnnnnnnn nnnnnnnnnn nnnnnnnnnn nnnnnnnnnn nnnnnnnnnn nnnnnnnnnn  43080
nnnnnnnnnn nnnnnnnnnn nnnnnnnnnn nnnnnnnnnn nnnnnnnnnn nnnnnnnnnn  43140
nnnnnnnnnn nnnnnnnnnn nnnnnnnnnn nnnnnnnnnn nnnnnnnnnn nnnnnnnnnn  43200
nnnnnnnnnn nnnnnnnnnn nnnnnnnnnn nnnnnnnnnn nnnnnnnnnn nnnnnnnnnn  43260
nnnnnnnnnn nnnnnnnnnn nnnnnnnnnn nnnnnnnnnn nnnnnnnnnn nnnnnnnnnn  43320
nnnnnnnnnn nnnnnnnnnn nnnnnnnnnn nnnnnnnnnn nnnnnnnnnn nnnnnnnnnn  43380
nnnnnnnnnn nnnnnnnnnn nnnnnnnnnn nnnnnnnnnn nnnnnnnnnn nnnnnnnnnn  43440
nnnnnnnnnn nnnnnnnnnn nnnnnnnnnn nnnnnnnnnn nnnnnnnnnn nnnnnnnnnn  43500
nnnnnnnnnn nnnnnnnnnn nnnnnnnnnn nnnnnnnnnn nnnnnnnnnn nnnnnnnnnn  43560
nnnnnnnnnn nnnnnnnnnn nnnnnnnnnn nnnnnnnnnn nnnnnnnnnn nnnnnnnnnn  43620
nnnnnnnnnn nnnnnnnnnn nnnnnnnnnn nnnnnnnnnn nnnnnnnnnn nnnnnnnnnn  43680
nnnnnnnnnn nnnnnnnnnn nnnnnnnnnn nnnnnnnnnn nnnnnnnnnn nnnnnnnnnn  43740
nnnnnnnnnn nnnnnnnnnn nnnnnnnnnn nnnnnnnnnn nnnnnnnnnn nnnnnnnnnn  43800
nnnnnnnnnn nnnnnnnnnn nnnnnnnnnn nnnnnnnnnn nnnnnnnnnn nnnnnnnnnn  43860
nnnnnnnnnn nnnnnnnnnn nnnnnnnnnn nnnnnnnnnn nnnnnnnnnn nnnnnnnnnn  43920
nnnnnnnnnn nnnnnnnnnn nnnnnnnnnn nnnnnnnnnn nnnnnnnnnn nnnnnnnnnn  43980
nnnnnnnnnn nnnnnnnnnn nnnnnnnnnn nnnnnnnnnn nnnnnnnnnn nnnnnnnnnn  44040
nnnnnnnnnn nnnnnnnnnn nnnnnnnnnn nnnnnnnnnn nnnnnnnnnn nnnnnnnnnn  44100
nnnnnnnnnn nnnnnnnnnn nnnnnnnnnn nnnnnnnnnn nnnnnnnnnn nnnnnnnnnn  44160
nnnnnnnnnn nnnnnnnnnn nnnnnnnnnn nnnnnnnnnn nnnnnnnnnn nnnnnnnnnn  44220
nnnnnnnnnn nnnnnnnnnn nnnnnnnnnn nnnnnnnnnn nnnnnnnnnn nnnnnnnnnn  44280
nnnnnnnnnn nnnnnnnnnn nnnnnnnnnn nnnnnnnnnn nnnnnnnnnn nnnnnnnnnn  44340
nnnnnnnnnn nnnnnnnnnn nnnnnnnnnn nnnnnnnnnn nnnnnnnnnn nnnnnnnnnn  44400
```

-continued

```
nnnnnnnnnn nnnnnnnnnn nnnnnnnnnn nnnnnnnnnn nnnnnnnnnn nnnnnnnnnn  44460
nnnnnnnnnn nnnnnnnnnn nnnnnnnnnn nnnnnnnnnn nnnnnnnnnn nnnnnnnnnn  44520
nnnnnnnnnn nnnnnnnnnn nnnnnnnnnn nnnnnnnnnn nnnnnnnnnn nnnnnnnnnn  44580
nnnnnnnnnn nnnnnnnnnn nnnnnnnnnn nnnnnnnnnn nnnnnnnnnn nnnnnnnnnn  44640
nnnnnnnnnn nnnnnnnnnn nnnnnnnnnn nnnnnnnnnn nnnnnnnnnn nnnnnnnnnn  44700
nnnnnnnnnn nnnnnnnnnn nnnnnnnnnn nnnnnnnnnn nnnnnnnnnn nnnnnnnnnn  44760
nnnnnnnnnn nnnnnnnnnn nnnnnnnnnn nnnnnnnnnn nnnnnnnnnn nnnnnnnnnn  44820
nnnnnnnnnn nnnnnnnnnn nnnnnnnnnn nnnnnnnnnn nnnnnnnnnn nnnnnnnnnn  44880
nnnnnnnnnn nnnnnnnnnn nnnnnnnnnn nnnnnnnnnn nnnnnnnnnn nnnnnnnnnn  44940
nnnnnnnnnn nnnnnnnnnn nnnnnnnnnn nnnnnnnnnn nnnnnnnnnn nnnnnnnnnn  45000
nnnnnnnnnn nnnnnnnnnn nnnnnnnnnn nnnnnnnnnn nnnnnnnnnn nnnnnnnnnn  45060
nnnnnnnnnn nnnnnnnnnn nnnnnnnnnn nnnnnnnnnn nnnnnnnnnn nnnnnnnnnn  45120
nnnnnnnnnn nnnnnnnnnn nnnnnnnnnn nnnnnnnnnn nnnnnnnnnn nnnnnnnnnn  45180
nnnnnnnnnn nnnnnnnnnn nnnnnnnnnn nnnnnnnnnn nnnnnnnnnn nnnnnnnnnn  45240
nnnnnnnnnn nnnnnnnnnn nnnnnnnnnn nnnnnnnnnn nnnnnnnnnn nnnnnnnnnn  45300
nnnnnnnnnn nnnnnnnnnn nnnnnnnnnn nnnnnnnnnn nnnnnnnnnn nnnnnnnnnn  45360
nnnnnnnnnn nnnnnnnnnn nnnnnnnnnn nnnnnnnnnn nnnnnnnnnn nnnnnnnnnn  45420
nnnnnnnnnn nnnnnnnnnn nnnnnnnnnn nnnnnnnnnn nnnnnnnnnn nnnnnnnnnn  45480
nnnnnnnnnn nnnnnnnnnn nnnnnnnnnn nnnnnnnnnn nnnnnnnnnn nnnnnnnnnn  45540
nnnnnnnnnn nnnnnnnnnn nnnnnnnnnn nnnnnnnnnn nnnnnnnnnn nnnnnnnnnn  45600
nnnnnnnnnn nnnnnnnnnn nnnnnnnnnn nnnnnnnnnn nnnnnnnnnn nnnnnnnnnn  45660
nnnnnnnnnn nnnnnnnnnn nnnnnnnnnn nnnnnnnnnn nnnnnnnnnn nnnnnnnnnn  45720
nnnnnnnnnn nnnnnnnnnn nnnnnnnnnn nnnnnnnnnn nnnnnnnnnn nnnnnnnnnn  45780
nnnnnnnnnn nnnnnnnnnn nnnnnnnnnn nnnnnnnnnn nnnnnnnnnn nnnnnnnnnn  45840
nnnnnnnnnn nnnnnnnnnn nnnnnnnnnn nnnnnnnnnn nnnnnnnnnn nnnnnnnnnn  45900
nnnnnnnnnn nnnnnnnnnn nnnnnnnnnn nnnnnnnnnn nnnnnnnnnn nnnnnnnnnn  45960
nnnnnnnnnn nnnnnnnnnn nnnnnnnnnn nnnnnnnnnn nnnnnnnnnn nnnnnnnnnn  46020
nnnnnnnnnn nnnnnnnnnn nnnnnnnnnn nnnnnnnnnn nnnnnnnnnn nnnnnnnnnn  46080
nnnnnnnnnn nnnnnnnnnn nnnnnnnnnn nnnnnnnnnn nnnnnnnnnn nnnnnnnnnn  46140
nnnnnnnnnn nnnnnnnnnn nnnnnnnnnn nnnnnnnnnn nnnnnnnnnn nnnnnnnnnn  46200
nnnnnnnnnn nnnnnnnnnn nnnnnnnnnn nnnnnnnnnn nnnnnnnnnn nnnnnnnnnn  46260
nnnnnnnnnn nnnnnnnnnn nnnnnnnnnn nnnnnnnnnn nnnnnnnnnn nnnnnnnnnn  46320
nnnnnnnnnn nnnnnnnnnn nnnnnnnnnn nnnnnnnnnn nnnnnnnnnn nnnnnnnnnn  46380
nnnnnnnnnn nnnnnnnnnn nnnnnnnnnn nnnnnnnnnn nnnnnnnnnn nnnnnnnnnn  46440
nnnnnnnnnn nnnnnnnnnn nnnnnnnnnn nnnnnnnnnn nnnnnnnnnn nnnnnnnnnn  46500
nnnnnnnnnn nnnnnnnnnn nnnnnnnnnn nnnnnnnnnn nnnnnnnnnn nnnnnnnnnn  46560
nnnnnnnnnn nnnnnnnnnn nnnnnnnnnn nnnnnnnnnn nnnnnnnnnn nnnnnnnnnn  46620
nnnnnnnnnn nnnnnnnnnn nnnnnnnnnn nnnnnnnnnn nnnnnnnnnn nnnnnnnnnn  46680
nnnnnnnnnn nnnnnnnnnn nnnnnnnnnn nnnnnnnnnn nnnnnnnnnn nnnnnnnnnn  46740
nnnnnnnnnn nnnnnnnnnn nnnnnnnnnn nnnnnnnnnn nnnnnnnnnn nnnnnnnnnn  46800
```

-continued

```
nnnnnnnnnn nnnnnnnnnn nnnnnnnnnn nnnnnnnnnn nnnnnnnnnn nnnnnnnnnn  46860
nnnnnnnnnn nnnnnnnnnn nnnnnnnnnn nnnnnnnnnn nnnnnnnnnn nnnnnnnnnn  46920
nnnnnnnnnn nnnnnnnnnn nnnnnnnnnn nnnnnnnnnn nnnnnnnnnn nnnnnnnnnn  46980
nnnnnnnnnn nnnnnnnnnn nnnnnnnnnn nnnnnnnnnn nnnnnnnnnn nnnnnnnnnn  47040
nnnnnnnnnn nnnnnnnnnn nnnnnnnnnn nnnnnnnnnn nnnnnnnnnn nnnnnnnnnn  47100
nnnnnnnnnn nnnnnnnnnn nnnnnnnnnn nnnnnnnnnn nnnnnnnnnn nnnnnnnnnn  47160
nnnnnnnnnn nnnnnnnnnn nnnnnnnnnn nnnnnnnnnn nnnnnnnnnn nnnnnnnnnn  47220
nnnnnnnnnn nnnnnnnnnn nnnnnnnnnn nnnnnnnnnn nnnnnnnnnn nnnnnnnnnn  47280
nnnnnnnnnn nnnnnnnnnn nnnnnnnnnn nnnnnnnnnn nnnnnnnnnn nnnnnnnnnn  47340
nnnnnnnnnn nnnnnnnnnn nnnnnnnnnn nnnnnnnnnn nnnnnnnnnn nnnnnnnnnn  47400
nnnnnnnnnn nnnnnnnnnn nnnnnnnnnn nnnnnnnnnn nnnnnnnnnn nnnnnnnnnn  47460
nnnnnnnnnn nnnnnnnnnn nnnnnnnnnn nnnnnnnnnn nnnnnnnnnn nnnnnnnnnn  47520
nnnnnnnnnn nnnnnnnnnn nnnnnnnnnn nnnnnnnnnn nnnnnnnnnn nnnnnnnnnn  47580
nnnnnnnnnn nnnnnnnnnn nnnnnnnnnn nnnnnnnnnn nnnnnnnnnn nnnnnnnnnn  47640
nnnnnnnnnn nnnnnnnnnn nnnnnnnnnn nnnnnnnnnn nnnnnnnnnn nnnnnnnnnn  47700
nnnnnnnnnn nnnnnnnnnn nnnnnnnnnn nnnnnnnnnn nnnnnnnnnn nnnnnnnnnn  47760
nnnnnnnnnn nnnnnnnnnn nnnnnnnnnn nnnnnnnnnn nnnnnnnnnn nnnnnnnnnn  47820
nnnnnnnnnn nnnnnnnnnn nnnnnnnnnn nnnnnnnnnn nnnnnnnnnn nnnnnnnnnn  47880
nnnnnnnnnn nnnnnnnnnn nnnnnnnnnn nnnnnnnnnn nnnnnnnnnn nnnnnnnnnn  47940
nnnnnnnnnn nnnnnnnnnn nnnnnnnnnn nnnnnnnnnn nnnnnnnnnn nnnnnnnnnn  48000
nnnnnnnnnn nnnnnnnnnn nnnnnnnnnn nnnnnnnnnn nnnnnnnnnn nnnnnnnnnn  48060
nnnnnnnnnn nnnnnnnnnn nnnnnnnnnn nnnnnnnnnn nnnnnnnnnn nnnnnnnnnn  48120
nnnnnnnnnn nnnnnnnnnn nnnnnnnnnn nnnnnnnnnn nnnnnnnnnn nnnnnnnnnn  48180
nnnnnnnnnn nnnnnnnnnn nnnnnnnnnn nnnnnnnnnn nnnnnnnnnn nnnnnnnnnn  48240
nnnnnnnnnn nnnnnnnnnn nnnnnnnnnn nnnnnnnnnn nnnnnnnnnn nnnnnnnnnn  48300
nnnnnnnnnn nnnnnnnnnn nnnnnnnnnn nnnnnnnnnn nnnnnnnnnn nnnnnnnnnn  48360
nnnnnnnnnn nnnnnnnnnn nnnnnnnnnn nnnnnnnnnn nnnnnnnnnn nnnnnnnnnn  48420
nnnnnnnnnn nnnnnnnnnn nnnnnnnnnn nnnnnnnnnn nnnnnnnnnn nnnnnnnnnn  48480
nnnnnnnnnn nnnnnnnnnn nnnnnnnnnn nnnnnnnnnn nnnnnnnnnn nnnnnnnnnn  48540
nnnnnnnnnn nnnnnnnnnn nnnnnnnnnn nnnnnnnnnn nnnnnnnnnn nnnnnnnnnn  48600
nnnnnnnnnn nnnnnnnnnn nnnnnnnnnn nnnnnnnnnn nnnnnnnnnn nnnnnnnnnn  48660
nnnnnnnnnn nnnnnnnnnn nnnnnnnnnn nnnnnnnnnn nnnnnnnnnn nnnnnnnnnn  48720
nnnnnnnnnn nnnnnnnnnn nnnnnnnnnn nnnnnnnnnn nnnnnnnnnn nnnnnnnnnn  48780
nnnnnnnnnn nnnnnnnnnn nnnnnnnnnn nnnnnnnnnn nnnnnnnnnn nnnnnnnnnn  48840
nnnnnnnnnn nnnnnnnnnn nnnnnnnnnn nnnnnnnnnn nnnnnnnnnn nnnnnnnnnn  48900
nnnnnnnnnn nnnnnnnnnn nnnnnnnnnn nnnnnnnnnn nnnnnnnnnn nnnnnnnnnn  48960
nnnnnnnnnn nnnnnnnnnn nnnnnnnnnn nnnnnnnnnn nnnnnnnnnn nnnnnnnnnn  49020
nnnnnnnnnn nnnnnnnnnn nnnnnnnnnn nnnnnnnnnn nnnnnnnnnn nnnnnnnnnn  49080
nnnnnnnnnn nnnnnnnnnn nnnnnnnnnn nnnnnnnnnn nnnnnnnnnn nnnnnnnnnn  49140
```

-continued nnnnnnnnnn nnnnnnnnnn nnnnnnnnnn nnnnnnnnnn nnnnnnnnnn nnnnnnnnnn 49200
nnnnnnnnnn nnnnnnnnnn nnnnnnnnnn nnnnnnnnnn nnnnnnnnnn nnnnnnnnnn 49260
nnnnnnnnnn nnnnnnnnnn nnnnnnnnnn nnnnnnnnnn nnnnnnnnnn nnnnnnnnnn 49320
nnnnnnnnnn nnnnnnnnnn nnnnnnnnnn nnnnnnnnnn nnnnnnnnnn nnnnnnnnnn 49380
nnnnnnnnnn nnnnnnnnnn nnnnnnnnnn nnnnnnnnnn nnnnnnnnnn nnnnnnnnnn 49440
nnnnnnnnnn nnnnnnnnnn nnnnnnnnnn nnnnnnnnnn nnnnnnnnnn nnnnnnnnnn 49500
nnnnnnnnnn nnnnnnnnnn nnnnnnnnnn nnnnnnnnnn nnnnnnnnnn nnnnnnnnnn 49560
nnnnnnnnnn nnnnnnnnnn nnnnnnnnnn nnnnnnnnnn nnnnnnnnnn nnnnnnnnnn 49620
nnnnnnnnnn nnnnnnnnnn nnnnnnnnnn nnnnnnnnnn nnnnnnnnnn nnnnnnnnnn 49680
nnnnnnnnnn nnnnnnnnnn nnnnnnnnnn nnnnnnnnnn nnnnnnnnnn nnnnnnnnnn 49740
nnnnnnnnnn nnnnnnnnnn nnnnnnnnnn nnnnnnnnnn nnnnnnnnnn nnnnnnnnnn 49800
nnnnnnnnnn nnnnnnnnnn nnnnnnnnnn nnnnnnnnnn nnnnnnnnnn nnnnnnnnnn 49860
nnnnnnnnnn nnnnnnnnnn nnnnnnnnnn nnnnnnnnnn nnnnnnnnnn nnnnnnnnnn 49920
nnnnnnnnnn nnnnnnnnnn nnnnnnnnnn nnnnnnnnnn nnnnnnnnnn nnnnnnnnnn 49980
nnnnnnnnnn nnnnnnnnnn nnnnnnnnnn nnnnnnnnnn nnnnnnnnnn nnnnnnnnnn 50040
nnnnnnnnnn nnnnnnnnnn nnnnnnnnnn nnnnnnnnnn nnnnnnnnnn nnnnnnnnnn 50100
nnnnnnnnnn nnnnnnnnnn nnnnnnnnnn nnnnnnnnnn nnnnnnnnnn nnnnnnnnnn 50160
nnnnnnnnnn nnnnnnnnnn nnnnnnnnnn nnnnnnnnnn nnnnnnnnnn nnnnnnnnnn 50220
nnnnnnnnnn nnnnnnnnnn nnnnnnnnnn nnnnnnnnnn nnnnnnnnnn nnnnnnnnnn 50280
nnnnnnnnnn nnnnnnnnnn nnnnnnnnnn nnnnnnnnnn nnnnnnnnnn nnnnnnnnnn 50340
nnnnnnnnnn nnnnnnnnnn nnnnnnnnnn nnnnnnnnnn nnnnnnnnnn nnnnnnnnnn 50400
nnnnnnnnnn nnnnnnnnnn nnnnnnnnnn nnnnnnnnnn nnnnnnnnnn nnnnnnnnnn 50460
nnnnnnnnnn nnnnnnnnnn nnnnnnnnnn nnnnnnnnnn nnnnnnnnnn nnnnnnnnnn 50520
nnnnnnnnnn nnnnnnnnnn nnnnnnnnnn nnnnnnnnnn nnnnnnnnnn nnnnnnnnnn 50580
nnnnnnnnnn nnnnnnnnnn nnnnnnnnnn nnnnnnnnnn nnnnnnnnnn nnnnnnnnnn 50640
nnnnnnnnnn nnnnnnnnnn nnnnnnnnnn nnnnnnnnnn nnnnnnnnnn nnnnnnnnnn 50700
nnnnnnnnnn nnnnnnnnnn nnnnnnnnnn nnnnnnnnnn nnnnnnnnnn nnnnnnnnnn 50760
nnnnnnnnnn nnnnnnnnnn nnnnnnnnnn nnnnnnnnnn nnnnnnnnnn nnnnnnnnnn 50820
nnnnnnnnnn nnnnnnnnnn nnnnnnnnnn nnnnnnnnnn nnnnnnnnnn nnnnnnnnnn 50880
nnnnnnnnnn nnnnnnnnnn nnnnnnnnnn nnnnnnnnnn nnnnnnnnnn nnnnnnnnnn 50940
nnnnnnnnnn nnnnnnnnnn nnnnnnnnnn nnnnnnnnnn nnnnnnnnnn nnnnnnnnnn 51000
nnnnnnnnnn nnnnnnnnnn nnnnnnnnnn nnnnnnnnnn nnnnnnnnnn nnnnnnnnnn 51060
nnnnnnnnnn nnnnnnnnnn nnnnnnnnnn nnnnnnnnnn nnnnnnnnnn nnnnnnnnnn 51120
nnnnnnnnnn nnnnnnnnnn nnnnnnnnnn nnnnnnnnnn nnnnnnnnnn nnnnnnnnnn 51180
nnnnnnnnnn nnnnnnnnnn nnnnnnnnnn nnnnnnnnnn nnnnnnnnnn nnnnnnnnnn 51240
nnnnnnnnnn nnnnnnnnnn nnnnnnnnnn nnnnnnnnnn nnnnnnnnnn nnnnnnnnnn 51300
nnnnnnnnnn nnnnnnnnnn nnnnnnnnnn nnnnnnnnnn nnnnnnnnnn nnnnnnnnnn 51360
nnnnnnnnnn nnnnnnnnnn nnnnnnnnnn nnnnnnnnnn nnnnnnnnnn nnnnnnnnnn 51420
nnnnnnnnnn nnnnnnnnnn nnnnnnnnnn nnnnnnnnnn nnnnnnnnnn nnnnnnnnnn 51480
nnnnnnnnnn nnnnnnnnnn nnnnnnnnnn nnnnnnnnnn nnnnnnnnnn nnnnnnnnnn 51540

-continued

```
nnnnnnnnnn nnnnnnnnnn nnnnnnnnnn nnnnnnnnnn nnnnnnnnnn nnnnnnnnnn  51600
nnnnnnnnnn nnnnnnnnnn nnnnnnnnnn nnnnnnnnnn nnnnnnnnnn nnnnnnnnnn  51660
nnnnnnnnnn nnnnnnnnnn nnnnnnnnnn nnnnnnnnnn nnnnnnnnnn nnnnnnnnnn  51720
nnnnnnnnnn nnnnnnnnnn nnnnnnnnnn nnnnnnnnnn nnnnnnnnnn nnnnnnnnnn  51780
nnnnnnnnnn nnnnnnnnnn nnnnnnnnnn nnnnnnnnnn nnnnnnnnnn nnnnnnnnnn  51840
nnnnnnnnnn nnnnnnnnnn nnnnnnnnnn nnnnnnnnnn nnnnnnnnnn nnnnnnnnnn  51900
nnnnnnnnnn nnnnnnnnnn nnnnnnnnnn nnnnnnnnnn nnnnnnnnnn nnnnnnnnnn  51960
nnnnnnnnnn nnnnnnnnnn nnnnnnnnnn nnnnnnnnnn nnnnnnnnnn nnnnnnnnnn  52020
nnnnnnnnnn nnnnnnnnnn nnnnnnnnnn nnnnnnnnnn nnnnnnnnnn nnnnnnnnnn  52080
nnnnnnnnnn nnnnnnnnnn nnnnnnnnnn nnnnnnnnnn nnnnnnnnnn nnnnnnnnnn  52140
nnnnnnnnnn nnnnnnnnnn nnnnnnnnnn nnnnnnnnnn nnnnnnnnnn nnnnnnnnnn  52200
nnnnnnnnnn nnnnnnnnnn nnnnnnnnnn nnnnnnnnnn nnnnnnnnnn nnnnnnnnnn  52260
nnnnnnnnnn nnnnnnnnnn nnnnnnnnnn nnnnnnnnnn nnnnnnnnnn nnnnnnnnnn  52320
nnnnnnnnnn nnnnnnnnnn nnnnnnnnnn nnnnnnnnnn nnnnnnnnnn nnnnnnnnnn  52380
nnnnnnnnnn nnnnnnnnnn nnnnnnnnnn nnnnnnnnnn nnnnnnnnnn nnnnnnnnnn  52440
nnnnnnnnnn nnnnnnnnnn nnnnnnnnnn nnnnnnnnnn nnnnnnnnnn nnnnnnnnnn  52500
nnnnnnnnnn nnnnnnnnnn nnnnnnnnnn nnnnnnnnnn nnnnnnnnnn nnnnnnnnnn  52560
nnnnnnnnnn nnnnnnnnnn nnnnnnnnnn nnnnnnnnnn nnnnnnnnnn nnnnnnnnnn  52620
nnnnnnnnnn nnnnnnnnnn nnnnnnnnnn nnnnnnnnnn nnnnnnnnnn nnnnnnnnnn  52680
nnnnnnnnnn nnnnnnnnnn nnnnnnnnnn nnnnnnnnnn nnnnnnnnnn nnnnnnnnnn  52740
nnnnnnnnnn nnnnnnnnnn nnnnnnnnnn nnnnnnnnnn nnnnnnnnnn nnnnnnnnnn  52800
nnnnnnnnnn nnnnnnnnnn nnnnnnnnnn nnnnnnnnnn nnnnnnnnnn nnnnnnnnnn  52860
nnnnnnnnnn nnnnnnnnnn nnnnnnnnnn nnnnnnnnnn nnnnnnnnnn nnnnnnnnnn  52920
nnnnnnnnnn nnnnnnnnnn nnnnnnnnnn nnnnnnnnnn nnnnnnnnnn nnnnnnnnnn  52980
nnnnnnnnnn nnnnnnnnnn nnnnnnnnnn nnnnnnnnnn nnnnnnnnnn nnnnnnnnnn  53040
nnnnnnnnnn nnnnnnnnnn nnnnnnnnnn nnnnnnnnnn nnnnnnnnnn nnnnnnnnnn  53100
nnnnnnnnnn nnnnnnnnnn nnnnnnnnnn nnnnnnnnnn nnnnnnnnnn nnnnnnnnnn  53160
nnnnnnnnnn nnnnnnnnnn nnnnnnnnnn nnnnnnnnnn nnnnnnnnnn nnnnnnnnnn  53220
nnnnnnnnnn nnnnnnnnnn nnnnnnnnnn nnnnnnnnnn nnnnnnnnnn nnnnnnnnnn  53280
nnnnnnnnnn nnnnnnnnnn nnnnnnnnnn nnnnnnnnnn nnnnnnnnnn nnnnnnnnnn  53340
nnnnnnnnnn nnnnnnnnnn nnnnnnnnnn nnnnnnnnnn nnnnnnnnnn nnnnnnnnnn  53400
nnnnnnnnnn nnnnnnnnnn nnnnnnnnnn nnnnnnnnnn nnnnnnnnnn nnnnnnnnnn  53460
nnnnnnnnnn nnnnnnnnnn nnnnnnnnnn nnnnnnnnnn nnnnnnnnnn nnnnnnnnnn  53520
nnnnnnnnnn nnnnnnnnnn nnnnnnnnnn nnnnnnnnnn nnnnnnnnnn nnnnnnnnnn  53580
nnnnnnnnnn nnnnnnnnnn nnnnnnnnnn nnnnnnnnnn nnnnnnnnnn nnnnnnnnnn  53640
nnnnnnnnnn nnnnnnnnnn nnnnnnnnnn nnnnnnnnnn nnnnnnnnnn nnnnnnnnnn  53700
nnnnnnnnnn nnnnnnnnnn nnnnnnnnnn nnnnnnnnnn nnnnnnnnnn nnnnnnnnnn  53760
nnnnnnnnnn nnnnnnnnnn nnnnnnnnnn nnnnnnnnnn nnnnnnnnnn nnnnnnnnnn  53820
nnnnnnnnnn nnnnnnnnnn nnnnnnnnnn nnnnnnnnnn nnnnnnnnnn nnnnnnnnnn  53880
```

-continued

```
nnnnnnnnnn nnnnnnnnnn nnnnnnnnnn nnnnnnnnnn nnnnnnnnnn nnnnnnnnnn  53940
nnnnnnnnnn nnnnnnnnnn nnnnnnnnnn nnnnnnnnnn nnnnnnnnnn nnnnnnnnnn  54000
nnnnnnnnnn nnnnnnnnnn nnnnnnnnnn nnnnnnnnnn nnnnnnnnnn nnnnnnnnnn  54060
nnnnnnnnnn nnnnnnnnnn nnnnnnnnnn nnnnnnnnnn nnnnnnnnnn nnnnnnnnnn  54120
nnnnnnnnnn nnnnnnnnnn nnnnnnnnnn nnnnnnnnnn nnnnnnnnnn nnnnnnnnnn  54180
nnnnnnnnnn nnnnnnnnnn nnnnnnnnnn nnnnnnnnnn nnnnnnnnnn nnnnnnnnnn  54240
nnnnnnnnnn nnnnnnnnnn nnnnnnnnnn nnnnnnnnnn nnnnnnnnnn nnnnnnnnnn  54300
nnnnnnnnnn nnnnnnnnnn nnnnnnnnnn nnnnnnnnnn nnnnnnnnnn nnnnnnnnnn  54360
nnnnnnnnnn nnnnnnnnnn nnnnnnnnnn nnnnnnnnnn nnnnnnnnnn nnnnnnnnnn  54420
nnnnnnnnnn nnnnnnnnnn nnnnnnnnnn nnnnnnnnnn nnnnnnnnnn nnnnnnnnnn  54480
nnnnnnnnnn nnnnnnnnnn nnnnnnnnnn nnnnnnnnnn nnnnnnnnnn nnnnnnnnnn  54540
nnnnnnnnnn nnnnnnnnnn nnnnnnnnnn nnnnnnnnnn nnnnnnnnnn nnnnnnnnnn  54600
nnnnnnnnnn nnnnnnnnnn nnnnnnnnnn nnnnnnnnnn nnnnnnnnnn nnnnnnnnnn  54660
nnnnnnnnnn nnnnnnnnnn nnnnnnnnnn nnnnnnnnnn nnnnnnnnnn nnnnnnnnnn  54720
nnnnnnnnnn nnnnnnnnnn nnnnnnnnnn nnnnnnnnnn nnnnnnnnnn nnnnnnnnnn  54780
nnnnttctaa taactgtgct ttctactaca ttaagcctat tttttttttt tttttttttt  54840
tttgagatgg agtcttgctc tgttacccag gctggagtgc agtggcacaa tatcggctca  54900
ctgcaaccct gcctcctggg ttcaagcgat ttcctgcct cagcctcctg agtagctggg  54960
atcacgggtg cccaccacca tgcctggcta atttttgtat ttttagtaga gatggggttt  55020
caccatgttg gctaggctgg tcttgaactc ttgaccttag gtgatccgcc tgcctcggcc  55080
tcccaaagta ttgggattac aggcatgagc cactgtgcct agcctgtgaa gctcatttct  55140
taaggctctg ataaatgtat atgttttagt ttcaaccaaa aggaaaagga acgtatttcc  55200
tagatttttg tatctcacct aattttcatc tttctggaat gcttaataca tatttttatg  55260
tacatacatt atttgttatt cttgagcctc ctcttgagtg aaaatttccc cttagatgac  55320
tcttggagct aatttatttc cttcccttta gctcactcac tcattcaatc attcaataac  55380
gagtgcgtta tcataccagg tactgttagg tagcaggttt acagggatga gcagaagaag  55440
caggccctct ctgccttctt tctttttcat cacactgaaa tcacagcgca ttgtgtgtgt  55500
gcaaaagtag agtgcagagg gaacatgcag aaaggagtta taggatagaa aaggtagcca  55560
aggaaagcag caagaacagc atgatttgtt cagggatctt taaatagctc atcattgttg  55620
gacagcaaag ggagagatgg ggaacgtggc aagatgagat gagaagggga gccggggtca  55680
agccatggag gacgctgaac ccctacaaag gaactaagcc tattgatgtg aacaggccac  55740
ttattttggg aacacgcctt tggtccaaag ggaagagggc acgaaacttc cttctctaaa  55800
aaacaaaaaa aaagaaactt gcatatatga gaaatacttt cttcactttg cagcatgaga  55860
aacggaatcc ctactaagga aataattctc ttattttttt tggaacagcg gtttttgaaa  55920
tttccagatg accccaaagt gagcagtgac tttcttgatc tgattcaaag cttgttgtgc  55980
ggccagaaag agagactgaa gtttgaaggt ctttgctgcc atcctttctt ctctaaaatt  56040
gactggaaca acattcgtaa ctgtaagtag ggctgttttc cttaatttgg gatgttggga  56100
ttatgaaaca ctcaagagag atctgagatt gttctggccc aaagaagctt ctgtaaatta  56160
cataaataaa ggctttaatt atctacagga gtagtaaagg ctaatgatgt agctgtcttt  56220
gagtaataat tctgccttaa aattgtttgt gtagaactgg gtcatttatc aaactctgtg  56280
```

-continued

```
tttatgtggc ctttagaata ttatccctca gtaagttaga ggcacagatt aatggagttt  56340
gaaggttgtc acttggtttg acacagtttc ttccaaaaaa gtggatctag gtatttcatt  56400
cacatatcag gaaaaagact cagattaggc aacatgccca ggttgttctg ctaatggctg  56460
agtttaaaca aaaaccataa acacctccct gtgtttattc atttgtttcc ctcgataata  56520
tttgtctttg ctcacaagca tgtaaaacct ataatgtata tgcacagtag attcattcat  56580
acatcacttt ttataatcag ttagtgcaaa ctgaatgaat tcattaaaaa caaagacctg  56640
gtttattatc aacagaaacc acacaatgct ctttttttctt ttaccagttg gtgatctttt  56700
aaaaatcctt ttaattcttg gatgtgttgt tgattgaatg tgttctactg aatgatcagc  56760
acggattaga gccagtagga aagcagttat cctgtttgag tatgtgtttt gtttttggtg  56820
atggagggag gttgggaaat ggaatctgtt tctaggtgtc aaaaccaggc ttctgattgg  56880
agatgtgtta taattataat tgcttgcacc ttcagctagg acatagtatg gtaaaaaatc  56940
agtattgtcc agttgtaaac cattttgatg gtttctctaa ccttctgctg aaatatttaa  57000
gtaggtagca tttccataaa tctttcttgg caaatgtttt tattattcgg gtggccacat  57060
tgctttattt ttctaaataa atagacatct ccccccaaat ctccaaggtt cagaccttct  57120
aatcagtaat atattttcag ggcattcttc cttttatgct tttagaaaga tgtaatagac  57180
tttcttttag atgctgttca agtacttaat cttttcttgt cttgcctttt tatctctgta  57240
atcttcttga ataagcagtt aatttttttt attcatgaac ctgctgatca tgtctaagaa  57300
tgtatctcca cttaagtaag tcagtgaatg gtgattacct gagtagagtt aaagtagtcc  57360
cccaccctcc tatctgtggc acatatgttc caagtctccc agtggatgtg tgaaactgat  57420
gatagtactg aaacccatct accttttttc ctgtgcatac atacctatgt tatataaagc  57480
ttaacttata aattaggcat aatatatttg actcccagct cccagtgtag tggctctgaa  57540
gactcacaaa atgtatttgc tttaaaaaat tctttttttt ttttttgaga cggagttttg  57600
ctcttgttgc ccaggctgga gtgcagtggt gcgacctcag ctcactgcaa cctccgcctc  57660
ttgggttcaa gcgattctcc tgcctcagcc tcccaagtag ctgggattat aggcatgcac  57720
caccacaccc agctaatttt ctatttttcg tagaaacggt ttttccatgt tggtcaggct  57780
gatcttgaac tcctgacctc aggtgatctg cctgcctcgg ccttccaaag tgctgggatt  57840
acaggtgtga gccaccacgc ctggccaaaa aattctttta atttaagtaa atctttattt  57900
atttactttt gagacagagt ctcactctgt gggccaggca ggaatgcagt ggtgtgatca  57960
cggctcactg cagcctcgac ctcccatgct caagcagtcc tcccacctca gcctcctaag  58020
tagctaggac tacaggtgtg tgccatcaca ctctgctaat ttttttgtat ttgtagagac  58080
gcggtttcac caggttgccc aggctggtct tgaactcctg agctcaagtg atcctcctgc  58140
tttggcctcc caaaatactg ggattacagg cgtgagccat tgcacccagc cctaatttta  58200
ataaatcttt tattttggaa tagtattaga tttatagaaa agttgcaaag atagtatgga  58260
agagttccca catacccttc acccagtttt ccccaacgtt aactcttttt tatatttatt  58320
tatttatttt ttgagacaca gtcttcccgt cgcccaggct ggagtgtggt ggcacgatct  58380
cggctcactg caacctccgc ctcctgggtt caagtgattc ttctgcctca gcctccgagt  58440
agctgggacc acaggtgtgc gccaccatgc ccggctactt tttgtatttt cagtagagac  58500
agggtttcac catgttggtc aggctgatct caagctcctg acctcaggtg atctgcctac  58560
cttagcctcc caaagtgctg ggattacaga catgagccac cgcacccagc cccagtgtt  58620
```

-continued

```
aactcttaca taacagtgtc actgtctaag tgtttgaaaa actatttgtc aaaactaata  58680
ttggtacatt attgttaact acacttcaga cttttttttgg attttaccaa ttctcccact  58740
catgtccctt ttctgtttca ggaatcaatc cgtggtacca tattgcagtt agggtgttta  58800
tatttgatgg gactggtcct agtttagata cttagtgtag ctcagccagc aggtgggatc  58860
ttcatgccca ccgaggattg gtattgtgtt ttcctggtgg ttttatggca tttccgacta  58920
tgcagagagg catggtatta acttcagtgt ctcctagcaa attttcctgt ttttcaccaa  58980
cctctgatcc ctgcattatt tgcaatcaac tcagagattt gtgattgaaa acattgcttg  59040
actccatgct ctttaagcta ttttctaact aggtaactgt aacataaatt atgcttttat  59100
ctagcactgt ttttcataaa cacatgttga gtgattttca tcaaccgaaa tacttcgaat  59160
cattaagttt cccaagttca tggatgctgc ttaaatgcct ggtggttcca ggctgtcgaa  59220
tatttctgcc ttctgcaata agagattgtc ccttgttaaa agcaacatta gcctttgtgc  59280
ggtttcaccc ccaattcttc tttttcttgt tgtaaccaat gaaaggaagt actgcttaac  59340
acagcaggta ataatcttct aaaactcatt atctcaagag gtggtcctgg caggatatat  59400
aaatgcaatt taagaaaggt cttggcaaat ttatgaatga cagaactggg agtggctacc  59460
gagagaaact aggatgcgcc tttgctttga cactgaggtc aggcgtagct tctgtaccct  59520
cctgggtcct gcctcttggg gttgctgcag gcagcacccc atgaaccagg catctgaccc  59580
agttccagga tacttattct tccagcaagt cgaacactct gtgatgagtg actgccatgc  59640
tcatgggtca ccaggctctc attattctgt ttcatttcca gcctcccaca agattggttt  59700
ttcagctgct tatttattat tatcattatt tcaaggctgc tttccaagtt tcagtggggg  59760
gtttcctaag cgtaccagct gccctggttg tgcagttccg gtgatgtttc agatgctggg  59820
ccggattctg gctgtaccca gcctgatctt tctgggcttc aggaaagctg aagccaatca  59880
gagctcctct ttcatgcctt tgggattatg cttaccttgc ctggcatcgt gtacctgctc  59940
ccatccatgg gaaagttttg ctgtctggta ctgtcttcta tcaacatctt ttaagatatc  60000
ttcccccgag gcatcgtgat gtcaacggaa ccagcacact tgtacgtttt atgcaagact  60060
gccatatctc aacagtgaga aatgcataat ggaagtggtg atcacggatt atttcctagg  60120
acattatggc taatgcgcta gagaactcgg atggtctgtt gcgtctgaca tgggcttttt  60180
ctcttgagtt gtctttcttt tgctattctc tgaaagaaac aattcttgcc acatgatcct  60240
gatttttcag gtcctcagca tttgttagca gaaagtacac tttgtttcca tccggcagtg  60300
actcagtggt ggtcccatgc tgatgaaacg ctgagatagt cttcttccaa ataggtatcg  60360
ttttgattgt tgctgcttat ttgctagctg gccctcaata gtgacaatga aacctcaagt  60420
gtataatatg gttgctcagt aatcctgagg gaagacagtc tttggtttgg gggataggga  60480
ttctgtgcct acttagcttc aggtgaaagt cttacaaatt tttgtgtgta gaaataagca  60540
ccatgtacct ccttgggttt tttctttttt tttctagtcc tttagtatgg tcaacaatat  60600
tgtttaggga gtacctattc tgtgctaacc actaggcatt caagtatatt acactatgct  60660
ccttcaaaac acttctgtca aatgtaagga ttattatacc cattttacag atgtggttac  60720
tgtggtaact tggccaaggt catagggcaa gtgaataagg gattctggat ttgggtggag  60780
gtctgtgtga ttccaaagcc catgctcttt ctacaatact atatatgcct ttgcataagt  60840
tattgttatt agtaataata tttgtgatga tggcaaataa taaaccatgt cacactagag  60900
agtgatttaa tctctaggtc tatttaagaa catttggaat tgcaggaatt ggattttttt  60960
ttttttttaa gtgatggagt cttgccatct ttgcccaggc tggtctcaaa cttgtgggct  61020
```

-continued caagtgatca tcctccctct gcctcccaaa gtgatgggat tacagatatg agccaccatg 61080
cccagcctag aattgcagga atttttgaat tgatgattca ttctgatatt tgaatttcta 61140
cagtatgtta agtgcaatgt caggtgctgg tgctgtggct ccattgatga acacatttgg 61200
gtatggccct accttcattg aatttagagt ctaagagcct aaccggtctt ttgcttgaat 61260
agagctgtag tcctgttaaa ttgctgtacc tccaaatggt gggaagttta atgcttcgta 61320
ggcctcccct cactagttta ctgaaccaca tgtgcttgat tttttttga gatggggtct 61380
cgctctgttg cccaggccgg agtgcagtgg cgtgatctcg gctcactgca agctccgcct 61440
cccaggttca cgccattctt ctgcctcagc ctcccgagta gctgggacta caggtgcccg 61500
ccaacacgcc cggctaattt ttttgtattt ttagtagaga cagggtttta ccatgttagc 61560
caggatggtc tcggtctgct gacctcgtga tccacctgcc tcagcctccc aaagtgctgg 61620
gattacaggc atgagccact gtgcctggcc ccacatgtgc ttgattttaa gcaaaataca 61680
gactataggc tgtgacctgg tgatctcttc cccacataca gcatcctgct aacctataac 61740
tctccccatg tctcagatct agcctgggaa aggacaatgt tggatcgatg gcccacttct 61800
aatcttggga tttctaatct caagatgagt tgagaagact caggatgtgt cctgttttct 61860
gtttatttag aacagggttt ctcagccttg gcactgttga catttggggc cagataattc 61920
tttgctgtgg gggctgttgt gtgaattgca ggatgttgaa cagcatcgct gtgctttctc 61980
catggatacc agtagcaccc tccccctgca gttgcaacaa ccaaaaatga ctctagacat 62040
tgcccagtct ccccttgggg gctacagtca ccttcagttg agaaccattg atttagaaga 62100
attggccagg ttattatcag gagagggaac atcacagtaa tctgaatctc tcaatactgc 62160
cactgttact gttaacgaac agcaaaacta ttacgtggag gcagtaggac cttgctactc 62220
agagtgtggt ccgtggaccg gcagcatcgg aatcatctag gagcttgtta gagcttcaga 62280
gactcaggcc tactgagtca gaagctgcat tttaataagg atccccaggg gatttctgtg 62340
catattagag ttgtgaagcc ctgcaagagg aagaaattgg atgctagcct cagagtttct 62400
tgctcatctt tgtgggtctt cctcgttttg tcttcgggct taaggtatgg ggaggccact 62460
ttttggctca ggactcctat gggtgaatgg gactgcttag aactgctggg ttttaggcct 62520
tgctttgagg aatttaaagc ttttctctta gatggacatt acatcgttca tatacttcaa 62580
aatggtggtt tgacctaatc tctgccttct gatagcaaaa agatatttcc ttgactccct 62640
gaaccccact ttactgttgt cccatattgg attttaatta agggtggaat aagtattctt 62700
cactaacatg tttatacatg tatgatatta ccatgccatt tattgagtgc ctagtatgtg 62760
ccaggagctc tgcaaagtgc tttatgctta ttattgttcc atttattctt ccccaaacct 62820
ctgtgaggca ggtcctatca ctagtccaca atacaaatga ggtcatggag cccgaagttg 62880
gcagtggtag gaatcaaact caggtctccc tgactctaaa ttctctttgc ctttgttttt 62940
ttgaaaaagt ggtatagccc atagcagaaa attcacatta tacagaaggt tatacggcga 63000
aaaatgcctc cttcccaccc cacgctcaac ccctctccct caagcgaacc actattgtca 63060
gtttctcata gaactttcca gaatattcta tgctcctata acactagcac aacctatcct 63120
cttaacaaca tctttatgct gcctcccaag aattcagtaa tttttttttt tttgagatgg 63180
agttttgctc tagttgccca ggctggagtg caatggcgtg atctcggctc attgcaacct 63240
ctgcctccca cgttcaagtg attctcttgc ctcagcctcc cgagtagctg ggattacagg 63300
catgcgccac tatgcttggc taattttgta tttttagtag agatggggtt tctccatgtt 63360

-continued

```
ggtcaggctg gtcttgaact cccaacctca ggtaatccgc ccacctcggc ctcccaaagt  63420
gttgagatta caggcgtgag ccaccgcacc tggccaaatt cagtaatttt tattggcagg  63480
ttattttccc gcatcattga aatgaatgaa gcaatcttta tacttcattc atttaagcat  63540
ggccctacca tgcttatcct tcgaatctgc cactcagcca ttggtttctg ataagcagtg  63600
ctcttctcaa atgaaaaccc cttatggctt tttttttttt ttaaacaagg ccacaggtga  63660
tatcatgatt ttgacattat tttttcattt attttgttta gtgtcctgcc tttagaattg  63720
cattatctca atggcttgtg catttagtgt gtgtgtgtgt gtgtgtgttg tgtgtgtgtg  63780
tgtgtggtat gtgagcacgc acatatttgt tttgggccct tttttttttt tttttgaga  63840
cagagtcttc ctctgtcagc caggctggag tgcagtggca caatctcggc tcactgcaac  63900
ttctgcctcc tgggttcaag caattctcct gcctcagcct cccacgcagc tgggattaca  63960
ggcatgcgcc accacgcctg gctaattttt ttgtattttt agtagagacg ggtttcaccg  64020
tgttggccag gctggtctcg aactcctgac ctcaggtaat ccgcccgcct cggcctccca  64080
aagtgctggg attacaggcg tgatgttttg ggccttttaa agttcatctt gtttgtgtat  64140
tcatttgttt ggggcctttt aaagttcttc ttgtttgagg cttcctgtca tttgaagggt  64200
tatctggtca tgttttgttt tctaagctag ttccatgagg atcatagata tgcttctctg  64260
ttaggcttgg ttggccctta aacttgtctt ccttttggac actcacttac ttcaggggca  64320
ggaggaagtg aggaagagga gttgggtctg tttggagtat cagcatggac gggaagggga  64380
gcaagaggga tgggatggta aagtagtgat ggtagaaatt caacttacta gaccaggagc  64440
gtgtgggcgc cacctactaa aacaaaaaag gaataatgaa gagctatagt cagtagctct  64500
tataatctct tatgggatat gtaggcaaat atttatgtgt ctcttcgggg ctgttctgtt  64560
tttagaaggt aaatgattgg taagaaaaaa taggccaaaa agagctaaat gcttatgaat  64620
taggattata ggattttccc ccactagtct gaatttagaa gctacttcca gagatgtcaa  64680
aaatatgtaa tattctactt tattccaaga taaattgagg gcaacttatt ctagaaataa  64740
ttgcaatatt aaaaatataa caatgaataa atagagaaat ctagatgaaa ggagtatgag  64800
gatagggaaa taaagttagg gttgaaagta aaaacaagga agttcctgtt aagttgccaa  64860
aggaagaatg atttgggact ctcagtctcc cagtgaccaa agcagaaagg agaatataaa  64920
cagttacaag agccccagtc gcatgaaaaa aaagtccaga atgctctgct cagaggagac  64980
ccaattttct gaatactgag ccctgaggaa tttcaccact gggtttccca taaatgagac  65040
cccctgtgac ctggtgggcc ccatccctcg gaagtgtacc ctggcatttc catagggactg  65100
cttccttctg ggcctcttag tgcaagccag cagtgcaatg ccacatccaa gtttggtaaa  65160
tcaattctaa gtgagataaa ttaatgcctt ttttgggggga agatgggaaa cagagtgggt  65220
ttgttggaga gcccataaat tggagtcttc aacccttaaa ttctcacttg cgggaaaacc  65280
tttcacaacc aagcaaacgt ggaaatgatt tggccaaaga ttcaaaatta tattaaacat  65340
ctgggactat attcagcagc caactttcta atcaattcta tgagtgtggt gattgcagtt  65400
atgctcattt tctgagggtg aagtttggat agaactaaaa agggcggttg gcaggaatca  65460
aaagagatga aagcctcagg acaaagagtt agaggcccag gtggttcatg actgagagtt  65520
tggaaatgat ttctggtgtc tcacttcaga gaaaataaat atagccaact ctgttcatcc  65580
gtggtgatgg aacattcaac tacagcactg gcagtttggg atctaagacc acccttccag  65640
cacttcaaaa ttctgactta taaaggacac acacaaagaa cagatagcca gatagagacc  65700
aaaataccca ctttattctt ggcagggcaa gcacccagta agctctgatg cagggctctg  65760
```

-continued

```
gtaaatttgc ccatcctacc aacagagaag aatggtggcc tcccctcatg aacggggtcg  65820
gagggggccc ttgccacaac agggggcctg atggaaataa gggggacaag agtgttcggt  65880
tggttgagtg cctgctatgc ctgtgcctag gcagtaaaag gggaagtttt aagtttggcc  65940
cttactttca agacatagta attctacctt ctagtaaaac atggccaaat aaatgtctgc  66000
ttttcatgag ccagataacc tccttcttct ttattggagg agtgagtaga agggtgagac  66060
tagccgggtg cgatgtctcc aacctgggcg aaagagcaag actccatctc aaaaaaaaaa  66120
aaaaaaatta agaataaatc ttttcactgt tggagaaaag ttttgagagg ccgaggtgag  66180
aggatcactt gaggccagga gtttgagact agcctgggca acatagcaag accccctgtct  66240
ctatcaaaaa ataataataa aaaaagctag ctgggtatgg tggtgtgcac ctgtaatccc  66300
agctacttgg gaggctgagg tgggaggatt gcttgagccc aggagttcaa gcttatagtg  66360
aactatgatt gcacccctgc actccctcct gggcatcaga gtgagacact gtctctaaaa  66420
aaaaaaagtt ggagaaaagg atactaaaga gataaaaggg tactaaagag atcgggaagg  66480
cagcaaagaa tgaatctagt ctgatgtgtt attgggtgta cgtaattcat ggcggaaggt  66540
gctgaaaggg aaggttgcct gggcctacag caagcaggtg ctgatgaact agctcctttg  66600
ctattactta aatgtgtcct ggttgggcca gatgtggtgg ctcacacctg taatcccagc  66660
actttgggag gccaaggcgg acggatcact tgaggtcagg agttcgagac cagcctggcc  66720
aacatggtaa aaccccgtct ctactaaaaa tacaaaaaaa gtatccaggc atggtggcag  66780
gtgcttgtaa tcccagctac ttgggaggct gaagcatgag aattccttga acccgggagg  66840
tggaggttgc agtgagccga gatcatgcca ctgcacttcc aacctgggca aaagagcaag  66900
actgagttct caaaaaaaaa aaaaaaaaaa attcctgggg aatatccacc agggtgaaaa  66960
attgggtata tccaaattca gctttgcaaa gaaatgcact catgactagt tgcaatttga  67020
aacgttcctc ttctgagtat ttctagccta tgtaggtgtt tcacagattg ctgagtacct  67080
agactgagag ggagagaaaa aaacaaagta aagctaaaat gttaagaagt ctggttaaag  67140
tgcaatccag aagtgaggga aagcatctct aaaagtatga atctttgggg aaacataact  67200
tgattaccaa aaacttaata ttaagcagcc tcataggaac atggcttttg ggtatggcga  67260
gagccagcta gagctcacat ctccattgaa atccaccacc agagaggtta tctgcctagt  67320
tgttggcagc cagaccctgg cattgtttag attgattgat ggaaggctac tttgggaatg  67380
ctggcttcct tattcattga ctttaaagac agcattgtaa aaattgatca ccagcccaaa  67440
tcaatgttac cctgaagtat ttttatgact ttttggggag gcaaagagat gggataattt  67500
ttgatttatt taagtctatt gcaaactgga actcctttgt cttctttttg aactaccttt  67560
tttgtttttt tgagagagag tcttgctttg ttacccagac tagaaagcag tgatgcagtc  67620
acagctgact gcagccttga cctcccagac tccgatgatc ctcccatctc tcccatgtgc  67680
atcaccacac ccggctaatt ttttgtattt tttgtagaga cagggttttg ccatgttgcc  67740
caggctggtc ttgaactcct agactgaagt gatccacctg ctttggcctc ctaaaatgct  67800
gggattacaa gtgttagcca ccaggcccgg tcttgaactt cgtatataca gtgtgttgtg  67860
tgggcaagtc atgcctgacc acttcctagt gggaggggag aaactagagg gcttgcctga  67920
ggctttaggc aatgtaatct gttctcttgg gatcaattac ttatgcatat ttagtagcca  67980
gctctatttg ctgatcacct aatctgttct cttcgttcat tcccatgaga cttcgatatg  68040
ggatatcttc ctcttcttcc cattgcagcc ttttctctca gagttgttcc catgataaga  68100
```

-continued

```
actcccatca aaatctctgc tctaacatca gttgtcagat tttgccactt ttttttttt  68160
tttttttctg agatgatgga atctcactct gctgcccagg ctggaggcag tgccaccatc  68220
tcggctcatt gcaacctctg tctcccgggt ttgagggatt ctcctgcctc agcctcccga  68280
gtagctgaga ttacaggagc accccaccac tccaggctaa tttttgtatt ttttttagta  68340
gagatgggct ttcaccatat tggccaggtt ggtctcaaac tcctgacctt aaatgatctg  68400
cctgtctctg cttcccaaag tgctgggatt acaggtgtga gccactacgc ccagccacat  68460
tttgttactt ctttctgtaa cctgaatgtg gaaaaactca ctgtctttcc tccactctca  68520
caccataact gtcaacacca cagaagactt ctgtgaccaa atatgtggtc accaccaagc  68580
aagcagtaag ttctgcagtg gacaccacta ggcgtcctcc agttcagttc tggcactatc  68640
cgcctggaga tagggctcaa tcccacaggt ggaggtctca gtccccaaga atgtcccctc  68700
ttcaggcacc agttgcaagt ccaggcctct ggaacttctc gctgactggc ttcaaattgg  68760
ggttcctgca gccccctctt tgagttcaat taattggcta gagctgctca cagaacttgg  68820
gaaaacacat ttactggttt attctaaagg acattgcaaa ggataaagat gaagaaatgc  68880
atagggcgag gtatgggggga aggggttgcga gcttccacgc cctccctggt cgccctccag  68940
gaacctccac gtgttcagct atccggaagc tctccaaact ctgtcctctt gggacctttc  69000
atggagacgc cattggatag gcatgatcaa caaccatgta gaaatgggat tgcacgaaaa  69060
ggctatgatc taatcctcat aggctgagtg gggaatccca gcaaggcctg tttgttcaga  69120
tccttctgta gcattcattc ctccaggtta tggggcagga ccccttctga aatggggtct  69180
tctgacctac aatcagacaa ggcagaggaa atttctttat ggccagctcc aagtcagaaa  69240
ggtgggggaa gattagagtc ctgccttgag cagatgaaag gagggctgga ggaggtcaga  69300
gagagagaga ttctgttttt caaggcctgc ttctaaagcc taaagcaccc ctaaataaca  69360
aaagattgta acaaggacta tgggagtcat aagccaggaa ccgtggatga aaacctatat  69420
atatgtatat atatatctca taataattca aacctgtctc ctgttaatcc catcctctct  69480
gtttctgtta tcatttcctt agtgtagatc tgcctaagtg tagaatttgt agaatttgtc  69540
atgttgacta ttgtagactt gtcttttaga gtttctagca ctagcctctt ccacccatca  69600
ctattgagat gattgtatcc gtctcagtac tgacactaac ccagcactct ggttttacat  69660
ctgtcaatcc atcaagactt cactttcact ttcttccctg cctcattatt cactatgctc  69720
ttgggccatt gctctggctt ctggggcttt tctaaagtag cacttttccc cactccagcc  69780
catgaagata ccttttaacc agctcttgag attaaatccc ctccgtgaca ctttcctgca  69840
ggaacttgca aaaaagtact gcattcccca ctggcaaaac ttgccatcag ccagtttatg  69900
tattctctgc ttttcacacc catatcttga cctctgaaca acacacatat tctcctcttc  69960
atttatttca cagttctgtc ttcataacat tgataagtat gatcacatta gcgctctaga  70020
ttttaagcaa ctggaagata gctatttttt tggtactctt cctttaaatt tgaacatagt  70080
gtctaattag tcaattaaca tttttttaaa agggcgaggg acatcatggt agagagaacg  70140
aagttgaacg tgtttttggt tgaatattag cgcatgccca ctgtattcta ggcacagtcc  70200
tgattcatta tatcatcaca caataattat ttatgtgcct tcatccttta tgacacagtg  70260
ctggctctta ttcatctccc atttctgcaa tccatggtga tgattaaaag tcttaggagt  70320
tttacgaggc tcagtatttt ttttttttaa tatgctagtt cttcatgaat acattgggta  70380
ctctgaagca tatcatttcc tgggtttcct gaagtggtat gttgcgtgga atggcacatt  70440
aggtctaaat aattatcccc tatgtaaggt tcttgttttt cattcattct cttaaaaaat  70500
```

-continued agatattaaa cattaaataa ggacagccag gtattgtttg aggtgttagt gggctatgct 70560
aaaaaatcaa aggtgggaat gaggcagctg gagctcaaag gagcatgtta gaaggagtcc 70620
caagaggaca aatccatttg gttcttcttt ccttgttttt tttcgaatat ttttgaggat 70680
gataattttt ttcccctcaa aagcttttaa tgaatgttag gattaaaaaa gagagagaga 70740
gaatttatag aagagaaatt aactatagct cctaaaatag ctctttgttt ctgaaagcct 70800
tgattctgct atctatttta taactgaaac aaaaacaaaa acaaaaacaa aaaacaacct 70860
caagaagtta cttgtatagc ctctgccact aaggagactg tgttctgatg ttacctcaaa 70920
caggctgatt tattaaaata tttaaaaata tatatggaaa tattttttc tatttttttt 70980
tttagtggct tttcccagtg aacaataggt cttactatat gatttcttat ttgtcattag 71040
tgaatgtggt gggtatgtgg cagctggggg agctgatgat tttataatac tgtatcagaa 71100
atgattagtg taggtactta ttaacatatt tctcagacag aacaatcttg acttttaaaa 71160
cctcttcatt taattcaaac atcaagtacc ctgtttgtgg cctgtgttat gttaggtgct 71220
ctctttacaa gacctatttt cttgctattt aattatatat ttgcttagca aatatttact 71280
ctgcacctac taggtacctg gcactgtgct gtgtactgag gtgccatgtg tacctccatc 71340
aacatagact caagatcaat atgatttcag tgaactaaaa atacctttat tgaagcaaaa 71400
aaaaatcaca ttttgtaagg atcaaaaaag agacatttta tataaggtac aagaaataga 71460
agaattatat ccccaagata tatgtgataa catacttgtt agtttttgga cgtgaccaga 71520
ttttacacaa tccttaaaaa atgcagcaac cagattttaa agtagttctc taatctctct 71580
ttctgtgccc cattagatgt atattggatc ttctcattct gtctttgtct tttgacctct 71640
catgttttcc gtctctttgt ctctgtgtgt tgcattgtac acaaatgctt cttgaactgt 71700
ggtgtgcaca tgaatcacct ggggaccttg ttacaacgta ggttctgatt ccatgggtat 71760
ggggcagggc ctgagattct tagagaatta aattctaacc agctcctgag tggtggtgat 71820
aatgccagtg tgtagaccat agcttaagta tcaaggttct atgtgattcc ctcagatcta 71880
actgctagtt cactaagttt ctcttcagct gtatctagtc tgctatttaa catattcagt 71940
gaatttttaa ccttaaattc aagaacaaga ctttttattt ctggaagttc agtttggttc 72000
ctttcaaatg tacctggttc tttttcaaag tgtcatgttc tttgataaga atttctacta 72060
atttaccttg ataataaaaa tttgtttcat ggctcatttt agattgttct tttatctgca 72120
gtttttggag ggctaattct cccatttctt gtatctgttg ttgcacccgt aaggtgtagt 72180
tgttgatttt tactttttaa ttgtgaattt atttctggta gggattggaa ggaggttgtt 72240
ggggtggggg tggggtgggg agaaaatcct gtgtgccctg ggttgcaaaa acacccctac 72300
aagttgttct ccacttgcat ctgccagtgc tccaagggct cagtgatcct ggaccagtag 72360
tcatgataat ttcttgaatt gtaacaggat actgtaaatg tggacactct acctgaggtt 72420
actgcttctt tctatctgct ttatttcctt cccactgaag ggccctggac aagggtaaac 72480
atctcatcac tttctgggtg gcagaatatt tccagttccc ccacttcttt ttggcttaag 72540
gctgtggctt tttcctctgc ctgaatgtgg ccctaagaag cccttctttt caaactttcc 72600
tgttgtactt gaccgactag ctgtctagag gtttatatcc ctagctttta atctttgctg 72660
tgaatatctt acctgttacc agctagtata tttcacattg acttctcttt ccttttttt 72720
tttttttttt tttttgagac ggtgtttcgc tcttgttccc caggctggag tgcagtggca 72780
cgatcttggc tcactgcaac ctccacctcc caggttcaag cgattctctt gcctcagcct 72840

-continued

```
cccaagtagc tgggactaca ggcatgcacc atcacatctg gctaattttt ttgtattttt  72900
aatagagatg gggttttacc atgttggcca ggctggcctt gaactcctga cctcaggtga  72960
tccacctgcc tcgccctccc aaggtgctgg gattacaggc atgagccact gtgcctggcc  73020
tacttcttct tccttttaac ttgaagatta tctgcccctt tttctaatct taaccgcatt  73080
aagctggctt tgagcatggc aagagtttta tagatgaatc ttattttata gtacaggatt  73140
tcaaaatcat aattatttca ctgagggtgg cttttaccct ccattaatta tacttctcac  73200
tcagaaatgg aattctattt tggtctccta aagataaatt agtatatagt ggaaaggaat  73260
tataaagttc tgctaggaat taaatgatat gattaacaca aacatccaca tggatgtgtc  73320
tctgccctgt gcaggaaaga tgaacattca gtacagattc tgctctatgt cactagcttt  73380
caagacctgc aggttctctc ctaagcatgc aattcctgtg agcagtagca ataatagcag  73440
gtcatatttg tggagtgatt actgtatgct aagaactgtg gtaaacactt ttatatggat  73500
tattttattt aaacctccta atagtccatt gaaatagata ttgccatgtt gaaaactgag  73560
gttcagagag gttaagtgac ttacccagtg tcacagaact agtaagtggt gcagctggga  73620
tttgaactga gattccagaa caattgccat taaccacttt gcttccatat tagtatcatc  73680
tgcaaatctc tctccataaa tttcctcagt ctttatctga gtttccttat ttcaggaagg  73740
aaaacttctg tttttgatcc ttatgaaata caatttccat taaaactttt tttttttgct  73800
attaaaaaag gtaccggata attgaaacca gactggattt gagcctgtgt tgatggaagt  73860
acacatggga tgtgggctga agtgttcaat ctaatttttc tttccatcag ctaattttta  73920
aagtattaag caagtagatt ctgacactaa cagggaagat ttaaattctc ttgagagact  73980
ggaggtgtta aataatttc tggtagtgca cattttacat cttaaatctt cctcactctc  74040
ccacctcatc tcaatgtacc tgaagctctg ggaatgttct tttgtacttc tcaggaacag  74100
ccagacctct ggcttcatct cctctcccct ccacatccct ttcctgctcc aattacttcc  74160
cagcgccact tggatgttgt tgtcatcggg gaactttgga aacagccaga tttttttgga  74220
gtctgtaagc agaaaacaga ctgcttgctg ctcatatctg gcacccagct ttgtccagaa  74280
aacgaggagt taaaaagaag tctgggctgt gaagggctgt gacaactgtc ctagggggag  74340
ctctagcgag ccctggcggg cagtgactca tgctgctctg tcactgggat cagcactggc  74400
ccctggcagg caggcggcag ccaggtgggg ttccagccag agcacgcacg cacggagccg  74460
ggagcatgca gcctgcactg cgggggatgt gatgctcggc tctaactcgc ctggctggcc  74520
cgccacggac gcctcagctt gcaaccatgg taacgtttct ggcgggggac acccccggga  74580
gcccaccgcg atgggcagcc tcctggtgac tgatggacga gtgtccacct cccagaccga  74640
gagcgcttag taggtcggag gaagtggaga ggatgtaaca cgcccccagc cgggagtgaa  74700
gccctgagga ggtaggagcc gcatatgtcc atccgtgcat tcccaccgtc agcgcgcagg  74760
ggtgctgtag atcaccggta ggaactttat ttggctggtg cttcattatg ctgattaaac  74820
tgcagtggat ttgatgggca tgattgcgct ggggaagatg cataatgaac taaaaaaaaa  74880
aaaaagtggt taataagatc tcggagtcga cttgtccggg tatgaatgaa gtagactgca  74940
gtggtatcct aacaggagtt ccagaacctc acacatccct tttcctggtc cttcctctta  75000
tcccggttaa tccacgaaat gtagaagttc catcttattt caacgattag tgctaatcat  75060
taataattta gacctgtctg gaggagggaa tccataggtt taggtctcct agcatcctgg  75120
cactagccag cagctgctct gtaggagcct tctggaaaca gcaggaagga gcggcttccc  75180
cacgagttcc ccaagtgctt tcgttggccc aagtgctttc gttggcccaa gtgacctgtt  75240
```

-continued

```
tgagtttgct cttcagttta ccccaggcgg gaaggcagcc tgtctgcggg ttggtggcca  75300
tgttggcaga gaaggggtta atctcttgtt gctgtaggag ccgaggttgc gagctagatt  75360
gaaagcaggc gctgcagtgc catcgccagc gccgaaggag taagacgatc ttctccgcaa  75420
cagtgttgaa tccggctgaa attttttttc ctccccgcct cctttcttgt ttttctttaa  75480
ccagctcctc ccccttcgt tcccaccctc aagtctgacg atgacacctc caattttgat  75540
gaaccagaga agaattcgtg ggtttcatcc tctccgtgcc agctgagccc ctcaggcttc  75600
tcgggtgaag aactgccgtt tgtggggttt tcgtacagca aggcactggg gattcttggt  75660
agatctgagt aagtgaaaat ttgactttct aaagggacct gcattgatgc aaggcttttg  75720
gagccaaagg tggtggtggg ggggtggggg aataggtggg gggagtgcag tggagggaag  75780
ctgctagtca cctgcattgg gaaagcagtc tacctgttag ggctttgcgg gggtagcctg  75840
ttaatattct cattttgcag tgtgtaaggt acctgttcct gtctgtggta tgataattgt  75900
caattgggta ctttgggtta gttttccaat ctttggtctt ctttaaaggg gagagagtgg  75960
gagatttcca gcagtgcaga tccccggtca aaggagaaat gtgcaggagt taagatgagc  76020
tgcccatcta tctaaccatc tatgtatctg tctctcaagt gggtggatgg gggttgctat  76080
cttggctgta taaagaatcc taaaaacctt gtctcataag ctagaggttt cctgatgggt  76140
ttaactgagc tgcaagtggc tgaaccagag ctctaacaga gagatggtgc tcggctcctc  76200
tccaagtatg ctgcaagatc agggatctgg cagctgagcc tctctgagct ggtggagcgc  76260
tggcagccag agaaagcccc gttactgtga gccaccagga gggagtgtga tgtagccgag  76320
tcattgattc acagaaactg ggcttcatag gggggaaaaa aaccaggaga ctagaaaatg  76380
gaaatataaa tatcactgta aacctcttga tctggtaggt ctttctccat tctcataaaa  76440
gctattgaaa aatgcattaa cagagcactt ggaattagag ggtcgaggct tccaggagcc  76500
tcctggaatt tctgtaaaat gcagtagctt ctgtggatgt gggaggtcag tatcttgcct  76560
cattctctca tgatacaatg acattctgtt ttcagaggag tgagttcccc agaagatctt  76620
ggactgatgg tgttatttgc cagccaccct ggtccctgca ctttcaggtt ctcagagggt  76680
aatgttgggt tagttgctgc ccacttagga gacgagcaga atttgatatt cttcttggca  76740
gcatctttcc ctctttgtgg tatttgtagc ttagatatcg atttataggg atgttatgtt  76800
ggttcctgga tggtgtctcc ctatgggtgc tattttgaca gtaacgttcc tgaaaagatt  76860
tcagagtgtt gtggggaatt gggcatttga tacgaaataa ggttgtgggc tgtgattgaa  76920
tgtgagggag gtttttatgt tgcaagatgt tgaagtggtc tttcttgatc ccctctctgg  76980
gggctgggtt tcaaattcag gttggatttt ggtagtgtta gatgtgcctc tctgtctgat  77040
ttgctccaca accccaaagc aatctggatg gtggtgggag aggcagagtg ctaactagct  77100
gttgaatgtg ccatcagatg ggtttgaaac ggctcagcag gattgggagg ttttgccatt  77160
ggcatcaaag agcagggcag aagcggaggc ctgatgttga aggatgcatg gttagtgggc  77220
agtataacct tgacacacgc agcacactga aggtcacacg tcgtactgga aggacgtgtg  77280
gagagttcta gttctggtta gcagtgggct ggctgggtca gaatgcaagc ttgcttgggt  77340
gttggtcagt gatctgaaag acgagggagg attcgaggga gttagatttc aggggaaaag  77400
gcagaatgat atgggagatc ttaggcattg caattaatct gaagcagtgt gtgattaatt  77460
gcttattttt caggaagact tgaatgacat ctttctgttt ctcacagaaa gctcagttta  77520
gggagctctc tgacagggac atctcagtat taaggctgag gcactcgata aatatttgtt  77580
```

-continued

```
gatttaattt acctatgatc ctttcctcca gaagtgttta tattgcttat tgtatttgaa  77640
gatgtgctat ctcacctctg gtagtttaaa ctatatcctt agagcacaaa acgagctgct  77700
gttcctgacc caacagaatg tttaataaga ttcttatttc aaaaaaggtc catgcaaata  77760
aaactgtgta tttcttattt ggacgatggc atcagagtat tcctatcatt ggggaacttt  77820
aacgtttttt caaagcttgg caacggggtt ggaatcagaa agattttctt tcatcttgcg  77880
tcttgttatg tgttattgct attggacttg gctactctgc tgtaggcagc cctgtgggtg  77940
atacctacaa gcatcatttt agaaattcat ccacctgttg gatgtagatg accctggaca  78000
tatcagattg tgattaatta gaaatctaat aaaagagagg cagtgatgaa attacttagc  78060
agctcctgca gttttattga caaaatttac ttggagagag ggggagacat tttctggggg  78120
taccaccttt gctgccagcg accctgtgtt tcttcctgag tttctttttc ttttctcacc  78180
attttcagca tcacaggttt ttatttacac acattgatta cctgtgctgt tactcattct  78240
tcacaccact gaggaaattg cagatgctgc tgtactgtgc taggtaaatt gacctcagat  78300
ttgttaccag tgaattgaat gaaatgttca gaggtggagc tgaatgaacg aggagttttt  78360
gtggagaaat tggcagtgag aatgatttaa attctgtgat agctcctcgt tttttgggat  78420
ccttattttg ggaccccaga ctatttttaa gccattgagt gcatcattat tttaggctga  78480
gcaagaatct tgatgacagc gtttcaatgg ctgaggcgta gtgggagttc cttgcagctt  78540
gagttggtgg gagctggaga gtttctagag aactaggttt ggttgtcttt ggggtggggt  78600
tatggtgaaa ttagtcttgg agagtgagta gctgtctgat gcttcttttc ctttttaacc  78660
agcaagagcc caaaccaaat ccccaagctc tgaatgcctg gctgttcctc tcagcctttc  78720
tttgcttgaa cttgacaata gtagggtagt aacaggaaac agcatgttaa agttttaaaa  78780
ataaaataga tctcagctct tttccttccc attagcaagg ggtacattta tttaggtttt  78840
tccttctaga ttgaggcact gcctcattta agttcttggt gaagccatgc atttctgcaa  78900
accataagta taaactctag aacgggggtg tccaatcttt tggcttcctt gggccacatg  78960
ggaagaagaa gaattgtctt gaggcacaca taaaatacac taatgatagc tgatgagcta  79020
aaaaaaaaaa aaaactcata aagttttaag aaagcttaca aacttgtaag ttttgagcca  79080
cattaaaaac catcctgggc tgcatgcagc ccccggggcc ttgggttgga caagcttgct  79140
gtagaaggta aaaatcagtt ggttttatgt ttttgtttta aacatgctgg ttgtatgctt  79200
ttggaagagt tggggaacac tgagggtaat gggatcttga tggggctgga atttgtggga  79260
agatggtgtc tgggtaggct gtttttagga aggggcactc tcttcctttt gattcagaga  79320
tttttccttt cttttcgggt ggttctgaaa acacagcgat ggatccaggc attcaaacac  79380
catggaggaa ggaagagtgg ctgttgccat tgcttcccga gttttctggg aaccagtttt  79440
tggtgcctct tccttgctct actggggctt ctctgcatgt cagtttcttc aactgcgaag  79500
tggaaggaca gcgatacttt tcttacagga cttttgcggg gatggatgaa atacgtaaaa  79560
cacttggtct agtacctggc acatggaaaa gccttggtaa atgttcactg ttgttatttt  79620
tgttattact aatacactag tccatgtatg tatagtgtcc tcctatacac accaagagaa  79680
tatggaaagg actcagcaat gattaggtag tccaaagtca taccagattg gaaaccaagc  79740
ttcccaggcc ctgggacttt tctgctagag acacttcacg gttctgacca actacaaaga  79800
gttaatatgc agttgccaaa tacctgttgg taaaaggtgg atgttgggga ggagtggatt  79860
ggggaacaga attagaaggt ccagtcccag aatgggtacc ttcccatcaa gttgaacaag  79920
tcaaaacagg ttatgttgaa acaactgaga gaaagtaaag caaacaccat tgctgcagaa  79980
```

-continued

```
tatcatggta caaattggac atctttggga gttagcggag taaggcaaaa tccagtgagg  80040
gacgcttaat gggtaatgcc aattcacaat tcttgttaaa ttacattgct gatcttcctt  80100
ggaatgtctg tccattcccc caagtagact gtgatctcaa ggcaaggctg ggtcttattc  80160
atcctggttt tcctggagca gtaaatactt gtgctgggac tgggcttata agcatactaa  80220
tggaaagtaa aatatttggg ttggtttttt aaaaagacag tggatttgga tcagtggaga  80280
ggaaggtaga gggaatttca ggtgggcagg gtgctaacaa cagcccatcc ttacagggca  80340
ccaactgtgt tctaggctgt gttccaacca ctttacacag atgaattcat ttaaattgca  80400
caaccagccc aagaggaagg taccattatt attctcattt tggatgtgag gaaactgagg  80460
cgtggggaga tcaaacaact tgcctaaagt tatgtagctt tgagtggctt agctgagatt  80520
tgaaccctgt gggtataaac gccacagatg ggaaatttgt gtggggtacc caggttcatg  80580
tgcttgttag aagtggaagc tatttgtaga gaatcacgaa tgatgaggtt ggggcagggt  80640
gtgatgggag ctgacaggca ggtctaaatg ctgggattca ttttcagtct ctgtgtttat  80700
tgagtaggta gacggtatag ctcttggatt tctcagattt tttcctcttt tcatttagag  80760
actcttatct ggtgtgtgtg tgcccgcaca catacataaa cccacgcgta tatactcttt  80820
ccctgaatgt tcttatttgc taaagcttaa gcttggcaaa gagaggaaac tgcactgacc  80880
ttactctcca ccatatcttc aggctgatca tacacaagtt gcttaataag catttggtta  80940
atccatctaa atcattctta tggctgcaac tctcattttg ttgatgactc tactatctat  81000
gtctattcac atctacattt tgtacttttg tttgcctccc atctgtcctg ggatggctga  81060
taccagtgga agacagcctg aactctccaa tcagtcctgt ttccttttta tgaaatactt  81120
ggaggttgga ggatcttccc ttaaaaagtg ttttcctttc tacatccagc caaaggctct  81180
tggtccttgt gcttgctacc tagatcccta ttggaaagag tcttgcctgc aatttgattt  81240
tttaaatagc agcaataaca gagtcgtctc tgctacacga agacatgcat ctgctgtatt  81300
tcccagacaa gttcaaaaac cttaactagc ttctgcccat ggttattgct ctcaagtgcc  81360
ttgtgttgtt cccatcccct cattatctgg attagatgtt taacatttgc ctgtgtgtgt  81420
tgtgttggat tttctcctct cctcttgctc attcaatttc ttccttctct tagccaagca  81480
cagcttgttc tcctacttgc cttattctgt tctctattta gactgtgcgt gcctgccttg  81540
cagccctggc aggaccattc caccgccttc tcatttgtct taaagatacc tttaggaaat  81600
ctaatccaga caatcctagc ccagtcctga agattaggct ccagaagatc tgtcaagtgt  81660
gtttttttgct ggcctacaca tgctaatttg catggttgcc tgggatccct taagaagaca  81720
gtcattgact aaatggcgct acatgttccc aagctctgcg ccagtctggc aactcttcct  81780
ttgtctacgt gaatttctcc tagttctttc tgctttgctt gctgttcatc tcctgacctc  81840
tctccgacaa acttcctgaa agaagagcct gcactcaaca cctctttttt ccacctcttc  81900
aacaatactg aaatgactgt ctcagaagcc gttgattgta cctaaccacc aaatctggtg  81960
atttccatct caccacgtga taccattaat actacctttc ttcgagacaa cgttctactt  82020
tcttctcttc tgtattatgg acacttggtt tccctcctac ctctctgact gtcattctca  82080
ctcttttgtg gctgccatca ggctcttgca atgtacgtac catctcctca agttccatcc  82140
tcagttatct ttctagttgg ttcttggtga tctcattcag ttccttgact ttagttctta  82200
cctccccatg gcctcctccc atcgtacact gtgttcctca tcaccaggat gttttaccag  82260
tttctcacca tcccatcctc tgttcccttc ctacatagac agacccactc gctcactcag  82320
```

-continued

```
taagccacta ggtgctagtt ttggcttctt cattttatgt aagaaactac caccttccct  82380
acccttctag gcaagaaagc tgagtcatcg taaattcttt tctgcctccc ccgccatccc  82440
atcagttgcc aatttctcca agtggtgcct ctaggatgcc acttgcatcc atacccatct  82500
ttcttcctca ttggcaccca tcatggactc ttgcttggtc tggtgcagta gcctcctcag  82560
tgattccctt gcctctggtt ttcctggctg taatccattc tccacaaagg gtggaattct  82620
tccaaagcat aggttggatg atgtcattca ccggcttaca ccttcaacag catcccagtg  82680
tgctcataat taatggctgc tcctgaactt ggtattcagt cttggtatgc caagacccca  82740
gcctgccggc tcatttgtgt ctcctcatcc cctactgaat cacttcaata gtgttgtctg  82800
gccaagctgt tcaaggctca ttaaggacag gaccaggtct tccttctttt gcctgaaaca  82860
gtgccttgcc cctggcaggt cttcaatgaa catttgttga attgaattag actaaaatgg  82920
ccagggatta taccaattcc ttctgcacag tgtagacaac tgctaatgga acctgttttc  82980
tgtagagcac ttcttgtgtt cccagaacta tgcgagtact ttatgtgcat tatctcatta  83040
aatcatcaca atctcactgt aactctatga ggtagctgat attatcccca ttttacaaat  83100
gaagacactg attcaggaag attagattat tttcctgagg ttctgaaggt agaaacacat  83160
ctaagacttg gagcaatatc tggttgcctc tagaccactg tactatctac cctgcctcta  83220
agagccatga ctttgctaga ttatgcagga gttatggact tgtctaatag taaaggtaaa  83280
agaattggtt ttaatgagaa tctactcttc taggtactat tctgagtgcc tgacaagcat  83340
tctcatgtag acccagcaat aactcattat tttacagata gagaaaatga tgatcatgat  83400
gcttgggtta cttcttaggt tcactcagct cacatctggc agagggtggt caacttttcc  83460
aagttttaac ttatttattt atttattttg agacagagtc tcattctgtt gcccacgctg  83520
gagtacggtg acacaatctc agcttattgc aacctccgcc tcccaggttc aagcgattct  83580
tgtgcctcag cctcccgtgt agctgggatt acaggtgcct gccaccacgc ccagctaatt  83640
ttgtttttgt atttttagta gaggctgggt ttcaccatgt tggccaggcc tgtcttgaac  83700
tcctgacctc aagtgatctg ccagcctcgg cctcccaaag tgttgtgatt acagatgtga  83760
gccaccacgc ctggctcaac ttttaacttt agaactgata taaacatgcc tatttttttg  83820
ggactgactg tagcataccc attcaaagtc caggctttgg aatcagacag acgtgggctg  83880
aactcagggt ttcacccctt gcttgttgtg tgaatgagac atttcactgc tttcagcctc  83940
aattccctca tctgtaaagt ggaaggtgta aggtcgccta tctgataggt ttgccatggg  84000
gatatgaagc acacttagtg ttggtgccat gagtagaatg agtgttcatt tcatatttgt  84060
taatgttatt taggtccgag gatgggtatg gggtgctttg gactctcttt ttctccctgc  84120
ttccgcctta taaagacatc ttgctggttt ctgcccattg agagaatcca gctccacgtg  84180
gggggcctga cagatgtcct aatatctcca tccaattttt tactctgaat ggagtctgtg  84240
atgtatcact tcaacctgca ctttctataa aatgctctcc aggcttctgg taggatccag  84300
tgccagtggg aagtgtgcat gttcccagcc tagatgtcac atgctcccac ccaccctgga  84360
agcacttggg tatcccctgg atgggtaagt ctgtgtgtca ttgtgccatt cctgtctcag  84420
aaccaatgct gggcatctct acttgcaggt gctggaaagc tttttcatgc cagcatacat  84480
gcagcacact tctcattttg gattccttta tcccacggtg acctttaaac tggctgcctg  84540
ggggcacaga agtactagca caccattcac ttatttattc attcattcat tcattcattc  84600
attcactcaa caaatatatt gttctagtcc ttaaggcaca actctgagca agacaggtaa  84660
ggtctttact ctcaagaagc tagcatttgg tggggagaaa caaaggagaa ataactactg  84720
```

-continued

```
tgcacatgtg aggcaattgc agatggtggt ctgcagaatt gggattgaga ctgcctgggg  84780
gtggccactt tagactgggt ccgcaaggaa aggttctctg agctgagcat gagtatttgt  84840
tcaagaaggc tgagttgcat cccaaggtga cacagctttt aagcccacac tgagcagctc  84900
tgaggtccta ggggctgttc gagaacctgg gatatagcac tgactatgag acaaaaatcc  84960
ctgtcttcat ggagcttaca tgatgggggc agattcacat tcattcattt gttcattaat  85020
tcattaattc attcagctat ttgagagcct actatgtgcc aagcactttc taggcactgg  85080
agaagtaaca gtgaatgcaa aggagcaagc atccctgccc acacagagtg cattcttcca  85140
gaatatcaat aaggagtcgg ttagcaaaaa taagtgggaa gagtattcca gagagaggaa  85200
aaaagggcaa aggccctgag gctgccacta acctatgggt gctcaatgaa cagaaggcat  85260
gtttgggtag gggtacttta aggatacaca aggaacatgg tctgagctga ggtcatcagg  85320
gcctttaggt atggactttg ctctaaattg cactgagtag gaagcttttg caggattttg  85380
aatagggtca tggaatatct gggtcttatt tcacaaagtg tgcctctgac cattgtgtgg  85440
agggtggata gtgagggaca agagttggat ccagggaggt aagtgtggtt attgcagtca  85500
tcccaggtga gaggcaatga aattaacctg caaagtgagg cactggctta gaggtgggaa  85560
ctgaattaaa aatcatggga ctagctattc ttttattaat agcatgattt ttgataaatg  85620
attctggagc tacatattaa tcatttcaaa gcaagtgctc taatttaact agagaccact  85680
gctggttgtg tgtgtgagtg catatgtgtg tatgtatatg agtatgtgtg gtgtgtgtca  85740
gtatgtatat gtgtgtatgg tatatatata aatatatata ttgtgtgtgg tgggggaggg  85800
ggggtgcccc aaagctagac agactctgac tgtctttagg ggaatagtgt ttttgatatt  85860
tccaggtgtt cctgatgggc accattgtta ttttatttta tttttatttt atttttgaga  85920
cggagtctca ctctgtcgcc aggctggagt gcagtggcgc tatctcggct caagacaacc  85980
tccgcctccc aggttcaagc aattctcctg cctcagcctc ccgagtagct aggactacag  86040
gtgcgtgcca ccacacccgg ccaccattgt gtattttaaa gtgtgcttat aaaattagtt  86100
cagagccaga tgtggtggcc cacgcctgta atccaagcac tttgggaggc cgaggcgggt  86160
ggatcatgag gtcaggagac cgagaccatc cttgccaacg gggtggtgaa accccatctc  86220
tactaaaaat acaaaaaaat tagctgggta cagtggcgcg tgcctgtagt cccaactact  86280
ccggaggaca aggcaggaga attgcttgaa cctgggaggt agaggttgca gtgagccgag  86340
atcgcaccac tgcactccag cctggtgaca gaacaagact ccatctctaa ataaataaat  86400
aaaacaagtt cacaaatttc ggaatgctca atcttaaaag ccagtatatt tttggaaacg  86460
gaatgctgat gagtttttta ttttttgcag catattacat cttgcagttg catgtatttt  86520
tagtgctgtt ggccagcact aaaggtgggg ccctcagctg agctaatttt gagtcccctc  86580
attttggctt caagtatact cattcttggt tttcccaaga atatctggga tttgtgatct  86640
gtgttatctg tggtttggtg tcgtattttg caggcatagg gtcctattcc taagggaata  86700
aatggatggc ttgatgctta agcacgaact taatcatcgc agtagtgatt aaagagtatt  86760
caacatgtac acttgcttgt aggaaggagt acacattgta ttctcttttg atatgcaata  86820
ttttattcat agccctatta agtaattttt tttaacaaag ttatatggat tatttacagg  86880
tacatcacgg gaaaactgca ttttataatt ttcactgaaa tgttgaggtt acatgtaaag  86940
caatttttat gtcatatctg atacatttta agaaaacatg tcttcctgtt acagcggtaa  87000
tgaccatgcc tgctctttct tctgtgtcat atgccattat ccctattaat actctttggg  87060
```

-continued

```
cttctataat tataaagcag atgtgtatat cagggagaga tgttgatttc agagtaagtt  87120
tttctagaaa atagaagctg gaaaaaaaag gaaaacccaa acttggcttc gtgctcgaag  87180
agacagcact gctgtgtgtg ggcgggtggc tgcgtgcacc cgctgctcag aagtgccttt  87240
tctctccatg gggataactg gctgtgtatc cgagatgtgg ccaggagtag gcaagcaacg  87300
tgtgggcagg ctgcatgttc ttttattagc atcttcattg tactgcatct cgtcgagccc  87360
agagcatgaa ctggcctggg tttctaatat ctaccctgct tcccacctaa ttactcccct  87420
gaaccctaaa gtgagggagg gagagttgct cttgtggggt gagctttccc tggggtggct  87480
gtgaaccaac ctggcatgtg gatgttcttg ggtatccaga gctgtcctgg actcaggctt  87540
ggagtcagct tcttagcact gaatgcagcc agtcatggat ggaggtcact gtatctcaca  87600
tgttccgctc tccctttcct ccatgacctt gcccctctga gcctctgtag cacttttctt  87660
gagtgtgtcc aaggccatct agctaagaag tagcagaaat gggatttgaa gccatgactg  87720
tttggtgata gagcctcagc tttgaactgg ggttctactg cctggcaccc ctgcacaaat  87780
catggtaacg tggtaggaga acatagaggt atagggcaag cccctcctta atgccatgaa  87840
taatacccat cttataggat tgtggggagg actcagtgaa gtaacccgtg aagcactaaa  87900
cacgtgcctg acacgtgctc aataaatgag cacttgtcct gatgacaaag gtcgtggcat  87960
taattctctc tcctaggttg ttacttcctt gaggacagga attgtggctt ccttaatggc  88020
cactgcagca gagtttctca agttggcact attgacattt tgggctggat aattcttgtt  88080
gtgggagctg tcctgtggat tgtaggatgt tgagcagcat ctttggcctc tacccgctac  88140
atattaatag cacccctagt catgaaaata aaatgtctag acattgccaa actgcccctg  88200
ttgagaacca ctggtctgca ggtatctctc atggggatca cagggctttt atattctctt  88260
ctctgtctct ctctctccct ctctgggtgt ctctctctct cacacacacg cttagagaag  88320
gtggttaaaa aaaattttgt tgaagtttga gaattttgag aacaaaggaa aaattttgga  88380
aggcatttta atgaacagat agactctgtc ccattccatg gtcaacagaa tttcataatt  88440
agatagtttg tttactgcaa ctctgcaccc cattgcccat cattttagag ttccaaccag  88500
ttagaggatt tttcttgcaa actttcctta aagcagtgat agtatcagct ctttaaataa  88560
tactatgctt gatgaagtgg tacttttcgg gataatttga gaccagccga cttgctgctt  88620
gaagaggaca gggctatatt tggtaataat atatatgtga taatatgtat gtaatattat  88680
tataatgtaa tatacaataa tatttggtgt aactggtgac tctgaggcca gtctttgatc  88740
gaacctctca agctatgatt tacattatgg tcaatgttag cataatgcaa ttatcagcaa  88800
tcacttgctg ttgctttgaa agtcagaagg atggctaata aaaatcttag aaaaagaaaa  88860
caggctgggc gcagtggctc acccctgtaa tcccagcact ttgggaggct gaggcgggca  88920
gatcatgagg tcaggagatc gagaccatcc tggccaacat ggtgaaaccc catctgtact  88980
agaatacaaa aaaaaaaaaa aaatttgctg ggcgtggtgg cgtgcgcctg tagtcccagc  89040
tactcgggag ctgagtcagg ggaatcgctt gaacccggga ggtggaggtt gcagtgagcc  89100
gagattgtgc cactgcactc cagcctggtg acagagtgag actccgtctc aaacaaaaca  89160
aaacaaaaca aaaaacaaaa aaagaaaatc ttagaaaaag aaaataaatt gtaatatttc  89220
agaatatttg ttggggagga tatgtgtgct caagaaatat atactgagaa cttaccattg  89280
atgctagaga ttgaattgcc ccatgtctac atgaaaaatg aatagaatat aaacatttta  89340
aattgagcca tgtctatctg tattatattt cttttataga aattcatgga aatggtatat  89400
tttaactgaa ttattaacac tggggacaat aggctttaat cattatctaa tacctgtacg  89460
```

-continued

```
ttgttttgaa attcatagcc caccaccatt aatttcaaaa ttgggttctt actcaaagag  89520
tgatgaaaag gcaccagtac caaatggtct ggccaaaatg ctacatggaa ctaaatgctg  89580
gggatggtca tacaatgagt tttaagtggc tagaccctaa atcagaagca ctttcttcta  89640
attagcacca tggttcttaa tcctttctgt acattacaat cgctcagcag cttaatacaa  89700
atgttgcttc ccggggccac actccacatc tttctgactc tctgatttaa ttggtccgaa  89760
tggggcctat acatcaggtg ttttttaaaa ggtctccaag tgattctaat gtgtacctgc  89820
attgaggacc agggaaggtg taggaagcct gataaccttt actctccagc ctcatcctcc  89880
aatcccatga ttgtttatgg gattgttgct acacacccag cttagtcata gcattcttac  89940
tctagctttt ttttagatgc aatttttatt tattcttaaa gaaaaagatt tctttagcac  90000
ctttattcta aagagctctt aattgctgtg cttagaactt ctaaacagtg agcatttgtc  90060
aaacatagaa tagcagaatg aaggggttgg acctcgggtg aggagggctg tcgcatggtc  90120
tctttcgagt gccggcgggt gggggctgca catctcctcg cttctgggcc cattgataag  90180
tgacctaaaa gtgcctttcg ttttttttgg tggggggtga aaaagcaatc tgttttgtac  90240
ccacagcggt gcactttaaa caggaagccc tactggggcc agccttctat gtgtcattaa  90300
gtttttcacg ccacatccta cctatcatca tgcacccatg tcatcgttct tttaaagggt  90360
gccagttttt tgcttaagca caaggagctg tgacctgtgt tgtcatccct gatgcatgtc  90420
atgcatgtga cttcatgaca tgtgggtgac ttttgatctc tgaaggacca gggacccagt  90480
ctgtggatca ccactctctc cgtgggtggt ttgggtcttg ttctctagcc cacccagcca  90540
ggtgcaatta ggaataaagg aaatagcaaa ggaattttgc tcaaggccat gccaagcatt  90600
tcatctcata tgaaaaggaa aagagagaga gtgtgtgtgt gttggctaga tttaggtaga  90660
aaacaggctg gtgagaagcg tagaacttgg ttaaaatttc tagccaaaag taagattttt  90720
aaaaagattt atttctggat ccaatccctg ttgcccattt ctatgaataa tcaccatttg  90780
ttttaatgtg aataatagca cacagcaaat tcagcccccct gagttttacc attttaagca  90840
attgctttag gcccgtgagg catgtactat ttatgaagtt gcatgggtag taatggaaaa  90900
cacaacaatg acagtagtaa caggtgacat ttgtcgaaca cttgcagtgt gccaggcact  90960
gtgctgagag cattacatgc attatttcat ttaatccttc caagaactct ttgaagtagg  91020
ttggtaatta tggccatttt acaattgagg aaactgaggt tcggagatgt caaataacta  91080
gtcagtggtg gggtcagat ttttcttttt tttttaaatt tatttgcttt tttttttttt  91140
ttttttgaga cggagtctca ctctgttgcc caggctgagt gctgtggtgc catcttggct  91200
cactgcaagt tccgcctccc gggttcacgc cattctcctg cctcagcctc cggagtagct  91260
gggactacag gcgcccacca ccaggcctgg ctaatttttt gtatttttag tagagacgag  91320
gtttcaccgt gttagccagg atggtctgga tctcctgacc tcgtgatccg cttgcctcgg  91380
ccccccaaag tgctgagatt acaggcatca gccaccgcgc ccggcctatt tgtttttttt  91440
tttaagagac aaggtcttgc tgtgttaccc agactggagt gcagtggtac aatcgtagct  91500
cactgtagcc ttgaactcct gggctcgagc gatcctccca ccccagcctc ccacgtagct  91560
gggactagag gcatgagcca ctatgcccga ctcattttta aacatttttt atagagacgg  91620
ctgggtgtgg tacctgtaat cccagcactt tgggagactg aggcgggcgg attgcttgag  91680
cccaggaatt tgagaccagc ctgggcaaca tggagaaacc ccgtgtctac aaaaaataca  91740
aaaatcagct gggtgtggtg gtgcgtgcct gtagttccag ttactgggga ggctgaggta  91800
```

-continued

```
agagaatcac ttgagtctgg gaagtcgagg ctgcagtgac ctgggaccac cgcactccag  91860

cctgggcatc ggagtgagac tgtctttcaa aaaataattt atttatttat tttaaaaata  91920

gagacagggt attgctgtgt tgcccaggcc cgtcttgaac ttctggcctc aagtgatcct  91980

tctgcctcgg cctcccaaag tgttgagatt ataggcatgt gccactgtgc ccagcctgag  92040

attttgaaca gaggagcatg atgctgggcg ttgactcatt tggctgtgag tgtggaaagc  92100

tgtcactgga gtacagcaag tcagcactat caagccagcc cttgtcattg ccaggagctg  92160

cggggagaga ggtgttttgc attgctgcag ggaactgacc tcttttagtc agggaagtag  92220

tttgggcagt agaaagcaga acttgcacct gctggtaaga tctgagtggt cactgacaac  92280

cagctctgca accctgttac cagggcaaca aagatgggcc caggggtagt ggtgggctct  92340

gccacatctc tctgtgcata agaacctttg gccacttgct ctggccttgt ctttcaccaa  92400

tcccagtgtt catatccagt gtaccaacca ctgagggcag ctgtcctgga atctgtctct  92460

catctctgcc cataattaac tgcttctggg cacagtgcat gagttacata gatgagtgtg  92520

ggtaagtttg ccctttctgt ggggggagca tccttttggt ccactctcag gagggcatcc  92580

tatgttattt ttgtgatatt ttcctaagag ttgtataagc aagtgcatca agccaacttg  92640

tctaccccag ctccctcttg agaccagcag aaactattta tcaactggca gtttacgtaa  92700

cctctctggg cctcaatttc ctcatataaa atgaggataa taaatcgtat ctgctcatag  92760

agttgctgtg gggagtaaag agttcaaatg tatctgtcag tgaaggaaaa aagaaaaaaa  92820

aacaaaaaca aagagttcaa atatatctag cgttcaaaca gaaccaggta tgcagccagt  92880

gcccaatagg tgtatgagtt tcctatggcc aatgtaacaa atgaccacaa acttagtggc  92940

ttaaaacaac acacatttat tattttacag ttctggaggt cagaagtcta agatgatgcc  93000

aggcttggtg gctcaagcct gtaatcccag cactttggga ggctgaggtg gcaggatcac  93060

ttgaggtcag gagttccaga ctagcctagc caacatggtg aaaccccatc tctactaaaa  93120

atacaaaaat tagtcaggca cggtcacgag cacctgtaat cccaactact caggaggctg  93180

aggcaggaga attgcttgaa cccaggaggt ggaggttgca gtgagccgag gttgcagtga  93240

gccgaggttg caccactgca ctccagcctg ggcaacagaa cgcgaccctg tttccaagaa  93300

aaaaaaaaag tccgggatga gttttactgg gctgagatca gtgtagacaa ggctgccctc  93360

tctctggagg ctctagggca gaatctgttt ccttgtcttt tccagcttct agaggttgcc  93420

tgcattcctt ggcttgtggc cccttcctcc gtgttcaaag ccattggtgt aacatcttca  93480

ggtctctgtg actccgatcc ttgcttccat cttataagga tccttgtgat ttcattgtac  93540

ccatccagat atcccaggag aatctttcca tcccaagatc cataacttaa atcccatctg  93600

caaagtccct tttgccatgt gtggtaatat attcacagct tgcagagatc aggacatggg  93660

catctttggg aaacgggaag gggcattat ttgacctaac atcaagagca tgagatgttt  93720

ttgtaaaatg aaacaaatgt tgcagcttcc taatgcagct tcttaggccc acctgcaggc  93780

ccccttgacg ttggtttttc tctacctagg tctgttgtgt cgggtctgga ctcccctgcc  93840

aagactagct ccatggaaaa gaaacttctc atcaaaagca aagagctaca agactctcag  93900

gacaagtgtc acaaggtatt tatttccgca gccggcctcc ttccttgctc caggatcctc  93960

ccgtccgtat atgccaaggg atccgcccgg ggccgctgct ggctctgagc cgcctgatcc  94020

gtagagagtg aggcgctcct gccttcgctg aagtcgcgcc tccagcagct cagagggaga  94080

tgaattcggg ccttgctgtt gctgtaaatc ctttaaatct aaaccagagg aggccctgga  94140

tttaaacagt ccgtttctca gcatgaccca gccagatgtc tgcttcttcc ggcaggtggc  94200
```

-continued

```
ctgggtcctc acctgtggct gagatacatc ccatctgctt tgagtgatgc gaagtctctc  94260
ttcctagtct tttaaaactc ctgcttatgt cactgcggcc actgtgttga ttacgctcaa  94320
cgtctcttaa cattcactgt tcctgcccag aggcaacgct ctggaaacta ataagtcact  94380
gcttgcctgg gactcctaag agtgcagacg aataaatatc tccttgccct gtcctggatt  94440
tgtcctctag atctttgcaa ggagatgggg ggggatcaag atggatttgg gataaaatta  94500
aagtgacgtc tgcaaaaaca aaacaaaaac aaaagcaaac aggtgaaaaa tgatgattgt  94560
ggcttccttg ctaactgggt tagagaagtg atcaagtgtg aaccgggact tgaatgagag  94620
gagtgactta gcatttggtg actgtcctta acgaagaact gtgcgctcct gggcgaagaa  94680
acaatggtat ttccatccca acttaacttt tggcgaatta gccttagccc agaccaccag  94740
gtggtttcgg aggctacttg agatgtgatt gctcctaatg aacctccacg ggccttttta  94800
acctgtcgat gtgtttattt cagatggagc aggaaatgac ccggttacat cggagagtgt  94860
cagaggtgga ggctgtgctt agtcagaagg aggtggagct gaaggcctct gagactcaga  94920
gatccctcct ggagcaggac cttgctacct acatcacaga atgcagtgtg agccttccct  94980
gaagcccccct tcccttggag gtggcacttc ctgttgtgtg tgtctcatcc tgtttcatga  95040
tgactccatg aggcacatca cagccaatgg cagagagtag agagagggag agcacaaaag  95100
caagatctgt gttttgcaga gtagtgagag ccaggcgtaa ggtccccaag aaatgagatt  95160
ggactcattt ccagcagaaa gtgcaggtag acggctggta ccatggagtc tggagatggg  95220
agtaattcat ctttgccgca agttgcaaaa gatcttaaca tctcccatcc cagcctctgt  95280
ggtctgcgtt gtgtctgaca tgagcagcct tgagaaccag actcccaact atgtacaaga  95340
aaacttactt tcaatcttcc tgacatcaaa ttttccattg gccagaacca gtgtagtgac  95400
aagaaaatag ccttgaaaac ccagaccctc tgtcattatt taccatgtga ctttcatttt  95460
ttctttcctt cacaagagta gactgtcttc ttctccattg tcttgttaaa tttttcattc  95520
aggtgttttt taatgtgccc aattaaacag tctcaagaag ttgaatcaca catttctaaa  95580
gtttttttca caagggagag gaaatctata gaacgtggct gattaagaat aactgctatg  95640
tttccattcc agacttggct gcctttcagt ggtgggtgaa gttattcagc tatgtatttc  95700
agatatagat ttcagtgcca ttgaagcatt aagggattct tatggatgaa aggtgtccag  95760
gaaaaataag ccaggaggta gaaatagacc acttggagtc ttaaatgaca actgggcaga  95820
ggatatgaag tcattgctac tttgaaagag gcatatgtac tttagggccc acaaataact  95880
gtagaaaaca ctttgtagct atccacatgg tggctgtaat agctactggg tcttaatagg  95940
ttttagtcct gaacatgcaa gtaagtatct cctaggacag gtagatggtg gcaggagaca  96000
ggctgatgca gtttccggct ggactaattt ttgtattgtt agtagagatg ggtttcatc  96060
atgttggtca ggcttgtctt gaactcctga cctcaggtga tccacccgcc tcgccctccc  96120
aaaatgctgg gattacaggc gtgagctact gcgcccagcc atttgtgtct cttaaaaaaa  96180
aaactaagaa aatgaaaaaa atgacattgg ccaattcatt aaaatgccac tcactgactg  96240
tggtatgaaa tggctttccc tttgatggac cgaagtctgt ctcattgtgt gagccacttg  96300
cagggctgag tatgactnnn nnnnnnnnnn nnnnnnnnnn nnnnnnnnnn nnnnnnnnnn  96360
nnnnnnnnnn nnnnnnnnnn nnnnnnnnnn nnnnnnnnnn nnnnnnnnnn nnnnnnnnnn  96420
nnnnnnnnnn nnnnnnnnnn nnnnnnnnnn nnnnnnnnnn nnnnnnnnnn nnnnnnnnnn  96480
nnnnnnnnnn nnnnnnnnnn nnnnnnnnnn nnnnnnnnnn nnnnnnnnnn nnnnnnnnnn  96540
```

-continued

```
nnnnnnnnnn nnnnnnnnnn nnnnnnnnnn nnnnnnnnnn nnnnnnnnnn nnnnnnnnnn  96600
nnnnnnnnnn nnnnnnnnnn nnnnnnnnnn nnnnnnnnnn nnnnnnnnnn nnnnnnnnnn  96660
nnnnnnnnnn nnnnnnnnnn nnnnnnnnnn nnnnnnnnnn nnnnnnnnnn nnnnnnnnnn  96720
nnnnnnnnnn nnnnnnnnnn nnnnnnnnnn nnnnnnnnnn nnnnnnnnnn nnnnnnnnnn  96780
nnnnnnnnnn nnnnnnnnnn nnnnnnnnnn nnnnnnnnnn nnnnnnnnnn nnnnnnnnnn  96840
nnnnnnnnnn nnnnnnnnnn nnnnnnnnnn nnnnnnnnnn nnnnnnnnnn nnnnnnnnnn  96900
nnnnnnnnnn nnnnnnnnnn nnnnnnnnnn nnnnnnnnnn nnnnnnnnnn nnnnnnnnnn  96960
nnnnnnnnnn nnnnnnnnnn nnnnnnnnnn nnnnnnnnnn nnnnnnnnnn nnnnnnnnnn  97020
nnnnnnnnnn nnnnnnnnnn nnnnnnnnnn nnnnnnnnnn nnnnnnnnnn nnnnnnnnnn  97080
nnnnnnnnnn nnnnnnnnnn nnnnnnnnnn nnnnnnnnnn nnnnnnnnnn nnnntcggcc  97140
tcccaagtgc tgggattaca ggcgtgagcc actgctcctg gcccccacgc cttttttttt  97200
ttttggagac agagtttcac tctgtcaccc agattggagt gctgtggcac aatctcagct  97260
cattgtgtcc tctgcctccc aggttcaagt gattcttgtg cctcagcctc ctgagtaggt  97320
ggaattacag gcgtgcacca caacacctgg ctaatttttg tatttttagt agagatgggg  97380
tttcaccatg ttggccaggc tggtctcgat ctcctgacct ccagtgatcc acttgcctag  97440
gcctcccaaa gtgttgggat tacaggcgtc agccaccatg cctggacccc tctgcccctt  97500
taagcactgc cacatattag atctacgaag gctttatgga tacaatccaa ggaagatgaa  97560
ccttgggcta gtgggataaa actaagcgca tgtagttaga atggaatgat ctggaaacca  97620
ggtcccaagt tggtctaaat tagactcatg ttgactatgt cacactgtaa accagtctaa  97680
atgctaataa gcatgcttga ccaaacactg ccctgcagcc ttcagagagg aagaaggaaa  97740
acataatttg tatcctctct ccctattttc tgagtctatg ggattcaaat tgtagctgcc  97800
atggaaactg tactttggaa tttctagagc ccttaatttt aacttaacat ataaaaacac  97860
ttttgtactg attttataat tattcatgat ggatgagaaa gtgaatgtct ttgacagtga  97920
gggaagctat ccgaatgcta ttttcttttt tttttttctt tcataaagat gcatatattt  97980
gcatgcttta tttacctggg gctaactctt gcatcttttg cagattccga caccatagct  98040
gagttacagg agctccagcc ttcggcaaag gacttcgaag tcagaagtct tgtaggttgt  98100
ggtcactttg ctgaagtgca ggtggtaaga gagaaagcaa ccggggacat ctatgctatg  98160
aaagtgatga agaagaaggc tttattggcc caggagcagg taggaggatt ttaacatcat  98220
gcttttccac tttctgtacc ggagtgttca ttgcaaagac gataatctgc tgcactggcg  98280
tctaggatca agcacgtttt cctctgtgac tctatattta attatagttg gggcaaaaag  98340
gtctctcatg ttcttagctc atcttcttga actgatgttg gctaattttg aaggctcaca  98400
aattcctctt gatgtatcat gtttctatcg ttgtaattta tttcagaacc aaggtggcct  98460
tttagctaat gaatttaaga tgatctttta tgaccattag ctgaggactc aggatataca  98520
tatggtgggg tgaatcagat tgcttttgta cacgctttag gtatttgtgt tgtgggcata  98580
tggatttggt tttaaaacag gcctttgaag aaatcaaata acattctttg ttatgtggct  98640
agggagttgc ttgtttgaga gcaggtagaa cgttatcttt tttgttgtgg tatttttctt  98700
tcttttaaac aaggctactg tctctagaca tattgattca tttgctgtgt tttagagaga  98760
tggccgtcag ccttggaatt cagagagtaa tttattactt acagacattt tagtgcacat  98820
gatatgtctg ataatgtacc cagctctgca ggaagcttgc aaaaggaata gaagtcccat  98880
ggttgctatt ttcagtgttt aaaaacaacc ttggaaagtg gaggaaaaat gcaaatgtat  98940
```

-continued

```
aaagcaggtg cttaccagct aaagtatcac agaagtggga gagcaattag caaattaatt  99000
aacgatgatg tgaggggaga tgttgtgggt gagcaaggga cagttaggga cagttctcac  99060
cgatgggggg aaatgtaggt tctcggcaga gagaagtgat gagaacatgt tgggtagaag  99120
tgtgacattc tggagtacta gaatgctatg caagtgtgtg tgtgtgggtg tgtgtgtgtg  99180
ttcagtggtt cagaacagac tgggaaatgg cgaaatgagg acatttgggt ggggaggggg  99240
aaatgggtgg gaaactcaag aaccttttttt taaaaaattg tggtaaaata tatataacat  99300
aaagtgtacc attttaacca tttttaaatg tgcaactgag tggtattcag tgcattcatg  99360
atgttgtaca accatgaccg ctctccattt ctagaatttt tctatcatcc caaacagaaa  99420
ctctctatcc attatacaat acctccccat tcccccaaga accagttttt gaattgcagt  99480
ttactttgtg aggctgttgg ggattattta ggcctctgga aggaggaggt tgggatcaga  99540
gtctggccct gtggacttca atgactttgt gtggcctcca atcagagaag cagcggaggg  99600
caggaagctg cttgtcagaa tctgagagtg atgtggcttc tttgtttagc aataaaatgt  99660
gagcacataa tagaaaggaa aagtgacagg acatggcaga taatttggaa gagaggagtg  99720
gaagatgctc actcagcctc ccagctcctg agaaagaact gtgtctcatc agttcatact  99780
acctgagcat ctgttgtatc tggtgtgttt ctaggtacct ggagaagagg cattacgtgt  99840
agccctgacc ttgtgatgct tatgtttttg atgggaaata gtgcgtgtaa aaagaaaata  99900
atccaacagg ccacacggca ggcaaacaat agagatattc aaataggtat accttcctcc  99960
aggtgaatgg cctgaaatga ccgtgtggaa gtgtgggctg ggggcttata aaattataca 100020
catacaggcg ctaactaaag ccgcctattc attccttaag aggatgcata gaaaagaaaa 100080
gtagggtcct ttaactgagc ccatttgaat ttagggcctg agagaagcag cacaagcagt 100140
gaagggaaga aaaagaagtg cccgagagga gggagggatt ctgttctgca gacaaggcct 100200
gccgcctggg agaggcccgc acgcccaccc agggttctct gacagctgga aggggtcttc 100260
agagactgtt tatattttat ttatttattt atttatttat tntgagacag agtctctgtc 100320
acccaggctg gagtgcagtg gtgcgatctc agctcactgc aagctccgcc tcccaggttc 100380
acaccattct cctatctcag cctcccgagt agctgggact acaggcgcct gccacaatgc 100440
ccggctaatt tttttgtaat tttagtagag acggggtttt acctgcgtta gccaggtatg 100500
gtcttgatct cctgacctca tgattcgccc acctcggcct cccaaagtgc tgggattaca 100560
ggtgtgagcc actgtgcctg gccgactgtt tctactattt tagagagagg gtctcactgt 100620
catctgtgct ggaatgcagt gatgcagtca tagctcactg caccctcaaa ctcctgggct 100680
taagcgaccc tcccgcctca gcctcttaag tagctgggac cataggcatg tgctgccaca 100740
cccagttaac tttattattt atttatttat ttagagaatg agtctcattc tgttgcccag 100800
gctagaggtg cagtggcacg atctcggctc actgcaaccc cgcctcccag gttcaagcga 100860
ttcttcttgc tcagcctcct gaatagctgg gattacaggc acctgccacc acacctggct 100920
aatttttgta tttttagtgc agaggggggn nnnnnnnnnn nnnnnnnnnn nnnnnnnnnn 100980
nnnnnnnnnn nnnnnnnnnn nnnnnnnnnn nnnnnnnnnn nnnnnnnnnn nnnnnnnnnn 101040
nnnnnnnnnn nnnnnnnnnn nnnnnnnnnn nnnnnnnnnn nnnnnnnnnn nnnnnnnnnn 101100
nnnnnnnnnn nnnnnnnnnn nnnnnnnnnn nnnnnnnnnn nnnnnnnnnn nnnnnnnnnn 101160
nnnnnnnnnn nnnnnnnnnn nnnnnnnnnn nnnnnnnnnn nnnnnnnnnn nnnnnnnnnn 101220
nnnnnnnnnn nnnnnnnnnn nnnnnnnnnn nnnnnnnnnn nnnnnnnnnn nnnnnnnnnn 101280
```

-continued nnnnnnnnnn nnnnnnnnnn nnnnnnnnnn nnnnnnnnnn nnnnnnnnnn nnnnnnnnnn 101340
nnnnnnnnnn nnnnnnnnnn nnnnnnnnnn nnnnnnnnnn nnnnnnnnnn nnnnnnnnnn 101400
nnnnnnnnnn nnnnnnnnnn nnnnnnnnnn nnnnnnnnnn nnnnnnnnnn nnnnnnnnnn 101460
nnnnnnnnnn nnnnnnnnnn nnnnnnnnnn nnnnnnnnnn nnnnnnnnnn nnnnnnnnnn 101520
nnnnnnnnnn nnnnnnnnnn nnnnnnnnnn nnnnnnnnnn nnnnnnnnnn nnnnnnnnnn 101580
nnnnnnnnnn nnnnnnnnnn nnnnnnnnnn nnnnnnnnnn nnnnnnnnnn nnnnnnnnnn 101640
nnnnnnnnnn nnnnnnnnnn nnnnnnnnnn nnnnnnnnnn nnnnnnnnnn nnnnnnnnnn 101700
nnnnnnnnnn nnnnnnnnnn nnnnnnnnnn nnnnnnnnnn nnnnnnnnnn nnnnnnnnnn 101760
nnnnnnnnnn nnnnnnnnnn nnnnnnnnnn nnnnnnnnnn nnnnnnnnnn nnnnnnnnnn 101820
nnnnnnnnnn nnnnnnnnnn nnnnnnnnnn nnnnnnnnnn nnnnnnnnnn nnnnnnnnnn 101880
nnnnnnnnnn nnnnnnnnnn nnnnnnnnnn nnnnnnnnnn nnnnnnnnnn nnnnnnnnnn 101940
nnnnnnnnnn nnnnnnnnnn nnnnnnnnnn nnnnnnnnnn nnnnnnnnnn nnnnnnnnnn 102000
nnnnnnnnnn nnnnnnnnnn nnnnnnnnnn nnnnnnnnnn nnnnnnnnnn nnnnnnnnnn 102060
nnnnnnnnnn nnnnnnnnnn nnnnnnnnnn nnnnnnnnnn nnnnnnnnnn nnnnnnnnnn 102120
nnnnnnnnnn nnnnnnnnnn nnnnnnnnnn nnnnnnnnnn nnnnnnnnnn nnnnnnnnnn 102180
nnnnnnnnnn nnnnnnnnnn nnnnnnnnnn nnnnnnnnnn nnnnnnnnnn nnnnnnnnnn 102240
nnnnnnnnnn nnnnnnnnnn nnnnnnnnnn nnnnnnnnnn nnnnnnnnnn nnnnnnnnnn 102300
nnnnnnnnnn nnnnnnnnnn nnnnnnnnnn nnnnnnnnnn nnnnnnnnnn nnnnnnnnnn 102360
nnnnnnnnnn nnnnnnnnnn nnnnnnnnnn nnnnnnnnnn nnnnnnnnnn nnnnnnnnnn 102420
nnnnnnnnnn nnnnnnnnnn nnnnnnnnnn nnnnnnnnnn nnnnnnnnnn nnnnnnnnnn 102480
nnnnnnnnnn nnnnnnnnnn nnnnnnnnnn nnnnnnnnnn nnnnnnnnnn nnnnnnnnnn 102540
nnnnnnnnnn nnnnnnnnnn nnnnnnnnnn nnnnnnnnnn nnnnnnnnnn nnnnnnnnnn 102600
nnnnnnnnnn nnnnnnnnnn nnnnnnnnnn nnnnnnnnnn nnnnnnnnnn nnnnnnnnnn 102660
nnnnnnnnnn nnnnnnnnnn nnnnnnnnnn nnnnnnnnnn nnnnnnnnnn nnnnnnnnnn 102720
nnnnnnnnnn nnnnnnnnnn nnnnnnnnnn nnnnnnnnnn nnnnnnnnnn nnnnnnnnnn 102780
nnnnnnnnnn nnnnnnnnnn nnnnnnnnnn nnnnnntata tgtgcataca gaatatatac 102840
acagaaatat atatgtacac atgcatagaa tatatttaca tatatatgca tatatataat 102900
ttatttattt taagcagttg atttatacag tttttgtttt tgtttttttt ttgagacaga 102960
gtctcactct gtcacccagg ctagagtgca gtggcgagat ctcagctcac tgcaacctct 103020
gcccccgggt tccagtgatt ctcctgcctc agctccacaa gtagcacacc accatgccca 103080
gctaattttt gtattttttt tagtagagac gaggtttcat catgttggcc aggctggtct 103140
cgaactcctg acctcaagtg atccgcccgc cttggcctcc caaagtgctg ggatttcagg 103200
cgtgagccac cacacctggc tcccataatg tcttttagaa taaaacgatc gagttgagga 103260
tcacacgtga cacttaattg tcctgtctct ttagtctcct tcaatctgga gcagttcttt 103320
gatttttcct ggactctcat gaccttgaca attctgatga ttataggcca gttattttgt 103380
aaaatttgaa tttgtctgat gttgcttatg tttagattta gggtcttggt ctttggccgg 103440
aatatctcag acaagatgct ctgttcttat tgcatcagag cagaagactc tctgtttcag 103500
ttgatcacat ttatgttgat gctcactttg atcacttgat taaggtggtg tcagttatgc 103560
ctttctactt gtagggttac tccttcctcc ttcgtgattt tatttatttt atttttctta 103620
gagacagggt cttgcttggt tgcccaagct ggagtgcagt ggtgggatct tggctcactg 103680

-continued cagccttgaa ctcctgggct caagtaatcc acctgccaca gcctcctgag taactgggac 103740
tgtaagcgaa caccaccaca cccagctact ttttgtattg tagagatggg gtctcactgt 103800
gttgtccagg ctggtctgta actcctggcc tcaagcagtc ttccggcctt ggcctcccga 103860
agtgctggga ttacaggcat gagccactgc acccagcctc ctttgtaatt aaaaaagtat 103920
tttatgggga gttactttca agtgatggaa atattttata tctatgtgga cttggatttt 103980
cctatttcag tcagtgagtt ataatccatt tctgtcacta gttttatact taaattgttc 104040
ccaacttggc cactgagaac ctttttaggt tagcttttgt gtccttttca catgtctcca 104100
agattcattg aatactttcc tgctttctgg tatagcaaga tgttcaggtt cttttggtac 104160
ttttactttc tctgccctgg ctctggcatc agtcatttct cagaggagcc ctgtgccttt 104220
cagtggacaa tggtgtttag aggccaagat ctggacattg ggtgttttca ttgctaccgg 104280
tgtgtcacta ctcccagacc cctttcagtg gacagcacta aggaatacac atacgtatat 104340
acaatatatc cacctacaca tgtgcgtgca ctcacacaca cacatataca ttacatctat 104400
atttgtgtat ccatgtctat atattgaaaa ttgtggctgg gcacagtggc ttatgccttt 104460
aatctcagca ttttgggagg ctgaggcaag aggatcacct gaagccagga gttcaacacc 104520
agcttgggaa acagagagag actctgtctc tacaaaaata aaaagggaaa accatgagtt 104580
cacacccgtg cccccagttc caatccaact tcacagggtt cattttagtt ttcacccttt 104640
ccatgtttgt aattctcttc tctgacatta tacccttaat atgtttactt attttatgca 104700
tctgtatgca tccaatctac tgtctttgtt ggtatcccac ctccccttgg tgggtccaga 104760
taatctgctc tgggttgccc tttcacgtgg atgtcttcct taccctgtgt gggcctgtga 104820
tactgggctg cccccacaca tgagtgctgc cctcctcacg ttgcttggga cggcactgtg 104880
tcctgggcca ccatgacttt tctcataact agcgtggatg cttaccttgt tccacaccag 104940
tgaatggctt caggaagaga agaggaagag aaaaatattt acatttaaag aaaggtagtt 105000
taaagaaata tgttaggtaa agaattgagc aggtaatata cggagctggc aaaaattgtg 105060
accaaagtag gtgaatgatt gagatttatg caattctggg ctaagtgaca gccccttccc 105120
tttcccttcc cttccccttc ccttcccttt tcttcccttt cccttccctt tccttccctt 105180
tcccttcccc ttcccttccc tttccttccc tttccctctt cttccttcct tccttctgtt 105240
ttcttttccc ttctttcctt tgcctttttt ttttttttaa agctagaaac atcagtttag 105300
gcataaagac agaggaaaag gcttcttttt cctctcacag ttctttataa ttgtctaagc 105360
agtttctttt ttccctaggt ttcatttttt gaggaagagc ggaacatatt atctcgaagc 105420
acaagcccgg gatcccccaa ttannnnnnn nnnnnnnnnn nnnnnnnnnn nnnnnnnnnn 105480
nnnnnnnnnn nnnnnnnnnn nnnnnnnnnn nnnnnnnnnn nnnnnnnnnn nnnnnnnnnn 105540
nnnnnnnnnn nnnnnnnnnn nnnnnnnnnn nnnnnnnnnn nnnnnnnnnn nnnnnnnnnn 105600
nnnnnnnnnn nnnnnnnnnn nnnnnnnnnn nnnnnnnnnn nnnnnnnnnn nnnnnnnnnn 105660
nnnnnnnnnn nnnnnnnnnn nnnnnnnnnn nnnnnnnnnn nnnnnnnnnn nnnnnnnnnn 105720
nnnnnnnnnn nnnnnnnnnn nnnnnnnnnn nnnnnnnnnn nnnnnnnnnn nnnnnnnnnn 105780
nnnnnnnnnn nnnnnnnnnn nnnnnnnnnn nnnnnnnnnn nnnnnnnnnn nnnnnnnnnn 105840
nnnnnnnnnn nnnnnnnnnn nnnnnnnnnn nnnnnnnnnn nnnnnnnnnn nnnnnnnnnn 105900
nnnnnnnnnn nnnnnnnnnn nnnnnnnnnn nnnnnnnnnn nnnnnnnnnn nnnnnnnnnn 105960
nnnnnnnnnn nnnnnnnnnn nnnnnnnnnn nnnnnnnnnn nnnnnnnnnn nnnnnnnnnn 106020

-continued

```
nnnnnnnnnn nnnnnnnnnn nnnnnnnnnn nnnnnnnnnn nnnnnnnnnn nnnnnnnnnn 106080
nnnnnnnnnn nnnnnnnnnn nnnnnnnnnn nnnnnnnnnn nnnnnnnnnn nnnnnnnnnn 106140
nnnnnnnnnn nnnnnnnnnn nnnnnnnnnn nnnnnnnnnn nnnnnnnnnn nnnnnnnnnn 106200
nnnnnnnnnn nnnnnnnnnn nnnnnnnnnn nnnnnnnnnn nnnnnnnnnn nnnnnnnnnn 106260
nnnnnnnnnn nnnnnnnnnn nnnnnnnnnn nnnnnnnnnn nnnnnnnnnn nnnnnnnnnn 106320
nnnnnnnnnn nnnnnnnnnn nnnnnnnnnn nnnnnnnnnn nnnnnnnnnn nnnnnnnnnn 106380
nnnnnnnnnn nnnnnnnnnn nnnnnnnnnn nnnnnnnnnn nnnnnnnnnn nnnnnnnnnn 106440
nnnnnnnnnn nnnnnnnnnn nnnnnnnnnn nnnnnnnnnn nnnnnnnnnn nnnatggagt 106500
cttgctctgt tgtccaggct ggagtgcagt ggtgtgatct tggctcactg caacctccgc 106560
ctcctgggtt gaagcgattc tcctgcctca gcccccctgaa tagctgggat tacaggcatg 106620
tgccaccacg cctggctaat ttttgtattt ttaatagaca cggggtttca ccatgttggt 106680
caggctggtc tcgaactcct gacctcaggt gatctgcatg cctaggcctc ccaaagtgct 106740
gggattacag gcatgagcca ctgcgcctgg ccaacttatt taactttttt gagacagggt 106800
ctcactctgt cacccaggct ggagtgcagt ggcatgatca tggctcactg cagcctcaaa 106860
ttgcagggct caagtgattc tcctgcttca ccttcctgat tagctgggac aacaggtaca 106920
aaccaccatg cctagctaat ttttaaattt tctgtagaga ctagggtctc actatgttgc 106980
ccaggctggt ttcgaactcc tgagctcaag agatcttcct gccttggcct tccaaagtgc 107040
tgggattaca ggtgtgagcc ccatgcccag ctccggtggg ggatatttct atatccacat 107100
gtgtatagtt tactttataa aaatggtatg ttactctgtg cttggctctc cagcttgctg 107160
ttgcctttca ccagtgtatc ccagacatcc tttcttcctt gtcagtaacg caggtctact 107220
ttattctttg agcagtggca taattttccc tgatgtgtat atatcataag ttagagaatg 107280
ctaaaattca ttttggggcc ttgtttaggt tcttgaggga ttaaattcct aaatttaaca 107340
agtgtatcct ggaaacaatt tttgttcctg attcagccct taaaagagga ctatcatgtt 107400
accttgaatg gagataaaca ggctcacgta agagaaaagg gtaagaggga tgaactccca 107460
cttatcttaa acttctactg gcccgttttt ggggaatttg ctgcttttat tcctgaccta 107520
aaataaataa gtttatgtgt cttggtttca tattagttga gaacccagtg cctggagaga 107580
agttttcctt gtcctctgag tgaggacatt cacatatgaa tctattggca gactggcttt 107640
gactgaccac acgtgccttc agaaccaatg ccacagctct taggtttatg gcctgaaaca 107700
ccctttcctt acatattgcc ttagaaactt tccttccttg agacatgggg catggaaccc 107760
tcaccttcac agatgacctt ggtgtgtttc tagggttgct ggtgttccag gacatctgtt 107820
gcagatgcag tatttacctt gtgctctctg catcataagc agcttctcat gtttgaatgt 107880
attaacagac ttttaatttt ttttattttt gagacaaagt ctcactctgt cacccaggct 107940
agtgttaccc aggctggagt gcaatgnnnn nnnnnnnnnn nnnnnnnnnn nnnnnnnnnn 108000
nnnnnnnnnn nnnnnnnnnn nnnnnnnnnn nnnnnnnnnn nnnnnnnnnn nnnnnnnnnn 108060
nnnnnnnnnn nnnnnnnnnn nnnnnnnnnn nnnnnnnnnn nnnnnnnnnn nnnnnnnnnn 108120
nnnnnnnnnn nnnnnnnnnn nnnnnnnnnn nnnnnnnnnn nnnnnnnnnn nnnnnnnnnn 108180
nnnnnnnnnn nnnnnnnnnn nnnnnnnnnn nnnnnnnnnn nnnnnnnnnn nnnnnnnnnn 108240
nnnnnnnnnn nnnnnnnnnn nnnnnnnnnn nnnnnnnnnn nnnnnnnnnn nnnnnnnnnn 108300
nnnnnnnnnn nnnnnnnnnn nnnnnnnnnn nnnnnnnnnn nnnnnnnnnn nnnnnnnnnn 108360
nnnnnnnnnn nnnnnnnnnn nnnnnnnnnn nnnnnnnnnn nnnnnnnnnn nnnnnnnnnn 108420
```

-continued nnnnnnnnnn nnnnnnnnnn nnnnnnnnnn nnnnnnnnnn nnnnnnnnnn nnnnnnnnnn 108480
nnnnnnnnnn nnnnnnnnnn nnnnnnnnnn nnnnnnnnnn nnnnnnnnnn nnnnnnnnnn 108540
nnnnnnnnnn nnnnnnnnnn nnnnnnnnnn nnnnnnnnnn nnnnnnnnnn nnnnnnnnnn 108600
nnnnnnnnnn nnnnnnnnnn nnnnnnnnnn nnnnnnnnnn nnnnnnnnnn nnnnnnnnnn 108660
nnnnnnnnnn nnnnnnnnnn nnnnnnnnnn nnnnnnnnnn nnnnnnnnnn nnnnnnnnnn 108720
nnnnnnnnnn nnnnnnnnnn nnnnnnnnnn nnnnnnnnnn nnnnnnnnnn nnnnnnnnnn 108780
nnnnnnnnnn nnnnnnnnnn nnnnnnnnnn nnnnnnnnnn nnnnnnnnnn nnnnnnnnnn 108840
nnnnnnnnnn nnnnnnnnnn nnnnnnnnnn nnnnnnnnnn nnnnnnnnnn nnnnnnnnnn 108900
nnnnnnnnnn nnnnnnnnnn nnnnnnnnnn nnnnnnnnnn nnnnnnnnnn nnnnnnnnnn 108960
nnnnnnnnnn nnnnnnnnnn nnnnnnnnnn nnnnnnnnnn nnnnnnnnnn nnnnnnnnnn 109020
nnnnnnnnnn nnnnnnnnnn nnnnnnnnnn nnnnnnnnnn nnnnnnnnnn nnnnnnnnnn 109080
nnnnnnnnnn nnnnnnnnnn nnnnnnnnnn nnnnnnnnnn nnnnnnnnnn nnnnnnnnnn 109140
nnnnnnnnnn nnnnnnnnnn nnnnnnnnnn nnnnnnnnnn nnnnnnnnnn nnnnnnnnnn 109200
nnnnnnnnnn nnnnnnnnnn nnnnnnnnnn nnnnnnnnnn nnnnnnnnnn nnnnnnnnnn 109260
nnnnnnnnnn nnnnnnnnnn nnnnnnnnnn nnnnnnnnnn nnnnnnnnnn nnnnnnnnnn 109320
nnnnnnnnnn nnnnnnnnnn nnnnnnnnnn nnnnnnnnnn nnnnnnnnnn nnnnnnnnnn 109380
nnnnnnnnnn nnnnnnnnnn nnnnnnnnnn nnnnnnnnnn nnnnnnnnnn nnnnnnnnnn 109440
nnnnnnnnnn nnnnnnnnnn nnnnnnnnnn nnnnnnnnnn nnnnnnnnnn nnnnnnnnnn 109500
nnnnnnnnnn nnnnnnnnnn nnnnnnnnnn nnnnnnnnnn nnnnnnnnnn nnnnnnnnnn 109560
nnnnnnnnnn nnnnnnnnnn nnnnnnnnnn nnnnnnnnnn nnnnnnnnnn nnnnnnnnnn 109620
nnnnnnnnnn nnnnnnnnnn nnnnnnnnnn nnnnnnnnnn nnnnnnnnnn nnnnnnnnnn 109680
nnnnnnnnnn nnnnnnnnnn nnnnnnnnnn nnnnnnnnnn nnnnnnnnnn nnnnnnnnnn 109740
nnnnnnnnnn nnnnnnnnnn nnnnnnnnnn nnnnnnnnnn nnnnnnnnnn nnnnnnnnnn 109800
nnnnnnnnnn nnnnnnnnnn nnnnnnnnnn nnnnnnnnnn nnnnnnnnnn nnnnnnnnnn 109860
nnnnnnnnnn nnnnnnnnnn nnnnnnnnnn nnnnnnnnnn nnnnnnnnnn nnnnnnnnnn 109920
nnnnnnnnnn nnnnnnnnnn nnnnnnnnnn nnnnnnnnnn nnnnnnnnnn nnnnnnnnnn 109980
nnnnnnnnnn nnnnnnnnnn nnnnnnnnnn nnnnnnnnnn nnnnnnnnnn nnnnnnnnnn 110040
nnnnnnnnnn nnnnnnnnnn nnnnnnnnnn nnnnnnnnnn nnnnnnnnnn nnnnnnnnnn 110100
nnnnnnnnnn nnnnnnnnnn nnnnnnnnnn nnnnnnnnnn nnnnnnnnnn nnnnnnnnnn 110160
nnnnnnnnnn nnnnnnnnnn nnnnnnnnnn nnnnnnnnnn nnnnnnnnnn nnnnnnnnnn 110220
nnnnnnnnnn nnnnnnnnnn nnnnnnnnnn nnnnnnnnnn nnnnnnnnnn nnnnnnnnnn 110280
nnnnnnnnnn nnnnnnnnnn nnnnnnnnnn nnnnnnnnnn nnnnnnnnnn nnnnnnnnnn 110340
nnnnnnnnnn nnnnnnnnnn nnnnnnnnnn nnnnnnnnnn nnnnnnnnnn nnnnnnnnnn 110400
nnnnnnnnnn nnnnnnnnnn nnnnnnnnnn nnnnnnnnnn nnnnnnnnnn nnnnnnnnnn 110460
nnnnnnnnnn nnnnnnnnnn nnnnnnnnnn nnnnnnnnnn nnnnnnnnnn nnnnnnnnnn 110520
nnnnnnnnnn nnnnnnnnnn nnnnnnnnnn nnnnnnnnnn nnnnnnnnnn nnnnnnnnnn 110580
nnnnnnnnnn nnnnnnnnnn nnnnnnnnnn nnnnnnnnnn nnnnnnnnnn nnnnnnnnnn 110640
nnnnnnnnnn nnnnnnnnnn nnnnnnnnnn nnnnnnnnnn nnnnnnnnnn nnnnnnnnnn 110700
nnnnnnnnnn nnnnnnnnnn nnnnnnnnnn nnnnnnnnnn nnnnnnnnnn nnnnnnnnnn 110760

-continued nnnnnnnnnn nnnnnnnnnn nnnnnnnnnn nnnnnnnnnn nnnnnnnnnn nnnnnnnnnn 110820
nnnnnnnnnn nnnnnnnnnn nnnnnnnnnn nnnnnnnnnn nnnnnnnnnn nnnnnnnnnn 110880
nnnnnnnnnn nnnnnnnnnn nnnnnnnnnn nnnnnnnnnn nnnnnnnnnn nnnnnnnnnn 110940
nnnnnnnnnn nnnnnnnnnn nnnnnnnnnn nnnnnnnnnn nnnnnnnnnn nnnnnnnnnn 111000
nnnnnnnnnn nnnnnnnnnn nnnnnnnnnn nnnnnnnnnn nnnnnnnnnn nnnnnnnnnn 111060
nnnnnnnnnn nnnnnnnnnn nnnnnnnnnn nnnnnnnnnn nnnnnnnnnn nnnnnnnnnn 111120
nnnnnnnnnn nnnnnnnnnn nnnnnnnnnn nnnnnnnnnn nnnnnnnnnn nnnnnnnnnn 111180
nnnnnnnnnn nnnnnnnnnn nnnnnnnnnn nnnnnnnnnn nnnnnnnnnn nnnnnnnnnn 111240
nnnnnnnnnn nnnnnnnnnn nnnnnnnnnn nnnnnnnnnn nnnnnnnnnn nnnnnnnnnn 111300
nnnnnnnnnn nnnnnnnnnn nnnnnnnnnn nnnnnnnnnn nnnnnnnnnn nnnnnnnnnn 111360
nnnnnnnnnn nnnnnnnnnn nnnnnnnnnn nnnnnnnnnn nnnnnnnnnn nnnnnnnnnn 111420
nnnnnnnnnn nnnnnnnnnn nnnnnnnnnn nnnnnnnnnn atattgaatc tgtgcaaagt 111480
cagctatcag tctgattgcc ctatcccaca aattgcatcc caggagatga ttagatgcaa 111540
taggtgaaag ttttcatgtt cctcagtggc attcagtgca tgaacaacca ttgtccacct 111600
aattcctctg catctacagc aagaaataga atttttgtgg agacttaaca tgctgtgtct 111660
tacttacata tgtatgcaaa aaaaaaaaaa aaagtcactt tttttctttt ttgagaccga 111720
gtcttgctct gtggcccagg ctggagcaca atcacggctc actgtaacct ccgctaccca 111780
ggttcaagtg attctcctgc ctcagcctcc ttgagtagct gggactacag gcacgtgcca 111840
ccatgcccag ctaatttttg tacttttagt agaaatgggg ttttgccatg ttggccaggc 111900
tggtctcgaa ctcctgacct caggtgatcc acctgtcttg gcctcccaaa gtgtgggatt 111960
acaggcgtga accaccaacg cctggccctg aagatacatt ttaaatcaat gaaaaaaaac 112020
aacaggattc tacctcctat ggtatatccc tcctggctgt ctcttctctc cagtcttgcc 112080
tctgctgtgt gggtttcagg catccatctt ctctactctg aattactgtg ataacctctg 112140
aagtattttc cctgccatct gtctggccct tctcccaggt cttccacata ctgcagccaa 112200
gtcagcccgc tgttgaaacc cttcaagact ccctgctgtc ctctggatga agtccagact 112260
cttccacgtg acttaccagg cctttcttgc acttgtcccc agccacttac tgtttctctc 112320
tttctacctt aacatcctga acttcctttg gttctttgac cttgcctctg accttttttcc 112380
atgctgttca ctctttccct gttcaccttg ctaactcctc tttctctttc tgggttggat 112440
cagatttcac ttcttccaga agcccttcct agaccctata cttctggaat ggcgcctttt 112500
gactgtacgc tcattgcacc ctgtacttct cctttatgag tgggtgctgg tctgtcccac 112560
taggctactt catccataaa gggagagtag agctttacca agtcaatgct taagcaatat 112620
ttattggatg aatgtgtgat taatttcata gaaatttgat gtgcattcaa atttacttat 112680
tgtattacgg aacttgcatt atattctcag tggagttatt ttctttcacg tgtgtaattc 112740
aagatagact cagtgagatt ttcaaaattt ggaatgcagt gcaaggaaat tgaacttgag 112800
ttcttttgca ttttgatggt taaaaatttc ccatttgtgg tgacatacca caataagcca 112860
gtgaatgtgg cttattgttt tctggtctat agaaaattgt cgcaaactct gtcataatgt 112920
ctggttctat ataacaaagc tagtcctgta ttctgcatgt ggctgatgga aacagtgctc 112980
tgttgatctg gttcatgaag aaatctgttc aattctgcat aacagatgcc ttcatcagtg 113040
tccttccatg aaggagctga tcttcacaaa gaacacatag ttttgcatcc caccacttgc 113100
agtnnnnnnn nnnnnnnnnn nnnnnnnnnn nnnnnnnnnn nnnnnnnnnn nnnnnnnnnn 113160

-continued nnnnnnnnnn nnnnnnnnnn nnnnnnnnnn nnnnnnnnnn nnnnnnnnnn nnnnnnnnnn 113220
nnnnnnnnnn nnnnnnnnnn nnnnnnnnnn nnnnnnnnnn nnnnnnnnnn nnnnnnnnnn 113280
nnnnnnnnnn nnnnnnnnnn nnnnnnnnnn nnnnnnnnnn nnnnnnnnnn nnnnnnnnnn 113340
nnnnnnnnnn nnnnnnnnnn nnnnnnnnnn nnnnnnnnnn nnnnnnnnnn nnnnnnnnnn 113400
nnnnnnncct actgtggttt tcttcagaat tacccttgct ctgagcctgc aattgactca 113460
tgaacttctt ttccatgttc taaccttaca atgacttcct tgtgttcact ccaaatgttt 113520
ttccctggtt gcatgtagag atgtattagc taaggtacat gcttagctgc tgtatcaaag 113580
agaccctaat gtacaaccca ggctggtaga gcagctctgc tgtatgtgtt aattcaggga 113640
cccaggttcc ttccatgttg tgactccccc cttccttagg atgttgtctt cttttacatg 113700
gctgaagttg ggccatttca tgtctctgtt ccagctgcct ggtaggaaaa aagaacagaa 113760
attcagagta agcaaattct ttttctatag atggatgcgg aagttggaca catcatttcc 113820
tctcacattt tctcggccag aacgtagtca tgtgactgca cgtctagctg ctaaggagac 113880
tgggaattta ctgtcggctg tgtggcctct gtcaagctaa aattcttatt actgtggaat 113940
aagggaagga tggatttggg ggcacaatta atagtctgtc acagaggcta aaacagctgc 114000
ttttggctgg gcacggtggc tcacacatgt aatttcagca ctttgggagg ccgaggcaag 114060
tggatcactt gagatcagga atttgagacc agcctggcca acatggtgaa accctgtctc 114120
tcctaaaaat atagaaatta gccgggcatg gtggcgggta cctgtaatcc gagctactcc 114180
agaggttgag gcaggagaat tgcttgaacc tggaaggcag aggttgcagt gagccaagat 114240
ggtgccactg cactccagcc tgggcgacag agcaagactc catctcaaaa aaaaaaaaaa 114300
aggttaaata aacagctgct tttgtaggtg atacaaggta cagctaagct ttgaagccag 114360
gcctgtagtt tcaccttcca tattcttact caaggcatta tacttctgga tctgaaacca 114420
ctggatctga tgccctgctt gggatgagtt ctttatatta tcttgctttc aacccacacc 114480
tgtgtaattt tatgggcagc gtttgtttcc tatataggaa caatttgaaa gtgggctgtt 114540
tctaggcttt catgaatagc aggctatgct gtcattggga atctggaggg agttaatgaa 114600
cacaacttca ttgtttactt tagtgaaatg tggcagctta tgatagtttt gacagtgaga 114660
catgtgctgt tttgatctct cagctaagat tatctgattt ttcaggcatg tctcaaaact 114720
caccaggcct gctcacatgc tgctgcttct gaagccaggg tttggaaacc agctgcccat 114780
cagaatgagg ctgtgactta gaatattggt tcttgtttta ttaccattcc ttgtttggtc 114840
tctccagagt cactggcctt ttccgcttca attttcttat cggtgaaatg agatattaat 114900
tcctcttatt gacttcaatt caattgctga gtgtattgtt gcctttggga agttctttga 114960
gttttctgtg cctttgaaat agttgttttt ttttattctg gtgttttgag gcatgtttca 115020
agtgagtgca tttacacttc taccatttta ggagccacaa ttcagttatg ttgtcccagc 115080
ttgcttggcc ccatccccag agtttctgat tcagtaggtc tggggtgggg cccaataatt 115140
tgcatttctt cttctttttt cgagacagag tctgactgtg tcatccaagc tggagtgcag 115200
tggcacgatc gtagctcatt gtagcctcaa actcctgggc tcaagccgtc ctcccacctc 115260
accctcctga gtagctggga ctataggcat atactaccat gccctgccac ctttttaatt 115320
ttttgtaagg atgggggtct cactgtgttg ctcaggctgg tcttgaattc ctgggctgaa 115380
gtgatcctcc tgcttcagcc tccccaaatg ccggcattcc tggcatgagc cactgcactt 115440
ggccaagact ttgcatttct aactagtttc caggtaatgc tgctgctggt gtagggacct 115500

-continued cattttgaga accattgttc tatagctgta gctatagtta gtttctggtt atagcttctt 115560
ccttttgtcc cttcagtaat agtgtacaca tccgaaatcc ctgtccttgc tctttcaggc 115620
ccaggcatgg tatctggtcc tcttctgttg ctagccctgg ggtgcttcat catcccaagt 115680
ttatttttct tctcctaacc tgaacctttg taaatagccc cttccctaat gaacgtcctc 115740
aattccctgt tttgcgtgtc ctgtctgttt cttggcaaga ctctggatga ttcagtactc 115800
aatgaggatt tttcgcatag atggatgaaa caggctgggt ttcatgtttt ctaagataaa 115860
ggtgcttctc tctttttctc ttggtcactt tgaccaagaa gaaaataaca gagtttttat 115920
tctcaagaag aataatatcg gggccactct gctcagaggc cactctgctt tgaggacccc 115980
ttctctcctc cctcatgcca aagatcagga acattgggca gagcggataa cgatgccgcc 116040
agcgtcatta cattttcacg gcactttcag ttgtgctgag cgtgcaaaca tttcaaggag 116100
acatttctaa gaggtggcta gcacagcatg cctctaatgc cctatgtgaa ttggaataga 116160
gtactaaaga actgttcaat attcacccca tccccgcata tgcaagcatg cacgtgggtt 116220
cattgtatat gtgtgtgtgc acgtgtgcac agacacattt gtccttcgtt tcaaatgcaa 116280
cacaatggat ggaaattgcc ttcctggtac tggggtatgg atgcaaacac caacagagaa 116340
gcagccgcta cttccaaact gaacacatgt gagatttgcc ctttaattag catctgcagc 116400
tgctgccatc agaagggtct gtctctgttg gcctgaaagt ctttgcttta aaagagcaag 116460
tccattatag ctccaagcca ggctcgtctg tcagctgctg tgctttctct gccatcagcg 116520
gggttgccac attgttttgg gctgtttcac tctaggactc tttcctcctc ctgtgccccc 116580
agcctttgat taccatgcct tggtgatcct catttgggtg acctgcagct gctcattgtg 116640
tgtgcaggag acatctccag tccttgtaag gagggaagat cactggcttc agtgctgatg 116700
gactggttat tttccagccc tttgtcgtca gtgatcttgt cttgatatgc agaaaggctc 116760
caggtagtca ctgaaaaaaa tataagcagc agaggtgatg gctatatgaa agtcacgttt 116820
catcaagggc attgctgcta tggaaacttt caattcactt ggagtaggga gccatattgg 116880
ttccacagcc tcctcagcag tgggtcccaa cacagtgctg ggctagctgc ctctgaatca 116940
ccgcagtagc tccttttact atagattcct gggtcccacc catggaatgt gatccatgaa 117000
gtctggggtt attccctgga atcctttaag ctccctaagt ggttgggatg ggaaagagat 117060
atgctttatg ttactatact tcttattatt attattttaa aattcttgcc gggcgcagtg 117120
gctcacacct gtaatcccag cacattggga gaccgaggcg ggtggatcac ttgaggtcag 117180
gagttcgaga ctggcctggc caacatgatg aaatcccgtc tctactaaaa atacaaaaat 117240
tagctgggca tggtggcgca tgactgtagt cccagccact ccggaggctg aggcaggaga 117300
atcgcttgaa cccgggaggc agaggttgca gtgagccgag atcgtggcac tgcactccag 117360
cctgggtaac agagtgagac ttcatctcaa aaaaaaccca aaaaaacaaa actctttttc 117420
attataccgg aacgtcagct ttatggagtc ggggattttt tctgttttat tcactgctgt 117480
ttccctaaca tctagaatag tggctggcac gataggcact caagtattga tttagatgag 117540
tctattttat tttcttttaa atttttaatt tttattagag gtggggtctg gctttgttgc 117600
ccaagctggt ctcaaaactc ctggcctcaa gcgattgtac tgcctcagcc tcccaaaggg 117660
ctaggatagg catgagccaa catgcctggc ttgtcttatt tttaacaagc acttctggtg 117720
attctgatgg acaatcaggc ttgggaagtt ctaacctaga ggacctacag ttgtcttggg 117780
gtagaagcca aggctatcct ggtttttaga atcagtgcct tactgggcat ctctgaagag 117840
taaaagtcag ggacagagtt acatttttgg acaaaaccag atgctgtgaa tggactcttg 117900

-continued gtcacaacct gggtggcgac ttggtcctta acttcttcat cattttctgc tgaccctgtt 117960
ctttggttca cagcaagtca cctgataaga agactcaaag actgctagtt tgttacttta 118020
gatgatgctt ttggaacctc ttggtaccat tttaacaatc caaacgtatt ttatgaaagc 118080
actcaagtcc tgggtcttta ttgtatcttt aagctctaac agcatgatga ttgaataagc 118140
tgtggttggc cacacacaag ccatcttccc catggcctcc attcatacta gaatgagcag 118200
ctataccccca gtagtatagt tttgggatat gggtaacatc ttgggatagc cacatttact 118260
tagtaaatgt ctggcttaca ttctcctaat ggtgcactgt tggaattttt ggtgtggtaa 118320
cctggaatag tgttggtggg tcaagtttga ttagcatctt tgataaggac ccggtctatt 118380
tagaggtttg tcattgagtg tgtctgtttt ggcctcatgt tgtgaagcat gctgtgtagc 118440
agctgttgta atttttgttg cttgttttct caatcaaccc tggttttgaa gaaatgggaa 118500
gttgttccac tcttagactg atctgacttg ggaggggatt ttcagttcag gaagttggat 118560
cttctgaatg gaagcaaaga atacatgtct ttttgccact ttacaagctg gctcttgttt 118620
tctgaactat tttactggtc attgcaaata gaatgtcagg agtagctgcc aaatactaag 118680
ttgtgttcag tttgtcagtt cttaagagtt gccggtggct gctctgctat gcgtatgact 118740
ttctcagcct taaacttaca agccatactg ttttttttcac atctttaata cagccatagg 118800
aaatttataa ctgtggcgtg tcgtcataaa tatgcattgt tcttatttta agacatttca 118860
gtactaaaag tataagtact tctgttatta tctgtgaatt tctttccttc ttcttttttt 118920
ggatatttaa gacctttttcg atgtcaatat atatttaaaa cagacatata aattagcatt 118980
cacccacata cccagggcct atggagaacc aggttgggat gagtgggtga gctacaggca 119040
gccaggtggc tcctgtgggc tcctcgagga ctggggtgag taactaatgt ctgctaggaa 119100
cttgggggaa agaaggtgtg tatgttaggt gctgcccccct tctaagtgtt cctcttgttc 119160
ataattgagt tttttttttt tttttttttt ttttagaagg agtctcgctc tgttgccagg 119220
ctggagtgca gtggtgtgat ctcagctcac tgcaacctct gcctcccggg ttcaagtgat 119280
tctcctgcct cagcctcccg agtagctggg actacaggca tgcaccacca tgcccagcta 119340
atttttgtat ttttagtaaa gacggggttt caccatgttg gccagggtgg tctcgatctc 119400
ttgaccttgt gatccgcctg cctcggcctc ccaaagtgct gggattacag gtgtgagcca 119460
ctgtgcccag cccataaatc aaaatttttt cagcaattgt tatacaagtg gaaccttact 119520
cttcaaatgc aattgtccag tgtctggctt aatgtctgct gttgtcagaa accatgtgaa 119580
tggagtagat tcccaggtta taaggagccc ccagggagga tgcgcgagtc actggcttct 119640
ccaggggtct ctggtttggg gttgccttgg tgctgggcac acttcctgga gattttactg 119700
gaccagcctg aggcctttgg ggctctgtgc agatgctcta cttctgactt gtctagagct 119760
ttcttctaat tctggactaa aagcaagcag gagtttggag gatgatggtg agaattcaca 119820
tccccgagtt ggcttttgga atgcagtagt ttgtgagatt tagtgttttt tttaagaagt 119880
atattcagat cttgcctttt tcccagaaag catatgagac aacttccaag acatttatag 119940
catggctaat aaaatgggaa atcagggcga aggacaggag aactcaataa gggttaacat 120000
ggctacagcg attgtctaaa tgggttcttt ttgctggcca gagcagaaag gatcatgcag 120060
taaagtgggg gggaagaaag ggaattgaat ggtaggtgaa gacttcatgt tggtgccagg 120120
cactgtgcca ggccctccta ggaccttgtc ttactcaatc ctcacacagt gctgcaagag 120180
gattagtctt atccctgttt tagagaggat gaaactgaaa ggcagcgagg tgaagtcacc 120240

-continued agcaggaggc tgaagccgcc caggctaact ggccttatag ctacctaggg actcaggaat 120300
atcacacctg tttatcatca aaaggagaaa ggatttcagt tccttggggt agaagagttt 120360
ctttttgcta atcaaacatt ttacttgagg cttcatattc ttcttcaaga tttttttcct 120420
gtgtatgtac caacacatgt aataattcct tgtttatttc aaaaaagggg ttgtacttta 120480
ttctttacaa gatttcactt tatattgtca tggacaattt tccatggcag tatgaataaa 120540
tggaatctgt ttgtttttaa tatctttgtc ttatcccatt gtttacatat gtcatatttt 120600
agccagtctc taactgatgg atagctgaat gatttccatg tttttttccc ctgttacaaa 120660
caatactgca aggaatctat ttatctttct atttatctgc aaactattgt aagtacctgt 120720
aaattgttag aagtggaatt actaggtcaa aggggatatt ttcacattta aattttgaat 120780
agaggctgtc agttgccttc cacactgact ataaaaggaa aagattgtat cacatttatt 120840
gcaagccttc tgtattctgc tgggtgctga ggggaataca gaaaggatat aagagtggtt 120900
gccctctagg aatatccgtc tacactgtac ctaatcctag ggaatgtctg gggtgtcaac 120960
ttgtgggtgg gaaagtgggt ggatttaatt caactgttca agcttgcctt gcaaacactg 121020
tgcatggtgt ctgggactag tctttcatta tattgattcc cctgggtaac agatgtaatt 121080
tccttagggc agggacttca tcctacatga cttacagcgt gccttacaca tcttctttgc 121140
tttgtggaga ccttgttatt ataacacgtc aggtgatatt cgaggatcta attgaggcat 121200
tccctatttt tgggtgtgtg aagaattaat aactttggca ttctatacag gtcatggaat 121260
atcagcctgg aggggacttg ctgtcacttt tgaatagata tgaggaccag ttagatgaaa 121320
acctgataca gttttaccta gctgagctga ttttggctgt tcacagcgtt catctgatgg 121380
gatacgtgca tcggtaagtg agactctggt agcattttta tgctgaggat tttcctgtgt 121440
cgcataagag ttcctgcatg gaaatgagtg gatgagtgat ttcaagatca agataacgcc 121500
nnnnnnnnnn nnnnnnnnnn nnnnnnnnnn nnnnnnnnnn nnnnnnnnnn nnnnnnnnnn 121560
nnnnnnnnnn nnnnnnnnnn nnnnnnnnnn nnnnnnnnnn nnnnnnnnnn nnnnnnnnnn 121620
nnnnnnnnnn nnnnnnnnnn nnnnnnnnnn nnnnnnnnnn nnnnnnnnnn nnnnnnnnnn 121680
nnnnnnnnnn nnnnnnnnnn nnnnnnnnnn nnnnnnnnnn nnnnnnnnnn nnnnnnnnnn 121740
nnnnnnnnnn nnnnnnnnnn nnnnnnnnnn nnnnnnnnnn nnnnnnnnnn nnnnnnnnnn 121800
nnnnnnnnnn nnnnnnnnnn nnnnnnnnnn nnnnnnnnnn nnnnnnnnnn nnnnnnnnnn 121860
nnnnnnnnnn nnnnnnnnnn nnnnnnnnnn nnnnnnnnnn nnnnnnnnnn nnnnnnnnnn 121920
nnnnnnnnnn nnnnnnnnnn nnnnnnnnnn nnnnnnnnnn nnnnnnnnnn nnnnnnnnnn 121980
nnnnnnnnnn nnnnnnnnnn nnnnnnnnnn nnnnnnnnnn nnnnnnnnnn nnnnnnnnnn 122040
nnnnnnnnnn nnnnnnnnnn nnnnnnnnnn nnnnnnnnnn nnnnnnnnnn nnnnnnnnnn 122100
nnnnnnnnnn nnnnnnnnnn nnnnnnnnnn nnnnnnnnnn nnnnnnnnnn nnnnnnnnnn 122160
nnnnnnnnnn nnnnnnnnnn nnnnnnnnnn nnnnnnnnnn nnnnnnnnnn nnnnnnnnnn 122220
nnnnnnnnnn nnnnnnnnnn nnnnnnnnnn nnnnnnnnnn nnnnnnnnnn nnnnnnnnnn 122280
nnnnnnnnnn nnnnnnnnnn nnnnnnnnnn nnnnnnnnnn nnnnnnnnnn nnnnnnnnnn 122340
nnnnnnnnnn nnnnnnnnnn nnnnnnnnnn nnnnnnnnnn nnnnnnnnnn nnnnnnnnnn 122400
nnnnnnnnnn nnnnnnnnnn nnnnnnnnnn nnnnnnnnnn nnnnnnnnnn nnnnnnnnnn 122460
nnnnnnnnnn nnnnnnnnnn nnnnnnnnnn nnnnnnnnnn nnnnnnnnnn nnnnnnnnnn 122520
nnnnnnnnnn nnnnnnnnnn nnnnnnnnnn nnnnnnnnnn nnnnnnnnnn nnnnnnnnnn 122580
nnnnnnnnnn nnnnnnnnnn nnnnnnnnnn nnnnnnnnnn nnnnnnnnnn nnnnnnnnnn 122640

-continued

```
nnnnnnnnnn nnnnnnnnnn nnnnnnnnnn nnnnnnnnnn nnnnnnnnnn nnnnnnnnnn 122700
nnnnnnnnnn nnnnnnnnnn nnnnnnnnnn nnnnnnnnnn nnnnnnnnnn nnnnnnnnnn 122760
nnnnnnnnnn nnnnnnnnnn nnnnnnnnnn nnnnnnnnnn nnnnnnnnnn nnnnnnnnnn 122820
nnnnnnnnnn nnnnnnnnnn nnnnnnnnnn nnnnnnnnnn nnnnnnnnnn nnnnnnnnnn 122880
nnnnnnnnnn nnnnnnnnnn nnnnnnnnnn nnnnnnnnnn nnnnnnnnnn nnnnnnnnnn 122940
nnnnnnnnnn nnnnnnnnnn nnnnnnnnnn nnnnnnnnnn nnnnnnnnnn nnnnnnnnnn 123000
nnnnnnnnnn nnnnnnnnnn nnnnnnnnnn nnnnnnnnnn nnnnnnnnnn nnnnnnnnnn 123060
nnnnnnnnnn nnnnnnnnnn nnnnnnnnnn nnnnnnnnnn nnnnnnnnnn nnnnnnnnnn 123120
nnnnnnnnnn nnnnnnnnnn nnnnnnnnnn nnnnnnnnnn nnnnnnnnnn nnnnnnnnnn 123180
nnnnnnnnnn nnnnnnnnnn nnnnnnnnnn nnnnnnnnnn nnnnnnnnnn nnnnnnnnnn 123240
nnnnnnnnnn nnnnnnnnnn nnnnnnnnnn nnnnnnnnnn nnnnnnnnnn nnnnnnnnnn 123300
nnnnnnnnnn nnnnnnnnnn nnnnnnnnnn nnnnnnnnnn nnnnnnnnnn nnnnnnnnnn 123360
nnnnnnnnnn nnnnnnnnnn nnnnnnnnnn nnnnnnnnnn nnnnnnnnnn nnnnnnnnnn 123420
nnnnnnnnnn nnnnnnnnnn nnnnnnnnnn nnnnnnnnnn nnnnnnnnnn nnnnnnnnnn 123480
nnnnnnnnnn nnnnnnnnnn nnnnnnnnnn nnnnnnnnnn nnnnnnnnnn nnnnnnnnnn 123540
nnnnnnnnnn nnnnnnnnnn nnnnnnnnnn nnnnnnnnnn nnnnnnnnnn nnnnnnnnnn 123600
nnnnnnnnnn nnnnnnnnnn nnnnnnnnnn nnnnnnnnnn nnnnnnnnnn nnnnnnnnnn 123660
nnnnnnnnnn nnnnnnnnnn nnnnnnnnnn nnnnnnnnnn nnnnnnnnnn nnnnnnnnnn 123720
nnnnnnnnnn nnnnaaaaaa ctgatgctag tgaaaatgca taatttaaga ggttagagaa 123780
gctgctcttc aaaatgcccc ccaagtctga gagttaaatc ctttacataa aggacaatat 123840
gtaaaatttt ctttttcttt tttctttttt tttgagacgg agtctcgctc tgtcccccag 123900
gctggagtgc agtggcgcga tctcggctca ctgcaagctc cgccccccctg ggttcacgcc 123960
attctcctgc ctcagcctcc cgagtagctg ggactgcaag cgcccgccac catgcccagc 124020
taattttttg tatttttagt agagacgggg tttcaccgtg ttagccagga tggtctcgat 124080
ctcctgacct cgtgatccac tcgcttcggc ctcccaaagt gctgggatta caggcataag 124140
ccactgcgcc cggctctttt ttttcttaaa ctgcttccag aaaagtggat attattaggt 124200
tgatgttaag aaaaggcttg gagttgcatt aactttttgc tttctagcat ctggcctgtc 124260
tgttctgcag acctgagacc tacttgagat aattttcttg gtgttcaggc ccttggaaaa 124320
ataagttccc tatgttgtcc agtgtcaaag tttctcaacc tcagcactat tctttttttc 124380
aggttatttt cttgtaatct gttcacttga tcattacatt aagaattaga ttatattgct 124440
ataactacaa agcattttat gttttaaaaa ttatgtacaa tttagaaaca ggcatgaaaa 124500
cttaggtatt aaatttagtg gaataaagca cagaaaaaaa gttaaaataa tgcagtttta 124560
tcacttagga ttaaacattt atatgggccg ggtgtagtgc ctcacacctg taatcccagc 124620
acgtttggag gtcgaggcgg gaggattgct ggagtttgag accagcctgg gcaacaaaat 124680
gagacctagt ctctacaaaa aatcaaaaaa ttagccagac atggtagtac atgcttgtag 124740
ctccagccac atgggaggcc aagacagtag gatcgctgga gcgaaggagg ttgaggctgc 124800
aatgaccgtg tttgcaccat tgcattccag cctgggcgac agaacaagac cctgtcttaa 124860
aacaaattta tatgctgcat tcgtgaaatt aaaaaaaaat catggattta gaaataaatt 124920
gaagcaaggt acattgacag tgtaacctca gcactactga cattttgatc tgaataattc 124980
```

-continued

```
tttgttgtgg gggatgcgct gtataagatg tttagctgca tccctgactc ctacctccta 125040
gatgccatta gcaccctccc ctccagatgt gataaccaaa aatgtctcta gacattgcca 125100
gatgtgcctg gggtaggagg gttgggggaa gtggggtttg agaaccctta gttgatcatg 125160
cctgcagtag gttgagaagc atcagaaagc taattaatta gacaggaata tgtgtttgca 125220
gtaagaaaac ctcagcaaac taatcaagtt ccaaagttac tgcttggtaa ataaatagga 125280
attaagaata agaccctatc tctgtgtctg gggtcattct cttcggagct cttggtggag 125340
agacagggtt cccagtttca attttttagt gcttcagact gccctttca gttataattg 125400
taacaacctt cactccaggt ggggagcctc ccaggtttat ttacaacaag gctcaatctc 125460
tgattatttt ggtcaaggag atatgacact ctataccaca cacttgagaa tattgcctct 125520
ctttttctct tgagctttta gggttggaac gtgacaggca gataaggaat tttttgcatt 125580
aagtgcaaag tcctttttct tatagaagag caataatctg cacactagat caagtcaagt 125640
gtggatataa aattataatt tttgggggga tatttttaat agtggttttg ggttaaacat 125700
atttccttta aatgaaatgt ctgtaggcct aaagtaggtt ctaaatgttg cctgtactca 125760
tagtatacca tataaaatat aatccacatt tactggaact accatatatt acttacccca 125820
aatcaatcaa tcccttccct atcacccccca cgtaagatct tcgtattttg gatacctgtg 125880
aatcttagat ctgttcagtt ttccattatc cattgtctta tttcaagctt ctcattcaga 125940
atgttgcttt ggagtatttt ctgttagtaa acacagggcc tagtgactct aggacctgct 126000
gtgtgactta ggtcacccac ttcactttat tagaatctca aagaatggtg aacagctgag 126060
ttccaatctg tctcatttgg ctctcatgaa aacagtcata aggagattgt agataaacca 126120
cattatatag catagtaagt gataatcaac cccatttggc agttgcaacc ccacaagaga 126180
tagccctttt tagatttgtg taggagtgaa aagctttatt ttccacaaga ggaacgacat 126240
agtaagaact cctttccccc ctgcttctgc aggtatatgc ttatgcccta ggcaacttga 126300
tgggtaaagt taggtttaaa tagttttatt tgtaagctct tctcttctct tctcttctct 126360
tctcttctct tctcttctct tcttttcttt caagacagag tcttgctctg tcacccaggc 126420
tggagtgcag tgggcgacct tggctcactg caacctccgc ctcctgggtt caagagattc 126480
tcctgcctca gctccccgag tagctgggat tacaggtgcc cgccaccatg cctggctaat 126540
ttttgtattt ttagtagaga tggggtttca ccatgttgaa gcattttagg aaaggggtta 126600
ggaggaggaa gacannnnnn nnnnnnnnnn nnnnnnnnnn nnnnnnnnnn nnnnnnnnnn 126660
nnnnnnnnnn nnnnnntctc cccctttctc ccaaaatatg gcagactctt ctgtccccta 126720
gtcattctca tatagtcttc tgaacttgtt tattttcttc cctgttaata cagtaaaaat 126780
taactaagtt ggccaggagt ggtggcacat gcctgtaatc ccagcacttt gggaggccga 126840
ggcgagcaga tcacctgagg tcaggagttt gagaccagcc tggccaacat ggtgaaaccc 126900
tgtctctact aaaaaaaaat tgtaaaagtt agctgggtgt ggtggtgcgc acctgtagtc 126960
ccagctattc gggaggctga ggcaggagaa ttgcttgaac ccaggggctg gaggttgcag 127020
tgagccaaga tcgcgccact gcactctagc ctgggcgaca gagcagtctt taaaaaaaaa 127080
aaaaaattaa ctaagttaag tagtacttgg gccctatcag atagtgtcct cctgcaggca 127140
ggctgggccc ctactacagt ttcactttta atatctcacc gagattagct gactgaattg 127200
ccaccagagg agagtgaaag catattgcaa aatcataatc aggacatgtg agattatgtg 127260
ttgaacaggt ttaatgtgct tgggggtcag tgactaatgg gaacttagca gtcattaact 127320
gtcattaaaa acgtttgtta attactatta cacacttaga gatttgttaa ttaacaaaga 127380
```

-continued gtaatgcctt tgctaatcac tattatgcac ttaagaggaa gccagtgggt atttttccct 127440
tcatagcttt ctagtacaaa ttaataaaat ttagaaaatt agaaaatgat tgtgcataaa 127500
tgtgtataat catgtatctg ttaggggcca aaaattagtt ggggaattat ctttctttga 127560
taagtcttat cattagtttg aaaatggggc attggcaatt catactgttt ggctgggttg 127620
tcctgagaaa cactccccag tcaattctgt ttttgcaact ctttggttgt gaacaagtga 127680
ctgccctgtg agctgcaaat aaggagaact gaatattcct gaacagtctg tggcaataaa 127740
aatgaaatcc agtaagtgca aatggtatgt attcaacaat tgcgtagtta ggtcctgcaa 127800
ggtaattaga cataaaggat aagtatttaa tcaacaatat agtagcattt tcattaccta 127860
gtcaaatcaa gatgttacag ttttccttct cttgttttgt tatttaaaaa atatctattg 127920
tggccaggct ccgtggctca cacttgtaat cccagcactt tgggaggcca agatgggtgg 127980
atcacgaggt caagagatcg agaccatcct ggccaaacat agtgaaaccc cgtctctact 128040
aaaaatacaa aaattatctg ggtgtggtgg catgcacctg tagtcgcagt tactcgagag 128100
gctgaggcaa gagaattgct tgaacctggg aggaggaggt tgcagtgagc tgagatcgca 128160
gcactgcact ccagcctggt gacagagcga gactccatct cggaaaaaaa aaaaaatcta 128220
ttggttattg ttggtgcatt ttaaccaaaa ccctttagtt taaccctaac ctgtgctgag 128280
ctctttaaca tttacataca tattaaaaaa cagaatcagc ccagatttcc caacatatta 128340
agtcttctcc ttgacttaag ctactttcag ttcttcaagc ttaagtcacc ctgtggtttt 128400
gtcttaggcc aaatattttc ccctttgtct ccccttctgt ctatcaagcc aagcctgcct 128460
gtgggttttg gatagtgtga ccatctggct ttcttgaagg ggcacttaca ggggaagttt 128520
tattgcccaa accggtggac aatccatgtc aggaatgatt atatcacact gctttctggg 128580
tttagggctt ggaaaaacct gtatcagagc gtgggcccta gggaagaggt aaaaagagag 128640
gagagggaag aataggtctg tttcatataa cgagaaagtc tcatggcaga ggaatggatg 128700
agattcaagt tacaggctgg aagagcttca tccagaatca gccccgggga gaggagacct 128760
catcacgtcc tcactaaaca ttcactttcc tctccacacc cagttaaagt aaagcaaatt 128820
tacttccttg gtgaaaagcc cagccttcaa ggtatgtgga cttacccaca aaatctcttg 128880
gctcactcag tttcacttac catcgtttaa tgaggaaaaa gttcttttgt accatgtaac 128940
tgctgacctg agagaagccc attatgatat agagttatag gacagctggc caacacacta 129000
tatagctaaa atcagggcct ctctgttttg atggggagaa aagttagaga aggaatcttt 129060
agacttcaaa tttcatggct cagtaaaacg tcaaaataat tttgaagacc aaaggggttg 129120
ccagcttact aggctgccta gacaggggtg ggtatgaggg gaagaaagcc tgcttctttc 129180
atcaacagca tatccagaaa caaaggacat ttaaacacta aaaaagtcag aaggacaaat 129240
tctcagaaaa aaaggacagt cctttaaatg ggttacattt agctttataa aatgccctcc 129300
tgtattgtcc taatctttct ttgccaaggt caagtgcttg ggtgccattg gattataagc 129360
ccctgggttt ctgaacggtg ggggagggaa ccacaggaac aagggttagg ggtgaggaaa 129420
aagaactcat taaccttggg ccctgggtgg aagttaatta tcatgtcttg ccctgtgggt 129480
gggttgaagt aggaacgtta attccaaagg cagttttcca aatttttgaa cttgagattt 129540
gtaatattat cttgccagtt agccaccagt tctcttctct tttttctttt cttttcttac 129600
agtctcgctg tcacccaggc tgcagtgtaa tggcgcaatc ttggctcact gcaacctccg 129660
cctcccaggt tcaagcgatt cttgtgcctc agcctcccga gtagctggga ccacaggtgt 129720

-continued

```
gcaccaccac acctgactaa tttttgtatt tttaatagag atggggcttc accatgttgg 129780
ccatgctggt ctcaaactcc tggcctcaaa tgatccaccc accttggcct cccaaagtgt 129840
tgggattaca ggcatgggcc actgcacctg gccaactgcc agttttctag taatggttag 129900
gttgatattt tagattcatt tttagagttt attatcattt tgctgttatc ataagagaag 129960
ttccatcatg tcaataactt gtattaggaa agacatcttc cattcccggt atatccaact 130020
ctcattcgta taactgaagg ctgtgtgtat atcatcaaca attcttgccc ttttgccctt 130080
ggattgcatt atatgctgtg tgcttttttt tttttttaaa ttagtaaagc gtttgcattt 130140
cctgacagtg tgccacttga cagctggttt aagtgcctgg gagaatagta atcagtggca 130200
aatcagcttg tgtctgaaat gtggctgttg gcagtctact tgaggataat tgaaagtttg 130260
ctgtattcgt tttattgatg ggattctagg tgaatgccaa actcccgatt gggaccccag 130320
attacatggc tcctgaagtg ctgactgtga tgaacgggga tggaaaaggc acctacggcc 130380
tggactgtga ctggtggtca gtgggcgtga ttgcctatga gatgatttat gggagatccc 130440
ccttcgcaga gggaacctct gccagaacct tcaataacat tatgaatttc caggtaaaga 130500
gtccttagaa gatttcgaag tcacattgag aaacgttatt taaaaattgt gcgaatgagg 130560
ctgggccgtg ggtggctcat gcctgtaatc ccggcacttt gggaggccga ggtgggtgga 130620
tcacgaggtc aggagatcga gaccatcctg gctaacatgg tgaaacccca tctctactaa 130680
aaaatacaaa aaaattagcc agttgtggtg gtgggcgcct gtagtcccag ctannnnnnn 130740
nnnnnnnnnn nnnnnnnnnn nnnnnnnnnn nnnnnnnnnn nnnnnnnnnn nnnnnnnnnn 130800
nnnnnnnnnn nnnnnnnnnn nnnnnnnnnn nnnnnnnnnn nnnnnnnnnn nnnnnnnnnn 130860
nnnnnnnnnn nnnnnnnnnn nnnnnnnnnn nnnnnnnnnn nnnnnnnnnn nnnnnnnnnn 130920
nnnnnnnnnn nnnnnnnnnn nnnnnnnnnn nnnnnnnnnn nnnnnnnnnn nnnnnnnnnn 130980
nnnnnnnnnn nnnnnnnnnn nnnnnnnnnn nnnnnnnnnn nnnnnnnnnn nnnnnnnnnn 131040
nnnnnnnnnn nnnnnnnnnn nnnnnnnnnn nnnnnnnnnn nnnnnnnnnn nnnnnnnnnn 131100
nnnnnnnnnn nnnnnnnnnn nnnnnnnnnn nnnnnnnnnn nnnnnnnnnn nnnnnnnnnn 131160
nnnnnnnnnn nnnnnnnnnn nnnnnnnnnn nnnnnnnnnn nnnnnnnnnn nnnnnnnnnn 131220
nnnnnnnnnn nnnnnnnnnn nnnnnnnnnn nnnnnnnnnn nnnnnnnnnn nnnnnnnnnn 131280
nnnnnnnnnn nnnnnnnnnn nnnnnnnnnn nnnnnnnnnn nnnnnnnnnn nnnnnnnnnn 131340
nnnnnnnnnn nnnnnnnnnn nnnnnnnnnn nnnnnnnnnn nnnnnnnnnn nnnnnnnnnn 131400
nnnnnnnnnn nnnnnnnnnn nnnnnnnnnn nnnnnnnnnn nnnnnnnnnn nnnnnnnnnn 131460
nnnnnnnnnn nnnnnnnnnn nnnnnnnnnn nnnnnnnnnn nnnnnnnnnn nnnnnnnnnn 131520
nnnnnnnnnn nnnnnnnnnn nnnnnnnnnn nnnnnnnnnn nnnnnnnnnn nnnnnnnnnn 131580
nnnnnnnnnn nnnnnnnnnn nnnnnnnnnn nnnnnnnnnn nnnnnnnnnn nnnnnnnnnn 131640
nnnnnnnnnn nnnnnnnnnn nnnnnnnnnn nnnnnnnnnn nnnnnnnnnn nnnnnnnnnn 131700
nnnnnnnnnn nnnnnnnnnn nnnnnnnnnn nnnnnnnnnn nnnnnnnnnn nnnnnnnnnn 131760
nnnnnnnnnn nnnnnnnnnn nnnnnnnnnn nnnnnnnnnn nnnnnnnnnn nnnnnnnnnn 131820
nnnnnnnnnn nnnnnnnnnn nnnnnnnnnn nnnnnnnnnn nnnnnnnnnn nnnnnnnnnn 131880
nnnnnnnnnn nnnnnnnnnn nnnnnnnnnn nnnnnnnnnn nnnnnnnnnn nnnnnnnnnn 131940
nnnnnnnnnn nnnnnnnnnn nnnnnnnnnn nnnnnnnnnn nnnnnnnnnn nnnnnnnnnn 132000
nnnnnnnnnn nnnnnnnnnn nnnnnnnnnn nnnnnnnnnn nnnnnnnnnn nnnnnnnnnn 132060
nnnnnnnnnn nnnnnnnnnn nnnnnnnnnn nnnnnnnnnn nnnnnnnnnn nnnnnnnnnn 132120
```

-continued

```
nnnnnnnnnn nnnnnnnnnn nnnnnnnnnn nnnnnnnnnn nnnnnnnnnn nnnnnnnnnn 132180
nnnnnnnnnn nnnnnnnnnn nnnnnnnnnn nnnnnnnnnn nnnnnnnnnn nnnnnnnnnn 132240
nnnnnnnnnn nnnnnnnnnn nnnnnnnnnn nnnnnnnnnn nnnnnnnnnn nnnnnnnnnn 132300
nnnnnnnnnn nnnnnnnnnn nnnnnnnnnn nnnnnnnnnn nnnnnnnnnn nnnnnnnnnn 132360
nnnnnnnnnn nnnnnnnnnn nnnnnnnnnn nnnnnnnnnn nnnnnnnnnn nnnnnnnnnn 132420
nnnnnnnnnn nnnnnnnnnn nnnnnnnnnn nnnnnnnnnn nnnnnnnnnn nnnnnnnnnn 132480
nnnnnnnnnn nnnnnnnnnn nnnnnnnnnn nnnnnnnnnn nnnnnnnnnn nnnnnnnnnn 132540
nnnnnnnnnn nnnnnnnnnn nnnnnnnnnn nnnnnnnnnn nnnnnnnnnn nnnnnnnnnn 132600
nnnnnnnnnn nnnnnnnnnn nnnnnnnnnn nnnnnnnnnn nnnnnnnnnn nnnnnnnnnn 132660
nnnnnnnnnn nnnnnnnnnn nnnnnnnnnn nnnnnnnnnn nnnnnnnnnn nnnnnnnnnn 132720
nnnnnnnnnn nnnnnnnnnn nnnnnnnnnn nnnnnnnnnn nnnnnnnnnn nnnnnnnnnn 132780
nnnnnnnnnn nnnnnnnnnn nnnnnnnnnn nnnnnnnnnn nnnnnnnnnn nnnnnnnnnn 132840
nnnnnnnnnn nnnnnnnnnn nnnnnnnnnn nnnnnnnnnn nnnnnnnnnn nnnnnnnnnn 132900
nnnnnnnnnn nnnnnnnnnn nnnnnnnnnn nnnnnnnnnn nnnnnnnnnn nnnnnnnnnn 132960
nnnnnnnnnn nnnnnnnnnn nnnnnnnnnn nnnnnnnnnn nnnnnnnnnn nnnnnnnnnn 133020
nnnnnnnnnn nnnnnnnnnn nnnnnnnnnn nnnnnnnnnn nnnnnnnnnn nnnnnnnnnn 133080
nnnnnnnnnn nnnnnnnnnn nnnnnnnnnn nnnnnnnnnn nnnnnnnnnn nnnnnnnnnn 133140
nnnnnnnnnn nnnnnnnnnn nnnnnnnnnn nnnnnnnnnn nnnnnnnnnn nnnnnnnnnn 133200
nnnnnnnnnn nnnnnnnnnn nnnnnnnnnn nnnnnnnnnn nnnnnnnnnn nnnnnnnnnn 133260
nnnnnnnnnn nnnnnnnnnn nnnnnnnnnn nnnnnnnnnn nnnnnnnnnn nnnnnnnnnn 133320
nnnnnnnnnn nnnnnnnnnn nnnnnnnnnn nnnnnnnnnn nnnnnnnnnn nnnnnnnnnn 133380
nnnnnnnnnn nnnnnnnnnn nnnnnnnnnn nnnnnnnnnn nnnnnnnnnn nnnnnnnnnn 133440
nnnnnnnnnn nnnnnnnnnn nnnnnnnnnn nnnnnnnnnn nnnnnnnnnn nnnnnnnnnn 133500
nnnnnnnnnn nnnnnnnnnn nnnnnnnnnn nnnnnnnnnn nnnnnnnnnn nnnnnnnnnn 133560
nnnnnnnnnn nnnnnnnnnn nnnnnnnnnn nnnnnnnnnn nnnnnnnnnn nnnnnnnnnn 133620
nnnnnnnnnn nnnnnnnnnn nnnnnnnnnn nnnnnnnnnn nnnnnnnnnn nnnnnnnnnn 133680
nnnnnnnnnn nnnnnnnnnn nnnnnnnnnn nnnnnnnnnn nnnnnnnnnn nnnnnnnnnn 133740
nnnnnnnnnn nnnnnnnnnn nnnnnnnnnn nnnnnnnnnn nnnnnnnnnn nnnnnnnnnn 133800
nnnnnnnnnn nnnnnnnnnn nnnnnnnnnn nnnnnnnnnn nnnnnnnnnn nnnnnnnnnn 133860
nnnnnnnnnn nnnnnnnnnn nnnnnnnnnn nnnnnnnnnn nnnnnnnnnn nnnnnnnnnn 133920
nnnnnnnnnn nnnnnnnnnn nnnnnnnnnn nnnnnnnnnn nnnnnnnnnn nnnnnnnnnn 133980
nnnnnnnnnn nnnnnnnnnn nnnnnnnnnn nnnnnnnnnn nnnnnnnnnn nnnnnnnnnn 134040
nnnnnnnnnn nnnnnnnnnn nnnnnnnnnn nnnnnnnnnn nnnnnnnnnn nnnnnnnnnn 134100
nnnnnnnnnn nnnnnnnnnn nnnnnnnnnn nnnnnnnnnn nnnnnnnnnn nnnnnnnnnn 134160
nnnnnnnnnn nnnnnnnnnn nnnnnnnnnn nnnnnnnnnn nnnnnnnnnn nnnnnnnnnn 134220
nnnnnnnnnn nnnnnnnnnn nnnnnnnnnn nnnnnnnnnn nnnnnnnnnn nnnnnnnnnn 134280
nnnnnnnnnn nnnnnnnnnn nnnnnnnnnn nnnnnnnnnn nnnnnnnnnn nnnnnnnnnn 134340
nnnnnnnnnn nnnnnnnnnn nnnnnnnnnn nnnnnnnnnn nnnnnnnnnn nnnnnnnnnn 134400
nnnnnnnnnn nnattgcttt atttttctaa ataaatagac atctcccccc aaatctccaa 134460
```

-continued

```
ggttcagacc ttctaatcag taatatattt tcagggcatt cttcctttta tgcttttaga 134520
aagatgtaat agactttctt ttagatgctg ttcaagtact taatcttttc ttgtcttgcc 134580
tttttatctc tgtaatcttc ttgaataagc agttaatttt ttttattcat gaacctgctg 134640
atcatgtcta agaatgtatc tccacttaag taagtcagtg aatggtgatt acctgagtag 134700
agttaaagta gtcccccacc ctcctatctg tggcacatat gttccaagtc tcccagtgga 134760
tgtgtgaaac tgatgatagt actgaaaccc atctaccttt tttcctgtgc atacatacct 134820
atgttatata aagcttaact tataaattag gcataatata tttgactccc agctcccagt 134880
gtagtggctc tgcagactca caaaatgtat ttgctttaaa aaattctttt tttttttttt 134940
gagacggagt tttgctcttg ttgcccaggc tggagtgcag tggtgcgacc tcagctcact 135000
gcaacctccg cctcttgggt tcaagcgatt ctcctgcctc agcctcccaa gtagctggga 135060
ttataggcat gcaccaccac acccagctaa ttttctattt ttcgtagaaa cggtttttcc 135120
atgttggtca ggctgatctt gaactcctga cctcaggtga tctgcctgcc tcggccttcc 135180
aaagtgctgg gattacaggt gtgagccacc acgcctggcc aaaaaattct tttaatttaa 135240
gtaaatcttt atttatttac ttttgagaca gagtctcact ctgtgggcca ggcaggaatg 135300
cagtggtgtg atcacggctc actgcagcct cgacctccca tgctcaagca gtcctcccac 135360
ctcagcctcc taagtagcta ggactacagg tgtgtgccat cacactctgc taattttttt 135420
gtatttgtag agacgcggtt tcaccaggtt gcccaggctg gtcttgaact cctgagctca 135480
agtgatcctc ctgctttggc ctcccaaaat actgggatta caggcgtgag ccattgcacc 135540
cagccctaat tttaataaat cttttatttt ggaatagtat tagatttata gaaaagttgc 135600
aaagatagta tggaagagtt cccacatacc cttcacccag ttttccccaa nnnnnnnnnn 135660
nnnnnnnnnn nnnnnnnnnn nnnnnnnnnn nnnnnnnnnn tatttattta tttatttttt 135720
gagacacagt cttcccgtcg cccaggctgg agtgtggtgg cacgatctcg gctcactgca 135780
acctccgcct cctgggttca agtgattctt ctgcctcagc ctccgagtag ctgggaccac 135840
aggtgtgcgc caccatgccc ggctactttt tgtattttca gtagagacag ggtttcacca 135900
tgttggtcag gctgatctca agctcctgac ctcaggtgat ctgcctacct tagcctccca 135960
aagtgctggg attacagaca tgagccaccg cacccagccc ccagtgttaa ctcttacata 136020
acagtgtcac tgtctaagtg tttgaaaaac tatttgtcaa aactaatatt ggtacattat 136080
tgttaactac acttcagact ttttttggat tttaccaatt ctcccactca tgtccctttt 136140
ctgtttcagg aatcaatccg tggtaccata ttgcagttag ggtgtttata tttgatggga 136200
ctggtcctag tttagatact tagtgtagct cagccagcag gtgggatctt catgcccacc 136260
gaggattggt attgtgtttt cctggtggtt ttatggcatt tccgactatg cagagaggca 136320
tggtattaac ttcagtgtct cctagcaaat tttcctgttt ttcaccaacc tctgatccct 136380
gcattatttg caatcaactc agagatttgt gattgaaaac attgcttgac tccatgctct 136440
ttaagctatt ttctaactag gtaactgtaa cataaattat gcttttatct agcactgttt 136500
ttcataaaca catgttgagt gattttcatc aaccgaaata cttcgaatca ttaagtttcc 136560
caagttcatg gatgctgctt aaatgcctgg tggttccagg ctgtcgaata tttctgcctt 136620
ctgcaataag agattgtccc ttgttaaaag caacattagc ctttgtgcgg tttcaccccc 136680
aattcttctt tttcttgttg taaccaatga aaggaagtac tgcttaacac agcaggtaat 136740
aatcttctaa aactcattat ctcaagaggt ggtcctggca ggatatataa atgcaattta 136800
agaaaggtct tggcaaattt atgaatgaca gaactgggag tggctaccga gagaaactag 136860
```

-continued

```
gatgcgcctt tgctttgaca ctgaggtcag gcgtagcttc tgtaccctcc tgggtcctgc 136920
ctcttggggt tgctgcaggc agcaccccat gaaccaggca tctgacccag ttccaggata 136980
cttattcttc cagcaagtcg aacactctgt gatgagtgac tgccatgctc atgggtcacc 137040
aggctctcat tattctgttt catttccagc ctcccacaag attggttttt cagctgctta 137100
tttattatta tcattatttc aaggctgctt tccaagtttc agtggggggt ttcctaagcg 137160
taccagctgc cctggttgtg cagttccggt gatgtttcag atgctgggcc ggattctggc 137220
tgtacccagc ctgatctttc tgggcttcag gaaagctgaa gccaatcaga gctcctcttt 137280
catgcctttg ggattatgct taccttgcct ggcatcgtgt acctgctccc atccatggga 137340
aagttttgct gtctggtact gtcttctatc aacatctttt aagatatctt cccccgaggc 137400
atcgtgatgt caacggaacc agcacacttg tacgttttat gcaagactgc catatctcaa 137460
cagtgagaaa tgcataatgg aagtggtgat cacggattat ttcctaggac attatggcta 137520
atgcgctaga gaactcggat ggtctgttgc gtctgacatg ggctttttct cttgagttgt 137580
ctttcttttg ctattctctg aaagaaacaa ttcttgccac atgatcctga tttttcaggt 137640
cctcagcatt tgttagcaga aagtacactt tgtttccatc cggcagtgac tcagtggtgg 137700
tcccatgctg atgaaacgct gagatagtct tcttccaaat aggtatcgtt ttgattgttg 137760
ctgcttattt gctagctggc cctcaatagt gacaatgaaa cctcaagtgt ataatatggt 137820
tgctcagtaa tcctgaggga agacagtctt tggtttgggg gatagggatt ctgtgcctac 137880
ttagcttcag gtgaaagtct tacaaatttt tgtgtgtaga aataagcacc atgtacctcc 137940
ttgggttttt tctttttttt tctagtcctt tagtatggtc aacaatattg tttagggagt 138000
acctattctg tgctaaccac taggcattca agtatattac actatgctcc ttcaaaacac 138060
ttctgtcaaa tgtaaggatt attataccca ttttacagat gtggttactg tggtaacttg 138120
gccaaggtca tagggcaagt gaataaggga ttctggattt gggtggaggt ctgtgtgatt 138180
ccaaagccca tgctctttct acaatactat atatgccttt gcataagtta ttgttattag 138240
taataatatt tgtgatgatg gcaaataata aaccatgtca cactagagag tgatttaatc 138300
tctaggtcta tttaagaaca tttggaattg caggaattgg attttttttt ttttttaagt 138360
gatggagtct tgccatcttt gcccaggctg gtctcaaact tgtgggctca agtgatcatc 138420
ctccctctgc ctcccaaagt gatgggatta cagatatgag ccaccatgcc cagcctagaa 138480
ttgcaggaat ttttgaattg atgattcatt ctgatatttg aatttctaca gtatgttaag 138540
tgcaatgtca ggtgctggtg ctgtggctcc attgatgaac acatttgggt atggccctac 138600
cttcattgaa tttagagtct aagagcctaa ccggtctttt gcttgaatag agctgtagtc 138660
ctgttaaatt gctgtacctc caaatggtgg gaagtttaat gcttcgtagg cctcccctca 138720
ctagtttact gaaccacatg tgcttgattt ttttttgann nnnnnnnnnn nnnnnnnnnn 138780
nnnnnnnnnn nnnnnnnnnn nnnnnnnnnn nnnnnnnnnn nnnnnnnnnn ctcactgcaa 138840
gctccgcctc ccaggttcac gccattcttc tgcctcagcc tcccgagtag ctgggactac 138900
aggtgcccgc caacacggcc cggctaattt ttttgtattt ttagtagaga cagggtttta 138960
ccatgttagc caggatggtc tcggtctgct gacctcgtga tccacctgcc tcagcctccc 139020
aaagtgctgg gattacaggc atgagccact gtgcctggcc ccacatgtgc ttgattttaa 139080
gcaaaataca gactataggc tgtgacctgg tgatctcttc cccacataca gcatcctgct 139140
aacctataac tctccccatg tctcagatct agcctgggaa aggacaatgt tggatcgatg 139200
```

-continued

```
gcccacttct aatcttggga tttctaatct caagatgagt tgagaagact caggatgtgt 139260
cctgttttct gtttatttag aacagggttt ctcagccttg gcactgttga catttggggc 139320
cagataattc tttgctgtgg gggctgttgt gtgaattgca ggatgttgaa cagcatcgct 139380
gtgctttctc catggatacc agtagcaccc tccccctgca gttgcaacaa ccaaaaatga 139440
ctctagacat tgcccagtct ccccttgggg gctacagtca ccttcagttg agaaccattg 139500
atttagaaga attggccagg ttattatcag gagagggaac atcacagtaa tctgaatctc 139560
tcaatactgc cactgttact gttaacgaac agcaaaacta ttacgtggag gcagtaggac 139620
cttgctactc agagtgtggt ccgtggaccg gcagcatcgg aatcatctag gagcttgtta 139680
gagcttcaga gactcaggcc tactgagtca gaagctgcat tttaataagg atccccaggg 139740
gatttctgtg catattagag ttgtgaagcc ctgcaagagg aagaaattgg atgctagcct 139800
cagagtttct tgctcatctt tgtgggtctt cctacgtttt gtcttcgggc ttaaggtatg 139860
gggaggccac tttttggctc aggactccta tgggtgaatg ggactgctta gaactgctgg 139920
gttttaggcc ttgctttgag gaatttaaag cttttctctt agatggacat tacatcgttc 139980
atatacttca aaatggtggt ttgacctaat ctctgccttc tgatagcaaa aagatatttc 140040
cttgactccc tgaaccccac tttactgttg tcccatattg gattttaatt aagggtggaa 140100
taagtattct tcactaacat gtttatacat gtatgatatt accatgccat ttattgagtg 140160
cctagtatgt gccaggagct ctgcaaagtg ctttatgctt attattgttc catttattct 140220
tccccaaacc tctgtgaggc aggtcctatc actagtccac aatacaaatg aggtcatgga 140280
gcccgaagtt ggcagtggta ggaatcaaac tcaggtctcc ctgactctaa attctctttg 140340
cctttgtttt tttgaaaaag tggtatagcc catagcagaa aattcacatt atacagaagg 140400
ttatacggcg aaaaatgcct ccttcccacc ccacgctcaa cccctctccc tcaagcggaa 140460
ccactattgt cagtttctca tagaactttc cagaatattc tatgctccta taacactagc 140520
acaacctatc ctcttaacaa catctttatg ctgcctccca agaattcagt aatttttttt 140580
tttttgagat ggagttttgc tctagttgcc caggctggag tgcaatggcg tgatctcggc 140640
tcattgcaac ctctgcctcc cacgttcaag tgattctctt gcctcagcct cccgagtagc 140700
tgggattaca ggcatgcgcc actatgcttg gctaattttg tatttttagt agagatgggg 140760
tttctcccat gttggtcagg ctggtcttga actcccaacc tcaggtaatc cgcccacctc 140820
ggcctcccaa agtgttgaga ttacaggcgt gagccaccgc acctggccaa attcagtaat 140880
ttttattggc aggttatttt cccgcatcat tnnnnnnnnn nnnnnnnnnn nnnnnnnnnn 140940
nnnnnnnnnn nnnnnnnnnn nnnnnnnnnn nnnnnnnnnn nnnnnnnnnn nnnnnnnnnn 141000
nnnnnnnnnn nnnnnnnnnn nnnnnnnnnn nnnnnnnnnn nnnnnnnnnn nnnnnnnnnn 141060
nnnnnnnnnn nnnnnnnnnn nnnnnnnnnn nnnnnnnnnn nnnnnnnnnn nnnnnnnnnn 141120
nnnnnnnnnn nnnnnnnnnn nnnnnnnnnn nnnnnnnnnn nnnnnnnnnn nnnnnnnnnn 141180
nnnnnnnnnn nnnnnnnnnn nnnnnnnnnn nnnnnnnnnn nnnnnnnnnn nnnnnnnnnn 141240
nnnnnnnnnn nnnnnnnnnn nnnnnnnnnn nnnnnnnnnn nnnnnnnnnn nnnnnnnnnn 141300
nnnnnnnnnn nnnnnnnnnn nnnnnnnnnn nnnnnnnnnn nnnnnnnnnn nnnnnnnnnn 141360
nnnnnnnnnn nnnnnnnnnn nnnnnnnnnn nnnnnnnnnn nnnnnnnnnn nnnnnnnnnn 141420
nnnnnnnnnn nnnnnnnnnn nnnnnnnnnn nnnnnnnnnn nnnnnnnnnn nnnnnnnnnn 141480
nnnnnnnnnn nnnnnnnnnn nnnnnnnnnn nnnnnnnnnn nnnnnnnnnn nnnnnnnnnn 141540
nnnnnnnnnn nnnnnnnnnn nnnnnnnnnn nnnnnnnnnn nnnnnnnnnn nnnnnnnnnn 141600
```

-continued nnnnnnnnnn nnnnnnnnnn nnnnnnnnnn nnnnnnnnnn nnnnnnnnnn nnnnnnnnnn 141660
nnnnnnnnnn nnnnnnnnnn nnnnnnnnnn nnnnnnnnnn nnnnnnnnnn nnnnnnnnnn 141720
nnnnnnnnnn nnnnnnnnnn nnnnnnnnnn nnnnnnnnnn nnnnnnnnnn nnnnnnnnnn 141780
nnnnnnnnnn nnnnnnnnnn nnnnnnnnnn nnnnnnnnnn nnnnnnnnnn nnnnnnnnnn 141840
nnnnnnnnnn nnnnnnnnnn nnnnnnnnnn nnnnnnnnnn nnnnnnnnnn nnnnnnnnnn 141900
nnnnnnnnnn nnnnnnnnnn nnnnnnnnnn nnnnnnnnnn nnnnnnnnnn nnnnnnnnnn 141960
nnnnnnnnnn nnnnnnnnnn nnnnnnnnnn nnnnnnnnnn nnnnnnnnnn nnnnnnnnnn 142020
nnnnnnnnnn nnnnnnnnnn nnnnnnnnnn nnnnnnnnnn nnnnnnnnnn nnnnnnnnnn 142080
nnnnnnnnnn nnnnnnnnnn nnnnnnnnnn nnnnnnnnnn nnnnnnnnnn nnnnnnnnnn 142140
nnnnnnnnnn nnnnnnnnnn nnnnnnnnnn nnnnnnnnnn nnnnnnnnnn nnnnnnnnnn 142200
nnnnnnnnnn nnnnnnnnnn nnnnnnnnnn nnnnnnnnnn nnnnnnnnnn nnnnnnnnnn 142260
nnnnnnnnnn nnnnnnnnnn nnnnnnnnnn nnnnnnnnnn nnnnnnnnnn nnnnnnnnnn 142320
nnnnnnnnnn nnnnnnnnnn nnnnnnnnnn nnnnnnnnnn nnnnnnnnnn nnnnnnnnnn 142380
nnnnnnnnnn nnnnnnnnnn nnnnnnnnnn nnnnnnnnnn nnnnnnnnnn nnnnnnnnnn 142440
nnnnnnnnnn nnnnnnnnnn nnnnnnnnnn nnnnnnnnnn nnnnnnnnnn nnnnnnnnnn 142500
nnnnnnnnnn nnnnnnnnnn nnnnnnnnnn nnnnnnnnnn nnnnnnnnnn nnnnnnnnnn 142560
nnnnnnnnnn nnnnnnnnnn nnnnnnnnnn nnnnnnnnnn nnnnnnnnnn nnnnnnnnnn 142620
nnnnnnnnnn nnnnnnnnnn nnnnnnnnnn nnnnnnnnnn nnnnnnnnnn nnnnnnnnnn 142680
nnnnnnnnnn nnnnnnnnnn nnnnnnnnnn nnnnnnnnnn nnnnnnnnnn nnnnnnnnnn 142740
nnnnnnnnnn nnnnnnnnnn nnnnnnnnnn nnnnnnnnnn nnnnnnnnnn nnnnnnnnnn 142800
nnnnnnnnnn nnnnnnnnnn nnnnnnnnnn nnnnnnnnnn nnnnnnnnnn nnnnnnnnnn 142860
nnnnnnnnnn nnnnnnnnnn nnnnnnnnnn nnnnnnnnnn nnnnnnnnnn nnnnnnnnnn 142920
nnnnnnnnnn nnnnnnnnnn nnnnnnnnnn nnnnnnnnnn nnnnnnnnnn nnnnnnnnnn 142980
nnnnnnnnnn nnnnnnnnnn nnnnnnnnnn nnnnnnnnnn nnnnnnnnnn nnnnnnnnnn 143040
nnnnnnnnnn nnnnnnnnnn nnnnnnnnnn nnnnnnnnnn nnnnnnnnnn nnnnnnnnnn 143100
nnnnnnnnnn nnnnnnnnnn nnnnnnnnnn nnnnnnnnnn nnnnnnnnnn nnnnnnnnnn 143160
nnnnnnnnnn nnnnnnnnnn nnnnnnnnnn nnnnnnnnnn nnnnnnnnnn nnnnnnnnnn 143220
nnnnnnnnnn nnnnnnnnnn nnnnnnnnnn nnnnnnnnnn nnnnnnnnnn nnnnnnnnnn 143280
nnnnnnnnnn nnnnnnnnnn nnnnnnnnnn nnnnnnnnnn nnnnnnnnnn nnnnnnnnnn 143340
nnnnnnnnnn nnnnnnnnnn nnnnnnnnnn nnnnnnnnnn nnnnnnnnnn nnnnnnnnnn 143400
nnnnnnnnnn nnnnnnnnnn nnnnnnnnnn nnnnnnnnnn nnnnnnnnnn nnnnnnnnnn 143460
nnnnnnnnnn nnnnnnnnnn nnnnnnnnnn nnnnnnnnnn nnnnnnnnnn nnnnnnnnnn 143520
nnnnnnnnnn nnnnnnnnnn nnnnnnnnnn nnnnnnnnnn nnnnnnnnnn nnnnnnnnnn 143580
nnnnnnnnnn nnnnnnnnnn nnnnnnnnnn nnnnnnnnnn nnnnnnnnnn nnnnnnnnnn 143640
nnnnnnnnnn nnnnnnnnnn nnnnnnnnnn nnnnnnnnnn nnnnnnnnnn nnnnnnnnnn 143700
nnnnnnnnnn nnnnnnnnnn nnnnnnnnnn nnnnnnnnnn nnnnnnnnnn nnnnnnnnnn 143760
nnnnnnnnnn nnnnnnnnnn nnnnnnnnnn nnnnnnnnnn nnnnnnnnnn nnnnnnnnnn 143820
nnnnnnnnnn nnnnnnnnnn nnnnnnnnnn nnnnnnnnnn nnnnnnnnnn nnnnnnnnnn 143880
nnnnnnnnnn nnnnnnnnnn nnnnnnnnnn nnnnnnnnnn nnnnnnnnnn nnnnnnnnnn 143940

-continued

```
nnnnnnnnnn nnnnnnnnnn nnnnnnnnnn nnnnnnnnnn nnnnnnnnnn nnnnnnnnnn 144000
nnnnnnnnnn nnnnnnnnnn nnnnnnnnnn nnnnnnnnnn nnnnnnnnnn nnnnnnnnnn 144060
nnnnnnnnnn nnnnnnnnnn nnnnnnnnnn nnnnnnnnnn nnnnnnnnnn nnnnnnnnnn 144120
nnnnnnnnnn nnnnnnnnnn nnnnnnnnnn nnnnnnnnnn nnnnnnnnnn nnnnnnnnnn 144180
nnnnnnnnnn nnnnnnnnnn nnnnnnnnnn nnnnnnnnnn nnnnnnnnnn nnnnnnnnnn 144240
nnnnnnnnnn nnnnnnnnnn nnnnnnnnnn nnnnnnnnnn nnnnnnnnnn nnnnnnnnnn 144300
nnnnnnnnnn nnnnnnnnnn nnnnnnnnnn nnnnnnnnnn nnnnnnnnnn nnnnnnnnnn 144360
nnnnnnnnnn nnnnnnnnnn nnnnnnnnnn nnnnnnnnnn nnnnnnnnnn nnnnnnnnnn 144420
nnnnnnnnnn nnnnnnnnnn nnnnnnnnnn nnnnnnnnnn nnnnnnnnnn nnnnnnnnnn 144480
nnnnnnnnnn nnnnnnnnnn nnnnnnnnnn nnnnnnnnnn nnnnnnnnnn nnnnnnnnnn 144540
nnnnnnnnnn nnnnnnnnnn nnnnnnnnnn nnnnnnnnnn nnnnnnnnnn nnnnnnnnnn 144600
nnnnnnnnnn nnnnnnnnnn nnnnnnnnnn nnnnnnnnnn nnnnnnnnnn nnnnnnnnnn 144660
nnnnnnnnnn nnnnnnnnnn nnnnnnnnnn nnnnnnnnnn nnnnnnnnnn nnnnnnnnnn 144720
nnnnnnnnnn nnnnnnnnnn nnnnnnnnnn nnnnnnnnnn nnnnnnnnnn nnnnnnnnnn 144780
nnnnnnnnnn nnnnnnnnnn nnnnnnnnnn nnnnnnnnnn nnnnnnnnnn nnnnnnnnnn 144840
nnnnnnnnnn nnnnnnnnnn nnnnnnnnnn nnnnnnnnnn nnnnnnnnnn nnnnnnnnnn 144900
nnnnnnnnnn nnnnnnnnnn nnnnnnnnnn nnnnnnnnnn nnnnnnnnnn nnnnnnnnnn 144960
nnnnnnnnnn nnnnnnnnnn nnnnnnnnnn nnnnnnnnnn nnnnnnnnnn nnnnnnnnnn 145020
nnnnnnnnnn nnnnnnnnnn nnnnnnnnnn nnnnnnnnnn nnnnnnnnnn nnnnnnnnnn 145080
nnnnnnnnnn nnnnnnnnnn nnnnnnnnnn nnnnnnnnnn nnnnnnnnnn nnnnnnnnnn 145140
nnnnnnnnnn nnnnnnnnnn nnnnnnnnnn nnnnnnnnnn nnnnnnnnnn nnnnnnnnnn 145200
nnnnnnnnnn nnnnnnnnnn nnnnnnnnnn nnnnnnnnnn nnnnnnnnnn nnnnnnnnnn 145260
nnnnnnnnnn nnnnnnnnnn nnnnnnnnnn nnnnnnnnnn nnnnnnnnnn nnnnnnnnnn 145320
nnnnnnnnnn nnnnnnnnnn nnnnnnnnnn nnnnnnnnnn nnnnnnnnnn nnnnnnnnnn 145380
nnnnnnnnnn nnnnnnnnnn nnnnnnnnnn nnnnnnnnnn nnnnnnnnnn nnnnnnnnnn 145440
nnnnnnnnnn nnnnnnnnnn nnnnnnnnnn nnnnnnnnnn nnnnnnnnnn nnnnnnnnnn 145500
nnnnnnnnnn nnnnnnnnnn nnnnnnnnnn nnnnnnnnnn nnnnnnnnnn nnnnnnnnnn 145560
nnnnnnnnnn nnnnnnnnnn nnnnnnnnnn nnnnnnnnnn nnnnnnnnnn nnnnnnnnnn 145620
nnnnnnnnnn nnnnnnnnnn nnnnnnnnnn nnnnnnnnnn nnnnnnnnnn nnnnnnnnnn 145680
nnnnnnnnnn nnnnnnnnnn nnnnnnnnnn nnnnnnnnnn nnnnnnnnnn nnnnnnnnnn 145740
nnnnnnnnnn nnnnnnnnnn nnnnnnnnnn nnnnnnnnnn nnnnnnnnnn nnnnnnnnnn 145800
nnnnnnnnnn nnnnnnnnnn nnnnnnnnnn nnnnnnnnnn nnnnnnnnnn nnnnnnnnnn 145860
nnnnnnnnnn nnnnnnnnnn nnnnnnnnnn nnnnnnnnnn nnnnnnnnnn nnnnnnnnnn 145920
nnnnnnnnnn nnnnnnnnnn nnnnnnnnnn nnnnnnnnnn nnnnnnnnnn nnnnnnnnnn 145980
nnnnnnnnnn nnnnnnnnnn nnnnnnnnnn nnnnnnnnnn nnnnnnnnnn nnnnnnnnnn 146040
nnnnnnnnnn nnnnnnnnnn nnnnnnnnnn nnnnnnnnnn nnnnnnnnnn nnnnnnnnnn 146100
nnnnnnnnnn nnnnnnnnnn nnnnnnnnnn nnnnnnnnnn nnnnnnnnnn nnnnnnnnnn 146160
nnnnnnnnnn nnnnnnnnnn nnnnnnnnnn nnnnnnnnnn nnnnnnnnnn nnnnnnnnnn 146220
nnnnnnnnnn nnnnnnnnnn nnnnnnnnnn nnnnnnnnnn nnnnnnnnnn nnnnnnnnnn 146280
nnnnnnnnnn nnnnnnnnnn nnnnnnnnnn nnnnnnnnnn nnnnnnnnnn nnnnnnnnnn 146340
```

-continued nnnnnnnnnn nnnnnnnnnn nnnnnnnnnn nnnnnnnnnn nnnnnnnnnn nnnnnnaatt 146400
caaaacctgt ctcctgttaa tcccatcctc tctgtttctg ttatcatttc cttagtgtag 146460
atctgcctaa gtgtagaatt tgtagaattt gtcatgttga ctattgtaga cttgtctttt 146520
agagtttcta gcactagcct cttccaccca tcactattga gatgattgta tccgtctcag 146580
tactgacact aacccagcac tctggtttta catctgtcaa tccatcaaga cttcactttc 146640
actttcttcc ctgcctcatt attcactatg ctcttgggcc attgctctgg cttctggggc 146700
ttttctaaag tagcactttt ccccactcca gcccatgaag ataccttttta accagctctt 146760
gagattaaat cccctccgtg acactttcct gcaggaactt gcaaaaaagt actgcattcc 146820
ccactggcaa aacttgccat cagccagttt atgtattctc tgcttttcac acccatatct 146880
tgacctctga acaacacaca tattctcctc ttcatttatt tcacagttct gtcttcataa 146940
cattgataag tatgatcaca ttagcgctct agattttaag caactggaag atagctattt 147000
ttttggtact cttcctttaa atttgaacat agtgtctaat tagtcaatta acattttttt 147060
aaaagggcga gggacatcat ggtagagaga acgaagttga acgtgttttt ggttgaatat 147120
tagcgcatgc ccactgtatt ctaggcacag tcctgattca ttatatcatc acacaataat 147180
tatttatgtg ccttcatcct ttatgacaca gtgctggctc ttattcatct cccatttctg 147240
caatccatgg tgatgattaa aagtcttagg agttttacga ggctcagtat tttttttttt 147300
taatatgcta gttcttcatg aatacattgg gtactctgaa gcatatcatt tcctgggttt 147360
cctgaagtgg tatgttgcgt ggaatggcac attaggtcta aataattatc ccctatgtaa 147420
ggggtcttgt ttttcattca ttctcttaaa aaatagatat taaacattaa ataaggacag 147480
ccaggnnnnn nnnnnnnnnn nnnnnnnnnn nnnnnnnnnn nnnnnnnnnn nnnnnnnnnn 147540
nnnnnnnnnn nnnnnnnnnn nnnnnnnnnn nnnnnnnnnn nnnnnnnnnn nnnnnnnnnn 147600
nnnnnnnnnn nnnnnnnnnn nnnnnnnnnn nnnnnnnnnn nnnnnnnnnn nnnnnnnnnn 147660
nnnnnnnnnn nnnnnnnnnn nnnnnnnnnn nnnnnnnnnn nnnnnnnnnn nnnnnnnnnn 147720
nnnnnnnnnn nnnnnnnnnn nnnnnnnnnn nnnnnnnnnn nnnnnnnnnn nnnnnnnnnn 147780
nnnnnnnnnn nnnnnnnnnn nnnnnnnnnn nnnnnnnnnn nnnnnnnnnn nnnnnnnnnn 147840
nnnnnnnnnn nnnnnnnnnn nnnnnnnnnn nnnnnnnnnn nnnnnnnnnn nnnnnnnnnn 147900
nnnnnnnnnn nnnnnnnnnn nnnnnnnnnn nnnnnnnnnn nnnnnnnnnn nnnnnnnnnn 147960
nnnnnnnnnn nnnnnnnnnn nnnnnnnnnn nnnnnnnnnn nnnnnnnnnn nnnnnnnnnn 148020
nnnnnnnnnn nnnnnnnnnn nnnnnnnnnn nnnnnnnnnn nnnnnnnnnn nnnnnnnnnn 148080
nnnnnnnnnn nnnnnnnnnn nnnnnnnnnn nnnnnnnnnn nnnnnnnnnn nnnnnnnnnn 148140
nnnnnnnnnn nnnnnnnnnn nnnnnnnnnn nnnnnnnnnn nnnnnnnnnn nnnnnnnnnn 148200
nnnnnnnnnn nnnnnnnnnn nnnnnnnnnn nnnnnnnnnn nnnnnnnnnn nnnnnnnnnn 148260
nnnnnnnnnn nnnnnnnnnn nnnnnnnnnn nnnnnnnnnn nnnnnnnnnn nnnnnnnnnn 148320
nnnnnnnnnn nnnnnnnnnn nnnnnnnnnn nnnnnnnnnn nnnnnnnnnn nnnnnnnnnn 148380
nnnnnnnnnn nnnnnnnnnn nnnnnnnnnn nnnnnnnnnn nnnnnnnnnn nnnnnnnnnn 148440
nnnnnnnnnn nnnnnnnnnn nnnnnnnnnn nnnnnnnnnn nnnnnnnnnn nnnnnnnnnn 148500
nnnnnnnnnn nnnnnnnnnn nnnnnnnnnn nnnnnnnnnn nnnnnnnnnn nnnnnnnnnn 148560
nnnnnnnnnn nnnnnnnnnn nnnnnnnnnn nnnnnnnnnn nnnnnnnnnn nnnnnnnnnn 148620
nnnnnnnnnn nnnnnnnnnn nnnnnnnnnn nnnnnnnnnn nnnnnnnnnn nnnnnnnnnn 148680

-continued nnnnnnnnnn nnnnnnnnnn nnnnnnnnnn nnnnnnnnnn nnnnnnnnnn nnnnnnnnnn 148740
nnnnnnnnnn nnnnnnnnnn nnnnnnnnnn nnnnnnnnnn nnnnnnnnnn nnnnnnnnnn 148800
nnnnnnnnnn nnnnnnnnnn nnnnnnnnnn nnnnnnnnnn nnnnnnnnnn nnnnnnnnnn 148860
nnnnnnnnnn nnnnnnnnnn nnnnnnnnnn nnnnnnnnnn nnnnnnnnnn nnnnnnnnnn 148920
nnnnnnnnnn nnnnnnnnnn nnnnnnnnnn nnnnnnnnnn nnnnnnnnnn nnnnnnnnnn 148980
nnnnnnnnnn nnnnnnnnnn nnnnnnnnnn nnnnnnnnnn nnnnnnnnnn nnnnnnnnnn 149040
nnnnnnnnnn nnnnnnnnnn nnnnnnnnnn nnnnnnnnnn nnnnnnnnnn nnnnnnnnnn 149100
nnnnnnnnnn nnnnnnnnnn nnnnnnnnnn nnnnnnnnnn nnnnnnnnnn nnnnnnnnnn 149160
nnnnnnnnnn nnnnnnnnnn nnnnnnnnnn nnnnnnnnnn nnnnnnnnnn nnnnnnnnnn 149220
nnnnnnnnnn nnnnnnnnnn nnnnnnnnnn nnnnnnnnnn nnnnnnnnnn nnnnnnnnnn 149280
nnnnnnnnnn nnnnnnnnnn nnnnnnnnnn nnnnnnnnnn nnnnnnnnnn nnnnnnnnnn 149340
nnnnnnnnnn nnnnnnnnnn nnnnnnnnnn nnnnnnnnnn nnnnnnnnnn nnnnnnnnnn 149400
nnnnnnnnnn nnnnnnnnnn nnnnnnnnnn nnnnnnnnnn nnnnnnnnnn nnnnnnnnnn 149460
nnnnnnnnnn nnnnnnnnnn nnnnnnnnnn nnnnnnnnnn nnnnnnnnnn nnnnnnnnnn 149520
nnnnnnnnnn nnnnnnnnnn nnnnnnnnnn nnnnnnnnnn nnnnnnnnnn nnnnnnnnnn 149580
nnnnnnnnnn nnnnnnnnnn nnnnnnnnnn nnnnnnnnnn nnnnnnnnnn nnnnnnnnnn 149640
nnnnnnnnnn nnnnnnnnnn nnnnnnnnnn nnnnnnnnnn nnnnnnnnnn nnnnnnnnnn 149700
nnnnnnnnnn nnnnnnnnnn nnnnnnnnnn nnnnnnnnnn nnnnnnnnnn nnnnnnnnnn 149760
nnnnnnnnnn nnnnnnnnnn nnnnnnnnnn nnnnnnnnnn nnnnnnnnnn nnnnnnnnnn 149820
nnnnnnnnnn nnnnnnnnnn nnnnnnnnnn nnnnnnnnnn nnnnnnnnnn nnnnnnnnnn 149880
nnnnnnnnnn nnnnnnnnnn nnnnnnnnnn nnnnnnnnnt tccttttttt tttttttttt 149940
ttttttgaga cggtgtttcg ctcttgttcc ccaggctgga gtgcagtggc acgatcttgg 150000
ctcactgcaa cctccacctc ccaggttcaa gcgattctct tgcctcagcc tcccaagtag 150060
ctgggactac aggcatgcac catcacatct ggctaatttt tttgtatttt taatagagat 150120
ggggttttac catgttggcc aggctggcct tgaactcctg acctcaggtg atccacctgc 150180
ctcgccctcc caaggtgctg ggattacagg catgagccac tgtgcctggc ctacttcttc 150240
ttccttttaa cttgaagatt atctgcccct ttttctaatc ttaaccgcat taagctggct 150300
ttgagcatgg caagagtttt atagatgaat cttattttat agtacaggat ttcaaaatca 150360
taattatttc actgagggtg gcttttaccc tccattaatt atacttctca ctcagaaatg 150420
gaattctatt ttggtctcct aaagataaat tagtatatag tggaaaggaa ttataaagtt 150480
ctgctaggaa ttaaatgata tgattaacac aaacatccac atggatgtgt ctctgccctg 150540
tgcaggaaag atgaacattc agtacagatt ctgctctatg tcactagctt tcaagacctg 150600
caggttctct cctaagcatg caattcctgt gagcagtagc aataatagca ggtcatattt 150660
gtggagtgat tactgtatgc taagaactgt ggtaaacact tttatatgga ttattttatt 150720
taaacctcct aatagtccat tgaaatagat attgccatgt tgaaaactga ggttcagaga 150780
ggttaagtga cttacccagt gtcacagaac tagtaagtgg tgcagctggg atttgaactg 150840
agattccaga acaattgcca ttaaccactt tgcttccata ttagtatcat ctgcaaatct 150900
ctctccataa atttcctcag tctttatctg agtttcctta tttcaggaag gaaaacttct 150960
gtttttgatc cttatgaaat acaatttcca ttaaaacttt tttttttgc tattaaaaaa 151020
ggtaccggat aattgaaacc agactggatt tgagcctgtg ttgatggaag tacacatggg 151080

-continued

```
atgtgggctg aagtgttcaa tctaattttt ctttccatca gctaattttt aaagtattaa 151140
gcaagtagat tctgacacta acagggaaga tttaaattct cttgagagac tggaggtgtt 151200
aaataatttt ctggtagtgc acattttaca tcttaaatct tcctcactct cccacctcat 151260
ctcaatgtac ctgaagctct gggaatgttc ttttgtactt ctcaggaaca gccagacctc 151320
tggcttcatc tcctctcccc tccacatccc tttcctgctc caattacttc ccagcgccac 151380
ttggatgttg ttgtcatcgg ggaactttgg aaacagccag atttttttgg agtctgtaag 151440
cagaaaacag actgcttgct gctcatatct ggcacccagc tttgtccaga aaacgaggag 151500
ttaaaaagaa gtctgggctg tgaagggctg tgacaactgt cctaggggga gctctagcga 151560
gccctggcgg gcagtgactc atgctgctct gtcactggga tcagcactgg cccctggcag 151620
gcaggcggca gccaggtggg gttccagcca gagcacgcac gcacggagcc gggagcatgc 151680
agcctgcact gcgggggatg tgatgctcgg ctctaactcg cctggctggc ccgccacgga 151740
cgcctcagct tgcaaccatg gtaacgtttc tggcgggggga cacccccggg agcccaccgc 151800
gatgggcagc ctcctggtga ctgatggacg agtgtccacc tcccagaccg agagcgctta 151860
gtaggtcgga ggaagtggag aggatgtaac acgcccccag ccgggagtga agccctgagg 151920
aggtaggagc cgcatatgtc catccgtgca ttcccaccgt cagcgcgcag gggtgctgta 151980
gatcaccggt aggaacttta tttggctggt gcttcattat gctgattaaa ctgcagtgga 152040
tttgatgggc atgattgcgc tggggaagat gcataatgaa ctaaaaaaaa aaaaaagtgg 152100
ttaataagat ctcggagtcg acttgtccgg gtatgaatga agtagactgc agtggtatcc 152160
taacaggagt tccagaacct cacacatccc ttttcctggt ccttcctctt atcccggtta 152220
atccacgaaa tgtagaagtt ccatcttatt tcaacgatta gtgctaatca ttaataattt 152280
agacctgtct ggaggaggga atccataggt ttaggtctcc tagcatcctg gcactagcca 152340
gcagctgctc tgtaggagcc ttctggaaac agcaggaagg agcggcttcc ccacgagttc 152400
cccaagtgct ttcgttggcc caagtgcttt cgttggccca agtgacctgt ttgagtttgc 152460
tcttcagttt accccaggcg ggaaggcagc ctgtctgcgg gttggtggcc atgttggcag 152520
agaaggggtt aatctcttgt tgctgtagga gccgaggttg cgagctagat tgaaagcagg 152580
cgctgcagtg ccatcgccag cgccgaagga gtaagacgat cttctccgca acagtgttga 152640
atccggctga aatttttttt cctccccgcc tcctttcttg tttttcttta accagctcct 152700
cccccttcg ttcccaccct caagtctgac gatgacacct ccaattttga tgaaccagag 152760
aagaattcgt gggtttcatc ctctccgtgc cagctgagcc cctcaggctt ctcgggtgaa 152820
gaactgccgt ttgtggggtt ttcgtacagc aaggcactgg ggattcttgg tagatctgag 152880
taagtgaaaa tttgactttc taaagggacc tgcattgatg caaggctttt ggagccaaag 152940
gtggtggtgg gggggtgggg gaataggtgg ggggagtgca gtggagggaa gctgctagtc 153000
acctgcattg ggaaagcagt ctacctgtta gggctttgcg ggggtagcct gttaatattc 153060
tcattttgca gtgtgtaagg tacctgttcc tgtctgtggt atgataattg tcaattgggt 153120
actttgggtt agttttccaa tctttggtct tctttaaagg ggagagagtg ggagatttcc 153180
agcagtgcag atccccggtc aaaggagaaa tgtgcaggag ttaagatgag ctgcccatct 153240
atctaaccat ctatgtatct gtctctcaag tgggtggatg ggggttgcta tcttggctgt 153300
ataaagaatc ctaaaaacct tgtctcataa gctagaggtt tcctgatggg tttaactgag 153360
ctgcaagtgg ctgaaccaga gctctaacag agagatggtg ctcggctcct ctccaagtat 153420
```

-continued

```
gctgcaagat cagggatctg gcagctgagc ctctctgagc tggtggagcg ctggcagcca 153480
gagaaagccc cgttactgtg agccaccagg agggagtgtg atgtagccga gtcattgatt 153540
cacagaaact gggcttcata gggggaaaaa aaaccaggag actagaaaat ggaaatataa 153600
atatcactgt aaacctcttg atctggtagg tctttctcca ttctcataaa agctattgaa 153660
aaatgcatta acagagcact tggaattaga gggtcgaggc ttccaggagc ctcctggaat 153720
ttctgtaaaa tgcagtagct tctgtggatg tgggaggtca gtatcttgcc tcattctctc 153780
atgatacaat gacattctgt tttcagagga gtgagttccc cagaagatct tggactgatg 153840
gtgttatttg ccagccaccc tggtccctgc actttcaggt tctcagaggg taatgttggg 153900
ttagttgctg cccacttagg agacgagcag aatttgatat tcttcttggc agcatctttc 153960
cctctttgtg gtatttgtag cttagatatc gatttatagg gatgttatgt tggttcctgg 154020
atggtgtctc cctatgggtg ctattttgac agtaacgttc ctgaaaagat ttcagagtgt 154080
tgtggggaat tgggcatttg atacgaaata aggttgtggg ctgtgattga atgtgaggga 154140
ggtttttatg ttgcaagatg ttgaagtggt ctttcttgat cccctctctg ggggctgggt 154200
ttcaaattca ggttggattt tggtagtgtt agatgtgcct ctctgtctga tttgctccac 154260
aaccccaaag caatctggat ggtggtggga gaggcagagt gctaactagc tgttgaatgt 154320
gccatcagat gggtttgaaa cggctcagca ggattgggag gttttgccat tggcatcaaa 154380
gagcagggca gaagcggagg cctgatgttg aaggatgcat ggttagtggg cagtataacc 154440
ttgacacacg cagcacactg aaggtcacac gtcgtactgg aaggacgtgt ggagagttct 154500
agttctggtt agcagtgggc tggctgggtc agaatgcaag cttgcttggg tgttggtcag 154560
tgatctgaaa gacgagggag gattcgaggg agttagattt caggggaaaa ggcagaatga 154620
tatgggagat cttaggcatt gcaattaatc tgaagcagtg tgtgattaat tgcttatttt 154680
tcaggaagac ttgaatgaca tctttctgtt tctcacagaa agctcagttt agggagctct 154740
ctgacaggga catctcagta ttaaggctga ggcactcgat aaatatttgt tgatttaatt 154800
tacctatgat cctttcctcc agaagtgttt atattgctta ttgtatttga agatgtgcta 154860
tctcacctct ggtagtttaa actatatcct tagagcacaa aacgagctgc tgttcctgac 154920
ccaacagaat gtttaataag attcttattt caaaaaaggt ccatgcaaat aaaactgtgt 154980
atttcttatt tggacgatgg catcagagta ttcctatcat tggggaactt taacgttttt 155040
tcaaagcttg gcaacggggt tggaatcaga aagattttct ttcatcttgc gtcttgttat 155100
gtgttattgc tattggactt ggctactctg ctgtaggcag ccctgtgggt gatacctaca 155160
agcatcattt tagaaattca tccacctgtt ggatgtagat gaccctggac atatcagatt 155220
gtgattaatt agaaatctaa taaaagagag gcagtgatga aattacttag cagctcctgc 155280
agttttattg acaaaattta cttggagaga gggggagaca ttttctgggg gtaccacctt 155340
tgctgccagc gaccctgtgt ttcttcctga gtttcttttt cttttctcac cattttcagc 155400
atcacaggtt tttatttaca cacattgatt acctgtgctg ttactcattc ttcacaccac 155460
tgaggaaatt gcagatgctg ctgtactgtg ctaggtaaat tgacctcaga tttgttacca 155520
gtgaattgaa tgaaatgttc agaggtggag ctgaatgaac gaggagtttt tgtggagaaa 155580
ttggcagtga gaatgattta aattctgtga tagctcctcg ttttttggga tccttatttt 155640
gggaccccag actattttta agccattgag tgcatcatta ttttaggctg agcaagaatc 155700
ttgatgacag cgtttcaatg gctgaggcgt agtgggagtt ccttgcagct tgagttggtg 155760
ggagctggag agtttctaga gaactaggtt tggttgtctt tggggtgggg ttatggtgaa 155820
```

-continued attagtcttg gagagtgagt agctgtctga tgcttctttt ccttttttaac cagcaagagc 155880
ccaaaccaaa tccccaagct ctgaatgcct ggctgttcct ctcagccttt ctttgcttga 155940
acttgacaat agtagggtag taacaggaaa cagcatgtta aagttttaaa aataaaatag 156000
atctcagctc ttttccttcc cattagcaag ggtacattt atttaggttt ttccttctag 156060
attgaggcac tgcctcattt aagttcttgg tgaagccatg catttctgca aaccataagt 156120
ataaactcta gaacgggggt gtccaatctt ttggcttcct tgggccacat gggaagaaga 156180
agaattgtct tgaggcacac ataaaataca ctaatgatag ctgatgagct aaaaaaaaaa 156240
aaaaactcat aaagttttaa gaaagcttac aaacttgtaa gttttgagcc acattaaaaa 156300
ccatcctggg ctgcatgcag cccccggggc cttgggttgg acaagcttgc tgtagaaggt 156360
aaaaatcagt tggttttatg tttttgtttt aaacatgctg gttgtatgct tttggaagag 156420
ttggggaaca ctgagggtaa tgggatcttg atggggctgg aatttgtggg aagatggtgt 156480
ctgggtaggc tgtttttagg aaggggcact ctcttccttt tgattcagag atttttcctt 156540
tcttttcggg tggttctgaa aacacagcga tggatccagg cattcaaaca ccatggagga 156600
aggaagagtg gctgttgcca ttgcttcccg agttttctgg gaaccagttt ttggtgcctc 156660
ttccttgctc tactggggct tctctgcatg tcagtttctt caactgcgaa gtggaaggac 156720
agcgatactt ttcttacagg acttttgcgg ggatggatga aatacgtaaa acacttggtc 156780
tagtacctgg cacatggaaa agccttggta aatgttcact gttgttattt ttgttattac 156840
taatacacta gtccatgtat gtatagtgtc ctcctataca caccaagaga atatggaaag 156900
gactcagcaa tgattaggta gtccaaagtc ataccagatt ggaaaccaag cttcccaggc 156960
cctgggactt ttctgctaga gacacttcac ggttctgacc aactacaaag agttaatatg 157020
cagttgccaa atacctgttg gtaaaaggtg gatgttgggg aggagtggat tggggaacag 157080
aattagaagg tccagtccca gaatgggtac cttcccatca agttgaacaa gtcaaaacag 157140
gttatgttga aacaactgag agaaagtaaa gcaaacacca ttgctgcaga atatcatggt 157200
acaaattgga catctttggg agttagcgga gtaaggcaaa atccagtgag ggacgcttaa 157260
tgggtaatgc caattcacaa ttcttgttaa attacattgc tgatcttcct tggaatgtct 157320
gtccattccc ccaagtagac tgtgatctca aggcaaggct gggtcttatt catcctggtt 157380
ttcctggagc agtaaatact tgtgctggga ctgggcttat aagcatacta atggaaagta 157440
aaatatttgg gttggttttt taaaaagaca gtggatttgg atcagtggag aggaaggtag 157500
agggaatttc aggtgggcag ggtgctaaca acagcccatc cttacagggc accaactgtg 157560
ttctaggctg tgttccaacc actttacaca gatgaattca tttaaattgc acaaccagcc 157620
caagaggaag gtaccattat tattctcatt ttggatgtga ggaaactgag gcgtggggag 157680
atcaaacaac ttgcctaaag ttatgtagct ttgagtggct tagctgagat ttgaaccctg 157740
tgggtataaa tgccacagat gggaaatttg tgtggggtac cccagggttc atgtgcttgt 157800
tagaagtgga agctatttgt agagaatcac gaatgatgag gttggggcag ggtgtgatgg 157860
gagctgacag gcaggtctaa atgctgggat tccattttca gtctctgtgt ttattgagta 157920
ggtagacggt atagctcttg gatttctcag attttttcct cttttcattt agagactctt 157980
atctggtgtg tgtgtgcccg cacacataca taaacccacg cgtatatact ctttccctga 158040
atgttcttat ttgctaaagc ttaagcttgg caaagagagg aaactgcact gaccttactc 158100
tccaccatat cttcaggctg atcatacaca agttgcttaa taagcatttg gttaatccat 158160

-continued ctaaatcatt cttatggctg caactctcat tttgttgatg actctactat ctatgtctat 158220
tcacatctac attttgtact tttgtttgcc tcccatctgt cctgggatgg ctgataccag 158280
tggaagacag cctgaactct ccaatcagtc ctgtttcctt tttatgaaat acttggaggt 158340
tggaggatct tcccttaaaa agtgttttcc tttctacatc cagccaaagg ctcttggtcc 158400
ttgtgcttgc tacctagatc cctattggaa agagtcttgc ctgcaatttg attttttaaa 158460
tagcagcaat aacagagtcg tctctgctac acgaagacat gcatctgctg tatttcccag 158520
acaagttcaa aaaccttaac tagcttctgc ccatggttat tgctctcaag tgccttgtgt 158580
tgttcccatc ccctcattat ctggattaga tgtttaacat ttgcctgtgt gtgttgtgtt 158640
ggattttctc ctctcctctt gctcattcaa tttcttcctt ctcttagcca agcacagctt 158700
gttctcctac ttgccttatt ctgttctcta tttagactgt gcgtgcctgc cttgcagccc 158760
tggcaggacc attccaccgc cttctcattt gtcttaaaga tacctttagg aaatctaatc 158820
cagacaatcc tagcccagtc ctgaagatta ggctccagaa gattctgtca agtgtgtttt 158880
ttgctggcct acacatgcta atttgcatgg ttgcctggga tcccttaaga agacagtcat 158940
tgactaaatg gcgctacatg ttcccaagct ctgcgccagt ctggcaactc ttcctttgtc 159000
tacgtgaatt tctcctagtt ctttctgctt tgcttgctgt tcatctcctg acctctctcc 159060
gacaaacttc nnnnnnnnnn nnnnnnnnnn nnnnnnnnnn nnnnnnnnnn nnnnnnnnnn 159120
nnnnnnnnnn nnnnnnnnnn nnnnnnnnnn nnnnnnnnnn nnnnnnnnnn nnnnnnnnnn 159180
nnnnnnnnnn nnnnnnnnnn nnnnnnnnnn nnnnnnnnnn nnnnnnnnnn nnnnnnnnnn 159240
nnnnnnnnnn nnnnnnnnnn nnnnnnnnnn nnnnnnnnnn nnnnnnnnnn nnnnnnnnnn 159300
nnnnnnnnnn nnnnnnnnnn nnnnnnnnnn nnnnnnnnnn nnnnnnnnnn nnnnnnnnnn 159360
nnnnnnnnnn nnnnnnnnnn nnnnnnnnnn nnnnnnnnnn nnnnnnnnnn nnnnnnnnnn 159420
nnnnnnnnnn nnnnnnnnnn nnnnnnnnnn nnnnnnnnnn nnnnnnnnnn nnnnnnnnnn 159480
nnnnnnnnnn nnnnnnnnnn nnnnnnnnnn nnnnnnnnnn nnnnnnnnnn nnnnnnnnnn 159540
nnnnnnnnnn nnnnnnnnnn nnnnnnnnnn nnnnnnnnnn nnnnnnnnnn nnnnnnnnnn 159600
nnnnnnnnnn nnnnnnnnnn nnnnnnnnnn nnnnnnnnnn nnnnnnnnnn nnnnnnnnnn 159660
nnnnnnnnnn nnnnnnnnnn nnnnnnnnnn nnnnnnnnnn nnnnnnnnnn nnnnnnnnnn 159720
nnnnnnnnnn nnnnnnnnnn nnnnnnnnnn nnnnnnnnnn nnnnnnnnnn nnnnnnnnnn 159780
nnnnnnnnnn nnnnnnnnnn nnnnnnnnnn nnnnnnnnnn nnnnnnnnnn nnnnnnnnnn 159840
nnnnnnnnnn nnnnnnnnnn nnnnnnnnnn nnnnnnnnnn nnnnnnnnnn nnnnnnnnnn 159900
nnnnnnnnnn nnnnnnnnnn nnnnnnnnnn nnnnnnnnnn nnnnnnnnnn nnnnnnnnnn 159960
nnnnnnnnnn nnnnnnnnnn nnnnnnnnnn nnnnnnnnnn nnnnnnnnnn nnnnnnnnnn 160020
nnnnnnnnnn nnnnnnnnnn nnnnnnnnnn nnnnnnnnnn nnnnnnnnnn nnnnnnnnnn 160080
nnnnnnnnnn nnnnnnnnnn nnnnnnnnnn nnnnnnnnnn nnnnnnnnnn nnnnnnnnnn 160140
nnnnnnnnnn nnnnnnnnnn nnnnnnnnnn nnnnnnnnnn nnnnnnnnnn nnnnnnnnnn 160200
nnnnnnnnnn nnnnnnnnnn nnnnnnnnnn nnnnnnnnnn nnnnnnnnnn nnnnnnnnnn 160260
nnnnnnnnnn nnnnnnnnnn nnnnnnnnnn nnnnnnnnnn nnnnnnnnnn nnnnnnnnnn 160320
nnnnnnnnnn nnnnnnnnnn nnnnnnnnnn nnnnnnnnnn nnnnnnnnnn nnnnnnnnnn 160380
nnnnnnnnnn nnnnnnnnnn nnnnnnnnnn nnnnnnnnnn nnnnnnnnnn nnnnnnnnnn 160440
nnnnnnnnnn nnnnnnnnnn nnnnnnnnnn nnnnnnnnnn nnnnnnnnnn nnnnnnnnnn 160500
nnnnnnnnnn nnnnnnnnnn nnnnnnnnnn nnnnnnnnnn nnnnnnnnnn nnnnnnnnnn 160560

-continued

```
nnnnnnnnnn nnnnnnnnnn nnnnnnnnnn nnnnnnnnnn nnnnnnnnnn nnnnnnnnnn 160620
nnnnnnnnnn nnnnnnnnnn nnnnnnnnnn nnnnnnnnnn nnnnnnnnnn nnnnnnnnnn 160680
nnnnnnnnnn nnnnnnnnnn nnnnnnnnnn nnnnnnnnnn nnnnnnnnnn nnnnnnnnnn 160740
nnnnnnnnnn nnnnnnnnnn nnnnnnnnnn nnnnnnnnnn nnnnnnnnnn nnnnnnnnnn 160800
nnnnnnnnnn nnnnnnnnnn nnnnnnnnnn nnnnnnnnnn nnnnnnnnnn nnnnnnnnnn 160860
nnnnnnnnnn nnnnnnnnnn nnnnnnnnnn nnnnnnnnnn nnnnnnnnnn nnnnnnnnnn 160920
nnnnnnnnnn nnnnnnnnnn nnnnnnnnnn nnnnnnnnnn nnnnnnnnnn nnnnnnnnnn 160980
nnnnnnnnnn nnnnnnnnnn nnnnnnnnnn nnnnnnnnnn nnnnnnnnnn nnnnnnnnnn 161040
nnnnnnnnnn nnnnnnnnnn nnnnnnnnnn nnnnnnnnnn nnnnnnnnnn nnnnnnnnnn 161100
nnnnnnnnnn nnnnnnnnnn nnnnnnnnnn nnnnnnnnnn nnnnnnnnnn nnnnnnnnnn 161160
nnnnnnnnnn nnnnnnnnnn nnnnnnnnnn nnnnnnnnnn nnnnnnnnnn nnnnnnnnnn 161220
nnnnnnnnnn nnnnnnnnnn nnnnnnnnnn nnnnnnnnnn nnnnnnnnnn nnnnnnnnnn 161280
nnnnnnnnnn nnnnnnnnnn nnnnnnnnnn nnnnnnnnnn nnnnnnnnnn nnnnnnnnnn 161340
nnnnnnnnnn nnnnnnnnnn nnnnnnnnnn nnnnnnnnnn nnnnnnnnnn nnnnnnnnnn 161400
nnnnnnnnnn nnnnnnnnnn nnnnnnnnnn nnnnnnnnnn nnnnnnnnnn nnnnnnnnnn 161460
nnnnnnnnnn nnnnnnnnnn nnnnnnnnnn nnnnnnnnnn nnnnnnnnnn nnnnnnnnnn 161520
nnnnnnnnnn nnnnnnnnnn nnnnnnnnnn nnnnnnnnnn nnnnnnnnnn nnnnnnnnnn 161580
nnnnnnnnnn nnnnnnnnnn nnnnnnnnnn nnnnnnnnnn nnnnnnnnnn nnnnnnnnnn 161640
nnnnnnnnnn nnnnnnnnnn nnnnnnnnnn nnnnnnnnnn nnnnnnnnnn nnnnnnnnnn 161700
nnnnnnnnnn nnnnnnnnnn nnnnnnnnnn nnnnnnnnnn nnnnnnnnnn nnnnnnnnnn 161760
nnnnnnnnnn nnnnnnnnnn nnnnnnnnnn nnnnnnnnnn nnnnnnnnnn nnnnnnnnnn 161820
nnnnnnnnnn nnnnnnnnnn nnnnnnnnnn nnnnnnnnnn nnnnnnnnnn nnnnnnnnnn 161880
nnnnnnnnnn nnnnnnnnnn nnnnnnnnnn nnnnnnnnnn nnnnnnnnnn nnnnnnnnnn 161940
nnnnnnnnnn nnnnnnnnnn nnnnnnnnnn nnnnnnnnnn nnnnnnnnnn nnnnnnnnnn 162000
nnnnnnnnnn nnnnnnnnnn nnnnnnnnnn nnnnnnnnnn nnnnnnnnnn nnnnnnnnnn 162060
nnnnnnnnnn nnnnnnnnnn nnnnnnnnnn nnnnnnnnnn nnnnnnnnnn nnnnnnnnnn 162120
nnnnnnnnnn nnnnnnnnnn nnnnnnnnnn nnnnnnnnnn nnnnnnnnnn nnnnnnnnnn 162180
nnnnnnnnnn nnnnnnnnnn nnnnnnnnnn nnnnnnnnnn nnnnnnnnnn nnnnnnnnnn 162240
nnnnnnnnnn nnnnnnnnnn nnnnnnnnnn nnnnnnnnnn nnnnnnnnnn nnnnnnnnnn 162300
nnnnnnnnnn nnnnnnnnnn nnnnnnnnnn nnnnnnnnnn nnnnnnnnnn nnnnnnnnnn 162360
nnnnnnnnnn nnnnnnnnnn nnnnnnnnnn nnnnnnnnnn nnnnnnnnnn nnnnnnnnnn 162420
nnnnnnnnnn nnnnnnnnnn nnnnnnnnnn nnnnnnnnnn nnnnnnnnnn nnnnnnnnnn 162480
nnnnnnnnnn nnnnnnnnnn nnnnnnnnnn nnnnnnnnnn nnnnnnnnnn nnnnnnnnnn 162540
nnnnnnnnnn nnnnnnnnnn nnnnnnnnnn nnnnnnnnnn nnnnnnnnnn nnnnnnnnnn 162600
nnnnnnnnnn nnnnnnnnnn nnnnnnnnnn nnnnnnnnnn nnnnnnnnnn nnnnnnnnnn 162660
nnnnnnnnnn nnnnnnnnnn nnnnnnnnnn nnnnnnnnnn nnnnnnnnnn nnnnnnnnnn 162720
nnnnnnnnnn nnnnnnnnnn nnnnnnnnnn nnnnnnnnnn nnnnnnnnnn nnnnnnnnnn 162780
nnnnnnnnnn nnnnnnnnnn nnnnnnnnnn nnnnnnnnnn nnnnnnnnnn nnnnnnnnnn 162840
nnnnnnnnnn nnnnnnnnnn nnnnnnnnnn nnnnnnnnnn nnnnnnnnnn nnnnnnnnnn 162900
```

-continued

```
nnnnnnnnnn nnnnnnnnnn nnnnnnnnnn nnnnnnnnnn nnnnnnnnnn nnnnnnnnnn 162960
nnnnnnnnnn nnnnnnnnnn nnnnnnnnnn nnnnnnnnnn nnnnnnnnnn nnnnnnnnnn 163020
nnnnnnnnnn nnnnnnnnnn nnnnnnnnnn nnnnnnnnnn nnnnnnnnnn nnnnnnnnnn 163080
nnnnnnnnnn nnnnnnnnnn nnnnnnnnnn nnnnnnnnnn nnnnnnnnnn nnnnnnnnnn 163140
nnnnnnnnnn nnnnnnnnnn nnnnnnnnnn nnnnnnnnnn nnnnnnnnnn nnnnnnnnnn 163200
nnnnnnnnnn nnnnnnnnnn nnnnnnnnnn nnnnnnnnnn nnnnnnnnnn nnnnnnnnnn 163260
nnnnnnnnnn nnnnnnnnnn nnnnnnnnnn nnnnnnnnnn nnnnnnnnnn nnnnnnnnnn 163320
nnnnnnnnnn nnnnnnnnnn nnnnnnnnnn nnnnnnnnnn nnnnnnnnnn nnnnnnnnnn 163380
nnnnnnnnnn nnnnnnnnnn nnnnnnnnnn nnnnnnnnnn nnnnnnnnnn nnnnnnnnnn 163440
nnnnnnnnnn nnnnnnnnnn nnnnnnnnnn nnnnnnnnnn nnnnnnnnnn nnnnnnnnnn 163500
nnnnnnnnnn nnnnnnnnnn nnnnnnnnnn nnnnnnnnnn nnnnnnnnnn nnnnnnnnnn 163560
nnnnnnnnnn nnnnnnnnnn nnnnnnnnnn nnnnnnnnnn nnnnnnnnnn nnnnnnnnnn 163620
nnnnnnnnnn nnnnnnnnnn nnnnnnnnnn nnnnnnnnnn nnnnnnnnnn nnnnnnnnnn 163680
nnnnnnnnnn nnnnnnnnnn nnnnnnnnnn nnnnnnnnnn nnnnnnnnnn nnnnnnnnnn 163740
nnnnnnnnnn nnnnnnnnnn nnnnnnnnnn nnnnnnnnnn nnnnnnnnnn nnnnnnnnnn 163800
nnnnnnnnnn nnnnnnnnnn nnnnnnnnnn nnnnnnnnnn nnnnnnnnnn nnnnnnnnnn 163860
nnnnnnnnnn nnnnnnnnnn nnnnnnnnnn nnnnnnnnnn nnnnnnnnnn nnnnnnnnnn 163920
nnnnnnnnnn nnnnnnnnnn nnnnnnnnnn nnnnnnnnnn nnnnnnnnnn nnnnnnnnnn 163980
nnnnnnnnnn nnnnnnnnnn nnnnnnnnnn nnnnnnnnnn nnnnnnnnnn nnnnnnnnnn 164040
nnnnnnnnnn nnnnnnnnnn nnnnnnnnnn nnnnnnnnnn nnnnnnnnnn nnnnnnnnnn 164100
nnnnnnnnnn nnnnnnnnnn nnnnnnnnnn nnnnnnnnnn nnnnnnnnnn nnnnnnnnnn 164160
nnnnnnnnnn nnnnnnnnnn nnnnnnnnnn nnnnnnnnnn nnnnnnnnnn nnnnnnnnnn 164220
nnnnnnnnnn nnnnnnnnnn nnnnnnnnnn nnnnnnnnnn nnnnnnnnnn nnnnnnnnnn 164280
nnnnnnnnnn nnnnnnnnnn nnnnnnnnnn nnnnnnnnnn nnnnnnnnnn nnnnnnnnnn 164340
nnnnnnnnnn nnnnnnnnnn nnnnnnnnnn nnnnatttca gagtaagttt ttctagaaaa 164400
tagaagctgg aaaaaaaagg aaaacccaaa cttggcttcg tgctcgaaga gacagcactg 164460
ctgtgtgtgg gcgggtggct gcgtgcaccc gctgctcaga agtgcctttt ctctccatgg 164520
ggataactgg ctgtgtatcc gagatgtggc caggagtagg caagcaacgt gtgggcaggc 164580
tgcatgttct tttattagca tcttcattgt actgcatctc gtcgagccca gagcatgaac 164640
tggcctgggt ttctaatatc taccctgctt cccacctaat tactcccctg aaccctaaag 164700
tgagggaggg agagttgctc ttgtggggtg agctttccct ggggtggctg tgaaccaacc 164760
tggcatgtgg atgttcttgg gtatccagag ctgtcctgga ctcaggcttg gagtcagctt 164820
cttagcactg aatgcagcca gtcatggatg gaggtcactg tatctcacat gttccgctct 164880
ccctttcctc catgaccttg cccctctgag cctctgtagc acttttcttg agtgtgtcca 164940
aggccatcta gctaagaagt agcagaaatg ggatttgaag ccatgactgt ttggtgatag 165000
agcctcagct ttgaactggg gttctactgc ctggcacccc tgcacaaatc atggtaacgt 165060
ggtaggagaa catagaggta tagggcaagc ccctccttaa tgccatgaat aatacccatc 165120
ttataggatt gtggggagga ctcagtgaag taacccgtga agcactaaac acgtgcctga 165180
cacgtgctca ataaatgagc acttgtcctg atgacaaagg tcgtggcatt aattctctct 165240
cctaggttgt tacttccttg aggacaggaa ttgtggcttc cttaatggcc actgcagcag 165300
```

-continued agtttctcaa gttggcacta ttgacatttt gggctggata attcttgttg tgggagctgt 165360
cctgtggatt gtaggatgtt gagcagcatc tttggcctct acccgctaca tattaatagc 165420
acccctagtc atgaaaataa aatgtctaga cattgccaaa ctgcccctgt tgagaaccac 165480
tggtctgcag gtatctctca tggggatcac agggctttta tattctcttc tctgtctctc 165540
tctctccctc tctgggtgtc tctctctctc acacacacgc ttagagaagg tggttaaaaa 165600
aaattttgtt gaagtttgag aattttgaga acaaaggaaa aattttggaa ggcattttaa 165660
tgaacagata gactctgtcc cattccatgg tcaacagaat ttcataatta gatagtttgt 165720
ttactgcaac tctgcacccc attgcccatc attttagagt tccaaccagt tagaggattt 165780
ttcttgcaaa ctttccttaa agcagtgata gtatcagctc tttaaataat actatgcttg 165840
atgaagtggt acttttcggg ataatttgag accagccgac ttgctgcttg aagaggacag 165900
ggctatattt ggtaataata tatatgtgat aatatgtatg taatattatt ataatgtaat 165960
atacaataat atttggtgta actggtgact ctgaggccag tctttgatcg aacctctcaa 166020
gctatgattt acattatggt caatgttagc ataatgcaat tatcagcaat cacttgctgt 166080
tgctttgaaa gtcagaagga tggctaataa aaatcttaga aaaagaaaac aggccgggtg 166140
cagtggctca cccctgtaat cccagcactt tgggaggctg aggcggacag atcatgaggt 166200
caggagatcg agaccatcct ggccaacatg gtgaaacccc atctgtacta gaatacaaaa 166260
aaaaaaaaaa aatttgctgg gcgtggtggc gtgcgcctgt agtcccagct actcgggagc 166320
tgagtcaggg gaatcgcttg aacccgggag gtggaggttg cagtgagccg agattgtgcc 166380
actgcactcc agcctggtga cagagtgaga ctccgtctca aacaaaacaa aacaaaacaa 166440
aaaacaaaaa aagaaaatct tagaaaaaga aaataaattg taatatttca gaatatttgt 166500
tggggaggat atgtgtgctc aagaaatata tactgagaac ttaccattga tgctagagat 166560
tgaattgccc catgtctaca tgaaaaatga atagaatata aacattttaa attgagccat 166620
gtctatctgt attatatttc ttttatagaa attcatggaa atggtatatt ttaactgaat 166680
tattaacact ggggacaata ggctttaatc attatctaat acctgtacgt tgttttgaaa 166740
ttcatagccc accaccatta atttcaaaat tgggttctta ctcaaagagt gatgaaaagg 166800
caccagtacc aaatggtctg gccaaaatgc tacatggaac taaatgctgg ggatggtcat 166860
acaatgagtt ttaagtggct agaccctaaa tcagaagcac tttcttctaa ttagcaccat 166920
ggttcttaat cctttctgta cattacaatc gctcagcagc ttaatacaaa tgttgcttcc 166980
cggggccaca ctccacatct ttctgactct ctgatttaat tggtccgaat ggggcctata 167040
catcaggtgt tttttaaaag gtctccaagt gattctaatg tgtacctgca ttgaggacca 167100
gggaaggtgt aggaagcctg ataaccttta ctctccagcc tcatcctcca atcccatgat 167160
tgtttatggg attgttgcta cacacccagc ttagtcatag cattcttact ctagcttttt 167220
tttagatgca atttttattt attcttaaag aaaaagattt ctttagcacc tttattctaa 167280
agagctctta attgctgtgc ttagaacttc taaacagtga gcatttgtca aacatagaat 167340
agcagaatga aggggttgga cctcgggtga ggagggctgt cgcatggtct ctttcgagtg 167400
ccggcgggtg ggggctgcac atctcctcgc ttctgggccc attgataagt gacctaaaag 167460
tgcctttcgt tttttttggt ggggggtgaa aaagcaatct gttttgtacc cacagcggtg 167520
cactttaaac aggaagccct actggggcca gccttctatg tgtcattaag tttttcacgc 167580
cacatcctac ctatcatcat gcacccatgt catcgttctt ttaaagggtg ccagtttttt 167640

-continued

```
gcttaagcac aaggagctgt gacctgtgtt gtcatccctg atgcatgtca tgcatgtgac 167700
ttcatgacat gtgggtgact tttgatctct gaaggaccag ggacccagtc tgtggatcac 167760
cactctctcc gtgggtggtt tgggtcttgt tctctagccc acccagccag gtgcaattag 167820
gaataaagga aatagcaaag gaattttgct caaggccatg ccaagcattt catctcatat 167880
gaaaaggaaa agagagagag tgtgtgtgtg ttggctagat ttaggtagaa aacaggctgg 167940
tgagaagcgt agaacttggt taaaatttct agccaaaagt aagattttta aaaagattta 168000
tttctggatc caatccctgt tgcccatttc tatgaataat caccatttgt tttaatgtga 168060
ataatagcac acagcaaatt cagccccctg agttttacca ttttaagcaa ttgctttagg 168120
cccgtgaggc atgtactatt tatgaagttg catgggtagt aatggaaaac acaacaatga 168180
cagtagtaac aggtgacatt tgtcgaacac ttgcagtgtg ccaggcactg tgctgagagc 168240
attacatgca ttatttcatt taatccttcc aagaactctt tgaagtaggt tggtaattat 168300
ggccatttta caattgagga aactgaggtt cggagatgtc aaataactag tcagtggtgg 168360
ggtcagattt ttcttttttt tttaaattta tttgcttttt tttttttttt ttttttttg 168420
agacggagtc tcactctgtt gcccaggctg annnnnnnnn nnnnnnnnnn nnnnnnnnnn 168480
nnnnnnnnnn nnnnnnnnnn nnnnnnnnnn nnnnnnnnnn nnnnnnnnnn nnnnnnnnnn 168540
nnnnnnnnnn nnnnnnnnnn nnnnnnnnnn nnnnnnnnnn nnnnnnnnnn nnnnnnnnnn 168600
nnnnnnnnnn nnnnnnnnnn nnnnnnnnnn nnnnnnnnnn nnnnnnnnnn nnnnnnnnnn 168660
nnnnnnnnnn nnnnnnnnnn nnnnnnnnnn nnnnnnnnnn nnnnnnnnnn nnnnnnnnnn 168720
nnnnnnnnnn nnnnnnnnnn nnnnnnnnnn nnnnnnnnnn nnnnnnnnnn nnnnnnnnnn 168780
nnnnnnnnnn nnnnnnnnnn nnnnnnnnnn nnnnnnnnnn nnnnnnnnnn nnnnnnnnnn 168840
nnnnnnnnnn nnnnnnnnnn nnnnnnnnnn nnnnnnnnnn nnnnnnnnnn nnnnnnnnnn 168900
nnnnnnnnnn nnnnnnnnnn nnnnnnnnnn nnnnnnnnnn nnnnnnnnnn nnnnnnnnnn 168960
nnnnnnnnnn nnnnnnnnnn nnnnnnnnnn nnnnnnnnnn nnnnnnnnnn nnnnnnnnnn 169020
nnnnnnnnnn nnnnnnnnnn nnnnnnnnnn nnnnnnnnnn nnnnnnnnnn nnnnnnnnnn 169080
nnnnnnnnnn nnnnnnnnnn nnnnnnnnnn nnnnnnnnnn nnnnnnnnnn nnnnnnnnnn 169140
nnnnnnnnnn nnnnnnnnnn nnnnnnnnnn nnnnnnnnnn nnnnnnnnnn nnnnnnnnnn 169200
nnnnnnnnnn nnnnnnnnnn nnnnnnnnnn nnnnnnnnnn nnnnnnnnnn nnnnnnnnnn 169260
nnnnnnnnnn nnnnnnnnnn nnnnnnnnnn nnnnnnnnnn nnnnnnnnnn nnnnnnnnnn 169320
nnnnnnnnnn nnnnnnnnnn nnnnnnnnnn nnnnnnnnnn nnnnnnnnnn nnnnnnnnnn 169380
nnnnnnnnnn nnnnnnnnnn nnnnnnnnnn nnnnnnnnnn nnnnnnnnnn nnnnnnnnnn 169440
nnnnnnnnnn nnnnnnnnnn nnnnnnnnnn nnnnnnnnnn nnnnnnnnnn nnnnnnnnnn 169500
nnnnnnnnnn nnnnnnnnnn nnnnnnnnnn nnnnnnnnnn nnnnnnnnnn nnnnnnnnnn 169560
nnnnnnnnnn nnnnnnnnnn nnnnnnnnnn nnnnnnnnnn nnnnnnnnnn nnnnnnnnnn 169620
nnnnnnnnnn nnnnnnnnnn nnnnnnnnnn nnnnnnnnnn nnnnnnnnnn nnnnnnnnnn 169680
nnnnnnnnnn nnnnnnnnnn nnnnnnnnnn nnnnnnnnnn nnnnnnnnnn nnnnnnnnnn 169740
nnnnnnnnnn nnnnnnnnnn nnnnnnnnnn nnnnnnnnnn nnnnnnnnnn nnnnnnnnnn 169800
nnnnnnnnnn nnnnnnnnnn nnnnnnnnnn nnnnnnnnnn nnnnnnnnnn nnnnnnnnnn 169860
nnnnnnnnnn nnnnnnnnnn nnnnnnnnnn nnnnnnnnnn nnnnnnnnnn nnnnnnnnnn 169920
nnnnnnnnnn nnnnnnnnnn nnnnnnnnnn nnnnnnnnnn nnnnnnnnnn nnnnnnnnnn 169980
nnnnnnnnnn nnnnnnnnnn nnnnnnnnnn nnnnnnnnnn nnnnnnnnnn nnnnnnnnnn 170040
```

-continued nnnnnnnnnn nnnnnnnnnn nnnnnnnnnn nnnnnnnnnn nnnnnnnnnn nnnnnnnnnn 170100
nnnnnnnnnn nnnnnnnnnn nnnnnnnnnn nnnnnnnnnn nnnnnnnnnn nnnnnnnnnn 170160
nnnnnnnnnn nnnnnnnnnn nnnnnnnnnn nnnnnnnnnn nnnnnnnnnn nnnnnnnnnn 170220
nnnnnnnnnn nnnnnnnnnn nnnnnnnnnn nnnnnnnnnn nnnnnnnnnn nnnnnnnnnn 170280
nnnnnnnnnn nnnnnnnnnn nnnnnnnnnn nnnnnnnnnn nnnnnnnnnn nnnnnnnnnn 170340
nnnnnnnnnn nnnnnnnnnn nnnnnnnnnn nnnnnnnnnn nnnnnnnnnn nnnnnnnnnn 170400
nnnnnnnnnn nnnnnnnnnn nnntggctta aaacaacaca catttattat tttacagttc 170460
tggaggtcag aagtctaaga tgatgccagg cttggtggct caagcctgta atcccagcac 170520
tttgggaggc tgaggtggca ggatcacttg aggtcaggag ttccagacta gcctagccaa 170580
catggtgaaa ccccatctct actaaaaata caaaaattag tcaggcacgg tcacgagcac 170640
ctgtaatccc aactactcag gaggctgagg caggagaatt gcttgaaccc aggaggtgga 170700
ggttgcagtg agccgaggtt gcagtgagcc gaggttgcac cactgcactc cagcctgggc 170760
aacagaacgc gaccctgttt ccaagaaaaa aaaaaagtcc gggatgagtt ttactgggct 170820
gagatcagtg tagacaaggc tgccctctct ctggaggctc tagggcagaa tctgtttcct 170880
tgtcttttcc agcttctaga ggttgcctgc attccttggc ttgtggcccc ttcctccgtg 170940
ttcaaagcca ttggtgtaac atcttcaggt ctctgtgact ccgatccttg cttccatctt 171000
ataaggatcc ttgtgatttc attgtaccca tccagatatc ccaggagaat ctttccatcc 171060
caagatccat aacttaaatc ccatctgcaa agtccctttt gccatgtgtg gtaatatatt 171120
cacagcttgc agagatcagg acatgggcat ctttgggaaa cgggaagggg gcattatttg 171180
acctaacatc aagagcatga gatgtttttg taaaatgaaa caaatgttgc agcttcctaa 171240
tgcagcttct taggcccacc tgcaggcccc cttgacgttg gtttttctct acctaggtct 171300
gttgtgtcgg gtctggactc ccctgccaag actagctcca tggaaaagaa acttctcatc 171360
aaaagcaaag agctacaaga ctctcaggac aagtgtcaca aggtatttat ttccgcagcc 171420
ggcctccttc cttgctccag gatcctcccg tccgtatatg ccaagggatc cgcccggggc 171480
cgctgctggc tctgagccgc ctgatccgta gagagtgagg cgctcctgcc ttcgctgaag 171540
tcgcgcctcc agcagctcag agggagatga attcgggcct tgctgttgct gtaaatcctt 171600
taaatctaaa ccagaggagg ccctggattt aaacagtccg tttctcagca tgacccagcc 171660
agatgtctgc ttcttccggc aggtggcctg ggtcctcacc tgtggctgag atacatccca 171720
tctgctttga gtgatgcgaa gtctctcttc ctagtctttt aaaactcctg cttatgtcac 171780
tgcggccact gtgttgatta cgctcaacgt ctcttaacat tcactgttcc tgcccagagg 171840
caacgctctg gaaactaata agtcactgct tgcctgggac tcctaagagt gcagacgaat 171900
aaatatctcc ttgccctgtc ctggatttgt cctctagatc tttgcaagga gatgggggg 171960
gatcaagatg gatttgggat aaaattaaag tgacgtctgc aaaaacaaaa caaaaacaaa 172020
agcaaacagg tgaaaaatga tgattgtggc ttccttgcta actgggttag agaagtgatc 172080
aagtgtgaac cgggacttga atgagaggag tgacttagca tttggtgact gtccttaacg 172140
aagaactgtg cgctcctggg cgaagaaaca atggtatttc catcccaact taacttttgg 172200
cgaattagcc ttagcccaga ccaccaggtg gtttcggagg ctacttgaga tgtgattgct 172260
cctaatgaac ctccacgggc ctttttaacc tgtcgatgtg tttatttcag atggagcagg 172320
aaatgacccg gttacatcgg agagtgtcag aggtggaggc tgtgcttagt cagaaggagg 172380

-continued

```
tggagctgaa ggcctctgag actcagagat ccctcctgga gcaggacctt gctacctaca 172440
tcacagaatg cagtgtgagc cttccctgaa gccccttcc cttggaggtg gcacttcctg 172500
ttgtgtgtgt ctcatcctgt ttcatgatga ctccatgagg cacatcacag ccaatggcag 172560
agagtagaga gagggagagc acaaaagcaa gatctgtgtt ttgcagagta gtgagagcca 172620
ggcgtaaggt ccccaagaaa tgagattgga ctcatttcca gcagaaagtg caggtagacg 172680
gctggtacca tggagtctgg agatgggagt aattcatctt tgccgcaagt tgcaaaagat 172740
cttaacatct cccatcccag cctctgtggt ctgcgttgtg tctgacatga gcagccttga 172800
gaaccagact cccaactatg tacaagaaaa cttactttca atcttcctga catcaaattt 172860
tccattggcc agaaccagtg tagtgacaag aaaatagcct tgaaaaccca gaccctctgt 172920
cattatttac catgtgactt tcattttttc tttccttcac aagagtagac tgtcttcttc 172980
tccattgtct tgttaaattt ttcattcagg tgttttttaa tgtgcccaat taaacagtct 173040
caagaagttg aatcacacat ttctaaagtt tttttcacaa gggagaggaa atctatagaa 173100
cgtggctgat taagaataac tgctatgttt ccattccaga cttggctgcc tttcagtggt 173160
gggtgaagtt attcagctat gtatttcaga tatagatttc agtgccatga agcataaggg 173220
nnnnnnnnnn nnnnnnnnnn nnnnnnnnnn nnnnnnnnnn nnnnnnnnnn nnnnnnnnnn 173280
nnnnnnnnnn nnnnnnnnnn nnnnnnnnnn nnnnnnnnnn nnnnnnnnnn nnnnnnnnnn 173340
nnnnnnnnnn nnnnnnnnnn nnnnnnnnnn nnnnnnnnnn nnnnnnnnnn nnnnnnnnnn 173400
nnnnnnnnnn nnnnnnnnnn nnnnnnnnnn nnnnnnnnnn nnnnnnnnnn nnnnnnnnnn 173460
nnnnnnnnnn nnnnnnnnnn nnnnnnnnnn nnnnnnnnnn nnnnnnnnnn tgattctcct 173520
gcctcagcct cccgagtagc tgggactaca ggcatgcacc accatgccca gctaattttt 173580
gtatttttag taaagacggg gtttcaccat gttggccagg gtggtctcga tctcttgacc 173640
ttgtgatccg cctgcctcgg cctcccaaag tgctgggatt acaggtgtga gccactgtgc 173700
ccagcccata aatcaaaatt ttttcagcaa ttgttataca agtggaacct tactcttcaa 173760
atgcaattgt ccagtgtctg gcttaatgtc tgctgttgtc agaaaccatg tgaatggagt 173820
agattcccag gttataagga gcccccaggg aggatgcgcg agtcactggc ttctccaggg 173880
gtctctggtt tggggttgcc ttggtgctgg gcacacttcc tggagatttt actggaccag 173940
cctgaggcct ttggggctct gtgcagatgc tctacttctg acttgtctag agctttcttc 174000
taattctgga ctaaaagcaa gcaggagttt ggaggatgat ggtgagaatt cacatccccg 174060
agttggcttt tggaatgcag tagtttgtga gatttagtgt ttttttaag aagtatattc 174120
agatcttgcc tttttcccag aaagcatatg agacaacttc caagacattt atagcatggc 174180
taataaaatg ggaaatcagg gcgaaggaca ggagaactca ataagggtta acatggctac 174240
agcgattgtc taaatgggtt ctttttgctg gccagagcag aaaggatcat gcagtaaagt 174300
ggggggggaag aaagggaatt gaatggtagg tgaagacttc atgttggtgc caggcactgt 174360
gccaggccct cctaggacct tgtcttactc aatcctcaca cagtgctgca agaggattag 174420
tcttatccct gttttagaga ggatgaaact gaaaggcagc gaggtgaagt caccagcagg 174480
aggctgaagc cgc                                                   174493
```

<210> SEQ ID NO 4
<211> LENGTH: 494
<212> TYPE: PRT
<213> ORGANISM: Mus Musculus

<400> SEQUENCE: 4

-continued

```
Met Leu Lys Phe Lys Tyr Gly Val Arg Asn Pro Pro Glu Ala Ser Ala
 1               5                  10                  15

Ser Glu Pro Ile Ala Ser Arg Ala Ser Arg Leu Asn Leu Phe Phe Gln
            20                  25                  30

Gly Lys Pro Pro Leu Met Thr Gln Gln Gln Met Ser Ala Leu Ser Arg
        35                  40                  45

Glu Gly Met Leu Asp Ala Leu Phe Ala Leu Phe Glu Glu Cys Ser Gln
    50                  55                  60

Pro Ala Leu Met Lys Met Lys His Val Ser Ser Phe Val Gln Lys Tyr
65                  70                  75                  80

Ser Asp Thr Ile Ala Glu Leu Arg Glu Leu Gln Pro Ser Ala Arg Asp
                85                  90                  95

Phe Glu Val Arg Ser Leu Val Gly Cys Gly His Phe Ala Glu Val Gln
            100                 105                 110

Val Val Arg Glu Lys Ala Thr Gly Asp Val Tyr Ala Met Lys Ile Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn Asn Leu Tyr Leu Val Met Glu Tyr
                165                 170                 175

Gln Pro Gly Gly Asp Phe Leu Ser Leu Leu Asn Arg Tyr Glu Asp Gln
            180                 185                 190

Leu Asp Glu Ser Met Ile Gln Phe Tyr Leu Ala Glu Leu Ile Leu Ala
        195                 200                 205

Val His Ser Val His Gln Met Gly Tyr Val His Arg Asp Ile Lys Pro
    210                 215                 220

Glu Asn Ile Leu Ile Asp Arg Thr Gly Glu Ile Lys Leu Val Asp Phe
225                 230                 235                 240

Gly Ser Ala Ala Lys Met Asn Ser Asn Lys Val Asp Ala Lys Leu Pro
                245                 250                 255

Ile Gly Thr Pro Asp Tyr Met Ala Pro Glu Val Leu Thr Val Met Asn
            260                 265                 270

Glu Asp Arg Arg Gly Thr Tyr Gly Leu Asp Cys Asp Trp Trp Ser Val
        275                 280                 285

Gly Val Val Ala Tyr Glu Met Val Tyr Gly Lys Thr Pro Phe Thr Glu
    290                 295                 300

Gly Thr Ser Ala Arg Thr Phe Asn Asn Ile Met Asn Phe Gln Arg Phe
305                 310                 315                 320

Leu Lys Phe Pro Asp Asp Pro Lys Val Ser Ser Glu Leu Leu Asp Leu
                325                 330                 335

Leu Gln Ser Leu Leu Cys Val Gln Lys Glu Arg Leu Lys Phe Glu Gly
            340                 345                 350

Leu Cys Cys His Pro Phe Phe Ala Arg Thr Asp Trp Asn Asn Ile Arg
        355                 360                 365

Asn Ser Pro Pro Pro Phe Val Pro Thr Leu Lys Ser Asp Asp Asp Thr
    370                 375                 380

Ser Asn Phe Asp Glu Pro Glu Lys Asn Ser Trp Ala Phe Ile Leu Cys
385                 390                 395                 400

Val Pro Ala Glu Pro Leu Ala Phe Ser Gly Glu Glu Leu Pro Phe Val
                405                 410                 415
```

-continued

```
Gly Phe Ser Tyr Ser Lys Ala Leu Gly Tyr Leu Gly Arg Ser Glu Ser
            420                 425                 430

Val Val Ser Ser Leu Asp Ser Pro Ala Lys Val Ser Ser Met Glu Lys
        435                 440                 445

Lys Leu Leu Ile Lys Ser Lys Glu Leu Gln Asp Ser Gln Asp Lys Cys
    450                 455                 460

His Lys Val Ser Ile Ser Thr Ala Gly Leu Arg Pro Cys Ser Arg Ile
465                 470                 475                 480

Leu Gln Ser Ile Tyr Ala Glu Gly Ser Ala Gly Gly His Cys
                485                 490
```